(12) United States Patent
Hasegawa et al.

(10) Patent No.: US 9,725,423 B2
(45) Date of Patent: Aug. 8, 2017

(54) TETRAZOLINONE COMPOUND AND APPLICATIONS THEREOF

(71) Applicant: SUMITOMO CHEMICAL COMPANY, LIMITED, Tokyo (JP)

(72) Inventors: Nao Hasegawa, Takarazuka (JP); Sadayuki Arimori, Takarazuka (JP); Yuichi Matsuzaki, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 14/647,215

(22) PCT Filed: Nov. 20, 2013

(86) PCT No.: PCT/JP2013/081828
§ 371 (c)(1),
(2) Date: May 26, 2015

(87) PCT Pub. No.: WO2014/084223
PCT Pub. Date: Jun. 5, 2014

(65) Prior Publication Data
US 2015/0299146 A1  Oct. 22, 2015

(30) Foreign Application Priority Data

Nov. 29, 2012 (JP) .................................. 2012-260680
Aug. 12, 2013 (JP) .................................. 2013-167312

(51) Int. Cl.

| C07D 257/04 | (2006.01) |
| C07D 405/12 | (2006.01) |
| C07D 409/12 | (2006.01) |
| A01N 43/713 | (2006.01) |
| A61K 31/41 | (2006.01) |
| A01N 43/76 | (2006.01) |
| C07D 401/12 | (2006.01) |
| C07D 403/12 | (2006.01) |
| C07D 407/12 | (2006.01) |
| C07D 413/12 | (2006.01) |

(52) U.S. Cl.
CPC ......... *C07D 257/04* (2013.01); *A01N 43/713* (2013.01); *A01N 43/76* (2013.01); *C07D 401/12* (2013.01); *C07D 403/12* (2013.01); *C07D 405/12* (2013.01); *C07D 407/12* (2013.01); *C07D 409/12* (2013.01); *C07D 413/12* (2013.01)

(58) Field of Classification Search
CPC .. C07D 257/04; C07D 405/12; C07D 409/12; A01N 43/713; A61K 31/41
USPC .................. 514/381, 382; 548/251
See application file for complete search history.

(56) References Cited

U.S. PATENT DOCUMENTS

| 6,583,090 B1 | 6/2003 | Gewehr et al. |
| 2013/0102568 A1 | 4/2013 | Fukumoto et al. |
| 2014/0323305 A1 | 10/2014 | Rheinheimer et al. |
| 2015/0031733 A1 | 1/2015 | Yoshimoto et al. |
| 2015/0051171 A1 | 2/2015 | Yoshimoto et al. |
| 2015/0203511 A1 | 7/2015 | Arimori et al. |
| 2015/0223460 A1 | 8/2015 | Arimori et al. |

FOREIGN PATENT DOCUMENTS

| DE | 199 00 571 A1 | 7/1999 | |
| JP | 9-208565 A | 8/1997 | |
| WO | WO 96/36229 A1 | 11/1996 | |
| WO | WO 9636229 A1 * | 11/1996 | ............. A01N 43/56 |
| WO | WO 2011/161945 A1 | 12/2011 | |
| WO | WO 2013/092224 A1 | 6/2013 | |
| WO | WO 2014/104268 A1 | 7/2014 | |
| WO | WO 2014/104382 A1 | 7/2014 | |
| WO | WO 2014/104384 A1 | 7/2014 | |
| WO | WO 2014/175465 A1 | 10/2014 | |

OTHER PUBLICATIONS

International Search Report issued in PCT/JP2013/081828, mailed on Feb. 4, 2014.
First Office Action (including an English translation thereof) issued in the corresponding Chinese Patent Application No. 201380061657.2 on Dec. 15, 2015.
Extended European Search Report, dated Apr. 15, 2016, for counterpart European Application No. 13857957.8.

* cited by examiner

*Primary Examiner* — Alicia L Otton
*Assistant Examiner* — Sagar Patel
(74) *Attorney, Agent, or Firm* — Birch, Stewart, Kolasch & Birch, LLP

(57) ABSTRACT

The compound represented by formula (1):

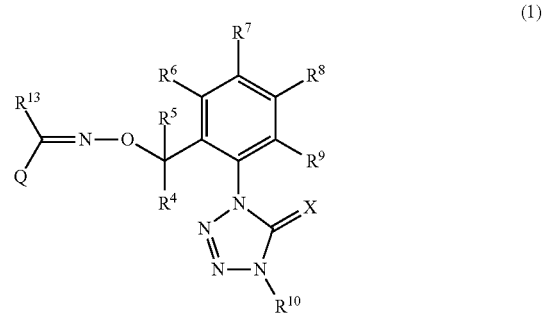

wherein
$R^4$ and $R^5$ each represents a hydrogen atom, a halogen atom, or a C1-C3 alkyl group; $R^6$ represents a C1-C4 alkyl group, a C3-C6 cycloalkyl group, or the like; $R^7$, $R^8$, and $R^9$ each represents a hydrogen atom, a halogen atom, or the like; $R^{10}$ represents a C1-C3 alkyl group, or the like; $R^{13}$ represents a C1-C3 alkyl group, or the like; and Q represents a phenyl group, or the like;
has an excellent control effect on pests.

5 Claims, No Drawings

TETRAZOLINONE COMPOUND AND APPLICATIONS THEREOF

TECHNICAL FIELD

The present invention relates to a tetrazolinone compound and applications thereof.

BACKGROUND ART

In order to control pests, various chemicals have been developed and applied for practical use. However, these chemicals may not exert sufficient effects.

Meanwhile, there has been known, as a pest control agent having a tetrazolinone ring, 1-methyl-4-{2-methyl-6-[1-(3-trifluoromethylphenyl)ethylideneaminooxymethyl]phenyl}-1,4-dihydrotetrazol-5-one represented by formula

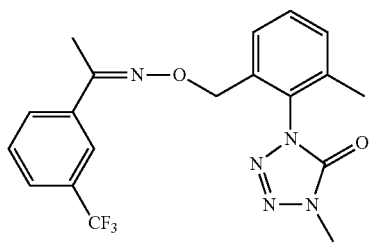

(A)

(JP 09-208565 A).

SUMMARY OF THE INVENTION

The present invention provides a compound having an excellent control effect on pests.

The present invention provides a tetrazolinone compound represented by formula (1):

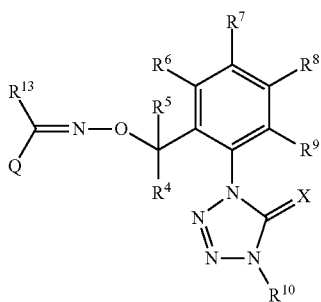

(1)

wherein
$R^4$ and $R^5$ each represents a hydrogen atom or a C1-C3 alkyl group;
$R^6$ represents a C1-C4 alkyl group, a C3-C6 cycloalkyl group, a C1-C4 haloalkyl group, a C3-C6 halocycloalkyl group, a halogen atom, a cyano group, a nitro group, a C2-C4 alkenyl group, a C2-C4 haloalkenyl group, a C2-C4 alkynyl group, a C2-C4 haloalkynyl group, a C1-C4 alkoxy group, a C1-C4 haloalkoxy group, a C1-C4 alkylthio group, or a C1-C4 haloalkylthio group;
$R^7$, $R^8$, and $R^9$ each represents a hydrogen atom or a halogen atom;
$R^{10}$ represents a C1-C3 alkyl group, a C1-C3 haloalkyl group, a C2-C3 alkenyl group, a C2-C3 haloalkenyl group, a C2-C3 alkynyl group, a C2-C3 haloalkynyl group, a C3-C5 cycloalkyl group, or a C3-C5 halocycloalkyl group;
X represents an oxygen atom or a sulfur atom;
$R^{13}$ represents a C1-C6 alkyl group, a C3-C6 cycloalkyl group, a hydrogen atom, a C1-C6 haloalkyl group, a C3-C6 halocycloalkyl group, a C2-C6 alkenyl group, a C2-C6 haloalkenyl group, a C2-C6 alkynyl group, a C2-C6 haloalkynyl group, a C1-C6 alkoxy group, or a C1-C6 alkylthio group; and
Q represents a phenyl group, a phenoxy group, a phenylthio group, a phenylamino group (provided that the phenyl moiety of the phenyl group, the phenoxy group, the phenylthio group, and the phenylamino group may form a four-membered ring, a five-membered ring, a six-membered ring, or a seven-membered ring together with the adjacent carbon atom; and the ring may contain one or more atoms selected from the group consisting of an oxygen atom, a sulfur atom, and a nitrogen atom as a ring-constituent atom, and may have an oxo group, a thioxo group, or a C1-C3 alkoxyimino group on the same carbon atom, and may have one or two oxide groups on the same sulfur atom; and the phenyl moiety and the ring may have one or more atoms or groups selected from Group $P^1$ and, when the number of atoms or groups selected from Group $P^1$ is two or more, the atoms or groups may be the same or different),
a five- or six-membered heterocyclyl group, a five- or six-membered heterocyclyloxy group, a five- or six-membered heterocyclylthio group, a five- or six-membered heterocyclylamino group (provided that the five- or six-membered heterocyclyl moiety of the five- or six-membered heterocyclyl group, the five- or six-membered heterocyclyloxy group, the five- or six-membered heterocyclylthio group, and the five- or six-membered heterocyclylamino group may form a four-membered ring, a five-membered ring, a six-membered ring, or a seven-membered ring together with the adjacent carbon atom; and the ring may contain one or more atoms selected from the group consisting of an oxygen atom, a sulfur atom, and a nitrogen atom as a ring-constituent atom; and the five- or six-membered heterocyclyl moiety and the ring may have an oxo group, a thioxo group, or a C1-C3 alkoxyimino group on the same carbon atom, and may have one or two oxide groups on the same sulfur atom, and may have one or more atoms or groups selected from Group $P^1$ and, when the number of atoms or groups selected from Group $P^1$ are two or more, the atoms or groups may be the same or different),
a C3-C6 cycloalkyl group, a C3-C6 cycloalkenyl group (provided that the C3-C6 cycloalkyl group and the C3-C6 cycloalkenyl group may form a four-membered ring, a five-membered ring, a six-membered ring, or a seven-membered ring together with the adjacent carbon atom; and the ring may contain one or more atoms selected from the group consisting of an oxygen atom, a sulfur atom, and a nitrogen atom as a ring-constituent atom, and may have one or two oxide groups on the same sulfur atom; and the ring, the C3-C6 cycloalkyl group, and the C3-C6 cycloalkenyl group may have an oxo group, a thioxo group, or a C1-C3 alkoxyimino group on the same carbon atom, and may have one or more atoms or groups selected from Group $P^1$ and, when the number of atoms or groups selected from Group $P^1$ is two or more, the atoms or groups may be the same or different),
a C1-C4 alkyl group (provided that the C1-C4 alkyl group may have an oxo group, a thioxo group, or a C1-C3 alkoxyimino group on the same carbon atom, and may have one or more atoms or groups selected from Group $P^1$ and, when the number of atoms or groups selected from Group $P^1$ is two or more, the atoms or groups may be the same or different), a C2-C4 alkenyl group, or a C2-C4 alkynyl group (provided that the C2-C4 alkenyl group and the C2-C4 alkynyl group may have one or more atoms or groups selected from Group $P^1$ and, when the number of atoms or groups selected from Group $P^1$ is two or more, the atoms or groups may be the same or different); or the substituents in Q and $R^{13}$ may form a five-membered ring, a six-membered ring, or a seven-membered ring together with the carbon atom or the nitrogen atom to which they are attached; and the ring may contain one or more atoms selected from the group consisting of an oxygen atom, a sulfur atom, and a nitrogen atom as a ring-constituent atom, and may contain one or more atoms or groups selected from Group $P^4$ as a substituent and, when the number of atoms or groups selected from Group $P^4$ is two or more, the atoms or groups may be the same or different:

Group $P^1$: Group consisting of a C1-C6 alkyl group optionally having an atom or a group selected from Group $P^3$, a C3-C6 cycloalkyl group optionally having an atom or a group selected from Group $P^3$, a phenyl group (provided that the phenyl group may form a four-membered ring, a five-membered ring, a six-membered ring, or a seven-membered ring together with the adjacent carbon atom; and the ring may contain one or more atoms selected from the group consisting of an oxygen atom, a sulfur atom, and a nitrogen atom as a ring-constituent atom, and may have an oxo group, a thioxo group, or a C1-C3 alkoxyimino group on the same carbon atom, and may have one or two oxide groups on same sulfur atom; and the phenyl group and the ring may have one or more atoms or group selected from Group $P^2$ and, when the number of atoms or groups selected from Group $P^2$ is two or more, the atoms or groups may be the same or different), a five- or six-membered heterocyclyl group (provided that the five- or six-membered heterocyclyl group may form a four-membered ring, a five-membered ring, a six-membered ring, or a seven-membered ring together with the adjacent carbon atom; the ring may contain one or more atoms selected from the group consisting of an oxygen atom, a sulfur atom, and a nitrogen atom as a ring-constituent atom; and the five- or six-membered heterocyclyl group and the ring may have an oxo group, a thioxo group, or a C1-C3 alkoxyimino group on the same carbon atom, and may have one or two oxide groups on the same sulfur atom, and may have one or more atoms or groups selected from Group $P^2$ and, when the number of atoms or groups selected from Group $P^2$ is two or more, the atoms or groups may be the same or different), a C1-C6 haloalkoxy group, a halogen atom, a nitro group, a C1-C6 alkoxy group, a C2-C6 alkenyl group, a C2-C6 haloalkenyl group, a C2-C6 alkynyl group, a C2-C6 haloalkynyl group, a C3-C6 alkenyloxy group, a C3-C6 haloalkenyloxy group, a C3-C6 alkynyloxy group, a C3-C6 haloalkynyloxy group, a C1-C8 alkylamino group, a C1-C8 haloalkylamino group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a cyano group, an amino group, a hydroxy group, a mercapto group, a pentafluorosulfanyl group, a C3-C9 trialkylsilyl group, a C2-C6 alkylcarbonyl group, a C2-C6 alkoxycarbonyl group, a C2-C8 alkylaminocarbonyl group, and a C2-C8 alkylcarbonylamino group;

Group $P^2$: Group consisting of a C1-C6 alkyl group optionally having an atom or a group selected from Group $P^3$, a C3-C6 cycloalkyl group optionally having an atom or a group selected from Group $P^3$, a C1-C6 alkoxy group, a C1-C6 haloalkoxy group, a halogen atom, a nitro group, a C2-C6 alkenyl group, a C2-C6 haloalkenyl group, a C2-C6 alkynyl group, a C2-C6 haloalkynyl group, a C3-C6 alkenyloxy group, a C3-C6 haloalkenyloxy group, a C3-C6 alkynyloxy group, a C3-C6 haloalkynyloxy group, a C1-C8 alkylamino group, a C1-C8 haloalkylamino group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a cyano group, an amino group, a hydroxy group, a mercapto group, a pentafluorosulfanyl group, a C3-C9 trialkylsilyl group, a C2-C6 alkylcarbonyl group, a C2-C6 alkoxycarbonyl group, a C2-C8 alkylaminocarbonyl group, and a C2-C8 alkylcarbonylamino group;

Group $P^3$: Group consisting of a halogen atom, a C3-C6 cycloalkyl group, a C3-C6 halocycloalkyl group, a C1-C4 alkoxy group, a C1-C4 haloalkoxy group, a C1-C4 alkylthio group, and a C1-C4 haloalkylthio group; and Group $P^4$: Group consisting of a halogen atom, a cyano group, a nitro group, a C1-C4 alkyl group, a C3-C6 cycloalkyl group, a C1-C4 haloalkyl group, a C3-C6 halocycloalkyl group, a C1-C4 alkoxy group, a C1-C4 haloalkoxy group, a C1-C4 alkylthio group, and a C1-C4 haloalkylthio group;

and its applications as a pest control agent; and a compound represented by formula (2):

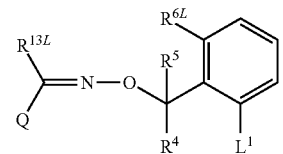

(2)

wherein
$R^{6L}$ represents a C1-C3 alkyl group optionally having one or more halogen atoms, a C3-C4 cycloalkyl group optionally having one or more halogen atoms, or a halogen atom;
$R^{13L}$ represents a C1-C3 alkyl group;
Q represents the following structure:

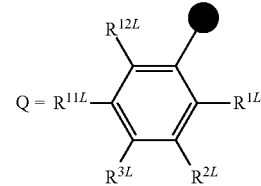

wherein $R^{1L}$, $R^{2L}$, $R^{3L}$, $R^{11L}$, and $R^{12L}$ each represents a hydrogen atom, a halogen atom, a cyano group, a nitro group,
a C1-C3 alkyl group optionally having one or more halogen atoms
a C1-C3 alkoxy group optionally having one or more halogen atoms, or
a C1-C3 alkylthio group optionally having one or more halogen atoms; and
the symbol ○ represents a binding site, or an indan-4-yl group, an indan-5-yl group, a 5,6,7,8-tetrahydronaphthalen-1-yl group, or a 5,6,7,8-tetrahydronaphthalen-2-yl group (provided that CH$_2$ constituting the ring of the indan-4-yl group, the indan-5-yl group, the 5,6,7,8-tetrahydronaphthalen-1-yl group, and the 5,6,7,8-tetrahydronaphthalen-2-yl group may be substituted with an oxygen atom, a sulfur atom, or a nitrogen atom, and the indan-4-yl group, the indan-5-yl group, the 5,6,7,8-tetrahydronaphthalen-1-yl group, and the 5,6,7,8-tetrahydronaphthalen-2-yl group may have atoms or groups selected from Group P$^4$ as a substituent): and Group P$^4$: Group consisting of a halogen atom, a cyano group, a nitro group, a C1-C4 alkyl group, a C3-C6 cycloalkyl group, a C1-C4 haloalkyl group, a C3-C6 halocycloalkyl group, a C1-C4 alkoxy group, a C1-C4 haloalkoxy group, a C1-C4 alkylthio group, and a C1-C4 haloalkylthio group); and L represents the following structure:

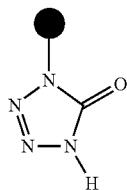

wherein the symbol ○ represents a binding site,
a nitro group, an amino group, an isocyanate group, a carboxyl group, C(O)Z$^{181}$ (provided that Z$^{181}$ represents a chlorine atom, a bromine atom, or an iodine atom), a C2-C6 alkoxycarbonyl group, C(O)N$_3$, NSO, C(O)NH$_2$, C(O)NHCl, C(O)NHBr, or C(O)NHOH, which is used in the production of the same.

MODE FOR CARRYING OUT THE INVENTION

The compound of the present invention (hereinafter referred to as the present compound) is a tetrazolinone compound represented by formula (1) mentioned above. A pest control agent containing the tetrazolinone compound represented by formula (1) is hereinafter referred to as the present control agent.

The present invention is also directed to a compound represented by formula (2) to be used in the production of the present compound.

Substituents as used herein will be mentioned in detail below.

The halogen atom is a fluorine atom, a chlorine atom, a bromine atom, or an iodine atom.

The C1-C6 alkyl group means a straight or branched alkyl group having 1 to 6 carbon atoms, and examples thereof include a methyl group, an ethyl group, a propyl group, an isopropyl group, a butyl group, an isobutyl group, a sec-butyl group, a tert-butyl group, a pentyl group, and a hexyl group.

The C1-C4 alkyl group is a methyl group, an ethyl group, a propyl group, an isopropyl group, a butyl group, an isobutyl group, a sec-butyl group, or a tert-butyl group.

The C1-C3 alkyl group is a methyl group, an ethyl group, a propyl group, or an isopropyl group.

The C1-C6 haloalkyl group means a group in which at least one hydrogen atom of a straight or branched alkyl group having 1 to 6 carbon atoms is substituted with a halogen atom, and examples thereof include a monofluoromethyl group, a monochloromethyl group, a dichloromethyl group, a difluoromethyl group, a trifluoromethyl group, a trichloromethyl group, a tribromomethyl group, a 2,2,2-trifluoroethyl group, a 2,2,2-trichloroethyl group, a pentafluoroethyl group, a chlorofluoromethyl group, a dichlorofluoromethyl group, a chlorodifluoromethyl group, a 2,2-difluoroethyl group, a 2-chloro-2-fluoroethyl group, a 2-chloro-2,2-difluoroethyl group, a 2,2-dichloro-2-fluoroethyl group, a 2-fluoropropyl group, a 3-fluoropropyl group, a 2,2-difluoropropyl group, a 3,3,3-trifluoropropyl group, a 3-(fluoromethyl)-2-fluoroethyl group, a 4-fluorobutyl group, and a 2,2-difluorohexyl group.

The C1-C4 haloalkyl group means a group in which at least one hydrogen atom of a straight or branched alkyl group having 1 to 4 carbon atoms is substituted with a halogen atom, and examples thereof include a monofluoromethyl group, a monochloromethyl group, a dichloromethyl group, a difluoromethyl group, a trifluoromethyl group, a trichloromethyl group, a tribromomethyl group, a 2,2,2-trifluoroethyl group, a 2,2,2-trichloroethyl group, a pentafluoroethyl group, a chlorofluoromethyl group, a dichlorofluoromethyl group, a chlorodifluoromethyl group, a 2,2-difluoroethyl group, a 2-chloro-2-fluoroethyl group, a 2-chloro-2,2-difluoroethyl group, a 2,2-dichloro-2-fluoroethyl group, a 2-fluoropropyl group, a 3-fluoropropyl group, a 2,2-difluoropropyl group, a 3,3,3-trifluoropropyl group, a 3-(fluoromethyl)-2-fluoroethyl group, and a 4-fluorobutyl group.

The C1-C3 haloalkyl group means a group in which at least one hydrogen atom of a straight or branched alkyl group having 1 to 3 carbon atoms is substituted with a halogen atom, and examples thereof include a chloromethyl group, a dichloromethyl group, a fluoromethyl group, a difluoromethyl group, a chlorofluoromethyl group, a dichlorofluoromethyl group, a chlorodifluoromethyl group, a trifluoromethyl group, a trichloromethyl group, a tribromomethyl group, a 2-fluoroethyl group, a 2,2-difluoroethyl group, a 2,2,2-trifluoroethyl group, a 2-chloroethyl group, a 2,2-dichloroethyl group, a 2,2,2-trichloroethyl group, a pentafluoroethyl group, a pentachloroethyl group, a 2-chloro-2-fluoroethyl group, a 2-chloro-2,2-difluoroethyl group, a 2-fluoropropyl group, a 3-fluoropropyl group, a 2,2-difluoropropyl group, a 2,3-difluoropropyl group, a 3,3,3-trifluoropropyl group, and a heptafluoropropyl group.

The C1-C4 fluoroalkyl group means a group in which at least one hydrogen atom of a straight or branched alkyl group having 1 to 4 carbon atoms is substituted with a fluorine atom, and examples thereof include a fluoromethyl group, a difluoromethyl group, a trifluoromethyl group, a 1,1-difluoroethyl group, a 1,2-difluoroethyl group, a 2,2-difluoroethyl group, a 1,1,2-trifluoroethyl group, a 1,2,2-trifluoroethyl group, a 2,2,2-trifluoroethyl group, a 1,1,2,2-tetrafluoroethyl group, a perfluoroethyl group, a 1,1-difluoropropyl group, a 1,2-difluoropropyl group, a perfluoropropyl group, a 1,1,2,2,3,3-hexafluoropropyl group, a perfluoroisopropyl group, and a perfluorobutyl group.

The C1-C3 alkyl group optionally having one or more halogen atoms means a group in which one or more hydrogen atoms of a straight or branched alkyl group having 1 to 3 carbon atoms may be substituted with a halogen atom, and examples thereof include a methyl group, an ethyl group, a propyl group, an isopropyl group, a chloromethyl group, a dichloromethyl group, a fluoromethyl group, a difluoromethyl group, a chlorofluoromethyl group, a dichlorofluoromethyl group, a chlorodifluoromethyl group, a trifluoromethyl group, a trichloromethyl group, a tribromomethyl group, a 2-fluoroethyl group, a 2,2-difluoroethyl group, a 2,2,2-trifluoroethyl group, a 2-chloroethyl group, a 2,2-dichloroethyl group, a 2,2,2-trichloroethyl group, a pentafluoroethyl group, a pentachloroethyl group, a 2-chloro-2-fluoroethyl group, a 2-chloro-2,2-difluoroethyl group, a 2-fluoropropyl group, a 3-fluoropropyl group, a 2,2-difluoropropyl group, a 2,3-difluoropropyl group, a 3,3,3-trifluoropropyl group, and a heptafluoropropyl group.

The C3-C6 cycloalkyl group is a cyclic alkyl group having 3 to 6 carbon atoms and may also be a cycloalkyl group having an alkyl group, and examples thereof include a cyclopropyl group, a cyclobutyl group, a cyclopentyl group, a cyclohexyl group, a 1-methylcyclopropyl group, a 2-methylcyclopropyl group, a 2,2-dimethylcyclopropyl group, and a 2,3-dimethylcyclopropyl group.

The C3-C5 cycloalkyl group means a cyclic alkyl group having 3 to 5 carbon atoms and may also be a cycloalkyl group having an alkyl group, and examples thereof include a cyclopropyl group, a cyclobutyl group, a cyclopentyl group, a 1-methylcyclopropyl group, a 2-methylcyclopropyl group, a 2,2-dimethylcyclopropyl group, and a 2,3-dimethylcyclopropyl group.

The C3-C4 cycloalkyl group is a cyclic alkyl group having 3 to 4 carbon atoms and may also be a cycloalkyl group having an alkyl group, and examples thereof include a cyclopropyl group, a cyclobutyl group, and a 1-methylcyclopropyl group.

The C3-C6 halocycloalkyl group represents a group in which at least one hydrogen atom of a cycloalkyl group having 3 to 6 carbon atoms is substituted with a halogen atom, and examples thereof include a 1-fluorocyclopropyl group, a 2-fluorocyclopropyl group, a 2,2-difluorocyclopropyl group, a 1-chlorocyclopropyl group, a 2-chloro-2-fluorocyclopropyl group, a 2,2-dichlorocyclopropyl group, a 2,2-dibromocyclopropyl group, a 2,2-difluoro-1-methylcyclopropyl group, a 2,2-dichloro-1-methylcyclopropyl group, a 2,2-dibromo-1-methylcyclopropyl group, a 1-(trifluoromethyl)cyclopropyl group, a 2,2,3,3-tetrafluorocyclobutyl group, a 1-fluorocyclobutyl group, a 1-chlorocyclobutyl group, 2,2,3,3-tetrafluorocyclobutyl group, a 2-chlorocyclopentyl group, a 3-chlorocyclopentyl group, a 3,3-difluorocyclopentyl group, a 1-fluorocyclohexyl group, a 2,2-difluorocyclohexyl group, a 3,3-difluorocyclohexyl group, and a 4,4-difluorocyclohexyl group.

The C3-C5 halocycloalkyl group is a group in which at least one hydrogen atom of a cycloalkyl group having 3 to 5 carbon atoms is substituted with a halogen atom, and examples thereof include a 1-fluorocyclopropyl group, a 2-fluorocyclopropyl group, a 2,2-difluorocyclopropyl group, a 1-chlorocyclopropyl group, a 2-chloro-2-fluorocyclopropyl group, a 2,2-dichlorocyclopropyl group, a 2,2-dibromocyclopropyl group, a 2,2-difluoro-1-methylcyclopropyl group, a 2,2-dichloro-1-methylcyclopropyl group, a 2,2-dibromo-1-methylcyclopropyl group, a 1-(trifluoromethyl)cyclopropyl group, a 2,2,3,3-tetrafluorocyclobutyl group, a 2,2,3,3-tetrafluorocyclobutyl group, a 2-chlorocyclopentyl group, and a 3-chlorocyclopentyl group.

The C3-C4 halocycloalkyl group is a group in which at least one hydrogen atom of a cyclic alkyl group having 3 to 4 carbon atoms is substituted with a halogen atom, and may be a cycloalkyl group having an alkyl group, and examples thereof include a 1-fluorocyclopropyl group, a 2-fluorocyclopropyl group, a 2,2-difluorocyclopropyl group, a cyclobutyl group, and a 1-methylcyclopropyl group.

The C3-C4 cycloalkyl group optionally having one or more halogen atoms is a group in which one or more hydrogen atoms of a cyclic alkyl group having 3 to 4 carbon atoms may be substituted with a halogen atom, and examples thereof include a cyclopropyl group, a cyclobutyl group, a 1-methylcyclopropyl group, a 1-fluorocyclopropyl group, a 2-fluorocyclopropyl group, a 2,2-difluorocyclopropyl group, a cyclobutyl group, and a 1-methylcyclopropyl group.

The C2-C6 alkenyl group means a straight or branched alkenyl group having 2 to 6 carbon atoms, and examples thereof include a vinyl group, a 1-propenyl group, an isopropenyl group, a 2-propenyl group, a 1-butenyl group, a 1-methyl-1-propenyl group, a 2-butenyl group, a 1-methyl-2-propenyl group, a 3-butenyl group, a 2-methyl-1-propenyl group, a 2-methyl-2-propenyl group, a 1,3-butadienyl group, a 1-pentenyl group, a 1-ethyl-2-propenyl group, a 2-pentenyl group, a 1-methyl-1-butenyl group, a 3-pentenyl group, a 1-methyl-2-butenyl group, a 4-pentenyl group, a 1-methyl-3-butenyl group, a 3-methyl-1-butenyl group, a 1,2-dimethyl-2-propenyl group, a 1,1-dimethyl-2-propenyl group, a 2-methyl-2-butenyl group, a 3-methyl-2-butenyl group, a 1,2-dimethyl-1-propenyl group, a 2-methyl-3-butenyl group, a 3-methyl-3-butenyl group, a 1,3-pentadienyl group, a 1-vinyl-2-propenyl group, a 1-hexenyl group, and a 5-hexenyl group.

The C2-C6 haloalkenyl group means a group in which at least one hydrogen atom of a straight or branched alkenyl group having 2 to 6 carbon atoms is substituted with a halogen atom, and examples thereof include a 2-chlorovinyl group, a 2-bromovinyl group, a 2-iodovinyl group, a 3-chloro-2-propenyl group, a 3-bromo-2-propenyl group, a 1-chloromethylvinyl group, a 2-bromo-1-methylvinyl group, a 1-trifluoromethylvinyl group, a 3,3,3-trichloro-1-propenyl group, a 3-bromo-3,3-difluoro-1-propenyl group, a 2,3,3,3-tetrachloro-1-propenyl group, a 1-trifluoromethyl-2,2-difluorovinyl group, a 2-chloro-2-propenyl group, a 3,3-difluoro-2-propenyl group, a 2,3,3-trichloro-2-propenyl group, a 4-bromo-3-chloro-3,4,4-trifluoro-1-butenyl group, a 1-bromomethyl-2-propenyl group, a 3-chloro-2-butenyl group, a 4,4,4-trifluoro-2-butenyl group, a 4-bromo-4,4-difluoro-2-butenyl group, a 3-bromo-3-butenyl group, a 3,4,4-trifluoro-3-butenyl group, a 3,4,4-tribromo-3-butenyl group, a 3-bromo-2-methyl-2-propenyl group, a 3,3-difluoro-2-methyl-2-propenyl group, a 3,3,3-trifluoro-2-methyl-1-propenyl group, a 3-chloro-4,4,4-trifluoro-2-butenyl group, a 3,3,3-trifluoro-1-methyl-1-propenyl group, a 3,4,4-trifluoro-1,3-butadienyl group, a 3,4-dibromo-1-pentenyl group, a 4,4-difluoro-3-methyl-3-butenyl group, a 3,3,4,4,5,5-heptafluoro-1-pentenyl group, a 5,5-difluoro-4-pentenyl group, a 4,5,5-trifluoro-4-pentenyl group, a 3,4,4,4-tetrafluoro-3-trifluoromethyl-1-butenyl group, a 4,4,4-trifluoro-3-methyl-2-butenyl group, a 3,5,5-trifluoro-2,4-pentadienyl group, a 4,4,5,5,6,6,6-heptafluoro-2-hexenyl group, a 3,4,4,5,5,5-hexafluoro-3-trifluoromethyl-1-pentenyl group, a 4,5,5,5-tetrafluoro-4-trifluoromethyl-2-pentenyl group, and a 5-bromo-4,5,5-trifluoro-4-trifluoromethyl-2-pentenyl group.

Examples of the C2-C4 alkenyl group include a vinyl group, a 1-propenyl group, an isopropenyl group, a 2-propenyl group, a 1-butenyl group, a 1-methyl-1-propenyl group, a 2-butenyl group, a 1-methyl-2-propenyl group, a 3-butenyl group, a 2-methyl-1-propenyl group, and a 2-methyl-2-propenyl group.

Examples of the C2-C3 alkenyl group includes a vinyl group, a 1-propenyl group, an isopropenyl group, and a 2-propenyl group.

The C2-C4 haloalkenyl group means a group in which at least one hydrogen atom of a straight or branched alkenyl group having 2 to 4 carbon atoms is substituted with a halogen atom, and examples thereof include a 2-chlorovinyl group, a 2-bromovinyl group, a 2-iodovinyl group, a 3-chloro-2-propenyl group, a 3-bromo-2-propenyl group, a 1-chloromethylvinyl group, a 2-bromo-1-methylvinyl group, a 1-trifluoromethylvinyl group, a 3,3,3-trichloro-1-propenyl group, a 3-bromo-3,3-difluoro-1-propenyl group, a 2,3,3,3-tetrachloro-1-propenyl group, a 1-trifluoromethyl-2,2-difluorovinyl group, a 2-chloro-2-propenyl group, a 3,3-difluoro-2-propenyl group, a 2,3,3-trichloro-2-propenyl group, a 4-bromo-3-chloro-3,4,4-trifluoro-1-butenyl group, a 1-bromomethyl-2-propenyl group, a 3-chloro-2-butenyl group, a 4,4,4-trifluoro-2-butenyl group, a 4-bromo-4,4-difluoro-2-butenyl group, a 3-bromo-3-butenyl group, a 3,4,4-trifluoro-3-butenyl group, a 3,4,4-tribromo-3-butenyl group, a 3-bromo-2-methyl-2-propenyl group, a 3,3-difluoro-2-methyl-2-propenyl group, a 3,3,3-trifluoro-2-methyl-1-propenyl group, a 3-chloro-4,4,4-trifluoro-2-butenyl group, a 3,3,3-trifluoro-1-methyl-1-propenyl group, and a 3,4,4-trifluoro-1,3-butadienyl group.

Examples of the C2-C3 haloalkenyl group include a 2-chlorovinyl group, a 2-bromovinyl group, a 2-iodovinyl group, a 3-chloro-2-propenyl group, a 3-bromo-2-propenyl group, a 1-chloromethylvinyl group, a 2-bromo-1-methylvinyl group, a 1-trifluoromethylvinyl group, a 3,3,3-trichloro-1-propenyl group, a 3-bromo-3,3-difluoro-1-propenyl group, a 2,3,3,3-tetrachloro-1-propenyl group, a 1-trifluoromethyl-2,2-difluorovinyl group, a 2-chloro-2-propenyl group, a 3,3-difluoro-2-propenyl group, and a 2,3,3-trichloro-2-propenyl group.

The C3-C6 cycloalkenyl group is a cycloalkenyl group having 3 to 6 carbon atoms or may be a cycloalkyl group having an alkyl group, and examples thereof include a cycloprop-1-enyl group, a cycloprop-2-enyl group, a cyclobut-1-enyl group, a cyclopent-1-enyl group, a cyclohex-1-enyl group, a cyclohex-3-enyl group, a cyclohex-4-enyl group, a 3-methylcyclopent-1-enyl group, a 5-methylcyclopent-1-enyl group, and a 3-methylcyclohexex-1-enyl group.

The C2-C6 alkynyl group means a straight or branched alkynyl group having 2 to 6 carbon atoms, and examples thereof include an ethynyl group, a propargyl group, a 1-butyn-3-yl group, a 3-methyl-1-butyn-3-yl group, a 2-butynyl group, a 3-butynyl group, a 2-pentynyl group, a 3-pentynyl group, a 4-pentynyl group, a 1-hexynyl group, and a 5-hexynyl group.

The C2-C6 haloalkynyl group means a group in which at least one hydrogen atom of a straight or branched alkynyl group having 2 to 6 carbon atoms is substituted with a halogen atom, and examples thereof include a fluoroethynyl group, a 3-fluoro-2-propynyl group, a 3-chloro-2-propynyl group, a 3-bromo-2-propynyl group, a 3-iodo-2-propynyl group, a 3-chloro-1-propynyl group, a 5-chloro-4-pentynyl group, a 3,3,3-trifluoro-1-propynyl group, a 3,3-difluoro-1-propynyl group, a 4,4,4-trifluoro-2-butynyl group, a perfluoro-2-butynyl group, a perfluoro-2-pentynyl group, a perfluoro-3-pentynyl group, and a perfluoro-1-hexynyl group.

The C2-C3 alkynyl group is an ethynyl group, a 1-propynyl group, or a 2-propynyl group.

Examples of the C2-C4 alkynyl group include an ethynyl group, a 2-propynyl group, a 2-butynyl group, and a 3-butynyl group.

The C2-C4 haloalkynyl group means a group in which at least one hydrogen atom of a straight or branched alkynyl group having 2 to 4 carbon atoms is substituted with a halogen atom, and examples thereof include a fluoroethynyl group, a 3-fluoro-2-propynyl group, and a 4,4,4-trifluoro-2-butynyl group.

Examples of the C2-C3 haloalkynyl group include a fluoroethynyl group, a 3-fluoro-2-propynyl group, a 3-chloro-2-propynyl group, a 3-bromo-2-propynyl group, a 3-iodo-2-propynyl group, a 3-chloro-1-propynyl group, a 3,3,3-trifluoro-1-propynyl group, and a 3,3-difluoro-1-propynyl group.

The C1-C6 alkoxy group represents a straight or branched alkoxy group having 1 to 6 carbon atoms, and examples thereof include a methoxy group, an ethoxy group, a propoxy group, an isopropoxy group, a butoxy group, an isobutoxy group, a sec-butoxy group, a tert-butoxy group, a pentyloxy group, an isoamyloxy group, a neopentyloxy group, a 2-pentyloxy group, a 3-pentyloxy group, a 2-methylbutoxy group, a hexyloxy group, an isohexyloxy group, a 3-methylpentyloxy group, and a 4-methylpentyloxy group.

The C1-C4 alkoxy group represents a straight or branched alkoxy group having 1 to 4 carbon atoms, and examples thereof include a methoxy group, an ethoxy group, a propoxy group, an isopropoxy group, a butoxy group, an isobutoxy group, a sec-butoxy group, and a tert-butoxy group.

Examples of the C1-C3 alkoxy group include a methoxy group, an ethoxy group, a propoxy group, an isopropoxy group, and a cyclopropoxy group.

The C1-C6 haloalkoxy group means a group in which at least one hydrogen atom of a straight or branched alkoxy group having 1 to 6 carbon atoms is substituted with a halogen atom, and examples thereof include a trifluoromethoxy group, a trichloromethoxy group, a chloromethoxy group, a dichloromethoxy group, a fluoromethoxy group, a difluoromethoxy group, a chlorofluoromethoxy group, a dichlorofluoromethoxy group, a chlorodifluoromethoxy group, a pentafluoroethoxy group, a pentachloroethoxy group, a 2,2,2-trichloroethoxy group, a 2,2,2-trifluoroethoxy group, a 2,2,2-tribromoethoxy group, a 2,2,2-triiodoethoxy group, a 2-fluoroethoxy group, a 2-chloroethoxy group, a 2,2-difluoroethoxy group, a 2-chloro-2-fluoroethoxy group, a 2-chloro-2,2-difluoroethoxy group, a heptafluoropropoxy group, a heptachloropropoxy group, a heptabromopropoxy group, a heptaiodopropoxy group, a 3,3,3-trifluoropropoxy group, a 3,3,3-trichloropropoxy group, a 3,3,3-tribromopropoxy group, a 3,3,3-triiodopropoxy group, a 2-fluoropropoxy group, a 3-fluoropropoxy group, a 2,2-difluoropropoxy group, a 2,3-difluoropropoxy group, a 2-chloropropoxy group, a 3-chloropropoxy group, a 2,3-dichloropropoxy group, a 2-bromopropoxy group, a 3-bromopropoxy group, a 3,3,3-trifluoropropoxy group, a nonafluorobutoxy group, a nonachlorobutoxy group, a nonabromobutoxy group, a nonaiodobutoxy group, a perfluoropentyloxy group, a perchloropentyloxy group, a perbromopentyloxy group, a perfluorohexyloxy group, a perchlorohexyloxy group, a perbromohexyloxy group, and a periodohexyloxy group.

The C1-C4 haloalkoxy group means a group in which at least one hydrogen atom of a straight or branched alkoxy group having 1 to 4 carbon atoms is substituted with a halogen atom, and examples thereof include a trifluoromethoxy group, a trichloromethoxy group, a chloromethoxy group, a dichloromethoxy group, a fluoromethoxy group, a difluoromethoxy group, a chlorofluoromethoxy group, a dichlorofluoromethoxy group, a chlorodifluoromethoxy group, a pentafluoroethoxy group, a pentachloroethoxy group, a 2,2,2-trichloroethoxy group, a 2,2,2-trifluoroethoxy group, a 2,2,2-tribromoethoxy group, a 2,2,2-triiodoethoxy group, a 2-fluoroethoxy group, a 2-chloroethoxy group, a 2,2-difluoroethoxy group, a 2,2,2-trifluoroethoxy group, a 2-chloro-2-fluoroethoxy group, a 2-chloro-2,2-difluoroethoxy group, a heptafluoropropoxy group, a heptachloropropoxy group, a heptabromopropoxy group, a heptaiodopropoxy group, a 3,3,3-trifluoropropoxy group, a 3,3,3-trichloropropoxy group, a 3,3,3-tribromopropoxy group, a 3,3,3-triiodopropoxy group, a 2-fluoropropoxy group, a 3-fluoropropoxy group, a 2,2-difluoropropoxy group, a 2,3-difluoropropoxy group, a 2-chloropropoxy group, a 3-chloropropoxy group, a 2,3-dichloropropoxy group, a 2-bromopropoxy group, a 3-bromopropoxy group, a 2,3,3-trifluoropropoxy group, a nonafluorobutoxy group, a nonachlorobutoxy group, a nonabromobutoxy group, and a nonaiodobutoxy group.

The C1-C3 haloalkoxy group means a group in which at least one hydrogen atom of a straight or branched alkoxy group having 1 to 3 carbon atoms is substituted with a halogen atom, and examples thereof include a trifluoromethoxy group, a trichloromethoxy group, a chloromethoxy group, a dichloromethoxy group, a fluoromethoxy group, a difluoromethoxy group, a chlorofluoromethoxy group, a dichlorofluoromethoxy group, a chlorodifluoromethoxy group, a pentafluoroethoxy group, a pentachloroethoxy group, a 2,2,2-trichloroethoxy group, a 2,2,2-trifluoroethoxy group, a 2,2,2-tribromoethoxy group, a 2,2,2-triiodoethoxy group, a 2-fluoroethoxy group, a 2-chloroethoxy group, a 2,2-difluoroethoxy group, a 2,2,2-trifluoroethoxy group, a 2-chloro-2-fluoroethoxy group, a 2-chloro-2,2-difluoroethoxy group, a heptafluoropropoxy group, a heptachloropropoxy group, a heptabromopropoxy group, a heptaiodopropoxy group, a 3,3,3-trifluoropropoxy group, a 3,3,3-trichloropropoxy group, a 3,3,3-tribromopropoxy group, a 3,3,3-triiodopropoxy group, a 2-fluoropropoxy group, a 3-fluoropropoxy group, a 2,2-difluoropropoxy group, a 2,3-difluoropropoxy group, a 2-chloropropoxy group, a 3-chloropropoxy group, a 2,3-dichloropropoxy group, a 2-bromopropoxy group, a 3-bromopropoxy group, and a 3,3,3-trifluoropropoxy group.

The C1-C4 fluoroalkoxy group means a group in which at least one hydrogen atom of a straight or branched alkoxy group having 1 to 4 carbon atoms is substituted with a fluorine atom, and examples thereof include a fluoromethoxy group, a difluoromethoxy group, a trifluoromethoxy group, a 1,1-difluoroethoxy group, a 1,2-difluoroethoxy group, a 2,2-difluoroethoxy group, a 1,1,2-trifluoroethoxy group, a 1,2,2-trifluoroethoxy group, a 2,2,2-trifluoroethoxy group, a 1,1,2,2-tetrafluoroethoxy group, a perfluoroethoxy group, a 1,1-difluoropropoxy group, a 1,2-difluoropropoxy group, a perfluoropropoxy group, a 2,2,2,2,2,2-hexafluoropropoxy group, a perfluoroisopropoxy group, and a perfluorobutoxy group.

The C1-C3 alkoxy group optionally having one or more halogen atoms represents a group in which one or more hydrogen atoms of a straight or branched alkoxy group having 1 to 3 carbon atoms may be substituted with a halogen atom, and examples thereof include a methoxy group, an ethoxy group, a propoxy group, an isopropoxy group, a cyclopropoxy group, a trifluoromethoxy group, a trichloromethoxy group, a chloromethoxy group, a dichloromethoxy group, a fluoromethoxy group, a difluoromethoxy group, a chlorofluoromethoxy group, a dichlorofluoromethoxy group, a chlorodifluoromethoxy group, a pentafluoroethoxy group, a pentachloroethoxy group, a 2,2,2-trichloroethoxy group, a 2,2,2-trifluoroethoxy group, a 2,2,2-tribromoethoxy group, a 2,2,2-triiodoethoxy group, a 2-fluoroethoxy group, a 2-chloroethoxy group, a 2,2-difluoroethoxy group, a 2,2,2-trifluoroethoxy group, a 2-chloro-2-fluoroethoxy group, a 2-chloro-2,2-difluoroethoxy group, a heptafluoropropoxy group, a heptachloropropoxy group, a heptabromopropoxy group, a heptaiodopropoxy group, a 3,3,3-trifluoropropoxy group, a 3,3,3-trichloropropoxy group, a 3,3,3-tribromopropoxy group, a 3,3,3-triiodopropoxy group, a 2-fluoropropoxy group, a 3-fluoropropoxy group, a 2,2-difluoropropoxy group, a 2,3-difluoropropoxy group, a 2-chloropropoxy group, a 3-chloropropoxy group, a 2,3-dichloropropoxy group, a 2-bromopropoxy group, a 3-bromopropoxy group, and a 3,3,3-trifluoropropoxy group.

The C3-C6 alkenyloxy group means a straight or branched alkenyloxy group having 3 to 6 carbon atoms, and examples thereof include a 2-propenyloxy group, a 2-butenyloxy group, a 1-methyl-2-propenyloxy group, a 3-butenyloxy group, a 2-methyl-2-propenyloxy group, a 2-pentenyloxy group, a 3-pentenyloxy group, a 4-pentenyloxy group, a 1-methyl-3-butenyloxy group, a 1,2-dimethyl-2-propenyloxy group, a 1,1-dimethyl-2-propenyloxy group, a 2-methyl-2-butenyloxy group, a 3-methyl-2-butenyloxy group, a 2-methyl-3-butenyloxy group, a 3-methyl-3-butenyloxy group, a 1-vinyl-2-propenyloxy group, and a 5-hexenyloxy group.

The C3-C6 haloalkenyloxy group means a group in which at least one hydrogen atom of a straight or branched alkenyloxy group having 3 to 6 carbon atoms is substituted with a halogen atom, and examples thereof include a 3-chloro-2-propenyloxy group, a 3-bromo-2-propenyloxy group, a 3-bromo-3,3-difluoro-1-propenyloxy group, a 2,3,3,3-tetrachloro-1-propenyloxy group, a 2-chloro-2-propenyloxy group, a 3,3-difluoro-2-propenyloxy group, a 2,3,3-trichloro-2-propenyloxy group, a 3,3-dichloro-2-propenyloxy group, a 3,3-dibromo-2-propenyloxy group, a 3-fluoro-3-chloro-2-propenyloxy group, a 4-bromo-3-chloro-3,4,4-trifluoro-1-butenyloxy group, a 1-bromomethyl-2-propenyloxy group, a 3-chloro-2-butenyloxy group, a 4,4,4-trifluoro-2-butenyloxy group, a 4-bromo-4,4-difluoro-2-butenyloxy group, a 3-bromo-3-butenyloxy group, a 3,4,4-trifluoro-3-butenyloxy group, a 3,4,4-tribromo-3-butenyloxy group, a 3-bromo-2-methyl-2-propenyloxy group, a 3,3-difluoro-2-methyl-2-propenyloxy group, a 3-chloro-4,4,4-trifluoro-2-butenyloxy group, a 4,4-difluoro-3-methyl-3-butenyloxy group, a 5,5-difluoro-4-pentenyloxy group, a 4,5,5-trifluoro-4-pentenyloxy group, a 4,4,4-trifluoro-3-methyl-2-butenyloxy group, a 3,5,5-trifluoro-2,4-pentadienyloxy group, a 4,4,5,5,6,6,6-heptafluoro-2-hexenyloxy group, a 4,5,5,5-tetrafluoro-4-trifluoromethyl-2-pentenyloxy group, and a 5-bromo-4,5,5-trifluoro-4-trifluoromethyl-2-pentenyloxy group.

The C3-C6 alkynyloxy group means a straight or branched alkynyloxy group having 3 to 6 carbon atoms, and examples thereof include a propargyloxy group, a 1-butyn-3-yloxy group, a 3-methyl-1-butyn-3-yloxy group, a 2-butynyloxy group, a 3-butynyloxy group, a 2-pentynyloxy group, a 3-pentynyloxy group, a 4-pentynyloxy group, and a 5-hexynyloxy group.

The C3-C6 haloalkynyloxy group means a group in which at least one hydrogen atom of a straight or branched alkynyloxy group having 3 to 6 carbon atoms is substituted with a halogen atom, and examples thereof include a 3-chloro-2-propynyloxy group, a 3-bromo-2-propynyloxy, a 3-iodo-2-propynyloxy group, a 5-chloro-4-pentynyloxy group, a 4,4,4-trifluoro-2-butynyloxy group, a perfluoro-2-butynyloxy group, a perfluoro-3-butynyloxy group, a perfluoro-2-pentynyloxy group, a perfluoro-3-pentynyloxy group, a perfluoro-4-pentynyloxy group, and a perfluoro-5-hexynyloxy group.

The C1-C6 alkylthio group is a straight or branched alkylthio group having 1 to 6 carbon atoms, and examples thereof include a methylthio group, an ethylthio group, a propylthio group, an isopropylthio group, a butylthio group, a sec-butylthio group, a tert-butylthio group, a pentylthio group, an isopentylthio group, a neopentylthio group, a hexylthio group, an isohexylthio group, and a sec-hexylthio group.

The C1-C6 haloalkylthio group means a group in which at least one hydrogen atom of a straight or branched alkylthio group having 1 to 6 carbon atoms is substituted with a halogen atom, and examples thereof include a monofluoromethylthio group, a difluoromethylthio group, a trifluoromethylthio group, a trichloromethylthio group, a tribromomethylthio group, a triiodomethylthio group, a chlorofluoromethylthio group, a pentafluoroethylthio group, a pentachloroethylthio group, a pentabromoethylthio group, a pentaiodoethylthio group, a 2,2,2-trichloroethylthio group, a 2,2,2-trifluoroethylthio group, a 2,2,2-tribromoethylthio group, a 2,2,2-triiodoethylthio group, a 2,2-difluoroethylthio group, a heptafluoropropylthio group, a heptachloropropylthio group, a heptabromopropylthio group, a heptaiodopropylthio group, a 3,3,3-trifluoropropylthio group, a 3,3,3-trichloropropylthio group, a 3,3,3-tribromopropylthio group, a 3,3,3-triiodopropylthio group, a 2,2-difluoropropylthio group, a 2,3,3-trifluoropropylthio group, a nonafluorobutylthio group, a nonachlorobutylthio group, a nonabromobutylthio group, a nonaiodobutylthio group, a perfluoropentylthio group, a perchloropentylthio group, a perbromopentylthio group, a perfluorohexylthio group, a perchlorohexylthio group, a perbromohexylthio group, and a periodohexylthio group.

Examples of the C1-C4 alkylthio group include a methylthio group, an ethylthio group, a propylthio group, an isopropylthio group, a butylthio group, an isobutylthio group, and a tert-butylthio group.

The C1-C4 haloalkylthio group means a group in which at least one hydrogen atom of a straight or branched alkylthio group having 1 to 4 carbon atoms is substituted with a halogen atom, and examples thereof include a monofluoromethylthio group, a difluoromethylthio group, a trifluoromethylthio group, a trichloromethylthio group, a tribromomethylthio group, a triiodomethylthio group, a chlorofluoromethylthio group, a pentafluoroethylthio group, a pentachloroethylthio group, a pentabromoethylthio group, a pentaiodoethylthio group, a 2,2,2-trichloroethylthio group, a 2,2,2-trifluoroethylthio group, a 2,2,2-trifluoroethylthio group, a 2,2,2-tribromoethylthio group, a 2,2,2-triiodoethylthio group, a 2,2-difluoroethylthio group, and a 2,2,2,2,2,2-hexafluoroisopropylthio group.

The C1-C3 alkylthio group is a methylthio group, an ethylthio group, a propylthio group, or an isopropylthio group.

The C1-C3 alkylthio group optionally having one or more halogen atoms means a group in which one or more hydrogen atoms of a straight or branched alkylthio group having 1 to 3 carbon atoms may be substituted with a halogen atom, and examples thereof include a methylthio group, an ethylthio group, a propylthio group, an isopropylthio group, a cyclopropylthio group, a trifluoromethylthio group, a difluoromethylthio group, and a pentafluoroethylthio group.

The C1-C8 alkylamino group means a group in which one hydrogen atom on nitrogen of an amino group is substituted with a straight or branched alkyl group having 1 to 8 carbon atoms, or an amino group in which two hydrogen atoms on nitrogen of an amino group are substituted with the same or different C1-C4 alkyl groups, and examples thereof include a methylamino group, an ethylamino group, a propylamino group, an isopropylamino group, an N,N-dimethylamino group, an N,N-diethylamino group, an N-ethyl-N-methylamino group, a butylamino group, a pentylamino group, a hexylamino group, an N,N-dibutylamino group, and an N-sec-butyl-N-methylamino group.

The C1-C8 haloalkylamino group means a group in which at least one hydrogen atom is substituted with a halogen atom among C1-C8 alkylamino groups, and examples thereof include a 2,2,2-trifluoroethylamino group, a N,N-(2,2-ditrifluoroethyl)amino group, a N,N-(2,2-ditrichloroethyl)amino group, and a pentafluoropropylamino group.

The C2-C6 alkylcarbonyl group means an alkylcarbonyl group having 2 to 6 carbon atoms, which has a straight or branched alkyl group having 1 to 5 carbon atoms, and examples thereof include a methylcarbonyl group (acetyl group), an ethylcarbonyl group, a propylcarbonyl group, an isopropylcarbonyl group, a pivaloyl group, a butylcarbonyl group, and a pentylcarbonyl group.

The C2-C6 alkoxycarbonyl group means an alkoxycarbonyl group having 2 to 6 carbon atoms, which has a straight or branched alkyl group having 1 to 5 carbon atoms, and examples thereof include a methoxycarbonyl group, an ethoxycarbonyl group, a propoxycarbonyl group, an isopropoxycarbonyl group, a butoxycarbonyl group, an isobutoxycarbonyl group, a sec-butoxycarbonyl group, a tert-butoxycarbonyl group, a pentyloxycarbonyl group, an isoamyloxycarbonyl group, a neopentyloxycarbonyl group, a 2-pentyloxycarbonyl group, a 3-pentyloxycarbonyl group, and a 2-methylbutoxycarbonyl group.

The C1-C8 alkylaminocarbonyl group means an alkylaminocarbonyl group having 2 to 8 carbon atoms, which has a carbamoyl group, or a straight or branched alkylamino group having 1 to 7 carbon atoms, and is an aminocarbonyl group in which one or two hydrogen atoms on nitrogen may be substituted with the same or different C1-C4 alkyl groups, and examples thereof include an aminocarbonyl group (carbamoyl group), a methylaminocarbonyl group, an ethylaminocarbonyl group, a propylaminocarbonyl group, an isopropylaminocarbonyl group, a butylaminocarbonyl group, an N,N-dimethylaminocarbonyl group, an N,N-diethylaminocarbonyl group, an N,N-dipropylaminocarbonyl group, and an N,N-diisopropylaminocarbonyl group.

The C1-C8 alkylcarbonylamino group means herein an aminocarbonyl group in which one hydrogen atom on nitrogen of an N-formylamino group, or an N-formylamino group or a C1-C4 alkylcarbonylamino group is substituted with a C1-C4 alkyl group, and examples thereof include an N-formylamino group, a N-formyl-N-methylamino group, an N-ethyl-N-formylamino group, an N-isopropyl-N-formylamino group, an N-acetylamino group, an N-methyl-N-acetylamino group, an N-tert-butyl-N-acetylamino group, a propanoylamino group, and an N-methylpropanoylamino group.

The C3-C9 trialkylsilyl group means a trialkylsilyl group having 3 to 9 carbon atoms, which has a straight or branched trialkyl group having 3 to 9 carbon atoms, and examples thereof include a trimethylsilyl group, a tert-butyldimethylsilyl group, a triethylsilyl group, an isopropyldimethylsilyl group, and a triisopropylsilyl group.

The C1-C6 alkylsulfonyl group means an alkylsulfonyl group having a straight or branched alkyl group having 1 to 6 carbon atoms, and examples thereof include a methylsulfonyl group, an ethylsulfonyl group, a propylsulfonyl group, an isopropylsulfonyl group, a butylsulfonyl group, an isobutylsulfonyl group, a sec-butylsulfonyl group, a pentylsulfonyl group, an isoamylsulfonyl group, a neopentylsulfonyl group, a 2-pentylsulfonyl group, a 3-pentylsulfonyl group, a 2-methylbutylsulfonyl group, a hexylsulfonyl group, an isohexylsulfonyl group, a 3-methylpentylsulfonyl group, and a 4-methylpentylsulfonyl group.

The C1-C6 haloalkylsulfonyl group means a group in which at least one hydrogen atom of a straight or branched alkylsulfonyl group having 1 to 6 carbon atoms is substituted with a halogen atom, and examples thereof include a trifluoromethylsulfonyl group, a trichloromethylsulfonyl group, a tribromomethylsulfonyl group, a triiodomethylsulfonyl group, a pentafluoroethylsulfonyl group, a pentachloroethylsulfonyl group, a pentabromoethylsulfonyl group, a pentaiodoethylsulfonyl group, a 2,2,2-trichloroethylsulfonyl group, a 2,2,2-trifluoroethylsulfonyl group, a 2,2,2-tribromoethylsulfonyl group, a 2,2,2-triiodoethylsulfonyl group, a heptafluoropropylsulfonyl group, a heptachloropropylsulfonyl group, a heptabromopropylsulfonyl group, a heptaiodopropylsulfonyl group, a 3,3,3-trifluoropropylsulfonyl group, a 3,3,3-trichloropropylsulfonyl group, a 3,3,3-tribromopropylsulfonyl group, a 3,3,3-triiodopropylsulfonyl group, a nonafluorobutylsulfonyl group, a nonachlorobutylsulfonyl group, a nonabromobutylsulfonyl group, a nonaiodobutylsulfonyl group, a perfluoropentylsulfonyl group, a perchloropentylsulfonyl group, a perbromopentylsulfonyl group, a perfluorohexylsulfonyl group, a perchlorohexylsulfonyl group, a perbromohexylsulfonyl group, and a periodohexylsulfonyl group.

The C1-C6 alkylsulfinyl group means a straight or branched alkylsulfinyl group having 1 to 6 carbon atoms, and examples thereof include a methylsulfinyl group, an ethylsulfinyl group, a propylsulfinyl group, an isopropylsulfinyl group, a butylsulfinyl group, an isobutylsulfinyl group, a sec-butylsulfinyl group, a pentylsulfinyl group, an isoamylsulfinyl group, a neopentylsulfinyl group, a 2-pentylsulfinyl group, a 3-pentylsulfinyl group, a 2-methylbutylsulfinyl group, a hexylsulfinyl group, an isohexylsulfinyl group, a 3-methylpentylsulfinyl group, and a 4-methylpentylsulfinyl group.

The C1-C6 haloalkylsulfinyl group means a group in which at least one hydrogen atom of a straight or branched alkylsulfinyl group having 1 to 6 carbon atoms is substituted with a halogen atom, and examples thereof include a trifluoromethylsulfinyl group, a trichloromethylsulfinyl group, a tribromomethylsulfinyl group, a triiodomethylsulfinyl group, a pentafluoroethylsulfinyl group, a pentachloroethylsulfinyl group, a pentabromoethylsulfinyl group, a pentaiodoethylsulfinyl group, a 2,2,2-trichloroethylsulfinyl group, a 2,2,2-trifluoroethylsulfinyl group, a 2,2,2-tribromoethylsulfinyl group, a 2,2,2-triiodoethylsulfinyl group, a heptafluoropropylsulfinyl group, a heptachloropropylsulfinyl group, a heptabromopropylsulfinyl group, a heptaiodopropylsulfinyl group, a 3,3,3-trifluoropropylsulfinyl group, a 3,3,3-trichloropropylsulfinyl group, a 3,3,3-tribromopropylsulfinyl group, a 3,3,3-triiodopropylsulfinyl group, a nonafluorobutylsulfinyl group, a nonachlorobutylsulfinyl group, a nonabromobutylsulfinyl group, a nonaiodobutylsulfinyl group, a perfluoropentylsulfinyl group, a perchloropentylsulfinyl group, a perbromopentylsulfinyl group, a perfluorohexylsulfinyl group, a perchlorohexylsulfinyl group, a perbromohexylsulfinyl group, and a periodohexylsulfinyl group.

Group P is Group consisting of a halogen atom, a C3-C6 cycloalkyl group, a C3-C6 halocycloalkyl group, a C1-C4 alkoxy group, a C1-C4 haloalkoxy group, a C1-C4 alkylthio group, and a C1-C4 haloalkylthio group.

The C1-C6 alkyl group optionally having an atom or a group selected from Group P means a C1-C6 alkyl in which a hydrogen atom attached to a carbon atom may be substituted with atoms or groups selected from Group P and, when the C1-C6 alkyl group has two or more atoms or groups selected from Group P, atoms or groups selected from Group P may be the same or different.

Examples of the C1-C6 alkyl group optionally having an atom or a group selected from Group P include a fluoromethyl group, a difluoromethyl group, a trifluoromethyl group, a trichloromethyl group, a tribromomethyl group, a 2,2,2-trifluoroethyl group, a 2,2,2-trichloroethyl group, a 3,3,3-trifluoropropyl group, a difluoromethyl group, a 2,2-difluoroethyl group, a 1,1-difluoroethyl group, a pentafluoroethyl group, a heptafluoroisopropyl group, a 1,1,2,2-tetrafluoroethyl group, a 2,2,3,3,3-pentafluoropropyl group, a 2,2,3,3,3-pentafluorobutyl group, a cyclopropylmethyl group, a cyclopropylethyl group, a cyclopropylpropyl group, a cyclopropylbutyl group, a cyclopropylpentyl group, a cyclopropylhexyl group, a cyclobutylmethyl group, a cyclobutylethyl group, a cyclobutylpropyl group, a cyclobutylbutyl group, a cyclopentylmethyl group, a cyclopentylethyl group, a cyclopentylpropyl group, a cyclohexylethyl group, a cyclohexylpropyl group, a 1-fluorocyclopropylmethyl group, a 1-fluorocyclopropylethyl group, a 1-fluorocyclopropylpropyl group, a 2,2-difluorocyclopropylmethyl group, a 2,2-difluorocyclopropylethyl group, a 2,2-difluorocyclopropylpropyl group, a pentafluorocyclopropylmethyl group, a pentafluorocyclopropylethyl group, a pentafluorocyclopropylpropyl group, a 1-chlorocyclopropylmethyl group, a 1-chlorocyclopropylethyl group, a 1-chlorocyclopropylpropyl group, a 2,2-dichlorocyclopropylmethyl group, a 2,2-dichlorocyclopropylethyl group, a 2,2-dichlorocyclopropylpropyl group, a pentachlorocyclopropylmethyl group, a pentachlorocyclopropylethyl group, a pentachlorocyclopropylpropyl group, a 1-fluorocyclobutylmethyl group, a 1-fluorocyclobutylethyl group, a 1-fluorocyclobutylpropyl group, a 2,2-difluorocyclobutylmethyl group, a 2,2-difluorocyclobutylethyl group, a 2,2-difluorocyclobutylpropyl group, a 1-chlorocyclobutylmethyl group, a 1-chlorocyclobutylethyl group, a 1-chlorocyclobutylpropyl group, a 2,2-dichlorocyclobutylmethyl group, a 2,2-dichlorocyclobutylethyl group, a 2,2-dichlorocyclobutylpropyl group, a 1-fluorocyclopentylmethyl group, a 1-fluorocyclopentylethyl group, a 1-fluorocyclopentylpropyl group, a 2,2-difluorocyclopentylmethyl group, a 2,2-difluorocyclopentylethyl group, a 2,2-difluorocyclopentylpropyl group, a 3,3-difluorocyclopentylmethyl group, a 3,3-difluorocyclopentylethyl group, a 3,3-difluorocyclopentylpropyl group, a 1-chlorocyclopentylmethyl group, a 1-chlorocyclopentylethyl group, a 1-chlorocyclopentylpropyl group, a 2,2-dichlorocyclopentylmethyl group, a 2,2-dichlorocyclopentylethyl group, a 2,2-dichlorocyclopentylpropyl group, a 3,3-dichlorocyclopentylmethyl group, a 3,3-dichlorocyclopentylethyl group, a 3,3-dichlorocyclopentylpropyl group, a 1-fluorocyclohexylmethyl group, a 1-fluorocyclohexylethyl group, a 1-fluorocyclohexylpropyl group, a 2,2-difluorocyclohexylmethyl group, a 2,2-difluorocyclohexylethyl group, a 2,2-difluorocyclohexylpropyl group, a 3,3-difluorocyclohexylmethyl group, a 3,3-difluorocyclohexylethyl group, a 3,3-difluorocyclohexylpropyl group, a 4,4-difluorocyclohexylmethyl group, a 4,4-difluorocyclohexylethyl group, a 4,4-difluorocyclohexylpropyl group, a 1-chlorocyclohexylmethyl group, a 1-chlorocyclohexylethyl group, a 1-chlorocyclohexylpropyl group, a 2,2-dichlorocyclohexylmethyl group, a 2,2-dichlorocyclohexylethyl group, a 2,2-dichlorocyclohexylpropyl group, a 3,3-dichlorocyclohexylmethyl group, a 3,3-dichlorocyclohexylethyl group, a 3,3-dichlorocyclohexylpropyl group, a methoxymethyl group, an ethoxymethyl group, an isopropoxymethyl group, a tert-butoxymethyl group, a 2-methoxyethyl group, a 2-ethoxyethyl group, a 2-tert-butoxyethyl group, a 3-methoxypropyl group, a 3-ethoxypropyl group, a trifluoromethoxymethyl group, a 2-trifluoromethoxyethyl group, a 3-trifluoromethoxypropyl group, a 4-trifluoromethoxybutyl group, a difluoromethoxymethyl group, a 2-difluoromethoxyethyl group, a 2-pentafluoroethoxyethyl group, a 3-pentafluoroethoxypropyl group, a 1,1,2,2-tetrafluoroethoxymethyl group, a 2-(1,1,2,2-tetrafluoroethoxyl)ethyl group, a methylthiomethyl group, a 2-methylthioethyl group, a 3-methylthiopropyl group, an ethylthiomethyl group, a 2-ethylthioethyl group, a 3-ethylthiopropyl group, a tert-butylthiomethyl group, a 2-(tert-butylthio)ethyl group, a 3-(tert-butylthio)propyl group, a trifluoromethylthiomethyl group, a 2-trifluoromethylthioethyl group, a trifluoromethylthiopropyl group, a cyanomethyl group, a 2-cyanoethyl group, a 3-cyanopropyl group, a 1-cyanoethyl group, a 2-cyano-2-methylethyl group, and a 2-cyano-2-methylpropyl group.

The C3-C6 cycloalkyl group optionally having an atom or a group selected from Group P means a C3-C6 cycloalkyl in which a hydrogen atom attached to a carbon atom may be substituted with atoms or groups selected from Group P and, when the C3-C6 cycloalkyl group has two or more atoms or groups selected from Group P, atoms or groups selected from Group P may be the same or different.

Examples of the C3-C6 cycloalkyl group optionally having an atom or a group selected from Group P include a 1-fluorocyclopropyl group, a 2,2-difluorocyclopropyl group, a 1-chloro-2-fluorocyclopropyl group, a 2,2-dichlorocyclopropyl group, a 2,2-dibromocyclopropyl group, a 2,2-difluoro-1-methylcyclopropyl group, a 2,2-dichloro-1-methylcyclopropyl group, a 2,2-dibromo-1-methylcyclopropyl group, a 1-trifluoromethylcyclopropyl group, a 2,2,3,3-tetrafluorocyclobutyl group, a 2,2,3,3-tetrafluorocyclobutyl group, a 2-chlorocyclopentyl group, a 3-chlorocyclopentyl group, a 3,3-difluorocyclopentyl group, a 1-fluorocyclohexyl group, a 2,2-difluorocyclohexyl group, a 3,3-difluorocyclohexyl group, a 4,4-difluorocyclohexyl group, a 1-cyclopropylcyclopropyl group, a 2-cyclopropylcyclopropyl group, a 2,2-biscyclopropylcyclopropyl group, a 2,3-biscyclopropylcyclopropyl group, a 1-cyclopropylcyclobutyl group, a 1-cyclobutylcyclobutyl group, a 2-cyclopropylcyclobutyl group, a 1-cyclopropylcyclopentyl group, a 2-cyclopropylcyclopentyl group, a 1-(1-fluorocyclopropyl)cyclopropyl group, a 1-(2,2-difluorocyclopropyl)cyclopropyl group, a 1-(1-chlorocyclopropyl)cyclopropyl group, a 1-(2,2-dichlorocyclopropyl)cyclopropyl group, a 1-methoxycyclopropyl group, a 1-methoxycyclobutyl group, a 1-methoxycyclopentyl group, a 1-methoxycyclohexyl group, a 2-methoxycyclopropyl group, a 2-methoxycyclobutyl group, a 2-methoxycyclopentyl group, a 2-methoxycyclohexyl group, a 2-ethoxycyclopropyl group, a 2-ethoxycyclobutyl group, a 2-ethoxycyclopentyl group, a 2-ethoxycyclohexyl group, a 1-ethoxycyclopropyl group, a 1-ethoxycyclobutyl group, a 1-ethoxycyclopentyl group, a 1-ethoxycyclohexyl group, a 1-isopropoxycyclopropyl group, a 1-isopropoxycyclobutyl group, a 1-isopropoxycyclopentyl group, a 1-isopropoxycyclohexyl group, a 1-trifluoromethoxycyclopropyl group, a 2-trifluoromethoxycyclopropyl group, a 1-difluoromethoxycyclopropyl group, a 2-difluoromethoxycyclopropyl group, a 1-(2,2-difluoroethoxyl)cyclopropyl group, a 2-(2,2-difluoroethoxyl)cyclopropyl group, a 1-methylthiocyclopropyl group, a 1-ethylthiocyclopropyl group, a 2-methylthiocyclopropyl group, a 2-ethylthiocyclopropyl group, a 1-trifluoromethylthiocyclopropyl group, a 2-trifluoromethylthiocyclopropyl group, a 1-cyanocyclopropyl group, a 2-cyanocyclopropyl group, and a 2,2-dicyanocyclopropyl group.

Having a C1-C3 alkoxyimino group on the same carbon atom means the following structure:

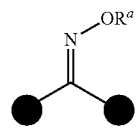

wherein $R^a$ represents a C1-C3 alkyl group.

Having an oxo group on the same carbon atom means the following structure.

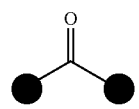

Having a thioxo group on the same carbon atom means the following structure.

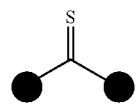

Having one oxide group on the same sulfur atom means the following structure.

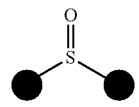

Having two oxide groups on the same sulfur atom means the following structure.

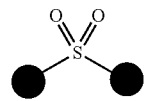

The phrase "the phenyl moiety of the phenyl group, the phenoxy group, the phenylthio group, and the phenylamino group may form a four-membered ring, a five-membered ring, a six-membered ring, or a seven-membered ring together with the adjacent carbon atom; and the ring may contain one or more atoms selected from the group consisting of an oxygen atom, a sulfur atom, and a nitrogen atom as a ring-constituent atom, and may have an oxo group, a thioxo group, or a C1-C3 alkoxyimino group on the same carbon atom, and may have one or two oxide groups on the same sulfur atom" includes, for example, the following structures:

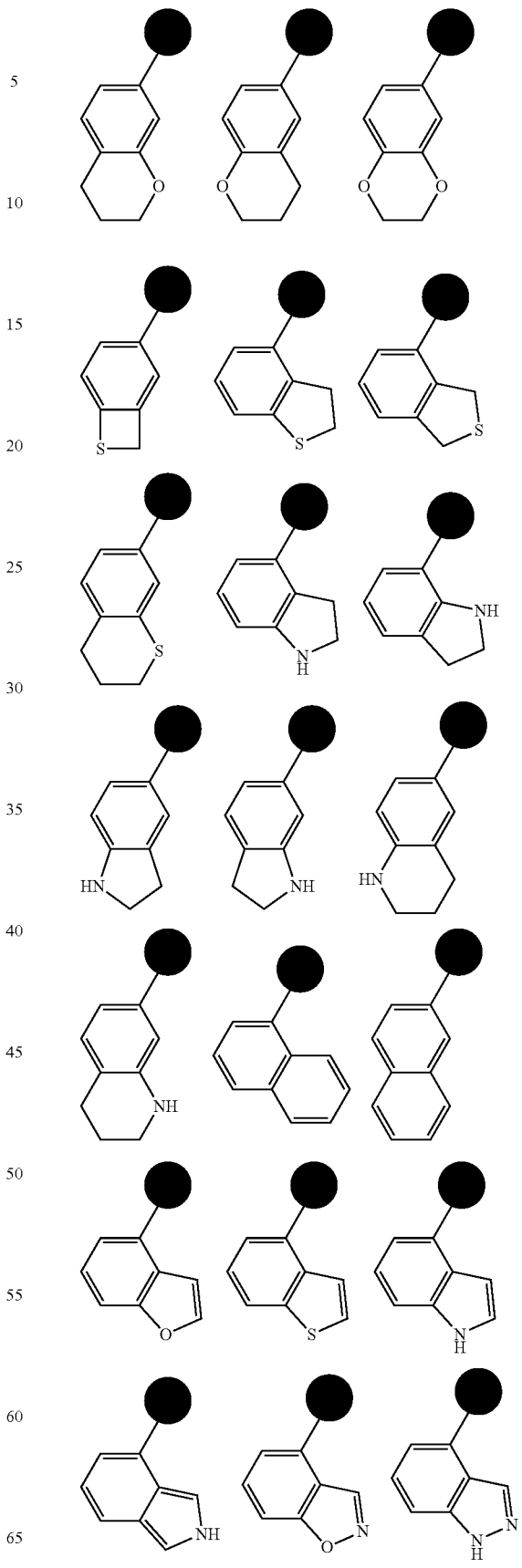

-continued

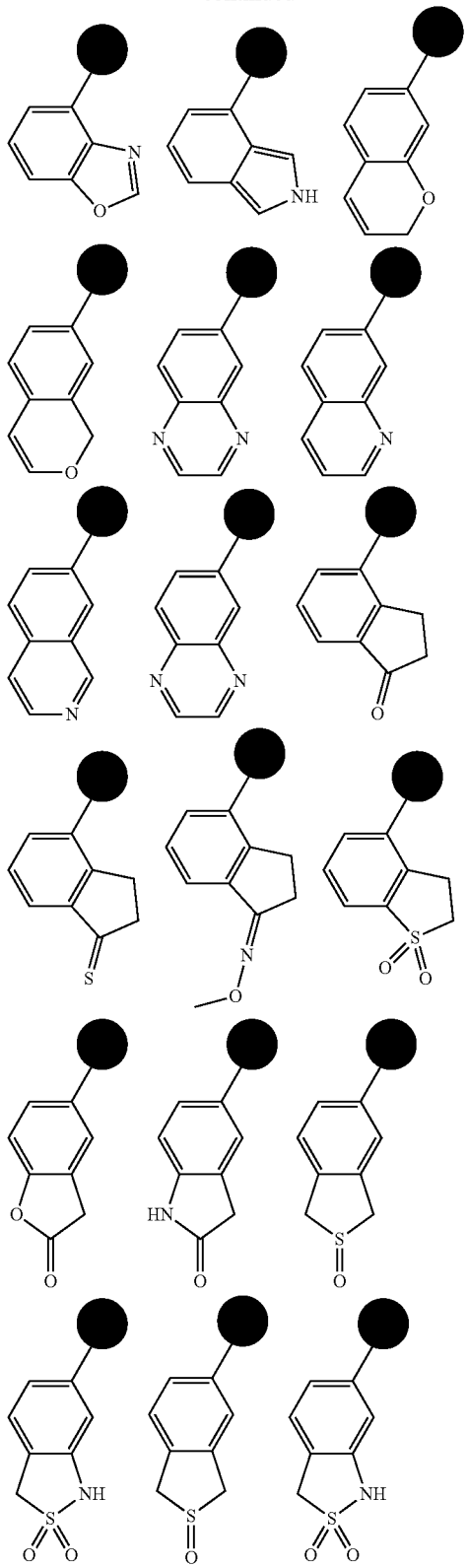

wherein the symbol ○ represents a binding site.

The phrase "the phenyl moiety of the phenyl group, the phenoxy group, the phenylthio group, and the phenylamino group may form a four-membered ring, a five-membered ring, a six-membered ring, or a seven-membered ring together with the adjacent carbon atom; and the ring may contain one or more atoms selected from the group consisting of an oxygen atom, a sulfur atom, and a nitrogen atom as a ring-constituent atom, and may have an oxo group, a thioxo group, or a C1-C3 alkoxyimino group on the same carbon atom, and may have one or two oxide groups on the same sulfur atom; and the phenyl moiety and the ring may have one or more atoms or groups selected from Group $P^1$ and, when the number of atoms or groups selected from Group $P^1$ is two or more, the atoms or groups may be the same or different" shows, for example, that a hydrogen atom of the above group may be substituted with atoms or groups selected from Group $P^1$.

Examples of the five- or six-membered heterocyclyl group include a pyrrolidin-2-yl group, a pyrrolidin-3-yl group, a pyrrolidin-3-yl group, an oxolan-2-yl group, an oxolan-3-yl group, a thiolan-2-yl group, a thiolan-3-yl group, a piperidin-2-yl group, a piperidin-3-yl group, a tetrahydrofuran-2-yl group, a tetrahydrothiopyran-2-yl group, a pyrrol-1-yl group, a pyrrol-2-yl group, a 1H-pyrrol-2-yl group, a furan-2-yl group, a thiophen-3-yl group, a 2-pyridinyl group, a 3-pyridinyl group, a 4-pyridinyl group, a pyrazin-2-yl group, a pyramidin-2-yl group, a pyramidin-5-yl group, an imidazol-2-yl group, an imidazol-4-yl group, an imidazol-5-yl group, a pyrazol-3-yl group, a pyrazol-4-yl group, a pyrazol-5-yl group, an oxazol-2-yl group, an oxazol-4-yl group, an oxazol-5-yl group, an isoxazol-3-yl group, an isoxazol-4-yl group, an isoxazol-5-yl group, a thiazol-2-yl group, a thiazol-4-yl group, a thiazol-5-yl group, an isothiazol-3-yl group, an isothiazol-4-yl group, an isothiazol-5-yl group, a 4,5-dihydro-1H-imidazol-2-yl group, and a 4,5-dihydro-1H-pyrazol-4-yl group.

Examples of the five- or six-membered heterocyclyloxy group include a pyrrolidin-2-yloxy group, a pyrrolidin-3-yloxy group, a pyrrolidin-3-yloxy group, an oxolan-2-yloxy group, an oxolan-3-yloxy group, a thiolan-2-yloxy group, a thiolan-3-yloxy group, a piperidin-2-yloxy group, a piperidin-3-yloxy group, a tetrahydrofuran-2-yloxy group, a tetrahydrothiopyran-2-yloxy group, a pyrrol-1-yloxy group, a pyrrol-2-yloxy group, a 1H-pyrrol-2-yloxy group, a furan-2-yloxy group, a thiophen-3-yloxy group, a 2-pyridinyloxy group, a 3-pyridinyloxy group, a 4-pyridinyloxy group, a pyrazin-2-yloxy group, a pyramidin-2-yloxy group, a pyramidin-5-yloxy group, an imidazol-2-yloxy group, an imidazol-4-yloxy group, an imidazol-5-yloxy group, a pyrazol-3-yloxy group, a pyrazol-4-yloxy group, a pyrazol-5-yloxy group, an oxazol-2-yloxy group, an oxazol-4-yloxy group, an oxazol-5-yloxy group, an isoxazol-3-yloxy group, an isoxazol-4-yloxy group, an isoxazol-5-yloxy group, a thiazol-2-yloxy group, a thiazol-4-yloxy group, a thiazol-5-yloxy group, an isothiazol-3-yloxy group, an isothiazol-4-yloxy group, an isothiazol-5-yloxy group, a 4,5-dihydro-1H-imidazol-2-yloxy group, and a 4,5-dihydro-1H-pyrazol-4-yloxy group.

Examples of the five- or six-membered heterocyclylthio group include a pyrrolidin-2-ylthio group, a pyrrolidin-3-ylthio group, a pyrrolidin-3-ylthio group, an oxolan-2-ylthio group, an oxolan-3-ylthio group, a thiolan-2-ylthio group, a thiolan-3-yllthio group, a piperidin-2-ylthio group, a piperidin-3-ylthio group, a tetrahydrofuran-2-ylthio group, a tetrahydrothiopyran-2-ylthio group, a pyrrol-1-ylthio group, a pyrrol-2-ylthio group, a 1H-pyrrol-2-ylthio group, a furan-2-ylthio group, a thiophen-3-ylthio group, a 2-pyridinylthio group, a 3-pyridinylthio group, a 4-pyridinylthio group, a pyrazin-2-ylthio group, a pyramidin-2-ylthio group, a pyramidin-5-ylthio group, an imidazol-2-ylthio group, an imidazol-4-ylthio group, an imidazol-5-ylthio group, a pyrazol- 3-ylthio group, a pyrazol-4-ylthio group, a pyrazol-5-ylthio group, an oxazol-2-ylthio group, an oxazol-4-ylthio group, an oxazol-5-ylthio group, an isoxazol-3-ylthio group, an isoxazol-4-ylthio group, an isoxazol-5-ylthio group, a thiazol-2-ylthio group, a thiazol-4-ylthio group, a thiazol-5-ylthio group, an isothiazol-3-ylthio group, an isothiazol-4-ylthio group, an isothiazol-5-ylthio group, a 4,5-dihydro-1H-imidazol-2-ylthio group, and a 4,5-dihydro-1H-pyrazol-4-ylthio group.

Examples of the five- or six-membered heterocyclylamino group include a pyrrolidin-2-ylamino group, a pyrrolidin-3-ylamino group, a pyrrolidin-3-ylamino group, an oxolan-2-ylamino group, an oxolan-3-ylamino group, a thiolan-2-ylamino group, a thiolan-3-ylamino group, a piperidin-2-ylamino group, a piperidin-3-ylamino group, a tetrahydrofuran-2-ylamino group, a tetrahydrothiopyran-2-ylamino group, a pyrrol-1-ylamino group, a pyrrol-2-ylamino group, a 1H-pyrrol-2-ylamino group, a furan-2-ylamino group, a thiophen-3-ylamino group, a 2-pyridinylamino group, a 3-pyridinylamino group, a 4-pyridinylamino group, a pyrazin-2-ylamino group, a pyramidin-2-ylamino group, a pyramidin-5-ylamino group, an imidazol-2-ylamino group, an imidazol-4-ylamino group, an imidazol-5-ylamino group, a pyrazol-3-ylamino group, a pyrazol-4-ylamino group, a pyrazol-5-ylamino group, an oxazol-2-ylamino group, an oxazol-4-ylamino group, an oxazol-5-ylamino group, an isoxazol-3-ylamino group, an isoxazol-4-ylamino group, an isoxazol-5-ylamino group, a thiazol-2-ylamino group, a thiazol-4-ylamino group, a thiazol-5-ylamino group, an isothiazol-3-ylamino group, an isothiazol-4-ylamino group, an isothiazol-5-ylamino group, a 4,5-dihydro-1H-imidazol-2-ylamino group, and a 4,5-dihydro-1H-pyrazol-4-ylamino group.

The phrase "the five- or six-membered heterocyclyl moiety of the five- or six-membered heterocyclyl group, the five- or six-membered heterocyclyloxy group, the five- or six-membered heterocyclylthio group, and the five- or six-membered heterocyclylamino group may form a four-membered ring, a five-membered ring, a six-membered ring, or a seven-membered ring together with the adjacent carbon atom; and the ring may contain one or more atoms selected from the group consisting of an oxygen atom, a sulfur atom, and a nitrogen atom as a ring-constituent atom; and the five- or six-membered heterocyclyl moiety and the ring may have an oxo group, a thioxo group, or a C1-C3 alkoxyimino group on the same carbon atom, and may have one or two oxide groups on the same sulfur atom" means that the five- or six-membered heterocyclyl moiety and the ring of each of the five- or six-membered heterocyclyl group, the five- or six-membered heterocyclyloxy group, the five- or six-membered heterocyclylthio group, and the five- or six-membered heterocyclylamino group include, for example, the following structures:

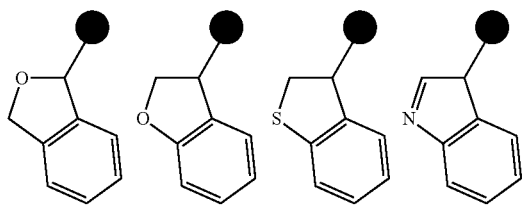

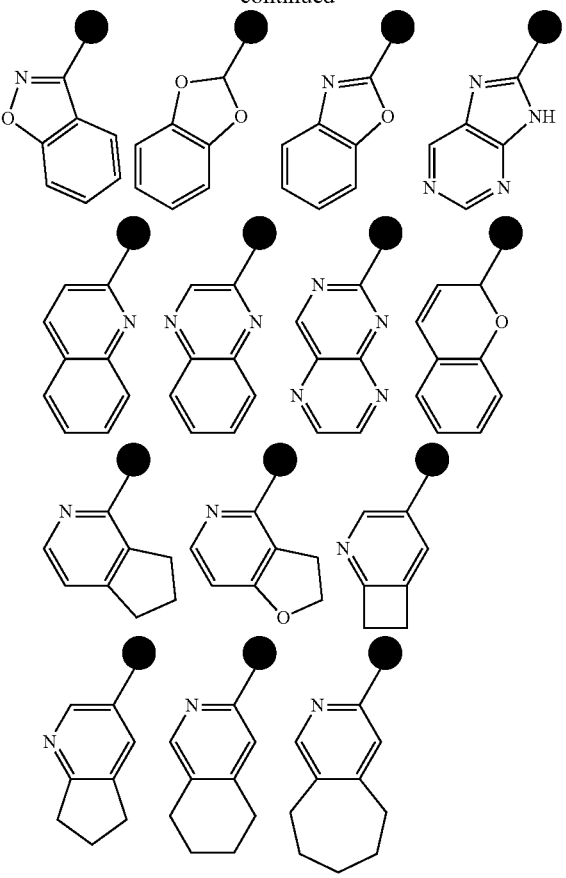

-continued wherein the symbol ○ represents a binding site.

The phrase "the five- or six-membered heterocyclyl moiety of the five- or six-membered heterocyclyl group, the five- or six-membered heterocyclyloxy group, the five- or six-membered heterocyclylthio group, and the five- or six-membered heterocyclylamino group may form a four-membered ring, a five-membered ring, a six-membered ring, or a seven-membered ring together with the adjacent carbon atom; and the ring may contain one or more atoms selected from the group consisting of an oxygen atom, a sulfur atom, and a nitrogen atom as a ring-constituent atom; and the five- or six-membered heterocyclyl moiety and the ring may have an oxo group, a thioxo group, or a C1-C3 alkoxyimino group on the same carbon atom, and may have one or two oxide groups on the same sulfur atom, and may have one or more atoms or groups selected from Group $P^1$ and, when the number of atoms or groups selected from Group $P^1$ is two or more, the atoms or groups may be the same or different" means that the five- or six-membered heterocyclyl moiety of the five- or six-membered heterocyclyl group, the five- or six-membered heterocyclyloxy group, the five- or six-membered heterocyclylthio group, and the five- or six-membered heterocyclylamino group and the hydrogen atom of the ring may be substituted with atoms or groups selected from Group $P^1$.

The phrase "the C3-C6 cycloalkyl group and the C3-C6 cycloalkenyl group may form a four-membered ring, a five-membered ring, a six-membered ring, or a seven-membered ring together with the adjacent carbon atom; and the ring contains one or more atoms selected from the group consisting of an oxygen atom, a sulfur atom, and a nitrogen atom as a ring-constituent atom, and may have one or two oxide groups on the same sulfur atom; and the ring, the C3-C6 cycloalkyl group, and the C3-C6 cycloalkenyl group may have an oxo group, a thioxo group, or a C1-C3 alkoxyimino group on the same carbon atom" shows, for example, the following structure:

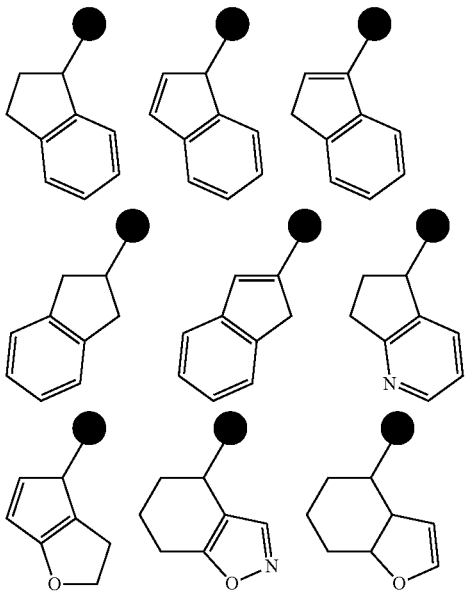

wherein the symbol ○ represents a binding site.

The phrase "the C3-C6 cycloalkyl group and the C3-C6 cycloalkenyl group may form a four-membered ring, a five-membered ring, a six-membered ring, or a seven-membered ring together with the adjacent carbon atom; and the ring may contain one or more atoms selected from the group consisting of an oxygen atom, a sulfur atom, and a nitrogen atom as a ring-constituent atom, and may have one or two oxide groups on the same sulfur atom; and the ring, the C3-C6 cycloalkyl group, and the C3-C6 cycloalkenyl group may have an oxo group, a thioxo group, or a C1-C3 alkoxyimino group on the same carbon atom, and may have one or more atoms or groups selected from Group $P^1$ and, when the number of atoms or groups selected from Group $P^1$ is two or more, the atoms or groups may be the same or different" shows, for example, the hydrogen atom of the ring, the C3-C6 cycloalkyl group, and the C3-C6 cycloalkenyl group may be substituted with atoms or groups selected from Group $P^1$.

The phrase "the C1-C4 alkyl group may have an oxo group, a thioxo group, or a C1-C3 alkoxyimino group on the same carbon atom, and may have one or more atoms or groups selected from Group $P^1$ and, when the number of atoms or groups selected from Group $P^1$ is two or more, the atoms or groups may be the same or different" shows, for example, a compound having an oxo group, a thioxo group, or a C1-C3 alkoxyimino group on the same carbon atom of the C1-C4 alkyl group, and the hydrogen atom of the C1-C4 alkyl moiety may be substituted with atoms or groups selected from Group P, and the compound may have an oxo group, a thioxo group, or a C1-C3 alkoxyimino group on the same carbon atom of the C1-C4 alkyl moiety.

The phrase "the C2-C4 alkenyl group and the C2-C4 alkynyl group may have one or more atoms or groups selected from Group $P^1$ and, when the number of atoms or groups selected from Group $P^1$ is two or more, the atoms or groups may be the same or different" shows, for example, the hydrogen atom on the C2-C4 alkenyl group and the C2-C4 alkynyl group may be substituted with one or more atoms selected from Group $P^1$.

The C1-C6 alkyl group optionally having an atom or a group selected from Group $P^3$ means a C1-C6 alkyl in which the hydrogen atom attached to the carbon atom may be substituted with atoms or groups selected from Group $P^3$ and, when the C1-C6 alkyl group has two or more atoms or groups selected from Group $P^3$, atoms or groups selected from Group $P^3$ may be the same or different.

Examples of the C1-C6 alkyl group optionally having an atom or a group selected from Group $P^3$ include a fluoromethyl group, a difluoromethyl group, a trifluoromethyl group, a trichloromethyl group, a tribromomethyl group, a 2,2,2-trifluoroethyl group, a 2,2,2-trichloroethyl group, a 3,3,3-trifluoropropyl group, a difluoromethyl group, a 2,2-difluoroethyl group, a 1,1-difluoroethyl group, a pentafluoroethyl group, a heptafluoroisopropyl group, a 1,1,2,2-tetrafluoroethyl group, a 2,2,3,3,3-pentafluoropropyl group, a 2,2,3,3,3-pentafluorobutyl group, a cyclopropylmethyl group, a cyclopropylethyl group, a cyclopropylpropyl group, a cyclopropylbutyl group, a cyclopropylpentyl group, a cyclopropylhexyl group, a cyclobutylmethyl group, a cyclobutylethyl group, a cyclobutylpropyl group, a cyclobutylbutyl group, a cyclopentylmethyl group, a cyclopentylethyl group, a cyclopentylpropyl group, a cyclohexylethyl group, a cyclohexylpropyl group, a 1-fluorocyclopropylmethyl group, a 1-fluorocyclopropylethyl group, a 1-fluorocyclopropylpropyl group, a 2,2-difluorocyclopropylmethyl group, a 2,2-difluorocyclopropylethyl group, a 2,2-difluorocyclopropylpropyl group, a pentafluorocyclopropylmethyl group, a pentafluorocyclopropylethyl group, a pentafluorocyclopropylpropyl group, a 1-chlorocyclopropylmethyl group, a 1-chlorocyclopropylethyl group, a 1-chlorocyclopropylpropyl group, a 2,2-dichlorocyclopropylmethyl group, a 2,2-dichlorocyclopropylethyl group, a 2,2-dichlorocyclopropylpropyl group, a pentachlorocyclopropylmethyl group, a pentachlorocyclopropylethyl group, a pentachlorocyclopropylpropyl group, a 1-fluorocyclobutylmethyl group, a 1-fluorocyclobutylethyl group, a 1-fluorocyclobutylpropyl group, a 2,2-difluorocyclobutylmethyl group, a 2,2-difluorocyclobutylethyl group, a 2,2-difluorocyclobutylpropyl group, a 1-chlorocyclobutylmethyl group, a 1-chlorocyclobutylethyl group, a 1-chlorocyclobutylpropyl group, a 2,2-dichlorocyclobutylmethyl group, a 2,2-dichlorocyclobutylethyl group, a 2,2-dichlorocyclobutylpropyl group, a 1-fluorocyclopentylmethyl group, a 1-fluorocyclopentylethyl group, a 1-fluorocyclopentylpropyl group, a 2,2-difluorocyclopentylmethyl group, a 2,2-difluorocyclopentylethyl group, a 2,2-difluorocyclopentylpropyl group, a 3,3, a-difluorocyclopentylmethyl group, a 3,3-difluorocyclopentylethyl group, a 3,3-difluorocyclopentylpropyl group, a 1-chlorocyclopentylmethyl group, a 1-chlorocyclopentylethyl group, a 1-chlorocyclopentylpropyl group, a 2,2-dichlorocyclopentylmethyl group, a 2,2-dichlorocyclopentylethyl group, a 2,2-dichlorocyclopentylpropyl group, a 3,3-dichlorocyclopentylmethyl group, a 3,3-dichlorocyclopentylethyl group, a 3,3-dichlorocyclopentylpropyl group, a 1-fluorocyclohexylmethyl group, a 1-fluorocyclohexylethyl group, a 1-fluorocyclohexylpropyl group, a 2,2-difluorocyclohexylmethyl group, a 2,2-difluorocyclohexylethyl group, a 2,2-difluorocyclohexylpropyl group, a 3,3-difluorocyclohexylmethyl group, a 3,3-difluorocyclohexylethyl group, a 3,3-difluorocyclohexylpropyl group, a 4,4-difluorocyclohexylmethyl group, a 4,4-difluorocyclohexylethyl group, a 4,4-difluorocyclohexylpropyl group, a 1-chlorocyclohexylmethyl group, a 1-chlorocyclohexylethyl group, a 1-chlorocyclohexylpropyl group, a 2,2-dichlorocyclohexylmethyl group, a 2,2-dichlorocyclohexylethyl group, a 2,2-dichlorocyclohexylpropyl group, a 3,3-dichlorocyclohexylmethyl group, a 3,3-dichlorocyclohexylethyl group, a 3,3-dichlorocyclohexylpropyl group, a methoxymethyl group, an ethoxymethyl group, an isopropoxymethyl group, a tert-butoxymethyl group, a 2-methoxyethyl group, a 2-ethoxyethyl group, a 2-tert-butoxyethyl group, a 3-methoxypropyl group, a 3-ethoxypropyl group, a trifluoromethoxymethyl group, a 2-trifluoromethoxyethyl group, a 3-trifluoromethoxypropyl group, a 4-trifluoromethoxybutyl group, a difluoromethoxymethyl group, a 2-difluoromethoxyethyl group, a 2-pentafluoroethoxyethyl group, a 3-pentafluoroethoxypropyl group, a 1,1,2,2-tetrafluoroethoxymethyl group, a 2-(1,1,2,2-tetrafluoroethoxy)ethyl group, a methylthiomethyl group, a 2-methylthioethyl group, a 3-methylthiopropyl group, an ethylthiomethyl group, a 2-ethylthioethyl group, a 3-ethylthiopropyl group, a tert-butylthiomethyl group, a 2-(tert-butylthio)ethyl group, a 3-(tert-butylthio)propyl group, a trifluoromethylthiomethyl group, a 2-trifluoromethylthioethyl group, a trifluoromethylthiopropyl group, a cyanomethyl group, a 2-cyanoethyl group, a 3-cyanopropyl group, a 1-cyanoethyl group, a 2-cyano-2-methylethyl group, and a 2-cyano-2-methylpropyl group.

The C3-C6 cycloalkyl group optionally having an atom or a group selected from Group $P^3$ means a C1-C6 alkyl in which the hydrogen atom attached to the carbon atoms may be substituted with atoms or groups selected from Group $P^3$ and, when the C1-C6 alkyl group has two or more atoms or groups selected from Group $P^3$, and atoms or groups selected from Group $P^3$ may be the same or different.

Examples of the C3-C6 cycloalkyl group optionally having an atom or a group selected from Group $P^3$ include a 1-fluorocyclopropyl group, a 2,2-difluorocyclopropyl group, a 1-chloro-2-fluorocyclopropyl group, a 2,2-dichlorocyclopropyl group, a 2,2-dibromocyclopropyl group, a 2,2-difluoro-1-methylcyclopropyl group, a 2,2-dichloro-1-methylcyclopropyl group, a 2,2-dibromo-1-methylcyclopropyl group, a 1-trifluoromethylcyclopropyl group, a 2,2,3,3-tetrafluorocyclobutyl group, a 2,2,3,3-tetrafluorocyclobutyl group, a 2-chlorocyclopentyl group, a 3-chlorocyclopentyl group, a 3,3-difluorocyclopentyl group, a 1-fluorocyclohexyl group, a 2,2-difluorocyclohexyl group, a 3,3-difluorocyclohexyl group, a 4,4-difluorocyclohexyl group, a 1-cyclopropylcyclopropyl group, a 2-cyclopropylcyclopropyl group, a 2,2-bis-cyclopropyl-cyclopropyl group, a 2,3-dicyclopropylcyclopropyl group, a 1-cyclopropylcyclobutyl group, a 1-cyclobutylcyclobutyl group, a 2-cyclopropylcyclobutyl group, a 1-cyclopropylcyclopentyl group, a 2-cyclopropylcyclopentyl group, a 1-(1-fluorocyclopropyl)cyclopropyl group, a 1-(2,2-difluorocyclopropyl)cyclopropyl group, a 1-(1-chlorocyclopropyl)cyclopropyl group, a 1-(2,2-dichlorocyclopropyl)cyclopropyl group, a 1-methoxycyclopropyl group, a 1-methoxycyclobutyl group, a 1-methoxycyclopentyl group, a 1-methoxycyclohexyl group, a 2-methoxycyclopropyl group, a 2-methoxycyclobutyl group, a 2-methoxycyclopentyl group, a 2-methoxycyclohexyl group, a 2-ethoxycyclopropyl group, a 2-ethoxycyclobutyl group, a 2-ethoxycyclopentyl group, a 2-ethoxycyclohexyl group, a 1-ethoxycyclopropyl group, a 1-ethoxycyclobutyl group, a 1-ethoxycyclopentyl group, a 1-ethoxycyclohexyl group, a 1-isopropoxycyclopropyl group, a 1-isopropoxycyclobutyl group, a 1-isopropoxycyclopentyl group, a 1-isopropoxycyclohexyl group, a 1-trifluoromethoxycyclopropyl group, a 2-trifluoromethoxycyclopropyl group, a 1-difluoromethoxycyclopropyl group, a 2-difluoromethoxycyclopropyl group, a 1-(2,2-difluoroethoxy)cyclopropyl group, a 2-(2,2-difluoroethoxy)cyclopropyl group, a 1-methylthiocyclopropyl group, a 1-ethylthiocyclopropyl group, a 2-methylthiocyclopropyl group, a 2-ethylthiocyclopropyl group, a 1-trifluoromethylthiocyclopropyl group, a 2-trifluoromethylthiocyclopropyl group, a 1-cyanocyclopropyl group, a 2-cyanocyclopropyl group, and a 2,2-dicyanocyclopropyl group.

The phrase "the indan-5-yl group, the 5,6,7,8-tetrahydronaphthalen-2-yl group, and the 2-naphthyl group may have atoms or groups selected from Group $P^4$ as the substituent" means that the hydrogen atom on the ring of the indan-5-yl group, the 5,6,7,8-tetrahydronaphthalen-2-yl group, and the 2-naphthyl group may be substituted with atoms or groups selected from Group $P^4$.

Group $P^5$ is Group consisting of a halogen atom, a C1-C3 alkyl group optionally having one or more halogen atoms, a C3-C4 cycloalkyl group optionally having one or more halogen atoms, and a C1-C3 alkoxy group optionally having one or more halogen atoms.

The term "phenyl group optionally having one or more same or different groups selected from Group $P^5$" means a phenyl group in which the hydrogen atom on the phenyl group may be substituted with atoms or groups selected from Group $P^5$ and, when the phenyl group has two or more atoms or groups selected from Group $P^5$, atoms or groups selected from Group $P^5$ may be the same or different.

Examples of the "phenyl group optionally having one or more same or different groups selected from Group $P^5$" include a phenyl group, a 2-fluorophenyl group, a 3-fluorophenyl group, a 4-fluorophenyl group, a 2,6-difluorophenyl group, a 3,5-difluorophenyl group, a 2-chlorophenyl group, a 3-chlorophenyl group, a 4-chlorophenyl group, a 2,6-dichlorophenyl group, a 3,5-dichlorophenyl group, a 2-bromophenyl group, a 3-bromophenyl group, a 4-bromophenyl group, a 2-trifluoromethylphenyl group, a 3-trifluoromethylphenyl group, a 4-trifluoromethylphenyl group, a 2-cyclopropylphenyl group, a 3-cyclopropylphenyl group, a 4-cyclopropylphenyl group, a 2-methoxyphenyl group, a 3-methoxyphenyl group, a 4-methoxyphenyl group, a 2,6-dimethoxyphenyl group, and a 3,5-dimethoxyphenyl group.

The formula (1-P) represents a compound represented by the following structure:

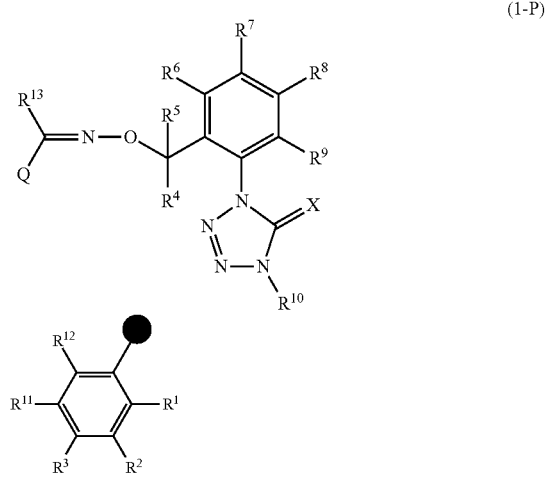

(1-P)

wherein
R$^4$ and R$^5$ each represents a hydrogen atom or a C1-C3 alkyl group;
R$^6$ represents a C1-C4 alkyl group, a C3-C6 cycloalkyl group, a C1-C4 haloalkyl group, a C3-C6 halocycloalkyl group, a halogen atom, a cyano group, a nitro group, a C2-C4 alkenyl group, a C2-C4 haloalkenyl group, a C2-C4 alkynyl group, a C2-C4 haloalkynyl group, a C1-C4 alkoxy group, a C1-C4 haloalkoxy group, a C1-C4 alkylthio group, or a C1-C4 haloalkylthio group;
R$^7$, R$^8$, and R$^9$ each represents a hydrogen atom or a halogen atom;
R$^{10}$ represents a C1-C3 alkyl group, a C1-C3 haloalkyl group, a C2-C3 alkenyl group, a C2-C3 haloalkenyl group, a C2-C3 alkynyl group, a C2-C3 haloalkynyl group, a C3-C5 cycloalkyl group, or a C3-C5 halocycloalkyl group;
X represents an oxygen atom or a sulfur atom;
R$^{13}$ represents a C1-C6 alkyl group, a C3-C6 cycloalkyl group, a hydrogen atom, a C1-C6 haloalkyl group, a C3-C6 halocycloalkyl group, a C2-C6 alkenyl group, a C2-C6 haloalkenyl group, a C2-C6 alkynyl group, a C2-C6 haloalkynyl group, a C1-C6 alkoxy group, or a C1-C6 alkylthio group;
R$^1$, R$^2$, R$^3$, R$^{11}$, and R$^{12}$ each represents a hydrogen atom, a C1-C6 alkyl group optionally having an atom or a group selected from Group P,
a C3-C6 cycloalkyl group optionally having an atom or a group Group selected from P,
a C1-C6 haloalkoxy group, a halogen atom, a nitro group, a C1-C6 alkoxy group, a C2-C6 alkenyl group, a C2-C6 haloalkenyl group, a C2-C6 alkynyl group, a C2-C6 haloalkynyl group, a C3-C6 alkenyloxy group, a C3-C6 haloalkenyloxy group, a C3-C6 alkynyloxy group, a C3-C6 haloalkynyloxy group, a C1-C8 alkylamino group, a C1-C8 haloalkylamino group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a cyano group, an amino group, a hydroxy group, a mercapto group, a pentafluorosulfanyl group, a C3-C9 trialkylsilyl group, a C2-C6 alkylcarbonyl group, a C2-C6 alkoxycarbonyl group, a C2-C8 alkylaminocarbonyl group, or a C2-C8 alkylcarbonylamino group;
or R$^1$ and R$^2$ form a four-membered ring, a five-membered ring, a six-membered ring, or a seven-membered ring together with the carbon atom to which they are attached, and the ring may contain one or more atoms selected from the group consisting of an oxygen atom and a sulfur atom as a ring-constituent atom, and the ring may have one or more atoms or groups selected from Group P as the substituent;
R$^2$ and R$^3$ form a four-membered ring, a five-membered ring, a six-membered ring, or a seven-membered ring together with the carbon atom to which they are attached, and the ring may contain one or more atoms selected from the group consisting of an oxygen atom and a sulfur atom as a ring-constituent atom, and the ring may have one or more atoms or groups selected from Group P as the substituent;
or, R$^{12}$ and R$^{13}$ form a five-membered ring, a six-membered ring, or a seven-membered ring together with the carbon atom to which they are attached, and the ring may contain one or more atoms selected from the group consisting of an oxygen atom and a sulfur atom as a ring-constituent atom, and the ring may have one or more atoms or groups selected from Group P as a substituent.

The phrase "R$^1$ and R$^2$ form a four-membered ring, a five-membered ring, a six-membered ring, or a seven-membered ring together with the carbon atom to which they are attached, and the ring may contain one or more atoms selected from the group consisting of an oxygen atom and a sulfur atom as a ring-constituent atom" means, for example, the following structures:

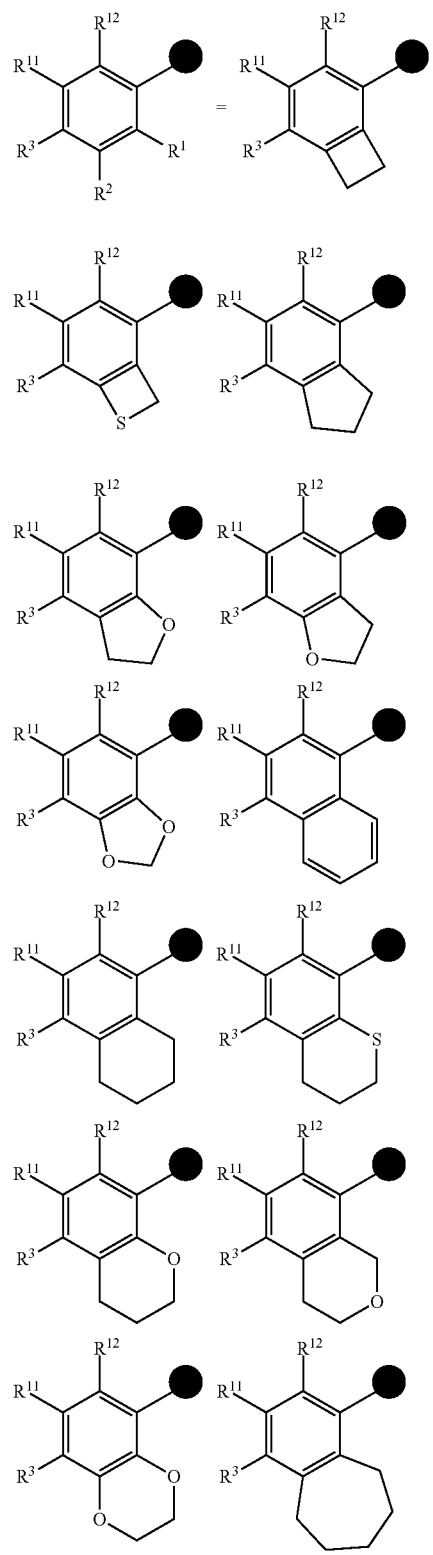

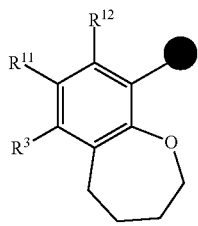

wherein symbols are as defined above.

The phrase "$R^1$ and $R^2$ form a four-membered ring, a five-membered ring, a six-membered ring, or a seven-membered ring together with the carbon atom to which they are attached, and the ring may contain one or more atoms selected from the group consisting of an oxygen atom and a sulfur atom as a ring-constituent atom, and the ring may have atoms or groups selected from Group P as the substituent" shows, for example, that the hydrogen atom on the ring is substituted with one or more atoms or groups selected from Group P.

The phrase "$R^1$ and $R^2$ form a four-membered ring or a five-membered ring together with the carbon atom to which they are attached, and the ring may contain one or more atoms selected from the group consisting of an oxygen atom, a sulfur atom, and a nitrogen atom as a ring-constituent atom" shows, for example, the following structures:

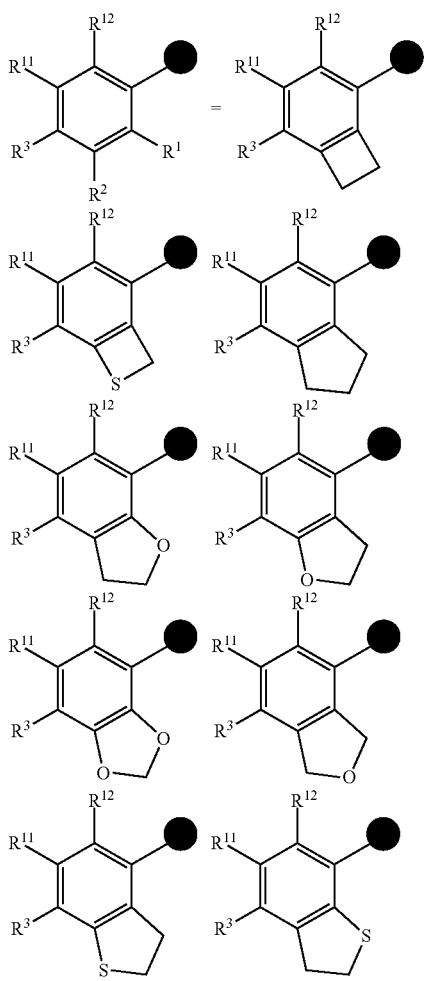

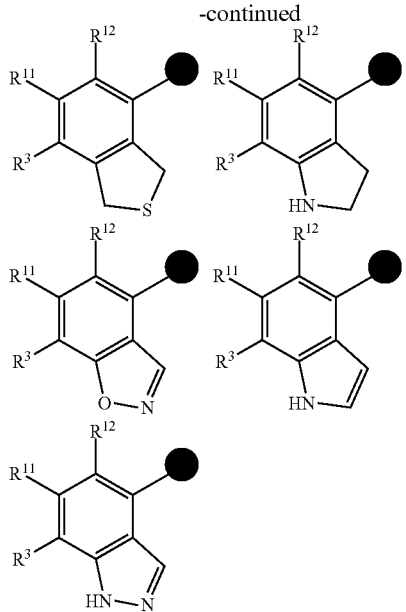

wherein symbols are as defined above.

The phrase "$R^1$ and $R^2$ form a four-membered ring or a five-membered ring together with the carbon atom to which they are attached, the ring may contain one or more atoms selected from the group consisting of an oxygen atom, a sulfur atom, and a nitrogen atom as a ring-constituent atom, and the ring may have one or more atoms or groups selected from Group $P^4$ as a substituent" shows, for example, that the hydrogen atom on the ring may be substituted with atoms or groups selected from Group $P^4$.

The phrase "$R^1$ and $R^2$ are combined to form -E-CH$_2$—CH$_2$— (provided that E is combined with the carbon atom to which $R^2$ is attached, and represents CH$_2$ or an oxygen atom)" shows, for example, the following structures:

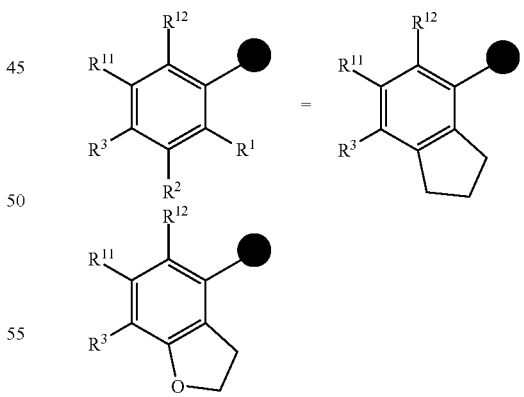

wherein symbols are as defined above.

The phrase "substituents in Q and $R^{13}$ form a five-membered ring, a six-membered ring, or a seven-membered ring together with the carbon atom or the nitrogen atom to which they are attached, and the ring may contain one or more atoms selected from the group consisting of an oxygen atom, a sulfur atom, and a nitrogen atom as a constituent atom" show, for example, the following structures:

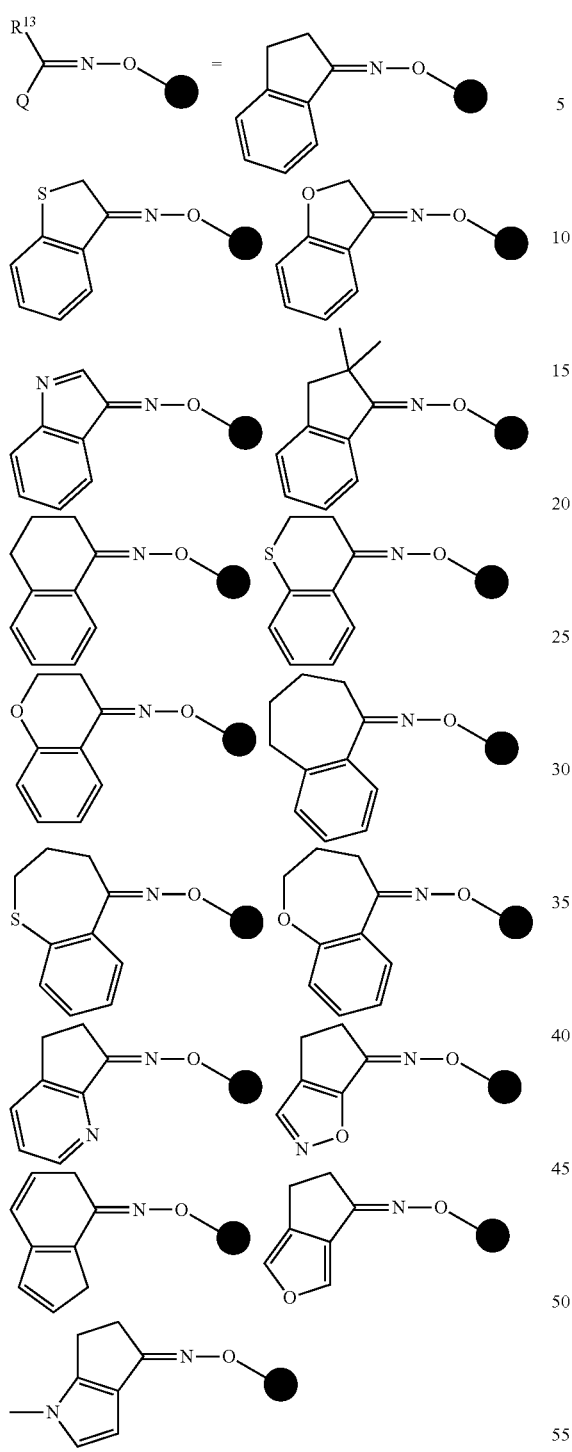

wherein symbols are as defined above.

The phrase "substituents in Q and $R^{13}$ form a five-membered ring, a six-membered ring together with the carbon atom or the nitrogen atom to which they are attached, or a seven-membered ring, and the ring may contain one or more atoms selected from the group consisting of an oxygen atom, a sulfur atom, and a nitrogen atom as a constituent atom, and may have one or more atoms or groups selected from Group $P^4$ as a substituent and, when the number of atoms or groups selected from Group $P^4$ is two or more, the atoms or groups may be the same or different" shows, for example, the nitrogen atom on the ring may be substituted with atoms or groups selected from Group $P^4$.

The phrase "$R^{1L}$ and $R^{2L}$ are combined to form $-E^L-CH_2-CH_2-$ (provided that $E^L$ is combined with the carbon atom to which $R^{2L}$ is attached, and represents $CH_2$ or an oxygen atom)" shows, for example, the following structures:

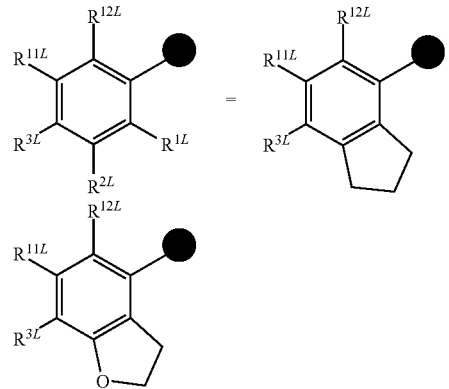

wherein symbols are as defined above.

The phrase "an indan-4-yl group, an indan-5-yl group, a 5,6,7,8-tetrahydronaphthalen-1-yl group, or a 5,6,7,8-tetrahydronaphthalen-2-yl group (provided that $CH_2$ constituting the ring of the indan-4-yl group, the indan-5-yl group, the 5,6,7,8-tetrahydronaphthalen-1-yl group, and the 5,6,7,8-tetrahydronaphthalen-2-yl group may be substituted with an oxygen atom, a sulfur atom, or a nitrogen atom" shows, for example, the following structures:

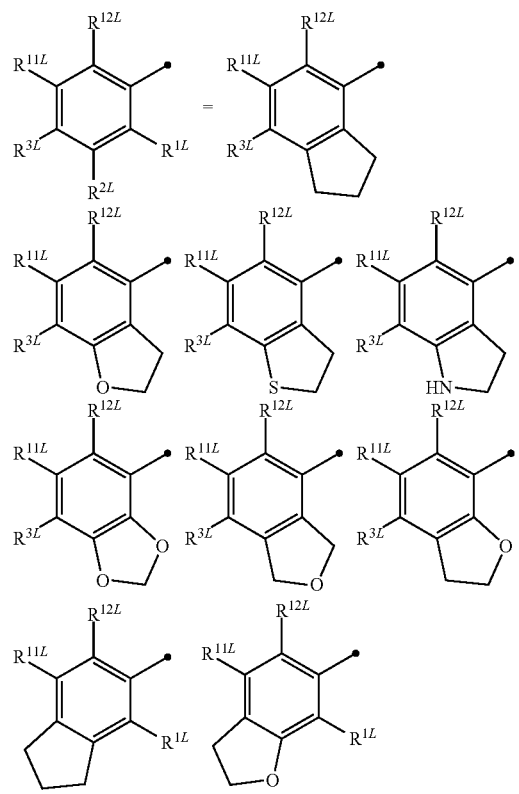

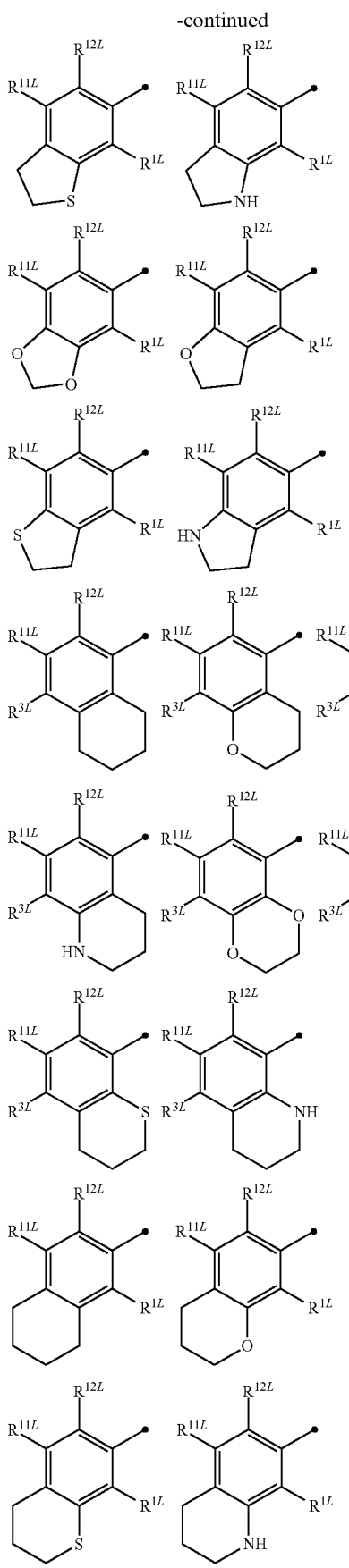

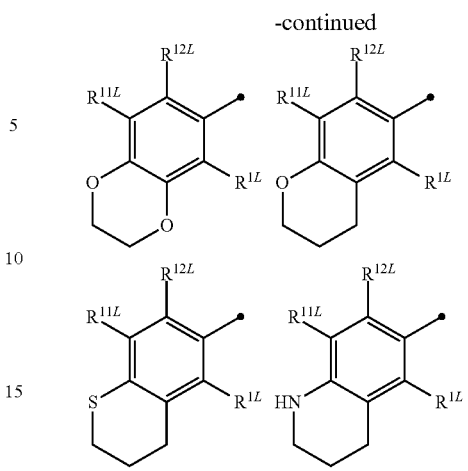

wherein symbols are as defined above.

The phrase "an indan-4-yl group, an indan-5-yl group, a 5,6,7,8-tetrahydronaphthalen-1-yl group, or a 5,6,7,8-tetrahydronaphthalen-2-yl group (provided that $CH_2$ constituting the ring of the indan-4-yl group, the indan-5-yl group, the 5,6,7,8-tetrahydronaphthalen-1-yl group, and the 5,6,7,8-tetrahydronaphthalen-2-yl group may be substituted with an oxygen atom, a sulfur atom, or a nitrogen atom, and also the indan-4-yl group, the indan-5-yl group, the 5,6,7,8-tetrahydronaphthalen-1-yl group, and the 5,6,7,8-tetrahydronaphthalen-2-yl group may have atoms or groups selected from Group $P^4$ as a substituent)" shows that the hydrogen atom on the ring may be substituted with atoms or groups selected from Group $P^4$.

The phrase "$R^2$ and $R^3$ form a four-membered ring, a five-membered ring, a six-membered ring, or a seven-membered ring together with the carbon atom to which they are attached, and the ring may contain one or more atoms selected from the group consisting of an oxygen atom and a sulfur atom as a ring-constituent atom" shows, for example, the following structures:

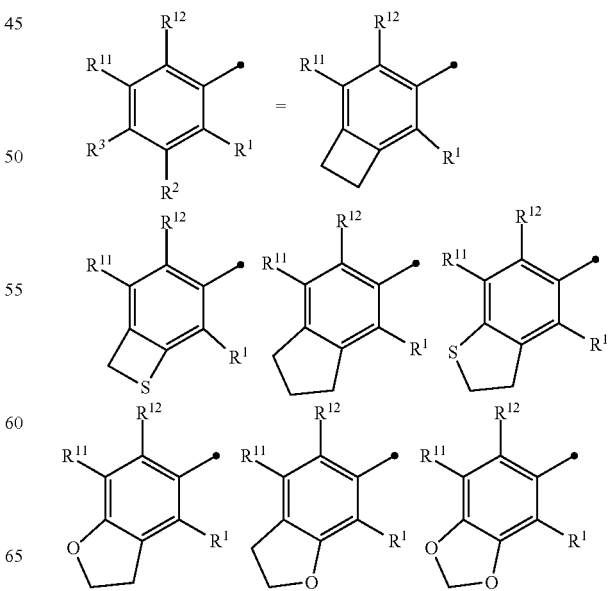

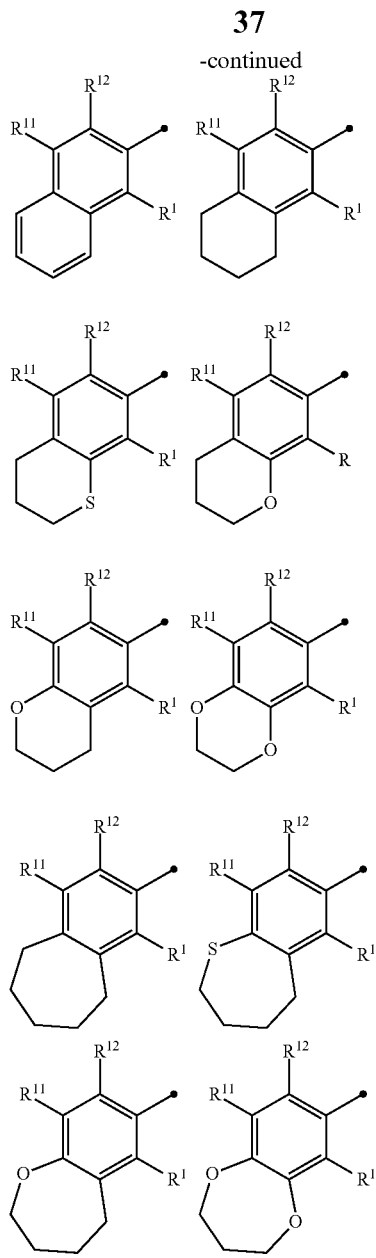

wherein symbols are as defined above.

The phrase "$R^2$ and $R^3$ form a four-membered ring, a five-membered ring, a six-membered ring, or a seven-membered ring together with the carbon atom to which they are attached, and the ring may contain one or more atoms selected from the group consisting of an oxygen atom and a sulfur atom as a ring-constituent atom, and the ring may have atoms or groups selected from Group P as a substituent" shows, for example, that the hydrogen atom on the ring may be substituted with one or more atoms or groups selected from Group P.

The phrase "$R^{12}$ and $R^{13}$ form a five-membered ring, a six-membered ring, or a seven-membered ring together with the carbon atom to which they are attached, and the ring may contain one or more atoms selected from the group consisting of an oxygen atom and a sulfur atom as a ring-constituent atom" shows, for example, the following structures:

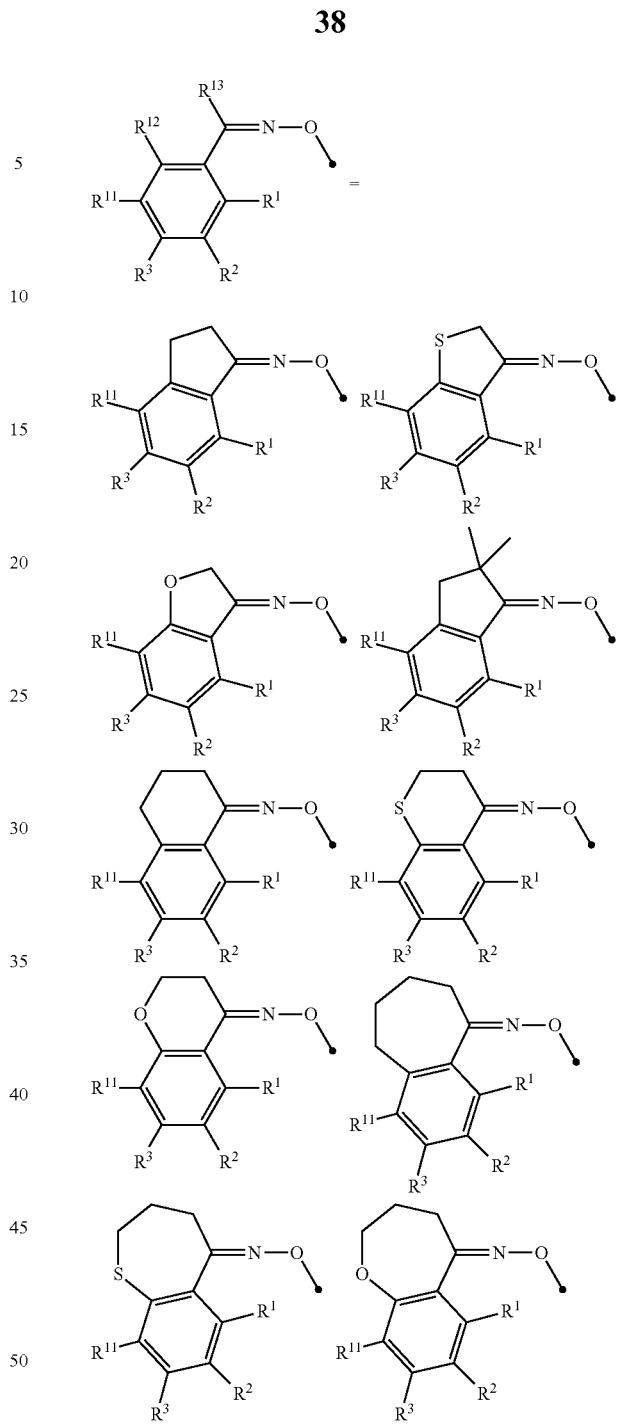

wherein symbols are as defined above.

The phrase "$R^{12}$ and R form a five-membered ring, a six-membered ring, or a seven-membered ring together with the carbon atom to which they are attached, and the ring may contain one or more atoms selected from the group consisting of an oxygen atom and a sulfur atom as a ring-constituent atom, and the ring may have one or more atoms or groups selected from Group P as a substituent" means, for example, the hydrogen atom on the ring is substituted with atoms or groups selected from Group P.

Examples of the present compound include compounds shown below: a compound represented by formula (1-P):

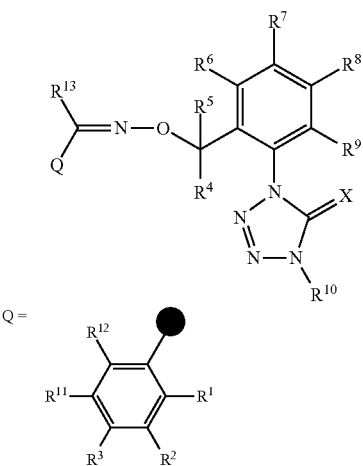

(1-P)

wherein symbols are as defined above;
a compound represented by formula (1-P), wherein X is an oxygen atom;
a compound represented by formula (1-P), wherein X is a sulfur atom;
a compound represented by formula (1-P), wherein $R^1$ is a hydrogen atom;
a compound represented by formula (1-P), wherein $R^1$ is a halogen atom;
a compound represented by formula (1-P), wherein $R^1$ is a C1-C6 alkyl group;
a compound represented by formula (1-P), wherein $R^1$ is a C1-C3 alkyl group;
a compound represented by formula (1-P), wherein $R^1$ is a methyl group; a compound represented by formula (1-P), wherein $R^1$ is a hydrogen atom or a C1-C6 alkyl group;
a compound represented by formula (1-P), wherein $R^1$ is a hydrogen atom or a C1-C3 alkyl group;
a compound represented by formula (1-P), wherein $R^1$ is a hydrogen atom or a methyl group;
a compound represented by formula (1-P), wherein $R^2$ is a hydrogen atom;
a compound represented by formula (1-P), wherein $R^2$ is a halogen atom;
a compound represented by formula (1-P), wherein $R^2$ is a C1-C6 alkyl group;
a compound represented by formula (1-P), wherein $R^2$ is a C1-C6 alkoxy group;
a compound represented by formula (1-P), wherein $R^2$ is a C1-C6 haloalkyl group;
a compound represented by formula (1-P), wherein $R^2$ is a C1-C6 haloalkoxy group;
a compound represented by formula (1-P), wherein $R^2$ is a halogen atom, a C1-C6 alkyl group, a C1-C6 alkoxy group, a C1-C6 haloalkyl group, or a C1-C6 haloalkoxy group;
a compound represented by formula (1-P), wherein $R^2$ is a halogen atom, a C1-C6 alkyl group, a C1-C6 alkoxy group, a C1-C6 haloalkyl group, or a C1-C6 haloalkoxy group;
a compound represented by formula (1-P), wherein $R^2$ is a halogen atom, a difluoromethyl group, a trifluoromethyl group, a difluoromethoxy group, a trifluoromethoxy group, or a 1,1,2,2-tetrafluoroethoxy group; a compound represented by formula (1-P), wherein $R^2$ is a chlorine atom, a trifluoromethyl group, a difluoromethoxy group, or a trifluoromethoxy group;
a compound represented by formula (1-P), wherein $R^1$ and $R^2$ form a five-membered ring or a six-membered ring together with the carbon atom to which they are attached;
a compound represented by formula (1-P), wherein $R^3$ is a hydrogen atom; a compound represented by formula (1-P), wherein $R^3$ is a halogen atom; a compound represented by formula (1-P), wherein $R^3$ is a C1-C6 alkyl group;
a compound represented by formula (1-P), wherein $R^3$ is a C1-C6 alkoxy group;
a compound represented by formula (1-P), wherein $R^3$ is a C1-C6 haloalkyl group;
a compound represented by formula (1-P), wherein $R^3$ is a C1-C6 haloalkoxy group;
a compound represented by formula (1-P), wherein $R^2$ and $R^3$ form a five-membered ring or a six-membered ring together with the carbon atom to which they are attached;
a compound represented by formula (1-P), wherein $R^3$ is a halogen atom, a C1-C6 alkyl group, a C1-C6 alkoxy group, a C1-C6 haloalkyl group, or a C1-C6 haloalkoxy group;
a compound represented by formula (1-P), wherein $R^3$ is a halogen atom, a difluoromethyl group, a trifluoromethyl group, a difluoromethoxy group, a trifluoromethoxy group, or a 1,1,2,2-tetrafluoroethoxy group;
a compound represented by formula (1-P), wherein $R^3$ is a chlorine atom, a trifluoromethyl group, a difluoromethoxy group, or a trifluoromethoxy group;
a compound represented by formula (1-P), wherein $R^4$ and $R^5$ are hydrogen atoms;
a compound represented by formula (1-P), wherein $R^6$ is a halogen atom; a compound represented by formula (1-P), wherein $R^6$ is a C1-C3 alkyl group;
a compound represented by formula (1-P), wherein $R^6$ is a C1-C3 haloalkyl group;
a compound represented by formula (1-P), wherein $R^6$ is a C2-C3 alkenyl group;
a compound represented by formula (1-P), wherein $R^6$ is a C2-C3 alkynyl group;
a compound represented by formula (1-P), wherein $R^6$ is a C1-C3 alkoxy group;
a compound represented by formula (1-P), wherein $R^6$ is a C1-C3 haloalkoxy group;
a compound represented by formula (1-P), wherein $R^6$ is a C1-C3 alkylthio group;
a compound represented by formula (1-P), wherein $R^6$ is a C3-C4 cycloalkyl group;
a compound represented by formula (1-P), wherein $R^6$ is a halogen atom, a C1-C3 alkyl group, a C1-C3 haloalkyl group, a C1-C3 alkoxy group, a C1-C3 haloalkoxy group, or a C3-C4 cycloalkyl group;
a compound represented by formula (1-P), wherein $R^6$ is a fluorine atom, a chlorine atom, a bromine atom, a methyl group, an ethyl group, a trifluoromethyl group, a difluoromethyl group, a methoxy group, an ethoxy group, a trifluoromethoxy group, a difluoromethoxy group, or a cyclopropyl group;
a compound represented by formula (1-P), wherein $R^6$ is a methyl group, an ethyl group, a difluoromethyl group, a trifluoromethyl group, or a cyclopropyl group;
a compound represented by formula (1-P), wherein $R^7$ is a hydrogen atom; a compound represented by formula (1-P), wherein $R^7$ is a hydrogen atom or a fluorine atom;
a compound represented by formula (1-P), wherein $R^8$ is a hydrogen atom; a compound represented by formula (1-P), wherein $R^8$ is a hydrogen atom or a fluorine atom;
a compound represented by formula (1-P), wherein $R^9$ is a hydrogen atom; a compound represented by formula (1-P), wherein $R^9$ is a hydrogen atom or a fluorine atom;

a compound represented by formula (1-P), wherein $R^7$, $R^8$, and $R^9$ are hydrogen atoms;
a compound represented by formula (1-P), wherein $R^7$, $R^8$, and $R^9$ are hydrogen atoms or fluorine atoms;
a compound represented by formula (1-P), wherein $R^{10}$ is a C1-C3 alkyl group;
a compound represented by formula (1-P), wherein $R^{10}$ is a C1-C3 haloalkyl group;
a compound represented by formula (1-P), wherein $R^{10}$ is a methyl group;
a compound represented by formula (1-P), wherein $R^{11}$ is a hydrogen atom;
a compound represented by formula (1-P), wherein $R^{11}$ is a halogen atom;
a compound represented by formula (1-P), wherein $R^{11}$ is a C1-C6 alkyl group;
a compound represented by formula (1-P), wherein $R^{11}$ is a C1-C6 alkoxy group;
a compound represented by formula (1-P), wherein $R^{11}$ is a C1-C6 haloalkyl group;
a compound represented by formula (1-P), wherein $R^{11}$ is a C1-C6 haloalkoxy group;
a compound represented by formula (1-P), wherein $R^{11}$ is a halogen atom, a C1-C6 alkyl group, a C1-C6 alkoxy group, a C1-C6 haloalkyl group, or a C1-C6 haloalkoxy group;
a compound represented by formula (1-P), wherein $R^{11}$ is a halogen atom, a difluoromethyl group, a trifluoromethyl group, a difluoromethoxy group, a trifluoromethoxy group, or a 1,1,2,2-tetrafluoroethoxy group; a compound represented by formula (1-P), wherein $R^{11}$ is a chlorine atom, a trifluoromethyl group, a difluoromethoxy group, or a trifluoromethoxy group;
a compound represented by formula (1-P), wherein $R^{12}$ is a hydrogen atom;
a compound represented by formula (1-P), wherein $R^{12}$ is a halogen atom;
a compound represented by formula (1-P), wherein $R^{12}$ is a C1-C6 alkyl group;
a compound represented by formula (1-P), wherein $R^{12}$ is a C1-C3 alkyl group;
a compound represented by formula (1-P), wherein $R^{12}$ is a methyl group;
a compound represented by formula (1-P), wherein $R^{12}$ is a hydrogen atom or a C1-C6 alkyl group;
a compound represented by formula (1-P), wherein $R^{12}$ is a hydrogen atom or a C1-C3 alkyl group;
a compound represented by formula (1-P), wherein $R^{12}$ is a hydrogen atom or a methyl group;
a compound represented by formula (1-P), wherein $R^1$ and $R^{12}$ are hydrogen atoms or C1-C3 alkyl groups;
a compound represented by formula (1-P), wherein $R^1$ and $R^{12}$ are hydrogen atoms or methyl groups;
a compound represented by formula (1-P), wherein $R^1$ and $R^{12}$ are hydrogen atoms;
a compound represented by formula (1-P), wherein $R^{13}$ is a hydrogen atom;
a compound represented by formula (1-P), wherein $R^{13}$ is a halogen atom;
a compound represented by formula (1-P), wherein $R^{13}$ is a C1-C4 alkyl group;
a compound represented by formula (1-P), wherein $R^{13}$ is a C2-C4 alkenyl group;
a compound represented by formula (1-P), wherein $R^{13}$ is a C2-C4 alkynyl group;
a compound represented by formula (1-P), wherein $R^3$ is a C1-C4 alkoxy group;
a compound represented by formula (1-P), wherein $R^{13}$ is a C1-C4 alkylthio group;
a compound represented by formula (1-P), wherein $R^{13}$ is a hydrogen atom, a halogen atom, a C1-C4 alkyl group, a C1-C4 alkoxy group, or a C1-C4 alkylthio group;
a compound represented by formula (1-P), wherein $R^{13}$ is a hydrogen atom or a C1-C4 alkyl group;
a compound represented by formula (1-P), wherein $R^{13}$ is a methyl group, an ethyl group, or a propyl group;
a compound represented by formula (1-P), wherein $R^2$ and $R^{11}$ each represents a halogen atom, a C1-C6 alkyl group, a C1-C6 alkoxy group, a C1-C6 haloalkyl group, or a C1-C6 haloalkoxy group;
a compound represented by formula (1-P), wherein $R^2$ and $R^{11}$ each represents a halogen atom, a difluoromethyl group, a trifluoromethyl group, a difluoromethoxy group, a trifluoromethoxy group, or a 1,1,2,2-tetrafluoroethoxy group;
a compound represented by formula (1-P), wherein $R^2$ and $R^{11}$ each represents a chlorine atom, a trifluoromethyl group, a difluoromethoxy group, or a trifluoromethoxy group;
a compound represented by formula (1-P), wherein $R^2$ and $R^3$ each represents a halogen atom, a C1-C6 alkyl group, a C1-C6 alkoxy group, a C1-C6 haloalkyl group, or a C1-C6 haloalkoxy group, or wherein $R^2$ and $R^3$ form a five-membered ring or a six-membered ring together with the carbon atom to which they are attached;
a compound represented by formula (1-P), wherein $R^2$ and $R^3$ each represents a halogen atom, a difluoromethyl group, a trifluoromethyl group, a difluoromethoxy group, a trifluoromethoxy group, or a 1,1,2,2-tetrafluoroethoxy group, or wherein $R^2$ and $R^3$ form a five-membered ring or a six-membered ring together with the carbon atom to which they are attached; a compound represented by formula (1-P), wherein $R^2$ and $R^3$ each represents a chlorine atom, a trifluoromethyl group, a difluoromethoxy group, or a trifluoromethoxy group compound, or wherein $R^2$ and $R^3$ form a five-membered ring or a six-membered ring together with the carbon atom to which they are attached;
a compound represented by formula (1-P), wherein $R^2$ and $R^3$ each represents a chlorine atom, a trifluoromethyl group, a difluoromethoxy group, or a trifluoromethoxy group;
a compound represented by formula (1-P), wherein $R^2$, $R^3$, and $R^{11}$ each represents a halogen atom, a C1-C6 alkyl group, a C1-C6 alkoxy group, a C1-C6 haloalkyl group, or a C1-C6 haloalkoxy group;
a compound represented by formula (1-P), wherein $R^2$, $R^3$, and $R^{11}$ each represents a halogen atom, a difluoromethyl group, a trifluoromethyl group, a difluoromethoxy group, a trifluoromethoxy group, or a 1,1,2,2-tetrafluoroethoxy group;
a compound represented by formula (1-P), wherein $R^2$, $R^3$, and $R^1$ each represents a chlorine atom, a trifluoromethyl group, a difluoromethoxy group, or a trifluoromethoxy group;
a compound represented by formula (1-P), wherein $R^4$, $R^5$, $R^7$, $R^8$, and $R^9$ are hydrogen atoms;
a compound represented by formula (1-P), wherein $R^4$, $R^5$, $R^7$, $R^8$, and $R^9$ are hydrogen atoms, and $R^{10}$ is a methyl group;
a compound represented by formula (1-P), wherein $R^4$, $R^5$, $R^7$, $R^8$, and $R^9$ are hydrogen atoms, $R^{10}$ is a methyl group, and X is an oxygen atom;
a compound represented by formula (1-P), wherein $R^4$, $R^5$, $R^7$, $R^8$, and $R^9$ are hydrogen atoms, $R^{10}$ is a methyl group, and X is a sulfur atom;
a compound represented by formula (1-P), wherein $R^1$ and $R^{12}$ each represents a hydrogen atom or a methyl group, $R^4$, $R^5$, $R^7$, $R^8$, and $R^9$ are hydrogen atoms, $R^{10}$ is a methyl group, and X is an oxygen atom;

a compound represented by formula (1-P), wherein $R^1$, $R^4$, $R^5$, $R^7$, $R^8$, $R^9$, and $R^{12}$ are hydrogen atoms, $R^{10}$ is a methyl group, and X is an oxygen atom;

a compound represented by formula (1-P), wherein $R^1$ and $R^{12}$ each represents a hydrogen atom or a methyl group, $R^3$, $R^4$, $R^5$, $R^7$, $R^8$, $R^9$, and $R^{11}$ are hydrogen atoms, $R^{10}$ is a methyl group, X is an oxygen atom, $R^2$ is a halogen atom, a C1-C6 alkyl group, a C1-C6 alkoxy group, a C1-C6 haloalkyl group, or a C1-C6 haloalkoxy group, $R^6$ is a halogen atom, a C1-C3 alkyl group, a C1-C3 haloalkyl group, a C1-C3 alkoxy group, a C1-C3 haloalkoxy group, or a C3-C4 cycloalkyl group, and $R^{13}$ is a hydrogen atom or a C1-C4 alkyl group;

a compound represented by formula (1-P), wherein $R^1$ and $R^{12}$ each represents a hydrogen atom or a methyl group, $R^3$, $R^4$, $R^5$, $R^7$, $R^8$, $R^9$, and $R^{11}$ are hydrogen atoms, $R^{10}$ is a methyl group, X is an oxygen atom, $R^2$ is a halogen atom, a C1-C6 alkyl group, a C1-C6 alkoxy group, a C1-C6 haloalkyl group, or a C1-C6 haloalkoxy group, $R^6$ is a halogen atom, a C1-C3 alkyl group, a C1-C3 haloalkyl group, a C1-C3 alkoxy group, a C1-C3 haloalkoxy group, or a C3-C4 cycloalkyl group, and $R^{13}$ is a methyl group, an ethyl group, or a propyl group;

a compound represented by formula (1-P), wherein $R^{11}$ and $R^{12}$ each represents a hydrogen atom or a methyl group, $R^3$, $R^4$, $R^5$, $R^7$, $R^8$, $R^9$, and $R^{11}$ are hydrogen atoms, $R^{10}$ is a methyl group, X is an oxygen atom, $R^2$ is a halogen atom, a C1-C6 alkyl group, a C1-C6 alkoxy group, a C1-C6 haloalkyl group, or a C1-C6 haloalkoxy group, $R^6$ is a fluorine atom, a chlorine atom, a bromine atom, a methyl group, an ethyl group, a trifluoromethyl group, a difluoromethyl group, a methoxy group, an ethoxy group, a trifluoromethoxy group, a difluoromethoxy group, or a cyclopropyl group, and $R^{13}$ is a hydrogen atom or a C1-C4 alkyl group; a compound represented by formula (1-P), wherein $R^1$ and $R^{12}$ each represents a hydrogen atom or a methyl group, $R^3$, $R^4$, $R^5$, $R^7$, $R^8$, $R^9$, and $R^{11}$ are hydrogen atoms, $R^{10}$ is a methyl group, X is an oxygen atom, $R^2$ is a halogen atom, a C1-C6 alkyl group, a C1-C6 alkoxy group, a C1-C6 haloalkyl group, or a C1-C6 haloalkoxy group, $R^6$ is a fluorine atom, a chlorine atom, a bromine atom, a methyl group, an ethyl group, a trifluoromethyl group, a difluoromethyl group, a methoxy group, an ethoxy group, a trifluoromethoxy group, a difluoromethoxy group, or a cyclopropyl group, and $R^{13}$ is a methyl group, an ethyl group, or a propyl group;

a compound represented by formula (1-P), wherein $R^{11}$ and $R^{12}$ each represents a hydrogen atom or a methyl group, $R^3$, $R^4$, $R^5$, $R^7$, $R^8$, $R^9$, and $R^{11}$ are hydrogen atoms, $R^{10}$ is a methyl group, X is an oxygen atom, $R^2$ is a halogen atom, a C1-C6 alkyl group, a C1-C6 alkoxy group, a C1-C6 haloalkyl group, or a C1-C6 haloalkoxy group, $R^6$ is a methyl group, an ethyl group, a difluoromethyl group, a trifluoromethyl group, or a cyclopropyl group, and $R^{13}$ is a hydrogen atom or a C1-C4 alkyl group; a compound represented by formula (1-P), wherein $R^1$ and $R^{12}$ each represents a hydrogen atom or a methyl group, $R^3$, $R^4$, $R^5$, $R^7$, $R^8$, $R^9$, and $R^{11}$ are hydrogen atoms, $R^{10}$ is a methyl group, X is an oxygen atom, $R^2$ is a halogen atom, a C1-C6 alkyl group, a C1-C6 alkoxy group, a C1-C6 haloalkyl group, or a C1-C6 haloalkoxy group, $R^6$ is a methyl group, an ethyl group, a difluoromethyl group, a trifluoromethyl group, or a cyclopropyl group, and $R^{13}$ is a methyl group, an ethyl group, or a propyl group;

a compound represented by formula (1-P), wherein $R^1$ and $R^{12}$ each represents a hydrogen atom or a methyl group, $R^3$, $R^4$, $R^5$, $R^7$, $R^8$, $R^9$, and $R^{11}$ are hydrogen atoms, $R^{10}$ is a methyl group, X is an oxygen atom, $R^2$ is a halogen atom, a difluoromethyl group, a trifluoromethyl group, a difluoromethoxy group, a trifluoromethoxy group, or a 1,1,2,2-tetrafluoroethoxy group, $R^6$ is a halogen atom, a C1-C3 alkyl group, a C1-C3 haloalkyl group, a C1-C3 alkoxy group, a C1-C3 haloalkoxy group, or a C3-C4 cycloalkyl group, and $R^{13}$ is a hydrogen atom or a C1-C4 alkyl group;

a compound represented by formula (1-P), wherein $R^{11}$ and $R^{12}$ each represents a hydrogen atom or a methyl group, $R^3$, $R^4$, $R^5$, $R^7$, $R^8$, $R^9$, and $R^{11}$ are hydrogen atoms, $R^{10}$ is a methyl group, X is an oxygen atom, $R^2$ is a halogen atom, a difluoromethyl group, a trifluoromethyl group, a difluoromethoxy group, a trifluoromethoxy group, or a 1,1,2,2-tetrafluoroethoxy group, $R^6$ is a halogen atom, a C1-C3 alkyl group, a C1-C3 haloalkyl group, a C1-C3 alkoxy group, a C1-C3 haloalkoxy group, or a C3-C4 cycloalkyl group, and $R^{13}$ is a methyl group, an ethyl group, or a propyl group;

a compound represented by formula (1-P), wherein $R^1$ and $R^{12}$ each represents a hydrogen atom or a methyl group, $R^3$, $R^4$, $R^5$, $R^7$, $R^8$, $R^9$, and $R^{11}$ are hydrogen atoms, $R^{10}$ is a methyl group, X is an oxygen atom, $R^2$ is a halogen atom, a difluoromethyl group, a trifluoromethyl group, a difluoromethoxy group, a trifluoromethoxy group, or a 1,1,2,2-tetrafluoroethoxy group, $R^6$ is a fluorine atom, a chlorine atom, a bromine atom, a methyl group, an ethyl group, a trifluoromethyl group, a difluoromethyl group, a methoxy group, an ethoxy group, a trifluoromethoxy group, a difluoromethoxy group, or a cyclopropyl group, and $R^{13}$ is a hydrogen atom or a C1-C4 alkyl group;

a compound represented by formula (1-P), wherein $R^1$ and $R^{12}$ each represents a hydrogen atom or a methyl group, $R^3$, $R^4$, $R^5$, $R^7$, $R^8$, $R^9$, and $R^{11}$ are hydrogen atoms, $R^{10}$ is a methyl group, X is an oxygen atom, $R^2$ is a halogen atom, a difluoromethyl group, a trifluoromethyl group, a difluoromethoxy group, a trifluoromethoxy group, or a 1,1,2,2-tetrafluoroethoxy group, $R^6$ is a fluorine atom, a chlorine atom, a bromine atom, a methyl group, an ethyl group, a trifluoromethyl group, a difluoromethyl group, a methoxy group, an ethoxy group, a trifluoromethoxy group, a difluoromethoxy group, or a cyclopropyl group, and $R^{13}$ is a methyl group, an ethyl group, or a propyl group; a compound represented by formula (1-P), wherein $R^{11}$ and $R^{12}$ each represents a hydrogen atom or a methyl group, $R^3$, $R^4$, $R^5$, $R^7$, $R^8$, $R^9$, and $R^{11}$ are hydrogen atoms, $R^{10}$ is a methyl group, X is an oxygen atom, $R^2$ is a halogen atom, a difluoromethyl group, a trifluoromethyl group, a difluoromethoxy group, a trifluoromethoxy group, or a 1,1,2,2-tetrafluoroethoxy group, $R^6$ is a methyl group, an ethyl group, a difluoromethyl group, a trifluoromethyl group, or a cyclopropyl group, and $R^{13}$ is a hydrogen atom or a C1-C4 alkyl group;

a compound represented by formula (1-P), wherein $R^1$ and $R^{12}$ each represents a hydrogen atom or a methyl group, $R^3$, $R^4$, $R^5$, $R^7$, $R^8$, $R^9$, and $R^{11}$ are hydrogen atoms, $R^{10}$ is a methyl group, X is an oxygen atom, $R^2$ is a halogen atom, a difluoromethyl group, a trifluoromethyl group, a difluoromethoxy group, a trifluoromethoxy group, or a 1,1,2,2-tetrafluoroethoxy group, $R^6$ is a methyl group, an ethyl group, a difluoromethyl group, a trifluoromethyl group, or a cyclopropyl group, and $R^{13}$ is a methyl group, an ethyl group, or a propyl group;

a compound represented by formula (1-P), wherein $R^1$ and $R^{12}$ each represents a hydrogen atom or a methyl group, $R^3$, $R^4$, $R^5$, $R^7$, $R^8$, $R^9$, and $R^{11}$ are hydrogen atoms, $R^{10}$ is a methyl group, X is an oxygen atom, $R^2$ is a chlorine atom, a trifluoromethyl group, a difluoromethoxy group, or a trifluoromethoxy group, $R^6$ is a halogen atom, a C1-C3 alkyl group, a C1-C3 haloalkyl group, a C1-C3 alkoxy group, a C1-C3 haloalkoxy group, or a C3-C4 cycloalkyl group, and $R^{13}$ is a hydrogen atom or a C1-C4 alkyl group;

a compound represented by formula (1-P), wherein $R^{11}$ and $R^{12}$ each represents a hydrogen atom or a methyl group, $R^3$, $R^4$, $R^5$, $R^7$, $R^8$, $R^9$, and $R^{11}$ are hydrogen atoms, $R^{10}$ is a methyl group, X is an oxygen atom, $R^2$ is a chlorine atom, a trifluoromethyl group, a difluoromethoxy group, or a trifluoromethoxy group, $R^6$ is a halogen atom, a C1-C3 alkyl group, a C1-C3 haloalkyl group, a C1-C3 alkoxy group, a C1-C3 haloalkoxy group, or a C3-C4 cycloalkyl group, and $R^{13}$ is a methyl group, an ethyl group, or a propyl group;

a compound represented by formula (1-P), wherein $R^{11}$ and $R^{12}$ each represents a hydrogen atom or a methyl group, $R^3$, $R^4$, $R^5$, $R^7$, $R^8$, $R^9$, and $R^{11}$ are hydrogen atoms, $R^{10}$ is a methyl group, X is an oxygen atom, $R^2$ is a chlorine atom, a trifluoromethyl group, a difluoromethoxy group, or a trifluoromethoxy group, $R^6$ is a fluorine atom, a chlorine atom, a bromine atom, a methyl group, an ethyl group, a trifluoromethyl group, a difluoromethyl group, a methoxy group, an ethoxy group, a trifluoromethoxy group, a difluoromethoxy group, or a cyclopropyl group, and $R^{13}$ is a hydrogen atom or a C1-C4 alkyl group;

a compound represented by formula (1-P), wherein $R^1$ and $R^{12}$ each represents a hydrogen atom or a methyl group, $R^3$, $R^4$, $R^5$, $R^7$, $R^8$, $R^9$, and $R^{11}$ are hydrogen atoms, $R^{10}$ is a methyl group, X is an oxygen atom, $R^2$ is a chlorine atom, a trifluoromethyl group, a difluoromethoxy group, or a trifluoromethoxy group, $R^6$ is a fluorine atom, a chlorine atom, a bromine atom, a methyl group, an ethyl group, a trifluoromethyl group, a difluoromethyl group, a methoxy group, an ethoxy group, a trifluoromethoxy group, a difluoromethoxy group, or a cyclopropyl group, and $R^{13}$ is a methyl group, an ethyl group, or a propyl group; a compound represented by formula (1-P), wherein $R^{11}$ and $R^{12}$ each represents a hydrogen atom or a methyl group, $R^3$, $R^4$, $R^5$, $R^7$, $R^8$, $R^9$, and $R^{11}$ are hydrogen atoms, $R^{10}$ is a methyl group, X is an oxygen atom, $R^2$ is a chlorine atom, a trifluoromethyl group, a difluoromethoxy group, or a trifluoromethoxy group, $R^6$ is a methyl group, an ethyl group, a difluoromethyl group, a trifluoromethyl group, or a cyclopropyl group, and $R^{13}$ is a hydrogen atom or a C1-C4 alkyl group;

a compound represented by formula (1-P), wherein $R^{11}$ and $R^{12}$ are hydrogen atoms or methyl groups, $R^3$, $R^4$, $R^5$, $R^7$, $R^8$, $R^9$, and $R^{11}$ are hydrogen atoms, $R^{10}$ is a methyl group, X is an oxygen atom, $R^2$ is a chlorine atom, a trifluoromethyl group, a difluoromethoxy group, or a trifluoromethoxy group, $R^6$ is a methyl group, an ethyl group, a difluoromethyl group, a trifluoromethyl group, or a cyclopropyl group, and $R^{13}$ is a methyl group, an ethyl group, or a propyl group;

a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a halogen atom, a C1-C6 alkyl group, a C1-C6 alkoxy group, a C1-C6 haloalkyl group, or a C1-C6 haloalkoxy group, $R^6$ is a halogen atom, a C1-C3 alkyl group, a C1-C3 haloalkyl group, a C1-C3 alkoxy group, a C1-C3 haloalkoxy group, or a C3-C4 cycloalkyl group, and $R^{13}$ is a hydrogen atom or a C1-C4 alkyl group;

a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a halogen atom, a C1-C6 alkyl group, a C1-C6 alkoxy group, a C1-C6 haloalkyl group, or a C1-C6 haloalkoxy group, $R^6$ is a halogen atom, a C1-C3 alkyl group, a C1-C3 haloalkyl group, a C1-C3 alkoxy group, a C1-C3 haloalkoxy group, or a C3-C4 cycloalkyl group, and $R^{13}$ is a methyl group, an ethyl group, or a propyl group;

a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a halogen atom, a C1-C6 alkyl group, a C1-C6 alkoxy group, a C1-C6 haloalkyl group, or a C1-C6 haloalkoxy group, $R^6$ is a fluorine atom, a chlorine atom, a bromine atom, a methyl group, an ethyl group, a trifluoromethyl group, a difluoromethyl group, a methoxy group, an ethoxy group, a trifluoromethoxy group, a difluoromethoxy group, or a cyclopropyl group, and $R^{13}$ is a hydrogen atom or a C1-C4 alkyl group; a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a halogen atom, a C1-C6 alkyl group, a C1-C6 alkoxy group, a C1-C6 haloalkyl group, or a C1-C6 haloalkoxy group, $R^6$ is a fluorine atom, a chlorine atom, a bromine atom, a methyl group, an ethyl group, a trifluoromethyl group, a difluoromethyl group, a methoxy group, an ethoxy group, a trifluoromethoxy group, a difluoromethoxy group, or a cyclopropyl group, and $R^{13}$ is a methyl group, an ethyl group, or a propyl group;

a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a halogen atom, a C1-C6 alkyl group, a C1-C6 alkoxy group, a C1-C6 haloalkyl group, or a C1-C6 haloalkoxy group, $R^6$ is a methyl group, an ethyl group, a difluoromethyl group, a trifluoromethyl group, or a cyclopropyl group, and $R^{13}$ is a hydrogen atom or a C1-C4 alkyl group; a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a halogen atom, a C1-C6 alkyl group, a C1-C6 alkoxy group, a C1-C6 haloalkyl group, or a C1-C6 haloalkoxy group, $R^6$ is a methyl group, an ethyl group, a difluoromethyl group, a trifluoromethyl group, or a cyclopropyl group, and $R^{13}$ is a methyl group, an ethyl group, or a propyl group;

a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a halogen atom, a difluoromethyl group, a trifluoromethyl group, a difluoromethoxy group, a trifluoromethoxy group, or a 1,1,2,2-tetrafluoroethoxy group, $R^6$ is a halogen atom, a C1-C3 alkyl group, a C1-C3 haloalkyl group, a C1-C3 alkoxy group, a C1-C3 haloalkoxy group, or a C3-C4 cycloalkyl group, and $R^{13}$ is a hydrogen atom or a C1-C4 alkyl group;

a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a halogen atom, a difluoromethyl group, a trifluoromethyl group, a difluoromethoxy group, a trifluoromethoxy group, or a 1,1,2,2-tetrafluoroethoxy group, $R^6$ is a halogen atom, a C1-C3 alkyl group, a C1-C3 haloalkyl group, a C1-C3 alkoxy group, a C1-C3 haloalkoxy group, or a C3-C4 cycloalkyl group, and $R^{13}$ is a methyl group, an ethyl group, or a propyl group;

a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a halogen atom, a difluoromethyl group, a trifluoromethyl group, a difluoromethoxy group, a trifluoromethoxy group, or a 1,1,2,2-tetrafluoroethoxy group, $R^6$ is a fluorine atom, a chlorine atom, a bromine atom, a methyl group, an ethyl group, a trifluoromethyl group, a difluoromethyl group, a methoxy group, an ethoxy group, a trifluoromethoxy group, a difluoromethoxy group, or a cyclopropyl group, and $R^{13}$ is a hydrogen atom or a C1-C4 alkyl group;

a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a halogen atom, a difluoromethyl group, a trifluoromethyl group, a difluoromethoxy group, a trifluoromethoxy group, or a 1,1,2,2-tetrafluoroethoxy group, $R^6$ is a fluorine atom, a chlorine atom, a bromine atom, a methyl group, an ethyl group, a trifluoromethyl group, a difluoromethyl group, a methoxy group, an ethoxy group, a trifluoromethoxy group, a difluoromethoxy group, or a cyclopropyl group, and $R^{13}$ is a methyl group, an ethyl group, or a propyl group; a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a halogen atom, a difluoromethyl group, a trifluoromethyl group, a difluoromethoxy group, a trifluoromethoxy group, or a 1,1,2,2-tetrafluoroethoxy group, $R^6$ is a methyl group, an ethyl group, a difluoromethyl group, a trifluoromethyl group, or a cyclopropyl group, and $R^{13}$ is a hydrogen atom or a C1-C4 alkyl group;

a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a halogen atom, a difluoromethyl group, a trifluoromethyl group, a difluoromethoxy group, a trifluoromethoxy group, or a 1,1,2,2-tetrafluoroethoxy group, $R^6$ is a methyl group, an ethyl group, a difluoromethyl group, a trifluoromethyl group, or a cyclopropyl group, and $R^{13}$ is a methyl group, an ethyl group, or a propyl group; a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a chlorine atom, a trifluoromethyl group, a difluoromethoxy group, or a trifluoromethoxy group, $R^6$ is a halogen atom, a C1-C3 alkyl group, a C1-C3 haloalkyl group, a C1-C3 alkoxy group, a C1-C3 haloalkoxy group, or a C3-C4 cycloalkyl group, and $R^{13}$ is a hydrogen atom or a C1-C4 alkyl group;

a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a chlorine atom, a trifluoromethyl group, a difluoromethoxy group, or a trifluoromethoxy group, $R^6$ is a halogen atom, a C1-C3 alkyl group, a C1-C3 haloalkyl group, a C1-C3 alkoxy group, a C1-C3 haloalkoxy group, or a C3-C4 cycloalkyl group, and $R^{13}$ is a methyl group, an ethyl group, or a propyl group;

a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a chlorine atom, a trifluoromethyl group, a difluoromethoxy group, or a trifluoromethoxy group, $R^6$ is a fluorine atom, a chlorine atom, a bromine atom, a methyl group, an ethyl group, a trifluoromethyl group, a difluoromethyl group, a methoxy group, an ethoxy group, a trifluoromethoxy group, a difluoromethoxy group, or a cyclopropyl group, and $R^{13}$ is a hydrogen atom or a C1-C4 alkyl group;

a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a chlorine atom, a trifluoromethyl group, a difluoromethoxy group, or a trifluoromethoxy group, $R^6$ is a fluorine atom, a chlorine atom, a bromine atom, a methyl group, an ethyl group, a trifluoromethyl group, a difluoromethyl group, a methoxy group, an ethoxy group, a trifluoromethoxy group, a difluoromethoxy group, or a cyclopropyl group, and $R^{13}$ is a methyl group, an ethyl group, or a propyl group; a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a chlorine atom, a trifluoromethyl group, a difluoromethoxy group, or a trifluoromethoxy group, $R^6$ is a methyl group, an ethyl group, a difluoromethyl group, a trifluoromethyl group, or a cyclopropyl group, and $R^{13}$ is a hydrogen atom or a C1-C4 alkyl group;

a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a chlorine atom, a trifluoromethyl group, a difluoromethoxy group, or a trifluoromethoxy group, $R^6$ is a methyl group, an ethyl group, a difluoromethyl group, a trifluoromethyl group, or a cyclopropyl group, and $R^{13}$ is a methyl group, an ethyl group, or a propyl group;

a compound represented by formula (1-P), wherein $R^1$, $R^2$, $R^4$, $R^5$, $R^7$, $R^8$, $R^9$, $R^{11}$, and $R^{12}$ are hydrogen atoms, $R^{10}$ is a methyl group, X is an oxygen atom, $R^3$ is a halogen atom, a C1-C6 alkyl group, a C1-C6 alkoxy group, a C1-C6 haloalkyl group, or a C1-C6 haloalkoxy group, $R^6$ is a halogen atom, a C1-C3 alkyl group, a C1-C3 haloalkyl group, a C1-C3 alkoxy group, a C1-C3 haloalkoxy group, or a C3-C4 cycloalkyl group, and $R^{13}$ is a hydrogen atom or a C1-C4 alkyl group;

a compound represented by formula (1-P), wherein $R^1$, $R^2$, $R^4$, $R^5$, $R^7$, $R^8$, $R^9$, $R^{11}$, and $R^{12}$ are hydrogen atoms, $R^{10}$ is a methyl group, X is an oxygen atom, $R^3$ is a halogen atom, a C1-C6 alkyl group, a C1-C6 alkoxy group, a C1-C6 haloalkyl group, or a C1-C6 haloalkoxy group, $R^6$ is a halogen atom, a C1-C3 alkyl group, a C1-C3 haloalkyl group, a C1-C3 alkoxy group, a C1-C3 haloalkoxy group, or a C3-C4 cycloalkyl group, and $R^{13}$ is a methyl group, an ethyl group, or a propyl group;

a compound represented by formula (1-P), wherein $R^1$, $R^2$, $R^4$, $R^5$, $R^7$, $R^8$, $R^9$, $R^{11}$, and $R^{12}$ are hydrogen atoms, $R^{10}$ is a methyl group, X is an oxygen atom, $R^3$ is a halogen atom, a C1-C6 alkyl group, a C1-C6 alkoxy group, a C1-C6 haloalkyl group, or a C1-C6 haloalkoxy group, $R^6$ is a fluorine atom, a chlorine atom, a bromine atom, a methyl group, an ethyl group, a trifluoromethyl group, a difluoromethyl group, a methoxy group, an ethoxy group, a trifluoromethoxy group, a difluoromethoxy group, or a cyclopropyl group, and $R^{13}$ is a hydrogen atom or a C1-C4 alkyl group; a compound represented by formula (1-P), wherein $R^1$, $R^2$, $R^4$, $R^5$, $R^7$, $R^8$, $R^9$, $R^{11}$, and $R^{12}$ are hydrogen atoms, $R^{10}$ is a methyl group, X is an oxygen atom, $R^3$ is a halogen atom, a C1-C6 alkyl group, a C1-C6 alkoxy group, a C1-C6 haloalkyl group, or a C1-C6 haloalkoxy group, $R^6$ is a fluorine atom, a chlorine atom, a bromine atom, a methyl group, an ethyl group, a trifluoromethyl group, a difluoromethyl group, a methoxy group, an ethoxy group, a trifluoromethoxy group, a difluoromethoxy group, or a cyclopropyl group, and $R^{13}$ is a methyl group, an ethyl group, or a propyl group;

a compound represented by formula (1-P), wherein $R^1$, $R^2$, $R^4$, $R^5$, $R^7$, $R^8$, $R^9$, $R^{11}$, and $R^{12}$ are hydrogen atoms, $R^{10}$ is a methyl group, X is an oxygen atom, $R^3$ is a halogen atom, a C1-C6 alkyl group, a C1-C6 alkoxy group, a C1-C6 haloalkyl group, or a C1-C6 haloalkoxy group, $R^6$ is a methyl group, an ethyl group, a difluoromethyl group, a trifluoromethyl group, or a cyclopropyl group, and $R^{13}$ is a hydrogen atom or a C1-C4 alkyl group; a compound represented by formula (1-P), wherein $R^1$, $R^2$, $R^4$, $R^5$, $R^7$, $R^8$, $R^9$, $R^{11}$, and $R^{12}$ are hydrogen atoms, $R^{10}$ is a methyl group, X is an oxygen atom, $R^3$ is a halogen atom, a C1-C6 alkyl group, a C1-C6 alkoxy group, a C1-C6 haloalkyl group, or a C1-C6 haloalkoxy group, $R^6$ is a methyl group, an ethyl group, a difluoromethyl group, a trifluoromethyl group, or a cyclopropyl group, and $R^{13}$ is a methyl group, an ethyl group, or a propyl group;

a compound represented by formula (1-P), wherein $R^1$, $R^2$, $R^4$, $R^5$, $R^7$, $R^8$, $R^9$, $R^{11}$, and $R^{12}$ are hydrogen atoms, $R^{10}$ is a methyl group, X is an oxygen atom, $R^3$ is a halogen atom, a difluoromethyl group, a trifluoromethyl group, a difluoromethoxy group, a trifluoromethoxy group, or a 1,1,2,2-tetrafluoroethoxy group, $R^6$ is a halogen atom, a C1-C3 alkyl group, a C1-C3 haloalkyl group, a C1-C3 alkoxy group, a C1-C3 haloalkoxy group, or a C3-C4 cycloalkyl group, and $R^{13}$ is a hydrogen atom or a C1-C4 alkyl group;

a compound represented by formula (1-P), wherein $R^1$, $R^2$, $R^4$, $R^5$, $R^7$, $R^8$, $R^9$, $R^{11}$, and $R^{12}$ are hydrogen atoms, $R^{10}$ is a methyl group, X is an oxygen atom, $R^3$ is a halogen atom, a difluoromethyl group, a trifluoromethyl group, a difluoromethoxy group, a trifluoromethoxy group, or a 1,1,2,2-tetrafluoroethoxy group, $R^6$ is a halogen atom, a C1-C3 alkyl group, a C1-C3 haloalkyl group, a C1-C3 alkoxy group, a C1-C3 haloalkoxy group, or a C3-C4 cycloalkyl group, and $R^{13}$ is a methyl group, an ethyl group, or a propyl group;

a compound represented by formula (1-P), wherein $R^1$, $R^2$, $R^4$, $R^5$, $R^7$, $R^8$, $R^9$, $R^{11}$, and $R^{12}$ are hydrogen atoms, $R^{10}$ is a methyl group, X is an oxygen atom, $R^3$ is a halogen atom, a difluoromethyl group, a trifluoromethyl group, a difluoromethoxy group, a trifluoromethoxy group, or a 1,1,2,2-tetrafluoroethoxy group, $R^6$ is a fluorine atom, a chlorine atom, a bromine atom, a methyl group, an ethyl group, a trifluoromethyl group, a difluoromethyl group, a methoxy group, an ethoxy group, a trifluoromethoxy group, a difluoromethoxy group, or a cyclopropyl group, and $R^{13}$ is a hydrogen atom or a C1-C4 alkyl group;

a compound represented by formula (1-P), wherein $R^1$, $R^2$, $R^4$, $R^5$, $R^7$, $R^8$, $R^9$, $R^{11}$, and $R^{12}$ are hydrogen atoms, $R^{10}$ is a methyl group, X is an oxygen atom, $R^3$ is a halogen atom, a difluoromethyl group, a trifluoromethyl group, a difluoromethoxy group, a trifluoromethoxy group, or a 1,1,2,2-tetrafluoroethoxy group, $R^6$ is a fluorine atom, a chlorine atom, a bromine atom, a methyl group, an ethyl group, a trifluoromethyl group, a difluoromethyl group, a methoxy group, an ethoxy group, a trifluoromethoxy group, a difluoromethoxy group, or a cyclopropyl group, and $R^{13}$ is a methyl group, an ethyl group, or a propyl group; a compound represented by formula (1-P), wherein $R^1$, $R^2$, $R^4$, $R^5$, $R^7$, $R^8$, $R^9$, $R^{11}$, and $R^{12}$ are hydrogen atoms, $R^{10}$ is a methyl group, X is an oxygen atom, $R^3$ is a halogen atom, a difluoromethyl group, a trifluoromethyl group, a difluoromethoxy group, a trifluoromethoxy group, or a 1,1,2,2-tetrafluoroethoxy group, $R^6$ is a methyl group, an ethyl group, a difluoromethyl group, a trifluoromethyl group, or a cyclopropyl group, and $R^{13}$ is a hydrogen atom or a C1-C4 alkyl group;

a compound represented by formula (1-P), wherein $R^1$, $R^2$, $R^4$, $R^5$, $R^7$, $R^8$, $R^9$, $R^{11}$, and $R^{12}$ are hydrogen atoms, $R^{10}$ is a methyl group, X is an oxygen atom, $R^3$ is a halogen atom, a difluoromethyl group, a trifluoromethyl group, a difluoromethoxy group, a trifluoromethoxy group, or a 1,1,2,2-tetrafluoroethoxy group, $R^6$ is a methyl group, an ethyl group, a difluoromethyl group, a trifluoromethyl group, or a cyclopropyl group, and $R^{13}$ is a methyl group, an ethyl group, or a propyl group; a compound represented by formula (1-P), wherein $R^1$, $R^2$, $R^4$, $R^5$, $R^7$, $R^8$, $R^9$, $R^{11}$, and $R^{12}$ are hydrogen atoms, $R^{10}$ is a methyl group, X is an oxygen atom, $R^3$ is a chlorine atom, a trifluoromethyl group, a difluoromethoxy group, or a trifluoromethoxy group, $R^6$ is a halogen atom, a C1-C3 alkyl group, a C1-C3 haloalkyl group, a C1-C3 alkoxy group, a C1-C3 haloalkoxy group, or a C3-C4 cycloalkyl group, and $R^{13}$ is a hydrogen atom or a C1-C4 alkyl group;

a compound represented by formula (1-P), wherein $R^1$, $R^2$, $R^4$, $R^5$, $R^7$, $R^8$, $R^9$, $R^{11}$, and $R^{12}$ are hydrogen atoms, $R^{10}$ is a methyl group, X is an oxygen atom, $R^3$ is a chlorine atom, a trifluoromethyl group, a difluoromethoxy group, or a trifluoromethoxy group, $R^6$ is a halogen atom, a C1-C3 alkyl group, a C1-C3 haloalkyl group, a C1-C3 alkoxy group, a C1-C3 haloalkoxy group, or a C3-C4 cycloalkyl group, and $R^{13}$ is a methyl group, an ethyl group, or a propyl group;

a compound represented by formula (1-P), wherein $R^1$, $R^2$, $R^4$, $R^5$, $R^7$, $R^8$, $R^9$, $R^{11}$, and $R^{12}$ are hydrogen atoms, $R^{10}$ is a methyl group, X is an oxygen atom, $R^3$ is a chlorine atom, a trifluoromethyl group, a difluoromethoxy group, or a trifluoromethoxy group, $R^6$ is a fluorine atom, a chlorine atom, a bromine atom, a methyl group, an ethyl group, a trifluoromethyl group, a difluoromethyl group, a methoxy group, an ethoxy group, a trifluoromethoxy group, a difluoromethoxy group, or a cyclopropyl group, and $R^{13}$ is a hydrogen atom or a C1-C4 alkyl group;

a compound represented by formula (1-P), wherein $R^1$, $R^2$, $R^4$, $R^5$, $R^7$, $R^8$, $R^9$, $R^{11}$, and $R^{12}$ are hydrogen atoms, $R^{10}$ is a methyl group, X is an oxygen atom, $R^3$ is a chlorine atom, a trifluoromethyl group, a difluoromethoxy group, or a trifluoromethoxy group, $R^6$ is a fluorine atom, a chlorine atom, a bromine atom, a methyl group, an ethyl group, a trifluoromethyl group, a difluoromethyl group, a methoxy group, an ethoxy group, a trifluoromethoxy group, a difluoromethoxy group, or a cyclopropyl group, and $R^{13}$ is a methyl group, an ethyl group, or a propyl group;

a compound represented by formula (1-P), wherein $R^1$, $R^2$, $R^4$, $R^5$, $R^7$, $R^8$, $R^9$, $R^{11}$, and $R^{12}$ are hydrogen atoms, $R^{10}$ is a methyl group, X is an oxygen atom, $R^3$ is a chlorine atom, a trifluoromethyl group, a difluoromethoxy group, or a trifluoromethoxy group, $R^6$ is a methyl group, an ethyl group, a difluoromethyl group, a trifluoromethyl group, or a cyclopropyl group, and $R^{13}$ is a hydrogen atom or a C1-C4 alkyl group;

a compound represented by formula (1-P), wherein $R^1$, $R^2$, $R^4$, $R^5$, $R^7$, $R^8$, $R^9$, $R^{11}$, and $R^{12}$ are hydrogen atoms, $R^{10}$ is a methyl group, X is an oxygen atom, $R^3$ is a chlorine atom, a trifluoromethyl group, a difluoromethoxy group, or a trifluoromethoxy group, $R^6$ is a methyl group, an ethyl group, a difluoromethyl group, a trifluoromethyl group, or a cyclopropyl group, and $R^{13}$ is a methyl group, an ethyl group, or a propyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a halogen atom, a C1-C6 alkyl group, a C1-C6 alkoxy group, a C1-C6 haloalkyl group, or a C1-C6 haloalkoxy group, $R^6$ is a halogen atom, a C1-C3 alkyl group, a C1-C3 haloalkyl group, a C1-C3 alkoxy group, a C1-C3 haloalkoxy group, or a C3-C4 cycloalkyl group, and $R^{13}$ is a hydrogen atom or a C1-C4 alkyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a halogen atom, a C1-C6 alkyl group, a C1-C6 alkoxy group, a C1-C6 haloalkyl group, or a C1-C6 haloalkoxy group, $R^6$ is a halogen atom, a C1-C3 alkyl group, a C1-C3 haloalkyl group, a C1-C3 alkoxy group, a C1-C3 haloalkoxy group, or a C3-C4 cycloalkyl group, and $R^{13}$ is a methyl group, an ethyl group, or a propyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a halogen atom, a C1-C6 alkyl group, a C1-C6 alkoxy group, a C1-C6 haloalkyl group, or a C1-C6 haloalkoxy group, $R^6$ is a fluorine atom, a chlorine atom, a bromine atom, a methyl group, an ethyl group, a trifluoromethyl group, a difluoromethyl group, a methoxy group, an ethoxy group, a trifluoromethoxy group, a difluoromethoxy group, or a cyclopropyl group, and $R^{13}$ is a hydrogen atom or a C1-C4 alkyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a halogen atom, a C1-C6 alkyl group, a C1-C6 alkoxy group, a C1-C6 haloalkyl group, or a C1-C6 haloalkoxy group, $R^6$ is a fluorine atom, a chlorine atom, a bromine atom, a methyl group, an ethyl group, a trifluoromethyl group, a difluoromethyl group, a methoxy group, an ethoxy group, a trifluoromethoxy group, a difluoromethoxy group, or a cyclopropyl group, and $R^{13}$ is a methyl group, an ethyl group, or a propyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a halogen atom, a C1-C6 alkyl group, a C1-C6 alkoxy group, a C1-C6 haloalkyl group, or a C1-C6 haloalkoxy group, $R^6$ is a methyl group, an ethyl group, a difluoromethyl group, a trifluoromethyl group, or a cyclopropyl group, and $R^{13}$ is a hydrogen atom or a C1-C4 alkyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a halogen atom, a C1-C6 alkyl group, a C1-C6 alkoxy group, a C1-C6 haloalkyl group, or a C1-C6 haloalkoxy group, $R^6$ is a methyl group, an ethyl group, a difluoromethyl group, a trifluoromethyl group, or a cyclopropyl group, and $R^{13}$ is a methyl group, an ethyl group, or a propyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a halogen atom, a difluoromethyl group, a trifluoromethyl group, a difluoromethoxy group, a trifluoromethoxy group, or a 1,1,2,2-tetrafluoroethoxy group, $R^6$ is a halogen atom, a C1-C3 alkyl group, a C1-C3 haloalkyl group, a C1-C3 alkoxy group, a C1-C3 haloalkoxy group, or a C3-C4 cycloalkyl group, and $R^{13}$ is a hydrogen atom or a C1-C4 alkyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a halogen atom, a difluoromethyl group, a trifluoromethyl group, a difluoromethoxy group, a trifluoromethoxy group, or a 1,1,2,2-tetrafluoroethoxy group, $R^6$ is a halogen atom, a C1-C3 alkyl group, a C1-C3 haloalkyl group, a C1-C3 alkoxy group, a C1-C3 haloalkoxy group, or a C3-C4 cycloalkyl group, and $R^{13}$ is a methyl group, an ethyl group, or a propyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a halogen atom, a difluoromethyl group, a trifluoromethyl group, a difluoromethoxy group, a trifluoromethoxy group, or a 1,1,2,2-tetrafluoroethoxy group, $R^6$ is a fluorine atom, a chlorine atom, a bromine atom, a methyl group, an ethyl group, a trifluoromethyl group, a difluoromethyl group, a methoxy group, an ethoxy group, a trifluoromethoxy group, a difluoromethoxy group, or a cyclopropyl group; $R^{13}$ is a hydrogen atom or a C1-C4 alkyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a halogen atom, a difluoromethyl group, a trifluoromethyl group, a difluoromethoxy group, a trifluoromethoxy group, or a 1,1,2,2-tetrafluoroethoxy group, $R^6$ is a fluorine atom, a chlorine atom, a bromine atom, a methyl group, an ethyl group, a trifluoromethyl group, a difluoromethyl group, a methoxy group, an ethoxy group, a trifluoromethoxy group, a difluoromethoxy group, or a cyclopropyl group, and $R^{13}$ is a methyl group, an ethyl group, or a propyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a halogen atom, a difluoromethyl group, a trifluoromethyl group, a difluoromethoxy group, a trifluoromethoxy group, or a 1,1,2,2-tetrafluoroethoxy group, $R^6$ is a methyl group, an ethyl group, a difluoromethyl group, a trifluoromethyl group, or a cyclopropyl group, and $R^{13}$ is a hydrogen atom or a C1-C4 alkyl group; a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a halogen atom, a difluoromethyl group, a trifluoromethyl group, a difluoromethoxy group, a trifluoromethoxy group, or a 1,1,2,2-tetrafluoroethoxy group, $R^6$ is a methyl group, an ethyl group, a difluoromethyl group, a trifluoromethyl group, or a cyclopropyl group, and $R^{13}$ is a methyl group, an ethyl group, or a propyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a chlorine atom, a trifluoromethyl group, a difluoromethoxy group, or a trifluoromethoxy group, $R^6$ is a halogen atom, a C1-C3 alkyl group, a C1-C3 haloalkyl group, a C1-C3 alkoxy group, a C1-C3 haloalkoxy group, or a C3-C4 cycloalkyl group, and $R^{13}$ is a hydrogen atom or a C1-C4 alkyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a chlorine atom, a trifluoromethyl group, a difluoromethoxy group, or a trifluoromethoxy group, $R^6$ is a halogen atom, a C1-C3 alkyl group, a C1-C3 haloalkyl group, a C1-C3 alkoxy group, a C1-C3 haloalkoxy group, or a C3-C4 cycloalkyl group, and $R^{13}$ is a methyl group, an ethyl group, or a propyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a chlorine atom, a trifluoromethyl group, a difluoromethoxy group, or a trifluoromethoxy group, $R^6$ is a fluorine atom, a chlorine atom, a bromine atom, a methyl group, an ethyl group, a trifluoromethyl group, a difluoromethyl group, a methoxy group, an ethoxy group, a trifluoromethoxy group, a difluoromethoxy group, or a cyclopropyl group, and $R^{13}$ is a hydrogen atom or a C1-C4 alkyl group; a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a chlorine atom, a trifluoromethyl group, a difluoromethoxy group, or a trifluoromethoxy group, $R^6$ is a fluorine atom, a chlorine atom, a bromine atom, a methyl group, an ethyl group, a trifluoromethyl group, a difluoromethyl group, a methoxy group, an ethoxy group, a trifluoromethoxy group, a difluoromethoxy group, or a cyclopropyl group, and $R^{13}$ is a methyl group, an ethyl group, or a propyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a chlorine atom, a trifluoromethyl group, a difluoromethoxy group, or a trifluoromethoxy group, $R^6$ is a methyl group, an ethyl group, a difluoromethyl group, a trifluoromethyl group, or a cyclopropyl group, and $R^{13}$ is a hydrogen atom or a C1-C4 alkyl group; a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a chlorine atom, a trifluoromethyl group, a difluoromethoxy group, or a trifluoromethoxy group, $R^6$ is a methyl group, an ethyl group, a difluoromethyl group, a trifluoromethyl group, or a cyclopropyl group, and $R^{13}$ is a methyl group, an ethyl group, or a propyl group;

a compound represented by formula (1-P), wherein $R^1$, $R^4$, $R^5$, $R^7$, $R^8$, $R^9$, and $R^{12}$ are hydrogen atoms, $R^{10}$ is a methyl group, X is an oxygen atom, $R^2$, $R^3$, and $R^{11}$ each represents a halogen atom, a C1-C6 alkyl group, a C1-C6 alkoxy group, a C1-C6 haloalkyl group, or a C1-C6 haloalkoxy group, $R^6$ is a halogen atom, a C1-C3 alkyl group, a C1-C3 haloalkyl group, a C1-C3 alkoxy group, a C1-C3 haloalkoxy group, or a C3-C4 cycloalkyl group, and $R^{13}$ is a hydrogen atom or a C1-C4 alkyl group;

a compound represented by formula (1-P), wherein $R^1$, $R^4$, $R^5$, $R^7$, $R^8$, $R^9$, and $R^{12}$ are hydrogen atoms, $R^{10}$ is a methyl group, X is an oxygen atom, $R^2$, $R^3$, and $R^{11}$ each represents a halogen atom, a C1-C6 alkyl group, a C1-C6 alkoxy group, a C1-C6 haloalkyl group, or a C1-C6 haloalkoxy group, $R^6$ is a halogen atom, a C1-C3 alkyl group, a C1-C3 haloalkyl group, a C1-C3 alkoxy group, a C1-C3 haloalkoxy group, or a C3-C4 cycloalkyl group, and $R^{13}$ is a methyl group, an ethyl group, or a propyl group;

a compound represented by formula (1-P), wherein $R^1$, $R^4$, $R^5$, $R^7$, $R^8$, $R^9$, and $R^{12}$ are hydrogen atoms, $R^{10}$ is a methyl group, X is an oxygen atom, $R^2$, $R^3$, and $R^1$ each represents a halogen atom, a C1-C6 alkyl group, a C1-C6 alkoxy group, a C1-C6 haloalkyl group, or a C1-C6 haloalkoxy group, $R^6$ is a fluorine atom, a chlorine atom, a bromine atom, a methyl group, an ethyl group, a trifluoromethyl group, a difluoromethyl group, a methoxy group, an ethoxy group, a trifluoromethoxy group, a difluoromethoxy group, or a cyclopropyl group, and $R^{13}$ is a hydrogen atom or a C1-C4 alkyl group;

a compound represented by formula (1-P), wherein $R^1$, $R^4$, $R^5$, $R^7$, $R^8$, $R^9$, and $R^{12}$ are hydrogen atoms, $R^{10}$ is a methyl group, X is an oxygen atom, $R^2$, $R^3$, and $R^{11}$ each represents a halogen atom, a C1-C6 alkyl group, a C1-C6 alkoxy group, a C1-C6 haloalkyl group, or a C1-C6 haloalkoxy group, $R^6$ is a fluorine atom, a chlorine atom, a bromine atom, a methyl group, an ethyl group, a trifluoromethyl group, a difluoromethyl group, a methoxy group, an ethoxy group, a trifluoromethoxy group, a difluoromethoxy group, or a cyclopropyl group, and $R^{13}$ is a methyl group, an ethyl group, or a propyl group;

a compound represented by formula (1-P), wherein $R^1$, $R^4$, $R^5$, $R^7$, $R^8$, $R^9$, and $R^{12}$ are hydrogen atoms, $R^{10}$ is a methyl group, X is an oxygen atom, $R^2$, $R^3$, and $R^1$ each represents a halogen atom, a C1-C6 alkyl group, a C1-C6 alkoxy group, a C1-C6 haloalkyl group, or a C1-C6 haloalkoxy group, $R^6$ is a methyl group, an ethyl group, a difluoromethyl group, a trifluoromethyl group, or a cyclopropyl group, and $R^{13}$ is a hydrogen atom or a C1-C4 alkyl group;

a compound represented by formula (1-P), wherein $R^1$, $R^4$, $R^5$, $R^7$, $R^8$, $R^9$, and $R^{12}$ are hydrogen atoms, $R^{10}$ is a methyl group, X is an oxygen atom, $R^2$, $R^3$, and $R^1$ each represents a halogen atom, a C1-C6 alkyl group, a C1-C6 alkoxy group, a C1-C6 haloalkyl group, or a C1-C6 haloalkoxy group, $R^6$ is a methyl group, an ethyl group, a difluoromethyl group, a trifluoromethyl group, or a cyclopropyl group, and $R^{13}$ is a methyl group, an ethyl group, or a propyl group;

a compound represented by formula (1-P), wherein $R^1$, $R^4$, $R^5$, $R^7$, $R^8$, $R^9$, and $R^{12}$ are hydrogen atoms, $R^{10}$ is a methyl group, X is an oxygen atom, $R^2$, $R^3$, and $R^{11}$ each represents a halogen atom, a difluoromethyl group, a trifluoromethyl group, a difluoromethoxy group, a trifluoromethoxy group, or a 1,1,2,2-tetrafluoroethoxy group, $R^6$ is a halogen atom, a C1-C3 alkyl group, a C1-C3 haloalkyl group, a C1-C3 alkoxy group, a C1-C3 haloalkoxy group, or a C3-C4 cycloalkyl group, and $R^{13}$ is a hydrogen atom or a C1-C4 alkyl group;

a compound represented by formula (1-P), wherein $R^1$, $R^4$, $R^5$, $R^7$, $R^8$, $R^9$, and $R^{12}$ are hydrogen atoms, $R^{10}$ is a methyl group, X is an oxygen atom, $R^2$, $R^3$, and $R^{11}$ each represents a halogen atom, a difluoromethyl group, a trifluoromethyl group, a difluoromethoxy group, a trifluoromethoxy group, or a 1,1,2,2-tetrafluoroethoxy group, $R^6$ is a halogen atom, a C1-C3 alkyl group, a C1-C3 haloalkyl group, a C1-C3 alkoxy group, a C1-C3 haloalkoxy group, or a C3-C4 cycloalkyl group, and $R^{13}$ is a methyl group, an ethyl group, or a propyl group;

a compound represented by formula (1-P), wherein $R^1$, $R^4$, $R^5$, $R^7$, $R^8$, $R^9$, and $R^{12}$ are hydrogen atoms, $R^{10}$ is a methyl group, X is an oxygen atom, $R^2$, $R^3$, and $R^{11}$ each represents a halogen atom, a difluoromethyl group, a trifluoromethyl group, a difluoromethoxy group, a trifluoromethoxy group, or a 1,1,2,2-tetrafluoroethoxy group, $R^6$ is a fluorine atom, a chlorine atom, a bromine atom, a methyl group, an ethyl group, a trifluoromethyl group, a difluoromethyl group, a methoxy group, an ethoxy group, a trifluoromethoxy group, a difluoromethoxy group, or a cyclopropyl group, and $R^{13}$ is a hydrogen atom or a C1-C4 alkyl group; a compound represented by formula (1-P), wherein $R^1$, $R^4$, $R^5$, $R^7$, $R^8$, $R^9$, and $R^{12}$ are hydrogen atoms, $R^{10}$ is a methyl group, X is an oxygen atom, $R^2$, $R^3$, and $R^{11}$ each represents a halogen atom, a difluoromethyl group, a trifluoromethyl group, a difluoromethoxy group, a trifluoromethoxy group, or a 1,1,2,2-tetrafluoroethoxy group, $R^6$ is a fluorine atom, a chlorine atom, a bromine atom, a methyl group, an ethyl group, a trifluoromethyl group, a difluoromethyl group, a methoxy group, an ethoxy group, a trifluoromethoxy group, a difluoromethoxy group, or a cyclopropyl group, and $R^{13}$ is a methyl group, an ethyl group, or a propyl group;

a compound represented by formula (1-P), wherein $R^1$, $R^4$, $R^5$, $R^7$, $R^8$, $R^9$, and $R^{12}$ are hydrogen atoms, $R^{10}$ is a methyl group, X is an oxygen atom, $R^2$, $R^3$, and $R^{11}$ each represents a halogen atom, a difluoromethyl group, a trifluoromethyl group, a difluoromethoxy group, a trifluoromethoxy group, or a 1,1,2,2-tetrafluoroethoxy group, $R^6$ is a methyl group, an ethyl group, a difluoromethyl group, a trifluoromethyl group, or a cyclopropyl group, and $R^{13}$ is a hydrogen atom or a C1-C4 alkyl group; a compound represented by formula (1-P), wherein $R^1$, $R^4$, $R^5$, $R^7$, $R^8$, $R^9$, and $R^{12}$ are hydrogen atoms, $R^{10}$ is a methyl group, X is an oxygen atom, $R^2$, $R^3$, and $R^{11}$ each represents a halogen atom, a difluoromethyl group, a trifluoromethyl group, a difluoromethoxy group, a trifluoromethoxy group, or a 1,1,2,2-tetrafluoroethoxy group, $R^6$ is a methyl group, an ethyl group, a difluoromethyl group, a trifluoromethyl group, or a cyclopropyl group, and $R^{13}$ is a methyl group, an ethyl group, or a propyl group;

a compound represented by formula (1-P), wherein $R^1$, $R^4$, $R^5$, $R^7$, $R^8$, $R^9$, and $R^{12}$ are hydrogen atoms, $R^{10}$ is a methyl group, X is an oxygen atom, $R^2$, $R^3$, and $R^1$ each represents a chlorine atom, a trifluoromethyl group, a difluoromethoxy group, or a trifluoromethoxy group, $R^6$ is a halogen atom, a C1-C3 alkyl group, a C1-C3 haloalkyl group, a C1-C3 alkoxy group, a C1-C3 haloalkoxy group, or a C3-C4 cycloalkyl group, and $R^{13}$ is a hydrogen atom or a C1-C4 alkyl group;

a compound represented by formula (1-P), wherein $R^1$, $R^4$, $R^5$, $R^7$, $R^8$, $R^9$, and $R^{12}$ are hydrogen atoms, $R^{10}$ is a methyl group, X is an oxygen atom, $R^2$, $R^3$, and $R^1$ each represents a chlorine atom, a trifluoromethyl group, a difluoromethoxy group, or a trifluoromethoxy group, $R^6$ is a halogen atom, a C1-C3 alkyl group, a C1-C3 haloalkyl group, a C1-C3 alkoxy group, a C1-C3 haloalkoxy group, or a C3-C4 cycloalkyl group, and $R^{13}$ is a methyl group, an ethyl group, or a propyl group;

a compound represented by formula (1-P), wherein $R^1$, $R^4$, $R^5$, $R^7$, $R^8$, $R^9$, and $R^{12}$ are hydrogen atoms, $R^{10}$ is a methyl group, X is an oxygen atom, $R^2$, $R^3$, and $R^1$ each represents a chlorine atom, a trifluoromethyl group, a difluoromethoxy group, or a trifluoromethoxy group, $R^6$ is a fluorine atom, a chlorine atom, a bromine atom, a methyl group, an ethyl group, a trifluoromethyl group, a difluoromethyl group, a methoxy group, an ethoxy group, a trifluoromethoxy group, a difluoromethoxy group, or a cyclopropyl group, and $R^{13}$ is a hydrogen atom or a C1-C4 alkyl group; a compound represented by formula (1-P), wherein $R^1$, $R^4$, $R^5$, $R^7$, $R^8$, $R^9$, and $R^{12}$ are hydrogen atoms, $R^{10}$ is a methyl group, X is an oxygen atom, $R^2$, $R^3$, and $R^1$ each represents a chlorine atom, a trifluoromethyl group, a difluoromethoxy group, or a trifluoromethoxy group, $R^6$ is a fluorine atom, a chlorine atom, a bromine atom, a methyl group, an ethyl group, a trifluoromethyl group, a difluoromethyl group, a methoxy group, an ethoxy group, a trifluoromethoxy group, a difluoromethoxy group, or a cyclopropyl group, and $R^{13}$ is a methyl group, an ethyl group, or a propyl group;

a compound represented by formula (1-P), wherein $R^1$, $R^4$, $R^5$, $R^7$, $R^8$, $R^9$, and $R^{12}$ are hydrogen atoms, $R^{10}$ is a methyl group, X is an oxygen atom, $R^2$, $R^3$, and $R^{11}$ each represents a chlorine atom, a trifluoromethyl group, a difluoromethoxy group, or a trifluoromethoxy group, $R^6$ is a methyl group, an ethyl group, a difluoromethyl group, a trifluoromethyl group, or a cyclopropyl group, and $R^{13}$ is a hydrogen atom or a C1-C4 alkyl group; a compound represented by formula (1-P), wherein $R^1$, $R^4$, $R^5$, $R^7$, $R^8$, $R^9$, and $R^{12}$ are hydrogen atoms, $R^{10}$ is a methyl group, X is an oxygen atom, $R^2$, $R^3$, and $R^{11}$ each represents a chlorine atom, a trifluoromethyl group, a difluoromethoxy group, or a trifluoromethoxy group, $R^6$ is a methyl group, an ethyl group, a difluoromethyl group, a trifluoromethyl group, or a cyclopropyl group, and $R^{13}$ is a methyl group, an ethyl group, or a propyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a halogen atom, a C1-C6 alkyl group, a C1-C6 alkoxy group, a C1-C6 haloalkyl group, or a C1-C6 haloalkoxy group, or $R^2$ and $R^3$ form a five-membered ring or a six-membered ring together with the carbon atom to which they are attached, $R^6$ is a halogen atom, a C1-C3 alkyl group, a C1-C3 haloalkyl group, a C1-C3 alkoxy group, a C1-C3 haloalkoxy group, or a C3-C4 cycloalkyl group, and $R^{13}$ is a hydrogen atom or a C1-C4 alkyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a halogen atom, a C1-C6 alkyl group, a C1-C6 alkoxy group, a C1-C6 haloalkyl group, or a C1-C6 haloalkoxy group, or $R^2$ and $R^3$ form a five-membered ring or a six-membered ring together with the carbon atom to which they are attached, $R^6$ is a halogen atom, a C1-C3 alkyl group, a C1-C3 haloalkyl group, a C1-C3 alkoxy group, a C1-C3 haloalkoxy group, or a C3-C4 cycloalkyl group, and $R^{13}$ is a methyl group, an ethyl group, or a propyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a halogen atom, a C1-C6 alkyl group, a C1-C6 alkoxy group, a C1-C6 haloalkyl group, or a C1-C6 haloalkoxy group, or $R^2$ and $R^3$ form a five-membered ring or a six-membered ring together with the carbon atom to which they are attached, $R^6$ is a fluorine atom, a chlorine atom, a bromine atom, a methyl group, an ethyl group, a trifluoromethyl group, a difluoromethyl group, a methoxy group, an ethoxy group, a trifluoromethoxy group, a difluoromethoxy group, or a cyclopropyl group, and $R^{13}$ is a hydrogen atom or a C1-C4 alkyl group; a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a halogen atom, a C1-C6 alkyl group, a C1-C6 alkoxy group, a C1-C6 haloalkyl group, or a C1-C6 haloalkoxy group, or $R^2$ and $R^3$ form a five-membered ring or a six-membered ring together with the carbon atom to which they are attached, $R^6$ is a fluorine atom, a chlorine atom, a bromine atom, a methyl group, an ethyl group, a trifluoromethyl group, a difluoromethyl group, a methoxy group, an ethoxy group, a trifluoromethoxy group, a difluoromethoxy group, or a cyclopropyl group, and $R^{13}$ is a methyl group, an ethyl group, or a propyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a halogen atom, a C1-C6 alkyl group, a C1-C6 alkoxy group, a C1-C6 haloalkyl group, or a C1-C6 haloalkoxy group, or $R^2$ and $R^3$ form a five-membered ring or a six-membered ring together with the carbon atom to which they are attached, $R^6$ is a methyl group, an ethyl group, a difluoromethyl group, a trifluoromethyl group, or a cyclopropyl group, and $R^{13}$ is a hydrogen atom or a C1-C4 alkyl group; a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a halogen atom, a C1-C6 alkyl group, a C1-C6 alkoxy group, a C1-C6 haloalkyl group, or a C1-C6 haloalkoxy group, or $R^2$ and $R^3$ form a five-membered ring or a six-membered ring together with the carbon atom to which they are attached, $R^6$ is a methyl group, an ethyl group, a difluoromethyl group, a trifluoromethyl group, or a cyclopropyl group, and $R^{13}$ is a methyl group, an ethyl group, or a propyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a halogen atom, a difluoromethyl group, a trifluoromethyl group, a difluoromethoxy group, a trifluoromethoxy group, or a 1,1,2,2-tetrafluoroethoxy group, or $R^2$ and $R^3$ form a five-membered ring or a six-membered ring together with the carbon atom to which they are attached, $R^6$ is a halogen atom, a C1-C3 alkyl group, a C1-C3 haloalkyl group, a C1-C3 alkoxy group, a C1-C3 haloalkoxy group, or a C3-C4 cycloalkyl group, and $R^{13}$ is a hydrogen atom or a C1-C4 alkyl group;

a compound represented by formula (1-P), wherein $R^1$, $R^4$, $R^5$, $R^7$, $R^8$, $R^9$, $R^{11}$ and $R^{12}$ are hydrogen atoms, $R^{10}$ is a methyl group, X is an oxygen atom, $R^2$ and $R^3$ each represents a halogen atom, a difluoromethyl group, a trifluoromethyl group, a difluoromethoxy group, a trifluoromethoxy group, or a 1,1,2,2-tetrafluoroethoxy group, or $R^2$ and $R^3$ form a five-membered ring or a six-membered ring together with the carbon atom to which they are attached, $R^6$ is a halogen atom, a C1-C3 alkyl group, a C1-C3 haloalkyl group, a C1-C3 alkoxy group, a C1-C3 haloalkoxy group, or a C3-C4 cycloalkyl group, and $R^{13}$ is a methyl group, an ethyl group, or a propyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a halogen atom, a difluoromethyl group, a trifluoromethyl group, a difluoromethoxy group, a trifluoromethoxy group, or a 1,1,2,2-tetrafluoroethoxy group, or $R^2$ and $R^3$ form a five-membered ring or a six-membered ring together with the carbon atom to which they are attached, $R^6$ is a fluorine atom, a chlorine atom, a bromine atom, a methyl group, an ethyl group, a trifluoromethyl group, a difluoromethyl group, a methoxy group, an ethoxy group, a trifluoromethoxy group, a difluoromethoxy group, or a cyclopropyl group, and $R^{13}$ is a hydrogen atom or a C1-C4 alkyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a halogen atom, a difluoromethyl group, a trifluoromethyl group, a difluoromethoxy group, a trifluoromethoxy group, or a 1,1,2,2-tetrafluoroethoxy group, or $R^2$ and $R^3$ form a five-membered ring or a six-membered ring together with the carbon atom to which they are attached, $R^6$ is a fluorine atom, a chlorine atom, a bromine atom, a methyl group, an ethyl group, a trifluoromethyl group, a difluoromethyl group, a methoxy group, an ethoxy group, a trifluoromethoxy group, a difluoromethoxy group, or a cyclopropyl group, and $R^{13}$ is a methyl group, an ethyl group, or a propyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a halogen atom, a difluoromethyl group, a trifluoromethyl group, a difluoromethoxy group, a trifluoromethoxy group, or a 1,1,2,2-tetrafluoroethoxy group, or $R^2$ and $R^3$ form a five-membered ring or a six-membered ring together with the carbon atom to which they are attached, $R^6$ is a methyl group, an ethyl group, a difluoromethyl group, a trifluoromethyl group, or a cyclopropyl group, and $R^{13}$ is a hydrogen atom or a C1-C4 alkyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a halogen atom, a difluoromethyl group, a trifluoromethyl group, a difluoromethoxy group, a trifluoromethoxy group, or a 1,1,2,2-tetrafluoroethoxy group, or $R^2$ and $R^3$ form a five-membered ring or a six-membered ring together with the carbon atom to which they are attached, $R^6$ is a methyl group, an ethyl group, a difluoromethyl group, a trifluoromethyl group, or a cyclopropyl group, and $R^{13}$ is a methyl group, an ethyl group, or a propyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a chlorine atom, a trifluoromethyl group, a difluoromethoxy group, or a trifluoromethoxy group, or $R^2$ and $R^3$ form a five-membered ring or a six-membered ring together with the carbon atom to which they are attached, $R^6$ is a halogen atom, a C1-C3 alkyl group, a C1-C3 haloalkyl group, a C1-C3 alkoxy group, a C1-C3 haloalkoxy group, or a C3-C4 cycloalkyl group, and $R^{13}$ is a hydrogen atom or a C1-C4 alkyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a chlorine atom, a trifluoromethyl group, a difluoromethoxy group, or a trifluoromethoxy group, or $R^2$ and $R^3$ form a five-membered ring or a six-membered ring together with the carbon atom to which they are attached, $R^6$ is a halogen atom, a C1-C3 alkyl group, a C1-C3 haloalkyl group, a C1-C3 alkoxy group, a C1-C3 haloalkoxy group, or a C3-C4 cycloalkyl group, and $R^{13}$ is a methyl group, an ethyl group, or a propyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a chlorine atom, a trifluoromethyl group, a difluoromethoxy group, or a trifluoromethoxy group, or $R^2$ and $R^3$ form a five-membered ring or a six-membered ring together with the carbon atom to which they are attached, $R^6$ is a fluorine atom, a chlorine atom, a bromine atom, a methyl group, an ethyl group, a trifluoromethyl group, a difluoromethyl group, a methoxy group, an ethoxy group, a trifluoromethoxy group, a difluoromethoxy group, or a cyclopropyl group, and $R^{13}$ is a hydrogen atom or a C1-C4 alkyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a chlorine atom, a trifluoromethyl group, a difluoromethoxy group, or a trifluoromethoxy group, or $R^2$ and $R^3$ form a five-membered ring or a six-membered ring together with the carbon atom to which they are attached, $R^6$ is a fluorine atom, a chlorine atom, a bromine atom, a methyl group, an ethyl group, a trifluoromethyl group, a difluoromethyl group, a methoxy group, an ethoxy group, a trifluoromethoxy group, a difluoromethoxy group, or a cyclopropyl group, and $R^{13}$ is a methyl group, an ethyl group, or a propyl group; a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a chlorine atom, a trifluoromethyl group, a difluoromethoxy group, or a trifluoromethoxy group, or $R^2$ and $R^3$ form a five-membered ring or a six-membered ring together with the carbon atom to which they are attached, $R^6$ is a methyl group, an ethyl group, a difluoromethyl group, a trifluoromethyl group, or a cyclopropyl group, and $R^{13}$ is a hydrogen atom or a C1-C4 alkyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a chlorine atom, a trifluoromethyl group, a difluoromethoxy group, or a trifluoromethoxy group, or $R^2$ and $R^3$ form a five-membered ring or a six-membered ring together with the carbon atom to which they are attached, $R^6$ is a methyl group, an ethyl group, a difluoromethyl group, a trifluoromethyl group, or a cyclopropyl group, and $R^{13}$ is a methyl group, an ethyl group, or a propyl group; a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a chlorine atom, a trifluoromethyl group, a difluoromethoxy group, or a trifluoromethoxy group, $R^6$ is a halogen atom, a C1-C3 alkyl group, a C1-C3 haloalkyl group, a C1-C3 alkoxy group, a C1-C3 haloalkoxy group, or a C3-C4 cycloalkyl group, and $R^{13}$ is a hydrogen atom or a C1-C4 alkyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a chlorine atom, a trifluoromethyl group, a difluoromethoxy group, or a trifluoromethoxy group, $R^6$ is a halogen atom, a C1-C3 alkyl group, a C1-C3 haloalkyl group, a C1-C3 alkoxy group, a C1-C3 haloalkoxy group, or a C3-C4 cycloalkyl group, and $R^{13}$ is a methyl group, an ethyl group, or a propyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a chlorine atom, a trifluoromethyl group, a difluoromethoxy group, or a trifluoromethoxy group, $R^6$ is a fluorine atom, a chlorine atom, a bromine atom, a methyl group, an ethyl group, a trifluoromethyl group, a difluoromethyl group, a methoxy group, an ethoxy group, a trifluoromethoxy group, a difluoromethoxy group, or a cyclopropyl group, and $R^{13}$ is a hydrogen atom or a C1-C4 alkyl group; a compound represented by formula (1-P), wherein $R^1$, $R^4$, $R^5$, $R^7$, $R^8$, $R^9$, $R^{11}$ and $R^{12}$ are hydrogen atoms, $R^{10}$ is a methyl group, X is an oxygen atom, $R^2$ and $R^3$ each represents a chlorine atom, a trifluoromethyl group, a difluoromethoxy group, or a trifluoromethoxy group, $R^6$ is a fluorine atom, a chlorine atom, a bromine atom, a methyl group, an ethyl group, a trifluoromethyl group, a difluoromethyl group, a methoxy group, an ethoxy group, a trifluoromethoxy group, a difluoromethoxy group, or a cyclopropyl group, and $R^{13}$ is a methyl group, an ethyl group, or a propyl group;

a compound represented by formula (1-P), wherein $R^1$, $R^2$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a chlorine atom, a trifluoromethyl group, a difluoromethoxy group, or a trifluoromethoxy group, $R^6$ is a methyl group, an ethyl group, a difluoromethyl group, a trifluoromethyl group, or a cyclopropyl group, and $R^{13}$ is a hydrogen atom or a C1-C4 alkyl group; a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a chlorine atom, a trifluoromethyl group, a difluoromethoxy group, or a trifluoromethoxy group, $R^6$ is a methyl group, an ethyl group, a difluoromethyl group, a trifluoromethyl group, or a cyclopropyl group, and $R^{13}$ is a methyl group, an ethyl group, or a propyl group;

a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a hydrogen atom, a halogen atom, a nitro group, a methyl group, a difluoromethyl group, a trifluoromethyl group, a methoxy group, an isopropoxy group, a pentyloxy group, a hexyloxy group, a difluoromethoxy group, a trifluoromethoxy group, a 1,1,2,2-tetrafluoroethoxy group, a cyano group, an aminocarbonyl group, or an N-methylaminocarbonyl group, $R^6$ is a halogen atom, a methyl group, an ethyl group, a trifluoromethyl group, a methoxy group, an ethoxy group, a thiomethyl group, or a cyclopropyl group, and $R^{13}$ is a hydrogen atom, a methyl group, an ethyl group, a propyl group, an isopropyl group, a butyl group, a hexyl group, a trifluoromethyl group, or a cyclopropyl group;

a compound represented by formula (1-P), wherein $R^1$, $R^3$, $R^4$, $R^5$, $R^7$, $R^8$, R' and $R^{12}$ are hydrogen atoms, $R^{10}$ is a methyl group, X is an oxygen atom, $R^2$ and $R^{11}$ are fluorine atoms, chlorine atoms, methyl groups, or trifluoromethyl groups, $R^6$ is a halogen atom, a methyl group, an ethyl group, a trifluoromethyl group, a methoxy group, an ethoxy group, a thiomethyl group, or a cyclopropyl group, and $R^{13}$ is a hydrogen atom, a methyl group, an ethyl group, a propyl group, an isopropyl group, a butyl group, a hexyl group, a trifluoromethyl group, or a cyclopropyl group;

a compound represented by formula (1-P), wherein $R^3$, $R^4$, $R^5$, $R^7$, $R^8$, $R^9$, $R^{11}$, and $R^{12}$ are hydrogen atoms, $R^{10}$ is a methyl group, X is an oxygen atom, Q is the following structure:

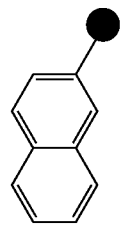

wherein the symbol ○ represents a binding site, $R^6$ is a halogen atom, a methyl group, an ethyl group, a trifluoromethyl group, a methoxy group, an ethoxy group, a thiomethyl group, or a cyclopropyl group, and $R^{13}$ is a hydrogen atom, a methyl group, an ethyl group, a propyl group, an isopropyl group, a butyl group, a hexyl group, a trifluoromethyl group, or a cyclopropyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ form a five-membered ring or a six-membered ring together with the carbon atom to which they are attached, $R^6$ is a halogen atom, a methyl group, an ethyl group, a trifluoromethyl group, a methoxy group, an ethoxy group, a thiomethyl group, or a cyclopropyl group, and $R^{13}$ is a hydrogen atom, a methyl group, an ethyl group, a propyl group, an isopropyl group, a butyl group, a hexyl group, a trifluoromethyl group, or a cyclopropyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a fluorine atom, a chlorine atom, or a bromine atom, $R^6$ is a halogen atom, a methyl group, an ethyl group, a trifluoromethyl group, a methoxy group, an ethoxy group, a thiomethyl group, or ncyclopropyl group, and $R^{13}$ is a hydrogen atom, a methyl group, an ethyl group, a propyl group, an isopropyl group, a butyl group, a hexyl group, a trifluoromethyl group, or a cyclopropyl group; a compound represented by formula (1-P), wherein $R^1$, $R^3$, $R^4$, $R^5$, $R^7$, $R^8$, $R^9$, and $R^{11}$ are hydrogen atoms, $R^{10}$ is a methyl group, X is an oxygen atom, $R^2$ is a hydrogen atom, a halogen atom, a nitro group, a methyl group, a difluoromethyl group, a trifluoromethyl group, a methoxy group, an isopropoxy group, a pentyloxy group, a hexyloxy group, a difluoromethoxy group, a trifluoromethoxy group, a 1,1,2,2-tetrafluoroethoxy group, a cyano group, an aminocarbonyl group, or an N-methylaminocarbonyl group, $R^6$ is a halogen atom, a methyl group, an ethyl group, a trifluoromethyl group, a methoxy group, an ethoxy group, a thiomethyl group, or a cyclopropyl group, $R^{12}$ and $R^{13}$ form a five-membered ring;

a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a halogen atom, a methyl group, a difluoromethyl group, a trifluoromethyl group, a 2,2,2-trifluoroethyl group, a 2,2,2,2,2,2-hexafluoroisopropyl group, a methoxy group, a difluoromethoxy group, a trifluoromethoxy group, a 1,1,2,2-tetrafluoroethoxy group, or a 2,2,2,2,2,2-hexafluoroisopropoxy group, $R^6$ is a halogen atom, a methyl group, an ethyl group, a difluoromethyl group, a trifluoromethyl group, a methoxy group, an ethoxy group, a difluoromethoxy group, a thiomethyl group, or a cyclopropyl group, and $R^{13}$ is a hydrogen atom, a halogen atom, a methyl group, an ethyl group, a propyl group, an isopropyl group, or a cyclopropyl group;

a compound represented by formula (1-P), wherein $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^1$ and $R^2$ form a five-membered ring or a six-membered ring together with the carbon atom to which they are attached, $R^6$ is a halogen atom, a methyl group, an ethyl group, a difluoromethyl group, a trifluoromethyl group, a methoxy group, an ethoxy group, a difluoromethoxy group, a thiomethyl group, or a cyclopropyl group, and $R^{13}$ is a hydrogen atom, a halogen atom, a methyl group, an ethyl group, a propyl group, an isopropyl group, or a cyclopropyl group;

a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a halogen atom, a C1-C6 alkyl group, a C1-C6 alkoxy group, a C1-C6 haloalkyl group, or a C1-C6 haloalkoxy group, $R^6$ is a halogen atom, $R^{13}$ is a hydrogen atom or a C1-C4 alkyl group;

a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a halogen atom, a C1-C6 alkyl group, a C1-C6 alkoxy group, a C1-C6 haloalkyl group, or a C1-C6 haloalkoxy group, $R^6$ is a halogen atom, and $R^{13}$ is a methyl group, an ethyl group, or a propyl group; a compound represented by formula (1-P), wherein $R^1$, $R^3$, $R^4$, $R^5$, $R^7$, $R^8$, $R^9$, $R^{11}$ and $R^{12}$ are hydrogen atoms, $R^{10}$ is a methyl group, X is an oxygen atom, $R^2$ is a halogen atom, a difluoromethyl group, a trifluoromethyl group, a difluoromethoxy group, a trifluoromethoxy group, or a 1,1,2,2-tetrafluoroethoxy group, $R^6$ is a halogen atom, and $R^{13}$ is a hydrogen atom or a C1-C4 alkyl group;

a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a halogen atom, a difluoromethyl group, a trifluoromethyl group, a difluoromethoxy group, a trifluoromethoxy group, or a 1,1,2,2-tetrafluoroethoxy group, $R^6$ is a halogen atom, and $R^{13}$ is a methyl group, an ethyl group, or a propyl group;

a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a chlorine atom, a trifluoromethyl group, a difluoromethoxy group, or a trifluoromethoxy group, $R^6$ is a halogen atom, $R^{13}$ is a hydrogen atom or a C1-C4 alkyl group;

a compound represented by formula (1-P), wherein $R^1$, $R^3$, $R^4$, $R^5$, $R^7$, $R^8$, $R^9$, $R^1$, $R^{12}$ are hydrogen atoms, $R^{10}$ is a methyl group, X is an oxygen atom, $R^2$ is a chlorine atom, a trifluoromethyl group, a difluoromethoxy group, or a trifluoromethoxy group, $R^6$ is a halogen atom, and $R^{13}$ is a methyl group, an ethyl group, or a propyl group;

a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a halogen atom, a C1-C6 alkyl group, a C1-C6 alkoxy group, a C1-C6 haloalkyl group, or a C1-C6 haloalkoxy group, $R^6$ is a C1-C3 alkyl group, and $R^{13}$ is a hydrogen atom or a C1-C4 alkyl group; a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a halogen atom, a C1-C6 alkyl group, a C1-C6 alkoxy group, a C1-C6 haloalkyl group, or a C1-C6 haloalkoxy group, $R^6$ is a C1-C3 alkyl group, and $R^{13}$ is a methyl group, an ethyl group, or a propyl group; a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a halogen atom, a difluoromethyl group, a trifluoromethyl group, a difluoromethoxy group, a trifluoromethoxy group, or a 1,1,2,2-tetrafluoroethoxy group, $R^6$ is a C1-C3 alkyl group, and $R^{13}$ is a hydrogen atom or a C1-C4 alkyl group;

a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a halogen atom, a difluoromethyl group, a trifluoromethyl group, a difluoromethoxy group, a trifluoromethoxy group, or a 1,1,2,2-tetrafluoroethoxy group, $R^6$ is a C1-C3 alkyl group, and $R^{13}$ is a methyl group, an ethyl group, or a propyl group;

a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a chlorine atom, a trifluoromethyl group, a difluoromethoxy group, or a trifluoromethoxy group, $R^6$ is a C1-C3 alkyl group, and $R^{13}$ is a hydrogen atom or a C1-C4 alkyl group;

a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a chlorine atom, a trifluoromethyl group, a difluoromethoxy group, or a trifluoromethoxy group, $R^6$ is a C1-C3 alkyl group, and $R^{13}$ is a methyl group, an ethyl group, or a propyl group;

a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a halogen atom, a C1-C6 alkyl group, a C1-C6 alkoxy group, a C1-C6 haloalkyl group, or a C1-C6 haloalkoxy group, $R^6$ is a C1-C3 haloalkyl group, and $R^{13}$ is a hydrogen atom or a C1-C4 alkyl group; a compound represented by formula (1-P), wherein $R^1$, $R^3$, $R^4$, $R^5$, $R^7$, $R^8$, $R^9$, $R^{11}$ and $R^{12}$ are hydrogen atoms, $R^{10}$ is a methyl group, X is an oxygen atom, $R^2$ is a halogen atom, a C1-C6 alkyl group, a C1-C6 alkoxy group, a C1-C6 haloalkyl group, or a C1-C6 haloalkoxy group, $R^6$ is a C1-C3 haloalkyl group, and $R^{13}$ is a methyl group, an ethyl group, or a propyl group;

a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a halogen atom, a difluoromethyl group, a trifluoromethyl group, a difluoromethoxy group, a trifluoromethoxy group, or a 1,1,2,2-tetrafluoroethoxy group, $R^6$ is a C1-C3 haloalkyl group, and $R^{13}$ is a hydrogen atom or a C1-C4 alkyl group;

a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a halogen atom, a difluoromethyl group, a trifluoromethyl group, a difluoromethoxy group, a trifluoromethoxy group, or a 1,1,2,2-tetrafluoroethoxy group, $R^6$ is a C1-C3 haloalkyl group, and $R^{13}$ is a methyl group, an ethyl group, or a propyl group;

a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a chlorine atom, a trifluoromethyl group, a difluoromethoxy group, or a trifluoromethoxy group, $R^6$ is a C1-C3 haloalkyl group, and $R^{13}$ is a hydrogen atom or a C1-C4 alkyl group;
a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a chlorine atom, a trifluoromethyl group, a difluoromethoxy group, or a trifluoromethoxy group, $R^6$ is a C1-C3 haloalkyl group, and $R^{13}$ is a methyl group, an ethyl group, or a propyl group;
a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a halogen atom, a C1-C6 alkyl group, a C1-C6 alkoxy group, a C1-C6 haloalkyl group, or a C1-C6 haloalkoxy group, $R^6$ is a methoxy group, and $R^{13}$ is a hydrogen atom or a C1-C4 alkyl group;
a compound represented by formula (1-P), wherein $R^1$, $R^3$, $R^4$, $R^5$, $R^7$, $R^8$, $R^9$, $R^{11}$, and $R^{12}$ is a hydrogen atom, $R^{10}$ is a methyl group, X is an oxygen atom, $R^2$ is a halogen atom, a C1-C6 alkyl group, a C1-C6 alkoxy group, a C1-C6 haloalkyl group, or a C1-C6 haloalkoxy group, $R^6$ is a methoxy group, and $R^{13}$ is a methyl group, an ethyl group, or a propyl group; a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a halogen atom, a difluoromethyl group, a trifluoromethyl group, a difluoromethoxy group, a trifluoromethoxy group, or a 1,1,2,2-tetrafluoroethoxy group, $R^6$ is a methoxy group, and $R^{13}$ is a hydrogen atom or a C1-C4 alkyl group;
a compound represented by formula (1-P), wherein $R^1$, $R^3$, $R^4$, $R^5$, $R^7$, $R^8$, $R^9$, $R^{11}$, and $R^{12}$ is a hydrogen atom, $R^{10}$ is a methyl group, X is an oxygen atom, $R^2$ is a halogen atom, a difluoromethyl group, a trifluoromethyl group, a difluoromethoxy group, a trifluoromethoxy group, or a 1,1,2,2-tetrafluoroethoxy group, $R^6$ is a methoxy group, and $R^{13}$ is a methyl group, an ethyl group, or a propyl group;
a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a chlorine atom, a trifluoromethyl group, a difluoromethoxy group, or a trifluoromethoxy group, $R^6$ is a methoxy group, and $R^{13}$ is a hydrogen atom or a C1-C4 alkyl group;
a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a chlorine atom, a trifluoromethyl group, a difluoromethoxy group, or a trifluoromethoxy group, $R^6$ is a methoxy group, and $R^{13}$ is a methyl group, an ethyl group, or a propyl group;
a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a halogen atom, a C1-C6 alkyl group, a C1-C6 alkoxy group, a C1-C6 haloalkyl group, or a C1-C6 haloalkoxy group, $R^6$ is a C1-C3 methylthio group, and $R^{13}$ is a hydrogen atom or a C1-C4 alkyl group; a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a halogen atom, a C1-C6 alkyl group, a C1-C6 alkoxy group, a C1-C6 haloalkyl group, or a C1-C6 haloalkoxy group, $R^6$ is a C1-C3 methylthio group, and $R^{13}$ is a methyl group, an ethyl group, or a propyl group;
a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a halogen atom, a difluoromethyl group, a trifluoromethyl group, a difluoromethoxy group, a trifluoromethoxy group, or a 1,1,2,2-tetrafluoroethoxy group, $R^6$ is a C1-C3 methylthio group, and $R^{13}$ is a hydrogen atom or a C1-C4 alkyl group;
a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a halogen atom, a difluoromethyl group, a trifluoromethyl group, a difluoromethoxy group, a trifluoromethoxy group, or a 1,1,2,2-tetrafluoroethoxy group, $R^6$ is a C1-C3 methylthio group, and $R^{13}$ is a methyl group, an ethyl group, or a propyl group;
a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a chlorine atom, a trifluoromethyl group, a difluoromethoxy group, or a trifluoromethoxy group, $R^6$ is a C1-C3 methylthio group, and $R^{13}$ is a hydrogen atom or a C1-C4 alkyl group;
a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a chlorine atom, a trifluoromethyl group, a difluoromethoxy group, or a trifluoromethoxy group, $R^6$ is a C1-C3 methylthio group, and $R^{13}$ is a methyl group, an ethyl group, or a propyl group;
a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a halogen atom, a C1-C6 alkyl group, a C1-C6 alkoxy group, a C1-C6 haloalkyl group, or a C1-C6 haloalkoxy group, $R^6$ is a C3-C4 cycloalkyl group, and $R^{13}$ is a hydrogen atom or a C1-C4 alkyl group; a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a halogen atom, a C1-C6 alkyl group, a C1-C6 alkoxy group, a C1-C6 haloalkyl group, or a C1-C6 haloalkoxy group, $R^6$ is a C3-C4 cycloalkyl group, and $R^{13}$ is a methyl group, an ethyl group, or a propyl group;
a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a halogen atom, a difluoromethyl group, a trifluoromethyl group, a difluoromethoxy group, a trifluoromethoxy group, or a 1,1,2,2-tetrafluoroethoxy group, $R^6$ is a C3-C4 cycloalkyl group, and $R^{13}$ is a hydrogen atom or a C1-C4 alkyl group;
a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a halogen atom, a difluoromethyl group, a trifluoromethyl group, a difluoromethoxy group, a trifluoromethoxy group, or a 1,1,2,2-tetrafluoroethoxy group, $R^6$ is a C3-C4 cycloalkyl group, and $R^{13}$ is a methyl group, an ethyl group, or a propyl group;
a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a chlorine atom, a trifluoromethyl group, a difluoromethoxy group, or a trifluoromethoxy group, $R^6$ is a C3-C4 cycloalkyl group, and $R^{13}$ is a hydrogen atom or a C1-C4 alkyl group;
a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a chlorine atom, a trifluoromethyl group, a difluoromethoxy group, or a trifluoromethoxy group, $R^6$ is a C3-C4 cycloalkyl group, and $R^{13}$ is a methyl group, an ethyl group, or a propyl group; a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a halogen atom, a C1-C6 alkyl group, a C1-C6 alkoxy group, a C1-C6 haloalkyl group, or a C1-C6 haloalkoxy group, $R^6$ is a methyl group, and $R^{13}$ is a hydrogen atom or a C1-C4 alkyl group;

a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a halogen atom, a C1-C6 alkyl group, a C1-C6 alkoxy group, a C1-C6 haloalkyl group, or a C1-C6 haloalkoxy group, $R^6$ is a methyl group, and $R^{13}$ is a methyl group, an ethyl group, or a propyl group; a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a halogen atom, a difluoromethyl group, a trifluoromethyl group, a difluoromethoxy group, a trifluoromethoxy group, or a 1,1,2,2-tetrafluoroethoxy group, $R^6$ is a methyl group, and $R^{13}$ is a hydrogen atom or a C1-C4 alkyl group;

a compound represented by formula (1-P), wherein $R^1$, $R^3$, $R^4$, $R^5$, $R^7$, $R^8$, $R^9$, $R^{11}$, and $R^{12}$ is a hydrogen atom, $R^{10}$ is a methyl group, X is an oxygen atom, $R^2$ is a halogen atom, a difluoromethyl group, a trifluoromethyl group, a difluoromethoxy group, a trifluoromethoxy group, or a 1,1,2,2-tetrafluoroethoxy group, $R^6$ is a methyl group, and $R^{13}$ is a methyl group, an ethyl group, or a propyl group;

a compound represented by formula (1-P), wherein $R^1$, $R^3$, $R^4$, $R^5$, $R^7$, $R^8$, $R^9$, $R^{11}$ and $R^{12}$ are hydrogen atoms, $R^{10}$ is a methyl group, X is an oxygen atom, $R^2$ is a chlorine atom, a trifluoromethyl group, a difluoromethoxy group, or a trifluoromethoxy group, $R^6$ is a methyl group, and $R^{13}$ is a hydrogen atom, or a C1-C4 alkyl group;

a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a chlorine atom, a trifluoromethyl group, a difluoromethoxy group, or a trifluoromethoxy group, $R^6$ is a methyl group, and $R^{13}$ is a methyl group, an ethyl group, or a propyl group;

a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a halogen atom, a C1-C6 alkyl group, a C1-C6 alkoxy group, a C1-C6 haloalkyl group, or a C1-C6 haloalkoxy group, $R^6$ is an ethyl group, and $R^{13}$ is a hydrogen atom or a C1-C4 alkyl group;

a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a halogen atom, a C1-C6 alkyl group, a C1-C6 alkoxy group, a C1-C6 haloalkyl group, or a C1-C6 haloalkoxy group, $R^6$ is an ethyl group, and $R^{13}$ is a methyl group, an ethyl group, or a propyl group; a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a halogen atom, a difluoromethyl group, a trifluoromethyl group, a difluoromethoxy group, a trifluoromethoxy group, or a 1,1,2,2-tetrafluoroethoxy group, $R^6$ is an ethyl group, and $R^{13}$ is a hydrogen atom or a C1-C4 alkyl group;

a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a halogen atom, a difluoromethyl group, a trifluoromethyl group, a difluoromethoxy group, a trifluoromethoxy group, or a 1,1,2,2-tetrafluoroethoxy group, $R^6$ is an ethyl group, and $R^{13}$ is a methyl group, an ethyl group, or a propyl group;

a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a chlorine atom, a trifluoromethyl group, a difluoromethoxy group, or a trifluoromethoxy group, $R^6$ is an ethyl group, and $R^{13}$ is a hydrogen atom, a C1-C4 alkyl group;

a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a chlorine atom, a trifluoromethyl group, a difluoromethoxy group, or a trifluoromethoxy group, $R^6$ is an ethyl group, and $R^{13}$ is a methyl group, an ethyl group, or a propyl group;

a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a halogen atom, a C1-C6 alkyl group, a C1-C6 alkoxy group, a C1-C6 haloalkyl group, or a C1-C6 haloalkoxy group, $R^6$ is a cyclopropyl group, and $R^{13}$ is a hydrogen atom or a C1-C4 alkyl group;

a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a halogen atom, a C1-C6 alkyl group, a C1-C6 alkoxy group, a C1-C6 haloalkyl group, or a C1-C6 haloalkoxy group, $R^6$ is a cyclopropyl group, and $R^{13}$ is a methyl group, an ethyl group, or a propyl group; a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a halogen atom, a difluoromethyl group, a trifluoromethyl group, a difluoromethoxy group, a trifluoromethoxy group, or a 1,1,2,2-tetrafluoroethoxy group, $R^6$ is a cyclopropyl group, and $R^{13}$ is a hydrogen atom or a C1-C4 alkyl group;

a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a halogen atom, a difluoromethyl group, a trifluoromethyl group, a difluoromethoxy group, a trifluoromethoxy group, or a 1,1,2,2-tetrafluoroethoxy group, $R^6$ is a cyclopropyl group, and $R^{13}$ is a methyl group, an ethyl group, or a propyl group;

a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a chlorine atom, a trifluoromethyl group, a difluoromethoxy group, or a trifluoromethoxy group, $R^6$ is a cyclopropyl group, and $R^{13}$ is a hydrogen atom or a C1-C4 alkyl group;

a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a chlorine atom, a trifluoromethyl group, a difluoromethoxy group, or a trifluoromethoxy group, $R^6$ is a cyclopropyl group, and $R^{13}$ is a methyl group, an ethyl group, or a propyl group;

a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a halogen atom, a C1-C6 alkyl group, a C1-C6 alkoxy group, a C1-C6 haloalkyl group, or a C1-C6 haloalkoxy group, $R^6$ is a trifluoromethyl group, and $R^{13}$ is a hydrogen atom or a C1-C4 alkyl group; a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a halogen atom, a C1-C6 alkyl group, a C1-C6 alkoxy group, a C1-C6 haloalkyl group, or a C1-C6 haloalkoxy group, $R^6$ is a trifluoromethyl group, and $R^{13}$ is a methyl group, an ethyl group, or a propyl group;

a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ is a halogen atom, a difluoromethyl group, a trifluoromethyl group, a difluoromethoxy group, a trifluoromethoxy group, or a 1,1,2,2- tetrafluoroethoxy group, $R^6$ is a trifluoromethyl group, and $R^{13}$ is a hydrogen atom or a C1-C4 alkyl group;

a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, $X$ is an oxygen atom, $R^2$ is a halogen atom, a difluoromethyl group, a trifluoromethyl group, a difluoromethoxy group, a trifluoromethoxy group, or a 1,1,2,2-tetrafluoroethoxy group, $R^6$ is a trifluoromethyl group, and $R^{13}$ is a methyl group, an ethyl group, or a propyl group;

a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, $X$ is an oxygen atom, $R^2$ is a chlorine atom, a trifluoromethyl group, a difluoromethoxy group, or a trifluoromethoxy group, $R^6$ is a trifluoromethyl group, and $R^{13}$ is a hydrogen atom or a C1-C4 alkyl group;

a compound represented by formula (1-P), wherein $R^1$, $R^3$, $R^4$, $R^5$, $R^7$, $R^8$, $R^9$, $R^{11}$, and $R^{12}$ are hydrogen atoms, $R^{10}$ is a methyl group, $X$ is an oxygen atom, $R^2$ is a chlorine atom, a trifluoromethyl group, a difluoromethoxy group, or a trifluoromethoxy group, $R^6$ is a trifluoromethyl group, and $R^{13}$ is a methyl group, an ethyl group, or a propyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, $X$ is an oxygen atom, $R^2$ and $R^3$ each represents a halogen atom, a C1-C6 alkyl group, a C1-C6 alkoxy group, a C1-C6 haloalkyl group, or a C1-C6 haloalkoxy group, or $R^2$ and $R^3$ form a five-membered ring or a six-membered ring together with the carbon atom to which they are attached, $R^6$ is a halogen atom, $R^{13}$ is a hydrogen atom or a C1-C4 alkyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, $X$ is an oxygen atom, $R^2$ and $R^3$ each represents a halogen atom, a C1-C6 alkyl group, a C1-C6 alkoxy group, a C1-C6 haloalkyl group, or a C1-C6 haloalkoxy group, or $R^2$ and $R^3$ form a five-membered ring or a six-membered ring together with the carbon atom to which they are attached, $R^6$ is a halogen atom, $R^{13}$ is a methyl group, an ethyl group, or a propyl group; a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, $X$ is an oxygen atom, $R^2$ and $R^3$ each represents a halogen atom, a difluoromethyl group, a trifluoromethyl group, a difluoromethoxy group, a trifluoromethoxy group, or a 1,1,2,2-tetrafluoroethoxy group, or $R^2$ and $R^3$ form a five-membered ring or a six-membered ring together with the carbon atom to which they are attached, $R^6$ is a halogen atom, $R^{13}$ is a hydrogen atom or a C1-C4 alkyl group;

a compound represented by formula (1-P), wherein $R^1$, $R^4$, $R^5$, $R^7$, $R^8$, $R^9$, $R^{11}$, and $R^{12}$ is a hydrogen atom, $R^{10}$ is a methyl group, $X$ is an oxygen atom, $R^2$ and $R^3$ each represents a halogen atom, a difluoromethyl group, a trifluoromethyl group, a difluoromethoxy group, a trifluoromethoxy group, or a 1,1,2,2-tetrafluoroethoxy group, or $R^2$ and $R^3$ form a five-membered ring or a six-membered ring together with the carbon atom to which they are attached, $R^6$ is a halogen atom, $R^{13}$ is a methyl group, an ethyl group, or a propyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, $X$ is an oxygen atom, $R^2$ and $R^3$ each represents a chlorine atom, a trifluoromethyl group, a difluoromethoxy group, or a trifluoromethoxy group, or $R^2$ and $R^3$ form a five-membered ring or a six-membered ring together with the carbon atom to which they are attached, $R^6$ is a halogen atom, $R^{13}$ is a hydrogen atom or a C1-C4 alkyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, $X$ is an oxygen atom, $R^2$ and $R^3$ each represents a chlorine atom, a trifluoromethyl group, a difluoromethoxy group, or a trifluoromethoxy group, or $R^2$ and $R^3$ form a five-membered ring or a six-membered ring together with the carbon atom to which they are attached, $R^6$ is a halogen atom, $R^{13}$ is a methyl group, an ethyl group, or a propyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, $X$ is an oxygen atom, $R^2$ and $R^3$ each represents a chlorine atom, a trifluoromethyl group, a difluoromethoxy group, or a trifluoromethoxy group, or $R^2$ and $R^3$ form a five-membered ring or a six-membered ring together with the carbon atom to which they are attached, $R^6$ is a halogen atom, $R^{13}$ is a hydrogen atom or a C1-C4 alkyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, $X$ is an oxygen atom, $R^2$ and $R^3$ each represents a chlorine atom, a trifluoromethyl group, a difluoromethoxy group, or a trifluoromethoxy group, or $R^2$ and $R^3$ form a five-membered ring or a six-membered ring together with the carbon atom to which they are attached, $R^6$ is a halogen atom, $R^{13}$ is a methyl group, an ethyl group, or a propyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, $X$ is an oxygen atom, $R^2$ and $R^3$ each represents a halogen atom, a C1-C6 alkyl group, a C1-C6 alkoxy group, a C1-C6 haloalkyl group, or a C1-C6 haloalkoxy group, or $R^2$ and $R^3$ form a five-membered ring or a six-membered ring together with the carbon atom to which they are attached, $R^6$ is a C1-C3 alkyl group, and $R^{13}$ is a hydrogen atom or a C1-C4 alkyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, $X$ is an oxygen atom, $R^2$ and $R^3$ each represents a halogen atom, a C1-C6 alkyl group, a C1-C6 alkoxy group, a C1-C6 haloalkyl group, or a C1-C6 haloalkoxy group, or $R^2$ and $R^3$ form a five-membered ring or a six-membered ring together with the carbon atom to which they are attached, $R^6$ is a C1-C3 alkyl group, and $R^{13}$ is a methyl group, an ethyl group, or a propyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, $X$ is an oxygen atom, $R^2$ and $R^3$ each represents a halogen atom, a difluoromethyl group, a trifluoromethyl group, a difluoromethoxy group, a trifluoromethoxy group, or a 1,1,2,2-tetrafluoroethoxy group, or $R^2$ and $R^3$ form a five-membered ring or a six-membered ring together with the carbon atom to which they are attached, $R^6$ is a C1-C3 alkyl group, and $R^{13}$ is a hydrogen atom or a C1-C4 alkyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, $X$ is an oxygen atom, $R^2$ and $R^3$ each represents a halogen atom, a difluoromethyl group, a trifluoromethyl group, a difluoromethoxy group, a trifluoromethoxy group, or a 1,1,2,2-tetrafluoroethoxy group, or $R^2$ and $R^3$ form a five-membered ring or a six-membered ring together with the carbon atom to which they are attached, $R^6$ is a C1-C3 alkyl group, and $R^{13}$ is a methyl group, an ethyl group, or a propyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, $X$ is an oxygen atom, $R^2$ and $R^3$ each represents a chlorine atom, a trifluoromethyl group, a difluoromethoxy group, or a trifluoromethoxy group, or $R^2$ and $R^3$ form a five-membered ring or a six-membered ring together with the carbon atom to which they are attached, $R^6$ is a C1-C3 alkyl group, and $R^{13}$ is a hydrogen atom or a C1-C4 alkyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a chlorine atom, a trifluoromethyl group, a difluoromethoxy group, or a trifluoromethoxy group, or $R^2$ and $R^3$ form a five-membered ring or a six-membered ring together with the carbon atom to which they are attached, $R^6$ is a C1-C3 alkyl group, and $R^{13}$ is a methyl group, an ethyl group, or a propyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a chlorine atom, a trifluoromethyl group, a difluoromethoxy group, or a trifluoromethoxy group, $R^6$ is a C1-C3 alkyl group, and $R^{13}$ is a hydrogen atom or a C1-C4 alkyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a chlorine atom, a trifluoromethyl group, a difluoromethoxy group, or a trifluoromethoxy group, $R^6$ is a C1-C3 alkyl group, and $R^{13}$ is a methyl group, an ethyl group, or a propyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a halogen atom, a C1-C6 alkyl group, a C1-C6 alkoxy group, a C1-C6 haloalkyl group, or a C1-C6 haloalkoxy group, or $R^2$ and $R^3$ form a five-membered ring or a six-membered ring together with the carbon atom to which they are attached, $R^6$ is a C1-C3 haloalkyl group, and $R^{13}$ is a hydrogen atom or a C1-C4 alkyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a halogen atom, a C1-C6 alkyl group, a C1-C6 alkoxy group, a C1-C6 haloalkyl group, or a C1-C6 haloalkoxy group, or $R^2$ and $R^3$ form a five-membered ring or a six-membered ring together with the carbon atom to which they are attached, $R^6$ is a C1-C3 haloalkyl group, and $R^{13}$ is a methyl group, an ethyl group, or a propyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a halogen atom, a difluoromethyl group, a trifluoromethyl group, a difluoromethoxy group, a trifluoromethoxy group, or a 1,1,2,2-tetrafluoroethoxy group, or $R^2$ and $R^3$ form a five-membered ring or a six-membered ring together with the carbon atom to which they are attached, $R^6$ is a C1-C3 haloalkyl group, and $R^{13}$ is a hydrogen atom or a C1-C4 alkyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a halogen atom, a difluoromethyl group, a trifluoromethyl group, a difluoromethoxy group, a trifluoromethoxy group, or a 1,1,2,2-tetrafluoroethoxy group, or $R^2$ and $R^3$ form a five-membered ring or a six-membered ring together with the carbon atom to which they are attached, $R^6$ is a C1-C3 haloalkyl group, and $R^{13}$ is a methyl group, an ethyl group, or a propyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a chlorine atom, a trifluoromethyl group, a difluoromethoxy group, or a trifluoromethoxy group, or $R^2$ and $R^3$ form a five-membered ring or a six-membered ring together with the carbon atom to which they are attached, $R^6$ is a C1-C3 haloalkyl group, and $R^{13}$ is a hydrogen atom or a C1-C4 alkyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a chlorine atom, a trifluoromethyl group, a difluoromethoxy group, or a trifluoromethoxy group, or $R^2$ and $R^3$ form a five-membered ring or a six-membered ring together with the carbon atom to which they are attached, $R^6$ is a C1-C3 haloalkyl group, and $R^{13}$ is a methyl group, an ethyl group, or a propyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a chlorine atom, a trifluoromethyl group, a difluoromethoxy group, or a trifluoromethoxy group, $R^6$ is a C1-C3 haloalkyl group, and $R^{13}$ is a hydrogen atom or a C1-C4 alkyl group; a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a chlorine atom, a trifluoromethyl group, a difluoromethoxy group, or a trifluoromethoxy group, $R^6$ is a C1-C3 haloalkyl group, and $R^{13}$ is a methyl group, an ethyl group, or a propyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a halogen atom, a C1-C6 alkyl group, a C1-C6 alkoxy group, a C1-C6 haloalkyl group, or a C1-C6 haloalkoxy group, or $R^2$ and $R^3$ form a five-membered ring or a six-membered ring together with the carbon atom to which they are attached, $R^6$ is a C1-C3 haloalkyl group, and $R^{13}$ is a hydrogen atom or a C1-C4 alkyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a halogen atom, a C1-C6 alkyl group, a C1-C6 alkoxy group, a C1-C6 haloalkyl group, or a C1-C6 haloalkoxy group, or $R^2$ and $R^3$ form a five-membered ring or a six-membered ring together with the carbon atom to which they are attached, $R^6$ is a C1-C3 haloalkyl group, and $R^{13}$ is a methyl group, an ethyl group, or a propyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a halogen atom, a difluoromethyl group, a trifluoromethyl group, a difluoromethoxy group, a trifluoromethoxy group, or a 1,1,2,2-tetrafluoroethoxy group, or $R^2$ and $R^3$ form a five-membered ring or a six-membered ring together with the carbon atom to which they are attached, $R^6$ is a C1-C3 haloalkyl group, and $R^{13}$ is a hydrogen atom or a C1-C4 alkyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a halogen atom, a difluoromethyl group, a trifluoromethyl group, a difluoromethoxy group, a trifluoromethoxy group, or a 1,1,2,2-tetrafluoroethoxy group, or $R^2$ and $R^3$ form a five-membered ring or a six-membered ring together with the carbon atom to which they are attached, $R^6$ is a C1-C3 haloalkyl group, and $R^{13}$ is a methyl group, an ethyl group, or a propyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a chlorine atom, a trifluoromethyl group, a difluoromethoxy group, or a trifluoromethoxy group, or $R^2$ and $R^3$ form a five-membered ring or a six-membered ring together with the carbon atom to which they are attached, $R^6$ is a C1-C3 haloalkyl group, and $R^{13}$ is a hydrogen atom or a C1-C4 alkyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a chlorine atom, a trifluoromethyl group, a difluoromethoxy group, or a trifluoromethoxy group, or $R^2$ and $R^3$ form a five-membered ring or a six-membered ring together with the carbon atom to which they are attached, $R^6$ is a C1-C3 haloalkyl group, and $R^{13}$ is a methyl group, an ethyl group, or a propyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a chlorine atom, a trifluoromethyl group, a difluoromethoxy group, or a trifluoromethoxy group, $R^6$ is a C1-C3 haloalkyl group, and $R^{13}$ is a hydrogen atom or a C1-C4 alkyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a chlorine atom, a trifluoromethyl group, a difluoromethoxy group, or a trifluoromethoxy group, $R^6$ is a C1-C3 haloalkyl group, and $R^{13}$ is a methyl group, an ethyl group, or a propyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a halogen atom, a C1-C6 alkyl group, a C1-C6 alkoxy group, a C1-C6 haloalkyl group, or a C1-C6 haloalkoxy group, or $R^2$ and $R^3$ form a five-membered ring or a six-membered ring together with the carbon atom to which they are attached, $R^6$ is a methoxy group, and $R^{13}$ is a hydrogen atom or a C1-C4 alkyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a halogen atom, a C1-C6 alkyl group, a C1-C6 alkoxy group, a C1-C6 haloalkyl group, or a C1-C6 haloalkoxy group, or $R^2$ and $R^3$ form a five-membered ring or a six-membered ring together with the carbon atom to which they are attached, $R^6$ is a methoxy group, and $R^{13}$ is a methyl group, an ethyl group, or a propyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a halogen atom, a difluoromethyl group, a trifluoromethyl group, a difluoromethoxy group, a trifluoromethoxy group, or a 1,1,2,2-tetrafluoroethoxy group, or $R^2$ and $R^3$ form a five-membered ring or a six-membered ring together with the carbon atom to which they are attached, $R^6$ is a methoxy group, and $R^{13}$ is a hydrogen atom or a C1-C4 alkyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a halogen atom, a difluoromethyl group, a trifluoromethyl group, a difluoromethoxy group, a trifluoromethoxy group, or a 1,1,2,2-tetrafluoroethoxy group, or $R^2$ and $R^3$ form a five-membered ring or a six-membered ring together with the carbon atom to which they are attached, $R^6$ is a methoxy group, and $R^{13}$ is a methyl group, an ethyl group, or a propyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a chlorine atom, a trifluoromethyl group, a difluoromethoxy group, or a trifluoromethoxy group, or $R^2$ and $R^3$ form a five-membered ring or a six-membered ring together with the carbon atom to which they are attached, $R^6$ is a methoxy group, and $R^{13}$ is a hydrogen atom or a C1-C4 alkyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a chlorine atom, a trifluoromethyl group, a difluoromethoxy group, or a trifluoromethoxy group, or $R^2$ and $R^3$ form a five-membered ring or a six-membered ring together with the carbon atom to which they are attached, $R^6$ is a methoxy group, and $R^{13}$ is a methyl group, an ethyl group, or a propyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a chlorine atom, a trifluoromethyl group, a difluoromethoxy group, or a trifluoromethoxy group, $R^6$ is a methoxy group, and $R^{13}$ is a hydrogen atom or a C1-C4 alkyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a chlorine atom, a trifluoromethyl group, a difluoromethoxy group, or a trifluoromethoxy group, $R^6$ is a methoxy group, and $R^{13}$ is a methyl group, an ethyl group, or a propyl group;

a compound represented by formula (1-P), wherein $R^1$, $R^4$, $R^5$, $R^7$, $R^8$, $R^9$, $R^{11}$ and $R^{12}$ are hydrogen atoms, $R^{10}$ is a methyl group, X is an oxygen atom, $R^2$ and $R^3$ each represents a halogen atom, a C1-C6 alkyl group, a C1-C6 alkoxy group, a C1-C6 haloalkyl group, or a C1-C6 haloalkoxy group, or $R^2$ and $R^3$ form a five-membered ring or a six-membered ring together with the carbon atom to which they are attached, $R^6$ is a methylthio group, and $R^{13}$ is a hydrogen atom or a C1-C4 alkyl group; a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a halogen atom, a C1-C6 alkyl group, a C1-C6 alkoxy group, a C1-C6 haloalkyl group, or a C1-C6 haloalkoxy group, or $R^2$ and $R^3$ form a five-membered ring or a six-membered ring together with the carbon atom to which they are attached, $R^6$ is a methylthio group, and $R^{13}$ is a methyl group, an ethyl group, or a propyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a halogen atom, a difluoromethyl group, a trifluoromethyl group, a difluoromethoxy group, a trifluoromethoxy group, or a 1,1,2,2-tetrafluoroethoxy group, or $R^2$ and $R^3$ form a five-membered ring or a six-membered ring together with the carbon atom to which they are attached, $R^6$ is a methylthio group, and $R^{13}$ is a hydrogen atom or a C1-C4 alkyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a halogen atom, a difluoromethyl group, a trifluoromethyl group, a difluoromethoxy group, a trifluoromethoxy group, or a 1,1,2,2-tetrafluoroethoxy group, or $R^2$ and $R^3$ form a five-membered ring or a six-membered ring together with the carbon atom to which they are attached, $R^6$ is a methylthio group, and $R^{13}$ is a methyl group, an ethyl group, or a propyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a chlorine atom, a trifluoromethyl group, a difluoromethoxy group, or a trifluoromethoxy group, or $R^2$ and $R^3$ form a five-membered ring or a six-membered ring together with the carbon atom to which they are attached, $R^6$ is a methylthio group, and $R^{13}$ is a hydrogen atom or a C1-C4 alkyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a chlorine atom, a trifluoromethyl group, a difluoromethoxy group, or a trifluoromethoxy group, or $R^2$ and $R^3$ form a five-membered ring or a six-membered ring together with the carbon atom to which they are attached, $R^6$ is a methylthio group, and $R^{13}$ is a methyl group, an ethyl group, or a propyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a chlorine atom, a trifluoromethyl group, a difluoromethoxy group, or a trifluoromethoxy group, $R^6$ is a methylthio group, and $R^{13}$ is a hydrogen atom or a C1-C4 alkyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a chlorine atom, a trifluoromethyl group, a difluoromethoxy group, or a trifluoromethoxy group, $R^6$ is a methylthio group, and $R^{13}$ is a methyl group, an ethyl group, or a propyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a halogen atom, a C1-C6 alkyl group, a C1-C6 alkoxy group, a C1-C6 haloalkyl group, or a C1-C6 haloalkoxy group, or $R^2$ and $R^3$ form a five-membered ring or a six-membered ring together with the carbon atom to which they are attached, $R^6$ is a C3-C4 cycloalkyl group, and $R^{13}$ is a hydrogen atom or a C1-C4 alkyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a halogen atom, a C1-C6 alkyl group, a C1-C6 alkoxy group, a C1-C6 haloalkyl group, or a C1-C6 haloalkoxy group, or $R^2$ and $R^3$ form a five-membered ring or a six-membered ring together with the carbon atom to which they are attached, $R^6$ is a C3-C4 cycloalkyl group, and $R^{13}$ is a methyl group, an ethyl group, or a propyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a halogen atom, a difluoromethyl group, a trifluoromethyl group, a difluoromethoxy group, a trifluoromethoxy group, or a 1,1,2,2-tetrafluoroethoxy group, or $R^2$ and $R^3$ form a five-membered ring or a six-membered ring together with the carbon atom to which they are attached, $R^6$ is a C3-C4 cycloalkyl group, and $R^{13}$ is a hydrogen atom or a C1-C4 alkyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a halogen atom, a difluoromethyl group, a trifluoromethyl group, a difluoromethoxy group, a trifluoromethoxy group, or a 1,1,2,2-tetrafluoroethoxy group, or $R^2$ and $R^3$ form a five-membered ring or a six-membered ring together with the carbon atom to which they are attached, $R^6$ is a C3-C4 cycloalkyl group, and $R^{13}$ is a methyl group, an ethyl group, or a propyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a chlorine atom, a trifluoromethyl group, a difluoromethoxy group, or a trifluoromethoxy group, or $R^2$ and $R^3$ form a five-membered ring or a six-membered ring together with the carbon atom to which they are attached, $R^6$ is a C3-C4 cycloalkyl group, and $R^{13}$ is a hydrogen atom or a C1-C4 alkyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a chlorine atom, a trifluoromethyl group, a difluoromethoxy group, or a trifluoromethoxy group, or $R^2$ and $R^3$ form a five-membered ring or a six-membered ring together with the carbon atom to which they are attached, $R^6$ is a C3-C4 cycloalkyl group, and $R^{13}$ is a methyl group, an ethyl group, or a propyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a chlorine atom, a trifluoromethyl group, a difluoromethoxy group, or a trifluoromethoxy group, $R^6$ is a C3-C4 cycloalkyl group, and $R^{13}$ is a hydrogen atom or a C1-C4 alkyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a chlorine atom, a trifluoromethyl group, a difluoromethoxy group, or a trifluoromethoxy group, $R^6$ is a C3-C4 cycloalkyl group, and $R^{13}$ is a methyl group, an ethyl group, or a propyl group;

a compound represented by formula (1-P), wherein $R^1$, $R^4$, $R^5$, $R^7$, $R^8$, $R^9$, $R^{11}$ and $R^{12}$ are hydrogen atoms, $R^{10}$ is a methyl group, X is an oxygen atom, $R^2$ and $R^3$ each represents a halogen atom, a C1-C6 alkyl group, a C1-C6 alkoxy group, a C1-C6 haloalkyl group, or a C1-C6 haloalkoxy group, or $R^2$ and $R^3$ form a five-membered ring or a six-membered ring together with the carbon atom to which they are attached, $R^6$ is a methyl group, and $R^{13}$ is a hydrogen atom or a C1-C4 alkyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a halogen atom, a C1-C6 alkyl group, a C1-C6 alkoxy group, a C1-C6 haloalkyl group, or a C1-C6 haloalkoxy group, or $R^2$ and $R^3$ form a five-membered ring or a six-membered ring together with the carbon atom to which they are attached, $R^6$ is a methyl group, and $R^{13}$ is a methyl group, an ethyl group, or a propyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a halogen atom, a difluoromethyl group, a trifluoromethyl group, a difluoromethoxy group, a trifluoromethoxy group, or a 1,1,2,2-tetrafluoroethoxy group, or $R^2$ and $R^3$ form a five-membered ring or a six-membered ring together with the carbon atom to which they are attached, $R^6$ is a methyl group, and $R^{13}$ is a hydrogen atom or a C1-C4 alkyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a halogen atom, a difluoromethyl group, a trifluoromethyl group, a difluoromethoxy group, a trifluoromethoxy group, or a 1,1,2,2-tetrafluoroethoxy group, or $R^2$ and $R^3$ form a five-membered ring or a six-membered ring together with the carbon atom to which they are attached, $R^6$ is a methyl group, and $R^{13}$ is a methyl group, an ethyl group, or a propyl group;

a compound represented by formula (1-P), wherein $R^1$, $R^4$, $R^5$, $R^7$, $R^8$, $R^9$, $R^{11}$ and $R^{12}$ are hydrogen atoms, $R^{10}$ is a methyl group, X is an oxygen atom, $R^2$ and $R^3$ each represents a chlorine atom, a trifluoromethyl group, a difluoromethoxy group, or a trifluoromethoxy group, or $R^2$ and $R^3$ form a five-membered ring or a six-membered ring together with the carbon atom to which they are attached, $R^6$ is a methyl group, and $R^{13}$ is a hydrogen atom or a C1-C4 alkyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a chlorine atom, a trifluoromethyl group, a difluoromethoxy group, or a trifluoromethoxy group, or $R^2$ and $R^3$ form a five-membered ring or a six-membered ring together with the carbon atom to which they are attached, $R^6$ is a methyl group, and $R^{13}$ is a methyl group, an ethyl group, or a propyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a chlorine atom, a trifluoromethyl group, a difluoromethoxy group, or a trifluoromethoxy group, $R^6$ is a methyl group, and $R^{13}$ is a hydrogen atom or a C1-C4 alkyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a chlorine atom, a trifluoromethyl group, a difluoromethoxy group, or a trifluoromethoxy group, $R^6$ is a methyl group, and $R^{13}$ is a methyl group, an ethyl group, or a propyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a halogen atom, a C1-C6 alkyl group, a C1-C6 alkoxy group, a C1-C6 haloalkyl group, or a C1-C6 haloalkoxy group, or $R^2$ and $R^3$ form a five-membered ring or a six-membered ring together with the carbon atom to which they are attached, $R^6$ is an ethyl group, and $R^{13}$ is a hydrogen atom or a C1-C4 alkyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a halogen atom, a C1-C6 alkyl group, a C1-C6 alkoxy group, a C1-C6 haloalkyl group, or a C1-C6 haloalkoxy group, or $R^2$ and $R^3$ form a five-membered ring or a six-membered ring together with the carbon atom to which they are attached, $R^6$ is an ethyl group, and $R^{13}$ is a methyl group, an ethyl group, or a propyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a halogen atom, a difluoromethyl group, a trifluoromethyl group, a difluoromethoxy group, a trifluoromethoxy group, or a 1,1,2,2-tetrafluoroethoxy group, or $R^2$ and $R^3$ form a five-membered ring or a six-membered ring together with the carbon atom to which they are attached, $R^6$ is an ethyl group, and $R^{13}$ is a hydrogen atom or a C1-C4 alkyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a halogen atom, a difluoromethyl group, a trifluoromethyl group, a difluoromethoxy group, a trifluoromethoxy group, or a 1,1,2,2-tetrafluoroethoxy group, or $R^2$ and $R^3$ form a five-membered ring or a six-membered ring together with the carbon atom to which they are attached, $R^6$ is an ethyl group, and $R^{13}$ is a methyl group, an ethyl group, or a propyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a chlorine atom, a trifluoromethyl group, a difluoromethoxy group, or a trifluoromethoxy group, or $R^2$ and $R^3$ form a five-membered ring or a six-membered ring together with the carbon atom to which they are attached, $R^6$ is an ethyl group, and $R^{13}$ is a hydrogen atom or a C1-C4 alkyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a chlorine atom, a trifluoromethyl group, a difluoromethoxy group, or a trifluoromethoxy group, or $R^2$ and $R^3$ form a five-membered ring or a six-membered ring together with the carbon atom to which they are attached, $R^6$ is an ethyl group, and $R^{13}$ is a methyl group, an ethyl group, or a propyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a chlorine atom, a trifluoromethyl group, a difluoromethoxy group, or a trifluoromethoxy group, $R^6$ is an ethyl group, and $R^{13}$ is a hydrogen atom or a C1-C4 alkyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a chlorine atom, a trifluoromethyl group, a difluoromethoxy group, or a trifluoromethoxy group, $R^6$ is an ethyl group, and $R^{13}$ is a methyl group, an ethyl group, or a propyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a halogen atom, a C1-C6 alkyl group, a C1-C6 alkoxy group, a C1-C6 haloalkyl group, or a C1-C6 haloalkoxy group, or $R^2$ and $R^3$ form a five-membered ring or a six-membered ring together with the carbon atom to which they are attached, $R^6$ is a cyclopropyl group, and $R^{13}$ is a hydrogen atom or a C1-C4 alkyl group; a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a halogen atom, a C1-C6 alkyl group, a C1-C6 alkoxy group, a C1-C6 haloalkyl group, or a C1-C6 haloalkoxy group, or $R^2$ and $R^3$ form a five-membered ring or a six-membered ring together with the carbon atom to which they are attached, $R^6$ is a cyclopropyl group, and $R^{13}$ is a methyl group, an ethyl group, or a propyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a halogen atom, a difluoromethyl group, a trifluoromethyl group, a difluoromethoxy group, a trifluoromethoxy group, or a 1,1,2,2-tetrafluoroethoxy group, or $R^2$ and $R^3$ form a five-membered ring or a six-membered ring together with the carbon atom to which they are attached, $R^6$ is a cyclopropyl group, and $R^{13}$ is a hydrogen atom or a C1-C4 alkyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a halogen atom, a difluoromethyl group, a trifluoromethyl group, a difluoromethoxy group, a trifluoromethoxy group, or a 1,1,2,2-tetrafluoroethoxy group, or $R^2$ and $R^3$ form a five-membered ring or a six-membered ring together with the carbon atom to which they are attached, $R^6$ is a cyclopropyl group, and $R^{13}$ is a methyl group, an ethyl group, or a propyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a chlorine atom, a trifluoromethyl group, a difluoromethoxy group, or a trifluoromethoxy group, or $R^2$ and $R^3$ form a five-membered ring or a six-membered ring together with the carbon atom to which they are attached, $R^6$ is a cyclopropyl group, and $R^{13}$ is a hydrogen atom or a C1-C4 alkyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a chlorine atom, a trifluoromethyl group, a difluoromethoxy group, or a trifluoromethoxy group, or $R^2$ and $R^3$ form a five-membered ring or a six-membered ring together with the carbon atom to which they are attached, $R^6$ is a cyclopropyl group, and $R^{13}$ is a methyl group, an ethyl group, or a propyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a chlorine atom, a trifluoromethyl group, a difluoromethoxy group, or a trifluoromethoxy group, $R^6$ is a cyclopropyl group, and $R^{13}$ is a hydrogen atom or a C1-C4 alkyl group; a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a chlorine atom, a trifluoromethyl group, a difluoromethoxy group, or a trifluoromethoxy group, $R^6$ is a cyclopropyl group, and $R^{13}$ is a methyl group, an ethyl group, or a propyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a halogen atom, a C1-C6 alkyl group, a C1-C6 alkoxy group, a C1-C6 haloalkyl group, or a C1-C6 haloalkoxy group, or $R^2$ and $R^3$ form a five-membered ring or a six-membered ring together with the carbon atom to which they are attached, $R^6$ is a trifluoromethyl group, and $R^{13}$ is a hydrogen atom or a C1-C4 alkyl group; a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a halogen atom, a C1-C6 alkyl group, a C1-C6 alkoxy group, a C1-C6 haloalkyl group, or a C1-C6 haloalkoxy group, or $R^2$ and $R^3$ form a five-membered ring or a six-membered ring together with the carbon atom to which they are attached, $R^6$ is a trifluoromethyl group, and $R^{13}$ is a methyl group, an ethyl group, or a propyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a halogen atom, a difluoromethyl group, a trifluoromethyl group, a difluoromethoxy group, a trifluoromethoxy group, or a 1,1,2,2-tetrafluoroethoxy group, or $R^2$ and $R^3$ form a five-membered ring or a six-membered ring together with the carbon atom to which they are attached, $R^6$ is a trifluoromethyl group, and $R^{13}$ is a hydrogen atom or a C1-C4 alkyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a halogen atom, a difluoromethyl group, a trifluoromethyl group, a difluoromethoxy group, a trifluoromethoxy group, or a 1,1,2,2-tetrafluoroethoxy group, or $R^2$ and $R^3$ form a five-membered ring or a six-membered ring together with the carbon atom to which they are attached, $R^6$ is a trifluoromethyl group, and $R^{13}$ is a methyl group, an ethyl group, or a propyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a chlorine atom, a trifluoromethyl group, a difluoromethoxy group, or a trifluoromethoxy group, or $R^2$ and $R^3$ form a five-membered ring or a six-membered ring together with the carbon atom to which they are attached, $R^6$ is a trifluoromethyl group, and $R^{13}$ is a hydrogen atom or a C1-C4 alkyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a chlorine atom, a trifluoromethyl group, a difluoromethoxy group, or a trifluoromethoxy group, or $R^2$ and $R^3$ form a five-membered ring or a six-membered ring together with the carbon atom to which they are attached, $R^6$ is a trifluoromethyl group, and $R^{13}$ is a methyl group, an ethyl group, or a propyl group;

a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a chlorine atom, a trifluoromethyl group, a difluoromethoxy group, or a trifluoromethoxy group, $R^6$ is a trifluoromethyl group, and $R^{13}$ is a hydrogen atom or a C1-C4 alkyl group; a compound represented by formula (1-P), wherein $R^1$, $R^4$, $R^5$, $R^7$, $R^8$, $R^9$, $R^{11}$, and $R^{12}$ are hydrogen atoms, $R^{10}$ is a methyl group, X is an oxygen atom, $R^2$ and $R^3$ each represents a chlorine atom, a trifluoromethyl group, a difluoromethoxy group, or a trifluoromethoxy group, $R^6$ is a trifluoromethyl group, and $R^{13}$ is a methyl group, an ethyl group, or a propyl group;

a compound represented by formula (1-P), wherein $R^1$, $R^3$, $R^4$, $R^5$, $R^7$, $R^8$, $R^9$, and $R^{12}$ is a hydrogen atom, $R^{10}$ is a methyl group, X is an oxygen atom, $R^2$ and $R^{11}$ each represents a halogen atom, a C1-C6 alkyl group, a C1-C6 alkoxy group, a C1-C6 haloalkyl group, or a C1-C6 haloalkoxy group, $R^6$ is a halogen atom, $R^{13}$ is a hydrogen atom or a C1-C4 alkyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a halogen atom, a C1-C6 alkyl group, a C1-C6 alkoxy group, a C1-C6 haloalkyl group, or a C1-C6 haloalkoxy group, $R^6$ is a halogen atom, $R^{13}$ is a methyl group, an ethyl group, or a propyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a halogen atom, a difluoromethyl group, a trifluoromethyl group, a difluoromethoxy group, a trifluoromethoxy group, or a 1,1,2,2-tetrafluoroethoxy group, $R^6$ is a halogen atom, $R^{13}$ is a hydrogen atom or a C1-C4 alkyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a halogen atom, a difluoromethyl group, a trifluoromethyl group, a difluoromethoxy group, a trifluoromethoxy group, or a 1,1,2,2-tetrafluoroethoxy group, $R^6$ is a halogen atom, $R^{13}$ is a methyl group, an ethyl group, or a propyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a chlorine atom, a trifluoromethyl group, a difluoromethoxy group, or a trifluoromethoxy group, $R^6$ is a halogen atom, $R^{13}$ is a hydrogen atom or a C1-C4 alkyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a chlorine atom, a trifluoromethyl group, a difluoromethoxy group, or a trifluoromethoxy group, $R^6$ is a halogen atom, $R^{13}$ is a methyl group, an ethyl group, or a propyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a halogen atom, a C1-C6 alkyl group, a C1-C6 alkoxy group, a C1-C6 haloalkyl group, or a C1-C6 haloalkoxy group, $R^6$ is a C1-C3 alkyl group, and $R^{13}$ is a hydrogen atom or a C1-C4 alkyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a halogen atom, a C1-C6 alkyl group, a C1-C6 alkoxy group, a C1-C6 haloalkyl group, or a C1-C6 haloalkoxy group, $R^6$ is a C1-C3 alkyl group, and $R^{13}$ is a methyl group, an ethyl group, or a propyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a halogen atom, a difluoromethyl group, a trifluoromethyl group, a difluoromethoxy group, a trifluoromethoxy group, or a 1,1,2,2-tetrafluoroethoxy group, $R^6$ is a C1-C3 alkyl group, and $R^{13}$ is a hydrogen atom or a C1-C4 alkyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a halogen atom, a difluoromethyl group, a trifluoromethyl group, a difluoromethoxy group, a trifluoromethoxy group, or a 1,1,2,2-tetrafluoroethoxy group, $R^6$ is a C1-C3 alkyl group, and $R^{13}$ is a methyl group, an ethyl group, or a propyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a chlorine atom, a trifluoromethyl group, a difluoromethoxy group, or a trifluoromethoxy group, $R^6$ is a C1-C3 alkyl group, and $R^{13}$ is a hydrogen atom or a C1-C4 alkyl group; a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a chlorine atom, a trifluoromethyl group, a difluoromethoxy group, or a trifluoromethoxy group, $R^6$ is a C1-C3 alkyl group, and $R^{13}$ is a methyl group, an ethyl group, or a propyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a halogen atom, a C1-C6 alkyl group, a C1-C6 alkoxy group, a C1-C6 haloalkyl group, or a C1-C6 haloalkoxy group, $R^6$ is a C1-C3 haloalkyl group, and $R^{13}$ is a hydrogen atom or a C1-C4 alkyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a halogen atom, a C1-C6 alkyl group, a C1-C6 alkoxy group, a C1-C6 haloalkyl group, or a C1-C6 haloalkoxy group, $R^6$ is a C1-C3 haloalkyl group, and $R^{13}$ is a methyl group, an ethyl group, or a propyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a halogen atom, a difluoromethyl group, a trifluoromethyl group, a difluoromethoxy group, a trifluoromethoxy group, or a 1,1,2,2-tetrafluoroethoxy group, $R^6$ is a C1-C3 haloalkyl group, and $R^{13}$ is a hydrogen atom or a C1-C4 alkyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a halogen atom, a difluoromethyl group, a trifluoromethyl group, a difluoromethoxy group, a trifluoromethoxy group, or a 1,1,2,2-tetrafluoroethoxy group, $R^6$ is a C1-C3 haloalkyl group, and $R^{13}$ is a methyl group, an ethyl group, or a propyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a chlorine atom, a trifluoromethyl group, a difluoromethoxy group, or a trifluoromethoxy group, $R^6$ is a C1-C3 haloalkyl group, and $R^{13}$ is a hydrogen atom or a C1-C4 alkyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a chlorine atom, a trifluoromethyl group, a difluoromethoxy group, or a trifluoromethoxy group, $R^6$ is a C1-C3 haloalkyl group, and $R^{13}$ is a methyl group, an ethyl group, or a propyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a halogen atom, a C1-C6 alkyl group, a C1-C6 alkoxy group, a C1-C6 haloalkyl group, or a C1-C6 haloalkoxy group, $R^6$ is a methoxy group, and $R^{13}$ is a hydrogen atom or a C1-C4 alkyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a halogen atom, a C1-C6 alkyl group, a C1-C6 alkoxy group, a C1-C6 haloalkyl group, or a C1-C6 haloalkoxy group, $R^6$ is a methoxy group, and $R^{13}$ is a methyl group, an ethyl group, or a propyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a halogen atom, a difluoromethyl group, a trifluoromethyl group, a difluoromethoxy group, a trifluoromethoxy group, or a 1,1,2,2-tetrafluoroethoxy group, $R^6$ is a methoxy group, and $R^{13}$ is a hydrogen atom or a C1-C4 alkyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a halogen atom, a difluoromethyl group, a trifluoromethyl group, a difluoromethoxy group, a trifluoromethoxy group, or a 1,1,2,2-tetrafluoroethoxy group, $R^6$ is a methoxy group, and $R^{13}$ is a methyl group, an ethyl group, or a propyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a chlorine atom, a trifluoromethyl group, a difluoromethoxy group, or a trifluoromethoxy group, $R^6$ is a methoxy group, and $R^{13}$ is a hydrogen atom or a C1-C4 alkyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a chlorine atom, a trifluoromethyl group, a difluoromethoxy group, or a trifluoromethoxy group, $R^6$ is a methoxy group, and $R^{13}$ is a methyl group, an ethyl group, or a propyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a halogen atom, a C1-C6 alkyl group, a C1-C6 alkoxy group, a C1-C6 haloalkyl group, or a C1-C6 haloalkoxy group, $R^6$ is a methylthio group, and $R^{13}$ is a hydrogen atom or a C1-C4 alkyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a halogen atom, a C1-C6 alkyl group, a C1-C6 alkoxy group, a C1-C6 haloalkyl group, or a C1-C6 haloalkoxy group, $R^6$ is a methylthio group, and $R^{13}$ is a methyl group, an ethyl group, or a propyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a halogen atom, a difluoromethyl group, a trifluoromethyl group, a difluoromethoxy group, a trifluoromethoxy group, or a 1,1,2,2-tetrafluoroethoxy group, $R^6$ is a methylthio group, and $R^{13}$ is a hydrogen atom or a C1-C4 alkyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a halogen atom, a difluoromethyl group, a trifluoromethyl group, a difluoromethoxy group, a trifluoromethoxy group, or a 1,1,2,2-tetrafluoroethoxy group, $R^6$ is a methylthio group, and $R^{13}$ is a methyl group, an ethyl group, or a propyl group; a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a chlorine atom, a trifluoromethyl group, a difluoromethoxy group, or a trifluoromethoxy group, $R^6$ is a methylthio group, and $R^{13}$ is a hydrogen atom or a C1-C4 alkyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a chlorine atom, a trifluoromethyl group, a difluoromethoxy group, or a trifluoromethoxy group, $R^6$ is a methylthio group, and $R^{13}$ is a methyl group, an ethyl group, or a propyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a halogen atom, a C1-C6 alkyl group, a C1-C6 alkoxy group, a C1-C6 haloalkyl group, or a C1-C6 haloalkoxy group, $R^6$ is a cycloalkyl group, and $R^{13}$ is a hydrogen atom or a C1-C4 alkyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a halogen atom, a C1-C6 alkyl group, a C1-C6 alkoxy group, a C1-C6 haloalkyl group, or a C1-C6 haloalkoxy group, $R^6$ is a cycloalkyl group, and $R^{13}$ is a methyl group, an ethyl group, or a propyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a halogen atom, a difluoromethyl group, a trifluoromethyl group, a difluoromethoxy group, a trifluoromethoxy group, or a 1,1,2,2-tetrafluoroethoxy group, $R^6$ is a cycloalkyl group, and $R^{13}$ is a hydrogen atom or a C1-C4 alkyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a halogen atom, a difluoromethyl group, a trifluoromethyl group, a difluoromethoxy group, a trifluoromethoxy group, or a 1,1,2,2-tetrafluoroethoxy group, $R^6$ is a cycloalkyl group, and $R^{13}$ is a methyl group, an ethyl group, or a propyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a chlorine atom, a trifluoromethyl group, a difluoromethoxy group, or a trifluoromethoxy group, $R^6$ is a cycloalkyl group, and $R^{13}$ is a hydrogen atom or a C1-C4 alkyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a chlorine atom, a trifluoromethyl group, a difluoromethoxy group, or a trifluoromethoxy group, $R^6$ is a cycloalkyl group, and $R^{13}$ is a methyl group, an ethyl group, or a propyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a halogen atom, a C1-C6 alkyl group, a C1-C6 alkoxy group, a C1-C6 haloalkyl group, or a C1-C6 haloalkoxy group, $R^6$ is a methyl group, and $R^{13}$ is a hydrogen atom or a C1-C4 alkyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a halogen atom, a C1-C6 alkyl group, a C1-C6 alkoxy group, a C1-C6 haloalkyl group, or a C1-C6 haloalkoxy group, $R^6$ is a methyl group, and $R^{13}$ is a methyl group, an ethyl group, or a propyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a halogen atom, a difluoromethyl group, a trifluoromethyl group, a difluoromethoxy group, a trifluoromethoxy group, or a 1,1,2,2-tetrafluoroethoxy group, $R^6$ is a methyl group, and $R^{13}$ is a hydrogen atom or a C1-C4 alkyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a halogen atom, a difluoromethyl group, a trifluoromethyl group, a difluoromethoxy group, a trifluoromethoxy group, or a 1,1,2,2-tetrafluoroethoxy group, $R^6$ is a methyl group, and $R^{13}$ is a methyl group, an ethyl group, or a propyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a chlorine atom, a trifluoromethyl group, a difluoromethoxy group, or a trifluoromethoxy group, $R^6$ is a methyl group, and $R^{13}$ are hydrogen atoms, C1-C4 alkyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a chlorine atom, a trifluoromethyl group, a difluoromethoxy group, or a trifluoromethoxy group, $R^6$ is a methyl group, and $R^{13}$ is a methyl group, an ethyl group, or a propyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a halogen atom, a C1-C6 alkyl group, a C1-C6 alkoxy group, a C1-C6 haloalkyl group, or a C1-C6 haloalkoxy group, $R^6$ is an ethyl group, and $R^{13}$ is a hydrogen atom or a C1-C4 alkyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a halogen atom, a C1-C6 alkyl group, a C1-C6 alkoxy group, a C1-C6 haloalkyl group, or a C1-C6 haloalkoxy group, $R^6$ is an ethyl group, and $R^{13}$ is a methyl group, an ethyl group, or a propyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a halogen atom, a difluoromethyl group, a trifluoromethyl group, a difluoromethoxy group, a trifluoromethoxy group, or a 1,1,2,2-tetrafluoroethoxy group, $R^6$ is an ethyl group, and $R^{13}$ is a hydrogen atom or a C1-C4 alkyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a halogen atom, a difluoromethyl group, a trifluoromethyl group, a difluoromethoxy group, a trifluoromethoxy group, or a 1,1,2,2-tetrafluoroethoxy group, $R^6$ is an ethyl group, and $R^{13}$ is a methyl group, an ethyl group, or a propyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a chlorine atom, a trifluoromethyl group, a difluoromethoxy group, or a trifluoromethoxy group, $R^6$ is an ethyl group, and $R^{13}$ is a hydrogen atom or a C1-C4 alkyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a chlorine atom, a trifluoromethyl group, a difluoromethoxy group, or a trifluoromethoxy group, $R^6$ is an ethyl group, and $R^{13}$ is a methyl group, an ethyl group, or a propyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a halogen atom, a C1-C6 alkyl group, a C1-C6 alkoxy group, a C1-C6 haloalkyl group, or a C1-C6 haloalkoxy group, $R^6$ is a cyclopropyl group, and $R^{13}$ is a hydrogen atom or a C1-C4 alkyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a halogen atom, a C1-C6 alkyl group, a C1-C6 alkoxy group, a C1-C6 haloalkyl group, or a C1-C6 haloalkoxy group, $R^6$ is a cyclopropyl group, and $R^{13}$ is a methyl group, an ethyl group, or a propyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a halogen atom, a difluoromethyl group, a trifluoromethyl group, a difluoromethoxy group, a trifluoromethoxy group, or a 1,1,2,2-tetrafluoroethoxy group, $R^6$ is a cyclopropyl group, and $R^{13}$ is a hydrogen atom or a C1-C4 alkyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a halogen atom, a difluoromethyl group, a trifluoromethyl group, a difluoromethoxy group, a trifluoromethoxy group, or a 1,1,2,2-tetrafluoroethoxy group, $R^6$ is a cyclopropyl group, and $R^{13}$ is a methyl group, an ethyl group, or a propyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a chlorine atom, a trifluoromethyl group, a difluoromethoxy group, or a trifluoromethoxy group, $R^6$ is a cyclopropyl group, and $R^{13}$ is a hydrogen atom or a C1-C4 alkyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a chlorine atom, a trifluoromethyl group, a difluoromethoxy group, or a trifluoromethoxy group, $R^6$ is a cyclopropyl group, and $R^{13}$ is a methyl group, an ethyl group, or a propyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a halogen atom, a C1-C6 alkyl group, a C1-C6 alkoxy group, a C1-C6 haloalkyl group, or a C1-C6 haloalkoxy group, $R^6$ is a trifluoromethyl group, and $R^{13}$ are hydrogen atoms, C1-C4 alkyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a halogen atom, a C1-C6 alkyl group, a C1-C6 alkoxy group, a C1-C6 haloalkyl group, or a C1-C6 haloalkoxy group, $R^6$ is a trifluoromethyl group, and $R^{13}$ is a methyl group, an ethyl group, or a propyl group;

a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a halogen atom, a difluoromethyl group, a trifluoromethyl group, a difluoromethoxy group, a trifluoromethoxy group, or a 1,1,2,2-tetrafluoroethoxy group, $R^6$ is a trifluoromethyl group, and $R^{13}$ is a hydrogen atom or a C1-C4 alkyl group;
a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a halogen atom, a difluoromethyl group, a trifluoromethyl group, a difluoromethoxy group, a trifluoromethoxy group, or a 1,1,2,2-tetrafluoroethoxy group, $R^6$ is a trifluoromethyl group, and $R^{13}$ is a methyl group, an ethyl group, or a propyl group; a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a chlorine atom, a trifluoromethyl group, a difluoromethoxy group, or a trifluoromethoxy group, $R^6$ is a trifluoromethyl group, and $R^{13}$ is a hydrogen atom or a C1-C4 alkyl group;
a compound represented by formula (1-P), wherein $R^1$, $R^3$, $R^4$, $R^5$, $R^7$, $R^8$, $R^9$, and $R^{12}$ are hydrogen atoms, $R^{10}$ is a methyl group, X is an oxygen atom, $R^2$ and $R^{11}$ each represents a chlorine atom, a trifluoromethyl group, a difluoromethoxy group, or a trifluoromethoxy group, $R^6$ is a trifluoromethyl group, and $R^{13}$ is a methyl group, an ethyl group, or a propyl group;
a compound represented by formula (1-P), wherein $R^1$, $R^2$, $R^3$, $R^{11}$, and $R^{12}$ are hydrogen atoms,
C1-C6 alkyl groups optionally having an atom or a group selected from Group P,
C1-C6 haloalkoxy groups, halogen atoms, nitro groups, C1-C6 alkoxy groups, C2-C6 alkynyloxy groups, C1-C8 alkylamino groups, cyano group, or C2-C8 alkylaminocarbonyl groups;
or, $R^1$ and $R^2$ form a five-membered ring or a six-membered ring together with the carbon atom to which they are attached, and the ring may contain one or more atoms selected from the group consisting of an oxygen atom and a sulfur atom as a ring-constituent atom, and the ring may have one or more atoms or groups selected from Group P as a substituent; or, $R^2$ and $R^3$ form a five-membered ring or a six-membered ring together with the carbon atom to which they are attached, and the ring may contain one or more atoms selected from the group consisting of an oxygen atom and a sulfur atom as a ring-constituent atom, and the ring may have one or more atoms or groups selected from Group P as a substituent;
$R^4$ and $R^5$ are hydrogen atoms;
$R^6$ is a C1-C4 alkyl group, a C3-C6 cycloalkyl group, a C1-C4 haloalkyl group, a halogen atom, a C1-C4 alkoxy group, or a C1-C4 alkylthio group;
$R^7$, $R^8$, and $R^9$ are hydrogen atoms;
$R^{10}$ is a C1-C3 alkyl group;
X is an oxygen atom; $R^{13}$ is a C1-C6 alkyl group, a C3-C6 cycloalkyl group, a hydrogen atom, or a C1-C6 haloalkyl group;
or, $R^{12}$ and $R^{13}$ form a five-membered ring together with the carbon atom to which they are attached, and the ring may contain one or more atoms selected from the group consisting of an oxygen atom and a sulfur atom as a ring-constituent atom, and the ring may have one or more atoms or groups selected from Group P as a substituent;
a compound represented by formula (1-P), wherein $R^1$, $R^2$, R, $R^{11}$, and $R^{12}$ are hydrogen atoms,
C1-C6 alkyl groups optionally having halogen,
C1-C6 haloalkoxy groups, halogen atoms, nitro groups, C1-C6 alkoxy groups, C2-C6 alkynyloxy groups, C1-C8 alkylamino groups, cyano group, or C2-C8 alkylaminocarbonyl groups;

or, $R^1$ and $R^2$ form a five-membered ring or a six-membered ring together with the carbon atom to which they are attached, and the ring may contain one or more atoms selected from the group consisting of an oxygen atom and a sulfur atom as a ring-constituent atom, and the ring may have one or more halogen atoms as a substituent;
or, $R^2$ and $R^3$ form a five-membered ring or a six-membered ring together with the carbon atom to which they are attached, and the ring may contain one or more oxygen atoms or sulfur atoms as the ring-constituent atom, and the ring may have halogen as a substituent;
$R^4$ and $R^5$ are hydrogen atoms;
$R^6$ is a C1-C3 alkyl group, a C3-C4 cycloalkyl group, a C1-C3 haloalkyl group, a halogen atom, a C1-C3 alkoxy group, or a C1-C3 alkylthio group;
$R^7$, $R^8$, and $R^9$ are hydrogen atoms;
$R^{10}$ is a methyl group;
X is an oxygen atom;
$R^{13}$ is a C1-C4 alkyl group, a C3-C4 cycloalkyl group, a hydrogen atom, or a C1-C4 haloalkyl group;
or, $R^{12}$ and $R^{13}$ form a five-membered ring together with the carbon atom to which they are attached, and the ring may contain one or more atoms selected from the group consisting of an oxygen atom and a sulfur atom as a ring-constituent atom, and the ring may have one or more halogen atoms as a substituent;
a compound represented by formula (1-P), wherein $R^1$, $R^2$, $R^3$, $R^{11}$, and $R^{12}$ are hydrogen atoms,
C1-C6 alkyl groups optionally having halogen,
C1-C6 haloalkoxy groups, halogen atoms, nitro groups, C1-C6 alkoxy groups, C2-C6 alkynyloxy groups, C1-C8 alkylamino groups, cyano groups, or C2-C8 alkylaminocarbonyl groups;
or, Q is any one of the following structures:

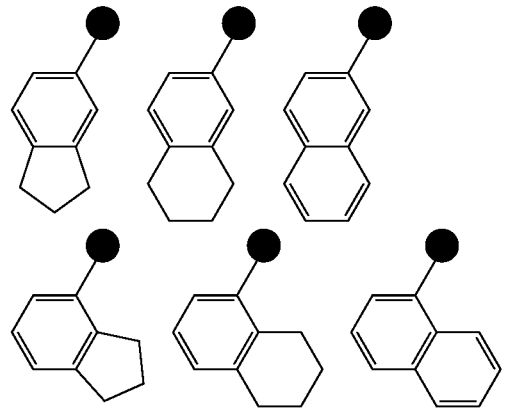

wherein the symbol ○ represents a binding site;
$R^4$ and $R^5$ are hydrogen atoms;
$R^6$ is a C1-C3 alkyl group, a C3-C4 cycloalkyl group, a C1-C3 haloalkyl group, a halogen atom, a C1-C3 alkoxy group, or a C1-C3 alkylthio group;
$R^7$, $R^8$ and $R^9$ are hydrogen atoms;
$R^{10}$ is a methyl group;
X is an oxygen atom;
$R^{13}$ is a C1-C4 alkyl group, a C3-C4 cycloalkyl group, a hydrogen atom, or a C1-C4 haloalkyl group;
or, $R^{12}$ and $R^{13}$ form a five-membered ring together with the carbon atom to which they are attached, and the ring may contain one or more atoms selected from the group consisting of an oxygen atom and a sulfur atom as a ring-constituent atom, and the may have a halogen atom as a substituent;
a compound represented by formula (1-P), wherein
$R^1$, $R^2$, $R^3$, $R^{11}$, and $R^{12}$ are hydrogen atoms,
C1-C4 alkyl groups optionally having halogen,
C1-C4 haloalkoxy groups, halogen atoms, nitro groups, or C1-C4 alkoxy groups;
or, Q is any one of the following structures:

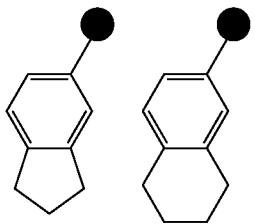

wherein the symbol ○ represents a binding site;
$R^4$ and $R^5$ are hydrogen atoms;
$R^6$ is a C1-C3 alkyl group, a C3-C4 cycloalkyl group, a C1-C3 haloalkyl group, a halogen atom, a C1-C3 alkoxy group, or a C1-C3 alkylthio group;
$R^7$, $R^8$, and $R^9$ are hydrogen atoms;
$R^{10}$ is a methyl group;
X is an oxygen atom;
$R^{13}$ is a C1-C4 alkyl group, a C3-C4 cycloalkyl group, a hydrogen atom, or a C1-C4 haloalkyl group;
a compound represented by formula (1-P), wherein
$R^4$, $R^5$, $R^7$, $R^8$, and $R^9$ are hydrogen atoms;
$R^{10}$ is a methyl group; and
X is an oxygen atom;
a compound represented by formula (1-P), wherein
$R^6$ is a C1-C3 alkyl group, a C3-C4 cycloalkyl group, a C1-C3 haloalkyl group, a C3-C4 halocycloalkyl group, a halogen atom, a C2-C3 alkenyl group, a C2-C3 alkynyl group, a C1-C3 alkoxy group, a C1-C3 haloalkoxy group, or a C1-C3 alkylthio group;
a compound represented by formula (1-P), wherein
$R^6$ is a C1-C3 alkyl group, a C3-C4 cycloalkyl group, a C1-C3 haloalkyl group, a C3-C4 halocycloalkyl group, a halogen atom, a C2-C3 alkenyl group, a C2-C3 alkynyl group, a C1-C3 alkoxy group, a C1-C3 haloalkoxy group, or a C1-C3 alkylthio group;
$R^1$, $R^2$, $R^3$, $R^{11}$, and $R^{12}$ each represents a hydrogen atom, a C1-C6 alkyl group optionally having an atom or a group selected from Group P,
a C3-C6 cycloalkyl group optionally having an atom or a group selected from Group P,
a C1-C6 haloalkoxy group, a halogen atom, a nitro group, a C1-C6 alkoxy group, a C2-C6 alkenyl group, a C2-C6 haloalkenyl group, a C2-C6 alkynyl group, a C2-C6 haloalkynyl group, a C3-C6 alkenyloxy group, a C3-C6 haloalkenyloxy group, a C3-C6 alkynyloxy group, a C3-C6 haloalkynyloxy group, a C1-C8 alkylamino group, a C1-C8 haloalkylamino group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a cyano group, an amino group, a hydroxy group, a mercapto group, a pentafluorosulfanyl group, a C3-C9 trialkylsilyl group, a C2-C6 alkylcarbonyl group, a C2-C6 alkoxycarbonyl group, a C2-C8 alkylaminocarbonyl group, or a C2-C8 alkylcarbonylamino group;
or, $R^1$ and $R^2$ form a four-membered ring, a five-membered ring, a six-membered ring, or a seven-membered ring together with the carbon atom to which they are attached, and the ring may contain one or more atoms selected from the group consisting of an oxygen atom and a sulfur atom as a ring-constituent atom, and the ring may have one or more atoms or groups selected from Group P as a substituent;
or, $R^2$ and $R^3$ form a four-membered ring, a five-membered ring, a six-membered ring, or a seven-membered ring together with the carbon atom to which they are attached, and the ring may contain one or more atoms selected from the group consisting of an oxygen atom and a sulfur atom as a ring-constituent atom, and the ring may have one or more atoms or groups selected from Group P as a substituent;
$R^4$ and $R^5$ each represents a hydrogen atom or a C1-C3 alkyl group;
$R^7$, $R^8$, and $R^9$ each represents a hydrogen atom or a halogen atom;
$R^{10}$ is a C1-C3 alkyl group, a C1-C3 haloalkyl group, a C2-C3 alkenyl group, a C2-C3 haloalkenyl group, a C2-C3 alkynyl group, a C2-C3 haloalkynyl group, a C3-C5 cycloalkyl group, or a C3-C5 halocycloalkyl group;
X is an oxygen atom or a sulfur atom;
$R^{13}$ is a C1-C6 alkyl group, a C3-C6 cycloalkyl group, a hydrogen atom, a halogen atom, a C1-C6 haloalkyl group, a C3-C6 halocycloalkyl group, a C2-C6 alkenyl group, a C2-C6 haloalkenyl group, a C2-C6 alkynyl group, a C2-C6 haloalkynyl group, a C1-C6 alkoxy group, or a C1-C6 alkylthio group;
or, $R^{12}$ and $R^{13}$ form a five-membered ring, a six-membered ring, or a seven-membered ring together with the carbon atom to which they are attached, and the ring may contain one or more atoms selected from the group consisting of an oxygen atom and a sulfur atom as a ring-constituent atom, and the ring may have one or more atoms or groups selected from Group P as a substituent;
a compound represented by formula (1-P), wherein
$R^4$, $R^5$, $R^7$, $R^8$, and $R^9$ are hydrogen atoms;
$R^{10}$ is a methyl group;
X is an oxygen atom;
$R^6$ is a C1-C3 alkyl group, a C3-C4 cycloalkyl group, a C1-C3 haloalkyl group, a C3-C4 halocycloalkyl group, a halogen atom, a C2-C3 alkenyl group, a C2-C3 alkynyl group, a C1-C3 alkoxy group, a C1-C3 haloalkoxy group, or a C1-C3 alkylthio group;
$R^1$, $R^2$, $R^3$, $R^{11}$, and $R^{12}$ each represents a hydrogen atom, a C1-C6 alkyl group optionally having an atom or a group selected from Group P,
a C3-C6 cycloalkyl group optionally having an atom or a group selected from Group P,
a C1-C6 haloalkoxy group, a halogen atom, a nitro group, a C1-C6 alkoxy group, a C2-C6 alkenyl group, a C2-C6 haloalkenyl group, a C2-C6 alkynyl group, a C2-C6 haloalkynyl group, a C3-C6 alkenyloxy group, a C3-C6 haloalkenyloxy group, a C3-C6 alkynyloxy group, a C3-C6 haloalkynyloxy group, a C1-C8 alkylamino group, a C1-C8 haloalkylamino group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a cyano group, an amino group, a hydroxy group, a mercapto group, a pentafluorosulfanyl group, a C3-C9 trialkylsilyl group, a C2-C6 alkylcarbonyl group, a C2-C6 alkoxycarbonyl group, a C2-C8 alkylaminocarbonyl group, or a C2-C8 alkylcarbonylamino group;
or, $R^1$ and $R^2$ form a four-membered ring, a five-membered ring, a six-membered ring, or a seven-membered ring together with the carbon atom to which they are attached, and the ring may contain one or more atoms selected from the group consisting of an oxygen atom and a sulfur atom as a ring-constituent atom, and the ring may have one or more atoms or groups selected from Group P as a substituent;
or, $R^2$ and $R^3$ form a four-membered ring, a five-membered ring, a six-membered ring, or a seven-membered ring together with the carbon atom to which they are attached, and the ring may contain one or more atoms selected from the group consisting of an oxygen atom and a sulfur atom as a ring-constituent atom, and the ring may have one or more atoms or groups selected from Group P as a substituent;
$R^{13}$ is a C1-C6 alkyl group, a C3-C6 cycloalkyl group, a hydrogen atom, a halogen atom, a C1-C6 haloalkyl group, a C3-C6 halocycloalkyl group, a C2-C6 alkenyl group, a C2-C6 haloalkenyl group, a C2-C6 alkynyl group, a C2-C6 haloalkynyl group, a C1-C6 alkoxy group, or a C1-C6 alkylthio group;
or, $R^{12}$ and $R^{13}$ form a five-membered ring, a six-membered ring, or a seven-membered ring together with the carbon atom to which they are attached, and the ring may contain one or more atoms selected from the group consisting of an oxygen atom and a sulfur atom as a ring-constituent atom, and the ring may have one or more atoms or groups selected from Group P as a substituent;
a compound represented by formula (1-P), wherein $R^{13}$ is a C1-C4 alkyl group, a C3-C4 cycloalkyl group, a hydrogen atom, a halogen atom, a C2-C4 alkenyl group, a C2-C4 alkynyl group, a C1-C4 alkoxy group, or a C1-C4 alkylthio group;
a compound represented by formula (1-P), wherein
$R^{13}$ is a C1-C4 alkyl group, a C3-C4 cycloalkyl group, a hydrogen atom, a halogen atom, a C2-C4 alkenyl group, a C2-C4 alkynyl group, a C1-C4 alkoxy group, or a C1-C4 alkylthio group;
$R^1$, $R^2$, $R^3$, $R^{11}$, and $R^{12}$ each represents a hydrogen atom, a C1-C6 alkyl group optionally having an atom or a group selected from Group P,
a C3-C6 cycloalkyl group optionally having an atom or a group selected from Group P,
a C1-C6 haloalkoxy group, a halogen atom, a nitro group, a C1-C6 alkoxy group, a C2-C6 alkenyl group, a C2-C6 haloalkenyl group, a C2-C6 alkynyl group, a C2-C6 haloalkynyl group, a C3-C6 alkenyloxy group, a C3-C6 haloalkenyloxy group, a C3-C6 alkynyloxy group, a C3-C6 haloalkynyloxy group, a C1-C8 alkylamino group, a C1-C8 haloalkylamino group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a cyano group, an amino group, a hydroxy group, a mercapto group, a pentafluorosulfanyl group, a C3-C9 trialkylsilyl group, a C2-C6 alkylcarbonyl group, a C2-C6 alkoxycarbonyl group, a C2-C8 alkylaminocarbonyl group, or a C2-C8 alkylcarbonylamino group;
or, $R^1$ and $R^2$ form a four-membered ring, a five-membered ring, a six-membered ring, or a seven-membered ring together with the carbon atom to which they are attached, and the ring may contain one or more atoms selected from the group consisting of an oxygen atom and a sulfur atom as a ring-constituent atom, and the ring may have one or more atoms or groups selected from Group P as a substituent;
or, $R^2$ and $R^3$ form a four-membered ring, a five-membered ring, a six-membered ring, or a seven-membered ring together with the carbon atom to which they are attached, and the ring may contain one or more atoms selected from the group consisting of an oxygen atom and a sulfur atom as a ring-constituent atom, and the ring may have one or more atoms or groups selected from Group P as a substituent;
$R^4$ and $R^5$ each represents a hydrogen atom or a C1-C3 alkyl group;
$R^6$ is a C1-C4 alkyl group, a C3-C6 cycloalkyl group, a C1-C4 haloalkyl group, a C3-C6 halocycloalkyl group, a halogen atom, a cyano group, a nitro group, a C2-C4 alkenyl group, a C2-C4 haloalkenyl group, a C2-C4 alkynyl group, a C2-C4 haloalkynyl group, a C1-C4 alkoxy group, a C1-C4 haloalkoxy group, a C1-C4 alkylthio group, or a C1-C4 haloalkylthio group;
$R^7$, $R^8$, and $R^9$ each represents a hydrogen atom or a halogen atom;
$R^{10}$ is a C1-C3 alkyl group, a C1-C3 haloalkyl group, a C2-C3 alkenyl group, a C2-C3 haloalkenyl group, a C2-C3 alkynyl group, a C2-C3 haloalkynyl group, a C3-C5 cycloalkyl group, or a C3-C5 halocycloalkyl group;
X is an oxygen atom or a sulfur atom;
a compound represented by formula (1-P), wherein
$R^4$, $R^5$, $R^7$, $R^8$, and $R^9$ are hydrogen atoms;
$R^{10}$ is a methyl group;
X is an oxygen atom;
$R^{13}$ is a C1-C4 alkyl group, a C3-C4 cycloalkyl group, a hydrogen atom, a halogen atom, a C2-C4 alkenyl group, a C2-C4 alkynyl group, a C1-C4 alkoxy group, or a C1-C4 alkylthio group;
$R^1$, $R^2$, $R^3$, $R^{11}$ and $R^{12}$ each represents a hydrogen atom, a C1-C6 alkyl group optionally having an atom or a group selected from Group P,
a C3-C6 cycloalkyl group optionally having an atom or a group selected from Group P,
a C1-C6 haloalkoxy group, a halogen atom, a nitro group, a C1-C6 alkoxy group, a C2-C6 alkenyl group, a C2-C6 haloalkenyl group, a C2-C6 alkynyl group, a C2-C6 haloalkynyl group, a C3-C6 alkenyloxy group, a C3-C6 haloalkenyloxy group, a C3-C6 alkynyloxy group, a C3-C6 haloalkynyloxy group, a C1-C8 alkylamino group, a C1-C8 haloalkylamino group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a cyano group, an amino group, a hydroxy group, a mercapto group, a pentafluorosulfanyl group, a C3-C9 trialkylsilyl group, a C2-C6 alkylcarbonyl group, a C2-C6 alkoxycarbonyl group, a C2-C8 alkylaminocarbonyl group, or a C2-C8 alkylcarbonylamino group;
or, $R^1$ and $R^2$ form a four-membered ring, a five-membered ring, a six-membered ring, or a seven-membered ring together with the carbon atom to which they are attached, and the ring may contain one or more atoms selected from the group consisting of an oxygen atom and a sulfur atom as a ring-constituent atom, and the ring may have one or more atoms or groups selected from Group P as a substituent;
or, $R^2$ and $R^3$ form a four-membered ring, a five-membered ring, a six-membered ring, or a seven-membered ring together with the carbon atom to which they are attached, and the ring may contain one or more atoms selected from the group consisting of an oxygen atom and a sulfur atom as a ring-constituent atom, and the ring may have one or more atoms or groups selected from Group P as a substituent; and
$R^6$ is a C1-C4 alkyl group, a C3-C6 cycloalkyl group, a C1-C4 haloalkyl group, a C3-C6 halocycloalkyl group, a halogen atom, a cyano group, a nitro group, a C2-C4 alkenyl group, a C2-C4 haloalkenyl group, a C2-C4 alkynyl group, a C2-C4 haloalkynyl group, a C1-C4 alkoxy group, a C1-C4 haloalkoxy group, a C1-C4 alkylthio group, or a C1-C4 haloalkylthio group;

a compound represented by formula (1-P), wherein
$R^6$ is a C1-C3 alkyl group, a C3-C4 cycloalkyl group, a C1-C3 haloalkyl group, a C3-C4 halocycloalkyl group, a halogen atom, a C2-C3 alkenyl group, a C2-C3 alkynyl group, a C1-C3 alkoxy group, a C1-C3 haloalkoxy group, or a C1-C3 alkylthio group;
$R^{13}$ is a C1-C4 alkyl group, a C3-C4 cycloalkyl group, a hydrogen atom, a halogen atom, a C2-C4 alkenyl group, a C2-C4 alkynyl group, a C1-C4 alkoxy group, or a C1-C4 alkylthio group;
$R^1$, $R^2$, $R^3$, $R^{11}$ and $R^{12}$ each represents a hydrogen atom, a C1-C6 alkyl group optionally having an atom or a group selected from Group P,
a C3-C6 cycloalkyl group optionally having an atom or a group selected from Group P,
a C1-C6 haloalkoxy group, a halogen atom, a nitro group, a C1-C6 alkoxy group, a C2-C6 alkenyl group, a C2-C6 haloalkenyl group, a C2-C6 alkynyl group, a C2-C6 haloalkynyl group, a C3-C6 alkenyloxy group, a C3-C6 haloalkenyloxy group, a C3-C6 alkynyloxy group, a C3-C6 haloalkynyloxy group, a C1-C8 alkylamino group, a C1-C8 haloalkylamino group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a cyano group, an amino group, a hydroxy group, a mercapto group, a pentafluorosulfanyl group, a C3-C9 trialkylsilyl group, a C2-C6 alkylcarbonyl group, a C2-C6 alkoxycarbonyl group, a C2-C8 alkylaminocarbonyl group or C2-C8 alkylcarbonylamino group;
or, $R^1$ and $R^2$ form a four-membered ring, a five-membered ring, a six-membered ring, or a seven-membered ring together with the carbon atom to which they are attached, and the ring may contain one or more atoms selected from the group consisting of an oxygen atom and a sulfur atom as a ring-constituent atom, and the ring may have one or more atoms or groups selected from Group P as a substituent;
or, $R^2$ and $R^3$ form a four-membered ring, a five-membered ring, a six-membered ring, or a seven-membered ring together with the carbon atom to which they are attached, and the ring may contain one or more atoms selected from the group consisting of an oxygen atom and a sulfur atom as a ring-constituent atom, and the ring may have one or more atoms or groups selected from Group P as a substituent;
$R^4$ and $R^5$ each represents a hydrogen atom or a C1-C3 alkyl group;
$R^7$, $R^8$, and $R^9$ each represents a hydrogen atom or a halogen atom;
$R^{10}$ is a C1-C3 alkyl group, a C1-C3 haloalkyl group, a C2-C3 alkenyl group, a C2-C3 haloalkenyl group, a C2-C3 alkynyl group, a C2-C3 haloalkynyl group, a C3-C5 cycloalkyl group, or a C3-C5 halocycloalkyl group;
X is an oxygen atom or a sulfur atom;
a compound represented by formula (1-P), wherein
$R^4$, $R^5$, $R^7$, $R^8$ and $R^9$ are hydrogen atoms;
$R^{10}$ is a methyl group;
X is an oxygen atom;
$R^6$ is a C1-C3 alkyl group, a C3-C4 cycloalkyl group, a C1-C3 haloalkyl group, a C3-C4 halocycloalkyl group, a halogen atom, a C2-C3 alkenyl group, a C2-C3 alkynyl group, a C1-C3 alkoxy group, a C1-C3 haloalkoxy group, or a C1-C3 alkylthio group;
$R^{13}$ is a C1-C4 alkyl group, a C3-C4 cycloalkyl group, a hydrogen atom, a halogen atom, a C2-C4 alkenyl group, a C2-C4 alkynyl group, a C1-C4 alkoxy group, or a C1-C4 alkylthio group;
$R^1$, $R^2$, $R^3$, $R^{11}$ and $R^{12}$ each represents a hydrogen atom,
a C1-C6 alkyl group optionally having an atom or a group selected from Group P,
a C3-C6 cycloalkyl group optionally having an atom or a group selected from Group P,
a C1-C6 haloalkoxy group, a halogen atom, a nitro group, a C1-C6 alkoxy group, a C2-C6 alkenyl group, a C2-C6 haloalkenyl group, a C2-C6 alkynyl group, a C2-C6 haloalkynyl group, a C3-C6 alkenyloxy group, a C3-C6 haloalkenyloxy group, a C3-C6 alkynyloxy group, a C3-C6 haloalkynyloxy group, a C1-C8 alkylamino group, a C1-C8 haloalkylamino group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a cyano group, an amino group, a hydroxy group, a mercapto group, a pentafluorosulfanyl group, a C3-C9 trialkylsilyl group, a C2-C6 alkylcarbonyl group, a C2-C6 alkoxycarbonyl group, a C2-C8 alkylaminocarbonyl group, or a C2-C8 alkylcarbonylamino group;
or, $R^1$ and $R^2$ form a four-membered ring, a five-membered ring, a six-membered ring, or a seven-membered ring together with the carbon atom to which they are attached, and the ring may contain one or more atoms selected from the group consisting of an oxygen atom and a sulfur atom as a ring-constituent atom, and the ring may have one or more atoms or groups selected from Group P as a substituent;
or, $R^2$ and $R^3$ form a four-membered ring, a five-membered ring, a six-membered ring together with the carbon atom to which they are attached, or a seven-membered ring, and the ring may contain one or more atoms selected from the group consisting of an oxygen atom and a sulfur atom as a ring-constituent atom, and the ring may have one or more atoms or groups selected from Group P as a substituent; a compound represented by formula (1-P), wherein
$R^1$ and $R^{12}$ are hydrogen atoms,
$R^2$, $R^3$, and $R^{11}$ each represents a hydrogen atom, a C1-C6 haloalkyl group, a C3-C6 halocycloalkyl group, a C1-C6 haloalkoxy group, a halogen atom, a nitro group, a C1-C6 alkyl group, a C3-C6 cycloalkyl group, a C1-C6 alkoxy group, a C2-C6 alkenyl group, a C2-C6 haloalkenyl group, a C2-C6 alkynyl group, a C2-C6 haloalkynyl group, a C3-C6 alkenyloxy group, a C3-C6 haloalkenyloxy group, a C3-C6 alkynyloxy group, a C3-C6 haloalkynyloxy group, a C1-C6 alkylthio group, or a C1-C6 haloalkylthio group;
or Q is any one of the following structures:

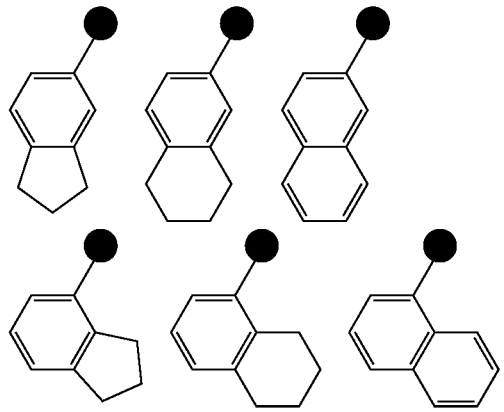

wherein the symbol ○ represents a binding site;
a compound represented by formula (1-P), wherein
$R^1$ and $R^{12}$ are hydrogen atoms,
$R^2$, $R^3$, and $R^{11}$ each represents a hydrogen atom, a C1-C6 haloalkyl group, a C3-C6 halocycloalkyl group, a C1-C6 haloalkoxy group, a halogen atom, a nitro group, a C1-C6 alkyl group, a C3-C6 cycloalkyl group, a C1-C6 alkoxy group, a C2-C6 alkenyl group, a C2-C6 haloalkenyl group, a C2-C6 alkynyl group, a C2-C6 haloalkynyl group, a C3-C6 alkenyloxy group, a C3-C6 haloalkenyloxy group, a C3-C6 alkynyloxy group, a C3-C6 haloalkynyloxy group, a C1-C6 alkylthio group, or a C1-C6 haloalkylthio group;

or Q is any one of the following structures:

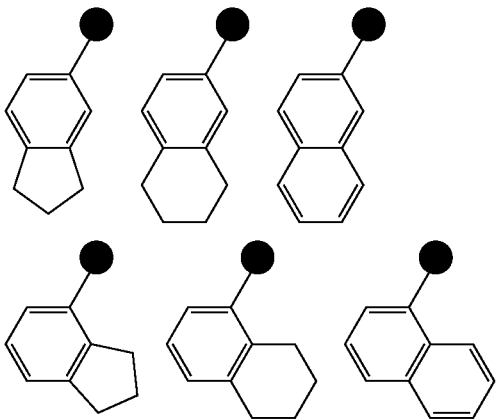

wherein the symbol ○ represents a binding site;
$R^4$ and $R^5$ each represents a hydrogen atom or a C1-C3 alkyl group;
$R^6$ is a C1-C4 alkyl group, a C3-C6 cycloalkyl group, a C1-C4 haloalkyl group, a C3-C6 halocycloalkyl group, a halogen atom, a cyano group, a nitro group, a C2-C4 alkenyl group, a C2-C4 haloalkenyl group, a C2-C4 alkynyl group, a C2-C4 haloalkynyl group, a C1-C4 alkoxy group, a C1-C4 haloalkoxy group, a C1-C4 alkylthio group, or a C1-C4 haloalkylthio group;
$R^7$, $R^8$, and $R^9$ each represents a hydrogen atom or a halogen atom;
$R^{10}$ is a C1-C3 alkyl group, a C1-C3 haloalkyl group, a C2-C3 alkenyl group, a C2-C3 haloalkenyl group, a C2-C3 alkynyl group, a C2-C3 haloalkynyl group, a C3-C5 cycloalkyl group, or a C3-C5 halocycloalkyl group;
X is an oxygen atom or a sulfur atom;
$R^{13}$ is a C1-C6 alkyl group, a C3-C6 cycloalkyl group, a hydrogen atom, a halogen atom, a C1-C6 haloalkyl group, a C3-C6 halocycloalkyl group, a C2-C6 alkenyl group, a C2-C6 haloalkenyl group, a C2-C6 alkynyl group, a C2-C6 haloalkynyl group, a C1-C6 alkoxy group, or a C1-C6 alkylthio group;
a compound represented by formula (1-P), wherein
$R^1$ and $R^{12}$ are hydrogen atoms,
$R^2$, $R^3$, and $R^{11}$ each represents a hydrogen atom, a C1-C6 haloalkyl group, a C3-C6 halocycloalkyl group, a C1-C6 haloalkoxy group, a halogen atom, a nitro group, a C1-C6 alkyl group, a C3-C6 cycloalkyl group, a C1-C6 alkoxy group, a C2-C6 alkenyl group, a C2-C6 haloalkenyl group, a C2-C6 alkynyl group, a C2-C6 haloalkynyl group, a C3-C6 alkenyloxy group, a C3-C6 haloalkenyloxy group, a C3-C6 alkynyloxy group, a C3-C6 haloalkynyloxy group, a C1-C6 alkylthio group, or a C1-C6 haloalkylthio group;

or Q is any one of the following structures:

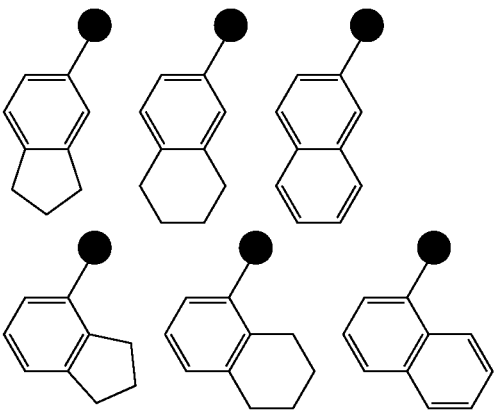

wherein the symbol ○ represents a binding site;
$R^4$, $R^5$, $R^7$, $R^8$, and $R^9$ are hydrogen atoms;
$R^{10}$ is a methyl group;
X is an oxygen atom;
$R^6$ is a C1-C4 alkyl group, a C3-C6 cycloalkyl group, a C1-C4 haloalkyl group, a C3-C6 halocycloalkyl group, a halogen atom, a cyano group, a nitro group, a C2-C4 alkenyl group, a C2-C4 haloalkenyl group, a C2-C4 alkynyl group, a C2-C4 haloalkynyl group, a C1-C4 alkoxy group, a C1-C4 haloalkoxy group, a C1-C4 alkylthio group, or a C1-C4 haloalkylthio group;
$R^{13}$ is a C1-C6 alkyl group, a C3-C6 cycloalkyl group, a hydrogen atom, a halogen atom, a C1-C6 haloalkyl group, a C3-C6 halocycloalkyl group, a C2-C6 alkenyl group, a C2-C6 haloalkenyl group, a C2-C6 alkynyl group, a C2-C6 haloalkynyl group, a C1-C6 alkoxy group, or a C1-C6 alkylthio group;
a compound represented by formula (1-P), wherein
$R^1$ and $R^{12}$ are hydrogen atoms,
$R^2$, $R^3$, and $R^{11}$ each represents a hydrogen atom, a C1-C6 haloalkyl group, a C3-C6 halocycloalkyl group, a C1-C6 haloalkoxy group, a halogen atom, a nitro group, a C1-C6 alkyl group, a C3-C6 cycloalkyl group, a C1-C6 alkoxy group, a C2-C6 alkenyl group, a C2-C6 haloalkenyl group, a C2-C6 alkynyl group, a C2-C6 haloalkynyl group, a C3-C6 alkenyloxy group, a C3-C6 haloalkenyloxy group, a C3-C6 alkynyloxy group, a C3-C6 haloalkynyloxy group, a C1-C6 alkylthio group, or a C1-C6 haloalkylthio group;

or Q is any one of the following structures:

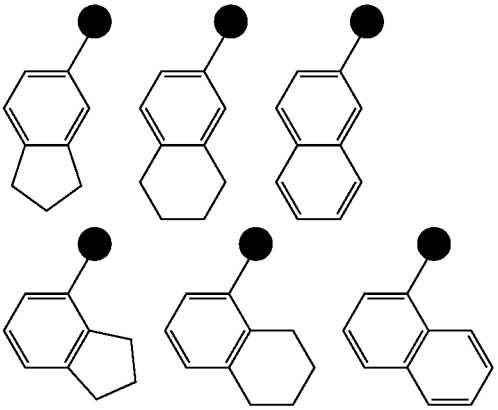

wherein the symbol ○ represents a binding site;
$R^4$, $R^5$, $R^7$, $R^8$, and $R^9$ are hydrogen atoms;
$R^{10}$ is a methyl group;

X is an oxygen atom;
R$^6$ is a C1-C3 alkyl group, a C3-C4 cycloalkyl group, a C1-C3 haloalkyl group, a C3-C4 halocycloalkyl group, a halogen atom, a C2-C3 alkenyl group, a C2-C3 alkynyl group, a C1-C3 alkoxy group, a C1-C3 haloalkoxy group, or a C1-C3 alkylthio group;
R$^{13}$ is a C1-C6 alkyl group, a C3-C6 cycloalkyl group, a hydrogen atom, a halogen atom, a C1-C6 haloalkyl group, a C3-C6 halocycloalkyl group, a C2-C6 alkenyl group, a C2-C6 haloalkenyl group, a C2-C6 alkynyl group, a C2-C6 haloalkynyl group, a C1-C6 alkoxy group, or a C1-C6 alkylthio group;
a compound represented by formula (1-P), wherein R$^1$ and R$^{12}$ are hydrogen atoms,
R$^2$, R$^3$, and R$^{11}$ each represents a hydrogen atom, a C1-C6 haloalkyl group, a C3-C6 halocycloalkyl group, a C1-C6 haloalkoxy group, a halogen atom, a nitro group, a C1-C6 alkyl group, a C3-C6 cycloalkyl group, a C1-C6 alkoxy group, a C2-C6 alkenyl group, a C2-C6 haloalkenyl group, a C2-C6 alkynyl group, a C2-C6 haloalkynyl group, a C3-C6 alkenyloxy group, a C3-C6 haloalkenyloxy group, a C3-C6 alkynyloxy group, a C3-C6 haloalkynyloxy group, a C1-C6 alkylthio group, or a C1-C6 haloalkylthio group;
or Q is any one of the following structures:

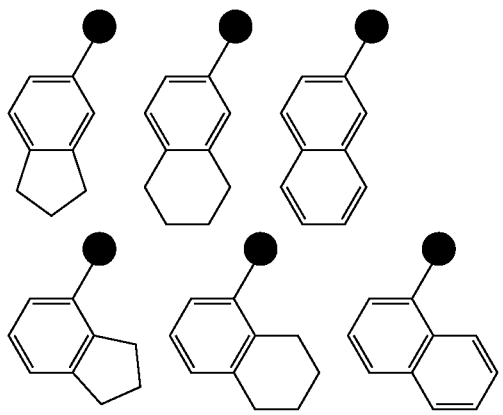

wherein the symbol ○ represents a binding site;
R$^4$, R$^5$, R$^7$, R$^8$, and R$^9$ are hydrogen atoms;
R$^{10}$ is a methyl group;
X is an oxygen atom;
R$^{13}$ is a C1-C4 alkyl group, a C3-C4 cycloalkyl group, a hydrogen atom, a halogen atom, a C2-C4 alkenyl group, a C2-C4 alkynyl group, a C1-C4 alkoxy group, or a C1-C4 alkylthio group; and
R$^6$ is a C1-C4 alkyl group, a C3-C6 cycloalkyl group, a C1-C4 haloalkyl group, a C3-C6 halocycloalkyl group, a halogen atom, a cyano group, a nitro group, a C2-C4 alkenyl group, a C2-C4 haloalkenyl group, a C2-C4 alkynyl group, a C2-C4 haloalkynyl group, a C1-C4 alkoxy group, a C1-C4 haloalkoxy group, a C1-C4 alkylthio group, or a C1-C4 haloalkylthio group;
a compound represented by formula (1-P), wherein R$^1$ and R$^{12}$ are hydrogen atoms,
R$^2$, R$^3$, and R$^1$ each represents a hydrogen atom, a C1-C6 haloalkyl group, a C3-C6 halocycloalkyl group, a C1-C6 haloalkoxy group, a halogen atom, a nitro group, a C1-C6 alkyl group, a C3-C6 cycloalkyl group, a C1-C6 alkoxy group, a C2-C6 alkenyl group, a C2-C6 haloalkenyl group, a C2-C6 alkynyl group, a C2-C6 haloalkynyl group, a C3-C6 alkenyloxy group, a C3-C6 haloalkenyloxy group, a C3-C6 alkynyloxy group, a C3-C6 haloalkynyloxy group, a C1-C6 alkylthio group, or a C1-C6 haloalkylthio group;
or Q is any one of the following structures:

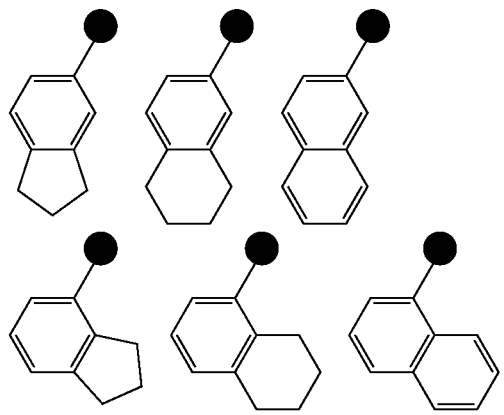

wherein the symbol ○ represents a binding site;
R$^4$, R$^5$, R$^7$, R$^8$, and R$^9$ are hydrogen atoms;
R$^{10}$ is a methyl group;
X is an oxygen atom;
R$^6$ is a C1-C3 alkyl group, a C3-C4 cycloalkyl group, a C1-C3 haloalkyl group, a C3-C4 halocycloalkyl group, a halogen atom, a C2-C3 alkenyl group, a C2-C3 alkynyl group, a C1-C3 alkoxy group, a C1-C3 haloalkoxy group, or a C1-C3 alkylthio group; and
R$^{13}$ is a C1-C4 alkyl group, a C3-C4 cycloalkyl group, a hydrogen atom, a halogen atom, a C2-C4 alkenyl group, a C2-C4 alkynyl group, a C1-C4 alkoxy group, or a C1-C4 alkylthio group;
a compound represented by formula (1-P), wherein R$^6$ is a C1-C3 alkyl group, a C3-C4 cycloalkyl group, a C1-C3 haloalkyl group, a halogen atom, a methoxy group, or a methylthio group;
a compound represented by formula (1-P), wherein R$^1$ and R$^{12}$ are hydrogen atoms,
R$^2$, R$^3$, and R$^1$ each represents a hydrogen atom, a C1-C6 haloalkyl group, a C3-C6 halocycloalkyl group, a C1-C6 haloalkoxy group, a halogen atom, a nitro group, a C1-C6 alkyl group, a C3-C6 cycloalkyl group, a C1-C6 alkoxy group, a C2-C6 alkenyl group, a C2-C6 haloalkenyl group, a C2-C6 alkynyl group, a C2-C6 haloalkynyl group, a C3-C6 alkenyloxy group, a C3-C6 haloalkenyloxy group, a C3-C6 alkynyloxy group, a C3-C6 haloalkynyloxy group, a C1-C6 alkylthio group, or a C1-C6 haloalkylthio group;
or Q is any one of the following structures:

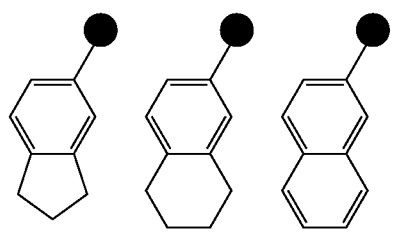

-continued

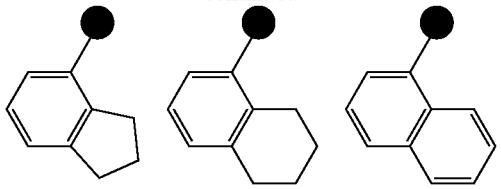

wherein the symbol ○ represents a binding site;
$R^4$, $R^5$, $R^7$, $R^8$, and $R^9$ are hydrogen atoms;
$R^{10}$ is a methyl group;
X is an oxygen atom;
$R^6$ is a C1-C3 alkyl group, a C3-C4 cycloalkyl group, a C1-C3 haloalkyl group, a halogen atom, a methoxy group, or a methylthio group; and
$R^{13}$ is a C1-C4 alkyl group, a C3-C4 cycloalkyl group, a hydrogen atom, a halogen atom, a C2-C4 alkenyl group, a C2-C4 alkynyl group, a C1-C4 alkoxy group, or a C1-C4 alkylthio group;
a compound represented by formula (1-P), wherein
$R^1$ and $R^{12}$ are hydrogen atoms;
$R^2$, $R^3$, and $R^{11}$ each represents a hydrogen atom, a C1-C4 fluoroalkyl group, a C1-C4 fluoroalkoxy group, a halogen atom, a nitro group, a methyl group, or a methoxy group;
or Q is any one of the following structures:

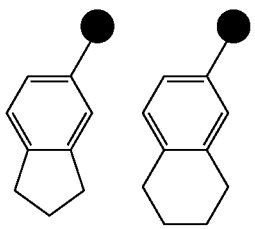

wherein the symbol ○ represents a binding site;
a compound represented by formula (1-P), wherein
$R^1$ and $R^{12}$ are hydrogen atoms;
$R^2$, $R^3$, and $R^1$ each represents a hydrogen atom, a C1-C4 fluoroalkyl group, a C1-C4 fluoroalkoxy group, a halogen atom, a nitro group, a methyl group, or a methoxy group;
or Q is any one of the following structures:

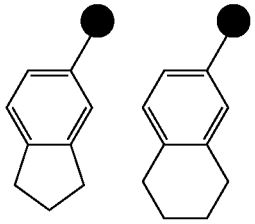

wherein the symbol ○ represents a binding site;
$R^4$, $R^5$, $R^7$, $R^8$, and $R^9$ are hydrogen atoms;
$R^{10}$ is a methyl group;
X is an oxygen atom;
$R^6$ is a C1-C3 alkyl group, a C3-C4 cycloalkyl group, a C1-C3 haloalkyl group, a C3-C4 halocycloalkyl group, a halogen atom, a C2-C3 alkenyl group, a C2-C3 alkynyl group, a C1-C3 alkoxy group, a C1-C3 haloalkoxy group, or a C1-C3 alkylthio group; and $R^{13}$ is a C1-C4 alkyl group, a C3-C4 cycloalkyl group, a hydrogen atom, a halogen atom, a C2-C4 alkenyl group, a C2-C4 alkynyl group, a C1-C4 alkoxy group, or a C1-C4 alkylthio group;
a compound represented by formula (1-P), wherein
$R^1$ and $R^{12}$ are hydrogen atoms;
$R^2$, $R^3$, and $R^{11}$ each represents a hydrogen atom, a C1-C4 fluoroalkyl group, a C1-C4 fluoroalkoxy group, a halogen atom, a nitro group, a methyl group, or a methoxy group;
or Q is any one of the following structures:

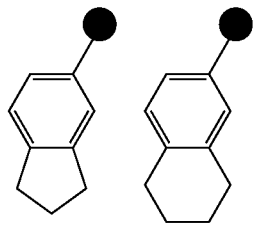

wherein the symbol ○ represents a binding site;
$R^4$, $R^5$, $R^7$, $R^8$, and $R^9$ are hydrogen atoms;
$R^{10}$ is a methyl group;
X is an oxygen atom;
$R^6$ is a C1-C3 alkyl group, a C3-C4 cycloalkyl group, a C1-C3 haloalkyl group, a halogen atom, a methoxy group, or a methylthio group; and $R^{13}$ is a C1-C4 alkyl group, a C3-C4 cycloalkyl group, a hydrogen atom, a halogen atom, a C2-C4 alkenyl group, a C2-C4 alkynyl group, a C1-C4 alkoxy group, or a C1-C4 alkylthio group;
a compound represented by formula (1-P), wherein $R^{11}$ and $R^{12}$ are hydrogen atoms;
$R^2$, $R^3$, and $R^{11}$ each represents a hydrogen atom, a C1-C4 fluoroalkyl group, a C1-C4 fluoroalkoxy group, a halogen atom, a nitro group, a methyl group, or a methoxy group;
or Q is any one of the following structures:

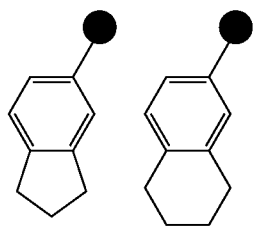

wherein the symbol ○ represents a binding site;
$R^4$, $R^5$, $R^7$, $R^8$, and $R^9$ are hydrogen atoms;
$R^{10}$ is a methyl group;
X is an oxygen atom;
$R^6$ is a methyl group, an ethyl group, a cyclopropyl group, a difluoromethyl group, or a trifluoromethyl group; and
$R^{13}$ is a methyl group, an ethyl group, or a propyl group;
a compound represented by formula (1-P), wherein
$R^1$ and $R^{12}$ represent a hydrogen atoms;
$R^2$, $R^3$, and $R^{11}$ each represents a hydrogen atom, a C1-C4 fluoroalkyl group, a C1-C4 fluoroalkoxy group, a halogen atom, a nitro group, a methyl group, or a methoxy group;

or Q is any one of the following structures:

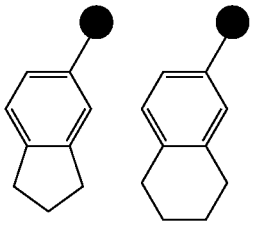

wherein the symbol ○ represents a binding site;
R⁴, R⁵, R⁷, R⁸, and R⁹ are hydrogen atoms;
R¹⁰ is a methyl group;
X is an oxygen atom;
R⁶ is a methyl group, an ethyl group, a cyclopropyl group, a difluoromethyl group, or a trifluoromethyl group; and
R¹³ is a methyl group, an ethyl group, or a propyl group;
a compound represented by formula (1-P), wherein
R¹, R³, R¹¹, and R¹² are hydrogen atoms;
R² is a C1-C4 fluoroalkyl group, a C1-C4 fluoroalkoxy group, or a halogen atom;
or R² and R³ form a five-membered ring or a six-membered ring together with the carbon atom to which they are attached;
a compound represented by formula (1-P), wherein
R¹, R³, R¹¹ and R¹² are hydrogen atoms;
R² is a C1-C4 fluoroalkyl group, a C1-C4 fluoroalkoxy group, or a halogen atom;
or R² and R³ form a five-membered ring or a six-membered ring together with the carbon atom to which they are attached;
R⁴, R⁵, R⁷, R⁸, and R⁹ are hydrogen atoms;
R¹⁰ is a methyl group;
X is an oxygen atom;
R⁶ is a C1-C3 alkyl group, a C3-C4 cycloalkyl group, a C1-C3 haloalkyl group, a halogen atom, a methoxy group, or a methylthio group; and
R¹³ is a C1-C4 alkyl group, a C3-C4 cycloalkyl group, a hydrogen atom, a halogen atom, a C2-C4 alkenyl group, a C2-C4 alkynyl group, a C1-C4 alkoxy group, or a C1-C4 alkylthio group;
a compound represented by formula (1-P), wherein R¹, R³, R¹¹, and R¹² are hydrogen atoms;
R² is a C1-C4 fluoroalkyl group, a C1-C4 fluoroalkoxy group, or a halogen atom;
or R² and R³ form a five-membered ring or a six-membered ring together with the carbon atom to which they are attached;
R⁴, R⁵, R⁷, R⁸, and R⁹ are hydrogen atoms;
R¹⁰ is a methyl group;
X is an oxygen atom;
R⁶ is a methyl group, an ethyl group, a cyclopropyl group, a difluoromethyl group, or a trifluoromethyl group; and
R¹³ is a methyl group, an ethyl group, or a propyl group;
a compound represented by formula (1-P), wherein
R⁶ is a methyl group, an ethyl group, a cyclopropyl group, a difluoromethyl group, or a trifluoromethyl group;
R¹³ is a methyl group, an ethyl group, or a propyl group;
R¹, R³, R¹¹, and R¹² are hydrogen atoms,
R² is a C1-C4 fluoroalkyl group, a C1-C4 fluoroalkoxy group, or a halogen atom;

or Q is any one of the following structures:


wherein the symbol ○ represents a binding site;
a compound represented by formula (1-P), wherein
R⁶ is a C1-C3 alkyl group optionally having one or more halogen atoms, or
a cyclopropyl group;
R¹³ is a C1-C3 alkyl group;
R¹, R³, R¹¹, and R¹² are hydrogen atoms;
R² is a C1-C4 fluoroalkyl group, a C1-C4 fluoroalkoxy group, or a halogen atom;
or Q is any one of the following structures:

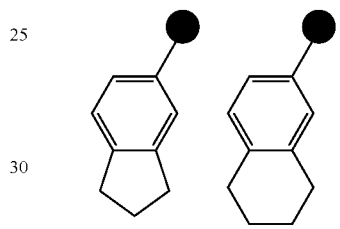

wherein the symbol ○ represents a binding site;
a compound represented by formula (1-P1):

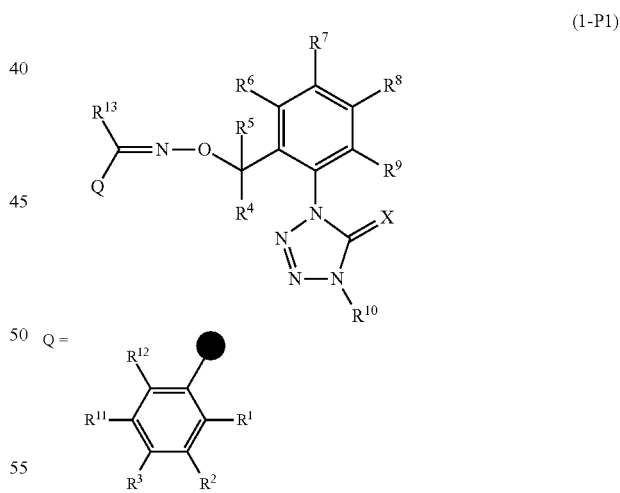

(1-P1)

wherein
R⁴ and R⁵ each represents a hydrogen atom or a C1-C3 alkyl group;
R⁶ represents a C1-C4 alkyl group, a C3-C6 cycloalkyl group, a C1-C4 haloalkyl group, a C3-C6 halocycloalkyl group, a halogen atom, a cyano group, a nitro group, a C2-C4 alkenyl group, a C2-C4 haloalkenyl group, a C2-C4 alkynyl group, a C2-C4 haloalkynyl group, a C1-C4 alkoxy group, a C1-C4 haloalkoxy group, a C1-C4 alkylthio group, or a C1-C4 haloalkylthio group;

$R^7$, $R^8$, and $R^9$ each represents a hydrogen atom or a halogen atom;
$R^{10}$ represents a C1-C3 alkyl group, a C1-C3 haloalkyl group, a C2-C3 alkenyl group, a C2-C3 haloalkenyl group, a C2-C3 alkynyl group, a C2-C3 haloalkynyl group, a C3-C5 cycloalkyl group, or a C3-C5 halocycloalkyl group;
X represents an oxygen atom or a sulfur atom;
$R^{13}$ represents a C1-C6 alkyl group, a C3-C6 cycloalkyl group, a hydrogen atom, a C1-C6 haloalkyl group, a C3-C6 halocycloalkyl group, a C2-C6 alkenyl group, a C2-C6 haloalkenyl group, a C2-C6 alkynyl group, a C2-C6 haloalkynyl group, a C1-C6 alkoxy group, or a C1-C6 alkylthio group;
$R^1$, $R^2$, $R^3$, R, and $R^{12}$ each represents a hydrogen atom, a C1-C6 alkyl group optionally having an atom or a group selected from Group $P^3$,
a C3-C6 cycloalkyl group optionally having an atom or a group selected from Group $P^3$,
a phenyl group (provided that the phenyl group may form a four-membered ring, a five-membered ring, a six-membered ring, or a seven-membered ring together with the adjacent carbon atom, and the ring may contain one or more atoms selected from the group consisting of an oxygen atom, a sulfur atom, and a nitrogen atom as a ring-constituent atom, and the same carbon atom may have an oxo group, a thioxo group, or a C1-C3 alkoxyimino group, and may have one or two oxide groups on the same sulfur atom, and the phenyl group and the ring may have one or more atoms or groups selected from Group $P^2$ and, when the number of atoms or groups selected from Group $P^2$ is two or more, the atoms or groups may be the same or different),
a C1-C6 haloalkoxy group, a halogen atom, a nitro group, a C1-C6 alkoxy group, a C2-C6 alkenyl group, a C2-C6 haloalkenyl group, a C2-C6 alkynyl group, a C2-C6 haloalkynyl group, a C3-C6 alkenyloxy group, a C3-C6 haloalkenyloxy group, a C3-C6 alkynyloxy group, a C3-C6 haloalkynyloxy group, a C1-C8 alkylamino group, a C1-C8 haloalkylamino group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a cyano group, an amino group, a hydroxy group, a mercapto group, a pentafluorosulfanyl group, a C3-C9 trialkylsilyl group, a C2-C6 alkylcarbonyl group, a C2-C6 alkoxycarbonyl group, a C2-C8 alkylaminocarbonyl group, or C2-C8 alkylcarbonylamino group;
or $R^1$ and $R^2$ form a four-membered ring, a five-membered ring, a six-membered ring, or a seven-membered ring together with the carbon atom to which they are attached, and the ring may contain one or more atoms selected from the group consisting of an oxygen atom, a sulfur atom, and a nitrogen atom as a ring-constituent atom, and the ring may have one or more atoms or groups selected from Group $P^4$ as substituent;
$R^2$ and $R^3$ form a four-membered ring, a five-membered ring, a six-membered ring, or a seven-membered ring together with the carbon atom to which they are attached, and the ring may contain one or more atoms selected from the group consisting of an oxygen atom, a sulfur atom, and a nitrogen atom as a ring-constituent atom, and the ring may have one or more atoms or groups selected from Group $P^4$ as a substituent;
or, $R^{12}$ and $R^{13}$ form a five-membered ring, a six-membered ring, or a seven-membered ring together with the carbon atom to which they are attached, and the ring may contain one or more atoms selected from the group consisting of an oxygen atom, a sulfur atom, and a nitrogen atom as a ring-constituent atom, and the ring may have one or more atoms or groups selected from Group $P^4$ as a substituent;
a compound represented by formula (1-P1), wherein
$R^1$, $R^2$, $R^3$, $R^{11}$ and $R^{12}$ each represents a hydrogen atom, C1-C6 alkyl group optionally having an atom or a group selected from Group $P^3$,
C3-C6 cycloalkyl group optionally having an atom or a group selected from Group P,
a C1-C6 haloalkoxy group, a halogen atom, a nitro group, a C1-C6 alkoxy group, a C2-C6 alkenyl group, a C2-C6 haloalkenyl group, a C2-C6 alkynyl group, a C2-C6 haloalkynyl group, a C3-C6 alkenyloxy group, a C3-C6 haloalkenyloxy group, a C3-C6 alkynyloxy group, a C3-C6 haloalkynyloxy group, a C1-C8 alkylamino group, a C1-C8 haloalkylamino group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a cyano group, an amino group, a hydroxy group, a mercapto group, a pentafluorosulfanyl group, a C3-C9 trialkylsilyl group, a C2-C6 alkylcarbonyl group, a C2-C6 alkoxycarbonyl group, a C2-C8 alkylaminocarbonyl group, or a C2-C8 alkylcarbonylamino group;
or $R^1$ and $R^2$ form a four-membered ring, a five-membered ring, a six-membered ring, or a seven-membered ring together with the carbon atom to which they are attached, and the ring may contain one or more atoms selected from the group consisting of an oxygen atom, a sulfur atom, and a nitrogen atom as a ring-constituent atom, and the ring may have one or more atoms or groups selected from Group $P^4$ as a substituent;
or, $R^2$ and $R^3$ form a four-membered ring, a five-membered ring, a six-membered ring, or a seven-membered ring together with the carbon atom to which they are attached, and the ring may have one or more atoms selected from the group consisting of an oxygen atom, a sulfur atom, and a nitrogen atom as a ring-constituent atom, and the ring may have one or more atoms or groups selected from Group $P^4$ as a substituent;
$R^4$ and $R^5$ each represents a hydrogen atom or a C1-C3 alkyl group;
$R^6$ is a C1-C4 alkyl group, a C3-C6 cycloalkyl group, a C1-C4 haloalkyl group, a C3-C6 halocycloalkyl group, a halogen atom, a cyano group, a nitro group, a C2-C4 alkenyl group, a C2-C4 haloalkenyl group, a C2-C4 alkynyl group, a C2-C4 haloalkynyl group, a C1-C4 alkoxy group, a C1-C4 haloalkoxy group, a C1-C4 alkylthio group, or a C1-C4 haloalkylthio group;
$R^7$, $R^8$ and $R^9$ each represents a hydrogen atom or a halogen atom;
$R^{10}$ is a C1-C3 alkyl group, a C1-C3 haloalkyl group, a C2-C3 alkenyl group, a C2-C3 haloalkenyl group, a C2-C3 alkynyl group, a C2-C3 haloalkynyl group, a C3-C5 cycloalkyl group, or a C3-C5 halocycloalkyl group;
X is an oxygen atom or a sulfur atom;
$R^{13}$ is a C1-C6 alkyl group, a C3-C6 cycloalkyl group, a hydrogen atom, a halogen atom, a C1-C6 haloalkyl group, a C3-C6 halocycloalkyl group, a C2-C6 alkenyl group, a C2-C6 haloalkenyl group, a C2-C6 alkynyl group, a C2-C6 haloalkynyl group, a C1-C6 alkoxy group, or a C1-C6 alkylthio group;
or $R^{12}$ and $R^{13}$ form a five-membered ring, a six-membered ring, or a seven-membered ring together with the carbon atom to which they are attached, and the ring may contain one or more atoms selected from the group consisting of an oxygen atom, a sulfur atom, and a nitrogen atom as a ring-constituent atom, and the ring may have one or more atoms or groups selected from Group $P^4$ as a substituent;

a compound represented by formula (1-P1), wherein $R^4$, $R^5$, $R^7$, $R^8$, and $R^9$ are hydrogen atoms;

$R^6$ is a C1-C4 alkyl group, a C3-C6 cycloalkyl group, a C1-C4 haloalkyl group, a halogen atom, a C1-C4 alkoxy group, a C1-C4 haloalkoxy group, or a C1-C4 alkylthio group;

$R^{10}$ is a C1-C3 alkyl group;

X is an oxygen atom;

$R^{13}$ is a C1-C6 alkyl group, a C3-C6 cycloalkyl group, a hydrogen atom, or a C1-C6 alkylthio group;

$R^{12}$ is a hydrogen atom or a C1-C6 alkyl group; or $R^{12}$ and $R^{13}$ form cyclopentane together with the carbon atom to which they are attached;

$R^1$ is a hydrogen atom, a halogen atom, a C1-C6 alkyl group, a C1-C6 haloalkyl group, a C1-C6 alkoxy group, or a phenyl group;

$R^2$ is a hydrogen atom, a C1-C6 alkyl group, a C1-C6 haloalkyl group, a C3-C6 cycloalkyl group, a C1-C6 haloalkoxy group, a halogen atom, a nitro group, a C1-C6 alkoxy group, a C3-C6 alkynyloxy group, a C1-C8 alkylamino group, a C1-C6 alkylthio group, a cyano group, a C2-C8 alkylcarbonylamino group, or a phenyl group;

$R^3$ is a hydrogen atom, a C1-C6 alkoxy group, a C1-C6 haloalkyl group, a C3-C6 cycloalkyl group, a halogen atom, or a phenyl group; or $R^1$ and $R^2$ form a five-membered ring or a six-membered ring together with the carbon atom to which they are attached, and the ring may contain one or more oxygen atoms as a ring-constituent atom, and the ring may have a halogen atom as a substituent; or $R^2$ and $R^3$ form a five-membered ring or a six-membered ring together with the carbon atom to which they are attached, and the ring may contain one or more oxygen atoms as a ring-constituent atom, and the ring may have a halogen atom as a substituent; and $R^{11}$ is a hydrogen atom, a C1-C6 alkyl group, a C1-C6 haloalkyl group, or a halogen atom;

a compound represented by formula (1-P1), wherein $R^4$, $R^5$, $R^7$, $R^8$, and $R^9$ are hydrogen atoms;

$R^6$ is a C1-C3 alkyl group, a C3-C4 cycloalkyl group, a C1-C3 haloalkyl group, a halogen atom, a C1-C3 alkoxy group, a C1-C3 haloalkoxy group, or a C1-C3 alkylthio group;

$R^{10}$ is a methyl group;

X is an oxygen atom;

$R^{13}$ is a C1-C3 alkyl group, a C3-C4 cycloalkyl group, a hydrogen atom, or a C1-C4 alkylthio group;

$R^{12}$ is a hydrogen atom or a C1-C6 alkyl group;

$R^1$ is a hydrogen atom, a halogen atom, a C1-C6 alkyl group, a C1-C6 haloalkyl group, a C1-C6 alkoxy group, or a phenyl group;

$R^2$ is a hydrogen atom, a C1-C6 haloalkyl group, a C1-C6 haloalkoxy group, a halogen atom, a nitro group, a C1-C6 alkyl group, a C3-C6 cycloalkyl group, a C1-C6 alkoxy group, a C3-C6 alkynyloxy group, a C1-C6 alkylthio group, or a phenyl group;

$R^3$ is a hydrogen atom, a C1-C6 alkoxy group, a C1-C6 haloalkyl group, a C3-C6 cycloalkyl group, or a halogen atom; or $R^1$ and $R^2$ form a four-membered ring, a five-membered ring, a six-membered ring, or a seven-membered ring together with the carbon atom to which they are attached, and the ring may contain one or more atoms selected from the group consisting of an oxygen atom, a sulfur atom, and a nitrogen atom as a ring-constituent atom, and the ring may have atoms or groups selected from Group $P^4$ as a substituent; or $R^2$ and $R^3$ form a four-membered ring, a five-membered ring, a six-membered ring, or a seven-membered ring together with the carbon atom to which they are attached, and the ring may contain one or more oxygen atoms, sulfur atoms, or nitrogen atoms as the ring-constituent atom, and the ring may have one or more atoms or groups selected from Group $P^4$ as a substituent;

$R^{11}$ is a hydrogen atom, a C1-C6 alkyl group, a C1-C6 haloalkyl group, or a halogen atom;

a compound represented by formula (1-P1), wherein $R^4$, $R^5$, $R^7$, $R^8$, and $R^9$ are hydrogen atoms;

$R^6$ is a C1-C3 alkyl group, a C3-C4 cycloalkyl group, a C1-C3 haloalkyl group, a halogen atom, a C1-C3 alkoxy group, a C1-C3 haloalkoxy group, or a C1-C3 alkylthio group;

$R^{10}$ is a methyl group;

X is an oxygen atom;

$R^{13}$ is a C1-C3 alkyl group, a C3-C4 cycloalkyl group, a hydrogen atom, or a C1-C4 alkylthio group;

$R^{12}$ is a hydrogen atom or a C1-C6 alkyl group;

$R^1$ is a hydrogen atom, a halogen atom, a C1-C6 alkyl group, a C1-C6 haloalkyl group, a C1-C6 alkoxy group, or a phenyl group;

$R^2$ is a hydrogen atom, a C1-C6 haloalkyl group, a C1-C6 haloalkoxy group, a halogen atom, a nitro group, a C1-C6 alkyl group, a C3-C6 cycloalkyl group, a C1-C6 alkoxy group, a C3-C6 alkynyloxy group, a C1-C6 alkylthio group, or a phenyl group;

$R^3$ is a hydrogen atom, a C1-C6 alkoxy group, a C1-C6 haloalkyl group, a C3-C6 cycloalkyl group, or a halogen atom; or $R^1$ and $R^2$ form a five-membered ring or a six-membered ring together with the carbon atom to which they are attached, and the ring may contain one or more oxygen atoms as the ring-constituent atom; or, $R^2$ and $R^3$ form a five-membered ring or a six-membered ring together with the carbon atom to which they are attached, and $R^{11}$ is a hydrogen atom, a C1-C6 alkyl group, a C1-C6 haloalkyl group, or a halogen atom;

a compound represented by formula (1-P1), wherein $R^4$, $R^5$, $R^7$, $R^8$, $R^9$, $R^{11}$, and $R^{12}$ are hydrogen atoms;

$R^{10}$ is a methyl group;

X is an oxygen atom;

$R^6$ is a C1-C3 alkyl group optionally having one or more halogen atoms, a C3-C4 cycloalkyl group optionally having one or more halogen atoms, a C1-C3 alkoxy group optionally having one or more halogen atoms, or a halogen atom;

$R^{13}$ is a C1-C4 alkyl group;

$R^3$ is a hydrogen atom or a C1-C3 alkoxy group optionally having one or more halogen atoms, and $R^1$ and $R^2$ form a four-membered ring or a five-membered ring together with the carbon atom to which they are attached, the ring may contain one or two atoms selected from the group consisting of an oxygen atom, a sulfur atom, and a nitrogen atom as a ring-constituent atom, and the ring may have one or more halogen atoms as a substituent;

a compound represented by formula (1-P1), wherein $R^4$, $R^5$, $R^7$, $R^8$, $R^9$, $R^{11}$, and $R^{12}$ are hydrogen atoms;

$R^{10}$ is a methyl group;

X is an oxygen atom;

$R^6$ is a C1-C3 alkyl group optionally having one or more halogen atoms;

$R^{13}$ is a C1-C4 alkyl group;

$R^3$ is a hydrogen atom or a C1-C3 alkoxy group optionally having one or more halogen atoms, and
$R^1$ and $R^2$ form a four-membered ring or a five-membered ring together with the carbon atom to which they are attached, the ring may contain one or two atoms selected from the group consisting of an oxygen atom, a sulfur atom, and a nitrogen atom as a ring-constituent atom, and the ring may have one or more halogen atoms as a substituent;
a compound represented by formula (1-P1), wherein
$R^4$, $R^5$, $R^7$, $R^8$, $R^9$, $R^{11}$, and $R^{12}$ are hydrogen atoms;
$R^{10}$ is a methyl group;
X is an oxygen atom;
$R^6$ is a C3-C4 cycloalkyl group optionally having one or more halogen atoms;
$R^{13}$ is a C1-C4 alkyl group;
$R^3$ is a hydrogen atom or a C1-C3 alkoxy group optionally having one or more halogen atoms, and
$R^1$ and $R^2$ form a four-membered ring or a five-membered ring together with the carbon atom to which they are attached, and the ring may contain one or two atoms selected from the group consisting of an oxygen atom, a sulfur atom, and a nitrogen atom as a ring-constituent atom, and the ring may have one or more halogen atoms as a substituent;
a compound represented by formula (1-P1), wherein
$R^4$, $R^5$, $R^7$, $R^8$, $R^9$, $R^{11}$, and $R^{12}$ are hydrogen atoms;
$R^{10}$ is a methyl group;
X is an oxygen atom;
$R^6$ is a C1-C3 alkoxy group optionally having one or more halogen atoms;
$R^{13}$ is a C1-C4 alkyl group;
$R^3$ is a hydrogen atom or a C1-C3 alkoxy group optionally having one or more halogen atoms, and
$R^1$ and $R^2$ form a four-membered ring or a five-membered ring together with the carbon atom to which they are attached, the ring may contain one or two atoms selected from the group consisting of an oxygen atom, a sulfur atom, and a nitrogen atom as a ring-constituent atom, and the ring may have one or more halogen atoms as a substituent;
a compound represented by formula (1-P1), wherein
$R^4$, $R^5$, $R^7$, $R^8$, $R^9$, $R^{11}$, and $R^{12}$ are hydrogen atoms;
$R^{10}$ is a methyl group;
X is an oxygen atom;
$R^6$ is a halogen atom;
$R^{13}$ is a C1-C4 alkyl group;
$R^3$ is a hydrogen atom or a C1-C3 alkoxy group optionally having one or more halogen atoms, and
$R^1$ and $R^2$ form a four-membered ring or a five-membered ring together with the carbon atom to which they are attached, the ring may contain one or two atoms selected from the group consisting of an oxygen atom, a sulfur atom, and a nitrogen atom as a ring-constituent atom, and the ring may have one or more halogen atoms as a substituent;
a compound represented by formula (1-P1), wherein
$R^4$, $R^5$, $R^7$, $R^8$, $R^9$, $R^{11}$, and $R^{12}$ are hydrogen atoms;
$R^{10}$ is a methyl group;
X is an oxygen atom;
$R^6$ is a C1-C3 alkyl group, a C3-C4 cycloalkyl group, a C1-C3 haloalkyl group, a halogen atom, or a methoxy group;
$R^{13}$ is a C1-C3 alkyl group;
$R^1$ and $R^2$ are combined to form -E-CH$_2$—CH$_2$— (provided that E is combined with a carbon atom to which $R^2$ is attached, and represents CH$_2$ or an oxygen atom); and
$R^3$ is a hydrogen atom or a C1-C3 alkoxy group optionally having one or more halogen atoms;
a compound represented by formula (1-P1), wherein
$R^4$, $R^5$, $R^7$, $R^8$, $R^9$, $R^{11}$, and $R^{12}$ are hydrogen atoms;
$R^{10}$ is a methyl group;
X is an oxygen atom;
$R^6$ is a C1-C3 alkyl group;
$R^{13}$ is a C1-C3 alkyl group;
$R^1$ and $R^2$ are combined to form -E-CH$_2$—CH$_2$—; and
$R^3$ is a hydrogen atom or a C1-C3 alkoxy group optionally having one or more halogen atoms;
a compound represented by formula (1-P1), wherein
$R^4$, $R^5$, $R^7$, $R^8$, $R^9$, $R^{11}$, and $R^{12}$ are hydrogen atoms;
$R^{10}$ is a methyl group;
X is an oxygen atom;
$R^6$ is a C3-C4 cycloalkyl group;
$R^{13}$ is a C1-C3 alkyl group;
$R^1$ and $R^2$ are combined to form -E-CH$_2$—CH$_2$—; and
$R^3$ is a hydrogen atom or a C1-C3 alkoxy group optionally having one or more halogen atoms;
a compound represented by formula (1-P1), wherein
$R^4$, $R^5$, $R^7$, $R^8$, $R^9$, $R^{11}$, and $R^{12}$ are hydrogen atoms; $R^{10}$ is a methyl group;
X is an oxygen atom;
$R^6$ is a C1-C3 haloalkyl group;
$R^{13}$ is a C1-C3 alkyl group;
$R^1$ and $R^2$ are combined to form -E-CH$_2$—CH$_2$—; and
$R^3$ is a hydrogen atom or a C1-C3 alkoxy group optionally having one or more halogen atoms;
a compound represented by formula (1-P1), wherein
$R^4$, $R^5$, $R^7$, $R^8$, $R^9$, $R^{11}$, and $R^{12}$ are hydrogen atoms;
$R^{10}$ is a methyl group;
X is an oxygen atom;
$R^6$ is a halogen atom;
$R^{13}$ is a C1-C3 alkyl group;
$R^1$ and $R^2$ are combined to form -E-CH$_2$—CH$_2$—; and
$R^3$ is a hydrogen atom or a C1-C3 alkoxy group optionally having one or more halogen atoms;
a compound represented by formula (1-P1), wherein
$R^4$, $R^5$, $R^7$, $R^8$, $R^9$, $R^{11}$, and $R^{12}$ are hydrogen atoms;
$R^{10}$ is a methyl group;
X is an oxygen atom;
$R^6$ is a methoxy group;
$R^{13}$ is a C1-C3 alkyl group;
$R^1$ and $R^2$ are combined to form -E-CH$_2$—CH$_2$—; and
$R^3$ is a hydrogen atom or a C1-C3 alkoxy group optionally having one or more halogen atoms;
a compound represented by formula (1-P1), wherein
$R^4$, $R^5$, $R^7$, $R^8$, $R^9$, $R^{11}$, and $R^{12}$ are hydrogen atoms;
$R^{10}$ is a methyl group;
X is an oxygen atom;
$R^6$ is a C1-C3 alkyl group, a C3-C4 cycloalkyl group, a C1-C3 haloalkyl group, a halogen atom, or a methoxy group;
$R^{13}$ is a C1-C3 alkyl group;
$R^1$ and $R^2$ are combined to form -E-CH$_2$—CH$_2$—; and
$R^3$ is a hydrogen atom or a methoxy group;
a compound represented by formula (1-P1), wherein
$R^4$, $R^5$, $R^7$, $R^8$, $R^9$, $R^{11}$, and $R^{12}$ are hydrogen atoms;
$R^{10}$ is a methyl group;
X is an oxygen atom;
$R^6$ is a C1-C3 alkyl group;
$R^{13}$ is a C1-C3 alkyl group;
$R^1$ and $R^2$ are combined to form -E-CH$_2$—CH$_2$—; and
$R^3$ is a hydrogen atom or a methoxy group;
a compound represented by formula (1-P1), wherein
$R^4$, $R^5$, $R^7$, $R^8$, $R^9$, $R^{11}$, and $R^{12}$ are hydrogen atoms;
$R^{10}$ is a methyl group;
X is an oxygen atom;
$R^6$ is a C3-C4 cycloalkyl group;
$R^{13}$ is a C1-C3 alkyl group;

$R^1$ and $R^2$ are combined to form -E-CH$_2$—CH$_2$—; and
$R^3$ is a hydrogen atom or a methoxy group;
a compound represented by formula (1-P1), wherein
$R^4$, $R^5$, $R^7$, $R^8$, $R^9$, $R^1$, and $R^1$ are hydrogen atoms;
$R^{10}$ is a methyl group;
X is an oxygen atom;
$R^6$ is a C1-C3 haloalkyl group;
$R^{13}$ is a C1-C3 alkyl group;
$R^1$ and $R^2$ are combined to form -E-CH$_2$—CH$_2$—; and
$R^3$ is a hydrogen atom or a methoxy group;
a compound represented by formula (1-P1), wherein
$R^4$, $R^5$, $R^7$, $R^8$, R, $R^{11}$, and $R^{12}$ are hydrogen atoms;
$R^{10}$ is a methyl group;
X is an oxygen atom;
$R^6$ is a halogen atom;
$R^{13}$ is a C1-C3 alkyl group;
$R^1$ and $R^2$ are combined to form -E-CH$_2$—CH$_2$—; and
$R^3$ is a hydrogen atom or a methoxy group;
a compound represented by formula (1-P1), wherein
$R^4$, $R^5$, $R^7$, $R^8$, $R^9$, $R^{11}$, and $R^{12}$ are hydrogen atoms;
$R^{10}$ is a methyl group;
X is an oxygen atom;
$R^6$ is a methoxy group;
$R^{13}$ is a C1-C3 alkyl group;
$R^1$ and $R^2$ are combined to form -E-CH$_2$—CH$_2$—; and
$R^3$ is a hydrogen atom or a methoxy group;
a compound represented by formula (1-Q):

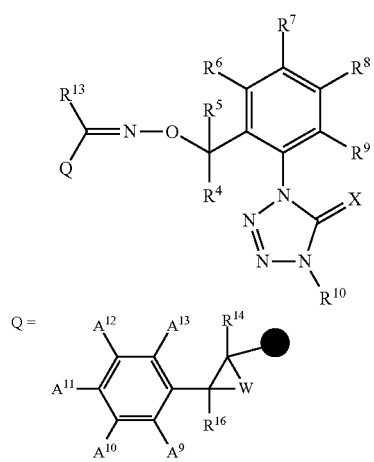

(1-Q)

wherein W represents CR$^{17}$R$^{18}$ or an oxygen atom;
$R^{14}$, $R^{16}$, $R^{17}$, and $R^{18}$ each represents a hydrogen atom, a halogen atom, or a C1-C3 alkyl group optionally having one or more halogen atoms;
$A^9$, $A^{10}$, $A^{11}$, $A^{12}$, and $A^{13}$ each represents a hydrogen atom, a halogen atom,
a cyano group, or a nitro group,
a C1-C3 alkyl group optionally having one or more halogen atoms,
a C3-C4 cycloalkyl group optionally having one or more halogen atoms,
a C1-C3 alkoxy group optionally having one or more halogen atoms, or
a C1-C3 alkylthio group optionally having one or more halogen atoms; and
the symbol ○ represents a binding site;
a compound represented by formula (1-Q), wherein
W is a CH$_2$;
$R^4$, $R^5$, $R^7$, $R^8$, $R^9$, $R^{14}$, and $R^{16}$ are hydrogen atoms;
$R^{10}$ is a methyl group;
X is an oxygen atom;
$R^6$ is a C1-C3 alkyl group optionally having one or more halogen atoms,
a C3-C4 cycloalkyl group optionally having one or more halogen atoms, or a halogen atom;
$R^{13}$ is a C1-C3 alkyl group; and
$A^9$, $A^{10}$, $A^{11}$, $A^{12}$, and $A^{13}$ each represents a hydrogen atom or a halogen atom;
a compound represented by formula (1-Q), wherein
W is a CH$_2$;
$R^4$, $R^5$, $R^7$, $R^8$, $R^9$, $R^4$, and $R^{16}$ are hydrogen atoms;
$R^{10}$ is a methyl group;
X is an oxygen atom;
$R^6$ is a C1-C3 alkyl group optionally having one or more halogen atoms;
$R^{13}$ is a C1-C3 alkyl group; and
$A^9$, $A^{10}$, $A^{11}$, $A^{12}$, and $A^{13}$ each represents a hydrogen atom or a halogen atom;
a compound represented by formula (1-Q), wherein
W is a CH$_2$;
$R^4$, $R^5$, $R^7$, $R^8$, $R^9$, $R^1$, and $R^1$ are hydrogen atoms;
$R^{10}$ is a methyl group;
X is an oxygen atom;
$R^6$ is a C3-C4 cycloalkyl group optionally having one or more halogen atoms;
$R^{13}$ is a C1-C3 alkyl group; and
$A^9$, $A^{10}$, $A^{11}$, $A^{12}$, and $A^{13}$ each represents a hydrogen atom or halogen atom;
a compound represented by formula (1-Q), wherein
W is a CH$_2$;
$R^4$, $R^5$, $R^7$, $R^8$, R, $R^{14}$, and $R^{16}$ are hydrogen atoms;
$R^{10}$ is a methyl group;
X is an oxygen atom;
$R^6$ is a halogen atom;
$R^{13}$ is a C1-C3 alkyl group; and
$A^9$, $A^{10}$, $A^{11}$, $A^{12}$, and $A^{13}$ each represents a hydrogen atom or a halogen atom;
a compound represented by formula (1-Q), wherein
W is a CH$_2$;
$R^4$, $R^5$, $R^7$, $R^8$, $R^9$, $R^4$, and $R^{16}$ are hydrogen atoms;
$R^{10}$ is a methyl group;
X is an oxygen atom;
$R^6$ is a C1-C3 alkyl group;
$R^{13}$ is a C1-C3 alkyl group; and
$A^9$, $A^{10}$, $A^{11}$, $A^{12}$, and $A^{13}$ each represents a hydrogen atom or a halogen atom;
a compound represented by formula (1-Q), wherein
W is a CH$_2$;
$R^4$, $R^5$, $R^7$, $R^8$, $R^9$, $R^{14}$, and $R^{16}$ are hydrogen atoms;
$R^6$ and $R^{13}$ are methyl groups;
X is an oxygen atom;
$R^6$ is a C1-C3 alkyl group; and
$A^9$, $A^{10}$, $A^{11}$, $A^{12}$, and $A^{13}$ each represents a hydrogen atom or a halogen atom;
a compound represented by formula (1-Q), wherein
W is a CH$_2$;
$R^4$, $R^5$, $R^7$, $R^8$, $R^9$, $R^1$, and $R^{16}$ are hydrogen atoms;
$R^6$ and $R^{10}$ are methyl groups;
X is an oxygen atom;
$R^{13}$ is a C1-C3 alkyl group; and
$A^9$, $A^{10}$, $A^{11}$, $A^{12}$, and $A^{13}$ each represents a hydrogen atom or halogen atom;
a compound represented by formula (1-Q), wherein
W is a CH$_2$;
$R^4$, $R^5$, $R^7$, $R^8$, $R^9$, $R^{14}$, and $R^{16}$ are hydrogen atoms;

$R^6$, $R^{10}$, and $R^{13}$ are methyl groups;
X is an oxygen atom; and
$A^9$, $A^{10}$, $A^{11}$, $A^{12}$, and $A^{13}$ each represents a hydrogen atom or a halogen atom;
a compound represented by formula (1-Q), wherein
W is a $CH_2$;
$R^4$, $R^5$, R, R, $R^9$, $R^{14}$, $R^{16}$, $A^{10}$, and $A^{12}$ are hydrogen atoms;
$R^{10}$ is a methyl group;
X is an oxygen atom;
$R^6$ is a C1-C3 alkyl group optionally having one or more halogen atoms,
a C3-C4 cycloalkyl group optionally having one or more halogen atoms, or a halogen atom;
$R^{13}$ is a C1-C3 alkyl group; and
$A^9$, $A^{11}$, and $A^{13}$ are hydrogen atoms or halogen atoms;
a compound represented by formula (1-Q), wherein
W is a $CH_2$;
$R^4$, $R^5$, $R^7$, $R^8$, $R^9$, $R^{14}$, $R^{16}$, $A^{10}$, and $A^{12}$ are hydrogen atoms;
$R^{10}$ is a methyl group;
X is an oxygen atom;
$R^6$ is a C1-C3 alkyl group optionally having one or more halogen atoms;
$R^{13}$ is a C1-C3 alkyl group; and
$A^9$, $A^{11}$, and $A^{13}$ are hydrogen atoms or halogen atoms;
a compound represented by formula (1-Q), wherein
W is a $CH_2$;
$R^4$, $R^5$, $R^7$, $R^8$, $R^9$, $R^{14}$, $R^{16}$, $A^{10}$, and $A^{12}$ are hydrogen atoms;
$R^{10}$ is a methyl group;
X is an oxygen atom;
$R^6$ is a C3-C4 cycloalkyl group optionally having one or more halogen atoms;
$R^{13}$ is a C1-C3 alkyl group; and
$A^9$, $A^{11}$, and $A^{13}$ are hydrogen atoms or halogen atoms;
a compound represented by formula (1-Q), wherein
W is a $CH_2$;
$R^4$, $R^5$, $R^7$, $R^8$, $R^9$, $R^{14}$, $R^{16}$, $A^{10}$, and $A^{12}$ are hydrogen atoms;
$R^{10}$ is a methyl group;
X is an oxygen atom;
$R^6$ is a halogen atom;
$R^{13}$ is a C1-C3 alkyl group; and
$A^9$, $A^{11}$, and $A^{13}$ are hydrogen atoms or halogen atoms;
a compound represented by formula (1-Q), wherein
W is a $CH_2$;
$R^4$, $R^5$, $R^7$, $R^8$, $R^9$, $R^{14}$, $R^{16}$, $A^{10}$, and $A^{12}$ are hydrogen atoms;
$R^{10}$ is a methyl group;
X is an oxygen atom;
$R^6$ is a C1-C3 alkyl group;
$R^{13}$ is a C1-C3 alkyl group; and
$A^9$, $A^{11}$, and $A^{13}$ are hydrogen atoms or halogen atoms;
a compound represented by formula (1-Q), wherein
W is a $CH_2$;
$R^4$, $R^5$, $R^7$, $R^8$, $R^9$, $R^{14}$, $R^{16}$, $A^{10}$, and $A^{12}$ are hydrogen atoms;
$R^{10}$ is a methyl group;
X is an oxygen atom;
$R^6$ is a methyl group;
$R^{13}$ is a methyl group; and
$A^9$, $A^{11}$, and $A^{13}$ are hydrogen atoms or halogen atoms;

a compound represented by formula (1-R):

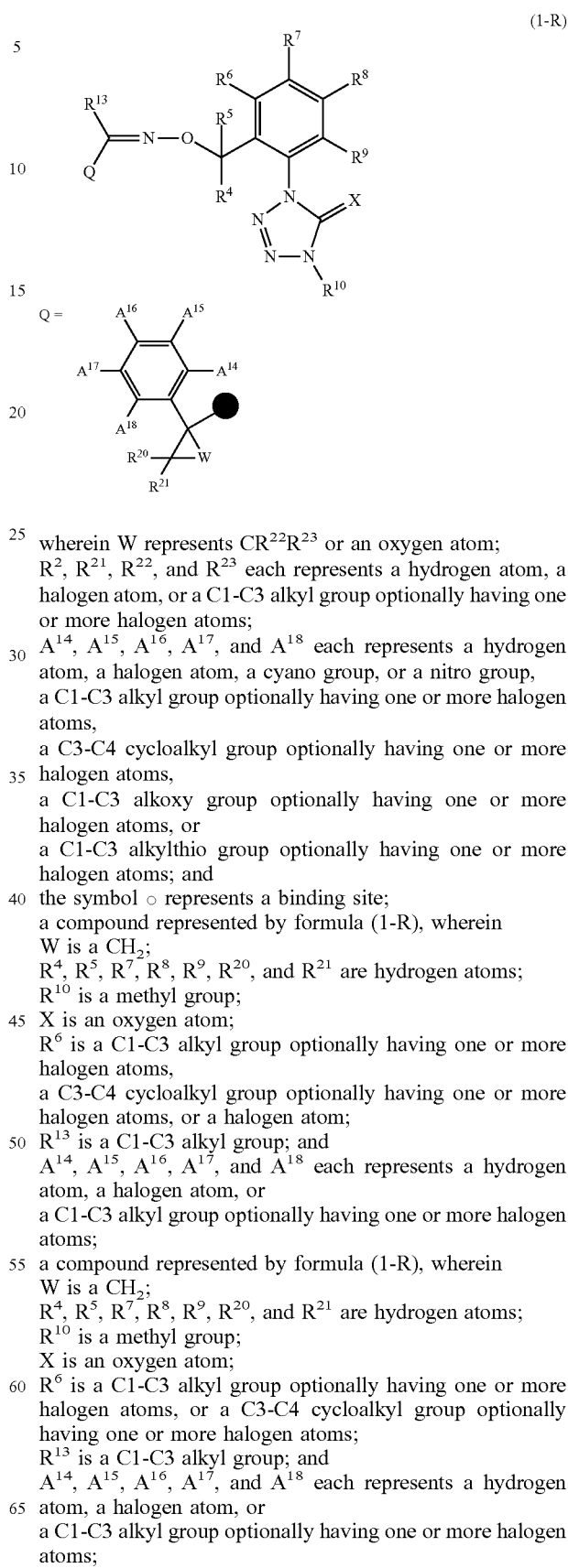

(1-R)

wherein W represents $CR^{22}R^{23}$ or an oxygen atom;
$R^2$, $R^{21}$, $R^{22}$, and $R^{23}$ each represents a hydrogen atom, a halogen atom, or a C1-C3 alkyl group optionally having one or more halogen atoms;
$A^{14}$, $A^{15}$, $A^{16}$, $A^{17}$, and $A^{18}$ each represents a hydrogen atom, a halogen atom, a cyano group, or a nitro group,
a C1-C3 alkyl group optionally having one or more halogen atoms,
a C3-C4 cycloalkyl group optionally having one or more halogen atoms,
a C1-C3 alkoxy group optionally having one or more halogen atoms, or
a C1-C3 alkylthio group optionally having one or more halogen atoms; and
the symbol ○ represents a binding site;
a compound represented by formula (1-R), wherein
W is a $CH_2$;
$R^4$, $R^5$, $R^7$, $R^8$, $R^9$, $R^{20}$, and $R^{21}$ are hydrogen atoms;
$R^{10}$ is a methyl group;
X is an oxygen atom;
$R^6$ is a C1-C3 alkyl group optionally having one or more halogen atoms,
a C3-C4 cycloalkyl group optionally having one or more halogen atoms, or a halogen atom;
$R^{13}$ is a C1-C3 alkyl group; and
$A^{14}$, $A^{15}$, $A^{16}$, $A^{17}$, and $A^{18}$ each represents a hydrogen atom, a halogen atom, or
a C1-C3 alkyl group optionally having one or more halogen atoms;
a compound represented by formula (1-R), wherein
W is a $CH_2$;
$R^4$, $R^5$, $R^7$, $R^8$, $R^9$, $R^{20}$, and $R^{21}$ are hydrogen atoms;
$R^{10}$ is a methyl group;
X is an oxygen atom;
$R^6$ is a C1-C3 alkyl group optionally having one or more halogen atoms, or a C3-C4 cycloalkyl group optionally having one or more halogen atoms;
$R^{13}$ is a C1-C3 alkyl group; and
$A^{14}$, $A^{15}$, $A^{16}$, $A^{17}$, and $A^{18}$ each represents a hydrogen atom, a halogen atom, or
a C1-C3 alkyl group optionally having one or more halogen atoms;

a compound represented by formula (1-R), wherein
W is a $CH_2$;
$R^4, R^5, R^7, R^8, R^9, R^{20}$, and $R^{21}$ are hydrogen atoms;
$R^{10}$ is a methyl group;
X is an oxygen atom;
$R^6$ is a C1-C3 alkyl group optionally having one or more halogen atoms;
$R^{13}$ is a C1-C3 alkyl group; and
$A^{14}, A^{15}, A^{16}, A^{17}$, and $A^{18}$ each represents a hydrogen atom, a halogen atom, or
a C1-C3 alkyl group optionally having one or more halogen atoms;
a compound represented by formula (1-R), wherein
W is a $CH_2$;
$R^4, R^5, R^7, R^8, R^9, R^{20}$, and $R^{21}$ are hydrogen atoms;
$R^{10}$ is a methyl group;
X is an oxygen atom;
$R^6$ is a C1-C3 alkyl group optionally having one or more halogen atoms,
a C3-C4 cycloalkyl group optionally having one or more halogen atoms,
or
a halogen atom;
$R^{13}$ is a C1-C3 alkyl group; and
$A^{14}, A^{15}, A^{16}, A^{17}$, and $A^{18}$ each represents a hydrogen atom, a halogen atom, or
a C1-C3 alkyl group optionally having one or more halogen atoms;
a compound represented by formula (1-R), wherein
W is a $CH_2$;
$R^4, R^5, R^7, R^8, R^9, R^{20}, R^{21}, A^{14}, A^{17}$, and $A^{18}$ are hydrogen atoms;
$R^{10}$ is a methyl group;
X is an oxygen atom;
$R^6$ is a C1-C3 alkyl group optionally having one or more halogen atoms, or a C3-C4 cycloalkyl group optionally having one or more halogen atoms;
$R^{13}$ is a C1-C3 alkyl group;
$A^{15}$ is a hydrogen atom or a C1-C3 alkyl group optionally having one or more halogen atoms; and
$A^{16}$ is a hydrogen atom or a halogen atom;
a compound represented by formula (1-R), wherein
W is a $CH_2$;
$R^4, R^5, R^7, R^8, R^9, R^{20}, R^{21}, A^{14}, A^{17}$, and $A^{18}$ are hydrogen atoms;
$R^{10}$ is a methyl group;
X is an oxygen atom;
$R^6$ is a C1-C3 alkyl group optionally having one or more halogen atoms;
$R^{13}$ is a C1-C3 alkyl group;
$A^{15}$ is a hydrogen atom or a C1-C3 alkyl group optionally having one or more halogen atoms, and
$A^{16}$ is a hydrogen atom or a halogen atom;
a compound represented by formula (1-S):

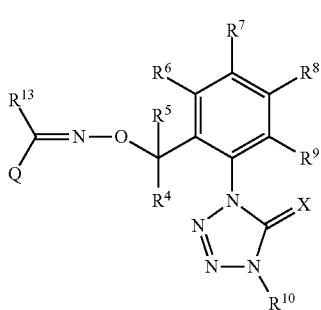

(1-S)

Q =

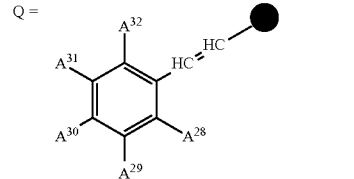

-continued wherein $A^{28}, A^{29}$, A, A, and $A^{32}$ each represents a hydrogen atom, a
halogen atom, a cyano group, or a nitro group,
a C1-C3 alkyl group optionally having one or more halogen atoms,
a C3-C4 cycloalkyl group optionally having one or more halogen atoms,
a C1-C3 alkoxy group optionally having one or more halogen atoms, or
a C1-C3 alkylthio group optionally having one or more halogen atoms; and
the symbol ○ represents a binding site;
a compound represented by formula (1-S), wherein
$R^4, R^5, R^7, R^8$, and $R^9$ are hydrogen atoms;
$R^{10}$ is a methyl group;
X is an oxygen atom;
$R^6$ is a C1-C3 alkyl group optionally having one or more halogen atoms,
a C3-C4 cycloalkyl group optionally having one or more halogen atoms, or
a halogen atom;
$R^{13}$ is a C1-C3 alkyl group; and
$A^{28}, A^{29}, A^{30}, A^{31}$, and $A^{32}$ each represents a hydrogen atom, a halogen atom or
a C1-C3 alkyl group optionally having one or more halogen atoms;
a compound represented by formula (1-S), wherein
$R^4, R^5, R^7, R^8$, and $R^9$ are hydrogen atoms;
$R^{10}$ is a methyl group;
X is an oxygen atom;
$R^6$ is a C1-C3 alkyl group optionally having one or more halogen atoms;
$R^{13}$ is a C1-C3 alkyl group; and
$A^{28}, A^{29}, A^{30}, A^{31}$, and $A^{32}$ each represents a hydrogen atom, a halogen atom, or
a C1-C3 alkyl group optionally having one or more halogen atoms;
a compound represented by formula (1-S), wherein
$R^4, R^5, R^7, R^8$, and $R^9$ are hydrogen atoms;
$R^{10}$ is a methyl group;
X is an oxygen atom;
$R^6$ is a C3-C4 cycloalkyl group optionally having one or more halogen atoms;
$R^{13}$ is a C1-C3 alkyl group; and
$A^{28}, A^{29}, A^{30}, A^{31}$, and $A^{32}$ each represents a hydrogen atom, a halogen atom, or
a C1-C3 alkyl group optionally having one or more halogen atoms;
a compound represented by formula (1-S), wherein
$R^4, R^5, R^7, R^8$, and $R^9$ are hydrogen atoms;
$R^{10}$ is a methyl group;
X is an oxygen atom;
$R^6$ is a halogen atom;
$R^{13}$ is a C1-C3 alkyl group; and
$A^{28}, A^{29}, A^{30}, A^{31}$, and $A^{32}$ each represents a hydrogen atom, a halogen atom, or a C1-C3 alkyl group optionally having one or more halogen atoms;
a compound represented by formula (1-S), wherein
$R^4$, $R^5$, $R^7$, $R^8$, and $R^9$ are hydrogen atoms;
$R^{10}$ is a methyl group;
X is an oxygen atom;
$R^6$ and $R^{13}$ are C1-C3 alkyl groups; and
$A^{28}$, $A^{29}$, $A^{30}$, $A^{31}$, and $A^{32}$ each represents a hydrogen atom, a halogen atom, or
a C1-C3 alkyl group optionally having one or more halogen atoms;
a compound represented by formula (1-S), wherein
$R^4$, $R^5$, $R^7$, $R^8$, and $R^9$ are hydrogen atoms;
$R^6$ and $R^{10}$ are methyl groups;
X is an oxygen atom;
$R^{13}$ is a C1-C3 alkyl group; and
$A^2$, $A^{29}$, A, $A^{31}$, and $A^{32}$ each represents a hydrogen atom, a halogen atom, or
a C1-C3 alkyl group optionally having one or more halogen atoms;
a compound represented by formula (1-S), wherein
$R^4$, $R^5$, $R^7$, $R^8$, and $R^9$ are hydrogen atoms;
$R^{10}$ and $R^{13}$ are methyl groups;
X is an oxygen atom;
$R^6$ is a C1-C3 alkyl group; and
$A^2$, $A^{29}$, A, $A^{31}$, and $A^{32}$ each represents a hydrogen atom, a halogen atom, or
a C1-C3 alkyl group optionally having one or more halogen atoms;
a compound represented by formula (1-S), wherein
$R^4$, $R^5$, $R^7$, $R^8$, and $R^9$ are hydrogen atoms;
$R^6$, $R^{10}$, and $R^{13}$ are methyl groups;
X is an oxygen atom; and
$A^{28}$, $A^{29}$, A, $A^{31}$, and $A^{32}$ each represents a hydrogen atom, a halogen atom, or
a C1-C3 alkyl group optionally having one or more halogen atoms;
a compound represented by formula (1-S), wherein
$R^4$, $R^5$, $R^7$, $R^8$, $R^9$, $A^{29}$, and $A^{31}$ are hydrogen atoms;
$R^{10}$ is a methyl group;
X is an oxygen atom;
$R^6$ is a C1-C3 alkyl group optionally having one or more halogen atoms,
a C3-C4 cycloalkyl group optionally having one or more halogen atoms, or
a halogen atom;
$R^{13}$ is a C1-C3 alkyl group; and
$A^{28}$, $A^{30}$, and $A^{32}$ are hydrogen atoms or halogen atoms;
a compound represented by formula (1-S), wherein
$R^4$, $R^5$, $R^7$, $R^8$, $R^9$, $A^{29}$, and $A^{31}$ are hydrogen atoms;
$R^{10}$ is a methyl group;
X is an oxygen atom;
$R^6$ is a C1-C3 alkyl group optionally having one or more halogen atoms;
$R^{13}$ is a C1-C3 alkyl group; and
$A^{28}$, $A^{30}$, and $A^{32}$ are hydrogen atoms or halogen atoms;
a compound represented by formula (1-S), wherein
$R^4$, $R^5$, $R^7$, $R^8$, $R^9$, $A^{29}$, and $A^{31}$ are hydrogen atoms;
$R^{10}$ is a methyl group;
X is an oxygen atom;
$R^6$ is a C3-C4 cycloalkyl group optionally having one or more halogen atoms;
$R^{13}$ is a C1-C3 alkyl group; and
$A^{28}$, $A^{30}$, and $A^{32}$ are hydrogen atoms or halogen atoms;
a compound represented by formula (1-S), wherein
$R^4$, $R^5$, $R^7$, $R^8$, $R^9$, $A^{29}$, and $A^{31}$ are hydrogen atoms;
$R^{10}$ is a methyl group;

X is an oxygen atom;
$R^6$ is a halogen atom;
$R^{13}$ is a C1-C3 alkyl group; and
$A^{28}$, $A^{30}$, and $A^{32}$ are hydrogen atoms or halogen atoms;
a compound represented by formula (1-S), wherein
$R^4$, $R^5$, $R^7$, $R^8$, $R^9$, $A^{29}$, and $A^{31}$ are hydrogen atoms;
$R^{10}$ is a methyl group;
X is an oxygen atom;
$R^6$ and $R^{13}$ are C1-C3 alkyl groups; and
$A^{28}$, $A^{29}$, $A^{30}$, $A^{31}$, and $A^{32}$ each represents a hydrogen atom, a halogen atom, or
a C1-C3 alkyl group optionally having one or more halogen atoms;
a compound represented by formula (1-S), wherein
$R^4$, $R^5$, $R^7$, $R^8$, $R^9$, $A^{29}$, and $A^{31}$ are hydrogen atoms;
$R^6$ and $R^{10}$ are methyl groups;
X is an oxygen atom;
$R^{13}$ is a C1-C3 alkyl group; and
$A^{28}$, $A^{30}$, and $A^{32}$ are hydrogen atoms or halogen atoms;
a compound represented by formula (1-S), wherein
$R^4$, $R^5$, $R^7$, $R^8$, $R^9$, $A^{29}$, and $A^{31}$ are hydrogen atoms;
$R^{10}$ and $R^{13}$ are methyl groups;
X is an oxygen atom;
$R^6$ is a C1-C3 alkyl group; and
$A^{28}$, $A^{30}$, and $A^{32}$ is a hydrogen atom or halogen atom;
a compound represented by formula (1-S), wherein
$R^4$, $R^5$, $R^7$, $R^8$, $R^9$, $A^{29}$, and $A^{31}$ are hydrogen atoms;
$R^6$, $R^{10}$, and $R^{13}$ are methyl groups;
X is an oxygen atom;
$A^{28}$, $A^{30}$, and $A^{32}$ are hydrogen atoms or halogen atoms;
a compound represented by formula (1-T):

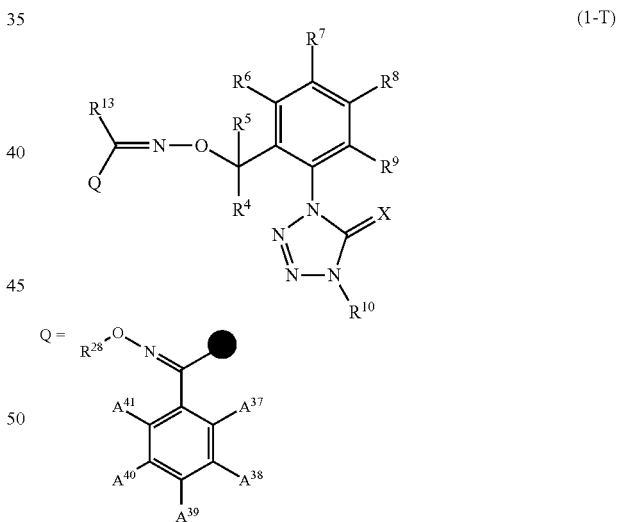

(1-T)

wherein $A^{37}$, $A^{38}$, $A^{39}$, $A^{40}$, and $A^{41}$ each represents a hydrogen atom, a halogen atom, a cyano group, or a nitro group,
a C1-C3 alkyl group optionally having one or more halogen atoms,
a C3-C4 cycloalkyl group optionally having one or more halogen atoms,
a C1-C3 alkoxy group optionally having one or more halogen atoms, or
a C1-C3 alkylthio group optionally having one or more halogen atoms; and
the symbol o represents a binding site;

a compound represented by formula (1-T), wherein
$R^4$, $R^5$, $R^7$, $R^8$, and $R^9$ are hydrogen atoms;
$R^{10}$ is a methyl group;
X is an oxygen atom;
$R^{28}$ is a C1-C3 alkyl group;
$R^6$ is a C1-C3 alkyl group optionally having one or more halogen atoms,
a C3-C4 cycloalkyl group optionally having one or more halogen atoms, or a halogen atom;
$R^{13}$ is a C1-C3 alkyl group; and
$A^3$, $A^{38}$, $A^{39}$, $A^{40}$ and $A^{41}$ each represents a hydrogen atom or halogen atom;
a compound represented by formula (1-T), wherein
$R^4$, $R^5$, $R^7$, $R^8$, and $R^9$ are hydrogen atoms;
$R^{10}$ is a methyl group;
X is an oxygen atom;
$R^{28}$ is a C1-C3 alkyl group;
$R^6$ is a C1-C3 alkyl group optionally having one or more halogen atoms;
$R^{13}$ is a C1-C3 alkyl group; and
$A^{37}$, $A^{38}$, $A^{39}$, $A^{40}$ and $A^{41}$ each represents a hydrogen atom or halogen atom;
a compound represented by formula (1-T), wherein
$R^4$, $R^5$, $R^7$, $R^8$, and $R^9$ are hydrogen atoms;
$R^{10}$ is a methyl group;
X is an oxygen atom;
$R^{28}$ is a C1-C3 alkyl group;
$R^6$ is a C3-C4 cycloalkyl group optionally having one or more halogen atoms;
$R^{13}$ is a C1-C3 alkyl group; and
$A^3$, $A^{38}$, $A^{39}$, $A^{40}$, and $A^{41}$ each represents a hydrogen atom or a halogen atom;
a compound represented by formula (1-T), wherein
$R^4$, $R^5$, $R^7$, $R^8$, and $R^9$ are hydrogen atoms;
$R^{10}$ is a methyl group;
X is an oxygen atom;
$R^{28}$ is a C1-C3 alkyl group;
$R^6$ is a halogen atom;
$R^{13}$ is a C1-C3 alkyl group; and
$A^{37}$, $A^{38}$, $A^{39}$, $A^{40}$, and $A^{41}$ each represents a hydrogen atom or a halogen atom;
a compound represented by formula (1-T), wherein
$R^4$, $R^5$, $R^7$, $R^8$, and $R^9$ are hydrogen atoms;
$R^{10}$ is a methyl group;
X is an oxygen atom;
$R^6$, $R^{13}$, and $R^{28}$ are C1-C3 alkyl groups; and
$A^{37}$, $A^{38}$, $A^{39}$, $A^{40}$, and $A^{41}$ each represents a hydrogen atom or halogen atom;
a compound represented by formula (1-T), wherein
$R^4$, $R^5$, $R^7$, $R^8$, and $R^9$ are hydrogen atoms;
$R^6$, $R^{10}$, $R^{13}$, and $R^{28}$ are methyl groups;
X is an oxygen atom; and
$A^{37}$, $A^{38}$, $A^{39}$, $A^{40}$, and $A^{41}$ each represents a hydrogen atom or halogen atom;
a compound represented by formula (1-T), wherein
$R^4$, $R^5$, $R^7$, R, $R^9$, $A^{37}$, $A^{38}$, $A^{40}$, and $A^{41}$ are hydrogen atoms;
$R^{10}$ is a methyl group;
X is an oxygen atom;
$R^{28}$ is a C1-C3 alkyl group;
$R^6$ is a C1-C3 alkyl group optionally having one or more halogen atoms,
a C3-C4 cycloalkyl group optionally having one or more halogen atoms, or a halogen atom;
$R^{13}$ is a C1-C3 alkyl group; and
$A^{39}$ is a hydrogen atom or a halogen atom;

a compound represented by formula (1-T), wherein
$R^4$, $R^5$, $R^7$, $R^8$, $R^9$, $A^{37}$, $A^{38}$, $A^{40}$, and $A^{41}$ are hydrogen atoms;
$R^{10}$ is a methyl group;
X is an oxygen atom;
$R^{13}$ and $R^{28}$ are C1-C3 alkyl groups;
$R^6$ is a halogen atom; and
$A^{39}$ is a hydrogen atom or a halogen atom;
a compound represented by formula (1-T), wherein
$R^4$, $R^5$, $R^7$, $R^8$, $R^9$, $A^{37}$, $A^{38}$, $A^{40}$, and $A^{41}$ are hydrogen atoms;
$R^{10}$ is a methyl group;
X is an oxygen atom;
$R^6$, $R^{13}$, and $R^{28}$ are C1-C3 alkyl groups; and
$A^{39}$ is a hydrogen atom or a halogen atom;
a compound represented by formula (1-T), wherein
$R^4$, $R^5$, $R^7$, $R^8$, $R^9$, $A^{37}$, $A^{38}$, $A^{40}$, and $A^{41}$ are hydrogen atoms;
$R^6$, $R^{10}$, $R^{13}$, and $R^{28}$ are methyl groups;
X is an oxygen atom; and
$A^{39}$ is a hydrogen atom or a halogen atom;
a compound represented by formula (1-V):

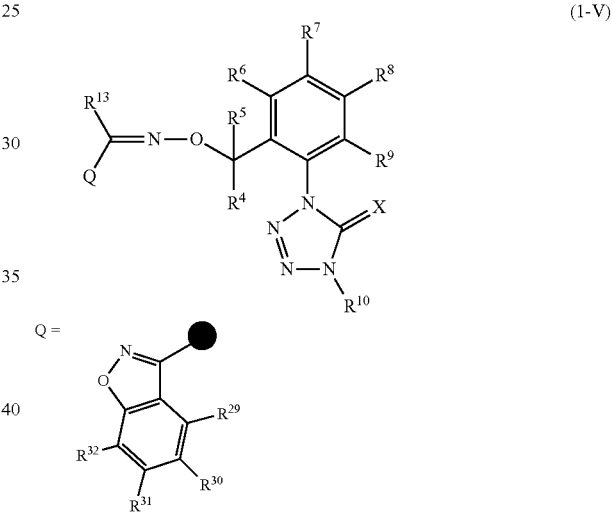

wherein $R^{29}$, $R^{30}$, $R^{31}$, and $R^{32}$ each represents a hydrogen atom, a halogen atom, a cyano group, a nitro group,
a C1-C3 alkyl group optionally having one or more halogen atoms,
a C3-C4 cycloalkyl group optionally having one or more halogen atoms,
a C1-C3 alkoxy group optionally having one or more halogen atoms, or
a C1-C3 alkylthio group optionally having one or more halogen atoms; and
the symbol o represents a binding site;
a compound represented by formula (1-V), wherein
$R^4$, $R^5$, $R^7$, $R^8$, and $R^9$ are hydrogen atoms;
$R^{10}$ is a methyl group;
X is an oxygen atom;
$R^6$ is a C1-C3 alkyl group optionally having one or more halogen atoms,
a C3-C4 cycloalkyl group optionally having one or more halogen atoms, or a halogen atom;
$R^{13}$ is a C1-C3 alkyl group; and
$R^{29}$, $R^{30}$, $R^{31}$, and $R^{32}$ each represents a hydrogen atom or a halogen atom;

a compound represented by formula (1-V), wherein
$R^4$, $R^5$, $R^7$, $R^8$, $R^1$, $R^{29}$, $R^{30}$, and $R^{32}$ are hydrogen atoms;
$R^{10}$ is a methyl group;
X is an oxygen atom;
$R^6$ is a C1-C3 alkyl group optionally having one or more halogen atoms,
a C3-C4 cycloalkyl group optionally having one or more halogen atoms, or a halogen atom;
$R^{13}$ is a C1-C3 alkyl group; and
$R^{31}$ is a halogen atom;
a compound represented by formula (1-V), wherein
$R^4$, $R^5$, $R^7$, $R^8$, and $R^9$ are hydrogen atoms;
$R^{10}$ is a methyl group;
X is an oxygen atom;
$R^6$ is a C1-C3 alkyl group optionally having one or more halogen atoms;
$R^{13}$ is a C1-C3 alkyl group; and
$R^{29}$, $R^{30}$, $R^{31}$, and $R^{32}$ each represents a hydrogen atom or a halogen atom;
a compound represented by formula (1-V), wherein
$R^4$, $R^5$, $R^7$, $R^8$, and $R^9$ are hydrogen atoms;
$R^{10}$ is a methyl group;
X is an oxygen atom;
$R^6$ is a C3-C4 cycloalkyl group optionally having one or more halogen atoms;
$R^{13}$ is a C1-C3 alkyl group; and
$R^{29}$, $R^{30}$, $R^{31}$, and $R^{32}$ each represents a hydrogen atom or halogen atom;
a compound represented by formula (1-V), wherein
$R^4$, $R^5$, $R^7$, $R^8$, and $R^9$ are hydrogen atoms;
$R^{10}$ is a methyl group;
X is an oxygen atom;
$R^6$ is a halogen atom;
$R^{13}$ is a C1-C3 alkyl group; and
$R^{29}$, $R^{30}$, $R^{31}$, and $R^{32}$ each represents a hydrogen atom or a halogen atom;
a compound represented by formula (1-V), wherein
$R^4$, $R^5$, $R^7$, $R^8$, $R^9$, $R^{29}$, $R^{30}$, and $R^{32}$ are hydrogen atoms;
$R^{10}$ is a methyl group;
X is an oxygen atom;
$R^6$ is a C1-C3 alkyl group optionally having one or more halogen atoms;
$R^{13}$ is a C1-C3 alkyl group; and
$R^{31}$ is a halogen atom;
a compound represented by formula (1-V), wherein
$R^4$, $R^5$, $R^7$, $R^8$, $R^1$, $R^{29}$, $R^{30}$, and $R^{32}$ are hydrogen atoms;
$R^{10}$ is a methyl group;
X is an oxygen atom;
$R^6$ is a C3-C4 cycloalkyl group optionally having one or more halogen atoms;
$R^{13}$ is a C1-C3 alkyl group; and
$R^{31}$ is a halogen atom;
a compound represented by formula (1-V), wherein
$R^4$, $R^5$, $R^7$, $R^8$, $R^1$, $R^{29}$, $R^{30}$, and $R^{32}$ are hydrogen atoms;
$R^{10}$ is a methyl group;
X is an oxygen atom;
$R^6$ is a halogen atom;
$R^{13}$ is a C1-C3 alkyl group; and
$R^{31}$ is a halogen atom;
a compound represented by formula (2), wherein
$R^{6L}$ is a C1-C3 alkyl group optionally having one or more halogen atoms;
$R^{13L}$ is a C1-C3 alkyl group;

Q is the following structure:

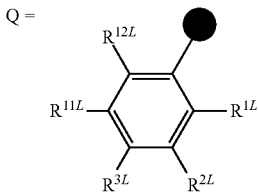

wherein $R^{1L}$ and $R^{2L}$ are combined to form -E-$CH_2$—$CH_2$— (provided that $E^L$ is combined with the carbon atom to which $R^{2L}$ is attached, and represents $CH_2$ or an oxygen atom); and
$L^1$ is the following structure:

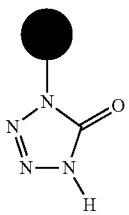

wherein the symbol ○ represents a binding site,
a nitro group, an amino group, an isocyanate group, a carboxyl group,
or a halocarbonyl group;
a compound represented by formula (2), wherein
$R^{6L}$ is a C1-C3 alkyl group optionally having one or more halogen atoms;
$R^{13L}$ is a C1-C3 alkyl group;
Q is the following structure:

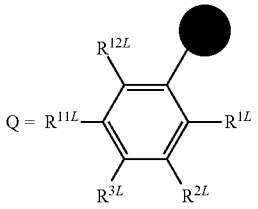

wherein $R^{1L}$ and $R^{2L}$ are combined to form -$E^L$-$CH_2$—$CH_2$—; and
$L^1$ is the following structure:

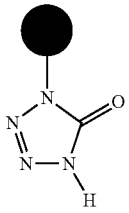

wherein the symbol ○ represents a binding site,
a nitro group, an amino group, or an isocyanate group;
a compound represented by formula (2), wherein
$R^{6L}$ is a C1-C3 alkyl group;
$R^{13L}$ is a C1-C3 alkyl group;

Q is the following structure:

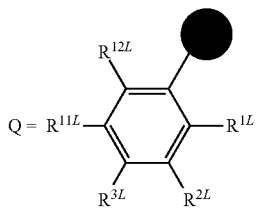

wherein $R^{1L}$ and $R^{2L}$ are combined to form $-E^L-CH_2-CH_2-$; and
$L^1$ is the following structure:

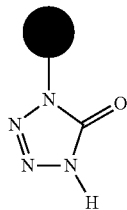

wherein the symbol ○ represents a binding site,
a nitro group, an amino group, an isocyanate group, a carboxyl group, or a halocarbonyl group; and
a compound represented by formula (2), wherein
$R^{6L}$ is a C1-C3 alkyl group;
$R^{13L}$ is a C1-C3 alkyl group; and
Q is the following structure:

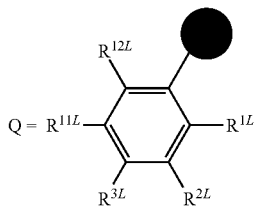

wherein $R^{1L}$ and $R^{2L}$ are combined to form $-E^L-CH_2-CH_2-$;
$L^1$ is the following structure:

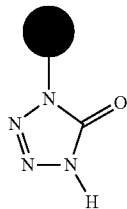

wherein the symbol ○ represents a binding site,
a nitro group, an amino group, or an isocyanate group.

As used herein, compounds represented by general formulas include individual stereoisomers and stereoisomer mixtures, such as all active geometrical isomers and optical isomers.

Next, a process for producing the present compound will be described.

The present compound can be produced by, for example, the following Production Processes.
(Production Process A)
The present compound represented by formula (1) can be produced by reacting a compound represented by formula (A-1) (hereinafter referred to as a compound (A-1)) with a compound represented by formula (A-2) (hereinafter referred to as a compound (A-2)) in the presence of a base:

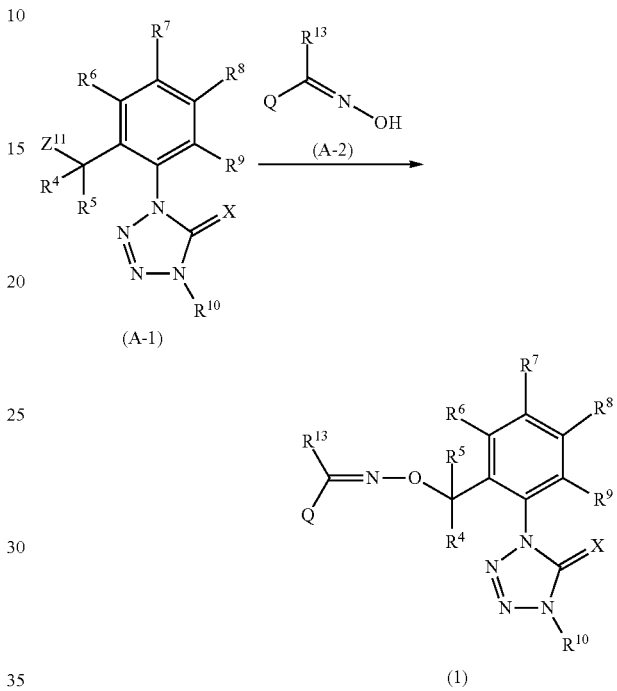

wherein $R^4$, $R^5$, $R^6$, $R^7$, $R^8$, $R^9$, $R^{10}$, $R^{13}$, Q, and X are as defined above, and $Z^1$ represents a leaving group such as a chlorine atom, a bromine atom, an iodine atom, a methanesulfonyloxy group, a trifluoromethanesulfonyloxy group, or a p-toluenesulfonyloxy group.

The reaction is usually performed in a solvent.

Examples of the solvent include hydrocarbons such as heptane, hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; water; and mixtures thereof.

Examples of the base include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; and alkali metal alkoxides such as sodium tert-butoxide and potassium tert-butoxide.

In the reaction, the compound (A-2) is usually used in the proportion within a range of 1 to 10 mols, and the base is usually used in the proportion within a range of 1 to 10 mols, based on 1 mol of the compound (A-1).

The reaction temperature is usually within a range of −20 to 150° C. The reaction time is usually within a range of 0.1 to 24 hours.

If necessary, sodium iodide, tetrabutylammonium iodide, and the like may be added in the reaction, and these compounds are usually used in the proportion of 0.001 to 1.2 mols based on 1 mol of the compound (A-1).

After completion of the reaction, the present compound represented by formula (1) can be isolated by performing post-treatment operations such as extraction of the reaction mixture with an organic solvent, and drying and concentration of the organic layer. The present compound represented by formula (1) can also be isolated by performing post-treatment operations such as filtration and concentration of the reaction mixture. The isolated present compound can be further purified by chromatography, recrystallization, and the like.

(Production Process B)

The present compound represented by formula (1) can be produced by reacting a compound represented by formula (B-1) (hereinafter referred to as a compound (B-1)) with a compound represented by formula (B-2) (hereinafter referred to as a compound (B-2)) in the presence of a base:

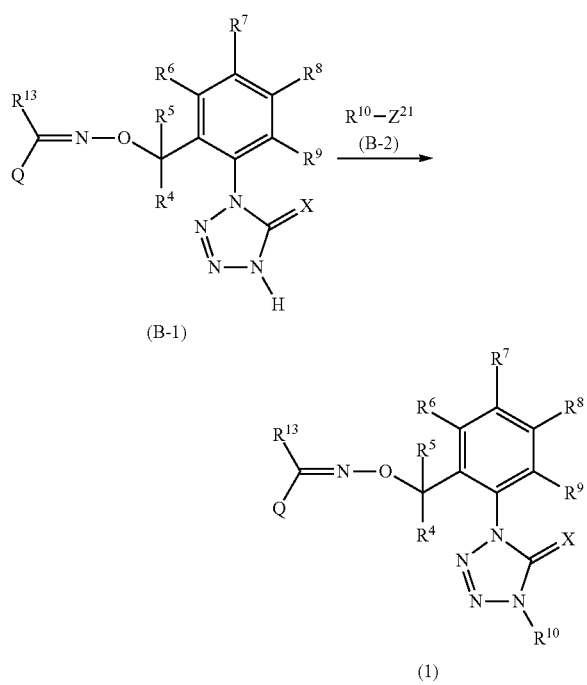

wherein $R^4$, $R^5$, $R^6$, $R^7$, $R^8$, $R^9$, $R^{10}$, $R^{13}$, Q, and X are as defined above, and $Z^{21}$ represents a leaving group such as a chlorine atom, a bromine atom, an iodine atom, a methanesulfonyloxy group, a methoxysulfonyloxy group, a trifluoromethanesulfonyloxy group, or a p-toluenesulfonyloxy group.

The reaction is usually performed in a solvent.

Examples of the solvent include hydrocarbons such as heptane, hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; water; and mixtures thereof.

It is possible to usually use, as the compound (B-2), commercially available compounds. Examples thereof include alkyl halides such as chlorodifluoromethane, methyl bromide, ethyl bromide, propyl bromide, methyl iodide, ethyl iodide, propyl bromide, allyl bromide, cyclopropyl bromide, and 1,1-difluoro-2-iodoethane; and alkyl or aryl sulfate esters such as dimethyl sulfate, methyl p-toluenesulfonate, ethyl p-toluenesulfonate, propyl p-toluenesulfonate, methyl methanesulfonate, ethyl methanesulfonate, and propyl methanesulfonate.

Examples of the base include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; alkali metal hydrides such as lithium hydride, sodium hydride, and potassium hydride; and alkali metal alkoxides such as sodium tert-butoxide, and potassium tert-butoxide.

In the reaction, the compound (B-2) is usually used in the proportion within a range of 1 to 10 mols, and the base is usually used in the proportion within a range of 1 to 10 mols, based on 1 mol of the compound (B-1).

The reaction temperature is usually within a range of −20 to 150° C. The reaction time is usually within a range of 0.1 to 24 hours.

After completion of the reaction, the present compound represented by formula (1) can be isolated by performing post-treatment operations such as extraction of the reaction mixture with an organic solvent, and drying and concentration of the organic layer. The present compound represented by formula (1) can also be isolated by performing post-treatment operations such as filtration and concentration of the reaction mixture. The isolated present compound can be further purified by chromatography, recrystallization, and the like.

(Production Process C)

Among the present compounds represented by formula (1), a compound represented by formula (1-S) in which X is a sulfur atom (hereinafter referred to as a compound (1-S)) can be produced from a compound in which X is an oxygen atom (hereinafter referred to as a compound (1-O)) among the present compounds represented by formula (1) by a known sulfidation reaction:

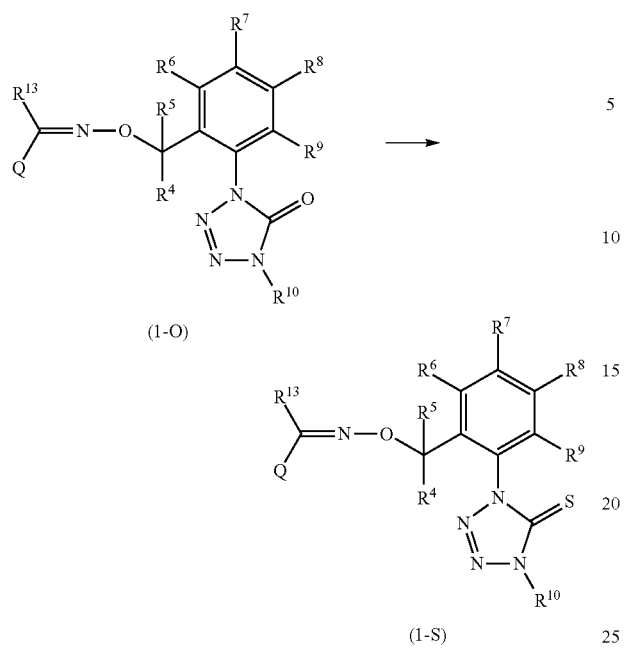

(1-O)

(1-S)

wherein $R^4$, $R^5$, $R^6$, $R^7$, $R^8$, $R^9$, $R^1$, R, and Q are as defined above.

The reaction is usually performed in a solvent.

Examples of the solvent include hydrocarbons such as heptane, hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; nitriles such as acetonitrile; and mixtures thereof.

Examples of the sulfurizing agent include phosphorous pentasulfide and Lawesson's reagent (2,4-Bis(4-methoxyphenyl)-1,3,2,4-dithiadiphosphetane 2,4-disulfide).

In the reaction, the sulfurizing agent is usually used in the proportion within a range of 0.5 to 10 mols based on 1 mol of the compound (1-O).

The reaction temperature is usually within a range of −20 to 150° C.

The reaction time is usually within a range of 0.1 to 24 hours.

In the reaction, if necessary, organic bases such as pyridine and triethylamine; and inorganic bases such as alkali metal hydroxide and alkali metal carbonate may be added, and the amount of the base to be added is usually within a range of 0.5 to 10 mols based on the compound (1-O).

After completion of the reaction, the present compound represented by formula (1-S) can be isolated by performing post-treatment operations such as extraction of the reaction mixture with an organic solvent, and drying and concentration of the organic layer. Alternatively, the present compound represented by formula (1-S) can be isolated by performing post-treatment operations such as filtration and concentration of the reaction mixture. The isolated present compound can be further purified by chromatography, recrystallization, and the like.

(Production Process D)

Among the present compounds represented by formula (1), a compound represented by formula (1-4-1) in which $R^6$ is $R^{41}$ (hereinafter referred to as a compound (1-4-1)) can be produced by subjecting a compound represented by formula (D-1) (hereinafter referred to as a compound (D-1)) and a compound represented by formula (D-2) (hereinafter referred to as a compound (D-2)) to a coupling reaction in the presence of a base and a catalyst:

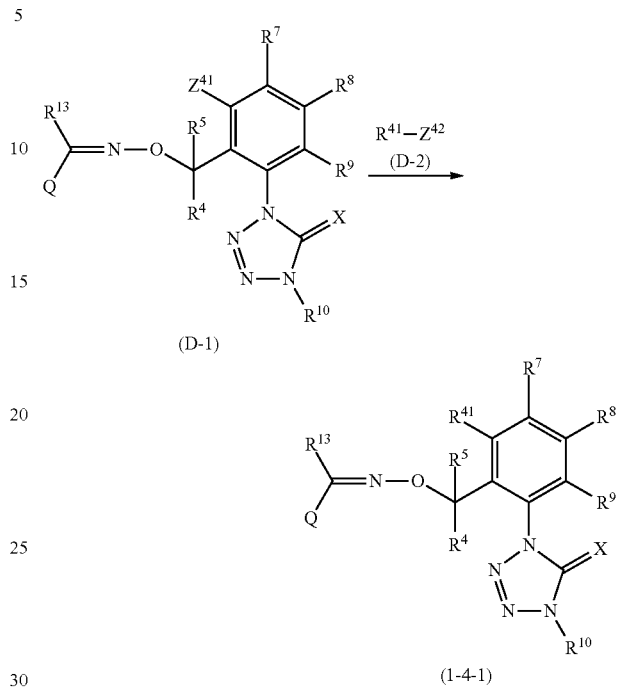

(D-1)

(1-4-1)

wherein $R^4$, $R^5$, $R^7$, $R^8$, $R^9$, $R^{10}$, $R^{13}$, Q, and X are as defined above, $Z^{41}$ represents a chlorine atom, a bromine atom, an iodine atom, or a trifluoromethanesulfonyloxy group, $R^{41}$ represents a C1-C4 alkyl group, a C1-C4 haloalkyl group, a C2-C4 alkenyl group, a C2-C4 haloalkenyl group, a C3-C6 cycloalkyl group, or a C3-C6 halocycloalkyl group, and $Z^{42}$ represents $B(OH)_2$, an alkoxyboryl group, or a trifluoroborate salt $BF_3^-K^-$.

The reaction is usually performed in a solvent.

Examples of the solvent include hydrocarbons such as heptane, hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; alcohols such as methanol, ethanol, propanol, and butanol; water; and mixtures thereof.

It is possible to usually use, as the compound (D-2), commercially available compounds, or those produced by a known method mentioned in N. Miyaura and A. Suzuki, Chem. Rev., 1995, 95, 2457. Regarding the compound (D-2) used in the reaction, borate ester derivatives can be produced by reacting ($R^{41}$—I) or ($R^{41}$—Br) with an alkyllithium such as butyllithium, followed by reaction with a borate ester. It is also possible to produce boronic acid derivatives by hydrolyzing the borate ester derivatives obtained by the above reaction, if necessary. It is also possible to obtain a trifluoroborate salt $BF_3$—K by fluorinating the borate ester with potassium hydrogenfluoride in accordance with a known method mentioned in Molander et al., Acc. Chem. Res., 2007, 40, 275.

Examples of the catalyst include palladium(II) acetate, dichlorobis(triphenylphosphine)palladium, tetrakistriphenylphosphinepalladium(0), palladium(II) acetate/triscyclohexylphosphine, bis(diphenylphoshineferrocenyl)palladium (II) dichloride, 1,3-bis(2,6-diisopropylphenyl)imidazol-2-ylidene (1,4-naphthoquinone)palladium dimer, aryl(chloro)(1,3-dimethyl-1,3-dihydro-2H-imidazol-2-ylidene) palladium, or palladium(II) acetate/dicyclohexyl(2',4',6'-triisopropylbiphenyl-2-yl)phosphine, and tris (dibenzylideneacetone)dipalladium.

Examples of the base include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; alkali metal phosphates such as tripotassium phosphate; and alkali metal alkoxides such as sodium ethoxide and potassium tert-butoxide.

In the reaction, the compound (D-2) is usually used in the proportion within a range of 1 to 10 mols, the base is usually used in the proportion within a range of 1 to 10 mols, and the catalyst is usually used in the proportion within a range of 0.0001 to 1 mol, based on 1 mol of the compound (D-1).

The reaction temperature is usually within a range of 0 to 150° C. The reaction time is usually within a range of 0.1 to 24 hours.

After completion of the reaction, the present compound represented by formula (1-4-1) can be isolated by performing post-treatment operations such as extraction of the reaction mixture with an organic solvent, and drying and concentration of the organic layer. Alternatively, the present compound represented by formula (1-4-1) can be isolated by performing post-treatment operations such as filtration and concentration of the reaction mixture. The isolated present compound can be further purified by chromatography, recrystallization, and the like.

According to the process for producing the compound (1-4-1), a compound represented by formula (1-4-2) in which $R^7$ is $R^{42}$ (hereinafter referred to as a compound (1-4-2)) among the present compounds represented by formula (1) can be produced by subjecting a compound represented by formula (D-3) (hereinafter referred to as a compound (D-3)) and a compound represented by formula (D-4) (hereinafter referred to as a compound (D-4)) to a coupling reaction in the presence of a base and a catalyst:

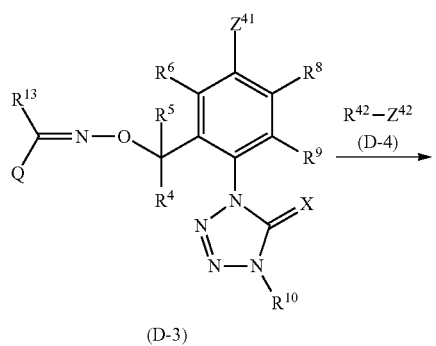

(D-3)

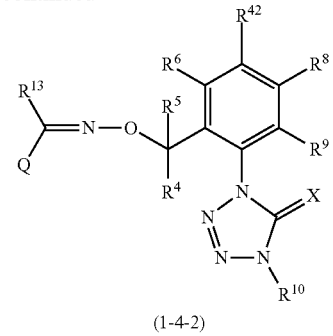

(1-4-2)

wherein $R^4$, $R^5$, $R^6$, $R^8$, $R^9$, $R^{10}$, $R^{13}$, Q, X, $Z^{41}$, and $Z^{42}$ are as defined above, and $R^{42}$ represents a C1-C3 alkyl group, a C1-C3 haloalkyl group, a C2-C3 alkenyl group, or a C2-C3 haloalkenyl group.

According to the process for producing the compound (1-4-1), a compound represented by formula (1-4-3) in which $R^8$ is $R^{42}$ (hereinafter referred to as a compound (1-4-3)) among the present compounds represented by formula (1) can be produced by subjecting a compound represented by formula (D-5) (hereinafter referred to as a compound (D-5)) and the compound (D-4) to a coupling reaction in the presence of a base and a catalyst:

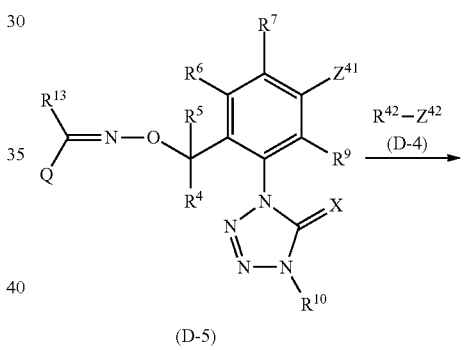

(D-5)

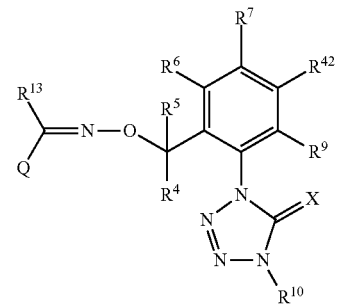

(1-4-3)

wherein $R^4$, $R^5$, $R^6$, $R^8$, $R^9$, $R^{10}$, $R^{13}$, $R^{42}$, Q, X, $Z^{41}$, and $Z^{42}$ are as defined above.

According to the process for producing the compound (1-4-1), a compound represented by formula (1-4-4) in which $R^9$ is $R^{42}$ (hereinafter referred to as a compound (1-4-4)) among the present compounds represented by formula (1) can be produced by subjecting a compound represented by formula (D-6) (hereinafter referred to as a compound (D-6)) and a compound (hereinafter referred to as a compound (D-4)) to a coupling reaction in the presence of a base and a catalyst:

127

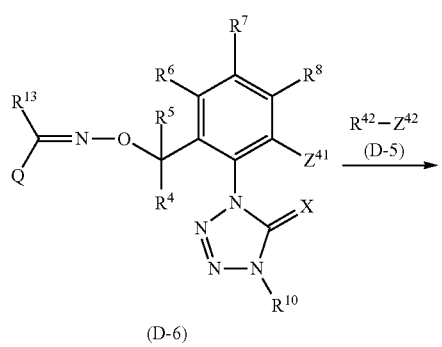

(D-6)

$R^{42}$—$Z^{42}$
(D-5)
→

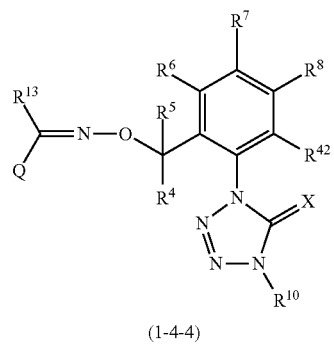

(1-4-4)

wherein $R^4$, $R^5$, $R^6$, $R^7$, $R^8$, $R^6$, $R^{13}$, $R^{42}$, Q, X, $Z^{41}$, and $Z^{42}$ are as defined above.

According to the Production Process D, it is possible to produce a compound in which $R^6$ is $R^{41}$, and one or more substituents selected from the group consisting of $R^7$, $R^8$, and $R^9$ is $R^{42}$ among the present compounds represented by formula (1).

The compound (1-4-1), the compound (1-4-2), the compound (1-4-3), and the compound (1-4-4) can be produced by using other known coupling reaction in place of the coupling reaction of the Production Process D.

(Production Process E)

A compound represented by formula (1-5) in which $R^1$ is $R^{51}$ (hereinafter referred to as a compound (1-5)) among the present compounds represented by formula (1) can be produced by subjecting a compound represented by formula (E-1) (hereinafter referred to as a compound (E-1)) and a compound represented by formula (E-2) (hereinafter referred to as a compound (E-2)) to a coupling reaction in the presence of a base and a catalyst:

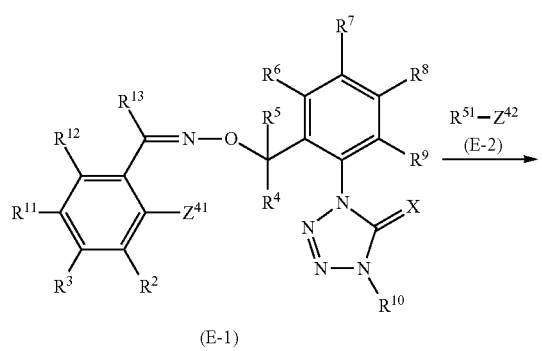

(E-1)

$R^{51}$—$Z^{42}$
(E-2)
→

128

-continued

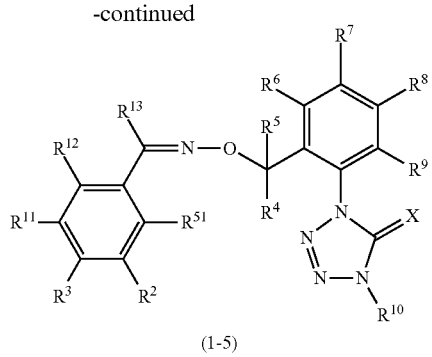

(1-5)

wherein $R^2$, $R^3$, $R^4$, $R^5$, $R^6$, $R^7$, $R^8$, $R^9$, $R^{10}$, $R^{11}$, $R^{12}$, $R^{13}$, X, $Z^{41}$, and $Z^{42}$ are as defined above, and $R^{51}$ represents a C1-C6 alkyl group, a C1-C6 haloalkyl group, a C2-C6 alkenyl group, a C2-C6 haloalkenyl group, a C2-C6 alkynyl group, a C2-C6 haloalkynyl group, a C3-C6 cycloalkyl group, or a C3-C6 halocycloalkyl group.

The reaction is usually performed in a solvent.

Examples of the solvent include hydrocarbons such as heptane, hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; alcohols such as methanol, ethanol, propanol, and butanol; water; and mixtures thereof.

It is also possible to usually use, as the compound (E-2), commercially available compounds, or those produced by a known method mentioned in N. Miyaura and A. Suzuki, Chem. Rev., 1995, 95, 2457. Regarding the compound (E-2) used in the reaction, borate ester derivatives can be produced by reacting ($R^{51}$—I) or ($R^{51}$—Br) with an alkyllithium such as butyllithium, followed by the reaction with a borate ester. It is also possible to produce boronic acid derivatives by hydrolyzing the borate ester derivatives obtained by the above reaction, if necessary. It is also possible to obtain a trifluoroborate salt $BF_3^-K^+$ by fluorinating the borate ester with potassium hydrogenfluoride in accordance with a known method mentioned in Molander et al., Acc. Chem. Res., 2007, 40, 275.

Examples of the catalyst include palladium(II) acetate, dichlorobis(triphenylphosphine)palladium, tetrakistriphenylphosphinepalladium(0), palladium(II) acetate/triscyclohexylphosphine, bis(diphenylphoshineferrocenyl)palladium (II) dichloride, 1,3-bis(2,6-diisopropylphenyl)imidazol-2-ylidene (1,4-naphthoquinone)palladium dimer, aryl(chloro)(1,3-dimethyl-1,3-dihydro-2H-imidazol-2-ylidene) palladium, or palladium(II) acetate/dicyclohexyl(2',4',6'-triisopropylbiphenyl-2-yl)phosphine, and tris(dibenzylideneacetone)dipalladium.

Examples of the base include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide;

alkali metal halides such as sodium fluoride, potassium fluoride, and cesium fluoride; alkali metal hydrides such as lithium hydride, sodium hydride, and potassium hydride; alkali metal phosphates such as tripotassium phosphate; and alkali metal alkoxides such as sodium ethoxide and potassium tert-butoxide.

In the reaction, the compound (E-2) is usually used in the proportion within a range of 1 to 10 mols, the base is usually used in the proportion within a range of 1 to 10 mols, and the catalyst is usually used in the proportion within a range of 0.0001 to 1 mol, based on 1 mol of the compound (E–1).

The reaction temperature is usually within a range of 0 to 150° C. The reaction time is usually within a range of 0.1 to 24 hours.

After completion of the reaction, the present compound represented by formula (1-5) can be isolated by performing post-treatment operations such as extraction of the reaction mixture with an organic solvent, and drying and concentration of the organic layer. The isolated present compound can be further purified by chromatography, recrystallization, and the like.

According to the process for producing the compound (1-5), a compound represented by formula (1-5-2) in which $R^2$ is $R^{51}$ (hereinafter referred to as a compound (1-5-2)) among the present compounds represented by formula (1) can be produced by subjecting a compound represented by formula (E-3) (hereinafter referred to as a compound (E-3)) and the compound (E-2) to a coupling reaction in the presence of a base and a catalyst:

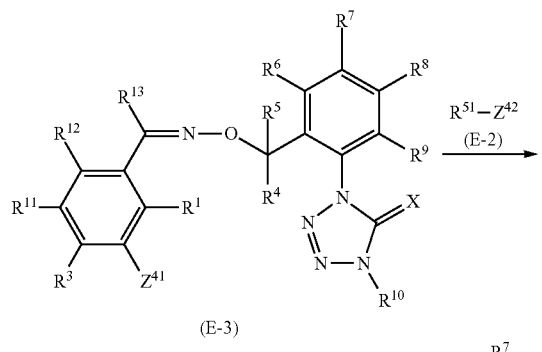

wherein $R^1$, $R^3$, $R^4$, $R^5$, $R^6$, $R^7$, $R^8$, $R^9$, $R^{10}$, $R^{11}$, $R^{12}$, $R^{13}$, $R^{51}$, X, $Z^{41}$, and $Z^{42}$ are as defined above.

According to the process for producing the compound (1-5-1), a compound represented by formula (1-5-3) in which $R^3$ is $R^{51}$ (hereinafter referred to as a compound (1-5-3)) among the present compounds represented by formula (1) can be produced by subjecting a compound represented by the following formula (E-4) (hereinafter referred to as a compound (E-4)) and the compound (E-2) to a coupling reaction in the presence of a base and a catalyst:

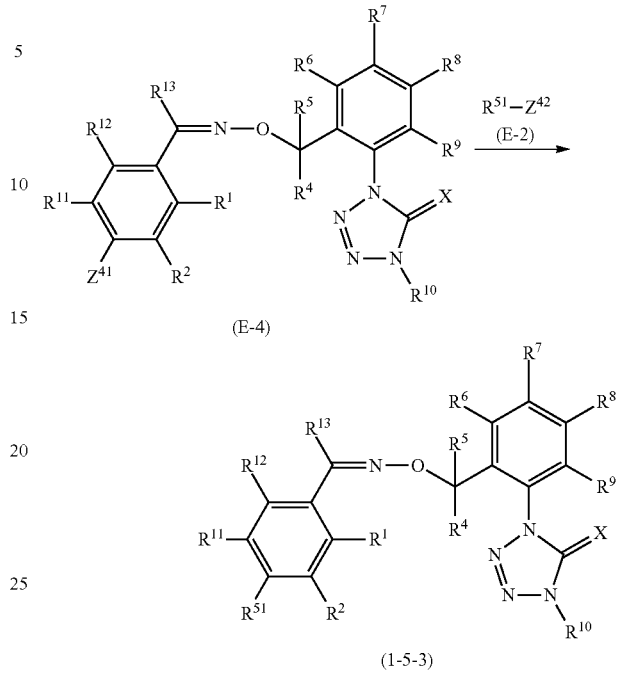

wherein $R^1$, $R^2$, $R^4$, $R^5$, $R^6$, $R^7$, $R^8$, $R^9$, $R^{10}$, $R^{11}$, $R^{12}$, $R^{13}$, $R^{51}$, X, $Z^{41}$, and $Z^{42}$ are as defined above.

According to the process for producing the compound (1-5), a compound represented by formula (1-5-4) in which $R^{11}$ is $R^{51}$ (hereinafter referred to as a compound (1-5-4)) among the present compounds represented by formula (1) can be produced by subjecting a compound represented by formula (E-5) (hereinafter referred to as a compound (E-5)) and the compound (E-2) to a coupling reaction in the presence of a base and a catalyst:

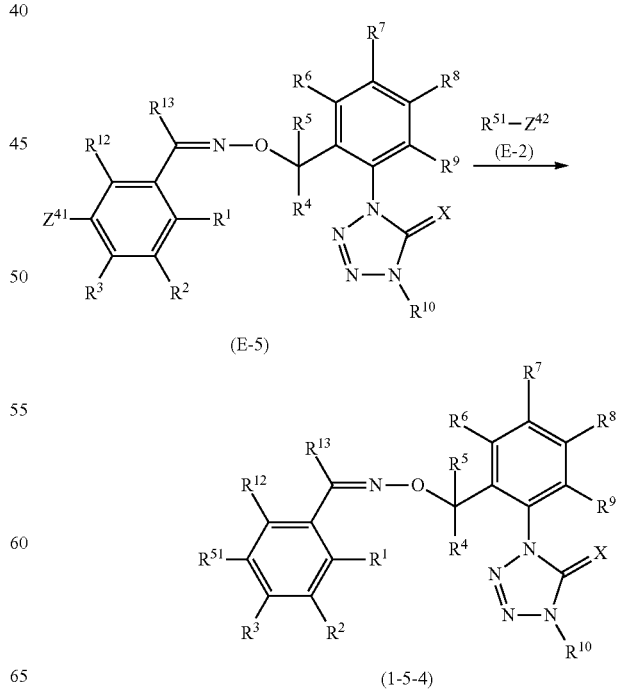

wherein $R^1$, $R^2$, $R^3$, $R^4$, $R^5$, $R^6$, $R^7$, $R^8$, $R^9$, $R^{10}$, $R^{12}$, $R^{13}$, $R^{51}$, X, $Z^{41}$ and $Z^{42}$ are as defined above.

According to the process for producing the compound (1-5-1), a compound represented by formula (1-5-5) in which $R^{12}$ is $R^{51}$ (hereinafter referred to as a compound (1-5-5)) among the present compounds represented by formula (1) can be produced by subjecting a compound represented by formula (E-6) (hereinafter referred to as a compound (E-6)) and the compound (E-2) to a coupling reaction in the presence of a base and a catalyst:

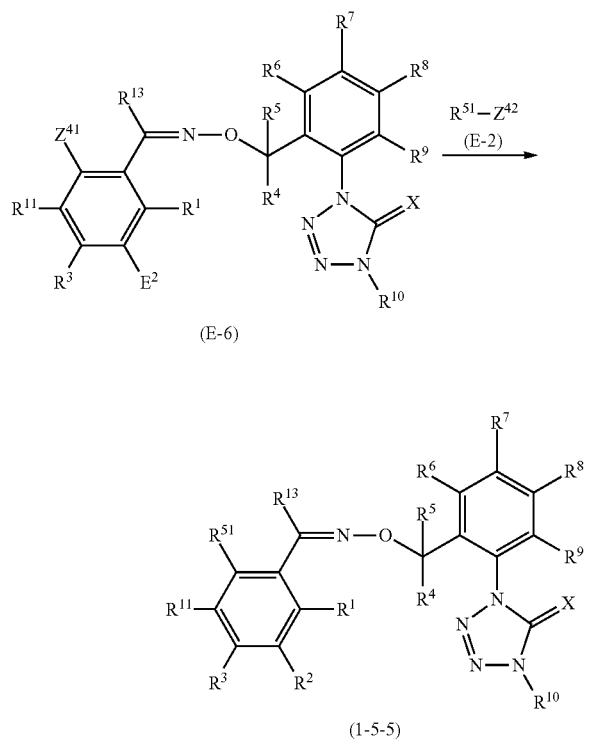

wherein $R^1$, $R^2$, $R^3$, $R^4$, $R^5$, $R^6$, $R^7$, $R^8$, $R^9$, $R^{10}$, $R^{11}$, $R^{13}$, $R^{51}$, X, $Z^{41}$ and $Z^{42}$ are as defined above.

According to the Production Process E, it is possible to produce a compound in which two or more substituents selected from the group consisting of $R^1$, $R^2$, $R^3$, and $R^{11}$ are $R^{51}$ among the compounds represented by formula (1).

It is also possible to produce the compound (1-5-1), the compound (1-5-2), the compound (1-5-3), the compound (1-5-4), and the compound (1-5-5) by using the other known coupling reaction in place of the coupling reaction of the Production Process E.

The process for producing a compound represented by formula (2) will be described in detail below.

a compound represented by formula (2) can be produced, for example, by the following Synthesis Process.

(Synthetic Process AA)

A compound represented by formula (2) (hereinafter referred to as a compound (2)) can be produced by reacting a compound represented by formula (2-3X) (hereinafter referred to as a compound (2-3X)) or a compound represented by formula (2-7) (hereinafter referred to as a compound (2-7)) with an azidizing agent:

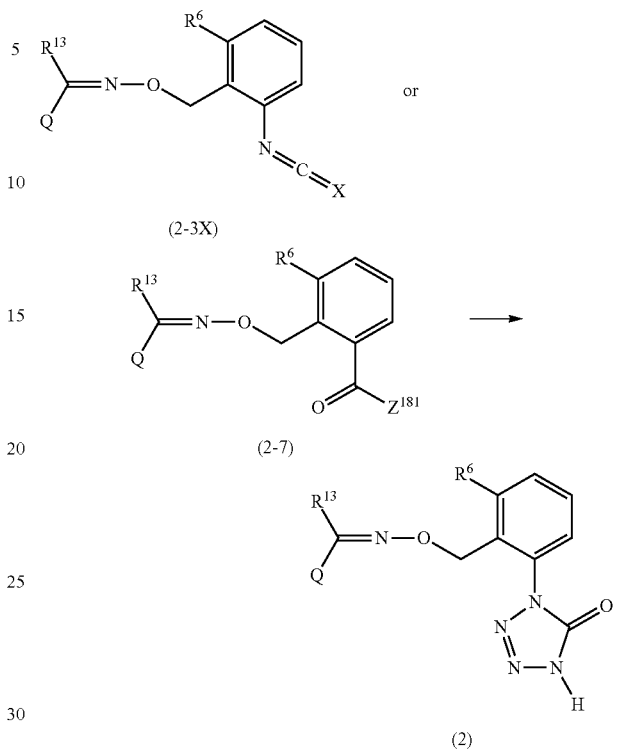

wherein $R^6$, $R^{13}$, Q, and X are as defined above, and $Z^8$ represents a chlorine atom, a bromine atom, or an iodine atom.

The reaction is usually performed in a solvent.

Examples of the solvent include hydrocarbons such as heptane, hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; and mixtures thereof.

Examples of the azidizing agent include inorganic azides such as sodium azide, barium azide, and lithium azide; and organic azides such as trimethylsilyl azide, and diphenylphosphoryl azide.

In the reaction, the azidizing agent is usually used in the proportion within a range of 1 to 10 mols based on 1 mol of the compound (2-3X) or the compound (2-7).

The reaction temperature is usually within a range of −20 to 150° C. The reaction time is usually within a range of 0.1 to 24 hours.

In the reaction, if necessary, Lewis acid such as aluminum chloride or zinc chloride may be added, and these compounds are usually used in the proportion within a range of 0.05 to 5 mols based on 1 mol of (2-3X) or the compound (2-7).

After completion of the reaction, the compound (3) can be isolated by performing post-treatment operations such as extraction of the reaction mixture with an organic solvent, and drying and concentration of the organic layer. The isolated compound (3) can also be further purified by chromatography, recrystallization, and the like.

(Synthetic Process A)

A compound represented by formula (2-1) in which $L^1$ is a nitro group in the compound (2) (hereinafter referred to as a compound (2-1)) can be produced by reacting a compound represented by formula (PA-1) (hereinafter referred to as a compound (PA-1)) with the compound (A-2) in the presence of a base:

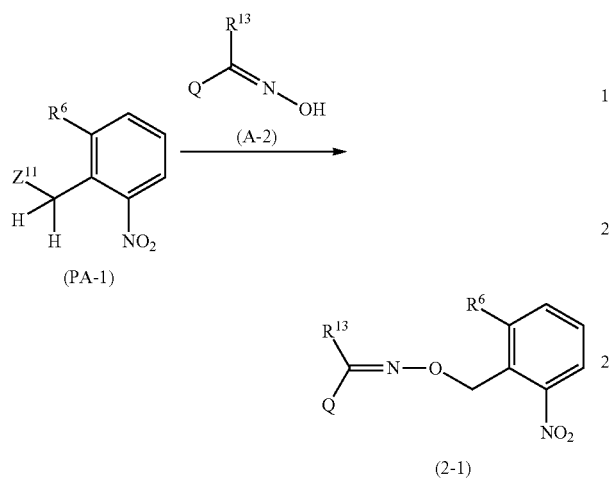

wherein $R^6$, $R^{13}$, Q, and $Z^{11}$ are as defined above

The reaction is usually performed in a solvent.

Examples of the solvent include hydrocarbons such as heptane, hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; water; and mixtures thereof.

Examples of the base include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; and alkali metal alkoxides such as sodium tert-butoxide, and potassium tert-butoxide.

In the reaction, the compound (PA-2) is usually used in the proportion within a range from 1 to 10 mols, and the base is usually used in the proportion within a range from 0.5 to 5 mols, based on 1 mol of the compound (PA-1).

The reaction temperature is usually within a range of −20 to 150° C. The reaction time is usually within a range of 0.1 to 24 hours.

In the reaction, if necessary, sodium iodide, tetrabutylammonium iodide, and the like may be added, and these compounds are usually used in the proportion within a range from 0.001 to 1.2 mols based on 1 mol of the compound (PA-1).

After completion of the reaction, the compound (2-1) can be isolated by performing post-treatment operations such as extraction of the reaction mixture with an organic solvent, and drying and concentration of the organic layer. The compound (2-1) can also be further purified by chromatography, recrystallization, and the like.

(Synthetic Process B)

A compound represented by formula (2-2) in which $L^1$ is an amino group in the compound (2) (hereinafter referred to as a compound (2-2)) can be produced by reacting the compound (2-1) with hydrogen in the presence of a catalyst:

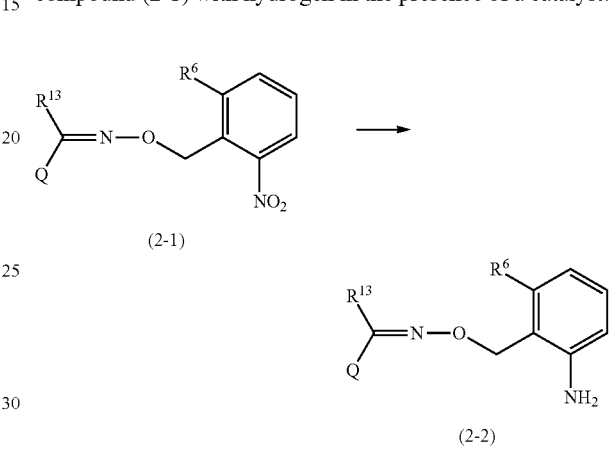

wherein $R^6$, $R^{13}$, and Q are as defined above.

The reaction is usually performed in a solvent.

Examples of the solvent include alcohols such as methanol, ethanol, propanol, and butanol; esters such as ethyl acetate and butyl acetate; halogenated hydrocarbons such as chloroform, 1,2-dichloroethane, and chlorobenzene; ethers such as tetrahydrofuran, 1,4-dioxane, ethylene glycol dimethyl ether, methyl tert-butyl ether, and diisopropyl ether; hydrocarbons such as heptane, hexane, cyclohexane, toluene, and xylene; water; and mixtures thereof.

Examples of the catalyst include palladium-supporting carbon (Pd/C), platinum-supporting carbon (Pt/C), osmium-supporting carbon (Os/C), ruthenium-supporting carbon (Ru/C), rhodium-supporting carbon (Rh/C), and Raney nickel.

The reaction temperature is usually within a range of −20 to 150° C. The reaction time is usually within a range of 0.1 to 24 hours.

In the reaction, the catalyst is usually used in the proportion of 0.01 to 1 mol, and hydrogen is usually used in the proportion within a range of 1 mol to a large excess of mols, based on 1 mol of the compound (2-1).

After completion of the reaction, the compound (2-2) can be isolated by performing post-treatment operations such as filtration of a catalyst and concentration of an organic layer. The isolated compound (2-2) can also be purified by operations such as chromatography and recrystallization.

(Synthetic Process D)

A compound represented by formula (2-3) in which L an isocyanate group in the compound (2) (hereinafter referred to as a compound (2-3)) can be produced by reacting the compound (2-2) with phosgenes:

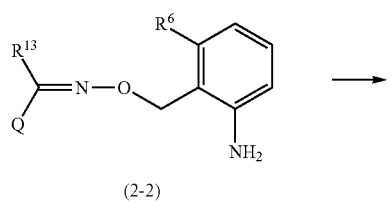

(2-2)

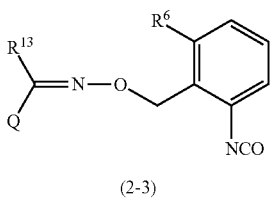

(2-3)

wherein $R^6$, $R^{13}$, and Q are as defined above

The reaction is usually performed in a solvent.

Examples of the solvent include hydrocarbons such as heptane, hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; esters such as ethyl acetate and methyl acetate; ketones such as acetone, methyl ethyl ketone, and methyl isobutyl ketone; nitriles such as acetonitrile; and mixtures thereof.

Examples of phosgenes include phosgene, diphosgene, and triphosgene.

In the reaction, phosgenes are usually used in the proportion within a range from 1 to 10 mols based on 1 mol of the compound (2-2).

The reaction temperature is usually within a range of −20 to 150° C. The reaction time is usually within a range of 0.1 to 24 hours.

In the reaction, if necessary, organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; and alkali metal hydrogen carbonates such as sodium hydrogen carbonate may be added, and these compounds are usually used in the proportion within a range of 0.05 to 5 mols based on 1 mol of the compound (2-2).

After completion of the reaction, the compound (2-3) can be isolated by performing post-treatment operations such as extraction of the reaction mixture with an organic solvent, and drying and concentration of the organic layer. The isolated compound (2-3) can also be further purified by operations such as chromatography and recrystallization.

(Synthetic Process E)

A compound represented by formula (2-4) in which L is NSO in the compound (2) (hereinafter referred to as a compound (2-4)) can be produced by reacting the compound (2-2) with thionyl chloride:

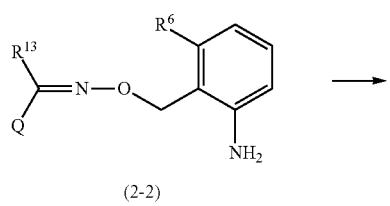

(2-2)

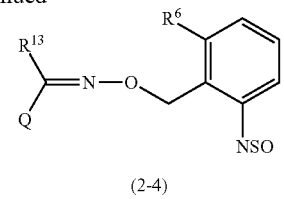

(2-4)

wherein $R^6$, $R^{13}$, and Q are as defined above.

The reaction is usually performed in a solvent.

Examples of the solvent include hydrocarbons such as heptane, hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; esters such as ethyl acetate and methyl acetate; ketones such as acetone, methyl ethyl ketone, and methyl isobutyl ketone; nitriles such as acetonitrile; and mixtures thereof.

In the reaction, thionyl chloride is usually used in the proportion within a range of 1 to 10 mols based on 1 mol of the compound (2-2).

The reaction temperature is usually within a range of −20 to 150° C. The reaction time is usually within a range of 0.1 to 24 hours.

After completion of the reaction, the compound (2-4) can be isolated by performing post-treatment operations such as extraction of the reaction mixture with an organic solvent, and drying and concentration of the organic layer. The isolated compound (2-4) can also be further purified by distillation operations such as chromatography and recrystallization.

(Synthetic Process F)

The compound (2-3) can also be produced by reacting the compound (2-4) with phosgenes:

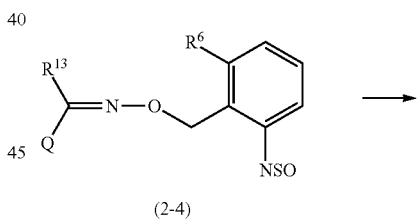

(2-4)

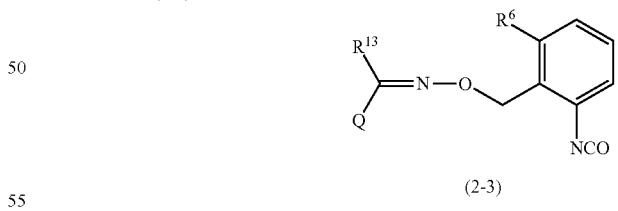

(2-3)

wherein $R^6$, $R^{13}$, and Q are as defined above.

The reaction is usually performed in a solvent.

Examples of the solvent include hydrocarbons such as heptane, hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; esters such as ethyl acetate and methyl acetate; ketones such as acetone, methyl ethyl ketone, and methyl isobutyl ketone; nitriles such as acetonitrile; and mixtures thereof.

Examples of phosgenes include phosgene, diphosgene, and triphosgene.

In the reaction, phosgenes are usually used in the proportion within a range of 1 to 10 mols based on 1 mol of the compound (2-4).

The reaction temperature is usually within a range of −20 to 150° C. The reaction time is usually within a range of 0.1 to 24 hours.

In the reaction, if necessary, organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; and alkali metal hydrogen carbonates such as sodium hydrogen carbonate may be added, and these compounds are usually used in the proportion within a range of 0.05 to 5 mols per 1 mol of the compound (2-4).

After completion of the reaction, the compound (2-3) can be isolated by performing post-treatment operations such as extraction of the reaction mixture with an organic solvent, and drying and concentration of the organic layer. The isolated compound (2-3) can also be further purified by operations such as chromatography and recrystallization.

(Synthetic Process G)

A compound represented by formula (2-5) in which $L^1$ is a C2-C6 alkoxycarbonyl group in the compound (2) (hereinafter referred to as a compound (2-5)) can be produced by reacting a compound (A-2) with a compound represented by formula (PG-1) (hereinafter referred to as a compound (PG-1)) in the presence of a base:

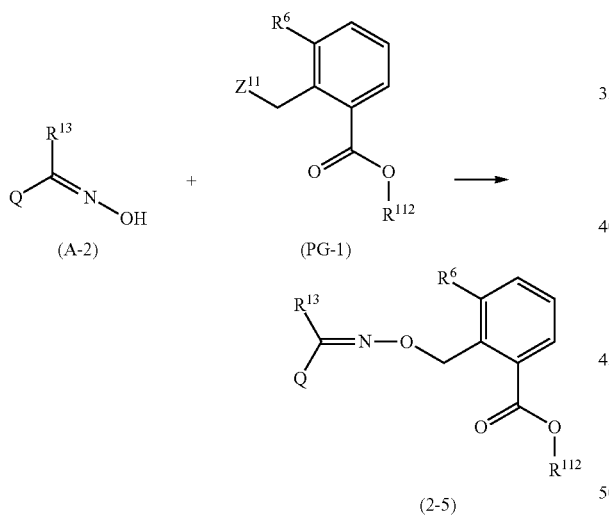

wherein $R^6$, $R^{13}$, Q, and $Z^{11}$ are as defined above, and $R^{112}$ represents a C1-C6 alkyl group.

The reaction is usually performed in a solvent.

Examples of the solvent include hydrocarbons such as heptane, hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; water; and mixtures thereof.

Examples of the base include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; and alkali metal alkoxides such as sodium tert-butoxide and potassium tert-butoxide.

In the reaction, the compound (PG-1) is usually used in the proportion within a range of 1 to 10 mols, and the base is usually used within a range of 0.5 to 5 mols, based on 1 mol of the compound (A-2).

The reaction temperature is usually within a range of −20 to 150° C. The reaction time is usually within a range of 0.1 to 24 hours.

In the reaction, if necessary, sodium iodide, tetrabutylammonium iodide may be added, and these compounds are usually used in the proportion within a range of 0.001 to 1.2 mols based on 1 mol of the compound (A-2).

After completion of the reaction, the compound (2-5) can be isolated by performing post-treatment operations such as extraction of the reaction mixture with an organic solvent, and drying and concentration of the organic layer. The isolated compound (2-5) can also be further purified by chromatography, recrystallization, and the like.

(Synthetic Process H)

A compound represented by formula (2-6) in which $L^1$ is a carboxyl group in the compound (2) (hereinafter referred to as a compound (2-6)) can be produced by reacting the compound (2-5) with a hydrolyzing agent:

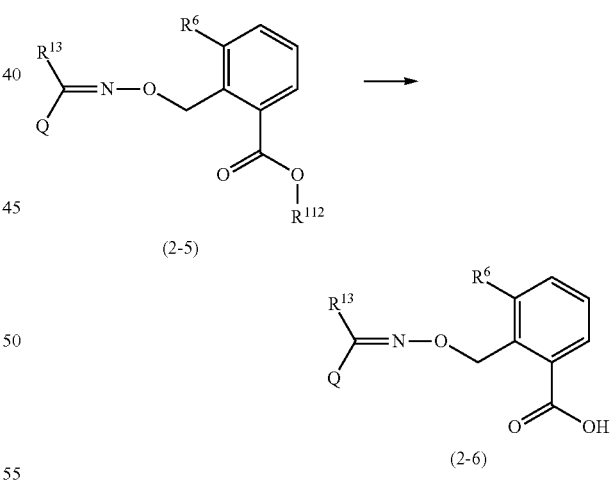

wherein $R^6$, $R^1$, $R^{12}$, and Q are as defined above.

The reaction is usually performed in a solvent.

Examples of the solvent include water; alcohols such as methanol, ethanol, propanol, and butanol; hydrocarbons such as heptane, hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; ketones such as acetone, methyl ethyl ketone, and methyl isobutyl ketone; and mixtures thereof.

Examples of the hydrolyzing agent bases such as an aqueous potassium hydroxide solution and an aqueous sodium hydroxide solution; and acids such as hydrochloric acid and sulfuric acid.

In the reaction, the hydrolyzing agent is usually used in the proportion within a range of 0.5 to 20 mols based on 1 mol of the compound (2-5).

The reaction temperature is usually within a range of −20 to 150° C. The reaction time is usually within a range of 0.1 to 72 hours.

After completion of the reaction, by performing post-treatment operations such as extraction of the reaction mixture with an organic solvent, and drying and concentration of the organic layer, a compound (2-6) can be isolated. The isolated compound (2-6) can also be further purified by operations such as chromatography and recrystallization.

(Synthetic Process I)

A compound represented by formula (2-7) in which $L^1$ is a halocarbonyl group in the compound (2) (hereinafter referred to as a compound (2-7)) can be produced by reacting the compound (2-6) with a halogenating agent:

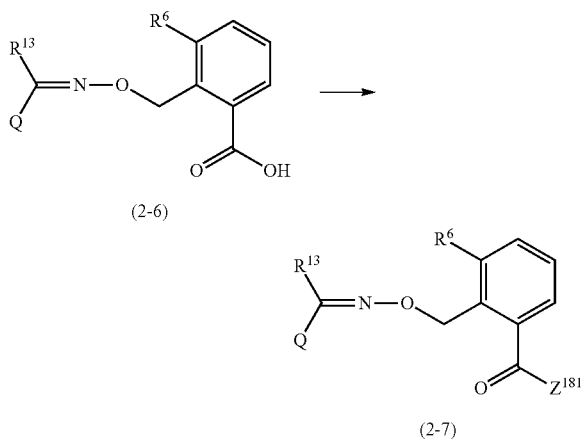

(2-6)

(2-7)

wherein $R^6$, $R^{13}$, Q, and $Z^{181}$ are as defined above.

The reaction is usually performed in a solvent.

Examples of the solvent include hydrocarbons such as heptane, hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; esters such as ethyl acetate and methyl acetate; ketones such as acetone, methyl ethyl ketone, and methyl isobutyl ketone; nitriles such as acetonitrile; and mixtures thereof.

Examples of the halogenating agent include phosphorus oxychloride, phosphorus trichloride, phosphorus pentachloride, thionyl chloride, phosphorus oxybromide, phosphorus tribromide, phosphorus pentabromide, phosphorus triiodide, oxalyl dichloride, oxalyl dibromide, triphosgene, diphosgene, phosgene and sulfuryl chloride.

In the reaction, the halogenating agent is usually used in the proportion within a range of 1 to 10 mols based on 1 mol of the compound (2-6).

The reaction temperature is usually within a range of −20 to 150° C. The reaction time is usually within a range of 0.1 to 24 hours.

In the reaction, a catalyst may be added, and N,N-dimethylformamide, triethylamine, diisopropylethylamine, and the like are used. The catalyst is usually used in the proportion within a range of 0.001 to 1 mol based on 1 mol of the compound (2-6).

In the reaction, if necessary, organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; and alkali metal hydrogen carbonates such as sodium hydrogen carbonate may be added, and these compounds are usually in the proportion within a range of 0.05 to 5 mols based on 1 mol of the compound (2-6).

After completion of the reaction, a compound (2-7) can be isolated by performing post-treatment operations such as extraction of the reaction mixture with an organic solvent, and drying and concentration of the organic layer. The isolated compound (2-7) may be further purified by operations such as chromatography and recrystallization.

(Synthetic Process J)

A compound represented by formula (2-8) in which L is $C(O)N_3$ in the compound (2) (hereinafter referred to as a compound (2-8)) can be produced by reacting the compound (2-7) with sodium azide:

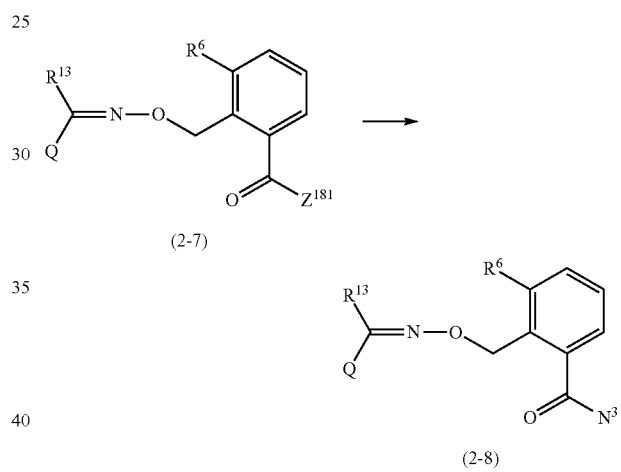

(2-7)

(2-8)

wherein $R^6$, $R^{13}$, Q, and $Z^{18}$ are as defined above.

The reaction is usually performed in a solvent.

Examples of the solvent include ethers such as tetrahydrofuran, 1,4-dioxane, ethylene glycol dimethyl ether, methyl tert-butyl ether, and diisopropyl ether; hydrocarbons such as heptane, hexane, cyclohexane, toluene, and xylene; halogenated hydrocarbons such as chloroform, 1,2-dichloroethane, and chlorobenzene; nitriles such as acetonitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; alcohols such as methanol, ethanol, propanol, and butanol; and mixtures thereof.

In the reaction, sodium azide is usually used in the proportion within a range of 1 to 10 mols based on 1 mol of the compound (2-7).

The reaction temperature is usually within a range of −20 to 50° C. The reaction time is usually within a range of 0.1 to 24 hours.

After completion of the reaction, a compound (2-8) can be isolated by performing post-treatment operations such as extraction of the reaction mixture with an organic solvent, and drying and concentration of the organic layer. The isolated compound (2-8) may be further purified by chromatography, recrystallization, and the like.

(Synthetic Process K)

A compound (2-3) can also be produced by heating the compound (2-8):

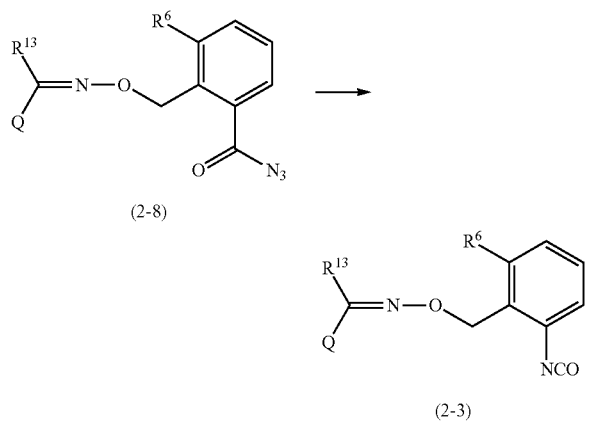

(2-8)

(2-3)

wherein $R^6$, $R^{13}$, and Q are as defined above.

The reaction is usually performed in a solvent.

Examples of the solvent include ethers such as tetrahydrofuran, 1,4-dioxane, ethylene glycol dimethyl ether, methyl tert-butyl ether, and diisopropyl ether; hydrocarbons such as heptane, hexane, cyclohexane, toluene, and xylene; halogenated hydrocarbons such as chloroform, 1,2-dichloroethane, and chlorobenzene; nitriles such as acetonitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; alcohols such as methanol, ethanol, propanol, and butanol; and mixtures thereof.

The reaction temperature is usually within a range of room temperature to 150° C. The reaction time is usually within a range of 0.1 to 24 hours.

After completion of the reaction, a compound (2-3) can be isolated by performing post-treatment operations such as extraction of the reaction mixture with an organic solvent, and drying and concentration of the organic layer. The isolated compound (2-3) can also be further purified by chromatography, recrystallization, and the like.

(Synthetic Process L)

A compound represented by formula (2-9) in which L is $C(O)NH_2$ in the compound (2) (hereinafter referred to as a compound (2-9)) can be produced by reacting the compound (2-7) with ammonia:

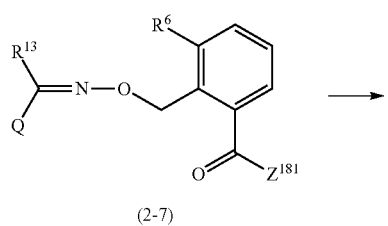

(2-7)

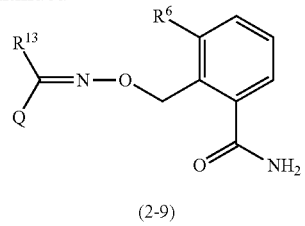

(2-9)

wherein $R^6$, $R^{13}$, Q, and $Z^{18}$ are as defined above.

The reaction is usually performed in a solvent.

Examples of the solvent include ethers such as tetrahydrofuran, 1,4-dioxane, ethylene glycol dimethyl ether, methyl tert-butyl ether, and diisopropyl ether; hydrocarbons such as heptane, hexane, cyclohexane, toluene, and xylene; halogenated hydrocarbons such as chloroform, 1,2-dichloroethane, and chlorobenzene; nitriles such as acetonitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; alcohols such as methanol, ethanol, propanol, and butanol; and mixtures thereof.

Ammonia may be in the form of a gas, or may be in the form of a solution dissolved in a solvent such as water, methanol, ethanol, tetrahydrofuran, 1,4-dioxane, or diethylether.

In the reaction, ammonia is usually used in the proportion within a range of 1 mol to a large excess of mols based on 1 mol of the compound (2-7) a large excess of mols.

The reaction temperature is usually within a range of −20 to 50° C. The reaction time is usually within a range of 0.1 to 24 hours.

After completion of the reaction, a compound (2-9) can be isolated by performing post-treatment operations such as extraction of the reaction mixture with an organic solvent, and drying and concentration of the organic layer. The isolated compound (2-9) can also be further purified by chromatography, recrystallization, and the like.

(Synthetic Process M)

The compound (2-3) can also be produced by reacting the compound (2-9) with hypochlorite or hypobromite:

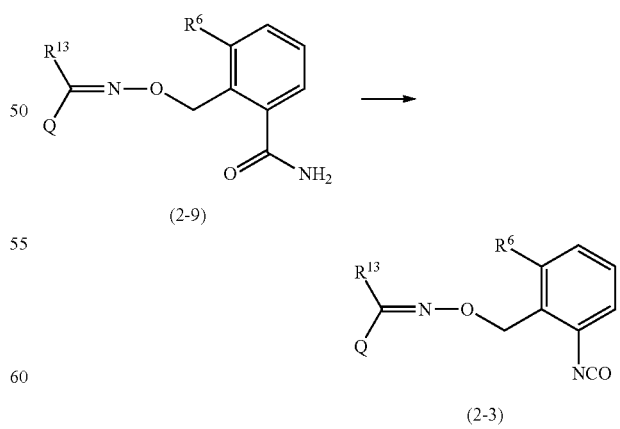

(2-9)

(2-3)

wherein $R^6$, $R^{13}$, and Q are as defined above.

The reaction is usually performed in a solvent.

Examples of the solvent include ethers such as tetrahydrofuran, 1,4-dioxane, ethylene glycol dimethyl ether, methyl tert-butyl ether, and diisopropyl ether; hydrocarbons such as heptane, hexane, cyclohexane, toluene, and xylene; halogenated hydrocarbons such as chloroform, 1,2-dichloroethane, and chlorobenzene; nitriles such as acetonitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; alcohols such as methanol, ethanol, propanol, and butanol; water; and mixtures thereof.

Examples of the hypochlorite and hypobromite include sodium hypobromite, sodium hypochlorite, potassium hypobromite, potassium hypochlorite, barium hypobromite, barium hypochlorite, calcium hypobromite, and calcium hypochlorite. It is also possible to use hypochlorite and hypobromite produced by mixing chlorine or bromine with sodium hydroxide, potassium hydroxide, barium hydroxide, calcium hydroxide.

The reaction temperature is usually within a range of 0 to 150° C. The reaction time is usually within a range of 0.1 to 24 hours.

In the reaction, hypochlorite is usually used in the proportion within a range of 1 to 10 mols based on 1 mol of the compound (2-9).

After completion of the reaction, by performing post-treatment operations such as extraction of the reaction mixture with an organic solvent, and drying and concentration of the organic layer, a compound (2-3) can be isolated. The isolated compound (2-3) can also be further purified by chromatography, recrystallization, and the like.

(Synthetic Process N)

A compound represented by formula (2-10) in which compound $L^1$ is C(O)NHOH in the compound (2) (hereinafter referred to as a compound (2-10)) can be produced by reacting the compound (2-7) with hydroxylamine:

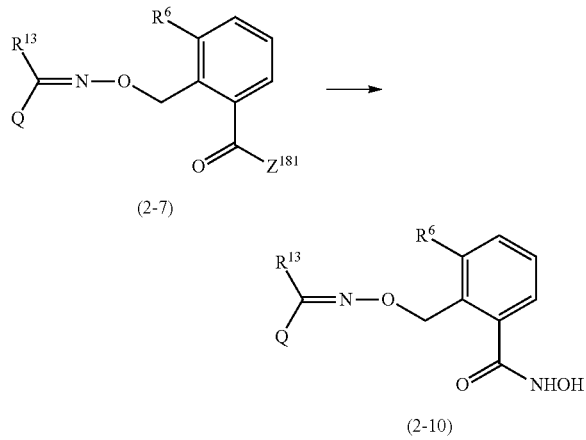

wherein $R^6$, $R^{13}$, Q, and $Z^{81}$ are as defined above.

The reaction is usually performed in a solvent.

Examples of the solvent include ethers such as tetrahydrofuran, 1,4-dioxane, ethylene glycol dimethyl ether, methyl tert-butyl ether, and diisopropyl ether; hydrocarbons such as heptane, hexane, cyclohexane, toluene, and xylene; halogenated hydrocarbons such as chloroform, 1,2-dichloroethane, and chlorobenzene; nitriles such as acetonitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; alcohols such as methanol, ethanol, propanol, and butanol; and mixtures thereof.

In the reaction, hydroxylamine is usually used in the proportion within a range of 1 to 10 mols based on 1 mol of the compound (2-7).

The reaction temperature is usually within a range of −20 to 50° C. The reaction time is usually within a range of 0.1 to 24 hours.

After completion of the reaction, a compound (2-10) can be isolated by performing post-treatment operations such as extraction of the reaction mixture with an organic solvent, and drying and concentration of the organic layer. The isolated compound (2-10) can also be further purified by chromatography, recrystallization, and the like.

(Synthetic Process O)

The compound (2-3) can also be produced by reacting the compound (2-10) with an acid halide.

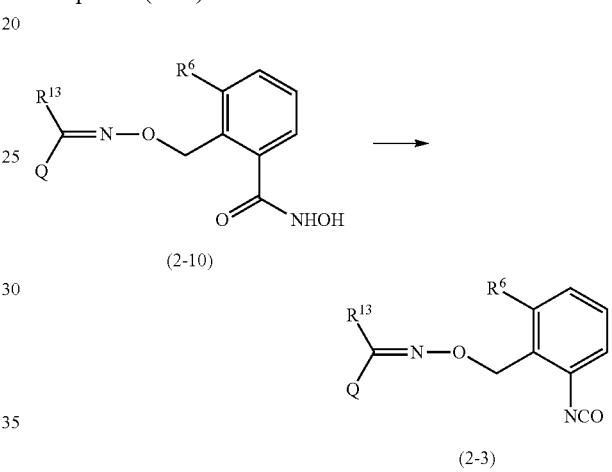

wherein $R^6$, $R^{13}$, and Q are as defined above

The reaction is usually performed in a solvent.

Examples of the solvent include ethers such as tetrahydrofuran, 1,4-dioxane, ethylene glycol dimethyl ether, methyl tert-butyl ether, and diisopropyl ether; hydrocarbons such as heptane, hexane, cyclohexane, toluene, and xylene; halogenated hydrocarbons such as chloroform, 1,2-dichloroethane, and chlorobenzene; nitriles such as acetonitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; alcohols such as methanol, ethanol, propanol, and butanol; water; and mixtures thereof.

Examples of the acid halide include acid anhydrides such as acetic anhydride, and propionic anhydride; acid halides such as acetyl chloride, acetyl bromide, and benzoyl chloride; sulfonyl chlorides such as paratoluenesulfonyl chloride and methanesulfonyl chloride; pyridine-sulfur trioxide complex, and thionyl chloride.

In the reaction, if necessary, bases such as pyridine, triethylamine, tributylamine, diazabicycloundecene, sodium hydroxide, and potassium hydroxide may be added, and these compounds are usually used in the proportion within a range of 1 to 10 mols based on 1 mol of the compound (2-10).

The reaction temperature is usually within a range of −20 to 150° C. The reaction time is usually within a range of 0.1 to 24 hours.

In the reaction, the acid halide is usually used in the proportion within a range of 1 to 10 mols based on 1 mol of the compound (2-10).

After completion of the reaction, a compound (2-3) can be isolated by performing post-treatment operations such as extraction of the reaction mixture with an organic solvent, and drying and concentration of the organic layer. The isolated compound (2-3) can also be further purified by chromatography, recrystallization, and the like.

(Synthetic Process P)

A compound represented by formula (2-11) in which $L^1$ is C(O)NHCl in the compound (2) (hereinafter referred to as a compound (2-11)) and a compound represented by formula (2-12) in which $L^1$ is C(O)NHBr (hereinafter referred to as a compound (2-12)) can be produced by reacting the compound (2-9) with a chlorinating agent or a brominating agent:

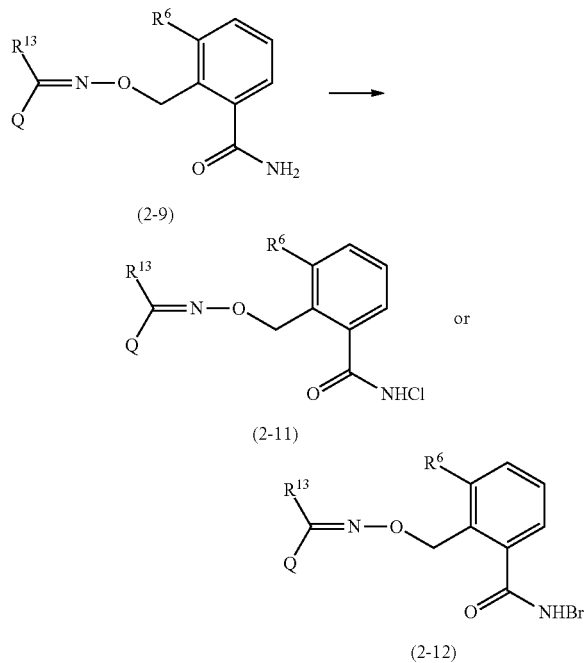

(2-9)

(2-11)

(2-12)

wherein $R^6$, $R^{13}$, and Q are as defined above.

The reaction is usually performed in a solvent.

Examples of the solvent include hydrocarbons such as heptane, hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; esters such as ethyl acetate and methyl acetate; ketones such as acetone, methyl ethyl ketone, and methyl isobutyl ketone; nitriles such as acetonitrile; and mixtures thereof.

Examples of the chlorinating agent or brominating agent include sodium hypochlorite, tert-butyl hypochlorite, trichloroisocyanuric acid, chlorine, sulfuryl chloride, sodium bromate, sodium bromite, hydrogen bromide, sodium bromide, and bromine.

In the reaction, the halogenating agent is usually used in the proportion within a range of 1 to 10 mols based on 1 mol of the compound (2-9).

The reaction temperature is usually within a range of −20 to 150° C. The reaction time is usually within a range of 0.1 to 24 hours.

In the reaction, a catalyst may be added, and dimethylformamide is used as the catalyst. The amount of the catalyst is usually within a range of 0.001 to 1 mol based on 1 mol of the compound (2-9).

After completion of the reaction, a compound (2-11) and a compound (2-12) can be isolated by performing post-treatment operations such as extraction of the reaction mixture with an organic solvent, and drying and concentration of the organic layer. The isolated compound (2-11) and compound (2-12) can also be further purified by operations such as chromatography and recrystallization.

(Synthetic Process Q)

The compound (2-3) can be produced by reacting the compound (2-11) or compound (2-12) with a base:

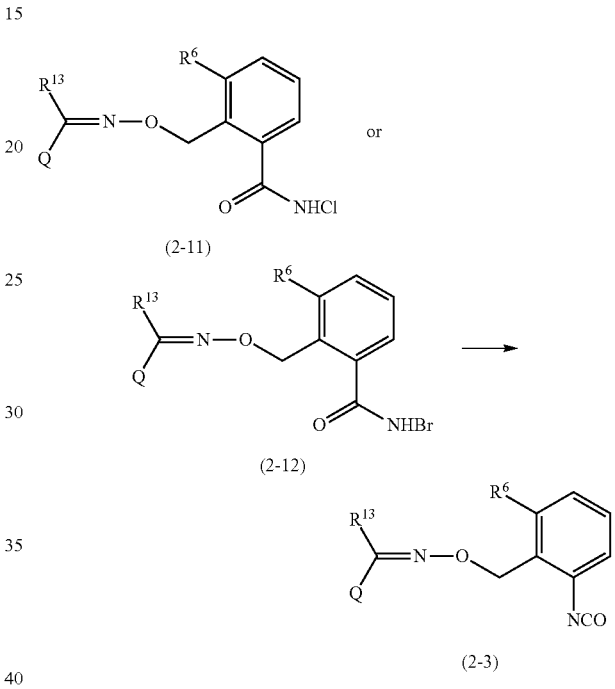

(2-11)

(2-12)

(2-3)

wherein $R^6$, $R^{13}$, and Q are as defined above.

The reaction is usually performed in a solvent.

Examples of the solvent include ethers such as tetrahydrofuran, 1,4-dioxane, ethylene glycol dimethyl ether, methyl tert-butyl ether, and diisopropyl ether; hydrocarbons such as heptane, hexane, cyclohexane, toluene, and xylene; halogenated hydrocarbons such as chloroform, 1,2-dichloroethane, and chlorobenzene; nitriles such as acetonitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; alcohols such as methanol, ethanol, propanol, and butanol; water; and mixtures thereof.

Examples of the base include pyridine, triethylamine, tributylamine, diazabicycloundecene, sodium hydroxide, potassium hydroxide, and the like.

In the reaction, the base is usually used in the proportion within a range of 1 to 10 mols based on 1 mol of the compound (2-11) or compound (2-12).

The reaction temperature is usually within a range of −20 to 150° C. The reaction time is usually within a range of 0.1 to 24 hours.

In the reaction, the base is usually used in the proportion within a range of 1 to 10 mols based on 1 mol of the compound (2-11) or compound (2-12).

After completion of the reaction, a compound (2-3) can be isolated by performing post-treatment operations such as extraction of the reaction mixture with an organic solvent, and drying and concentration of the organic layer. The isolated compound (2-3) can also be further purified by chromatography, recrystallization, and the like.

The process for synthesizing an intermediate compound will be mentioned in detail below.

(Reference Production Process XA)

A compound represented by formula (XA3) (hereinafter referred to as a compound (XA3)) can be produced by reacting a compound represented by formula (XA1) (hereinafter referred to as a compound (XA1)) or a compound represented by formula (XA2) (hereinafter referred to as a compound (XA2)) with an azidizing agent:

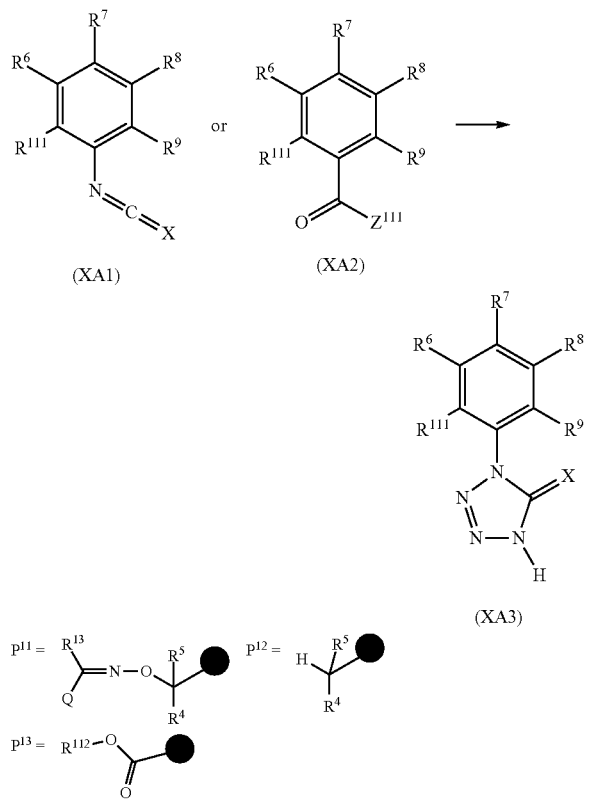

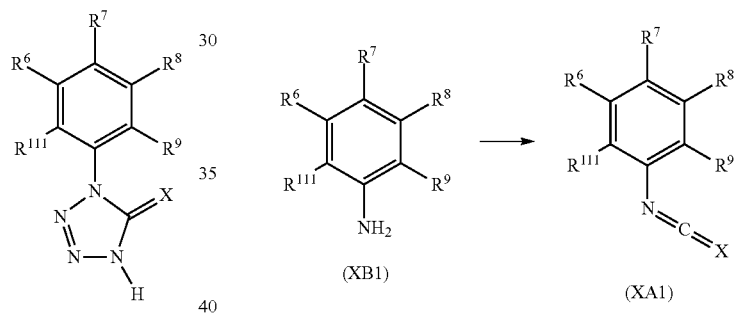

wherein $R^4$, $R^5$, $R^6$, $R^7$, $R^8$, $R^9$, $R^{13}$, $R^{112}$, Q, and X are as defined above, $R^{111}$ represents $P^{11}$, $P^{12}$, or $P^{13}$, $Z^{111}$ represents a chlorine atom or bromine atom, and the symbol ○ represents a binding site.

The reaction is usually performed in a solvent.

Examples of the solvent include hydrocarbons such as heptane, hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; and mixtures thereof.

Examples of the azidizing agent include inorganic azides such as sodium azide, barium azide, and lithium azide; and organic azides such as trimethylsilyl azide and diphenylphosphoryl azide.

In the reaction, the azidizing agent is usually used in the proportion within a range of 1 to 10 mols based on 1 mol of the compound (XA1) or compound (XA2).

The reaction temperature is usually within a range of −20 to 150° C. The reaction time is usually within a range of 0.1 to 24 hours.

In the reaction, if necessary, Lewis acid such as aluminum chloride or zinc chloride may be added, and these compounds are usually used in the proportion within a range of 0.05 to 5 mols based on 1 mol of the compound (XA1) or compound (XA2).

After completion of the reaction, a compound (XA3) can be isolated by performing post-treatment operations such as extraction of the reaction mixture with an organic solvent, and drying and concentration of the organic layer. The isolated compound (XA3) can also be further purified by chromatography, recrystallization, and the like.

(Reference Production Process XB)

The compound (XA1) can be produced by reacting a compound represented by the following formula (XB1) (hereinafter referred to as a compound (XB1)) with an isocyanating agent:

wherein $R^6$, $R^7$, $R^8$, $R^9$, $R^{111}$, and X are as defined above.

The reaction is usually performed in a solvent.

Examples of the solvent include hydrocarbons such as heptane, hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; esters such as ethyl acetate and methyl acetate; ketones such as acetone, methyl ethyl ketone, and methyl isobutyl ketone; nitriles such as acetonitrile; and mixtures thereof.

Examples of the isocyanating agent include phosgene, diphosgene, triphosgene, thiophosgene, N,N-carbodiimidazole, and N,N-thiocarbodiimidazole.

In the reaction, the isocyanating agent is usually used in the proportion within a range of 1 to 10 mols based on 1 mol of the compound (XB1).

The reaction temperature is usually within a range of −20 to 150° C. The reaction time is usually within a range of 0.1 to 24 hours.

In the reaction, if necessary, organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; or alkali metal hydrogen carbonates such as sodium hydrogen carbonate may be added, and these compounds are usually used in the proportion within a range of 0.05 to 5 mols based on 1 mol of the compound (XB1).

After completion of the reaction, a compound (XA1) can be isolated by performing post-treatment operations such as extraction of the reaction mixture with an organic solvent, and drying and concentration of the organic layer. The compound may be further purified by operations such as distillation, chromatography, and recrystallization.

(Reference Production Process XC)

The compound (XA2) can be produced by reaction a compound represented by formula (XC1) (hereinafter referred to as a compound (XC1)) with a halogenating agent:

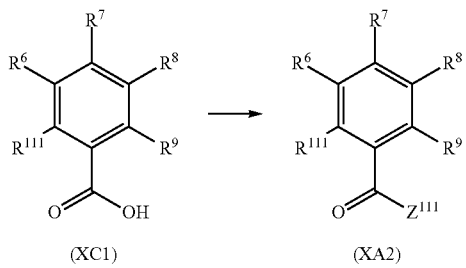

(XC1)          (XA2)

wherein $R^6$, $R^7$, $R^8$, $R^9$, $R^{111}$, and $Z^{111}$ are as defined above.

The reaction is usually performed in a solvent.

Examples of the solvent include hydrocarbons such as heptane, hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; esters such as ethyl acetate and methyl acetate; ketones such as acetone, methyl ethyl ketone, and methyl isobutyl ketone; nitriles such as acetonitrile; and mixtures thereof.

Examples of the halogenating agent include phosphorus oxychloride, phosphorus trichloride, phosphorus pentachloride, thionyl chloride, phosphorus oxybromide, phosphorus tribromide, phosphorus pentabromide, phosphorus triiodide, oxalyl dichloride, oxalyl dibromide, triphosgene, diphosgene, phosgene and sulfuryl chloride.

In the reaction, the halogenating agent is usually used in the proportion within a range of 1 to 10 mols based on 1 mol of the compound (XC1).

The reaction temperature is usually within a range of −20 to 150° C. The reaction time is usually within a range of 0.1 to 24 hours.

In the reaction, a catalyst may be added, and N,N-dimethylformamide is used as the catalyst. The amount of the catalyst is usually within a range of 0.001 to 1 mol based on 1 mol of the compound (XC1).

In the reaction, if necessary, organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; and alkali metal hydrogen carbonates such as sodium hydrogen carbonate may be added, and these compounds are usually in the proportion within a range of 0.05 to 5 mols based on 1 mol of the compound (XC1).

After completion of the reaction, a compound (XA2) can be isolated by performing post-treatment operations such as extraction of the reaction mixture with an organic solvent, and drying and concentration of the organic layer. The compound may be further purified by operations such as distillation, chromatography, and recrystallization.

(Reference Production Process XD)

The compound (XA1) can be produced by reacting a compound (XB1) with a carbamating agent to obtain a compound represented by formula (XD1) (hereinafter referred to as a compound (XD1)), and reacting the compound (XD1) with an isocyanating agent:

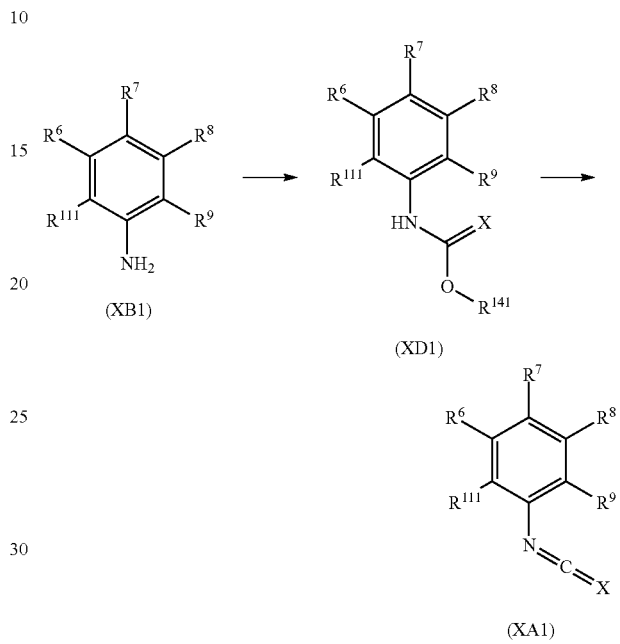

wherein $R^6$, $R^7$, $R^8$, $R^9$, $R^{111}$, and X are as defined above, and $R^{141}$ represents a C1-C6 alkyl group or a phenyl group.

The process for producing the compound (XD1) from the compound (XB1) will be described below.

The reaction is usually performed in a solvent.

Examples of the solvent include hydrocarbons such as heptane, hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; water; and mixtures thereof.

Examples of the carbamating agent include phenyl chlorocarbonate, methyl chlorocarbonate, ethyl chlorocarbonate, propyl chlorocarbonate, isopropyl chlorocarbonate, butyl chlorocarbonate, tert-butyl chlorocarbonate, di-tert-butyl dicarbonate, dimethyl dicarbonate, diethyl dicarbonate, phenyl chlorothioformate, methyl chlorothioformate, and ethyl chlorothioformate.

In the reaction, the carbamating agent is usually used in the proportion within a range of 1 to 10 mols based on 1 mol of the compound (XB1).

The reaction temperature is usually within a range of −20 to 150° C. The reaction time is usually within a range of 0.1 to 24 hours.

In the reaction, if necessary, organic bases such as triethylamine, pyridine, N-methylmorpholine, 4-dimethylaminopyridine, diisopropylethylamine, and diazabicycloundecene; and bases, for example, alkali metal carbonates such as lithium carbonate, sodium carbonate, and potassium carbonate, and alkali metal hydrogen carbonates such as sodium hydrogen carbonate may be added, and these bases are usually used in the proportion within a range of 0.05 to 5 mols based on 1 mol of the compound (XB1).

After completion of the reaction, a compound (XD1) can be isolated by performing post-treatment operations such as extraction of the reaction mixture with an organic solvent, and drying and concentration of the organic layer. The compound may be further purified by operations such as distillation, chromatography, and recrystallization.

The process for producing a compound (XA1) from a compound (XD1) will be described below.

The reaction is usually performed in a solvent.

Examples of the solvent include ethers such as tetrahydrofuran, 1,4-dioxane, ethylene glycol dimethyl ether, methyl tert-butyl ether, and diisopropyl ether; aromatic hydrocarbons such as toluene and xylene; halogenated hydrocarbons such as chloroform, 1,2-dichloroethane, and chlorobenzene; nitriles such as acetonitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; and mixtures thereof.

It is possible to use, as the isocyanating agent, for example, pentachloride, phosphorus oxychloride, diphosphorus pentaoxide, trichlorosilane, dichlorosilane, monochlorosilane, boron trichloride, 2-chloro-1,3,2-benzodioxaborole, silane diiodide, methyltrichlorosilane, dimethyldichlorosilane, and chlorotrimethylsilane.

In the reaction, the isocyanating agent is usually used in the proportion within a range of 1 to 10 mols based on 1 mol of the compound (XD1).

The reaction temperature is usually within a range of $-20$ to $250°$ C. The reaction time is usually within a range of 0.1 to 24 hours.

In the reaction, if necessary, organic bases such as triethylamine, pyridine, N-methylmorpholine, 4-dimethylaminopyridine, diisopropylethylamine, and diazabicycloundecene; bases, for example, alkali metal carbonates such as lithium carbonate, sodium carbonate, and potassium carbonate, and alkali metal hydrogen carbonates such as sodium hydrogen carbonate, and these bases may be usually used in the proportion within a range of 0.05 to 5 mols based on 1 mol of the compound (XD1).

After completion of the reaction, a compound (XA1) can be isolated by performing post-treatment operations such as extraction of the reaction mixture with an organic solvent, and drying and concentration of the organic layer. The compound may be further purified by operations such as distillation, chromatography, and recrystallization.

(Reference Production Process XE)

A compound represented by formula (XE2) (hereinafter referred to as a compound (XE2)) can be produced by reacting a compound represented by formula (XE1) (hereinafter referred to as a compound (XE1)) with hydrogen in the presence of a catalyst:

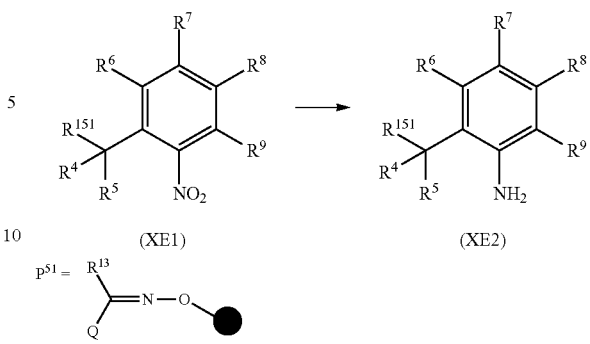

Wherein $R^4$, $R^5$, $R^6$, $R^7$, $R^8$, $R^9$, Q, and $R^{13}$ are as defined above, $R^{151}$ represents a hydrogen atom or $P^{51}$, and the symbol ○ represents a binding site.

The reaction is usually performed in a solvent.

Examples of the solvent include alcohols such as methanol, ethanol, propanol, and butanol; esters such as ethyl acetate and butyl acetate; halogenated hydrocarbons such as chloroform, 1,2-dichloroethane, and chlorobenzene; ethers such as tetrahydrofuran, 1,4-dioxane, ethylene glycol dimethyl ether, methyl tert-butyl ether, and diisopropyl ether; hydrocarbons such as heptane, hexane, cyclohexane, toluene, and xylene; acetic acid, water; and mixtures thereof.

Examples of the catalyst include palladium-supporting carbon (Pd/C), platinum-supporting carbon (Pt/C), osmium-supporting carbon (Os/C), ruthenium-supporting carbon (Ru/C), rhodium-supporting carbon (Rh/C), and Raney nickel.

In the reaction, the catalyst is usually used in the proportion within a range of 0.1 to 1 mol, and hydrogen is used in an excess amount based on 1 mol of the compound (XE1).

The reaction temperature is usually within a range of $-20$ to $150°$ C. The reaction time is usually within a range of 0.1 to 24 hours.

After completion of the reaction, a compound (XE2) can be isolated by performing post-treatment operations such as concentration of the organic layer after filtration of the catalyst. The compound may be further purified by operations such as distillation, chromatography, and recrystallization.

(Reference Production Process XF)

The compound (XE2) can be produced by reacting the compound (XE1) with a reducing agent in the presence of an acid:

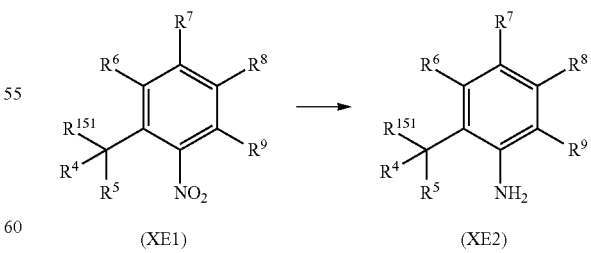

wherein $R^4$, R, $R^6$, $R^7$, $R^8$, $R^9$, and $R^{151}$ are as defined above.

The reaction is usually performed in a solvent.

Examples of the solvent include aliphatic carboxylic acids such as acetic acid; alcohols such as methanol and ethanol; water; and mixtures thereof.

Examples of the reducing agent include tin compounds such as tin chloride; zinc compounds such as zinc chloride; and iron.

Examples of the acid include hydrochloric acid, sulfuric acid, acetic acid, and aqueous ammonium chloride solution.

In the reaction, the reducing agent is usually used in the proportion within a range of 1 to 30 mols, and the acid is usually used in the proportion within a range of 1 to 100 mols, based on 1 mol of the compound (XE1).

The reaction temperature is usually within a range of −20 to 150° C. The reaction time is usually within a range of 0.1 to 24 hours.

After completion of the reaction, a compound (XE2) can be isolated by performing post-treatment operations such as extraction of the reaction mixture with an organic solvent, and drying and concentration of the organic layer. The compound may be further purified by operations such as distillation, chromatography, and recrystallization.

(Reference Production Process XG)

A compound represented by formula (XG2) (hereinafter referred to as a compound (XG2)) can be produced by reacting a compound represented by formula (XG1) (hereinafter referred to as a compound (XG1)) with a compound (B-2) in the presence of a base:

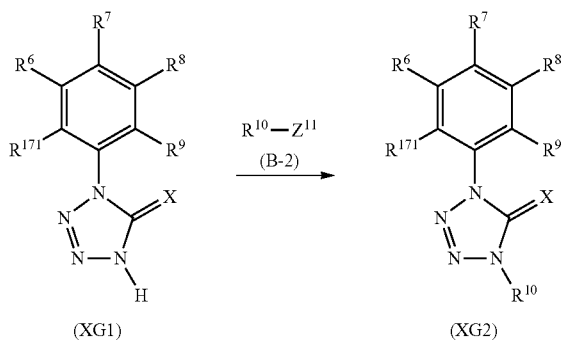

Wherein $R^6$, $R^7$, $R^8$, $R^9$, $R^{10}$, X, and $Z^{11}$ are as defined above, and $R^{171}$ represents $P^{12}$ or $P^{13}$.

The reaction can be carried out according to the Production Process B.

(Reference Production Process XH)

A compound represented by formula (XH2) (hereinafter referred to as a compound (XH2)) can be produced by reacting a compound represented by formula (XH1) (hereinafter referred to as a compound (XH1)) with a halogenating agent in the presence of a radical initiator:

Wherein $R^4$, $R^5$, $R^6$, $R^7$, $R^8$, $R^9$, $R^{10}$, $Z^{181}$, and X are as defined above, and $R^{181}$ represents $P^{81}$ or a nitro group.

The reaction is usually performed in a solvent.

Examples of the solvent include hydrocarbons such as heptane, hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; esters such as ethyl acetate and methyl acetate; ketones such as acetone, methyl ethyl ketone, and methyl isobutyl ketone; nitriles such as acetonitrile; and mixtures thereof.

The halogenating agent is a chlorinating agent, a brominating agent, or an iodinating agent, and examples thereof include chlorine, bromine, iodine, sulfuryl chloride, N-chlorosuccinimide, N-bromosuccinimide, 1,3-dibromo-5,5-dimethylhydantoin, iodosuccinimide, tert-butyl hypochlorite, N-chloroglutarimide, N-bromoglutarimide, N-chloro-N-cyclohexyl-benzenesulfonimide, and N-bromophthalimide.

Examples of the radical initiator include benzoyl peroxide, azobisisobutyronitrile (AIBN), 1,1-azobis(cyanocyclohexane), diacyl peroxide, dialkyl peroxydicarbonate, tert-alkyl peroxyester, monoperoxycarbonate, di(tert-alkylperoxy)ketal and ketone peroxide, and triethylborane.

In the reaction, the halogenating agent is usually used in the proportion within a range of 1 to 10 mols, and the radical initiator is usually used in the proportion within a range of 0.01 to 5 mols, based on 1 mol of the compound (XH1).

The reaction temperature is usually within a range of −20 to 150° C. The reaction time is usually within a range of 0.1 to 24 hours.

After completion of the reaction, a compound (XH2) can be isolated by performing post-treatment operations such as extraction of the reaction mixture with an organic solvent, and drying and concentration of the organic layer. The compound may be further purified by operations such as distillation, chromatography, and recrystallization.

(Reference Production Process XI)

A compound represented by formula (XI2) (hereinafter referred to as a compound (XI2)) can be produced by subjecting a compound represented by the following formula (XI1) (hereinafter referred to as a compound (XI1)) and the compound (D-2) to a coupling reaction in the presence of a base and a catalyst:

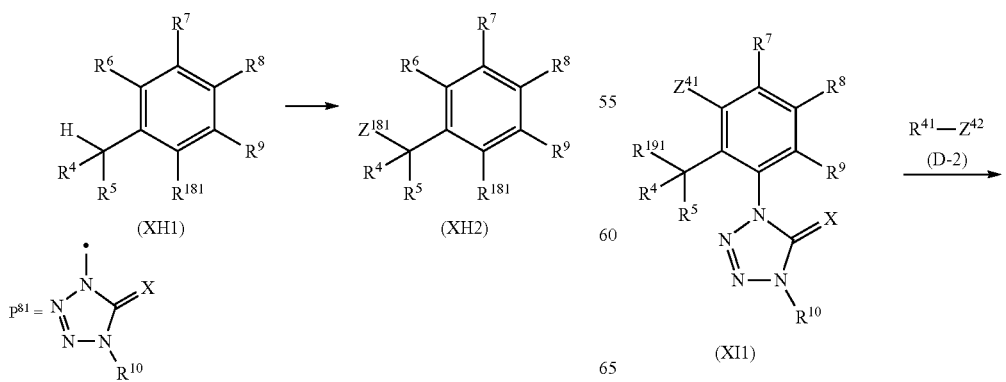

-continued

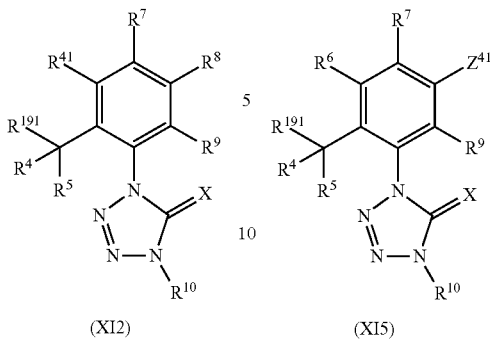

wherein $R^{191}$ represents a hydrogen atom or an $OR^{112}$ group, and $R^4$, $R^5$, $R^7$, $R^8$, $R^9$, $R^{10}$, $R^{41}$, X, $Z^{41}$, and $Z^{42}$ are as defined above.

The reaction can be carried out according to the Production Process D.

A compound represented by formula (XI4) (hereinafter referred to as a compound (XI4)) can be produced by subjecting compound represented by formula (XI3) (hereinafter referred to as a compound (XI3)) and a compound (D-4) to a coupling reaction in the presence of a base and a catalyst:

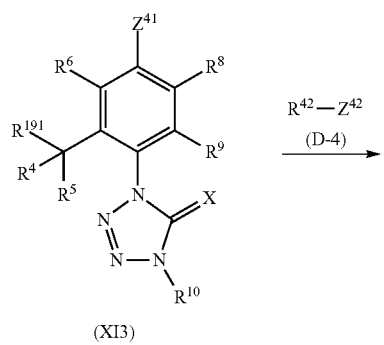

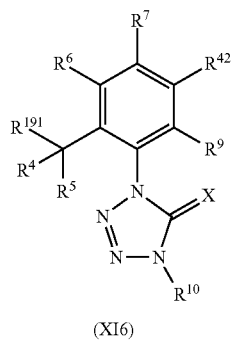

wherein $R^4$, $R^5$, $R^6$, $R^8$, $R^9$, $R^{10}$, $R^{42}$, $R^{191}$, X, $Z^{41}$, and $Z^{42}$ are as defined above.

The reaction can be carried out according to the Production Process D.

A compound represented by formula (XI6) (hereinafter referred to as a compound (XI6)) can be produced by subjecting a compound represented by formula (XI5) (hereinafter referred to as a compound (XI5)) and the compound (D-4) to a coupling reaction in the presence of a base and a catalyst:

wherein $R^4$, $R^5$, $R^6$, $R^8$, $R^9$, $R^{10}$, $R^{42}$, $R^{191}$, X, $Z^{41}$, and $Z^{42}$ are as defined above.

The reaction can be carried out according to the Production Process D.

A compound represented by formula (XI8) (hereinafter referred to as a compound (XI8)) can be produced by subjecting a compound represented by formula (XI7) (hereinafter referred to as a compound (XI7)) and the compound (D-4) to a coupling reaction in the presence of a base and a catalyst:

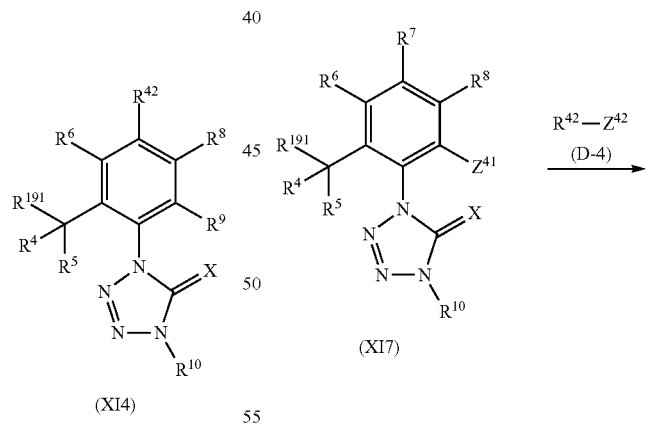

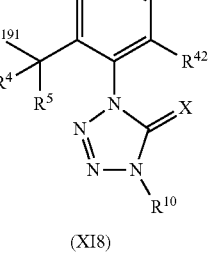

wherein $R^4$, $R^5$, $R^6$, $R^7$, $R^8$, $R^{10}$, $R^{42}$, $R^{191}$, X, $Z^{41}$, and $Z^{42}$ are as defined above The reaction can be carried out according to the Production Process D.

(Reference Production Process XJ)

A compound represented by formula (XJ2) (hereinafter referred to as a compound (XJ2)) can be produced by subjecting a compound represented by formula (XJ1) (hereinafter referred to as a compound (XJ1)) and the compound (D-2) a coupling reaction in the presence of a base and a catalyst:

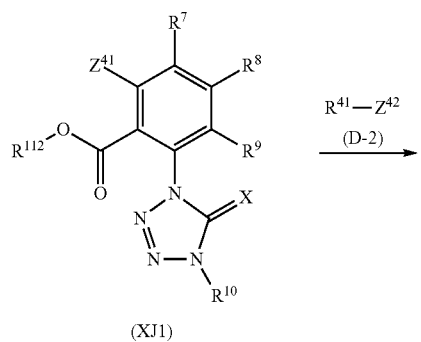

(XJ1)

$R^{41}-Z^{42}$
(D-2)
→

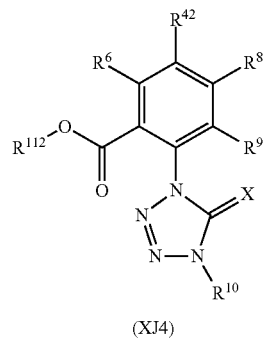

(XJ2)

wherein $R^7$, $R^8$, $R^9$, $R^{10}$, $R^{41}$, $R^{112}$, X, $Z^{41}$, and $Z^{42}$ are as defined above.

The reaction can be carried out according to the Production Process D.

A compound represented by formula (XJ4) (hereinafter referred to as a compound (XJ4)) can be produced by subjecting a compound represented by the following formula (XJ3) (hereinafter referred to as a compound (XJ3)) and the compound (D-4) to a coupling reaction in the presence of a base and a catalyst:

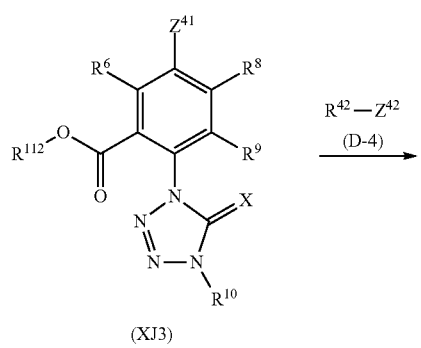

(XJ3)

$R^{42}-Z^{42}$
(D-4)
→

(XJ4)

wherein $R^6$, $R^8$, $R^9$, $R^{10}$, $R^{42}$, $R^{112}$, X, $Z^{41}$, and $Z^{42}$ are as defined above.

The reaction can be carried out according to the Production Process D.

A compound represented by formula (XJ6) (hereinafter referred to as a compound (XJ6)) can be produced by subjecting a compound represented by formula (XJ5) (hereinafter referred to as a compound (XJ5)) and the compound (D-4) to a coupling reaction in the presence of a base and a catalyst:

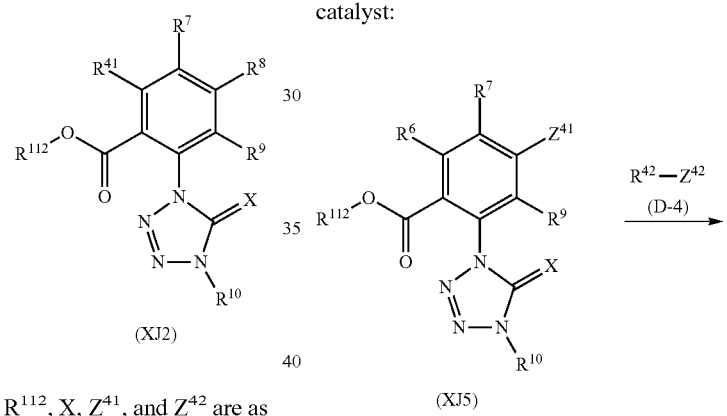

(XJ5)  $R^{42}-Z^{42}$ (D-4) →  (XJ6)

wherein $R^6$, $R^7$, $R^9$, $R^{10}$, $R^{42}$, $R^{112}$, X, $Z^{41}$, and $Z^{42}$ are as defined above.

The reaction can be carried out according to the Production Process D.

A compound represented by formula (XJ8) (hereinafter referred to as a compound (XJ8)) can be produced by subjecting a compound represented by formula (XJ7) (hereinafter referred to as a compound (XJ7)) and the compound (D-4) to a coupling reaction in the presence of a base and a catalyst:

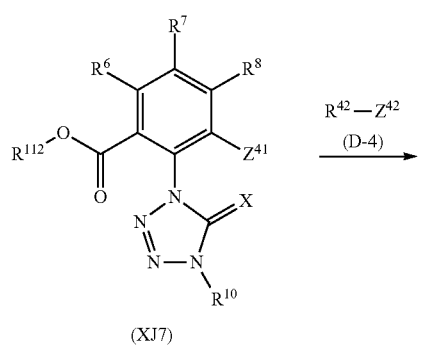

(XJ7)

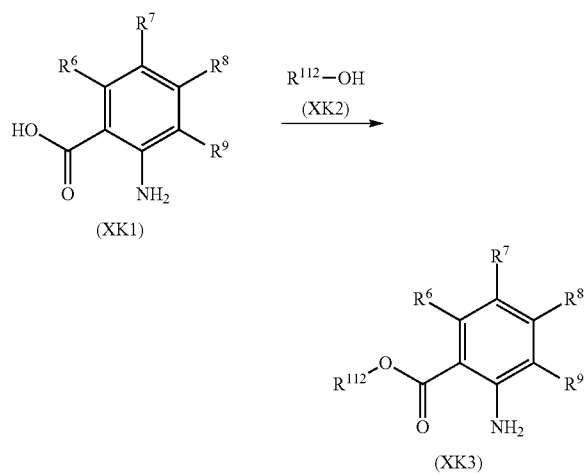

wherein $R^6$, $R^7$, $R^8$, $R^{10}$, R, $R^{112}$, X, $Z^{41}$, and $Z^{42}$ are as defined above.

The reaction can be carried out according to the Production Process D.

(Reference Production Process XK)

A compound represented by formula (XK3) (hereinafter referred to as a compound (XK3)) can be produced by reacting a compound represented by the following formula (XK1) (hereinafter referred to as a compound (XK1)) with a compound represented by formula (XK2) (hereinafter referred to as a compound (XK2)) in the presence of a reaction accelerator:

wherein $R^6$, $R^7$, $R^8$, $R^9$, and $R^{112}$ are as defined above.

The reaction is usually performed in a solvent.

Examples of the solvent include hydrocarbons such as heptane, hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; and mixtures thereof, and the compound (XK2) may be used as the solvent.

Examples of the compound (XK2) usable in the reaction include methyl alcohol, ethyl alcohol, propyl alcohol, isopropyl alcohol, butyl alcohol, sec-butyl alcohol, tert-butyl alcohol, and pentanol.

Examples of the reaction accelerator include acids such as hydrochloric acid and sulfuric acid; carbodiimides such as dicyclohexylcarbodiimide, diisopropylcarbodiimide, and N'-(3-dimethylaminopropyl)-N-ethylcarbodiimide; organic acids such as methanesulfonic acid and toluenesulfonic acid; Mitsunobu reaction reagents such as triphenylphosphine/diethyl azodicarboxylate; thionyl chloride, and boron trifluoride-ethyl ether complex.

In the reaction, the reaction accelerator is usually used in the proportion within a range of 0.01 to 10 mols based on 1 mol of the compound (XK1).

In the reaction, if necessary, organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate may be added, and these compounds are usually used in the proportion within a range of 0.001 to 5 mols based on 1 mol of the compound (XK1).

In the reaction, an excess amount of compound (XK2) is used based on the compound (XK1).

The reaction temperature is usually within a range of −78 to 100° C. The reaction time is usually within a range of 0.1 to 24 hours.

After completion of the reaction, an compound (XK3) can be isolated by performing post-treatment operations such as extraction of the reaction mixture with an organic solvent, and drying and concentration of the organic layer. The compound may be further purified by operations such as distillation, chromatography, and recrystallization.

(Reference Production Process XL)

The compound (XK3) can be produced by reacting the compound (XK1) with a halogenating agent to obtain the compound represented by following formula (XL1) (hereinafter referred to as a compound (XL1)), and then reacting the compound (XL1) with the compound (XK2):

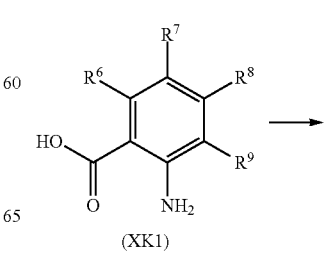

-continued

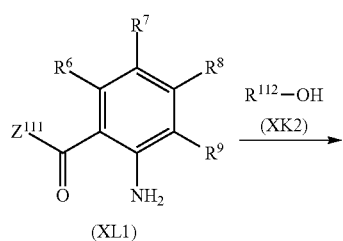

(XL1)

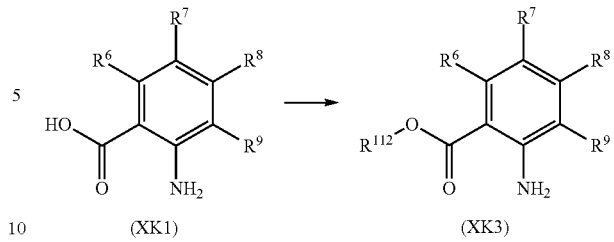

wherein $R^6$, $R^7$, $R^8$, $R^9$, and $R^{12}$ are as defined above.

The reaction is usually performed in a solvent.

Examples of the solvent include hydrocarbons such as heptane, hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; water; and mixtures thereof.

Examples of the alkylating agent include diazo compounds such as diazomethane and trimethylsilyldiazomethane; alkyl halides such as chlorodifluoromethane, methyl bromide, ethyl bromide, propyl bromide, methyl iodide, ethyl iodide, propyl bromide, allyl bromide, cyclopropyl bromide, benzyl bromide, and 1,1-difluoro-2-iodoethane; dialkyl sulfates such as dimethyl sulfate, diethyl sulfate, and dipropyl sulfate; and alkyl or aryl sulfate esters, such as methyl p-toluenesulfonate, ethyl p-toluenesulfonate, propyl p-toluenesulfonate, methyl methanesulfonate, ethyl methanesulfonate, and propyl methanesulfonate.

In the reaction, the alkylating agent is usually used in the proportion within a range of 1 to 10 mols based on 1 mol of the compound (XK1).

In the reaction, if necessary, additives may be added. Examples of additives include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate; and quaternary ammonium salts such as tetrabutylammonium hydroxide. These additives are usually used in the proportion within a range of 0.001 to 5 mols based on 1 mol of the compound (XK1).

The reaction temperature is usually within a range from −78 to 100° C. The reaction time is usually within a range of 0.1 to 24 hours.

After completion of the reaction, a compound (XK3) can be isolated by performing post-treatment operations such as extraction of the reaction mixture with an organic solvent, and drying and concentration of the organic layer. The compound may be further purified by operations such as distillation, chromatography, and recrystallization.

(Reference Production Process XN)

A compound represented by formula (XN2) (hereinafter referred to as a compound (XN2)) can be produced by reacting a compound represented by formula (XN1) (hereinafter referred to as a compound (XN1)) with a reducing agent:

wherein $R^6$, $R^7$, $R^8$, $R^9$, $R^{112}$, and $Z^{111}$ are as defined above.

The process for reacting the compound (XK1) with a halogenating agent to produce the compound (XL1) can be carried out according to the Reference Production Process XC.

The process for producing the compound (XK3) from the compound (XL1) will be described below.

The reaction is usually performed in a solvent.

Examples of the solvent include hydrocarbons such as heptane, hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; and mixtures thereof, and the compound (XK2) can be used as the solvent.

Examples of the compound (XK2) include methyl alcohol, ethyl alcohol, propyl alcohol, isopropyl alcohol, butyl alcohol, sec-butyl alcohol, tert-butyl alcohol, and pentanol.

In the reaction, the compound (XK2) is usually used in the proportion within a range of 1 to 50 mols based on 1 mol of the compound (XL1).

The reaction temperature is usually within a range of −78 to 100° C. The reaction time is usually within a range of 0.1 to 24 hours.

After completion of the reaction, a compound (XK3) can be isolated by performing post-treatment operations such as extraction of the reaction mixture with an organic solvent, and drying and concentration of the organic layer. The compound may be further purified by operations such as distillation, chromatography, and recrystallization.

(Reference Production Process XM)

The compound (XK3) can be produced by reacting the compound (XK1) with an alkylating agent:

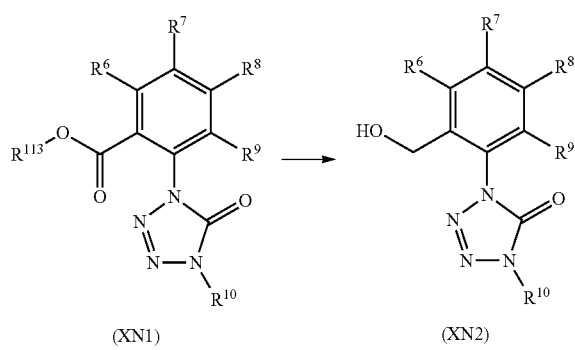

(XN1) → (XN2)

wherein $R^6$, $R^7$, $R^8$, $R^9$, and $R^{10}$ are as defined above, and $R^{113}$ represents a hydrogen atom or a C1-C3 alkyl group.

The reaction is usually performed in a solvent.

Examples of the solvent include hydrocarbons such as heptane, hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; alcohols such as methanol, ethanol, propanol, and butanol; water; and mixtures thereof.

Examples of the reducing agent include lithium triethylborohydride, aluminum diisobutylhydride, lithium aminoborohydride, lithium borohydride, sodium borohydride, borane, borane dimethyl sulfide complex, and borane tetrahydrofuran complex.

In the reaction, the reducing agent is usually used in the proportion of 1 to 10 mols based on 1 mol of the compound (XN1).

The reaction temperature is usually within a range from −78 to 100° C. The reaction time is usually within a range of 0.1 to 24 hours.

After completion of the reaction, a compound (XN2) can be isolated by performing post-treatment operations such as extraction of the reaction mixture with an organic solvent, and drying and concentration of the organic layer. The compound may be further purified by operations such as distillation, chromatography, and recrystallization.

(Reference Production Process XO)

A compound represented by formula (XO2) (hereinafter referred to as a compound (XO2)) can be produced by reacting a compound represented by formula (XO1) (hereinafter referred to as a compound (XO1)) with a reducing agent:

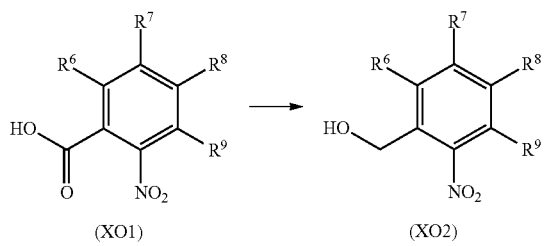

(XO1) → (XO2)

wherein $R^6$, $R^7$, $R^8$, and $R^9$ are as defined above.

The reaction is usually performed in a solvent.

Examples of the solvent include hydrocarbons such as heptane, hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; sulfoxides such as dimethyl sulfoxide; nitriles such as acetonitrile; alcohols such as methanol, ethanol, propanol, and butanol; water; and mixtures thereof.

Examples of the reducing agent include borane, borane tetrahydrofuran complex, and borane dimethyl sulfide complex. It is also possible to use borane to be generated by mixing a borohydride such as sodium borohydride or potassium borohydride with an acid such as sulfuric acid, hydrochloric acid, methanesulfonic acid, or boron trifluoride diethyl ether complex.

In the reaction, the reducing agent is usually used in the proportion within a range of 1 to 10 mols based on 1 mol of the compound (XO1).

The reaction temperature is usually within a range from −20 to 100° C. The reaction time is usually within a range of 0.1 to 72 hours.

After completion of the reaction, a compound (XO2) can be isolated by performing post-treatment operations such as extraction of the reaction mixture with an organic solvent, and drying and concentration of the organic layer. The compound may be further purified by operations such as distillation, chromatography, and recrystallization.

(Reference Production Process XP)

A compound represented by formula (XP2) (hereinafter referred to as a compound (XP2)) can be produced by reacting the compound (XH2) with a compound represented by formula (XP1) (hereinafter referred to as a compound (XP1)):

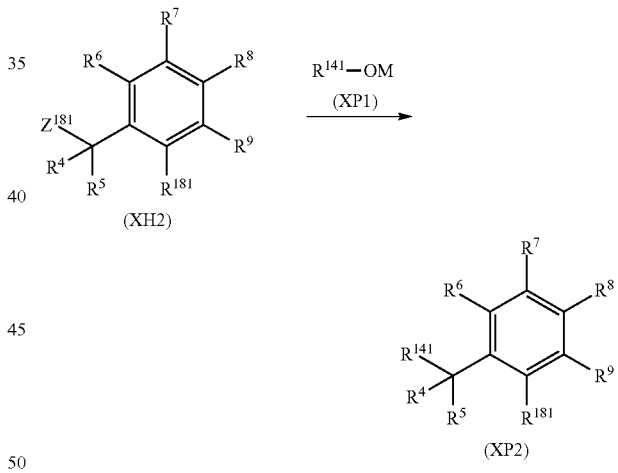

wherein $R^4$, $R^5$, $R^6$, $R^7$, $R^8$, $R^9$, $R^{141}$, $R^{181}$, and $Z^{181}$ are as defined above, and M represents sodium, potassium, or lithium.

The reaction is usually performed in a solvent.

Examples of the solvent include ethers such as tetrahydrofuran, 1,4-dioxane, ethylene glycol dimethyl ether, methyl tert-butyl ether, and diisopropyl ether; hydrocarbons such as heptane, hexane, cyclohexane, toluene, and xylene; halogenated hydrocarbons such as chloroform, 1,2-dichloroethane, and chlorobenzene; nitriles such as acetonitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; alcohols such as methanol, ethanol, propanol, and butanol; and mixtures thereof.

Examples of the compound (XI1) include sodium methoxide, sodium ethoxide, sodium propoxide, sodium butoxide, sodium isopropoxide, sodium sec-butoxide, sodium tert-butoxide, potassium methoxide, potassium ethoxide, potassium propoxide, potassium butoxide, potassium isopropoxide, potassium sec-butoxide, potassium tert-butoxide, and sodium phenoxide.

In the reaction, the compound (XP1) is usually used in the proportion within a range of 1 to 10 mols based on 1 mol of the compound (XH2).

The reaction temperature is usually within a range of −20 to 150° C. The reaction time is usually within a range of 0.1 to 24 hours.

After completion of the reaction, a compound (XP2) can be isolated by performing post-treatment operations such as extraction of the reaction mixture with an organic solvent, and drying and concentration of the organic layer. The compound may be further purified by operations such as distillation, chromatography, and recrystallization.

(Reference Production Process XQ)

A compound represented by formula (XQ1) (hereinafter referred to as a compound (XQ1)) can be produced by reacting the compound (XH2) with water in the presence of a base:

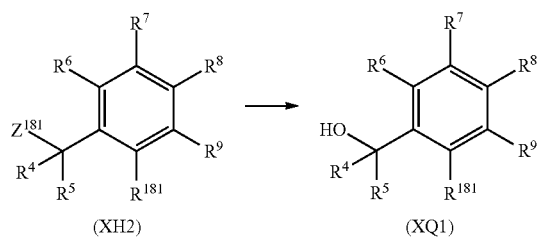

(XH2)            (XQ1)

wherein $R^4$, $R^5$, $R^6$, $R^7$, $R^8$, $R^9$, $R^{181}$, and $Z^{181}$ are as defined above.

The reaction is usually performed in water, or a solvent containing water.

Examples of the solvent include ethers such as tetrahydrofuran, 1,4-dioxane, ethylene glycol dimethyl ether, methyl tert-butyl ether, and diisopropyl ether; hydrocarbons such as heptane, hexane, cyclohexane, toluene, and xylene; halogenated hydrocarbons such as chloroform, 1,2-dichloroethane, and chlorobenzene; nitriles such as acetonitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; alcohols such as methanol, ethanol, propanol, and butanol; and mixtures thereof.

Examples of the base include organic bases such as triethylamine, pyridine, N-methylmorpholine, 4-dimethylaminopyridine, diisopropylethylamine, and diazabicycloundecene; metal organic acid salts such as lithium formate, lithium acetate, sodium formate, sodium acetate, potassium formate, and potassium acetate; metal nitrates such as silver nitrate and sodium nitrate; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide; and alkali metal alkoxides such as sodium ethoxide and potassium tert-butoxide.

In the reaction, the base is usually used in the proportion within a range of 1 to 100 mols based on 1 mol of the compound (XH2).

In the reaction, water is usually used in the proportion within a range of 1 mol to a large excess amount of mols based on 1 mol of the compound (XH2).

The reaction temperature is usually within a range of −20 to 150° C. The reaction time is usually within a range of 0.1 to 24 hours.

After completion of the reaction, a compound (XQ1) can be isolated by performing post-treatment operations such as extraction of the reaction mixture with an organic solvent, and drying and concentration of the organic layer. The compound may be further purified by operations such as distillation, chromatography, and recrystallization.

(Reference Production Process XR)

The compound (XH2) can be produced by reacting a compound (XP2) with a halogenating agent:

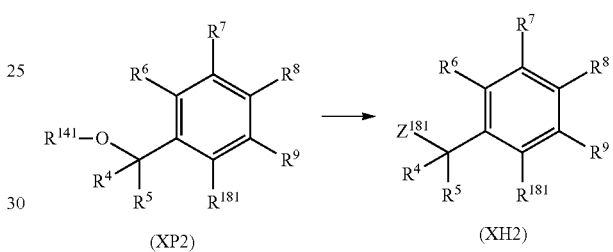

(XP2)            (XH2)

wherein $R^4$, $R^5$, $R^6$, $R^7$, $R^8$, $R^9$, $R^{141}$, $R^{181}$ and $Z^{181}$ are as defined above.

The reaction is usually performed in a solvent.

Examples of the solvent include hydrocarbons such as heptane, hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; esters such as ethyl acetate and methyl acetate; ketones such as acetone, methyl ethyl ketone, and methyl isobutyl ketone; nitriles such as acetonitrile; organic acids such as formic acid, acetic acid, and trifluoroacetic acid; water; and mixtures thereof.

Examples of the halogenating agent include hydrochloric acid, hydrobromic acid, and hydroiodic acid.

In the reaction, the halogenating agent is usually used in the proportion within a range of 1 mol or more based on 1 mol of the compound (XP2).

The reaction temperature is usually within a range of −20 to 150° C. The reaction time is usually within a range of 0.1 to 24 hours.

After completion of the reaction, a compound (XH2) can be isolated by performing post-treatment operations such as extraction of the reaction mixture with an organic solvent, and drying and concentration of the organic layer. The compound may be further purified by operations such as distillation, chromatography, and recrystallization.

(Reference Production Process XS)

The compound (XH2) can be produced by reacting a compound (XQ1) with a halogenating agent:

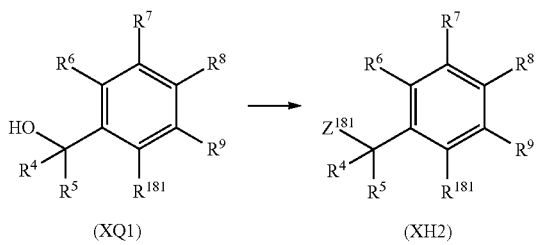

(XQ1) (XH2)

wherein $R^4$, $R^5$, $R^6$, $R^7$, $R^8$, $R^9$, $R^{181}$, and $Z^{181}$ are as defined above.

The reaction is usually performed in a solvent.

Examples of the solvent include hydrocarbons such as heptane, hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; esters such as ethyl acetate and methyl acetate; ketones such as acetone, methyl ethyl ketone, and methyl isobutyl ketone; nitriles such as acetonitrile; organic acids such as formic acid, acetic acid, and trifluoroacetic acid; water; and mixtures thereof.

Examples of the halogenating agent used in the reaction bromine, include chlorine, sulfuryl chloride, hydrochloric acid, hydrobromic acid, hydroiodic acid, boron tribromide, phosphorus tribromide, trimethylsilyl chloride, trimethylsilyl bromide, trimethylsilyl iodide, thionyl chloride, thionyl bromide, phosphorus oxychloride, phosphorus trichloride, phosphorus pentachloride, thionyl chloride, phosphorus oxybromide, phosphorus pentabromide, phosphorus triiodide, oxalyl dichloride, oxalyl dibromide, acetyl chloride, carbon tetrabromide, N-bromosuccinimide, lithium chloride, sodium iodide, and acetyl bromide.

In the reaction, the halogenating agent is usually used in the proportion within a range of 1 to 10 mols based on 1 mol of the compound (XQ1).

In order to enable the reaction to proceed, additives may be used depending on the halogenating agent to be used. Examples of additives include zinc chloride for, acetyl chloride, triphenylphosphine for carbon tetrabromide, dimethyl sulfide for N-bromosuccinimide, boron trifluoride diethyl ether complex for sodium iodide, boron trifluoride diethyl ether complex for acetyl bromide, triethylamine and methanesulfonyl chloride for lithium chloride, aluminum chloride for sodium iodide, and trimethylsilyl chloride for sodium iodide. The amount of additives to be used is usually within a range of 0.01 to mols based on 1 mol of the compound (XQ1).

The reaction temperature is usually within a range of −20 to 150° C. The reaction time is usually within a range of 0.1 to 24 hours.

After completion of the reaction, a compound (XH2) can be isolated by performing post-treatment operations such as extraction of the reaction mixture with an organic solvent, and drying and concentration of the organic layer. The compound may be further purified by operations such as distillation, chromatography, and recrystallization.

(Reference Production Process YA)

The compound (A-2) can be produced by reacting a compound represented by formula (YA1) (hereinafter referred to as a compound (YA1)) with hydroxylamine or a salt thereof:

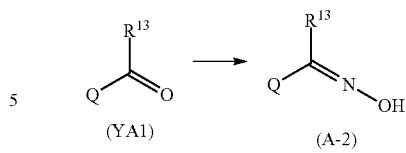

(YA1) (A-2)

wherein $R^{13}$ and Q are as defined above.

The reaction is usually performed in a solvent.

Examples of the solvent include alcohols such as methanol, ethanol, propanol, and butanol; water, hydrocarbons such as heptane, hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; sulfoxides such as dimethyl sulfoxide; nitriles such as acetonitrile; and mixtures thereof.

Examples of the hydroxylamine salt include hydroxylamine hydrochloride, hydroxylamine sulfate, and hydroxylamine carbonate.

In the reaction, hydroxylamine or a salt thereof is usually used in the proportion of 1 to 10 mols based on 1 mol of the compound (YA1).

In the reaction, if necessary, additives may be added, and examples of additive include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate; alkali metal acetates such as sodium acetate and potassium acetate; and quaternary ammonium salts such as tetrabutylammonium hydroxide. These additives are usually used in the proportion within a range of 0.5 to 10 mols based on 1 mol of the compound (YA1).

The reaction temperature is usually within a range of 20 to 150° C. The reaction time is usually within a range of 0.1 to 72 hours.

After completion of the reaction, a compound (A-2) can be isolated by performing post-treatment operations such as extraction of the reaction mixture with an organic solvent, and drying and concentration of the organic layer. The compound may be further purified by operations such as distillation, chromatography, and recrystallization.

(Reference Production Process YB)

The compound (YA1) can be produced by reacting a compound represented by formula (YB1) (hereinafter referred to as a compound (YB1)) with a compound represented by formula (YB2) (hereinafter referred to as a compound (YB2)):

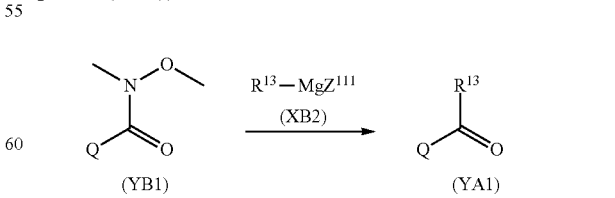

(YB1) (YA1)

wherein $R^{13}$, Q, and $Z^{111}$ are as defined above.

The reaction is usually performed in a solvent.

Examples of the solvent include hydrocarbons such as heptane, hexane, cyclohexane, toluene, and xylene; ethers such as tetrahydrofuran, 1,4-dioxane, ethylene glycol dimethyl ether, methyl tert-butyl ether, and diisopropyl ether; and mixtures thereof.

Examples of the compound (YB2) include alkylmagnesium halides such as methylmagnesium chloride, methylmagnesium bromide, ethylmagnesium chloride, ethylmagnesium bromide, propylmagnesium chloride, propylmagnesium bromide, isopropylmagnesium chloride, isopropylmagnesium bromide, cyclopropylmagnesium chloride, cyclopropylmagnesium bromide, butylmagnesium chloride, butylmagnesium bromide, pentylmagnesium chloride, pentylmagnesium bromide, hexylmagnesium chloride, and hexylmagnesium bromide; and organic magnesium reagents such as vinylmagnesium chloride, vinylmagnesium bromide, ethynylmagnesium chloride, and ethynylmagnesium bromide.

In the reaction, the compound (YB2) is usually used in the proportion within a range of 0.5 to 10 mols based on 1 mol of the compound (YB1).

The reaction temperature is usually within a range of −90 to 100° C. The reaction time is usually within a range of 0.1 to 72 hours.

After completion of the reaction, a compound (YA1) can be isolated by performing post-treatment operations such as extraction of the reaction mixture with an organic solvent, and drying and concentration of the organic layer. The compound may be further purified by operations such as distillation, chromatography, and recrystallization.

(Reference Production Process YC)

The compound (YB1) can be produced by a compound represented by formula (YC1) (hereinafter referred to as a compound (YC1)) with N,O-dimethylhydroxylamine or a salt thereof:

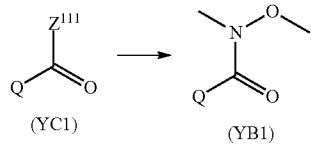

(YC1) (YB1)

wherein Q and $Z^{111}$ are as defined above.

The reaction is usually performed in a solvent.

Examples of the solvent include hydrocarbons such as heptane, hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; esters such as ethyl acetate and methyl acetate; sulfoxides such as dimethyl sulfoxide; ketones such as acetone, methyl ethyl ketone, and methyl isobutyl ketone; nitriles such as acetonitrile; and mixtures thereof.

Examples of the N,O-dimethyl-hydroxylamine salt include N,O-dimethyl-hydroxylamine hydrochloride and N,O-dimethyl-hydroxylamine sulfate.

Examples of the acid include hydrochloric acid, sulfuric acid, nitric acid, acetic acid, trifluoroacetic acid, and p-toluenesulfonic acid, and examples of the base include organic bases such as triethylamine, pyridine, N-methylmorpholine, 4-dimethylaminopyridine, diisopropylethylamine, and diazabicycloundecene; metal hydrides such as sodium hydride and potassium hydride; metal organic acid salts such as lithium formate, lithium acetate, sodium formate, sodium acetate, potassium formate, and potassium acetate; metal nitrates such as silver nitrate and sodium nitrate; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide; and alkali metal alkoxides such as sodium ethoxide and potassium tert-butoxide.

In the reaction, N,O-dimethyl-hydroxylamine or a salt thereof is usually used in the proportion within a range of 1 to 10 mols, and the acid or base is usually used in the proportion within a range of 1 to 15 mols, based on the compound (YC1).

The reaction temperature is usually within a range of −20 to 150° C. The reaction time is usually within a range of 0.1 to 24 hours.

After completion of the reaction, a compound (YB1) can be isolated by performing post-treatment operations such as extraction of the reaction mixture with an organic solvent, and drying and concentration of the organic layer. The isolated compound (YB1) can also be further purified by chromatography, recrystallization, and the like.

(Reference Production Process YD)

The compound (YC1) can be produced by a compound represented by formula (YD1) (hereinafter referred to as a compound (YD1)) with a halogenating agent:

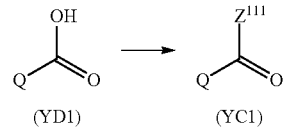

(YD1) (YC1)

wherein Q and $Z^1$ are as defined above.

The reaction is usually performed in a solvent.

Examples of the solvent include hydrocarbons such as heptane, hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; esters such as ethyl acetate and methyl acetate; nitriles such as acetonitrile; and mixtures thereof.

Examples of the halogenating agent include phosphorus oxychloride, phosphorus trichloride, phosphorus pentachloride, thionyl chloride, phosphorus oxybromide, phosphorus tribromide, phosphorus pentabromide, phosphorus triiodide, oxalyl dichloride, oxalyl dibromide, triphosgene, diphosgene, phosgene, and sulfuryl chloride.

In the reaction, the halogenating agent is usually used in the proportion within a range of 1 to 10 mols based on 1 mol of the compound (YD1).

The reaction temperature is usually within a range of −20 to 150° C. The reaction time is usually within a range of 0.1 to 24 hours.

In the reaction, a catalyst may be added and, for example, N,N-dimethylformamide is used as the catalyst. The catalyst is usually used in the proportion within a range of 0.001 to 1 mol based on 1 mol of the compound (YD1).

In the reaction, if necessary, organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; and alkali metal hydrogen carbonates such as sodium hydrogen carbonate may be further added, and these compounds are usually used in the proportion within a range of 0.05 to 5 mols based on 1 mol of the compound (YD1).

After completion of the reaction, a compound (YC1) can be isolated by performing post-treatment operations such as extraction of the reaction mixture with an organic solvent, and drying and concentration of the organic layer. The compound may be further purified by operations such as distillation, chromatography, and recrystallization.

(Reference Production Process YE)

The compound (YD1) can be produced by reacting a compound represented by formula (YE1) (hereinafter referred to as a compound (YE1)) with a hydrolyzing agent:

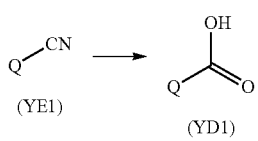

wherein Q is as defined above.

The reaction is usually performed in a solvent.

Examples of the solvent include water; alcohols such as methanol, ethanol, propanol, and butanol; hydrocarbons such as heptane, hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; ketones such as acetone, methyl ethyl ketone, and methyl isobutyl ketone; and mixtures thereof.

Examples of the hydrolyzing agent include bases such as aqueous potassium hydroxide solution; bases such as aqueous sodium hydroxide solution; and acids such as hydrochloric acid and sulfuric acid.

In the reaction, the hydrolyzing agent is usually used in the proportion within a range of 1 to 20 mols based on 1 mol of the compound (YE1).

The reaction temperature is usually within a range of −20 to 150° C. The reaction time is usually within a range of 0.1 to 72 hours.

After completion of the reaction, a compound (YD1) can be isolated by performing post-treatment operations such as extraction of the reaction mixture with an organic solvent, and drying and concentration of the organic layer. The compound may be further purified by operations such as distillation, chromatography, and recrystallization.

Although a form used for the present compound may be the present compound as itself, the present compound is usually prepared by mixing the present compound with solid carriers, liquid carriers, gas carriers, surfactants and the others, and if necessary, adding stickers, dispersers and stabilizers, to formulate into wettable powders, water dispersible granules, flowables, granules, dry flowables, emulsifiable concentrates, aqueous solutions, oil solutions, smoking agents, aerosols, microcapsules and the others, In these formulations, the present compound is contained in a range of usually 0.1 to 99%, preferably 0.2 to 90% by weight.

Examples of the solid carrier include clays (for example, kaolin, diatomaceous earth, synthetic hydrated silicon dioxide, Fubasami clay, bentonite and acid clay), talcs or the other inorganic minerals (for example, sericite, quartz powder, sulfur powder, activated charcoal, calcium carbonate and hydrated silica) in the form of fine powders or particulates, and examples of the liquid carries include water, alcohols (for example, methanol and ethanol), ketones (for example, acetone and methyl ethyl ketone), aromatic hydrocarbons (for example, benzene, toluene, xylene, ethylbenzene and methyl naphthalene), aliphatic hydrocarbons (for example, hexane, cyclohexane and kerosene), esters (for example, ethyl acetate and butyl acetate), nitriles (for example, acetonitrile and isobutyronitrile), ethers (for example, dioxane and diisopropylether), acid amides (for example, N,N-dimethyl formamide which may be referred to DMF) and dimethylacetamide), halogenated hydrocarbons (for example, dichloroethane, trichloro ethylene and carbon tetrachloride) and the others.

Examples of the surfactants include alkyl sulfates, alkyl sulfonates, alkyl aryl sulfonates, alkyl aryl ethers and polyoxyethylenated compounds thereof, polyethylene glycol ethers, polyol esters and sugar alcohol derivatives Examples of other auxiliary agents for formulation include stickers, dispersers and stabilizers, specifically casein, gelatin, polysaccharides (for example, starch, gum arabic, cellulose derivatives and alginic acid), lignin derivatives, bentonite, sugars, water-soluble synthetic polymers (for example, polyvinyl alcohol, polyvinyl pyrrolidone and polyacrylic acids), PAP (acidic isopropyl phosphate), BHT (2,6-di-tert-butyl-4-methylphenol), BHA (a mixture of 2-tert-butyl-4-methoxyphenol and 3-tert-butyl-4-methoxyphenol), vegetable oils, mineral oils and fatty acids or fatty acid esters thereof.

The method for applying the present control agent is not particularly limited, as far as the applying form is a form by which the present compound may be applied substantially, and includes, for example, an application to plants such as a foliage application; an application to area for cultivating plants such as a soil treatment; and an application to seeds such as seed disinfection.

The present compound may be used by mixing with various oil such as mineral oil and plant oil, or with surfactant. Examples of the oil and the surfactant include Nimbus (Registered Trademark), Assist (Registered Trademark), Aureo (Registered Trademark), Iharol (Registered Trademark), Silwet L-77 (Registered Trademark), Break-Thru (Registered Trademark), Sundancell (Registered Trademark), Induce (Registered Trademark), Penetrator (Registered Trademark), AgriDex (Registered Trademark). Lutensol A8 (Registered Trademark), NP-7 (Registered Trademark), Triton (Registered Trademark), Nufilm (Registered Trademark), Emulgator NP7 (Registered Trademark), Emulad (Registered Trademark), TRITON X 45 (Registered Trademark), AGRAL 90 (Registered Trademark), AGROTIN(Registered Trademark), ARPON(Registered Trademark), EnSpray N(Registered Trademark) and BANOLE (Registered Trademark).

The present control agent can be used by mixing with, or can be used simultaneously under non-mixing condition with, other fungicide, insecticide, acaricide, nematocide or plant growth regulator.

Examples of the other fungicide include the followings.

(1) Axzole Type Fungicide

Propiconazole, prothioconazole, triadimenol, prochloraz, penconazole, tebuconazole, flusilazole, diniconazole, bromuconazole, epoxyconazole, difenoconazole, cyproconazole, metconazole, triflumizole, tetraconazole, myclobutanil, fenbuconazole, hexaconazole, fluquinconazole, triticonazole, bitertanol, imazalil, flutriafol, simeconazole, ipconazole, and the like;

(2) Amine Type Fungicide

Fenpropimorph, tridemorph, fenpropidin, spiroxamine, and the like;

(3) Benzimidazole Type Fungicide
Carbendazim, benomyl, thiabendazole, thiophanate-methyl), and the like;
(4) Dicarboxyimide Type Fungicide
Procymidone, iprodione, vinclozolin, and the like;
(5) Aniline Pyrimidine Type Fungicide
Cyprodinil, pyrimethanil. Mepanipyrim, and the like;
(6) Phenylpyrrole Type Fungicide
Fenpiclonil, fludioxonil) and the like;
(7) Strobilurin Type Fungicide
kresoxim-methyl, azoxystrobin, trifloxystrobin, fluoxastrobin, picoxystrobin, pyraclostrobin, dimoxystrobin, pyribencarb, metominostrobin, orysastrobin, enestrobin, pyraoxystrobin, pyrametostrobin, flufenoxystrobin, fenaminstrobin, enoxastrobin, coumoxystrobin, pyriminostrobin, triclopyricarb, mandestrobin, and the like;
(8) Phenylamide Type Fungicide
Metalaxyl, metalaxyl-M or mefenoxam, benalaxyl, benalaxyl-M or kiralaxyl, and the like;
(9) Carboxylic Acid Amide Type Fungicide
Dimethomorph, iprovalicarb, benthivalicarb-isopropyl, mandipropamid, valiphenal, and the like
(10) Carboxyamide Type Fungicide
Carboxin, mepronil, flutolanil, thifluzamide, furametpyr, boscalid, penthiopyrad, fluopyram, bixafen, penflufen, sedaxane, fluxapyroxad, isopyrazam, benzovindiflupyr, isofetamid, N-[2-(3,4-difluorophenyl)phenyl]-3-trifluoromethylpyrazin-2-carboxylic acid amide, N-(1,1,3-trimethylindan-4-yl)-1-methyl-3-difluoromethylpyrazol-4-carboxylic acid amide (including mixture of racemate or enantiomer, R-enantiomer and S-enantiomer in any ratio), and the like;
(11) Other Fungicide
Diethofencarb; thiuram; fluazinam; mancozeb; chlorothalonil; captan; dichlofluanid; folpet; quinoxyfen; fenhexanid; fanoxadon; fenamidon; zoxamide; ethaboxam; amisulbrom; cyazofamid; metrafenone; pyriofenone; cyflufenamid; proquinazid; flusulfamide; fluopicolide; fosetyl; cymoxanil; pencycuron; tolclofos-methyl; carpropamid; diclocymet; fenoxanil; tricyclazole; pyroquilon; probenazole; isotianil; tiadinil; tebufloquin; diclomezine; kasugamycin; ferimzone; fthalide; validamycin; hydroxyisoxazole; iminoctadine acetate; isoprothiolane; oxolinic acid; oxytetracycline; streptomycin; copper oxychloride; copper hydroxide; copper hydroxide sulfate; organocopper; sulfur; ametoctradin; fenpyrazamine; oxathiapiprolin; 3-chloro-4-(2,6-difluorophenyl)-6-methyl-5-phenylpyridazine; 3-cyano-4-(2,6-difluorophenyl)-6-methyl-5-phenylpyridazine, and the like:
Examples of the other insecticide include the followings.
(1) Organophosphorus Type Compound
Acephate, Aluminiumphosphide, butathiofos, cadusafos, chlorethoxyfos, chlorfenvinphos, chlorpyrifos, chlorpyrifos-methyl, cyanophos:CYAP, diazinon, DCIP (dichlorodiisopropyl ether), ECP (dichlofenthion), DDVP (dichlorvos), dimethoate, dimethylvinphos, disulfoton, EPN, ethion, ethoprophos, etrimfos, fenthion:MPP, MEP (fenitrothion), fosthiazate, formothion, Hydrogen phosphide, isofenphos, isoxathion, malathion, mesulfenfos, DMTP (methidathion), monocrotophos, BRP (naled), ESP (oxydeprofos), parathion, phosalone, PMP (phosmet), pirimiphos-methyl, pyridafenthion, quinalphos, PAP (phenthoate), profenofos, propaphos, prothiofos, pyraclorfos, salithion, sulprofos, tebupirimfos, temephos, tetrachlorvinphos, terbufos, thiometon, DEP (trichlorphon, vamidothion, phorate, cadusafos, and the like;
(2) Carbamate Type Compound
Alanycarb, bendiocarb, benfuracarb, BPMC, carbaryl, carbofuran, carbosulfan, cloethocarb, ethiofencarb, fenobucarb, fenothiocarb, fenoxycarb, furathiocarb, MIPC (isoprocarb), metolcarb, methomyl, methiocarb, NAC, oxamyl, pirimicarb, PHC (propoxur), XMC, thiodicarb, xylylcarb, aldicarb, and the like;
(3) Synthetic Pyrethroid Compound
Acrinathrin, allethrin, benfluthrin, beta-cyfluthrin, bifenthrin, cycloprothrin, cyfluthrin, cyhalothrin, cypermethrin, deltamethrin, esfenvalerate, ethofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, tetramethrin, phenothrin, cyphenothrin, alpha-cypermethrin, beta-cypermethrin, theta-cypermethrin, zeta-cypermethrin, lambda-cyhalothrin, gamma-cyhalothrin, furamethrin, tau-fluvalinate, halfenprox, protrifenbute, 2,3,5,6-tetrafluoro-4-(methoxy)benzyl (EZ)-(1RS,3RS;1RS,3SR)-2,2-dimethyl-3-prop-1-enylcyclopropanecarbo xylate, 2,3,5,6-tetrafluoro-4-methylbenzyl (EZ)-(1RS,3RS;1RS,3SR)-2,2-dimethyl-3-prop-1-enylcyclopropanecarbo xylate, 2,3,5,6-tetrafluoro-4-(methoxymethyl)benzyl (1RS,3RS;1RS,3SR)-2,2-dimethyl-3-(2-methyl-1-propenyl)cyclopropane carboxylate, and the like;
(4) Nereistoxin Compound
Cartap, bensultap, thiocyclam, monosultap, bisultap, and the like;
(5) Neonicotinoid Compound
Imidacloprid, nitenpyram, acetamiprid, thiamethoxam, thiacloprid, dinotefuran, clothianidin), and the like;
(6) Benzoylurea Compound
Chlorfluazuron, bistrifluron, diafenthiuron, diflubenzuron, fluazuron, flucycloxuron, flufenoxuron, hexaflumuron, lufenuron, novaluron, noviflumuron, teflubenzuron, triflumuron, triazuron, and the like;
(7) Phenylpyrazole Compound
Acetoprole, ethiprole, fipronil, vaniliprole, pyriprole, pyrafluprole, and the like;
(8) Bt-Toxin Insecticide
living spore and δ-endotoxin deribed from *Bacillus thuringiensis* and a mixture thereof;
(9) Hydrazine Compound
Chromafenozide, halofenozide, methoxyfenozide, tebufenozide, and the like;
(10) Organic Chloride Compound
Aldrin, dieldrin, dienochlor, endosulfan, methoxychlor, and the like;
(11) Natural Insecticide
machine oil, nicotine-sulfate);
(12) Other Insecticide
avermectin-B, bromopropylate, buprofezin, chlorphenapyr, cyromazine, D-D(1,3-Dichloropropene, emamectin-benzoate, fenazaquin, flupyrazofos, hydroprene, methoprene, indoxacarb, metoxadiazone, milbemycin-A, pymetrozine, pyridalyl, pyriproxyfen, spinosad, sulfluramid, tolfenpyrad, triazamate, flubendiamide, doramectin, lepimectin, Arsenic acid, benclothiaz, Calcium cyanamide, Calcium polysulfide, chlordane, DDT, DSP, flufenerim, flonicamid, flurimfen, formetanate, metam-ammonium, metam-sodium, Methyl bromide, Potassium oleate, spiromesifen, Sulfur, metaflumizone, spirotetramat, pyrifluquinazone, spinetoram, chlorantraniliprole, cyantraniliprole, cyclaniliprole, sulfoxaflor, flupyradifurone, and the like:
Examples of the other acaricide (acaricidal active ingredient) include acequinocyl, amitraz, benzoximate, bifenaate, bromopropylate, chinomethionat, chlorobenzilate, CPCBS (chlorfenson, clofentezine, cyflumetofen, dicofol, etoxazole, fenbutatin oxide, fenothiocarb, fenpyroximate, fluacrypyrim, fluproxyfen, hexythiazox, BPPS (propargite), polynactins, pyridaben, Pyrimidifen, tebufenpyrad, tetradifon, spirodiclofen, spiromesifen, spirotetramat, amidoflumet, cyenopyrafen, and the like.

Examples of the nematocide (nematocidal active ingredient) include DCIP, fosthiazate, levamisole hydrochloride, methyisothiocyanate, morantel tartarate, imicyafos, fluensulfone, and the like.

Examples of the plant growth regulator include the followings; Ethephon, chlormequat-chloride, mepiquat-chloride, Gibberellin A represented by Gibberellin A$^3$, abscisic acid, Kinetin, benzyladenine, 1,3-diphenylurea, forchlorfenuron, thidiazuron, 4-oxo-4-(2-phenylethyl)aminobutyric acid, methyl 5-(trifluoromethyl)benzo[b]thiophene-2-carboxylate, 5-(trifluoromethyl)benzo[b]thiophene-2-carboxylic acid, and the like.

More specifically, the present compound can be used in the following forms;

a composition for controlling pest comprising any one compound selected from compounds 1 to 159, 201 to 219 and 251 to 266, and prothioconazole in a ratio of 0.1:1, a composition for controlling pest comprising any one compound selected from compounds 1 to 159, 201 to 219 and 251 to 266, and prothioconazole in a ratio of 1:1, a composition for controlling pest comprising any one compound selected from compounds 1 to 159, 201 to 219 and 251 to 266, and prothioconazole in a ratio of 10:1, a composition for controlling pest comprising any one compound selected from compounds 1 to 159, 201 to 219 and 251 to 266, and bromuconazole in a ratio of 0.1:1, a composition for controlling pest comprising anyone compound selected from compounds 1 to 159, 201 to 219 and 251 to 266, and bromuconazole in a ratio of 1:1, a composition for controlling pest comprising any one compound selected from compounds 1 to 159, 201 to 219 and 251 to 266, and bromuconazole in a ratio of 10:1, a composition for controlling pest comprising any one compound selected from compounds 1 to 159, 201 to 219 and 251 to 266, and metconazole in a ratio of 0.1:1, a composition for controlling pest comprising any one compound selected from compounds 1 to 159, 201 to 219 and 251 to 266, and metconazole in a ratio of 1:1, a composition for controlling pest comprising anyone compound selected from compounds 1 to 159, 201 to 219 and 251 to 266, and metconazole in a ratio of 10:1, a composition for controlling pest comprising any one compound selected from compounds 1 to 159, 201 to 219 and 251 to 266, and tebuconazole in a ratio of 0.1:1, a composition for controlling pest comprising any one compound selected from compounds 1 to 159, 201 to 219 and 251 to 266, and tebuconazole in a ratio of 1:1, a composition for controlling pest comprising any one compound selected from compounds 1 to 159, 201 to 219 and 251 to 266, and tebuconazole in a ratio of 10:1, a composition for controlling pest comprising any one compound selected from compounds 1 to 159, 201 to 219 and 251 to 266, and tetraconazole in a ratio of 0.1:1, a composition for controlling pest comprising anyone compound selected from compounds 1 to 159, 201 to 219 and 251 to 266, and tetraconazole in a ratio of 1:1, a composition for controlling pest comprising any one compound selected from compounds 1 to 159, 201 to 219 and 251 to 266, and tetraconazole in a ratio of 10:1, a composition for controlling pest comprising any one compound selected from compounds 1 to 159, 201 to 219 and 251 to 266, and cyproconazole in a ratio of 0.1:1, a composition for controlling pest comprising any one compound selected from compounds 1 to 159, 201 to 219 and 251 to 266, and cyproconazole in a ratio of 1:1, a composition for controlling pest comprising anyone compound selected from compounds 1 to 159, 201 to 219 and 251 to 266, and cyproconazole in a ratio of 10:1, a composition for controlling pest comprising any one compound selected from compounds 1 to 159, 201 to 219 and 251 to 266, and flusilazole in a ratio of 0.1:1, a composition for controlling pest comprising any one compound selected from compounds 1 to 159, 201 to 219 and 251 to 266, and flusilazole in a ratio of 1:1, a composition for controlling pest comprising any one compound selected from compounds 1 to 159, 201 to 219 and 251 to 266, and flusilazole in a ratio of 10:1, a composition for controlling pest comprising any one compound selected from compounds 1 to 159, 201 to 219 and 251 to 266, and prochloraz in a ratio of 0.1:1, a composition for controlling pest comprising anyone compound selected from compounds 1 to 159, 201 to 219 and 251 to 266, and prochloraz in a ratio of 1:1, a composition for controlling pest comprising any one compound selected from compounds 1 to 159, 201 to 219 and 251 to 266, and prochloraz in a ratio of 10:1, a composition for controlling pest comprising any one compound selected from compounds 1 to 159, 201 to 219 and 251 to 266, and azoxystrobin in a ratio of 0.1:1, a composition for controlling pest comprising any one compound selected from compounds 1 to 159, 201 to 219 and 251 to 266, and azoxystrobin in a ratio of 1:1, a composition for controlling pest comprising any one compound selected from compounds 1 to 159, 201 to 219 and 251 to 266, and azoxystrobin in a ratio of 10:1, a composition for controlling pest comprising any one compound selected from compounds 1 to 159, 201 to 219 and 251 to 266, and pyraclostrobin in a ratio of 0.1:1, a composition for controlling pest comprising any one compound selected from compounds 1 to 159, 201 to 219 and 251 to 266, and pyraclostrobin in a ratio of 1:1, a composition for controlling pest comprising any one compound selected from compounds 1 to 159, 201 to 219 and 251 to 266, and pyraclostrobin in a ratio of 10:1, a composition for controlling pest comprising any one compound selected from compounds 1 to 159, 201 to 219 and 251 to 266, and picoxystrobin in a ratio of 0.1:1, a composition for controlling pest comprising anyone compound selected from compounds 1 to 159, 201 to 219 and 251 to 266, and picoxystrobin in a ratio of 1:1, a composition for controlling pest comprising any one compound selected from compounds 1 to 159, 201 to 219 and 251 to 266, and picoxystrobin in a ratio of 10:1, a composition for controlling pest comprising any one compound selected from compounds 1 to 159, 201 to 219 and 251 to 266, and fluoxastrobin in a ratio of 0.1:1, a composition for controlling pest comprising any one compound selected from compounds 1 to 159, 201 to 219 and 251 to 266, and fluoxastrobin in a ratio of 1:1, a composition for controlling pest comprising any one compound selected from compounds 1 to 159, 201 to 219 and 251 to 266, and fluoxastrobin in a ratio of 10:1, a composition for controlling pest comprising anyone compound selected from compounds 1 to 159, 201 to 219 and 251 to 266, and trifloxystrobin in a ratio of 0.1:1, a composition for controlling pest comprising any one compound selected from compounds 1 to 159, 201 to 219 and 251 to 266, and trifloxystrobin in a ratio of 1:1, a composition for controlling pest comprising any one compound selected from compounds 1 to 159, 201 to 219 and 251 to 266, and trifloxystrobin in a ratio of 10:1, a composition for controlling pest comprising any one compound selected from compounds 1 to 159, 201 to 219 and 251 to 266, and mandestrobin in a ratio of 0.1:1, a composition for controlling pest comprising anyone compound selected from compounds 1 to 159, 201 to 219 and 251 to 266, and mandestrobin in a ratio of 1:1, a composition for controlling pest comprising any one compound selected from compounds 1 to 159, 201 to 219 and 251 to 266, and mandestrobin in a ratio of 10:1, a composition for controlling pest comprising any one compound selected from compounds 1 to 159, 201 to 219 and 251 to 266, and fluoxastrobin in a ratio of 0.1:1, a composition for controlling pest comprising any one compound selected from compounds 1 to 159, 201 to 219 and 251 to 266, and fluoxastrobin in a ratio of 1:1, a composition for controlling pest comprising any one compound selected from compounds 1 to 159, 201 to 219 and 251 to 266, and fluoxastrobin in a ratio of 10:1, a composition for controlling pest comprising anyone compound selected from compounds 1 to 159, 201 to 219 and 251 to 266, and bixafen in a ratio of 0.1:1, a composition for controlling pest comprising any one compound selected from compounds 1 to 159, 201 to 219 and 251 to 266, and bixafen in a ratio of 1:1, a composition for controlling pest comprising any one compound selected from compounds 1 to 159, 201 to 219 and 251 to 266, and bixafen in a ratio of 10:1, a composition for controlling pest comprising any one compound selected from compounds 1 to 159, 201 to 219 and 251 to 266, and isopyrazam in a ratio of 0.1:1, a composition for controlling pest comprising anyone compound selected from compounds 1 to 159, 201 to 219 and 251 to 266, and isopyrazam in a ratio of 1:1, a composition for controlling pest comprising any one compound selected from compounds 1 to 159, 201 to 219 and 251 to 266, and isopyrazam in a ratio of 10:1, a composition for controlling pest comprising any one compound selected from compounds 1 to 159, 201 to 219 and 251 to 266, and fluopyram in a ratio of 0.1:1, a composition for controlling pest comprising any one compound selected from compounds 1 to 159, 201 to 219 and 251 to 266, and fluopyram in a ratio of 1:1, a composition for controlling pest comprising any one compound selected from compounds 1 to 159, 201 to 219 and 251 to 266, and fluopyram in a ratio of 10:1, a composition for controlling pest comprising anyone compound selected from compounds 1 to 159, 201 to 219 and 251 to 266, and penthiopyrad in a ratio of 0.1:1, a composition for controlling pest comprising any one compound selected from compounds 1 to 159, 201 to 219 and 251 to 266, and penthiopyrad in a ratio of 1:1, a composition for controlling pest comprising any one compound selected from compounds 1 to 159, 201 to 219 and 251 to 266, and penthiopyrad in a ratio of 10:1, a composition for controlling pest comprising any one compound selected from compounds 1 to 159, 201 to 219 and 251 to 266, and benzovindiflupyr in a ratio of 0.1:1, a composition for controlling pest comprising any one compound selected from compounds 1 to 159, 201 to 219 and 251 to 266, and benzovindiflupyr in a ratio of 1:1, a composition for controlling pest comprising any one compound selected from compounds 1 to 159, 201 to 219 and 251 to 266, and benzovindiflupyr in a ratio of 10:1, a composition for controlling pest comprising any one compound selected from compounds 1 to 159, 201 to 219 and 251 to 266, and fluxapyroxad in a ratio of 0.1:1, a composition for controlling pest comprising any one compound selected from compounds 1 to 159, 201 to 219 and 251 to 266, and fluxapyroxad in a ratio of 1:1, a composition for controlling pest comprising any one compound selected from compounds 1 to 159, 201 to 219 and 251 to 266, and fluxapyroxad in a ratio of 10:1, a composition for controlling pest comprising anyone compound selected from compounds 1 to 159, 201 to 219 and 251 to 266, and boscalid in a ratio of 0.1:1, a composition for controlling pest comprising any one compound selected from compounds 1 to 159, 201 to 219 and 251 to 266, and boscalid in a ratio of 1:1, a composition for controlling pest comprising any one compound selected from compounds 1 to 159, 201 to 219 and 251 to 266, and boscalid in a ratio of 10:1, a composition for controlling pest comprising any one compound selected from compounds 1 to 159, 201 to 219 and 251 to 266, and N-[2-(3,4-difluorophenyl)phenyl]-3-trifluoromethylpyrazin-2-carboxylic acid amide in a ratio of 0.1:1, a composition for controlling pest comprising any one compound selected from compounds 1 to 159, 201 to 219 and 251 to 266, and N-[2-(3,4-difluorophenyl)phenyl]-3-trifluoromethylpyrazin-2-carboxylic acid amide in a ratio of 1:1, a composition for controlling pest comprising any one compound selected from compounds 1 to 159, 201 to 219 and 251 to 266, and N-[2-(3,4-difluorophenyl)phenyl]-3-trifluoromethylpyrazin-2-carboxylic acid amide in a ratio of 10:1, a composition for controlling pest comprising any one compound selected from compounds 1 to 159, 201 to 219 and 251 to 266, and N-(1,1,3-trimethylindan-4-yl)-1-methyl-3-difluoromethylpyrazol-4-carboxylic acid amide in a ratio of 0.1:1, a composition for controlling pest comprising any one compound selected from compounds 1 to 159, 201 to 219 and 251 to 266, and N-(1,1,3-trimethylindan-4-yl)-1-methyl-3-difluoromethylpyrazol-4-carboxylic acid amide in a ratio of 1:1, a composition for controlling pest comprising any one compound selected from compounds 1 to 159, 201 to 219 and 251 to 266, and N-(1,1,3-trimethylindan-4-yl)-1-methyl-3-difluoromethylpyrazol-4-carboxylic acid amide in a ratio of 10:1, a composition for controlling pest comprising any one compound selected from compounds 1 to 159, 201 to 219 and 251 to 266, and 3-chloro-4-(2,6-difluorophenyl)-6-methyl-5-phenylpyridazine in a ratio of 0.1:1, a composition for controlling pest comprising anyone compound selected from compounds 1 to 159, 201 to 219 and 251 to 266, and 3-chloro-4-(2,6-difluorophenyl)-6-methyl-5-phenylpyridazine in a ratio of 1:1, a composition for controlling pest comprising any one compound selected from compounds 1 to 159, 201 to 219 and 251 to 266, and 3-chloro-4-(2,6-difluorophenyl)-6-methyl-5-phenylpyridazine in a ratio of 10:1, a composition for controlling pest comprising any one compound selected from compounds 1 to 159, 201 to 219 and 251 to 266, and 3-cyano-4-(2,6-difluorophenyl)-6-methyl-5-phenylpyridazine in a ratio of 0.1:1, a composition for controlling pest comprising any one compound selected from compounds 1 to 159, 201 to 219 and 251 to 266, and 3-cyano-4-(2,6-difluorophenyl)-6-methyl-5-phenylpyridazine in a ratio of 1:1,
a composition for controlling pest comprising any one compound selected from compounds 1 to 159, 201 to 219 and 251 to 266, and 3-cyano-4-(2,6-difluorophenyl)-6-methyl-5-phenylpyridazine in a ratio of 10:1,
a composition for controlling pest comprising any one compound selected from compounds 1 to 159, 201 to 219 and 251 to 266, and fenpropimorph in a ratio of 0.1:1,
a composition for controlling pest comprising any one compound selected from compounds 1 to 159, 201 to 219 and 251 to 266, and fenpropimorph in a ratio of 1:1,
a composition for controlling pest comprising any one compound selected from compounds 1 to 159, 201 to 219 and 251 to 266, and fenpropimorph in a ratio of 10:1,
a composition for controlling pest comprising any one compound selected from compounds 1 to 159, 201 to 219 and 251 to 266, and fenpropidin in a ratio of 0.1:1,
a composition for controlling pest comprising anyone compound selected from compounds 1 to 159, 201 to 219 and 251 to 266, and fenpropidin in a ratio of 1:1,
a composition for controlling pest comprising any one compound selected from compounds 1 to 159, 201 to 219 and 251 to 266, and fenpropidin in a ratio of 10:1,
a composition for controlling pest comprising any one compound selected from compounds 1 to 159, 201 to 219 and 251 to 266, and spiroxamine in a ratio of 0.1:1,
a composition for controlling pest comprising any one compound selected from compounds 1 to 159, 201 to 219 and 251 to 266, and spiroxamine in a ratio of 1:1,
a composition for controlling pest comprising any one compound selected from compounds 1 to 159, 201 to 219 and 251 to 266, and spiroxamine in a ratio of 10:1,
a composition for controlling pest comprising any one compound selected from compounds 1 to 159, 201 to 219 and 251 to 266, and cyprodinil in a ratio of 0.1:1,
a composition for controlling pest comprising any one compound selected from compounds 1 to 159, 201 to 219 and 251 to 266, and cyprodinil in a ratio of 1:1,
a composition for controlling pest comprising any one compound selected from compounds 1 to 159, 201 to 219 and 251 to 266, and cyprodinil in a ratio of 10:1,
a composition for controlling pest comprising any one compound selected from compounds 1 to 159, 201 to 219 and 251 to 266, and fludioxonil in a ratio of 0.1:1,
a composition for controlling pest comprising anyone compound selected from compounds 1 to 159, 201 to 219 and 251 to 266, and fludioxonil in a ratio of 1:1,
a composition for controlling pest comprising any one compound selected from compounds 1 to 159, 201 to 219 and 251 to 266, and fludioxonil in a ratio of 10:1,
a composition for controlling pest comprising any one compound selected from compounds 1 to 159, 201 to 219 and 251 to 266, and procymidone in a ratio of 0.1:1,
a composition for controlling pest comprising any one compound selected from compounds 1 to 159, 201 to 219 and 251 to 266, and procymidone in a ratio of 1:1,
a composition for controlling pest comprising any one compound selected from compounds 1 to 159, 201 to 219 and 251 to 266, and procymidone in a ratio of 10:1,
a composition for controlling pest comprising anyone compound selected from compounds 1 to 159, 201 to 219 and 251 to 266, and iprodione in a ratio of 0.1:1,
a composition for controlling pest comprising any one compound selected from compounds 1 to 159, 201 to 219 and 251 to 266, and iprodione in a ratio of 1:1,
a composition for controlling pest comprising any one compound selected from compounds 1 to 159, 201 to 219 and 251 to 266, and iprodione in a ratio of 10:1,
a composition for controlling pest comprising any one compound selected from compounds 1 to 159, 201 to 219 and 251 to 266, and thiophanate-methyl in a ratio of 0.1:1,
a composition for controlling pest comprising anyone compound selected from compounds 1 to 159, 201 to 219 and 251 to 266, and thiophanate-methyl in a ratio of 1:1,
a composition for controlling pest comprising any one compound selected from compounds 1 to 159, 201 to 219 and 251 to 266, and thiophanate-methyl in a ratio of 10:1,
a composition for controlling pest comprising any one compound selected from compounds 1 to 159, 201 to 219 and 251 to 266, and carbendazim in a ratio of 0.1:1,
a composition for controlling pest comprising any one compound selected from compounds 1 to 159, 201 to 219 and 251 to 266, and carbendazim in a ratio of 1:1,
a composition for controlling pest comprising any one compound selected from compounds 1 to 159, 201 to 219 and 251 to 266, and carbendazim in a ratio of 10:1,
a composition for controlling pest comprising anyone compound selected from compounds 1 to 159, 201 to 219 and 251 to 266, and diethofencarb in a ratio of 0.1:1,
a composition for controlling pest comprising any one compound selected from compounds 1 to 159, 201 to 219 and 251 to 266, and diethofencarb in a ratio of 1:1,
a composition for controlling pest comprising any one compound selected from compounds 1 to 159, 201 to 219 and 251 to 266, and diethofencarb in a ratio of 10:1,
a composition for controlling pest comprising any one compound selected from compounds 1 to 159, 201 to 219 and 251 to 266, and fenpyrazamine in a ratio of 0.1:1,
a composition for controlling pest comprising anyone compound selected from compounds 1 to 159, 201 to 219 and 251 to 266, and fenpyrazamine in a ratio of 1:1,
a composition for controlling pest comprising any one compound selected from compounds 1 to 159, 201 to 219 and 251 to 266, and fenpyrazamine in a ratio of 10:1,
a composition for controlling pest comprising any one compound selected from compounds 1 to 159, 201 to 219 and 251 to 266, and chlorothalonil in a ratio of 0.1:1,
a composition for controlling pest comprising any one compound selected from compounds 1 to 159, 201 to 219 and 251 to 266, and chlorothalonil in a ratio of 1:1,
a composition for controlling pest comprising any one compound selected from compounds 1 to 159, 201 to 219 and 251 to 266, and chlorothalonil in a ratio of 10:1,
a composition for controlling pest comprising anyone compound selected from compounds 1 to 159, 201 to 219 and 251 to 266, and mancozeb in a ratio of 0.1:1,
a composition for controlling pest comprising any one compound selected from compounds 1 to 159, 201 to 219 and 251 to 266, and mancozeb in a ratio of 1:1,
a composition for controlling pest comprising any one compound selected from compounds 1 to 159, 201 to 219 and 251 to 266, and mancozeb in a ratio of 10:1,
a composition for controlling pest comprising any one compound selected from compounds 1 to 159, 201 to 219 and 251 to 266, and folpet in a ratio of 0.1:1,
a composition for controlling pest comprising any one compound selected from compounds 1 to 159, 201 to 219 and 251 to 266, and folpet in a ratio of 1:1,
a composition for controlling pest comprising any one compound selected from compounds 1 to 159, 201 to 219 and 251 to 266, and folpet in a ratio of 10:1, a composition for controlling pest comprising any one compound selected from compounds 1 to 159, 201 to 219 and 251 to 266, and metiram in a ratio of 0.1:1, a composition for controlling pest comprising any one compound selected from compounds 1 to 159, 201 to 219 and 251 to 266, and metiram in a ratio of 1:1, a composition for controlling pest comprising any one compound selected from compounds 1 to 159, 201 to 219 and 251 to 266, and metiram in a ratio of 10:1, a composition for controlling pest comprising anyone compound selected from compounds 1 to 159, 201 to 219 and 251 to 266, and clothianidin in a ratio of 1:1, a composition for controlling pest comprising any one compound selected from compounds 1 to 159, 201 to 219 and 251 to 266, and clothianidin in a ratio of 1:10, a composition for controlling pest comprising any one compound selected from compounds 1 to 159, 201 to 219 and 251 to 266, and clothianidin in a ratio of 1:50, a composition for controlling pest comprising any one compound selected from compounds 1 to 159, 201 to 219 and 251 to 266, and imidacloprid in a ratio of 1:1, a composition for controlling pest comprising any one compound selected from compounds 1 to 159, 201 to 219 and 251 to 266, and imidacloprid in a ratio of 1:10, a composition for controlling pest comprising anyone compound selected from compounds 1 to 159, 201 to 219 and 251 to 266, and imidacloprid in a ratio of 1:50, a composition for controlling pest comprising any one compound selected from compounds 1 to 159, 201 to 219 and 251 to 266, and thiamethoxam in a ratio of 1:1, a composition for controlling pest comprising any one compound selected from compounds 1 to 159, 201 to 219 and 251 to 266, and thiamethoxam in a ratio of 1:10, a composition for controlling pest comprising any one compound selected from compounds 1 to 159, 201 to 219 and 251 to 266, and thiamethoxam in a ratio of 1:50, a composition for controlling pest comprising anyone compound selected from compounds 1 to 159, 201 to 219 and 251 to 266, and dinotefuran in a ratio of 1:1, a composition for controlling pest comprising any one compound selected from compounds 1 to 159, 201 to 219 and 251 to 266, and dinotefuran in a ratio of 1:10, a composition for controlling pest comprising any one compound selected from compounds 1 to 159, 201 to 219 and 251 to 266, and dinotefuran in a ratio of 1:50, a composition for controlling pest comprising any one compound selected from compounds 1 to 159, 201 to 219 and 251 to 266, and sulfoxaflor in a ratio of 1:1, a composition for controlling pest comprising any one compound selected from compounds 1 to 159, 201 to 219 and 251 to 266, and sulfoxaflor in a ratio of 1:10, a composition for controlling pest comprising anyone compound selected from compounds 1 to 159, 201 to 219 and 251 to 266, and sulfoxaflor in a ratio of 1:50, a composition for controlling pest comprising any one compound selected from compounds 1 to 159, 201 to 219 and 251 to 266, and chlorantraniliprole in a ratio of 1:1, a composition for controlling pest comprising any one compound selected from compounds 1 to 159, 201 to 219 and 251 to 266, and chlorantraniliprole in a ratio of 1:10, a composition for controlling pest comprising any one compound selected from compounds 1 to 159, 201 to 219 and 251 to 266, and chlorantraniliprole in a ratio of 1:50, a composition for controlling pest comprising anyone compound selected from compounds 1 to 159, 201 to 219 and 251 to 266, and abamectin in a ratio of 1:1, a composition for controlling pest comprising any one compound selected from compounds 1 to 159, 201 to 219 and 251 to 266, and abamectin in a ratio of 1:10, a composition for controlling pest comprising any one compound selected from compounds 1 to 159, 201 to 219 and 251 to 266, and abamectin in a ratio of 1:50, a composition for controlling pest comprising any one compound selected from compounds 1 to 159, 201 to 219 and 251 to 266, and 4-oxo-4-(2-phenylethyl)aminobutyric acid in a ratio of 5:1, a composition for controlling pest comprising any one compound selected from compounds 1 to 159, 201 to 219 and 251 to 266, and 4-oxo-4-(2-phenylethyl)aminobutyric acid in a ratio of 1:10, a composition for controlling pest comprising anyone compound selected from compounds 1 to 159, 201 to 219 and 251 to 266, and 4-oxo-4-(2-phenylethyl)aminobutyric acid in a ratio of 1:50, a composition for controlling pest comprising any one compound selected from compounds 1 to 159, 201 to 219 and 251 to 266, and methyl 5-(trifluoromethyl)benzo[b]thiophene-2-carboxylate in a ratio of 5:1, a composition for controlling pest comprising any one compound selected from compounds 1 to 159, 201 to 219 and 251 to 266, and methyl 5-(trifluoromethyl)benzo[b]thiophene-2-carboxylate in a ratio of 1:10, a composition for controlling pest comprising anyone compound selected from compounds 1 to 159, 201 to 219 and 251 to 266, and methyl 5-(trifluoromethyl)benzo[b]thiophene-2-carboxylate in a ratio of 1:50, a composition for controlling pest comprising any one compound selected from compounds 1 to 159, 201 to 219 and 251 to 266, and 5-(trifluoromethyl)benzo[b]thiophene-2-carboxylic acid in a ratio of 5:1, a composition for controlling pest comprising any one compound selected from compounds 1 to 159, 201 to 219 and 251 to 266, and 5-(trifluoromethyl)benzo[b]thiophene-2-carboxylic acid in a ratio of 1:10, a composition for controlling pest comprising anyone compound selected from compounds 1 to 159, 201 to 219 and 251 to 266, and 5-(trifluoromethyl)benzo[b]thiophene-2-carboxylic acid in a ratio of 1:50.

The application dose varies depending on weather conditions, dosage forms, timing of application, methods of application, areas to be applied, target diseases and target crops etc., but is in the range of usually from 1 to 500 g, and preferably from 2 to 200 g per 1,000 m$^2$ of the area to be applied. The emulsifiable concentrate, the wettable powder or the suspension concentrate, etc., is usually applied by diluting it with water. In this case, the concentration of the present compound after dilution is in the range of usually 0.0005 to 2% by weight, and preferably 0.005 to 1% by weight. The dust formulation or the granular formulation etc., is usually applied as itself without diluting it. In the application to seeds, the amount of the present compound is in the range of usually from 0.001 to 100 g, and preferably from 0.01 to 50 g per 1 kg of the seeds.

Herein, examples of the place where the pests live include paddy fields, fields, tea gardens, orchards, non-agricultural lands, houses, nursery trays, nursery boxes, nursery soils and nursery bed.

Also, in another embodiment, for example, the present compound can be administered to the inside (inside of the body) or the outside (body surface) of the below-mentioned vertebrate to exterminate systemically or unsystemically the living things or parasites which are parasitic on the vertebrate. Examples of a method of the internal medication include an oral administration, an anal administration, a transplantation, an administration via injection subcutaneously, intramuscularly or intravenously. Examples of a method of outside medication include a transdermal administration. Also, the present compound can be ingested to a livestock animal so as to exterminate sanitary insects which occur in the excrement of the animal.

When the present compound is applied to the animals such as the livestock animal and pets on which pests are parasitic, the dose varies depending on the administration method etc., but it is desirable in general to administer the present compound so that a dose of the active ingredient (the present compound or salts thereof) is in the range of generally from 0.1 mg to 2,000 mg and preferably 0.5 mg to 1,000 mg per 1 kg of body weight of the animal.

The present compound can be used as agent for controlling plant disease in agricultural lands such as fields, paddy fields, lawns, orchards. The compound of the present invention can control diseases occurred in the agricultural lands or the others for cultivating the following "plant".

Crops:
corn, rice, wheat, barley, rye, oat, sorghum, cotton, soybean, peanut, buckwheat, beet, rapeseed, sunflower, sugar cane, tobacco, and the others;

Vegetables:
solanaceous vegetables (for example, eggplant, tomato, pimento, pepper and potato),
cucurbitaceous vegetables (for example, cucumber, pumpkin, zucchini, water melon and melon),
cruciferous vegetables (for example, Japanese radish, white turnip, horseradish, kohlrabi, Chinese cabbage, cabbage, leaf mustard, broccoli, cauliflower),
asteraceous vegetables (for example, burdock, crown daisy, artichoke and lettuce),
liliaceous vegetables (for example, green onion, onion, garlic and asparagus),
ammiaceous vegetables (for example, carrot, parsley, celery and parsnip),
chenopodiaceous vegetables (for example, spinach and Swiss chard), lamiaceous vegetables (for example, *Perilla frutescens*, mint and basil),
strawberry, sweet potato, *Dioscorea japonica*, colocasia and the others;

Flowers:
Ornamental Foliage Plants:
Fruits:
pomaceous fruits (for example, apple, pear, Japanese pear, Chinese quince and quince),
stone fruits (for example, peach, plum, nectarine, *Prunus mume*, cherry fruit, apricot and prune),
citrus fruits (for example, Citrus unshiu, orange, lemon, lime and grapefruit),
nuts (for example, chestnut, walnuts, hazelnuts, almond, pistachio, cashew nuts and macadamia nuts),
berry fruits (for example, blueberry, cranberry, blackberry and raspberry),
grape, kaki persimmon, olive, Japanese plum, banana, coffee, date palm, coconuts, and the others;

Trees Other than Fruit Trees:
tea, mulberry, flowering plant, roadside trees (for example, ash, birch, dogwood, *Eucalyptus, Ginkgo biloba*, lilac, maple, *Quercus*, poplar, Judas tree, *Liquidambar formosana*, plane tree, *zelkova*, Japanese arborvitae, fir wood, hemlock, juniper, *Pinus, Picea*, and *Taxus cuspidate*);
and the others.

The above-mentioned "plant" includes genetically modified crops.

The pests on which the present compound has a control efficacy include plant pathogens such as filamentous fungus, as well as harmful arthropods such as harmful insects and harmful mites, and nemathelminth such as nematodes, and specifically include the following examples, but are not limited thereto.

Rice diseases: blast (*Magnaporthe grisea*), brown spot (*Cochliobolus miyabeanus*), sheath blight (*Rhizoctonia solani*), bakanae disease (*Gibberella fujikuroi*), and downy mildew (*Sclerophthora macrospora*);

Wheat diseases: powdery mildew (*Erysiphe graminis*), fusarium blight (*Fusarium gaminearum, F. avenaceum, F. culmorum, Microdochium nivale*), rust (*Puccinia striiformis, P. graminis, P. recondita*), snow mould (*Micronectriella nivale*), typhula snow blight (*Typhula* sp.), loose smut (*Ustilago tritici*), stinking smut (*Tilletia caries, T. controversa*), eyespot (*Pseudocercosporella herpotrichoides*), leaf blotch (*Septoria tritici*), glume blotch (*Stagonospora nodorum*), tan spot (*Pyrenophora tritici-repentis*), rhizoctonia seeding blight (*Rhizoctonia solani*), and take all disease (*Gaeumannomyces graminis*);

Barly diseases: powdery mildew (*Erysiphe graminis*), fusarium blight (*Fusarium gaminearum, F. avenaceum, F. culmorum, Microdochium nivale*), rust (*Puccinia striiformis, P. graminis, P. hordei*), loose smut (*Ustilago nuda*), scald (*Rhynchosporium secalis*), net blotch (*Pyrenophora teres*), spot blotch (*Cochliobolus sativus*), leaf stripe (*Pyrenophora graminea*), Ramularia disease (*Ramularia collo-cygni*), and rhizoctonia seeding blight (*Rhizoctonia solani*);

Corn diseases: rust (*Puccinia sorghi*), southern rust (*Puccinia polysora*), northern leaf blight (*Setosphaeria turcica*), southern leaf blight (*Cochliobolus heterostrophus*), anthracnose (*Colletotrichum* gfaminicola), gray leaf spot (*Cercospora zeae-maydis*), eyespot (*Kabatiella zeae*), and phaeosphaeria leaf spot (*Phaeosphaeria maydis*);

Cotton diseases: anthracnose (*Colletotrichum gossypii*), grey mildew (*Ramuraria areola*), alternaria leaf spot (*Alternaria macrospora, A. gossypii*);

Coffee diseases: rust (*Hemileia vastatrix*);

Rape seed diseases: sclerotinia rot (*Sclerotinia sclerotiorum*), black spot (*Alternaria brassicae*), and black leg (*Phoma lingam*);

Citrus diseases: melanose (*Diaporthe citri*), scab (*Elsinoe fawcetti*), and fruit rot (*Penicillium digitatum, P. italicum*);

Apple diseases: blossom blight (*Monilinia mali*), canker (*Valsa ceratosperma*), powdery mildew (*Podosphaera leucotricha*), alternaria leaf spot (*Alternaria alternata* apple pathotype), scab (*Venturia inaequalis*), and bitter rot (*Colletotrichum acutatum*);

Pear diseases: scab (*Venturia nashicola, V. pirina*), black spot (*Alternaria alternata* Japanese pear pathotype) and rust (*Gymnosporangium haraeanum*);

Peach diseases: brown rot (*Monilinia fructicola*), scab (*Cladosporium carpophilum*) and Phomopsis rot (*Phomopsis* sp.);

Grapes diseases: anthracnose (*Elsinoe ampelina*), ripe rot (*Glomerella cingulata*), powdery mildew (*Uncinula necator*), rust (*Phakopsora ampelopsidis*), black rot (*Guignardia bidwellii*), and downy mildew (*Plasmopara viticola*);

Diseases of Japanese persimmon: anthracnose (*Gloeosporium kaki*) and leaf spot (*Cercospora kaki, Mycosphaerella nawae*);

Diseases of gourd family: anthracnose (*Colletotrichum lagenarium*), powdery mildew (*Sphaerotheca fuliginea*), gummy stem blight (*Didymella bryoniae*), target spot (*Corynespora cassiicola*), fusarium wilt (*Fusarium oxysporum), downy mildew (*Pseudoperonospora cubensis*), phytophthora rot (*Phytophthora* sp.) and damping-off (*Pythium* sp.);

Tomato diseases: early blight (*Alternaria solani*), leaf mold (*Cladosporium fulvum*), leaf mold (*Pseudocercospora fuligena*), and late blight (*Phytophthora infestans*);

Eggplant disease: brown spot (*Phomopsis vexans*) and powdery mildew (*Erysiphe cichoracearum*);

Diseases of Cruciferous Vegetables: alternaria leaf spot (*Alternaria japonica*), white spot (*Cercosporella brassicae*), clubroot (*Plasmodiophora parasitica*), downy mildew (*Peronospora parasitica*);

Welsh onion diseases: rust (*Puccinia allii*);

Soybean diseases: purple stain (*Cercospora kikuchii*), sphaceloma scad (*Elsinoe glycines*), pod and stem blight (*Diaporthe phaseolorum* var. *sojae*), rust (*phakopsora pachyrhizi*), target spot (*Corynespora cassiicola*), anthracnose (*Colletotrithum glycines, C. truncatum*), Rhizoctonia aerial blight (*Rhizoctonia solani*), septoria brown spot (*Septoria glycines*), and frog eye leaf spot (*Cercospora sojina*);

Kindney bean diseases: anthracnose (*Colletotrichum lindemthianum*);

Peanut diseases: early leaf spot (*Cercospora personata*), late leaf spot (*Cercospora arachidicola*) and southern blight (*Sclerotium rolfsii*);

Garden pea diseases: powdery mildew (*Erysiphe pisi*);

Potato diseases: early blight (*Alternaria solani*), late blight (*Phytophthora infestans*), and verticillium wilt (*verticillium albo-atrum, V. dahliae, V. nigrescens*);

Strawberry diseases: powdery mildew (*Sphaerotheca humuli*);

Tea diseases: net blister blight (*Exobasidium reticulatum*), white scab (*Elsinoe leucospila*), gray blight (*Pestalotiopsis* sp.) and anthracnose (*Colletotrichum theae-sinensis*);

Tabacco diseases: brown spot (*Alternaria longipes*), powdery mildew (*Erysiphe cichoracearum*), anthracnose (*Colletotrichum tabacum*), downy mildew (*Peronospora tabacina*), and black shank (*Phytophthora nicotianae*);

Sugar beet diseases: cercospora leaf spot (*Cercospora beticola*), leaf blight (*Thanatephorus cucumeris*), root rot (*Thanatephorus cucumeris*) and aphanomyces root rot (*Aphanomyces sochlioides*);

Rose diseases: black spot (*Diplocarpon rosae*) and powdery mildew (*Sphaerotheca pannosa*);

Diseases of Chrysanthemum: leaf blight (*Septoria chrysanthemi-indici*) and white rust (*Puccinia horiana*);

Onion diseases: botrytis leaf blight (*Botrytis cinerea, B. byssoidea, B. squamosa*), gray-mold neck rot (*Botrytis slli*), and small sclerotial rot (*Botrytis squamosa*);

Various crops diseases: gray mold (*Botrytis cinerea*), and sclerotinia rot (*Sclerotinia sclerotiorum*);

Diseases of Japanese radish: alternaria leaf spot (*Alternaria brassicicola*);

Turfgrass diseases: dollar spot (*Sclerotinia homeocarpa*), brown patch and large patch (*Rhizoctonia solani*); and Banana diseases: Sigatoka disease (*Mycosphaerella fijiensis, Mycosphaerella musicola*).

Hemiptera:

Delphacidae (for example, *Laodelphax striatellus, Nilaparvata lugens*, or *Sogatella furcifera*);

Deltocephalidae (for example, *Nephotettix cincticeps*, or *Nephotettix virescens*);

Aphididae (for example, *Aphis gossypii, Myzus persicae, Brevicoryne brassicae, Macrosiphum euphorbiae, Aulacorthum solani, Rhopalosiphum padi, Toxoptera citricidus*);

Pentatomidae (for example, *Nezara antennata, Riptortus clavetus, Leptocorisa chinensis, Eysarcoris parvus, Halyomorpha mista*, or *Lygus lineolaris*);

Aleyrodidae (for example, *Trialeurodes vaporariorum*, or *Bemisia argentifolii*);

Coccoidea (for example, *Aonidiella aurantii, Comstockaspis perniciosa, Unaspis citri, Ceroplastes rubens*, or *Icerya purchasi*);

Tingidae;

Psyllidae;

Bed bugs (*Cimex lectularius*) and the others;

Lepidoptera:

Pyralidae (for example, *Chilo suppressalis, Tryporyza incertulas, Cnaphalocrocis medinalis, Notarcha derogata, Plodia interpunctella, Ostrinia furnacalis, Hellula undalis, Pediasia teterrellus*);

Noctuidae (for example, *Spodoptera litura, Spodoptera exigua, Pseudaletia separata, Mamestra brassicae, Agrotis ipsilon, Plusia nigrisigna, Trichoplusia* spp., *Heliothis* spp, or *Helicoverpa* spp.;

Pieridae (for example, *Pieris rapae*);

Tortricidae (for example, *Adoxophyes* spp., *Grapholita molesta, Cydia pomonella, Leguminivora glycinivorella, Matsumuraeses azukivora, Adophyes orana fasciata, Adoxophyes* sp., *Homona magnanima, Archips fuscocupreanus, Cydia pomonella*);

Gracillariidae (for example, *Caloptilia theivora, Phyllonorycter ringoneella*);

Carposinidae (for example, *Carposina niponensis*);

Lyonetiidae (for example, *Lyonetia* spp.);

Lymantriidae (for example, *Lymantria* spp., or *Euproctis* spp.);

Yponomeutidae (for example, *Plutella xylostella*);

Gelechiidae (for example, *Pectinophora gossypiella* or *Phthorimaea operculella*);

Arctiidae (for example, *Hyphantria cunea*); Tineidae (for example, *Tinea translucens*, or *Tineola bisselliella*); and the others;

Thysanoptera:

Thysanoptera (for example, *Frankliniella occidentalis, Thrips palmi, Scirtothrips dorsalis, Thrips tabaci, Frankliniella intonsa, Frankliniella fusca*);

Diptera:

*Musca domestica, Culex popiens pallens, Tabanus trigonus, Hylemya antiqua, Hylemya platura, Anopheles sinensis, Agromyza oryzae, Hydrellia griseola, Chlorops oryzae, Dacus cucurbitae, Ceratitis capitata, Liriomyza trifolii*, and the others;

Coleoptera:

*Epilachna vigintioctopunctata, Aulacophora femoralis, Phyllotreta striolata, Oulema oryzae, Echinocnemus squameus, Lissorhoptrus oryzophilus, Anthonomus grandis, Callosobruchus chinensis, Sphenophorus venatus, Popillia japonica, Anomala cuprea, Diabrotica* spp., *Leptinotarsa decemlineata, Agriotes* spp., *Lasioderma serricorne, Anthrenus verbasci, Tribolium castaneum, Lyctus brunneus, Anoplophora malasiaca, Tomicus piniperda*), and the others;

Orthoptera:

*Locusta migratoria, Gryllotalpa africana, Oxya yezoensis, Oxya japanica*, and the others;

Hymenoptera:

*Athalia rosae, Acromyrmex* spp., *Solenopsis* spp., and the others;

Nematodes:

*Aphelenchoides besseyi, Nothotylenchus acris, Heterodera glycines, Meloidogyne incognita, Pratylenchus, Nacobbus aberrans*, and the others;

Blattariae:
*Blattella germanica, Periplaneta fuliginosa, Periplaneta americana, Periplaneta brunnea, Blatta orientalis*, and the others;
Acarina:
*Tetranychidae* (for example, *Tetranychus urticae, Panonychus citri*, or *Oligonychus* spp.);
*Eriophyidae* (for example, *Aculops pelekassi*);
*Tarsonemidae* (for example, *Polyphagotarsonemus latus*);
*Tenuipalpidae;*
Tuckerellidae;
*Acaridae* (for example, *Tyrophagus putrescentiae*);
Pyroglyphidae (for example, *Dermatophagoides farinae*, or *Dermatophagoides ptrenyssnus*);
Cheyletidae (for example, *Cheyletus eruditus, Cheyletus malaccensis*, or *Cheyletus moorei*);
Dermanyssidae;
and the others.

Also the formulation comprising the present compound can be used in the field relating to a treatment of livestock diseases or livestock industry, and for example, can exterminate the living things or parasites which are parasitic on the inside and/or the outside of a vertebrate such as human being, cow, sheep, pig, poultry, dog, cat and fish, so as to maintain public health. Examples of the pests include *Isodes* spp. (for example, *Isodes scapularis*), *Boophilus* spp. (for example, *Boophilus microplus*), *Amblyomma* spp., *Hyalomma* spp., *Rhipicephalus* spp. (for example, *Rhipicephalus sanguineus*), *Haemaphysalis* spp. (for example, *Haemaphysalis longicornis*), *dermacentor* spp., *Ornithodoros* spp. (for example, *Ornithodoros moubata*), *Dermahyssus gallinae, Ornithonyssus sylviarum, Sarcoptes* spp. (for example, *Sarcoptes scabiei*), *Psoroptes* spp., *Chorioptes* spp., *Demodex* spp., *Eutrombicula* spp., *Ades* spp. (for example, *Aedes albopictus*), *Anopheles* spp., *Culex* spp., *Culicodes* spp., *Musca* spp., *Hypoderma* spp., *Gasterophilus* spp., *Haematobia* spp., *Tabanus* spp., *Simulium* spp., *Triatoma* spp., *Phthiraptera* (for example, *Damalinia* spp.), *Linognathus* spp., *Haematopinus* spp., *Ctenocephalides* spp. (for example, *Ctenocephalides felis*) *Xenosylla* spp., *monomorium pharaonis* and nematodes [for example, hairworm (for example, *Nippostrongylus brasiliensis, Trichostrongylus axei, Trichostrongylus colubriformis*), *Trichinella* spp. (for example, *Trichinella spiriralis*), *Haemonchus contortus, Nematodirus* spp. (for example, *Nematodirus battus*), *Ostertagia circumcincta, Cooperia* spp., *Hymenolepis nana*, and the others.

EXAMPLES

The present invention will be more specifically described below by way of Examples such as Production Examples, Formulation Examples, and Test Examples, but the present invention is not limited only to these Examples.

In the following Production Examples of the present compounds, an intermediate produced in the following Reference Production Example is mentioned as C4A (numeric portion means the number of Reference Production Example. In this case, this means an intermediate produced in Reference Production Example 4).

First, Production Examples will be shown.

Production Example 1

A mixture of 0.59 g of C2A, 0.38 g of C55A, 0.35 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 1-{3-chloro-2-[1-(3-difluoromethylphenyl)ethylideneaminooxymethyl]phenyl}-4-methyl-1,4-dihydrotetrazol-5-one (hereinafter referred to as the present compound 1).

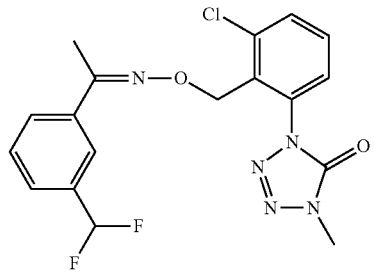 [SMILES: CC(=NOCc1c(Cl)cccc1-n1nnn(C)c1=O)c1cccc(C(F)F)c1]

$^1$H-NMR (CDCl$_3$) δ(ppm): 7.71 (1H, s), 7.65 (1H, d, J=7.2 Hz), 7.60 (1H, d, J=7.2 Hz), 7.51-7.41 (3H, m), 7.33 (1H, d, J=7.2 Hz), 6.67 (1H, t, J=56.3 Hz), 5.46 (2H, s), 3.61 (3H, s), 2.10 (3H, s).

Production Example 2

A mixture of 0.52 g of C11A, 0.34 g of C55A, 0.31 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 1-{3-methyl-2-[1-(3-difluoromethylphenyl)ethylideneaminooxymethyl]phenyl}-4-methyl-1,4-dihydrotetrazol-5-one (hereinafter referred to as the present compound 2).

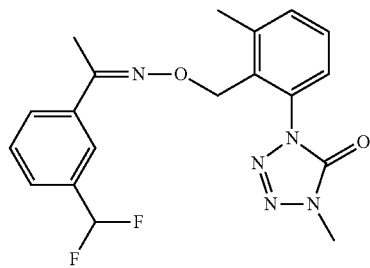 [SMILES: CC(=NOCc1c(C)cccc1-n1nnn(C)c1=O)c1cccc(C(F)F)c1]

$^1$H-NMR (CDCl$_3$) δ(ppm): 7.74 (1H, s), 7.66 (1H, d, J=7.8 Hz), 7.49 (1H, d, J=7.8 Hz), 7.45-7.38 (3H, m), 7.23 (1H, t, J=4.6 Hz), 6.67 (1H, t, J=56.3 Hz), 5.26 (2H, s), 3.65 (3H, s), 2.55 (3H, s), 2.13 (3H, s).

Production Example 3

A mixture of 0.40 g of C2A, 0.25 g of C40A, 0.24 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 1-[2-(1-benzo

[1,3]dioxan-5-yl-ethylideneaminooxymethyl)-3-chlorophenyl]-4-methyl-1,4-dihydrotetrazol-5-one (hereinafter referred to as the present compound 3).

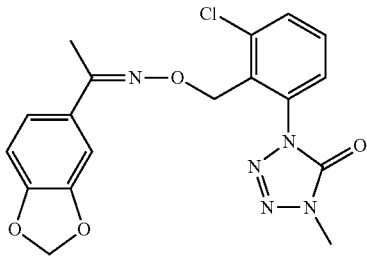 [SMILES: CC(=NOCc1c(Cl)cccc1-n1nnn(C)c1=O)c1ccc2c(c1)OCO2]

$^1$H-NMR (CDCl$_3$) δ(ppm): 7.58 (1H, dd, J=8.1, 1.5 Hz), 7.41 (1H, t, J=8.1 Hz), 7.32 (1H, dd, J=7.9, 1.3 Hz), 7.11 (1H, d, J=1.7 Hz), 7.00 (1H, dd, J=8.2, 1.8 Hz), 6.75 (1H, d, J=8.3 Hz), 5.96 (2H, s), 5.43 (2H, s), 3.63 (3H, s), 2.03 (3H, s).

Production Example 4

A mixture of 0.40 g of C2A, 0.22 g of C20A, 0.24 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 3-{1-[2-chloro-6-(4-methyl-5-oxo-4,5-dihydrotetrazol-1-yl)benzyloxyimino]ethyl}benzonitrile (hereinafter referred to as the present compound 4).

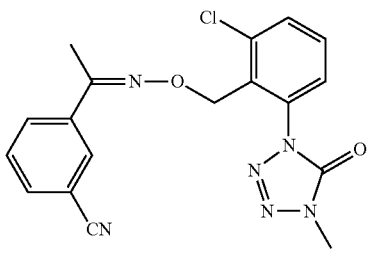 [SMILES: CC(=NOCc1c(Cl)cccc1-n1nnn(C)c1=O)c1cccc(C#N)c1]

$^1$H-NMR (CDCl$_3$) δ(ppm): 7.9 (1H, t, J=1.5 Hz), 7.78 (1H, dq, J=8.1, 1.0 Hz), 7.61 (2H, dt, J=7.9, 1.3 Hz), 7.44 (2H, t, J=8.1 Hz), 7.34 (1H, dd, J=7.8, 1.2 Hz), 5.46 (2H, s), 3.67 (3H, s), 2.09 (3H, s).

Production Example 5

A mixture of 0.40 g of C2A, 0.22 g of C21A, 0.24 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 1-{3-chloro-2-[1-(3-methoxyphenyl)ethylideneaminooxymethyl]phenyl}-4-methyl-1,4-dihydrotetrazol-5-one (hereinafter referred to as the present compound 5).

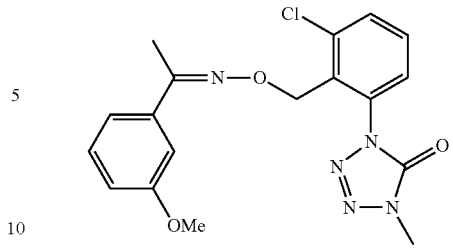

$^1$H-NMR (CDCl$_3$) δ(ppm): 7.59 (1H, dd, J=8.2 1.3 Hz), 7.42 (1H, t, J=8.1 Hz), 7.32 (1H, dd, J=8.1, 1.2 Hz), 7.23 (1H, d, J=8.1 Hz), 7.14-7.10 (2H, m), 6.88 (1H, dq, J=8.2, 1.2 Hz), 5.46 (2H, s), 3.83 (3H, s), 3.59 (3H, s), 2.07 (3H, s).

Production Example 6

A mixture of 0.40 g of C2A, 0.23 g of C22A, 0.24 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 1-{3-chloro-2-[1-(3-nitrophenyl)ethylideneaminooxymethyl]phenyl}-4-methyl-1,4-dihydrotetrazol-5-one (hereinafter referred to as the present compound 6).

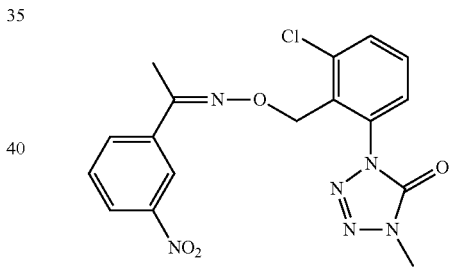

$^1$H-NMR (CDCl$_3$) δ(ppm): 8.39 (1H, t, J=1.9 Hz), 8.19 (1H, d, J=8.2 Hz), 7.91 (1H, d, J=7.7 Hz), 7.61 (1H, d, J=8.0 Hz), 7.51 (1H, t, J=8.0 Hz), 7.44 (1H, t, J=8.1 Hz), 7.34 (1H, d, J=8.0 Hz), 5.48 (2H, s), 3.67 (3H, s), 2.14 (3H, s).

Production Example 7

A mixture of 0.40 g of C11A, 0.30 g of C42A, 0.24 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 1-{3-methyl-2-[1-(3-tri fluoromethylphenyl)ethylideneaminooxymethyl]phenyl}-4-methyl-1,4-dihydrotetrazol-5-one (hereinafter referred to as the present compound 7).

191

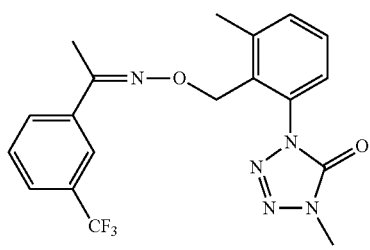

¹H-NMR (CDCl₃) δ(ppm): 7.84 (1H, s), 7.75 (1H, d, J=7.8 Hz), 7.58 (1H, d, J=7.8 Hz), 7.46 (1H, t, J=7.8 Hz), 7.38 (2H, m), 7.23 (1H, t, J=4.6 Hz), 5.27 (2H, s), 3.66 (3H, s), 2.56 (3H, s), 2.13 (3H, s).

Production Example 8

A mixture of 0.40 g of C2A, 0.30 g of C56A, 0.24 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 1-{3-chloro-2-[1-(2,2-difluorobenzo[1,3]dioxoyl-5yl)ethylideneaminooxymethyl]phenyl}-4-methyl-1,4-dihydrotetrazol-5-one (hereinafter referred to as the present compound 8).

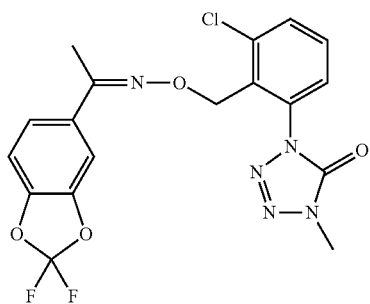 [SMILES: CC(=NOCc1c(Cl)cccc1-n1nnn(C)c1=O)c1ccc2c(c1)OC(F)(F)O2]

¹H-NMR (CDCl₃) δ(ppm): 7.60 (1H, dd, J=8.2, 1.3 Hz), 7.43 (1H, t, J=8.1 Hz), 7.35-7.32 (2H, m), 7.24 (1H, dd, J=8.5, 1.7 Hz), 7.00 (1H, d, J=8.3 Hz), 5.44 (2H, s), 3.65 (3H, s), 2.06 (3H, s).

Production Example 9

A mixture of 0.40 g of C2A, 0.35 g of C57A, 0.24 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 1-(3-chloro-2-{1-[3-(1,1,2,2-tetrafluoroethoxyl)phenyl]ethylideneaminooxymethyl]phenyl}-4-methyl-1,4-dihydrotetrazol-5-one (hereinafter referred to as the present compound 9).

192

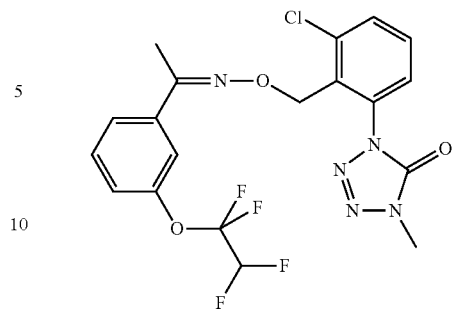

¹H-NMR (CDCl₃) δ(ppm): 7.60 (1H, dd, J=8.1, 1.2 Hz), 7.48-7.41 (3H, m), 7.36-7.32 (2H, m), 7.19 (1H, dq, J=8.2, 1.1 Hz), 5.93 (1H, tt, J=53.1, 2.9 Hz), 5.46 (2H, s), 3.61 (3H, s), 2.08 (3H, s).

Production Example 10

A mixture of 0.40 g of C2A, 0.23 g of C23A, 0.24 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 1-{3-chloro-2-[1-(3,5-dimethylphenyl)ethylideneaminooxymethyl]phenyl}-4-methyl-1,4-dihydrotetrazol-5-one (hereinafter referred to as the present compound 10).

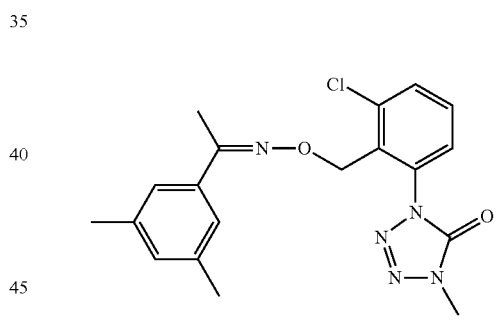

¹H-NMR (CDCl₃) δ(ppm): 7.58 (1H, dd, J=8.1, 1.0 Hz), 7.41 (1H, t, J=8.1 Hz), 7.32 (1H, d, J=7.6 Hz), 7.16 (2H, s), 6.97 (1H, s), 5.45 (2H, s), 3.58 (3H, s), 2.31 (6H, s), 2.05 (3H, s).

Production Example 11

A mixture of 0.40 g of C2A, 0.28 g of C58A, 0.24 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 1-{3-chloro-2-[1-(3-difluoromethoxyphenyl)ethylideneaminooxymethyl]phenyl}-4-methyl-1,4-dihydrotetrazol-5-one (hereinafter referred to as the present compound 11).

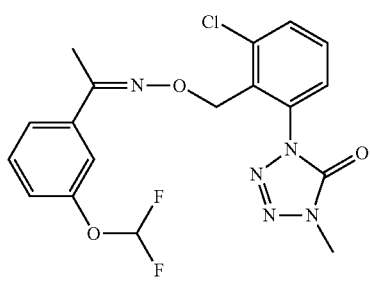 [SMILES: CC(=NOCc1c(Cl)cccc1-n1nnn(C)c1=O)c1cccc(OC(F)F)c1]

¹H-NMR (CDCl₃) δ(ppm): 7.59 (1H, dd, J=8.2, 1.3 Hz), 7.43 (1H, t, J=8.1 Hz), 7.38-7.30 (4H, m), 7.09 (1H, d, J=8.5 Hz), 6.58 (1H, t, J=73.9 Hz), 5.44 (2H, s), 3.63 (3H, s), 2.08 (3H, s).

Production Example 12

A mixture of 0.30 g of C8A, 0.21 g of C42A, 0.23 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 1-{3-methoxy-2-[1-(3-trifluoromethylphenyl)ethylideneaminooxymethyl]phenyl}-4-methyl-1,4-dihydrotetrazol-5-one (hereinafter referred to as the present compound 12).

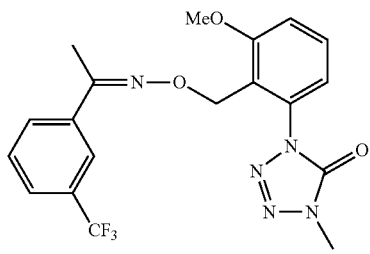 [SMILES: COc1cccc(-n2nnn(C)c2=O)c1CON=C(C)c1cccc(C(F)(F)F)c1]

¹H-NMR (CDCl₃) δ(ppm): 7.82 (1H, s), 7.73 (1H, d, J=7.8 Hz), 7.58 (1H, d, J=7.8 Hz), 7.45 (2H, m), 7.09 (1H, d, J=8.5 Hz), 7.01 (1H, d, J=8.1 Hz), 5.40 (2H, s), 3.93 (3H, s), 3.59 (3H, s), 2.08 (3H, s).

Production Example 13

A mixture of 0.40 g of C2A, 0.20 g of C24A, 0.24 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 1-[3-chloro-2-(indan-1-ylideneaminooxymethyl]phenyl)-4-methyl-1,4-dihydrotetrazol-5-one (hereinafter referred to as the present compound 13).

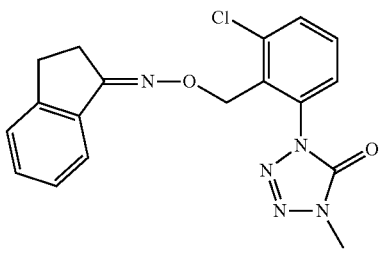 [SMILES: Cn1nnn(-c2cccc(Cl)c2CON=C2CCc3ccccc32)c1=O]

¹H-NMR (CDCl₃) δ(ppm): 7.60-7.56 (2H, m), 7.41 (1H, t, J=8.1 Hz), 7.33-7.20 (4H, m), 5.41 (2H, s), 3.64 (3H, s), 2.97-2.94 (2H, m), 2.74-2.71 (2H, m).

Production Example 14

A mixture of 0.40 g of C2A, 0.22 g of C25A, 0.24 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 1-[3-chloro-2-(6-methylindan-1-ylideneaminooxymethyl]phenyl)-4-methyl-1,4-dihydrotetrazol-5-one (hereinafter referred to as the present compound 14).

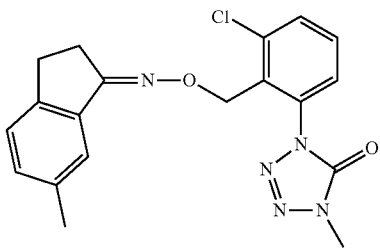

¹H-NMR (CDCl₃) δ(ppm): 7.58 (1H, dd, J=8.1, 1.2 Hz), 7.41 (2H, t, J=8.1 Hz), 7.32 (1H, dd, J=7.8, 1.2 Hz), 7.16-7.11 (2H, m), 5.41 (2H, s), 3.65 (3H, s), 2.92-2.89 (2H, m), 2.73-2.70 (2H, m), 2.35 (3H, s).

Production Example 15

A mixture of 0.40 g of C2A, 0.26 g of C26A, 0.24 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 1-{3-chloro-2-[1-(naphthalen-2-yl)ethylideneaminooxymethyl]phenyl}-4-methyl-1,4-dihydrotetrazol-5-one (hereinafter referred to as the present compound 15).

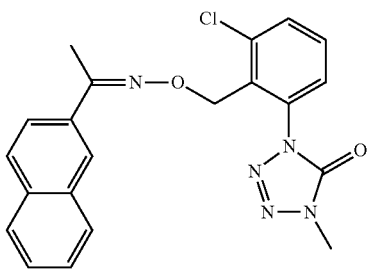 [SMILES: CC(=NOCc1c(Cl)cccc1-n1nnn(C)c1=O)c1ccc2ccccc2c1]

¹H-NMR (CDCl₃) δ(ppm): 7.94 (1H, s), 7.86-7.77 (4H, m), 7.61 (1H, d, J=8.2 Hz), 7.49-7.41 (3H, m), 7.35 (1H, d, J=8.0 Hz), 5.52 (2H, s), 3.57 (3H, s), 2.20 (3H, s).

Production Example 16

A mixture of 0.40 g of C2A, 0.24 g of C28A, 0.24 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 1-{3-chloro-2-[1-(3-chlorophenyl)ethylideneaminooxymethyl]phenyl}-4-methyl-1,4-dihydrotetrazol-5-one (hereinafter referred to as the present compound 16).

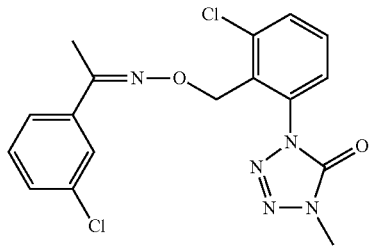 [SMILES: CC(=NOCc1c(Cl)cccc1-n1nnn(C)c1=O)c1cccc(Cl)c1]

¹H-NMR (CDCl₃) δ(ppm): 7.59 (1H, dd, J=8.2, 1.3 Hz), 7.55 (1H, t, J=1.7 Hz), 7.45-7.41 (2H, m), 7.34-7.24 (3H, m), 5.46 (2H, s), 3.62 (3H, s), 2.06 (3H, s).

Production Example 17

A mixture of 0.40 g of C2A, 0.21 g of C46A, 0.24 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 1-{3-chloro-2-[1-(3-methylphenyl)ethylideneaminooxymethyl]phenyl}-4-methyl-1,4-dihydrotetrazol-5-one (hereinafter referred to as the present compound 17).

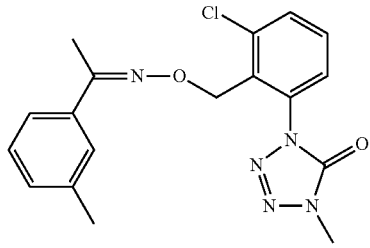 [SMILES: CC(=NOCc1c(Cl)cccc1-n1nnn(C)c1=O)c1cccc(C)c1]

¹H-NMR (CDCl₃) δ(ppm): 7.59 (1H, dd, J=8.1, 1.2 Hz), 7.42 (1H, t, J=8.1 Hz), 7.38-7.32 (3H, m), 7.22 (1H, t, J=7.7 Hz), 7.15 (1H, d, J=7.3 Hz), 5.46 (2H, s), 3.58 (3H, s), 2.36 (3H, s), 2.07 (3H, s).

Production Example 18

A mixture of 0.40 g of C2A, 0.28 g of C29A, 0.24 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 1-{3-chloro-2-[1-(2-trifluoromethylphenyl)ethylideneaminooxymethyl]phenyl}-4-methyl-1,4-dihydrotetrazol-5-one (hereinafter referred to as the present compound 18).

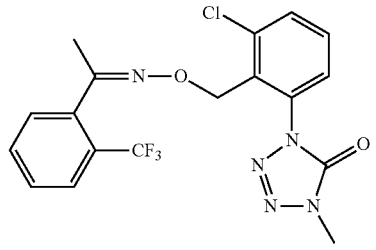 [SMILES: CC(=NOCc1c(Cl)cccc1-n1nnn(C)c1=O)c1ccccc1C(F)(F)F]

¹H-NMR (CDCl₃) δ(ppm): 7.65 (1H, d, J=7.8 Hz), 7.58 (1H, dd, J=8.1, 1.2 Hz), 7.53 (1H, t, J=7.2 Hz), 7.47-7.41 (2H, m), 7.34 (1H, dd, J=7.8, 3.9 Hz), 7.28-7.25 (1H, m), 5.43 (2H, s), 3.59 (3H, s), 2.02 (3H, s).

Production Example 19

A mixture of 0.40 g of C2A, 0.24 g of C30A, 0.24 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 1-{3-chloro-2-[1-(indan-5-yl)ethylideneaminooxymethyl]phenyl}-4-methyl-1,4-dihydrotetrazol-5-one (hereinafter referred to as the present compound 19).

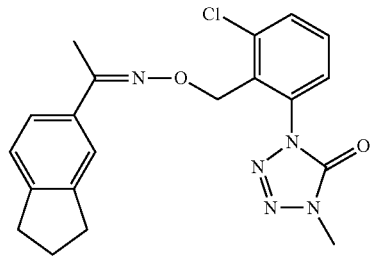 [SMILES: CC(=NOCc1c(Cl)cccc1-n1nnn(C)c1=O)c1ccc2c(c1)CCC2]

¹H-NMR (CDCl₃) δ(ppm): 7.58 (1H, dt, J=8.1, 1.2 Hz), 7.43-7.39 (2H, m), 7.33-7.30 (2H, m), 7.17 (1H, d, J=8.0 Hz), 5.45 (2H, s), 3.59 (3H, s), 2.89 (4H, m), 2.17 (3H, s), 2.08-2.04 (2H, m).

Production Example 20

A mixture of 0.40 g of C2A, 0.28 g of C31A, 0.28 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 1-{3-chloro-2-[1-(3,5-dichlorophenyl)ethylideneaminooxymethyl]phenyl}-4-methyl-1,4-dihydrotetrazol-5-one (hereinafter referred to as the present compound 20).

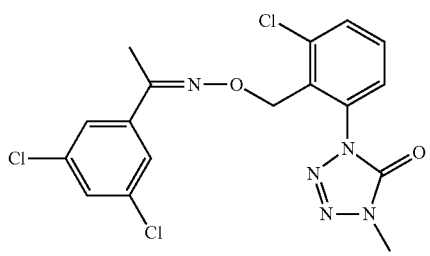 [SMILES: CC(=NOCc1c(Cl)cccc1-n1nnn(C)c1=O)c1cc(Cl)cc(Cl)c1]

¹H-NMR (CDCl₃) δ(ppm): 7.60 (1H, d, J=8.1 Hz), 7.46-7.42 (3H, m), 7.34-7.31 (2H, m), 5.45 (2H, s), 3.66 (3H, s), 2.04 (3H, s).

Production Example 21

A mixture of 0.40 g of C2A, 0.25 g of C32A, 0.24 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 1-[3-chloro-2-(6-chloroindan-1-ylideneaminooxymethyl]phenyl)-4-methyl-1,4-dihydrotetrazol-5-one (hereinafter referred to as the present compound 21).

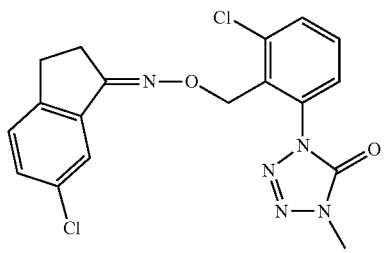 [SMILES: Cn1nnn(-c2cccc(Cl)c2CON=C2CCc3ccc(Cl)cc32)c1=O]

¹H-NMR (CDCl₃) δ(ppm): 7.59 (1H, dd, J=8.2, 1.3 Hz), 7.55 (1H, d, J=2.0 Hz), 7.42 (1H, t, J=8.1 Hz), 7.33 (1H, dd, J=8.1, 1.2 Hz), 7.24 (1H, d, J=2.2 Hz), 7.17 (1H, d, J=8.1 Hz), 5.41 (2H, s), 3.69 (3H, s), 2.94-2.90 (2H, m), 2.75-2.72 (2H, m).

Production Example 22

A mixture of 0.40 g of C2A, 0.37 g of C33A, 0.24 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 1-{3-chloro-2-[1-(3,5-ditrifluoromethylphenyl)ethylideneaminooxymethyl]phenyl}-4-methyl-1,4-dihydrotetrazol-5-one (hereinafter referred to as the present compound 22).

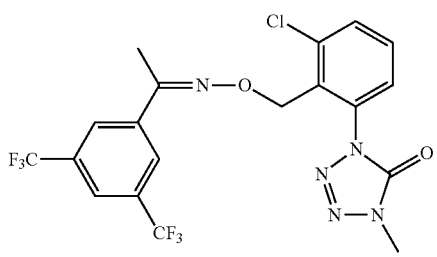 [SMILES: CC(=NOCc1c(Cl)cccc1-n1nnn(C)c1=O)c1cc(C(F)(F)F)cc(C(F)(F)F)c1]

¹H-NMR (CDCl₃) δ(ppm): 8.00 (2H, s), 7.83 (1H, s), 7.61 (1H, dd, J=8.3, 1.2 Hz), 7.45 (1H, t, J=8.1 Hz), 7.33 (1H, dd, J=8.1, 1.2 Hz), 5.46 (2H, s), 3.67 (3H, s), 2.14 (3H, s).

Production Example 23

A mixture of 0.40 g of C2A, 0.27 g of C42A, 0.24 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 1-{3-chloro-2-[1-(3-trifluoromethylphenyl)ethylideneaminooxymethyl]phenyl}-4-methyl-1,4-dihydrotetrazol-5-one (hereinafter referred to as the present compound 23).

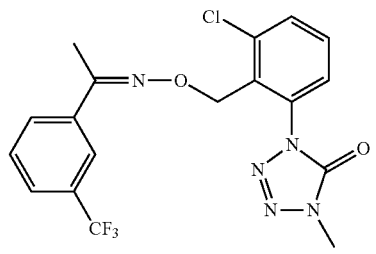

¹H-NMR (CDCl₃) δ(ppm): 7.81 (1H, s), 7.74 (1H, d, J=7.8 Hz), 7.61-7.58 (2H, m), 7.47-7.41 (2H, m), 7.33 (1H, dd, J=8.1, 1.2 Hz), 5.47 (2H, s), 3.62 (3H, s), 2.11 (3H, s).

Production Example 24

A mixture of 0.40 g of C2A, 0.19 g of acetophenone oxime, 0.24 g of potassium carbonate, and 10 mL of acetonitrile was stirred while heating under reflux for 7 hours. After cooling to room temperature, the reaction mixture was filtered and the filtrate was concentrated.

The obtained residue was subjected to silica gel column chromatography to obtain 1-[3-chloro-2-(1-phenylethylideneaminooxymethyl)phenyl]-4-methyl-1,4-dihydrotetrazol-5-one (hereinafter referred to as the present compound 24).

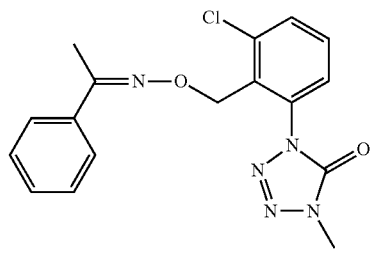 [SMILES: CC(=NOCc1c(Cl)cccc1-n1nnn(C)c1=O)c1ccccc1]

¹H-NMR (CDCl₃) δ(ppm): 7.66 (2H, d, J=8.5 Hz), 7.59 (3H, t, J=7.6 Hz), 7.43 (1H, t, J=8.1 Hz), 7.33 (2H, d, J=7.3 Hz), 5.47 (2H, s), 3.62 (3H, s), 2.10 (3H, s).

Production Example 25

A mixture of 0.40 g of C2A, 0.30 g of C34A, 0.24 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 1-{3-chloro-2-

[1-(3-trifluoromethoxyphenyl)ethylideneaminooxymethyl]phenyl}-4-methyl-1,4-dihydrotetrazol-5-one (hereinafter referred to as the present compound 25).

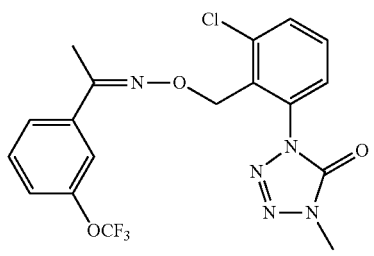

¹H-NMR (CDCl₃) δ(ppm): 7.60 (1H, d, J=8.2 Hz), 7.49-7.41 (3H, m), 7.38-7.32 (2H, m), 7.19 (1H, d, J=8.2 Hz), 5.46 (2H, s), 3.62 (3H, s), 2.08 (3H, s).

Production Example 26

A mixture of 0.40 g of C2A, 0.26 g of C35A, 0.24 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 1-[3-chloro-2-(2,2,2-trifluoro-1-phenylethylideneaminooxymethyl)phenyl]-4-methyl-1,4-dihydrotetrazol-5-one (hereinafter referred to as the present compound 26).

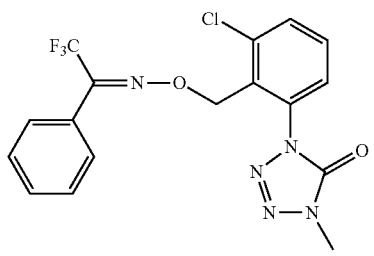 [SMILES: Cn1nnn(-c2cccc(Cl)c2CON=C(c2ccccc2)C(F)(F)F)c1=O]

¹H-NMR (CDCl₃) δ(ppm): 7.58 (1H, dd, J=8.1, 1.2 Hz), 7.47-7.34 (7H, m), 5.53 (2H, s), 3.59 (3H, s).

Production Example 27

A mixture of 0.40 g of C2A, 0.28 g of C36A, 0.24 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 1-{3-chloro-2-[1-(4-trifluoromethylphenyl)ethylideneaminooxymethyl]phenyl}-4-methyl-1,4-dihydrotetrazol-5-one (hereinafter referred to as the present compound 27).

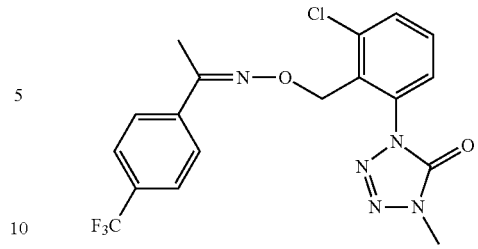

¹H-NMR (CDCl₃) δ(ppm): 7.66 (2H, d, J=8.3 Hz), 7.61-7.57 (3H, m), 7.44 (1H, t, J=8.1 Hz), 7.33 (1H, d, J=7.8 Hz), 5.47 (2H, s), 3.62 (3H, s), 2.10 (3H, s).

Production Example 28

A mixture of 0.40 g of C2A, 0.24 g of C37A, 0.24 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 1-{3-chloro-2-[1-(3,5-difluorophenyl)ethylideneaminooxymethyl]phenyl}-4-methyl-1,4-dihydrotetrazol-5-one (hereinafter referred to as the present compound 28).

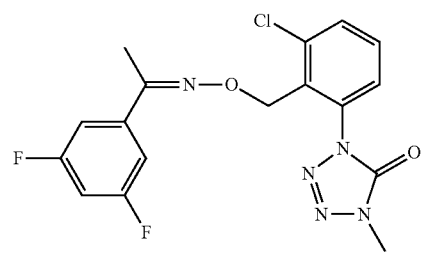 [SMILES: CC(=NOCc1c(Cl)cccc1-n1nnn(C)c1=O)c1cc(F)cc(F)c1]

¹H-NMR (CDCl₃) δ(ppm): 7.60 (1H, dd, J=8.1, 1.2 Hz), 7.43 (1H, t, J=8.1 Hz), 7.33 (1H, dd, J=7.8, 1.2 Hz), 7.08 (2H, dd, J=8.8, 2.2 Hz), 6.77 (1H, tt, J=8.8, 2.4 Hz), 5.46 (2H, s), 3.66 (3H, s), 2.04 (3H, s).

Production Example 29

A mixture of 0.30 g of C17A, 0.21 g of C42A, 0.17 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.34 g of 1-{3-cyclopropyl-2-[1-(3-trifluoromethylphenyl)ethylideneaminooxym ethyl]phenyl}-4-methyl-1,4-dihydrotetrazol-5-one (hereinafter referred to as the present compound 29).

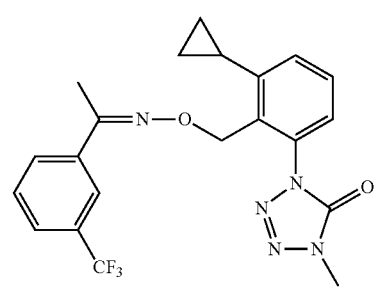

$^1$H-NMR (CDCl$_3$) δ(ppm): 7.84 (1H, s), 7.75 (1H, d, J=7.7 Hz), 7.58 (1H, d, J=7.7 Hz), 7.46 (1H, t, J=7.9 Hz), 7.39 (1H, t, J=7.9 Hz), 7.27-7.21 (2H, m), 5.50 (2H, s), 3.64 (3H, s), 2.27-2.20 (1H, m), 2.12 (3H, s), 1.08-1.03 (2H, m), 0.81-0.77 (2H, m).

Production Example 30

A mixture of 0.30 g of C14A, 0.22 g of C42A, 0.18 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.35 g of 1-{3-ethyl-2-[1-(3-trifluoromethylphenyl)ethylideneaminooxymethyl]phenyl}-4-methyl-1,4-dihydrotetrazol-5-one (hereinafter referred to as the present compound 30).

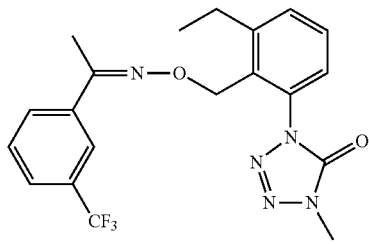 [SMILES: CCc1cccc(-n2nnn(C)c2=O)c1CON=C(C)c1cccc(C(F)(F)F)c1]

$^1$H-NMR (CDCl$_3$) δ(ppm): 7.84 (1H, s), 7.75 (1H, d, J=8.0 Hz), 7.59 (1H, d, J=7.7 Hz), 7.47 (1H, d, J=8.0 Hz), 7.44-7.41 (2H, m), 7.23 (1H, dd, J=6.0, 3.4 Hz), 5.30 (2H, s), 3.63 (3H, s), 2.91 (2H, q, J=7.6 Hz), 2.12 (3H, s), 1.31 (3H, t, J=7.5 Hz).

Production Example 31

A mixture of 0.56 g of C11A, 0.34 g of C28A, 0.36 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.50 g of 1-{3-methyl-2-[1-(3-chlorophenyl)ethylideneaminooxymethyl]phenyl}-4-methyl-1,4-dihydrotetrazol-5-one (hereinafter referred to as the present compound 31).

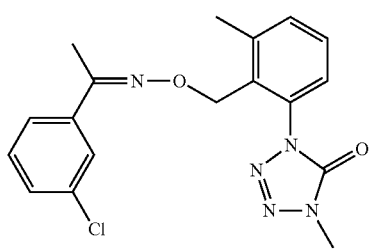

$^1$H-NMR (CDCl$_3$) δ(ppm): 7.58 (1H, t, J=1.8 Hz), 7.44 (1H, dt, J=7.3, 1.6 Hz), 7.39-7.38 (2H, m), 7.32-7.28 (2H, m), 7.25-7.21 (1H, m), 5.26 (2H, s), 3.66 (3H, s), 2.55 (3H, s), 2.08 (3H, s).

Production Example 32

A mixture of 0.56 g of C11A, 0.44 g of C34A, 0.36 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.60 g of 1-{3-methyl-2-[1-(3-trifluoromethoxyphenyl)ethylideneaminooxymethyl]phenyl}-4-methyl-1,4-dihydrotetrazol-5-one (hereinafter referred to as the present compound 32).

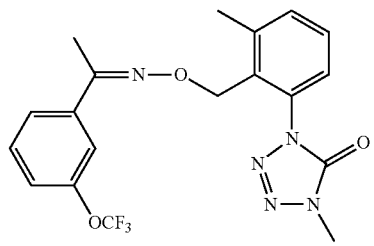

$^1$H-NMR (CDCl$_3$) δ(ppm): 7.51-7.45 (2H, m), 7.39-7.34 (3H, m), 7.25-7.17 (2H, m), 5.26 (2H, s), 3.66 (3H, s), 2.55 (3H, s), 2.10 (3H, s).

Production Example 33

A mixture of 0.56 g of C11A, 0.50 g of C57A, 0.36 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.65 g of 1-(3-methyl-2-{1-[3-(1,1,2,2-tetrafluoroethoxyl)phenyl]ethylideneaminooxymethyl}phenyl)-4-methyl-1,4-dihydrotetrazol-5-one (hereinafter referred to as the present compound 33).

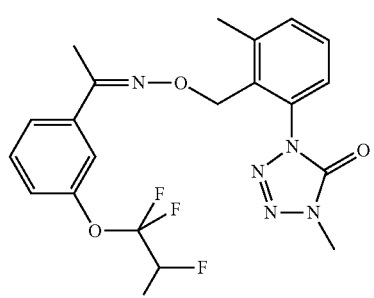

$^1$H-NMR (CDCl$_3$) δ(ppm): 7.48 (1H, dt, J=7.8, 1.3 Hz), 7.44 (1H, s), 7.38-7.32 (3H, m), 7.24-7.17 (2H, m), 5.93 (1H, tt, J=53.1, 2.9 Hz), 5.26 (2H, s), 3.65 (3H, s), 2.55 (3H, s), 2.10 (3H, s).

Production Example 34

A mixture of 0.56 g of C11A, 0.33 g of C21A, 0.36 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.36 g of 1-{3-methyl-2-[1-(3-methoxyphenyl)ethylideneaminooxymethyl]phenyl}-4-methyl-1,4-dihydrotetrazol-5-one (hereinafter referred to as the present compound 34).

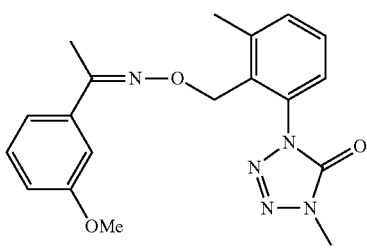

¹H-NMR (CDCl₃) δ(ppm): 7.37-7.35 (2H, m), 7.26-7.20 (2H, m), 7.16-7.12 (2H, m), 6.88 (1H, dd, J=8.2, 2.6 Hz), 5.25 (2H, s), 3.82 (3H, s), 3.63 (3H, s), 2.54 (3H, s), 2.09 (3H, s).

Production Example 35

A mixture of 0.56 g of C11A, 0.35 g of C30A, 0.36 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.24 g of 1-{3-methyl-2-[1-(indan-5-yl)ethylideneaminooxymethyl]phenyl}-4-methyl-1,4-dihydrotetrazol-5-one (hereinafter referred to as the present compound 35).

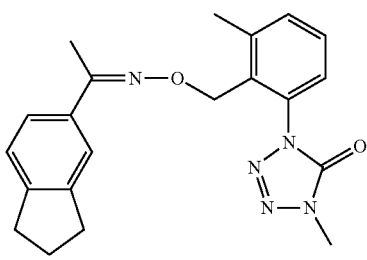 [SMILES: CC(=NOCc1c(C)cccc1-n1nnn(C)c1=O)c1ccc2c(c1)CCC2]

¹H-NMR (CDCl₃) δ(ppm): 7.45 (1H, s), 7.36-7.32 (3H, m), 7.25-7.16 (2H, m), 5.24 (2H, s), 3.63 (3H, s), 2.92-2.86 (4H, m), 2.54 (3H, s), 2.09 (3H, s), 2.09-2.02 (2H, m).

Production Example 36

A mixture of 0.56 g of C11A, 0.37 g of C26A, 0.36 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.47 g of 1-[3-methyl-2-(1-naphthalen-2-ylethylideneaminooxymethyl)phenyl]-4-methyl-1,4-dihydrotetrazol-5-one (hereinafter referred to as the present compound 36).

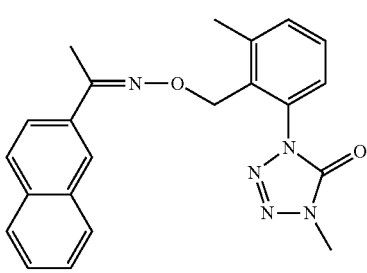 [SMILES: CC(=NOCc1c(C)cccc1-n1nnn(C)c1=O)c1ccc2ccccc2c1]

¹H-NMR (CDCl₃) δ(ppm): 7.84-7.75 (5H, m), 7.47-7.21 (5H, m), 5.31 (2H, s), 3.59 (3H, s), 2.56 (3H, s), 2.21 (3H, s).

Production Example 37

A mixture of 0.56 g of C11A, 0.36 g of C22A, 0.36 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.42 g of 1-{3-methyl-2-[1-(3-nitrophenyl)ethylideneaminooxymethyl]phenyl}-4-methyl-1,4-dihydrotetrazol-5-one (hereinafter referred to as the present compound 37).

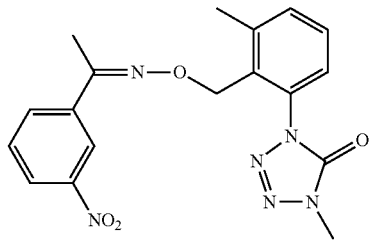 [SMILES: CC(=NOCc1c(C)cccc1-n1nnn(C)c1=O)c1cccc([N+](=O)[O-])c1]

¹H-NMR (CDCl₃) δ(ppm): 8.40 (1H, s), 8.18-8.15 (1H, m), 7.93-7.90 (1H, m), 7.50 (1H, t, J=7.9 Hz), 7.38 (2H, d, J=5.1 Hz), 7.23 (1H, t, J=4.5 Hz), 5.29 (2H, s), 3.69 (3H, s), 2.56 (3H, s), 2.15 (3H, s).

Production Example 38

A mixture of 0.56 g of C11A, 0.33 g of C23A, 0.36 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.51 g of 1-{3-methyl-2-[1-(3,5-dimethylphenyl)ethylideneaminooxymethyl]phen yl}-4-methyl-1,4-dihydrotetrazol-5-one (hereinafter referred to as the present compound 38).

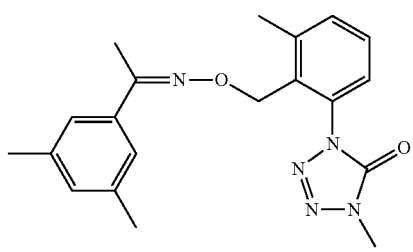 [SMILES: CC(=NOCc1c(C)cccc1-n1nnn(C)c1=O)c1cc(C)cc(C)c1]

¹H-NMR (CDCl₃) δ(ppm): 7.37-7.36 (2H, m), 7.25-7.19 (3H, m), 6.97 (1H, bs), 5.24 (2H, s), 3.63 (3H, s), 2.54 (3H, s), 2.32 (6H, s), 2.08 (3H, s).

Production Example 39

A mixture of 0.56 g of C11A, 0.41 g of C31A, 0.36 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.54 g of 1-{3-methyl-2-[1-(3,5-dichlorophenyl)ethylideneaminooxymethyl]phenyl}-4-methyl-1,4-dihydrotetrazol-5-one (hereinafter referred to as the present compound 39).

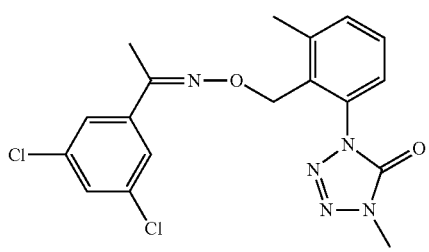 [SMILES: CC(=NOCc1c(C)cccc1-n1nnn(C)c1=O)c1cc(Cl)cc(Cl)c1]

$^1$H-NMR (CDCl$_3$) δ(ppm): 7.46-7.23 (6H, m), 5.26 (2H, s), 3.68 (3H, s), 2.54 (3H, s), 2.06 (3H, s).

Production Example 40

A mixture of 0.56 g of C11A, 0.37 g of C33A, 0.36 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.43 g of 1-{3-methyl-2-[1-(3,5-ditrifluoromethylphenyl)ethylideneaminooxymethyl]phenyl}-4-methyl-1,4-dihydrotetrazol-5-one (hereinafter referred to as the present compound 40).

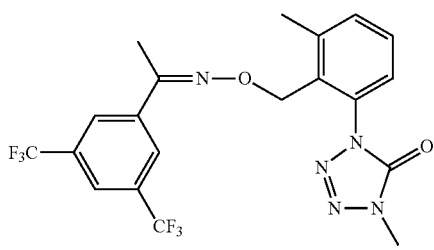 [SMILES: CC(=NOCc1c(C)cccc1-n1nnn(C)c1=O)c1cc(C(F)(F)F)cc(C(F)(F)F)c1]

$^1$H-NMR (CDCl$_3$) δ(ppm): 8.02 (2H, bs), 7.83 (1H, bs), 7.40-7.39 (2H, m), 7.23 (1H, t, J=4.8 Hz), 5.29 (2H, s), 3.68 (3H, s), 2.54 (3H, s), 2.16 (3H, s).

Production Example 41

A mixture of 0.45 g of C8A, 0.25 g of C28A, 0.28 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.25 g of 1-{3-methoxy-2-[1-(3-chlorophenyl)ethylideneaminooxymethyl]phenyl}-4-methyl-1,4-dihydrotetrazol-5-one (hereinafter referred to as the present compound 41).

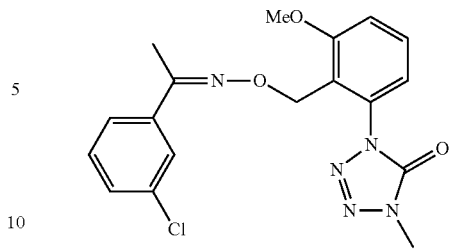

$^1$H-NMR (CDCl$_3$) δ(ppm): 7.56 (1H, m), 7.45-7.40 (2H, m), 7.30-7.23 (2H, m), 7.07 (1H, d, J=8.5 Hz), 7.01 (1H, d, J=8.0 Hz), 5.40 (2H, s), 3.92 (3H, s), 3.58 (3H, s), 2.03 (3H, s).

Production Example 42

A mixture of 0.45 g of C8A, 0.33 g of C34A, 0.28 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.35 g of 1-{3-methoxy-2-[1-(3-trifluoromethoxyphenyl)ethylideneaminooxymethyl]phenyl}-4-methyl-1,4-dihydrotetrazol-5-one (hereinafter referred to as the present compound 42).

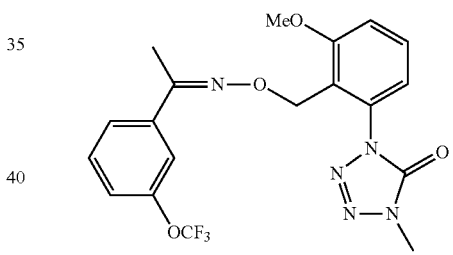

$^1$H-NMR (CDCl$_3$) δ(ppm): 7.48-7.41 (3H, m), 7.34 (1H, t, J=7.9 Hz), 7.19-7.16 (1H, m), 7.07 (1H, dd, J=8.2, 0.8 Hz), 7.01 (1H, dd, J=8.2, 0.8 Hz), 5.40 (2H, s), 3.92 (3H, s), 3.57 (3H, s), 2.05 (3H, s).

Production Example 43

A mixture of 0.45 g of C8A, 0.38 g of C57A, 0.28 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.30 g of 1-(3-methoxy-2-{1-[3-(1,1,2,2-tetrafluoroethoxy)phenyl]ethylideneaminooxymethyl}phenyl)-4-methyl-1,4-dihydrotetrazol-5-one (hereinafter referred to as the present compound 43).

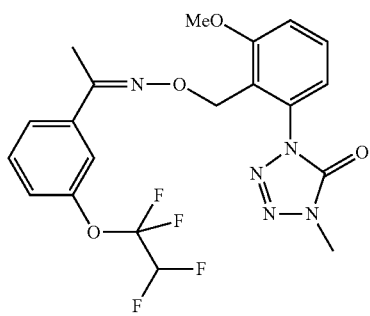 [SMILES: COc1cccc(-n2nnn(C)c2=O)c1CON=C(C)c1cccc(OC(F)(F)C(F)F)c1]

$^1$H-NMR (CDCl$_3$) δ(ppm): 7.47-7.41 (3H, m), 7.34 (1H, t, J=8.0 Hz), 7.19-7.17 (1H, m), 7.07 (1H, dd, J=8.5, 0.7 Hz), 7.01 (1H, dd, J=8.0, 1.0 Hz), 5.93 (1H, tt, J=53.0, 2.9 Hz), 5.40 (2H, s), 3.92 (3H, s), 3.57 (3H, s), 2.05 (3H, s).

Production Example 44

A mixture of 0.45 g of C8A, 0.25 g of C21A, 0.28 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.32 g of 1-{3-methoxy-2-[1-(3-methoxyphenyl)ethylideneaminooxymethyl]phenyl}-4-methyl-1,4-dihydrotetrazol-5-one (hereinafter referred to as the present compound 44).

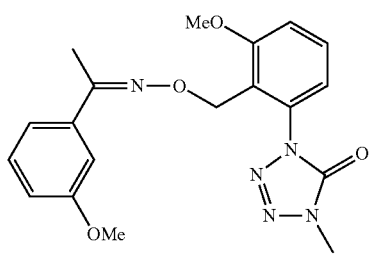 [SMILES: COc1cccc(C(C)=NOCc2c(OC)cccc2-n2nnn(C)c2=O)c1]

$^1$H-NMR (CDCl$_3$) δ(ppm): 7.43 (1H, t, J=8.2 Hz), 7.23 (1H, d, J=8.2 Hz), 7.13-7.11 (2H, m), 7.07 (1H, d, J=8.5 Hz), 7.00 (1H, d, J=8.0 Hz), 6.89-6.86 (1H, m), 5.39 (2H, s), 3.92 (3H, s), 3.82 (3H, s), 3.55 (3H, s), 2.04 (3H, s).

Production Example 45

A mixture of 0.45 g of C8A, 0.27 g of C22A, 0.28 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.38 g of 1-{3-methoxy-2-[1-(3-nitrophenyl)ethyl ideneaminooxymethyl]phenyl}-4-methyl-1,4-dihydrotetrazol-5-one (hereinafter referred to as the present compound 45).

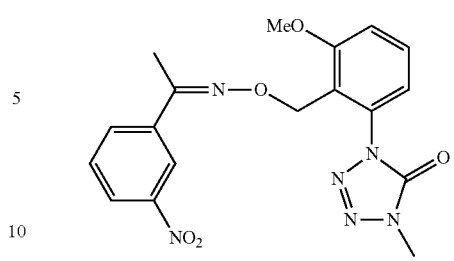

$^1$H-NMR (CDCl$_3$) δ(ppm): 8.39 (1H, t, J=2.1 Hz), 8.16 (1H, dq, J=8.2, 1.1 Hz), 7.89 (1H, dq, J=7.8, 0.89 Hz), 7.49 (1H, t, J=8.1 Hz), 7.45 (1H, t, J=8.1 Hz), 7.09 (1H, d, J=8.5 Hz), 7.01 (1H, d, J=8.0 Hz), 5.41 (2H, s), 3.94 (3H, s), 3.63 (3H, s), 2.10 (3H, s).

Production Example 46

A mixture of 0.45 g of C8A, 0.26 g of C30A, 0.28 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.25 g of 1-{3-methoxy-2-[1-(indan-5-yl)ethylideneaminooxymethyl]phenyl}-4-m ethyl-1,4-dihydrotetrazol-5-one (hereinafter referred to as the present compound 46).

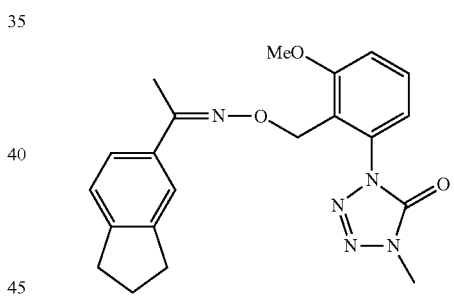

$^1$H-NMR (CDCl$_3$) δ(ppm): 7.43-7.40 (2H, m), 7.32-7.30 (1H, m), 7.17 (1H, d, J=7.7 Hz), 7.03 (2H, dd, J=19.3, 8.2 Hz), 5.39 (2H, s), 3.90 (3H, s), 3.54 (3H, s), 2.89 (4H, m), 2.07-2.03 (2H, m), 2.04 (3H, s).

Production Example 47

A mixture of 0.45 g of C8A, 0.28 g of C26A, 0.28 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.38 g of 1-{3-methoxy-2-[1-(naphthalen-2-yl)ethylideneaminooxymethyl]phenyl}-4-methyl-1,4-dihydrotetrazol-5-one (hereinafter referred to as the present compound 47).

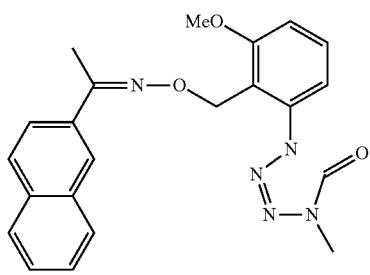 [SMILES: COc1cccc(N/N=N\N(C)C=O)c1CON=C(C)c1ccc2ccccc2c1]

¹H-NMR (CDCl₃) δ(ppm): 7.93 (1H, s), 7.85-7.76 (4H, m), 7.48-7.42 (3H, m), 7.08 (1H, d, J=8.5 Hz), 7.02 (1H, d, J=8.1 Hz), 5.46 (2H, s), 3.93 (3H, s), 3.51 (3H, s), 2.17 (3H, s).

Production Example 48

A mixture of 0.45 g of C8A, 0.24 g of C23A, 0.28 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.27 g of 1-{3-methoxy-2-[1-(3,5-dimethylphenyl)ethylideneaminooxymethyl]phenyl}-4-methyl-1,4-dihydrotetrazol-5-one (hereinafter referred to as the present compound 48).

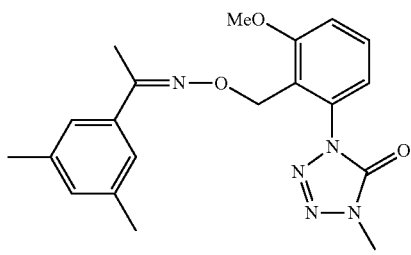 [SMILES: COc1cccc(-n2nnn(C)c2=O)c1CON=C(C)c1cc(C)cc(C)c1]

¹H-NMR (CDCl₃) δ(ppm): 7.42 (1H, t, J=8.2 Hz), 7.17 (2H, s), 7.06 (1H, d, J=8.5 Hz), 7.01 (1H, d, J=8.0 Hz), 6.96 (1H, s), 5.39 (2H, s), 3.91 (3H, s), 3.54 (3H, s), 2.31 (6H, s), 2.03 (3H, s).

Production Example 49

A mixture of 0.45 g of C8A, 0.30 g of C31A, 0.28 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.48 g of 1-{3-methoxy-2-[1-(3,5-dichlorophenyl)ethylideneaminooxymethyl]phenyl}-4-methyl-1,4-dihydrotetrazol-5-one (hereinafter referred to as the present compound 49).

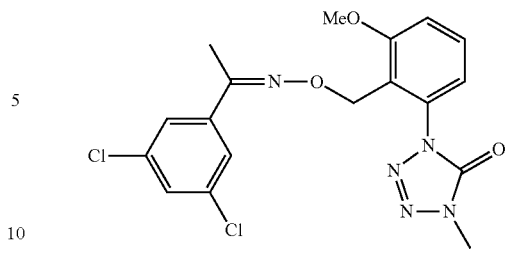

¹H-NMR (CDCl₃) δ(ppm): 7.46-7.42 (3H, m), 7.30 (1H, t, J=1.8 Hz), 7.04 (2H, dd, J=27.2, 8.1 Hz), 5.39 (2H, s), 3.93 (3H, s), 3.63 (3H, s), 2.01 (3H, s).

Production Example 50

A mixture of 0.42 g of C11A, 0.28 g of C38A, 0.28 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 1-methyl-4-{3-methyl-2-[1-(3-trifluoromethylphenyl)methylideneaminooxymethyl]phenyl}-1,4-dihydrotetrazol-5-one (hereinafter referred to as the present compound 50).

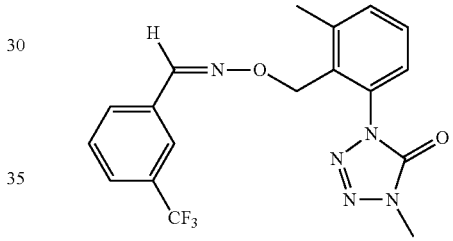

¹H-NMR (CDCl₃) δ(ppm): 7.98 (1H, s), 7.79 (1H, s), 7.66 (1H, d, J=7.8 Hz), 7.58 (1H, d, J=7.6 Hz), 7.45 (1H, t, J=7.8 Hz), 7.41-7.37 (2H, m), 7.25-7.23 (1H, m), 5.24 (2H, s), 3.69 (3H, s), 2.54 (3H, s).

Production Example 51

A mixture of 0.42 g of C11A, 0.33 g of C39A, 0.28 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 1-methyl-4-{3-methyl-2-[1-(3-trifluoromethylphenyl)propylideneaminooxymethyl]phenyl}-1,4-dihydrotetrazol-5-one (hereinafter referred to as the present compound 51).

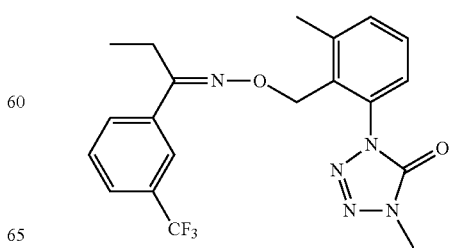

¹H-NMR (CDCl₃) δ(ppm): 7.84 (1H, s), 7.74 (1H, d, J=7.8 Hz), 7.58 (1H, d, J=7.8 Hz), 7.46 (1H, t, J=7.8 Hz), 7.40-7.36 (2H, m), 7.25-7.22 (1H, m), 5.25 (2H, s), 3.66 (3H, s), 2.65 (2H, q, J=7.6 Hz), 2.55 (3H, s), 1.04 (3H, t, J=7.6 Hz).

Production Example 52

A mixture of 0.42 g of C11A, 0.37 g of C64A, 0.28 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.34 g of 1-{3-methyl-2-[2,2-dimethyl-1-(3-trifluoromethylphenyl)pyrrolideneaminooxymethyl]phenyl}-4-methyl-1,4-dihydrotetrazol-5-one (hereinafter referred to as the present compound 52).

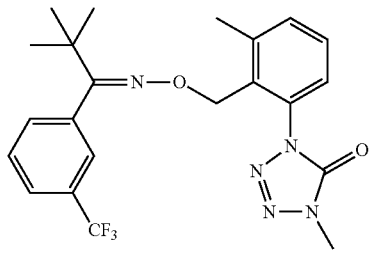 [SMILES: Cc1cccc(-n2nnn(C)c2=O)c1CON=C(c1cccc(C(F)(F)F)c1)C(C)(C)C]

¹H-NMR (CDCl₃) δ(ppm): 7.54 (1H, d, J=7.3 Hz), 7.43 (1H, t, J=7.8 Hz), 7.32-7.29 (2H, m), 7.16 (1H, d, J=7.3 Hz), 7.11 (1H, s), 7.07 (1H, d, J=7.6 Hz), 5.00 (2H, s), 3.64 (3H, s), 2.27 (3H, s), 1.03 (9H, s).

Production Example 53

A mixture of 0.46 g of C17A, 0.25 g of C28A, 0.28 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.42 g of 1-{3-cyclopropyl-2-[1-(3-chlorophenyl)ethylideneaminooxymethyl]phenyl}-4-methyl-1,4-dihydrotetrazol-5-one (hereinafter referred to as the present compound 53).

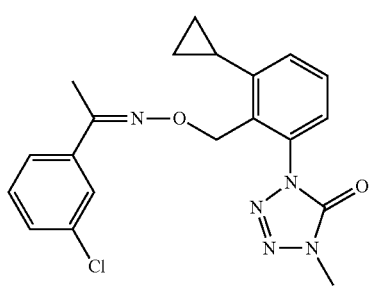 [SMILES: CC(=NOCc1c(C2CC2)cccc1-n1nnn(C)c1=O)c1cccc(Cl)c1]

¹H-NMR (CDCl₃) δ(ppm): 7.58 (1H, t, J=1.6 Hz), 7.44 (1H, dt, J=7.3, 1.6 Hz), 7.39 (1H, t, J=7.9 Hz), 7.31-7.20 (4H, m), 5.49 (2H, s), 3.64 (3H, s), 2.30-2.19 (1H, m), 2.08 (3H, s), 1.06-1.04 (2H, m), 0.79-0.77 (2H, m).

Production Example 54

A mixture of 0.46 g of C17A, 0.33 g of C34A, 0.28 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.55 g of 1-{3-cyclopropyl-2-[1-(3-trifluoromethoxyphenyl)ethylideneaminooxymethyl]phenyl}-4-methyl-1,4-dihydrotetrazol-5-one (hereinafter referred to as the present compound 54).

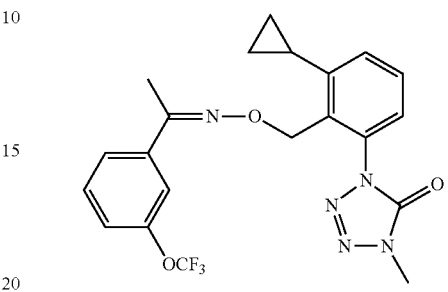

¹H-NMR (CDCl₃) δ(ppm): 7.45-7.39 (4H, m), 7.25-7.19 (3H, m), 5.50 (2H, s), 3.64 (3H, s), 2.27-2.20 (1H, m), 2.09 (3H, s), 1.08-1.03 (2H, m), 0.80-0.76 (2H, m).

Production Example 55

A mixture of 0.46 g of C17A, 0.50 g of C57A, 0.28 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.16 g of 1-(3-cyclopropyl-2-{1-[3-(1,1,2,2-tetrafluoroethoxy)phenyl]ethylideneaminooxymethyl}phenyl)-4-methyl-1,4-dihydrotetrazol-5-one (hereinafter referred to as the present compound 55).

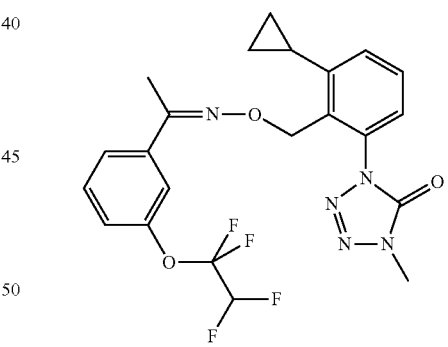

¹H-NMR (CDCl₃) δ(ppm): 7.48-7.45 (2H, m), 7.41-7.33 (2H, m), 7.23-7.19 (3H, m), 5.93 (1H, tt, J=53.2, 2.9 Hz), 5.50 (2H, s), 3.63 (3H, s), 2.28-2.20 (1H, m), 2.09 (3H, s), 1.07-1.02 (2H, m), 0.79-0.76 (2H, m).

Production Example 56

A mixture of 0.46 g of C17A, 0.33 g of C21A, 0.28 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.31 g of 1-{3-cyclopropyl-2-[1-(3-methoxyphenyl)ethylideneaminooxymethyl]phenyl}-4-methyl-1,4-dihydrotetrazol-5-one (hereinafter referred to as the present compound 56).

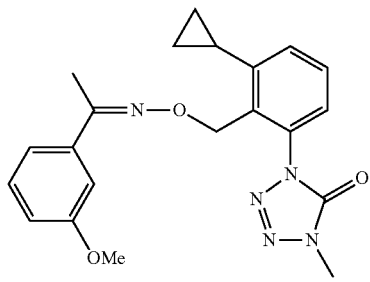 [SMILES: COc1cccc(C(C)=NOCc2c(C3CC3)cccc2-n2nnn(C)c2=O)c1]

¹H-NMR (CDCl₃) δ(ppm): 7.38 (1H, t, J=7.9 Hz), 7.25-7.22 (3H, m), 7.16-7.12 (2H, m), 6.88 (1H, dq, J=8.2, 1.9 Hz), 5.48 (2H, s), 3.83 (3H, s), 3.62 (3H, s), 2.31-2.19 (1H, m), 2.09 (3H, s), 1.05-1.03 (2H, m), 0.78-0.77 (2H, m).

Production Example 57

A mixture of 0.46 g of C17A, 0.27 g of C22A, 0.28 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.36 g of 1-{3-cyclopropyl-2-[1-(3-nitrophenyl)ethylideneaminooxymethyl]phen yl}-4-methyl-1,4-dihydrotetrazol-5-one (hereinafter referred to as the present compound 57).

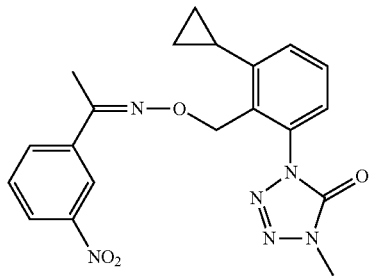 [SMILES: CC(=NOCc1c(C2CC2)cccc1-n1nnn(C)c1=O)c1cccc([N+](=O)[O-])c1]

¹H-NMR (CDCl₃) δ(ppm): 8.42 (1H, t, J=1.8 Hz), 8.18 (1H, dq, J=8.2, 1.2 Hz), 7.92 (1H, dq, J=7.8, 0.9 Hz), 7.51 (1H, t, J=8.2 Hz), 7.40 (1H, t, J=7.8 Hz), 7.25-7.22 (2H, m), 5.51 (2H, s), 3.68 (3H, s), 2.28-2.20 (1H, m), 2.15 (3H, s), 1.08-1.06 (2H, m), 0.81-0.77 (2H, m).

Production Example 58

A mixture of 0.46 g of C17A, 0.26 g of C30A, 0.28 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.36 g of 1-{3-cyclopropyl-2-[1-(indan-5-yl)ethylideneaminooxymethyl]phenyl}-4-methyl-1,4-dihydrotetrazol-5-one (hereinafter referred to as the present compound 58).

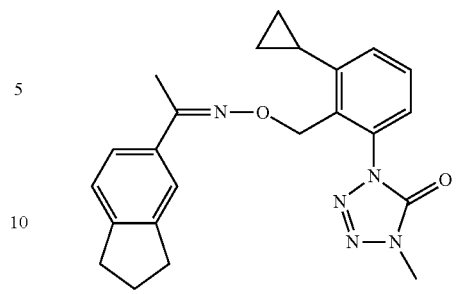

¹H-NMR (CDCl₃) δ(ppm): 7.45 (1H, s), 7.37 (1H, t, J=7.9 Hz), 7.33 (1H, dd, J=7.9, 1.6 Hz), 7.23-7.17 (3H, m), 5.47 (2H, s), 3.61 (3H, s), 2.89 (4H, m), 2.27-2.20 (1H, m), 2.09 (3H, s), 2.06-2.03 (2H, m), 1.06-1.01 (2H, m), 0.79-0.75 (2H, m).

Production Example 59

A mixture of 0.46 g of C17A, 0.28 g of C26A, 0.28 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.47 g of 1-{3-cyclopropyl-2-[1-(naphthalen-2-yl)ethylideneaminooxymethyl]phenyl}-4-methyl-1,4-dihydrotetrazol-5-one (hereinafter referred to as the present compound 59).

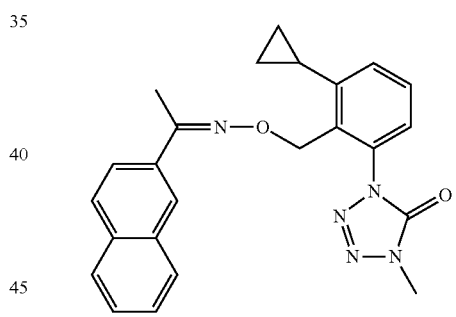

¹H-NMR (CDCl₃) δ(ppm): 7.94 (1H, s), 7.84-7.76 (4H, m), 7.48-7.44 (2H, m), 7.37 (1H, t, J=7.9 Hz), 7.22 (2H, d, J=8.0 Hz), 5.55 (2H, s), 3.57 (3H, s), 2.29-2.24 (1H, m), 2.21 (3H, s), 1.07-1.02 (2H, m), 0.80-0.76 (2H, m).

Production Example 60

A mixture of 0.46 g of C17A, 0.24 g of C23A, 0.28 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.42 g of 1-{3-cyclopropyl-2-[1-(3,5-dimethylphenyl)ethylideneaminooxymethyl]phenyl}-4-methyl-1,4-dihydrotetrazol-5-one (hereinafter referred to as the present compound 60).

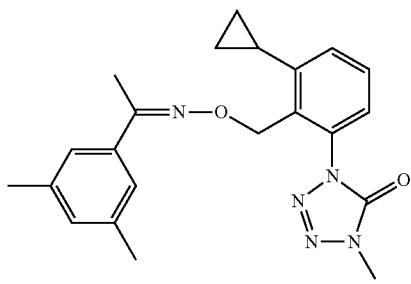 [SMILES: CC(=NOCc1c(C2CC2)cccc1-n1nnn(C)c1=O)c1cc(C)cc(C)c1]

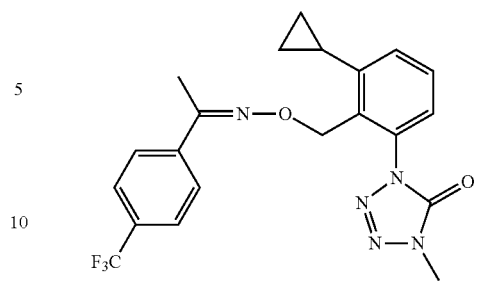

¹H-NMR (CDCl₃) δ(ppm): 7.37 (1H, t, J=7.9 Hz), 7.25-7.19 (4H, m), 6.97 (1H, s), 5.47 (2H, s), 3.61 (3H, s), 2.31 (6H, s), 2.29-2.20 (1H, m), 2.08 (3H, s), 1.06-1.01 (2H, m), 0.79-0.75 (2H, m).

Production Example 61

A mixture of 0.46 g of C17A, 0.30 g of C31A, 0.28 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.46 g of 1-{3-cyclopropyl-2-[1-(3,5-dichlorophenyl)ethylideneaminooxymethyl]phenyl}-4-methyl-1,4-dihydrotetrazol-5-one (hereinafter referred to as the present compound 61).

¹H-NMR (CDCl₃) δ(ppm): 7.69 (2H, d, J=8.2 Hz), 7.59 (2H, d, J=8.2 Hz), 7.40 (1H, t, J=7.9 Hz), 7.25-7.21 (2H, m), 5.51 (2H, s), 3.63 (3H, s), 2.28-2.18 (1H, m), 2.12 (3H, s), 1.08-1.03 (2H, m), 0.80-0.76 (2H, m).

Production Example 63

A mixture of 0.42 g of C11A, 0.39 g of C74A, 0.28 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.10 g of 1-methyl-4-{3-methyl-2-[2,2,2-trifluoro-1-(3-trifluoromethylphenyl)ethylideneaminooxymethyl]phenyl}-1,4-dihydrotetrazol-5-one (hereinafter referred to as the present compound 63).

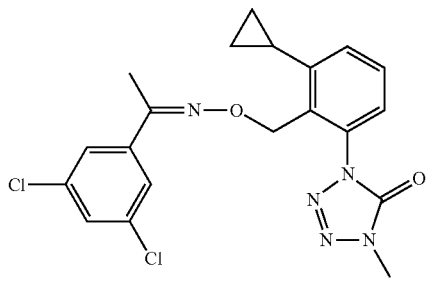 [SMILES: CC(=NOCc1c(C2CC2)cccc1-n1nnn(C)c1=O)c1cc(Cl)cc(Cl)c1]

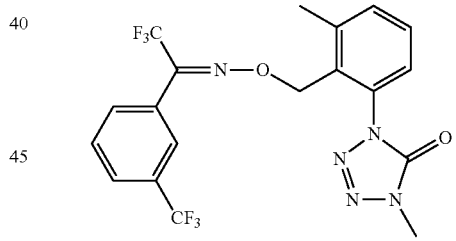

¹H-NMR (CDCl₃) δ(ppm): 7.46 (2H, d, J=1.7 Hz), 7.40 (1H, t, J=7.9 Hz), 7.32 (1H, t, J=1.9 Hz), 7.23 (2H, t, J=8.0 Hz), 5.49 (2H, s), 3.67 (3H, s), 2.26-2.17 (1H, m), 2.06 (3H, s), 1.08-1.04 (2H, m), 0.80-0.76 (2H, m).

Production Example 62

A mixture of 0.31 g of C17A, 0.20 g of C36A, 0.18 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.42 g of 1-{3-cyclopropyl-2-[1-(4-trifluoromethylphenyl)ethylideneaminooxymethyl]phenyl}-4-methyl-1,4-dihydrotetrazol-5-one (hereinafter referred to as the present compound 62).

¹H-NMR (CDCl₃) δ(ppm): 7.70-7.67 (1H, m), 7.62 (1H, s), 7.54 (2H, d, J=5.1 Hz), 7.43-7.36 (2H, m), 7.29-7.23 (1H, m), 5.32 (2H, s), 3.65 (3H, s), 2.44 (3H, s).

Production Example 64

A mixture of 0.60 g of C9A, 1.00 g of C42A, 0.56 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 1.26 g of 1-{3-trifluoromethyl-2-[1-(3-trifluoromethylphenyl)ethylideneaminooxymethyl]phenyl}-4-methyl-1,4-dihydrotetrazol-5-one (hereinafter referred to as the present compound 64).

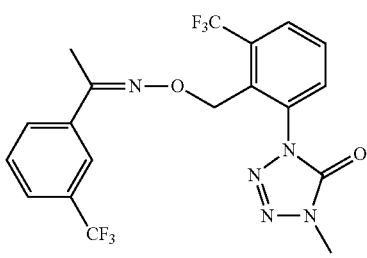 [SMILES: CC(=NOCc1c(-n2nnn(C)c2=O)cccc1C(F)(F)F)c1cccc(C(F)(F)F)c1]

¹H-NMR (CDCl₃) δ(ppm): 7.89 (1H, dd, J=6.5, 2.7 Hz), 7.79 (1H, s), 7.72 (1H, d, J=8.0 Hz), 7.65-7.58 (3H, m), 7.45 (1H, t, J=7.7 Hz), 5.52 (2H, s), 3.58 (3H, s), 2.06 (3H, s).

Production Example 65

A mixture of 0.50 g of C11A, 0.35 g of C19A, 0.28 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.46 g of 1-{3-methyl-2-[1-(3-bromo-4-fluorophenyl)ethylideneaminooxymethyl]phenyl}-4-methyl-1,4-dihydrotetrazol-5-one (hereinafter referred to as the present compound 65).

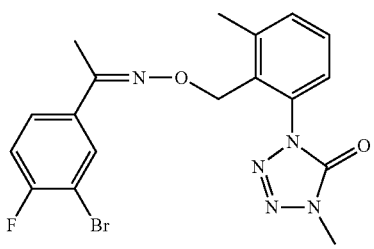

¹H-NMR (CDCl₃) δ(ppm): 7.79 (1H, dd, J=6.6, 2.30 Hz), 7.49 (1H, dq, J=8.7, 2.3 Hz), 7.39-7.39 (1H, m), 7.38 (1H, s), 7.25-7.20 (1H, m), 7.08 (1H, t, J=8.5 Hz), 5.24 (2H, s), 3.67 (3H, s), 2.54 (3H, s), 2.07 (3H, s).

Production Example 66

A mixture of 0.50 g of C11A, 0.31 g of C43A, 0.28 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.50 g of 1-{3-methyl-2-[1-(3,4dichlorophenyl)ethylideneaminooxymethyl]phenyl}-4-methyl-1,4-dihydrotetrazol-5-one (hereinafter referred to as the present compound 66).

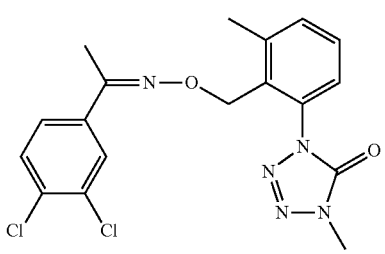 [SMILES: CC(=NOCc1c(C)cccc1-n1nnn(C)c1=O)c1ccc(Cl)c(Cl)c1]

¹H-NMR (CDCl₃) δ(ppm): 7.67 (1H, dd, J=1.5, 0.7 Hz), 7.41-7.36 (4H, m), 7.24-7.20 (1H, m), 5.25 (2H, s), 3.66 (3H, s), 2.54 (3H, s), 2.06 (3H, s).

Production Example 67

A mixture of 0.50 g of C11A, 0.26 g of C44A, 0.28 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.38 g of 1-{3-methyl-2-[1-(3,4-difluorophenyl)ethylideneaminooxymethyl]phen yl}-4-methyl-1,4-dihydrotetrazol-5-one (hereinafter referred to as the present compound 67).

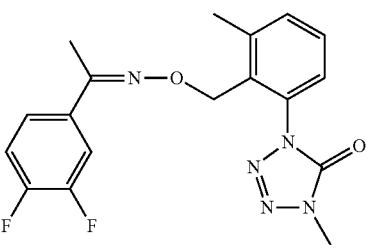 [SMILES: CC(=NOCc1c(C)cccc1-n1nnn(C)c1=O)c1ccc(F)c(F)c1]

¹H-NMR (CDCl₃) δ(ppm): 7.47-7.37 (3H, m), 7.30-7.27 (1H, m), 7.25-7.20 (1H, m), 7.15-7.08 (1H, m), 5.24 (2H, s), 3.67 (3H, s), 2.55 (3H, s), 2.07 (3H, s).

Production Example 68

A mixture of 0.47 g of C13A, 0.30 g of C42A, 0.28 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.38 g of 1-{3-ethoxy-2-[1-(3-trifluoromethylphenyl)ethylideneaminooxymethyl]phenyl}-4-methyl-1,4-dihydrotetrazol-5-one (hereinafter referred to as the present compound 68).

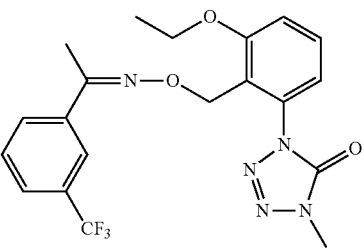 [SMILES: CCOc1cccc(-n2nnn(C)c2=O)c1CON=C(C)c1cccc(C(F)(F)F)c1]

¹H-NMR (CDCl₃) δ(ppm): 7.84 (1H, s), 7.72 (1H, d, J=7.8 Hz), 7.56 (1H, d, J=7.8 Hz), 7.46-7.38 (2H, m), 7.05 (1H, d, J=8.2 Hz), 6.99 (1H, d, J=8.0 Hz), 5.43 (2H, s), 4.13 (2H, q, J=7.0 Hz), 3.57 (3H, s), 2.07 (3H, s), 1.46 (3H, t, J=7.0 Hz).

Production Example 69

A mixture of 0.42 g of C11A, 0.28 g of C45A, 0.28 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.39 g of 1-{3-methyl-2-[1-(5,6,7,8-tetrahydronaphthalen-2-yl)ethyl-ideneaminooxymethyl]phenyl}-4-methyl-1,4-dihydrotetrazol-5-one (hereinafter referred to as the present compound 69).

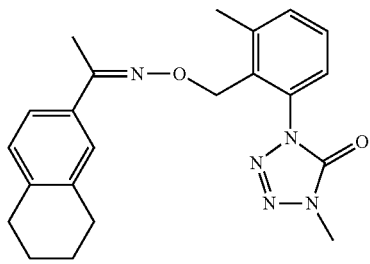 [SMILES: CC(=NOCc1c(C)cccc1-n1nnn(C)c1=O)c1ccc2c(c1)CCCC2]

¹H-NMR (CDCl₃) δ(ppm): 7.36 (2H, d, J=4.8 Hz), 7.28 (2H, d, J=7.1 Hz), 7.21 (1H, t, J=4.6 Hz), 7.02 (1H, d, J=8.5 Hz), 5.23 (2H, s), 3.64 (3H, s), 2.80-2.71 (4H, m), 2.54 (3H, s), 2.07 (3H, s), 1.81-1.75 (4H, m).

Production Example 70

A mixture of 0.42 g of C11A, 0.53 g of C59A, 0.28 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography and further subjected to gel permeation chromatography to obtain 0.40 g of 1-{2-[cyclopropyl(3-trifluoromethylphenyl)methylideneaminooxymethyl]-3-methylphenyl}-4-methyl-1,4-dihydrotetrazol-5-one (hereinafter referred to as the present compound 70).

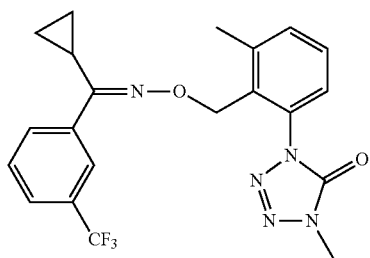 [SMILES: Cc1cccc(-n2nnn(C)c2=O)c1CON=C(c1cccc(C(F)(F)F)c1)C1CC1]

¹H-NMR (CDCl₃) δ(ppm): 7.66 (0.8H, s), 7.59-7.56 (2.0H, m), 7.51-7.40 (1.4H, m), 7.39-7.30 (2.0H, m), 7.23 (0.8H, t, J=4.6 Hz), 5.24 (1.6H, s), 5.05 (0.4H, s), 3.62 (0.6H, s), 3.61 (2.4H, s), 2.55 (2.4H, s), 2.37 (0.6H, s), 2.04-1.97 (0.8H, m), 1.61-1.54 (0.2H, m), 0.90-0.85 (1.6H, m), 0.78-0.72 (0.8H, m), 0.54-0.50 (1.6H, m).

Production Example 71

A mixture of 0.42 g of C11A, 0.23 g of C46A, 0.28 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.36 g of 1-{3-methyl-2-[1-(3-methylphenyl)ethylideneaminooxymethyl]phenyl}-4-methyl-1,4-dihydrotetrazol-5-one (hereinafter referred to as the present compound 71).

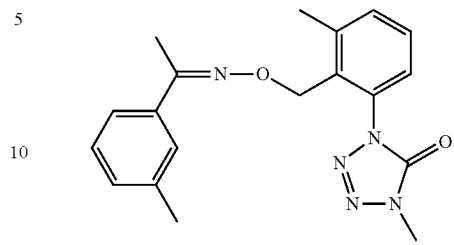

¹H-NMR (CDCl₃) δ(ppm): 7.41 (1H, s), 7.37-7.34 (3H, m), 7.25-7.20 (2H, m), 7.14 (1H, d, J=7.6 Hz), 5.25 (2H, s), 3.62 (3H, s), 2.55 (3H, s), 2.36 (3H, s), 2.09 (3H, s).

Production Example 72

A mixture of 0.42 g of C11A, 0.35 g of C67A, 0.28 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.40 g of 1-{3-methyl-2-[1-(3-hexyloxyphenyl) ethyl ideneaminooxymethyl]phenyl}-4-methyl-1,4-dihydrotetrazol-5-one (hereinafter referred to as the present compound 72).

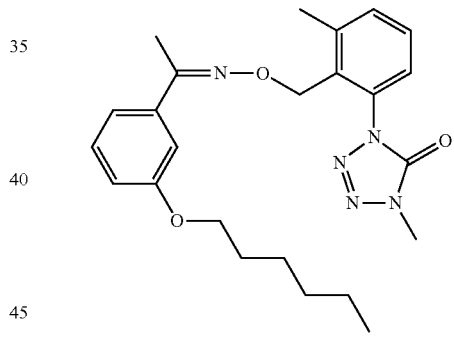

¹H-NMR (CDCl₃) δ(ppm): 7.36 (2H, d, J=5.3 Hz), 7.25-7.20 (2H, m), 7.14-7.10 (2H, m), 6.88-6.85 (1H, m), 5.25 (2H, s), 3.97 (2H, t, J=6.5 Hz), 3.63 (3H, s), 2.54 (3H, s), 2.09 (3H, s), 1.81-1.74 (2H, m), 1.50-1.43 (2H, m), 1.37-1.32 (4H, m), 0.93-0.89 (3H, m).

Production Example 73

A mixture of 0.42 g of C11A, 0.35 g of C60A, 0.28 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography and further subjected to gel permeation chromatography to obtain 0.46 g of 1-methyl-4-{3-methyl-2-[2-methyl-1-(3-trifluoromethyl-phenyl)propylideneaminooxymethyl]phenyl}-4-methyl-1,4-dihydrotetrazol-5-one (hereinafter referred to as the present compound 73).

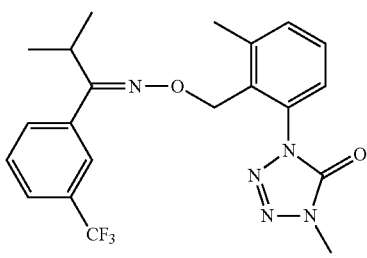 [SMILES: Cc1cccc(-n2nnn(C)c2=O)c1CON=C(c1cccc(C(F)(F)F)c1)C(C)C]

¹H-NMR (CDCl₃) δ(ppm): 7.61-7.53 (2.1H, m), 7.47-7.41 (1.1H, m), 7.39-7.29 (2.5H, m), 7.26-7.22 (0.8H, m), 7.18 (0.5H, dd, J=7.2, 1.7 Hz), 5.20 (1.0H, s), 5.06 (1.0H, s), 3.62 (1.5H, s), 3.62 (1.5H, s), 3.37 (0.5H, sep, J=7.1 Hz), 3.37 (0.5H, sep, J=6.9 Hz), 2.54 (1.5H, s), 2.35 (1.5H, s), 1.10 (3.0H, d, J=7.1 Hz), 1.00 (3.0H, d, J=6.9 Hz).

Production Example 74

A mixture of 0.42 g of C11A, 0.29 g of C65A, 0.28 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.46 g of N-(3-{1-[2-methyl-6-(4-methyl-5-oxo-4,5-dihydrotetrazol-1-yl)benzyloxyamino]ethyl}phenyl)acetamide (hereinafter referred to as the present compound 74).

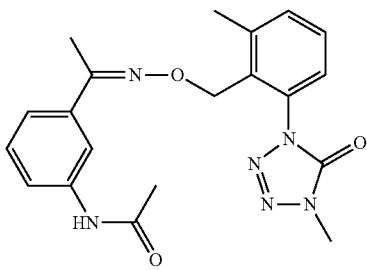 [SMILES: CC(=O)Nc1cccc(C(C)=NOCc2c(C)cccc2-n2nnn(C)c2=O)c1]

¹H-NMR (CDCl₃) δ(ppm): 8.07 (1H, bs), 7.97 (1H, d, J=8.0 Hz), 7.49 (1H, s), 7.41-7.36 (2H, m), 7.28-7.24 (2H, m), 7.15 (1H, d, J=8.0 Hz), 5.25 (2H, s), 3.67 (3H, s), 2.55 (3H, s), 2.20 (3H, s), 2.09 (3H, s).

Production Example 75

A mixture of 0.42 g of C11A, 0.35 g of C66A, 0.28 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.31 g of N-methyl-N-(3-{1-[2-methyl-6-(4-methyl-5-oxo-4,5-dihydrotetrazol-1-yl)benzyloxyimino]ethyl}phenyl)acetamide (hereinafter referred to as the present compound 75).

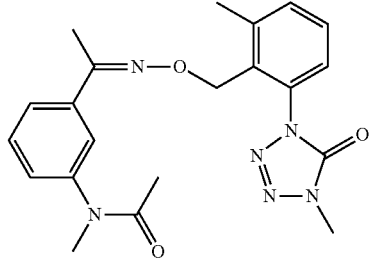 [SMILES: CC(=O)N(C)c1cccc(C(C)=NOCc2c(C)cccc2-n2nnn(C)c2=O)c1]

¹H-NMR (CDCl₃) δ(ppm): 7.52-7.36 (5H, m), 7.22 (1H, t, J=4.7 Hz), 7.15 (1H, d, J=7.8 Hz), 5.25 (2H, s), 3.68 (3H, s), 3.27 (3H, s), 2.56 (3H, s), 2.11 (3H, s), 1.87 (3H, s).

Production Example 76

A mixture of 0.28 g of C11A, 0.18 g of C68A, 0.18 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.09 g of 1-{3-methyl-2-[1-(3-isopropoxyphenyl)ethylideneiminooxymethyl]phen yl}-4-methyl-1,4-dihydrotetrazol-5-one (hereinafter referred to as the present compound 76).

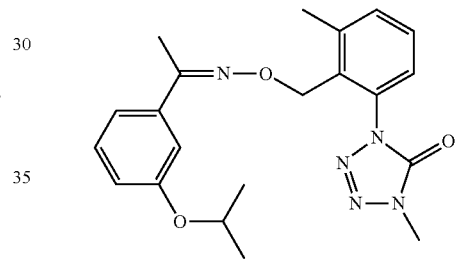

¹H-NMR (CDCl₃) δ(ppm): 7.37 (2H, d, J=4.8 Hz), 7.24-7.20 (2H, m), 7.12-7.10 (2H, m), 6.87-6.84 (1H, m), 5.25 (2H, s), 4.58 (1H, sep, J=6.1 Hz), 3.64 (3H, s), 2.55 (3H, s), 2.08 (3H, s), 1.33 (6H, d, J=6.2 Hz).

Production Example 77

A mixture of 0.28 g of C11A, 0.22 g of C70A, 0.18 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.23 g of 1-{3-methyl-2-[1-(3-trifluoromethylphenyl)butylideneaminooxymethyl]phenyl}-4-methyl-1,4-dihydrotetrazol-5-one (hereinafter referred to as the present compound 77).

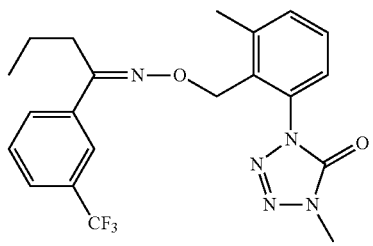 [SMILES: CCCC(=NOCc1c(C)cccc1-n1nnn(C)c1=O)c1cccc(C(F)(F)F)c1]

$^1$H-NMR (CDCl$_3$) δ(ppm): 7.83 (1H, s), 7.73 (1H, d, J=7.8 Hz), 7.58 (1H, d, J=8.0 Hz), 7.46 (1H, t, J=7.9 Hz), 7.38 (2H, m), 7.23 (1H, t, J=4.7 Hz), 5.25 (2H, s), 3.67 (3H, s), 2.64-2.60 (2H, m), 2.56 (3H, s), 1.51-1.38 (2H, m), 0.89 (3H, t, J=7.4 Hz).

Production Example 78

A mixture of 0.28 g of C11A, 0.26 g of C50A, 0.18 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.16 g of 1-{3-methyl-2-[1-(3-iodophenyl)ethylideneaminooxymethyl]phenyl}-4-methyl-1,4-dihydrotetrazol-5-one (hereinafter referred to as the present compound 78).

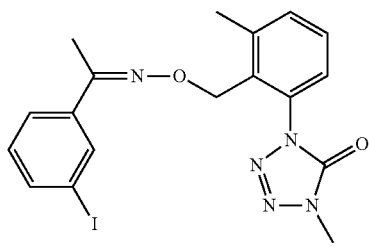 [SMILES: CC(=NOCc1c(C)cccc1-n1nnn(C)c1=O)c1cccc(I)c1]

$^1$H-NMR (CDCl$_3$) δ(ppm): 7.93 (1H, t, J=1.6 Hz), 7.66 (1H, dq, J=7.8, 0.92 Hz), 7.52 (1H, dq, J=7.9, 0.92 Hz), 7.39-7.38 (2H, m), 7.23 (1H, t, J=4.6 Hz), 7.07 (1H, t, J=7.7 Hz), 5.26 (2H, s), 3.66 (3H, s), 2.55 (3H, s), 2.07 (3H, s).

Production Example 79

A mixture of 0.28 g of C11A, 0.20 g of C51A, 0.18 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.29 g of 1-{3-methyl-2-[1-(3-bromophenyl)ethylideneaminooxymethyl]phenyl}-4-methyl-1,4-dihydrotetrazol-5-one (hereinafter referred to as the present compound 79).

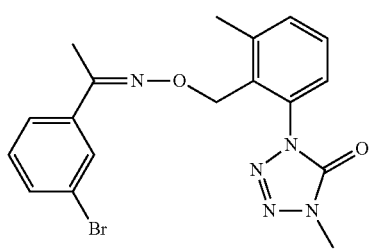

$^1$H-NMR (CDCl$_3$) δ(ppm): 7.74 (1H, t, J=1.8 Hz), 7.50-7.44 (2H, m), 7.38-7.37 (2H, m), 7.25-7.18 (2H, m), 5.26 (2H, s), 3.66 (3H, s), 2.55 (3H, s), 2.08 (3H, s).

Production Example 80

A mixture of 0.42 g of C11A, 0.38 g of 1-(3-trifluoromethylphenyl)pentan-1-one oxime mentioned in Reference Production Example 61, 0.28 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.50 g of 1-{3-methyl-2-[1-(3-trifluoromethylphenyl)pentylideneaminooxymethyl]phenyl}-4-methyl-1,4-dihydrotetrazol-5-one (hereinafter referred to as the present compound 80).

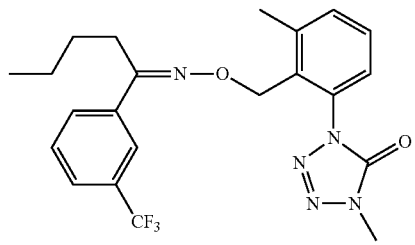 [SMILES: CCCCC(=NOCc1c(C)cccc1-n1nnn(C)c1=O)c1cccc(C(F)(F)F)c1]

$^1$H-NMR (CDCl$_3$) δ(ppm): 7.83 (1H, s), 7.72 (1H, d, J=7.8 Hz), 7.58 (1H, d, J=7.8 Hz), 7.46 (1H, t, J=7.9 Hz), 7.38 (2H, d, J=5.3 Hz), 7.22 (1H, t, J=4.6 Hz), 5.24 (2H, s), 3.67 (3H, s), 2.63 (2H, t, J=7.7 Hz), 2.56 (3H, s), 1.43-1.25 (4H, m), 0.86 (3H, t, J=7.2 Hz).

Production Example 81

A mixture of 0.28 g of C11A, 0.27 g of C62A, 0.18 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.36 g of 1-{3-methyl-2-[1-(3-trifluoromethylphenyl)heptylideneaminooxymethyl]phenyl}-4-methyl-1,4-dihydrotetrazol-5-one (hereinafter referred to as the present compound 81).

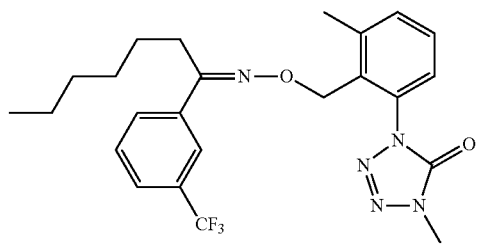 [SMILES: CCCCCCC(=NOCc1c(C)cccc1-n1nnn(C)c1=O)c1cccc(C(F)(F)F)c1]

$^1$H-NMR (CDCl$_3$) δ(ppm): 7.82 (1H, s), 7.71 (1H, d, J=7.8 Hz), 7.57 (1H, d, J=7.8 Hz), 7.45 (1H, t, J=7.9 Hz), 7.38 (2H, d, J=4.1 Hz), 7.22 (1H, t, J=4.6 Hz), 5.23 (2H, s), 3.66 (3H, s), 2.62 (2H, t, J=7.9 Hz), 2.55 (3H, s), 1.43-1.36 (2H, m), 1.31-1.20 (6H, m), 0.83 (3H, t, J=6.1 Hz).

Production Example 82

A mixture of 0.28 g of C11A, 0.25 g of C63A, 0.18 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.31 g of 1-methyl-4-{3-methyl-2-[3-methyl-1-(3-trifluoromethylphenyl)butylideneaminooxymethyl]phenyl}-4-methyl-1,4-dihydrotetrazol-5-one (hereinafter referred to as the present compound 82).

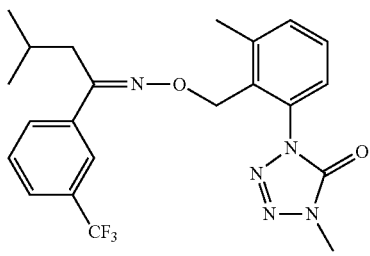 [SMILES: Cc1cccc(-n2nnn(C)c2=O)c1CON=C(CC(C)C)c1cccc(C(F)(F)F)c1]

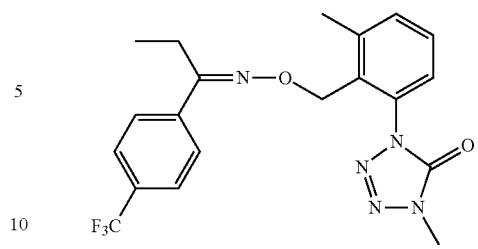

¹H-NMR (CDCl₃) δ(ppm): 7.82 (1H, s), 7.72 (1H, d, J=7.8 Hz), 7.57 (1H, d, J=7.8 Hz), 7.45 (1H, t, J=7.8 Hz), 7.38-7.37 (2H, m), 7.22 (1H, t, J=4.7 Hz), 5.23 (2H, s), 3.65 (3H, s), 2.56 (5H, m), 1.80 (1H, sep, J=6.8 Hz), 0.82 (6H, d, J=6.7 Hz).

¹H-NMR (CDCl₃) δ(ppm): 7.68 (2H, d, J=8.5 Hz), 7.59 (2H, d, J=8.5 Hz), 7.39-7.37 (2H, m), 7.25-7.21 (1H, m), 5.25 (2H, s), 3.66 (3H, s), 2.65 (2H, q, J=7.7 Hz), 2.55 (3H, s), 1.03 (3H, t, J=7.6 Hz).

Production Example 83

A mixture of 0.28 g of C11A, 0.22 g of C47A, 0.18 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.19 g of 1-{3-methyl-2-[1-(2-trifluoromethylphenyl) propylideneaminooxymethyl]phenyl}-4-methyl-1,4-dihydrotetrazol-5-one (hereinafter referred to as the present compound 83).

Production Example 85

A mixture of 0.28 g of C11A, 0.22 g of C69A, 0.18 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.25 g of 1-{3-methyl-2-[1-(3-pentyloxyphenyl)ethylideneaminooxymethyl]phenyl}-4-methyl-1,4-dihydrotetrazol-5-one (hereinafter referred to as the present compound 85).

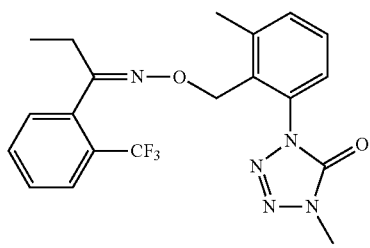 [SMILES: CCC(=NOCc1c(C)cccc1-n1nnn(C)c1=O)c1ccccc1C(F)(F)F]

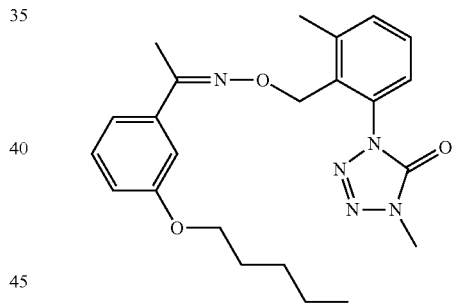

¹H-NMR (CDCl₃) δ(ppm): 7.68 (1H, d, J=8.0 Hz), 7.54 (1H, t, J=6.6 Hz), 7.46 (1H, t, J=8.0 Hz), 7.39-7.38 (2H, m), 7.29-7.28 (1H, m), 7.24-7.22 (1H, m), 5.17 (2H, s), 3.65 (3H, s), 2.58 (2H, q, J=7.7 Hz), 2.52 (3H, s), 0.88 (3H, t, J=7.7 Hz).

¹H-NMR (CDCl₃) δ(ppm): 7.37 (2H, d, J=4.4 Hz), 7.25-7.21 (2H, m), 7.13-7.11 (2H, m), 6.88-6.86 (1H, m), 5.25 (2H, s), 3.97 (2H, t, J=6.5 Hz), 3.64 (3H, s), 2.55 (3H, s), 2.09 (3H, s), 1.82-1.75 (2H, m), 1.49-1.34 (4H, m), 0.94 (3H, t, J=7.1 Hz).

Production Example 84

A mixture of 0.28 g of C11A, 0.22 g of C48A, 0.18 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.32 g of 1-{3-methyl-2-[1-(4-trifluoromethylphenyl)propylideneaminooxymethyl]phenyl}-4-methyl-1,4-dihydrotetrazol-5-one (hereinafter referred to as the present compound 84).

Production Example 86

A mixture of 0.31 g of C17A, 0.20 g of C58A, 0.18 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.40 g of 1-{3-cyclopropy-2-[1-(3-difluoromethoxyphenyl)ethylideneaminooxymethyl]phenyl}-4-methyl-1,4-dihydrotetrazol-5-one (hereinafter referred to as the present compound 86).

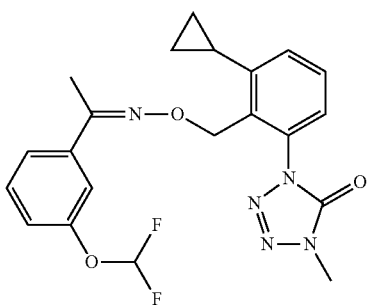 [SMILES: CC(=NOCc1c(C2CC2)cccc1-n1nnn(C)c1=O)c1cccc(OC(F)F)c1]

$^1$H-NMR (CDCl$_3$) δ(ppm): 7.41-7.36 (3H, m), 7.32 (1H, t, J=7.9 Hz), 7.22 (2H, t, J=8.7 Hz), 7.09 (1H, dd, J=7.8, 1.6 Hz), 6.58 (1H, t, J=74.0 Hz), 5.48 (2H, s), 3.65 (3H, s), 2.30-2.20 (1H, m), 2.09 (3H, s), 1.08-1.03 (2H, m), 0.80-0.76 (2H, m).

Production Example 87

A mixture of 0.28 g of C11A, 0.20 g of C71A, 0.18 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.27 g of 1-(3-methyl-2-{1-[3-(butyn-2-yloxy)phenyl]ethylideneaminooxymethyl)phenyl-4-methyl-1,4-dihydrotetrazol-5-one (hereinafter referred to as the present compound 87).

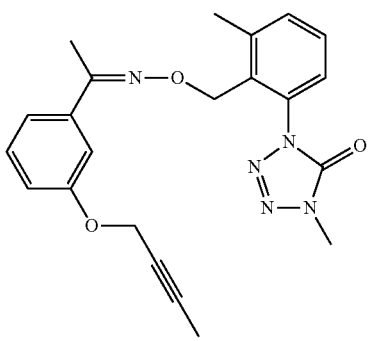 [SMILES: CC#CCOc1cccc(C(C)=NOCc2c(C)cccc2-n2nnn(C)c2=O)c1]

$^1$H-NMR (CDCl$_3$) δ(ppm): 7.36 (2H, d, J=4.4 Hz), 7.27-7.16 (4H, m), 6.95-6.93 (1H, m), 5.25 (2H, s), 4.68-4.65 (2H, m), 3.64 (3H, s), 2.55 (3H, s), 2.09 (3H, s), 1.87-1.85 (3H, m).

Production Example 88

A mixture of 0.28 g of C11A, 0.22 g of C72A, 0.18 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.16 g of 1-(3-methyl-2-{1-[3-(pentyn-2-yloxy)phenyl] ethylideneaminooxymethyl}phenyl)-4-methyl-1,4-dihydrotetrazol-5-one (hereinafter referred to as the present compound 88).

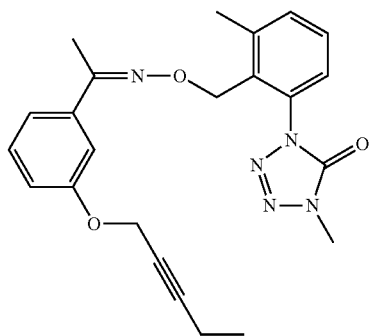 [SMILES: CCC#CCOc1cccc(C(C)=NOCc2c(C)cccc2-n2nnn(C)c2=O)c1]

$^1$H-NMR (CDCl$_3$) δ(ppm): 7.36 (2H, d, J=4.6 Hz), 7.26-7.16 (4H, m), 6.94 (1H, dd, J=7.9, 2.4 Hz), 5.25 (2H, s), 4.68 (2H, t, J=2.3 Hz), 3.63 (3H, s), 2.54 (3H, s), 2.23 (2H, tq, J=7.6, 2.3 Hz), 2.09 (3H, s), 1.13 (3H, t, J=7.6 Hz).

Production Example 89

A mixture of 0.31 g of C17A, 0.19 g of C55A, 0.18 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 1-{3-cyclopropyl-2-[1-(3-difluoromethylphenyl)ethylideneaminooxymethyl]phenyl}-4-methyl-1,4-dihydrotetrazol-5-one (hereinafter referred to as the present compound 89).

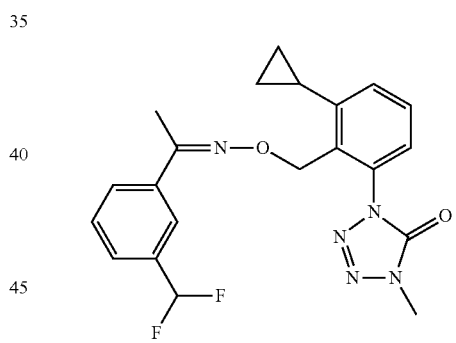

$^1$H-NMR (CDCl$_3$) δ(ppm): 7.75 (1H, s), 7.67 (1H, d, J=7.6 Hz), 7.49 (1H, d, J=7.6 Hz), 7.4 (1H, d, J=7.8 Hz), 7.39 (1H, t, J=7.7 Hz), 7.23 (2H, t, J=7.7 Hz), 6.67 (1H, t, J=56.3 Hz), 5.49 (2H, s), 3.63 (3H, s), 2.30-2.18 (1H, m), 2.12 (3H, s), 1.08-1.03 (2H, m), 0.80-0.76 (2H, m).

Production Example 90

A mixture of 0.31 g of C17A, 0.18 g of C40A, 0.18 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 1-[2-(1-benzo[1,3]dioxan-5-yl-ethylideneaminooxymethyl)-3-cyclopropylphenyl]-4-methyl-1,4-dihydrotetrazol-5-one (hereinafter referred to as the present compound 90).

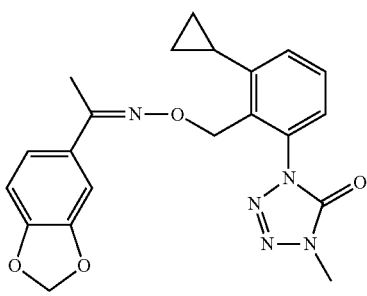 [SMILES: CC(=NOCc1c(C2CC2)cccc1-n1nnn(C)c1=O)c1ccc2c(c1)OCO2]

¹H-NMR (CDCl₃) δ(ppm): 7.38 (1H, t, J=7.8 Hz), 7.22 (2H, t, J=7.6 Hz), 7.14 (1H, s), 7.02 (1H, dd, J=8.1, 1.7 Hz), 6.76 (1H, d, J=8.2 Hz), 5.96 (2H, s), 5.45 (2H, s), 3.65 (3H, s), 2.27-2.20 (1H, m), 2.05 (3H, s), 1.07-1.02 (2H, m), 0.79-0.75 (2H, m).

Production Example 91

A mixture of 0.31 g of C17A, 0.22 g of C56A, 0.18 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 1-{3-cyclopropyl-2-[1-(2,2-difluorobenzo[1,3]dioxol-5-yl)ethylideneaminooxymethyl]phenyl}-4-methyl-1,4-dihydrotetrazol-5-one (hereinafter referred to as the present compound 91).

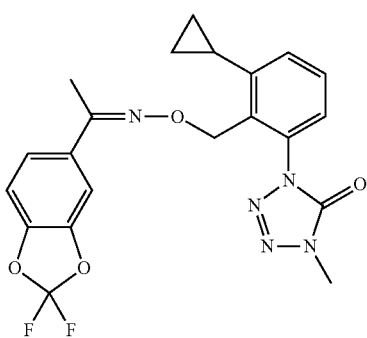 [SMILES: CC(=NOCc1c(C2CC2)cccc1-n1nnn(C)c1=O)c1ccc2c(c1)OC(F)(F)O2]

¹H-NMR (CDCl₃) δ(ppm): 7.41-7.37 (2H, m), 7.27-7.21 (3H, m), 7.00 (1H, d, J=8.5 Hz), 5.47 (2H, s), 3.66 (3H, s), 2.26-2.19 (1H, m), 2.08 (3H, s), 1.08-1.02 (2H, m), 0.80-0.76 (2H, m).

Production Example 92

A mixture of 0.31 g of C18A, 0.20 g of C42A, 0.18 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography and further subjected to gel permeation chromatography to obtain 0.26 g of 1-{3-methylthio-2-[1-(3-trifluoromethylphenyl)ethylideneaminooxymethyl]phenyl}-4-methyl-1,4-dihydrotetrazol-5-one (hereinafter referred to as the present compound 92).

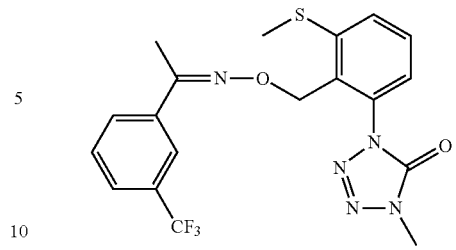

¹H-NMR (CDCl₃) δ(ppm): 7.85 (1H, s), 7.75 (1H, d, J=8.0 Hz), 7.58 (1H, d, J=7.8 Hz), 7.50-7.43 (3H, m), 7.20 (1H, dd, J=7.3, 1.8 Hz), 5.42 (2H, s), 3.64 (3H, s), 2.55 (3H, s), 2.13 (3H, s).

Production Example 93

A mixture of 0.35 g of C5A, 0.20 g of C42A, 0.18 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.30 g of 1-{3-bromo-2-[1-(3-trifluoromethylphenyl)ethylideneaminooxymethyl]phenyl}-4-methyl-1,4-dihydrotetrazol-5-one (hereinafter referred to as the present compound 93).

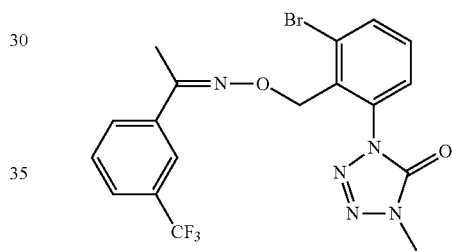

¹H-NMR (CDCl₃) δ(ppm): 7.82 (1H, s), 7.78 (1H, dd, J=6.8, 2.6 Hz), 7.74 (1H, d, J=8.0 Hz), 7.58 (1H, d, J=7.8 Hz), 7.45 (1H, t, J=7.9 Hz), 7.38-7.32 (2H, m), 5.47 (2H, s), 3.62 (3H, s), 2.11 (3H, s).

Production Example 94

A mixture of 0.16 g of C7A, 0.20 g of C42A, 0.18 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.11 g of 1-{3-iodo-2-[1-(3-trifluoromethylphenyl)ethylideneaminooxymethyl]phenyl}-4-methyl-1,4-dihydrotetrazol-5-one (hereinafter referred to as the present compound 94).

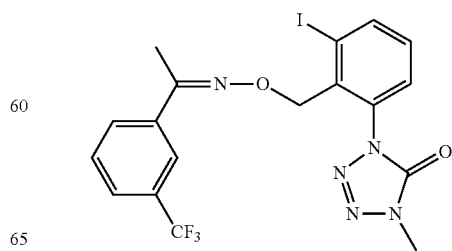

¹H-NMR (CDCl₃) δ(ppm): 8.06 (1H, d, J=8.0 Hz), 7.85 (1H, s), 7.75 (1H, d, J=8.0 Hz), 7.59 (1H, d, J=8.0 Hz), 7.45 (1H, t, J=7.8 Hz), 7.38 (1H, dd, J=7.9, 1.0 Hz), 7.17 (1H, t, J=7.9 Hz), 5.43 (2H, s), 3.63 (3H, s), 2.14 (3H, s).

Production Example 95

A mixture of 0.28 g of C11A, 0.19 g of C27A, 0.18 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.29 g of 1-{3-methyl-2-[1-(naphthalen-1-yl)ethylideneaminooxymethyl]-phenyl}-4-methyl-1,4-dihydrotetrazol-5-one (hereinafter referred to as the present compound 95).

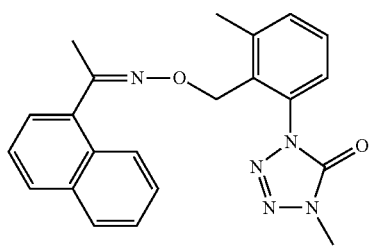 [SMILES: CC(=NOCc1c(C)cccc1-n1nnn(C)c1=O)c1cccc2ccccc12]

¹H-NMR (CDCl₃) δ(ppm): 7.92-7.89 (1H, m), 7.85-7.81 (2H, m), 7.48-7.37 (6H, m), 7.29-7.27 (1H, m), 5.32 (2H, s), 3.57 (3H, s), 2.56 (3H, s), 2.22 (3H, s).

Production Example 96

A mixture of 0.28 g of C11A, 0.15 g of C52A, 0.18 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.15 g of 1-{3-methyl-2-[1-(2-methylphenyl)ethylideneaminooxymethyl]phenyl}-4-methyl-1,4-dihydrotetrazol-5-one (hereinafter referred to as the present compound 96).

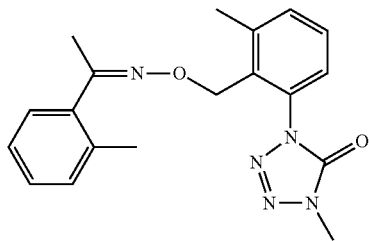 [SMILES: CC(=NOCc1c(C)cccc1-n1nnn(C)c1=O)c1ccccc1C]

¹H-NMR (CDCl₃) δ(ppm): 7.38-7.37 (2H, m), 7.25-7.19 (2H, m), 7.17-7.15 (3H, m), 5.24 (2H, s), 3.62 (3H, s), 2.53 (3H, s), 2.22 (3H, s), 2.04 (3H, s).

Production Example 97

A mixture of 0.42 g of C11A, 0.25 g of C54A, 0.28 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 1-{3-methyl-2-[1-(2-methoxyphenyl)ethylideneaminooxymethyl]phenyl}-4-methyl-1,4-dihydrotetrazol-5-one (hereinafter referred to as the present compound 97).

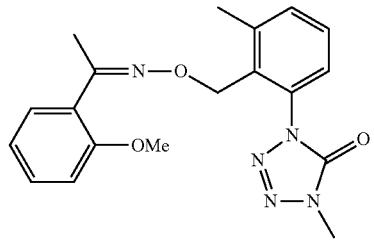 [SMILES: COc1ccccc1C(C)=NOCc1c(C)cccc1-n1nnn(C)c1=O]

¹H-NMR (CDCl₃) δ(ppm): 7.38-7.37 (2H, m), 7.31 (1H, td, J=7.8, 1.7 Hz), 7.25-7.21 (2H, m), 6.94-6.86 (2H, m), 5.23 (2H, s), 3.80 (3H, s), 3.65 (3H, s), 2.54 (3H, s), 2.06 (3H, s).

Production Example 98

A mixture of 0.42 g of C11A, 0.25 g of C53A, 0.28 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 1-{3-methyl-2-[1-(2-chlorophenyl)ethylideneaminooxymethyl]-phenyl}-4-methyl-1,4-dihydrotetrazol-5-one (hereinafter referred to as the present compound 98).

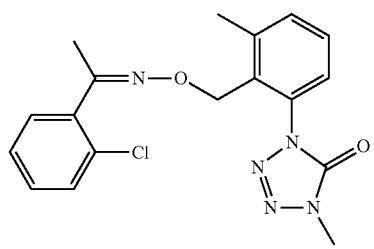 [SMILES: CC(=NOCc1c(C)cccc1-n1nnn(C)c1=O)c1ccccc1Cl]

¹H-NMR (CDCl₃) δ(ppm): 7.39-7.23 (7H, m), 5.25 (2H, s), 3.65 (3H, s), 2.54 (3H, s), 2.09 (3H, s).

Production Example 99

A mixture of 0.28 g of C11A, 0.24 g of C49A, 0.18 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.26 g of 1-{3-methyl-2-[1-(3-fluoro-5-trifluoromethylphenyl)propylideneaminooxymethyl]phenyl}-4-methyl-1,4-dihydrotetrazol-5-one (hereinafter referred to as the present compound 99).

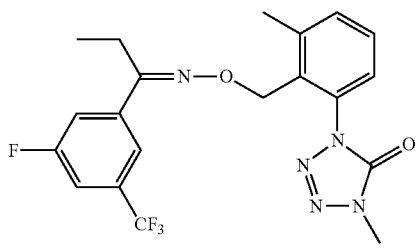 [SMILES: CCC(=NOCc1c(C)cccc1-n1nnn(C)c1=O)c1cc(F)cc(C(F)(F)F)c1]

¹H-NMR (CDCl₃) δ(ppm): 7.62 (1H, s), 7.47 (1H, dt, J=9.8, 1.8 Hz), 7.40-7.38 (2H, m), 7.29 (1H, d, J=8.2 Hz), 7.23 (1H, t, J=4.7 Hz), 5.25 (2H, s), 3.69 (3H, s), 2.62 (2H, q, J=7.6 Hz), 2.55 (3H, s), 1.04 (3H, t, J=7.6 Hz).

Production Example 100

A mixture of 0.46 g of C17A, 0.33 g of C39A, 0.28 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.45 g of 1-{3-cyclopropyl-2-[1-(3-trifluoromethylphenyl)propylideneaminooxymethyl]phenyl}-4-methyl-1,4-dihydrotetrazol-5-one (hereinafter referred to as the present compound 100).

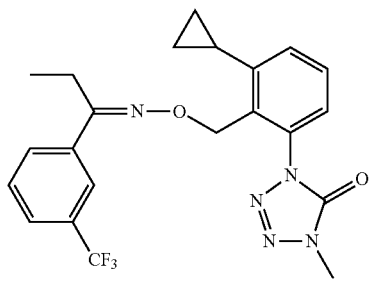 [SMILES: CCC(=NOCc1c(C2CC2)cccc1-n1nnn(C)c1=O)c1cccc(C(F)(F)F)c1]

¹H-NMR (CDCl₃) δ(ppm): 7.84 (1H, s), 7.74 (1H, d, J=7.8 Hz), 7.59 (1H, d, J=7.8 Hz), 7.46 (1H, t, J=7.8 Hz), 7.40 (1H, t, J=7.8 Hz), 7.22 (2H, m), 5.46 (2H, s), 3.65 (3H, s), 2.65 (2H, q, J=7.6 Hz), 2.30-2.21 (1H, m), 1.08-1.01 (5H, m), 0.80-0.76 (2H, m).

Production Example 101

A mixture of 0.44 g of C14A, 0.33 g of C39A, 0.28 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.48 g of 1-{3-ethyl-2-[1-(3-trifluoromethylphenyl)propylideneaminooxymethyl]phenyl}-4-methyl-1,4-dihydrotetrazol-5-one (hereinafter referred to as the present compound 101).

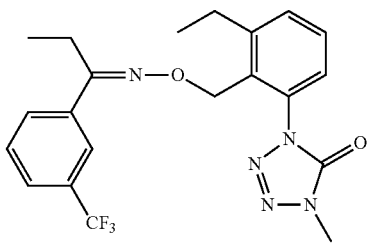 [SMILES: CCC(=NOCc1c(CC)cccc1-n1nnn(C)c1=O)c1cccc(C(F)(F)F)c1]

¹H-NMR (CDCl₃) δ(ppm): 7.84 (1H, s), 7.74 (1H, d, J=7.8 Hz), 7.59 (1H, d, J=7.8 Hz), 7.48 (1H, d, J=7.8 Hz), 7.45-7.41 (2H, m), 7.23 (1H, dd, J=6.1, 3.1 Hz), 5.27 (2H, s), 3.64 (3H, s), 2.91 (2H, q, J=7.6 Hz), 2.64 (2H, q, J=7.6 Hz), 1.31 (3H, t, J=7.6 Hz), 1.02 (3H, t, J=7.6 Hz).

Production Example 102

A mixture of 0.50 g of C9A, 0.33 g of C39A, 0.28 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.77 g of 1-methyl-4-{3-trifluoromethyl-2-[1-(3-trifluoromethylphenyl)propylideneaminooxymethyl]phenyl}-1,4-dihydrotetrazol-5-one (hereinafter referred to as the present compound 102).

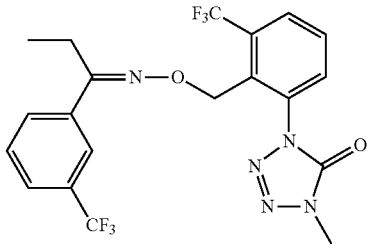 [SMILES: CCC(=NOCc1c(-n2nnn(C)c2=O)cccc1C(F)(F)F)c1cccc(C(F)(F)F)c1]

¹H-NMR (CDCl₃) δ(ppm): 7.90 (1H, dd, J=6.8, 2.4 Hz), 7.79 (1H, s), 7.71 (1H, d, J=7.8 Hz), 7.66-7.58 (3H, m), 7.46 (1H, t, J=7.8 Hz), 5.49 (2H, s), 3.58 (3H, s), 2.58 (2H, q, J=7.6 Hz), 0.99 (3H, t, J=7.7 Hz).

Production Example 103

A mixture of 0.30 g of C2A, 0.18 g of C41A, 0.18 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.22 g of 1-[3-chloro-2-(4-chloroindan-1-ylideneaminooxymethyl)phenyl]-4-methyl-1,4-dihydrotetrazol-5-one (hereinafter referred to as the present compound 103).

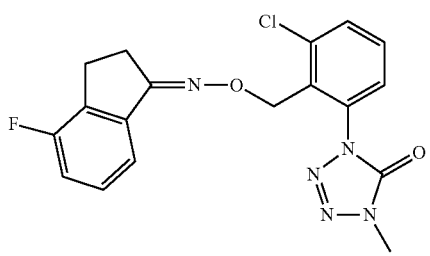 [SMILES: Cn1nnn(-c2cccc(Cl)c2CON=C2CCc3c(F)cccc32)c1=O]

¹H-NMR (CDCl₃) δ(ppm): 7.58 (1H, d, J=8.0 Hz), 7.48 (1H, d, J=7.6 Hz), 7.41 (1H, t, J=8.0 Hz), 7.30 (2H, dd, J=14.8, 7.9 Hz), 7.17 (1H, t, J=7.8 Hz), 5.40 (2H, s), 3.66 (3H, s), 2.97-2.94 (2H, m), 2.76-2.73 (2H, m).

Production Example 104

A mixture of 0.23 g of C2A, 0.14 g of C45A, 0.14 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.03 g of 1-{3-chloro-2-[1-(5,6,7,8-tetrahydronaphthalen-2-yl)ethylideneaminooxymethyl]phenyl}-4-methyl-1,4-dihydrotetrazol-5-one (hereinafter referred to as the present compound 104).

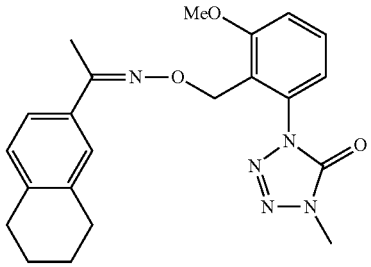

¹H-NMR (CDCl₃) δ(ppm): 7.42 (1H, t, J=8.2 Hz), 7.29-7.26 (2H, m), 7.06 (1H, d, J=8.5 Hz), 7.01 (2H, dt, J=8.1, 1.6 Hz), 5.38 (2H, s), 3.91 (3H, s), 3.56 (3H, s), 2.78-2.73 (4H, m), 2.02 (3H, s), 1.80-1.76 (4H, m).

Production Example 106

A mixture of 0.23 g of C17A, 0.14 g of C45A, 0.14 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.26 g of 1-{3-cyclopropyl-2-[1-(5,6,7,8-tetrahydronaphthalen-2-yl)ethylideneaminooxymethyl]phenyl}-4-methyl-1,4-dihydrotetrazol-5-one (hereinafter referred to as the present compound 106).

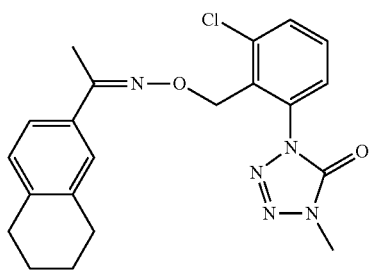

¹H-NMR (CDCl₃) δ(ppm): 7.57 (1H, dd, J=8.0, 1.1 Hz), 7.40 (1H, t, J=8.0 Hz), 7.32 (1H, dd, J=8.0, 1.1 Hz), 7.28-7.25 (2H, m), 7.01 (1H, d, J=8.0 Hz), 5.44 (2H, s), 3.59 (3H, s), 2.76-2.74 (4H, m), 2.04 (3H, s), 1.79-1.76 (4H, m).

Production Example 105

A mixture of 0.22 g of C8A, 0.14 g of C45A, 0.14 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.11 g of 1-{3-methoxy-2-[1-(5,6,7,8-tetrahydronaphthalen-2-yl)ethylideneaminooxymethyl]phenyl}-4-methyl-1,4-dihydrotetrazol-5-one (hereinafter referred to as the present compound 105).

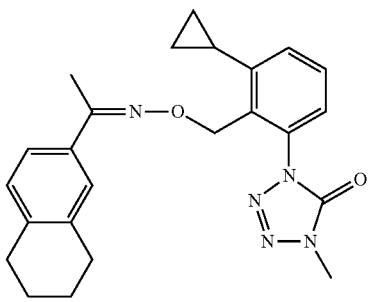

¹H-NMR (CDCl₃) δ(ppm): 7.37 (1H, t, J=7.9 Hz), 7.29-7.28 (2H, m), 7.23-7.19 (2H, m), 7.02 (1H, d, J=8.5 Hz), 5.46 (2H, s), 3.62 (3H, s), 2.78-2.73 (4H, m), 2.29-2.20 (1H, m), 2.07 (3H, s), 1.80-1.75 (4H, m), 1.06-1.01 (2H, m), 0.79-0.75 (2H, m).

Production Example 107

A mixture of 0.22 g of C14A, 0.14 g of C45A, 0.14 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 1-{3-ethyl-2-[1-(5,6,7,8-tetrahydronaphthalen-2-yl)ethylideneaminooxymethyl]phenyl}-4-methyl-1,4-dihydrotetrazol-5-one (hereinafter referred to as the present compound 107).

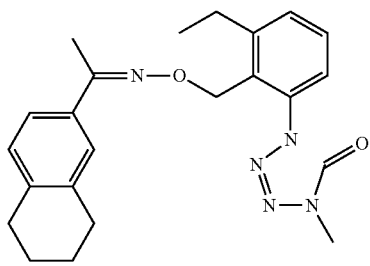

$^1$H-NMR (CDCl$_3$) δ(ppm): 7.41-7.40 (2H, m), 7.29-7.27 (2H, m), 7.23-7.21 (1H, m), 7.02 (1H, d, J=8.5 Hz), 5.26 (2H, s), 3.61 (3H, s), 2.89 (2H, q, J=7.6 Hz), 2.78-2.73 (4H, m), 2.06 (3H, s), 1.80-1.76 (4H, m), 1.29 (3H, t, J=7.6 Hz).

Production Example 108

A mixture of 0.26 g of C5A, 0.14 g of C45A, 0.14 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 1-{3-bromo-2-[1-(5,6,7,8-tetrahydronaphthalen-2-yl)ethylideneaminooxymethyl]phenyl}-4-methyl-1,4-dihydrotetrazol-5-one (hereinafter referred to as the present compound 108).

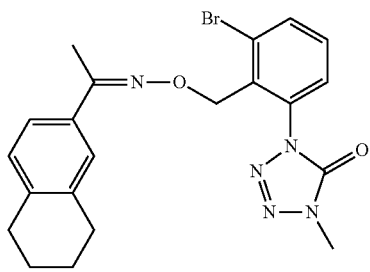 [SMILES: CC(=NOCc1c(Cl)cccc1-n1nnn(C)c1=O)c1ccc2c(c1)CCCC2]

$^1$H-NMR (CDCl$_3$) δ(ppm): 7.76 (1H, dd, J=7.6, 1.1 Hz), 7.37-7.27 (4H, m), 7.01 (1H, d, J=7.8 Hz), 5.44 (2H, s), 3.59 (3H, s), 2.78-2.73 (4H, m), 2.05 (3H, s), 1.79-1.76 (4H, m).

Production Example 109

A mixture of 0.28 g of C11A, 0.19 g of C73A, 0.27 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.20 g of 1-{2-[1-(3-dimethylaminophenyl)ethylideneaminooxymethyl]-3-methylphenyl}-4-methyl-1,4-dihydrotetrazol-5-one (hereinafter referred to as the present compound 109).

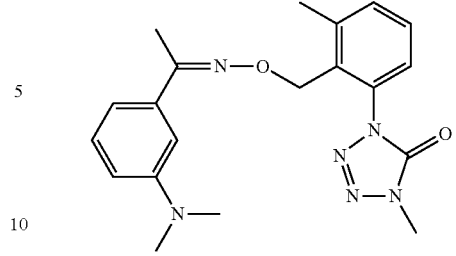

$^1$H-NMR (CDCl$_3$) δ(ppm): 7.37 (2H, d, J=4.8 Hz), 7.23-7.18 (2H, m), 6.96-6.95 (1H, m), 6.88 (1H, d, J=7.8 Hz), 6.73 (1H, dd, J=8.2, 2.8 Hz), 5.25 (2H, s), 3.63 (3H, s), 2.96 (6H, s), 2.55 (3H, s), 2.10 (3H, s).

Production Example 110

A mixture of 0.28 g of C11A, 0.18 g of C101A, 0.26 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.18 g of 1-[2-(1-indan-4-ylethylideneaminooxymethyl)-3-methylphenyl]-4-methyl-1,4-dihydrotetrazol-5-one (hereinafter referred to as the present compound 110).

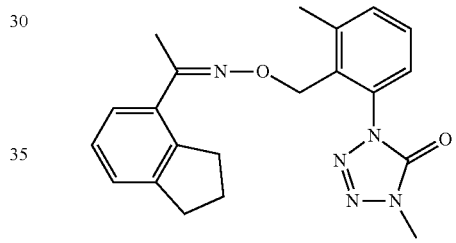

$^1$H-NMR (CDCl$_3$) δ(ppm): 7.37-7.36 (2H, m), 7.24-7.18 (2H, m), 7.13-7.12 (2H, m), 5.26 (2H, s), 3.61 (3H, s), 2.90-2.84 (4H, m), 2.53 (3H, s), 2.07 (3H, s), 2.01-1.94 (2H, m).

Production Example 111

A mixture of 0.35 g of C5A, 0.22 g of C39A, 0.26 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.35 g of 1-{3-bromo-2-[1-(3-trifluoromethylphenyl)propylideneaminooxymethyl]phenyl}-4-methyl-1,4-dihydrotetrazol-5-one (hereinafter referred to as the present compound 111).

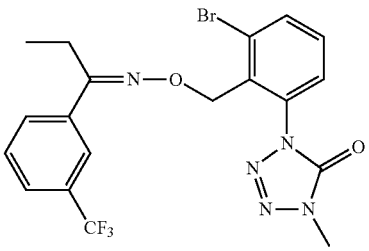 [SMILES: CCC(=NOCc1c(Br)cccc1-n1nnn(C)c1=O)c1cccc(C(F)(F)F)c1]

$^1$H-NMR (CDCl$_3$) δ(ppm): 7.82 (1H, s), 7.78 (1H, dd, J=6.9, 2.3 Hz), 7.73 (1H, d, J=7.8 Hz), 7.58 (1H, d, J=7.8 Hz), 7.46 (1H, t, J=7.8 Hz), 7.38-7.34 (2H, m), 5.43 (2H, s), 3.63 (3H, s), 2.64 (2H, q, J=7.6 Hz), 1.04 (3H, t, J=7.6 Hz).

Production Example 112

A mixture of 0.34 g of C9A, 0.17 g of C28A, 0.20 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.18 g of 1-{2-[1-(3-chlorophenyl)ethylideneaminooxymethyl]-3-trifluoromethylphenyl}-4-methyl-1,4-dihydrotetrazol-5-one (hereinafter referred to as the present compound 112).

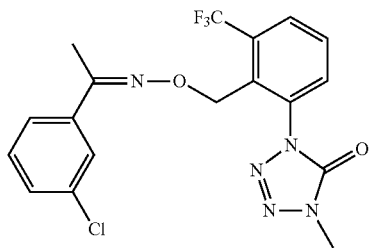 [SMILES: CC(=NOCc1c(-n2nnn(C)c2=O)cccc1C(F)(F)F)c1cccc(Cl)c1]

$^1$H-NMR (CDCl$_3$) δ(ppm): 7.90-7.88 (1H, m), 7.64-7.59 (2H, m), 7.53 (1H, t, J=1.8 Hz), 7.41 (1H, dt, J=7.6, 1.5 Hz), 7.31 (1H, dt, J=8.0, 1.7 Hz), 7.28-7.24 (1H, m), 5.51 (2H, s), 3.58 (3H, s), 2.02 (3H, s).

Production Example 113

A mixture of 0.34 g of C9A, 0.17 g of C21A, 0.20 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.18 g of 1-{2-[1-(3-methoxyphenyl)ethylideneaminooxymethyl]-3-trifluoromethylphenyl}-4-methyl-1,4-dihydrotetrazol-5-one (hereinafter referred to as the present compound 113).

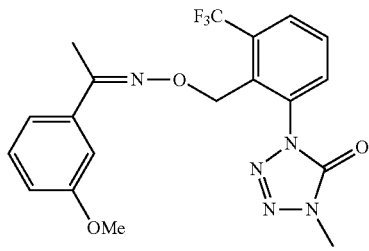 [SMILES: COc1cccc(C(C)=NOCc2c(-n3nnn(C)c3=O)cccc2C(F)(F)F)c1]

$^1$H-NMR (CDCl$_3$) δ(ppm): 7.88-7.87 (1H, m), 7.60-7.60 (2H, m), 7.23 (1H, d, J=7.6 Hz), 7.12-7.09 (2H, m), 6.89-6.87 (1H, m), 5.51 (2H, s), 3.81 (3H, s), 3.54 (3H, s), 2.03 (3H, s).

Production Example 114

A mixture of 0.34 g of C9A, 0.22 g of C34A, 0.20 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.25 g of 1-{2-[1-(3-trifluoromethoxyphenyl)ethylideneaminooxymethyl]-3-trifluoromethylphenyl}-4-methyl-1,4-dihydrotetrazol-5-one (hereinafter referred to as the present compound 114).

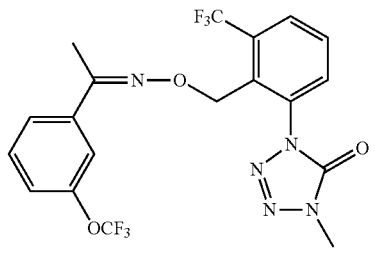

$^1$H-NMR (CDCl$_3$) δ(ppm): 7.89 (1H, dd, J=6.1, 3.3 Hz), 7.64-7.59 (2H, m), 7.46 (1H, d, J=8.0 Hz), 7.41 (1H, s), 7.35 (1H, t, J=8.0 Hz), 7.19 (1H, d, J=8.0 Hz), 5.51 (2H, s), 3.57 (3H, s), 2.03 (3H, s).

Production Example 115

A mixture of 0.34 g of C9A, 0.18 g of C30A, 0.20 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.18 g of 1-[2-(1-indan-5-ylethylideneaminooxymethyl)-3-trifluoromethylphenyl]-4-methyl-1,4-dihydrotetrazol-5-one (hereinafter referred to as the present compound 115).

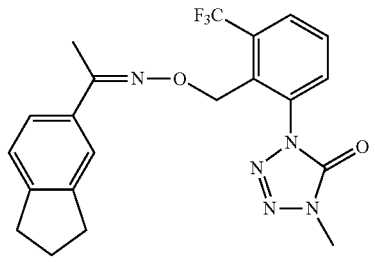 [SMILES: CC(=NOCc1c(-n2nnn(C)c2=O)cccc1C(F)(F)F)c1ccc2c(c1)CCC2]

$^1$H-NMR (CDCl$_3$) δ(ppm): 7.87 (1H, t, J=4.6 Hz), 7.61-7.59 (2H, m), 7.41 (1H, s), 7.30 (1H, d, J=7.7 Hz), 7.17 (1H, d, J=8.0 Hz), 5.49 (2H, s), 3.53 (3H, s), 2.91-2.86 (4H, m), 2.10-2.04 (2H, m), 2.02 (3H, s).

Production Example 116

A mixture of 0.34 g of C9A, 0.19 g of C45A, 0.20 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.14 g of 1-{2-[1-(5,6,7,8-tetrahydronaphthalen-2-yl)ethylideneaminooxymethyl]-3-trifluoromethylphenyl}-4-methyl-1,4-dihydrotetrazol-5-one (hereinafter referred to as the present compound 116).

241

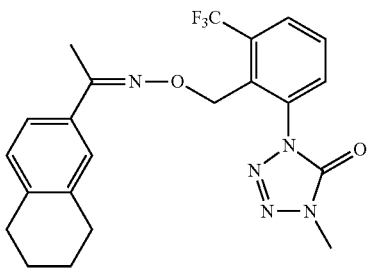 [SMILES: CC(=NOCc1c(-n2nnn(C)c2=O)cccc1C(F)(F)F)c1ccc2c(c1)CCCC2]

¹H-NMR (CDCl₃) δ(ppm): 7.87 (1H, t, J=4.7 Hz), 7.59 (2H, d, J=4.4 Hz), 7.27-7.24 (2H, m), 7.01 (1H, d, J=7.8 Hz), 5.48 (2H, s), 3.54 (3H, s), 2.77-2.73 (4H, m), 2.01 (3H, s), 1.79-1.76 (4H, m).

Production Example 117

A mixture of 0.19 g of C9A, 0.19 g of C26A, 0.20 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.21 g of 1-{2-(1-naphthalen-2-ylethylideneaminooxymethyl)-3-trifluoromethyl phenyl]-4-methyl-1,4-dihydrotetrazol-5-one (hereinafter referred to as the present compound 117).

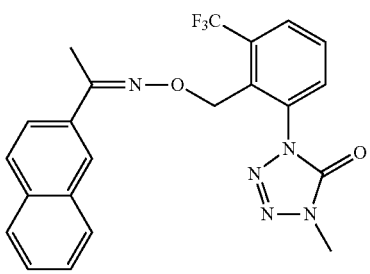

¹H-NMR (CDCl₃) δ(ppm): 7.92 (1H, s), 7.89 (1H, t, J=4.7 Hz), 7.85-7.78 (4H, m), 7.62-7.61 (2H, m), 7.50-7.46 (2H, m), 5.56 (2H, s), 3.49 (3H, s), 2.16 (3H, s).

Production Example 118

A mixture of 0.28 g of C11A, 0.23 g of C102A, 0.20 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.23 g of 1-{2-[1-(3-trifluoromethoxyphenyl)propylideneaminooxymethyl]-3-methylphenyl}-4-methyl-1,4-dihydrotetrazol-5-one (hereinafter referred to as the present compound 118).

242

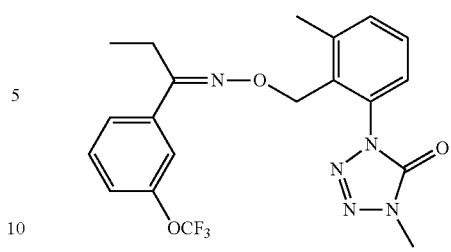

¹H-NMR (CDCl₃) δ(ppm): 7.49 (1H, d, J=7.8 Hz), 7.45 (1H, s), 7.39-7.34 (3H, m), 7.25-7.17 (2H, m), 5.24 (2H, s), 3.66 (3H, s), 2.62 (2H, q, J=7.6 Hz), 2.55 (3H, s), 1.03 (3H, t, J=7.6 Hz).

Production Example 119

A mixture of 0.30 g of C14A, 0.23 g of C102A, 0.20 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.16 of 1-{3-ethyl-2-[1-(3-trifluoromethoxyphenyl)propylideneaminooxymethyl]phenyl}-4-methyl-1,4-dihydrotetrazol-5-one (hereinafter referred to as the present compound 119).

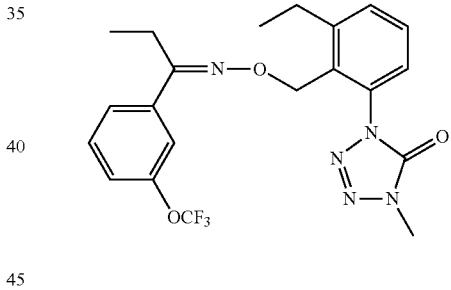

¹H-NMR (CDCl₃) δ(ppm): 7.49 (1H, d, J=8.0 Hz), 7.46-7.41 (3H, m), 7.37 (1H, t, J=7.9 Hz), 7.23 (1H, dd, J=6.3, 2.9 Hz), 7.19 (1H, d, J=8.2 Hz), 5.27 (2H, s), 3.64 (3H, s), 2.91 (2H, q, J=7.6 Hz), 2.61 (2H, q, J=7.6 Hz), 1.30 (3H, t, J=7.6 Hz), 1.02 (3H, t, J=7.6 Hz).

Production Example 120

A mixture of 0.31 g of C17A, 0.23 g of C102A, 0.20 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.18 g of 1-{3-cyclopropyl-2-[1-(3-trifluoromethoxyphenyl)propylideneaminooxymethyl]phenyl}-4-methyl-1,4-dihydrotetrazol-5-one (hereinafter referred to as the present compound 120).

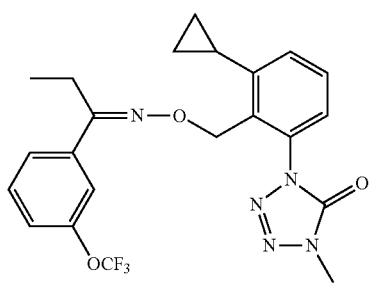 [SMILES: CCC(=NOCc1c(C2CC2)cccc1-n1nnn(C)c1=O)c1cccc(OC(F)(F)F)c1]

¹H-NMR (CDCl₃) δ(ppm): 7.49 (1H, d, J=7.8 Hz), 7.45 (1H, s), 7.42-7.34 (2H, m), 7.23-7.18 (3H, m), 5.46 (2H, s), 3.65 (3H, s), 2.61 (2H, q, J=7.6 Hz), 2.28-2.21 (1H, m), 1.07-1.01 (5H, m), 0.80-0.76 (2H, m).

Production Example 121

A mixture of 0.35 g of C5A, 0.23 g of C102A, 0.20 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.18 g of 1-{3-bromo-2-[1-(3-trifluoromethoxyphenyl)propylideneaminooxymethyl]phenyl}-4-methyl-1,4-dihydrotetrazol-5-one (hereinafter referred to as the present compound 121).

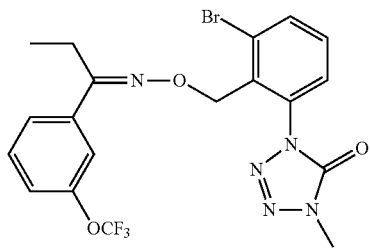 [SMILES: CCC(=NOCc1c(Br)cccc1-n1nnn(C)c1=O)c1cccc(OC(F)(F)F)c1]

¹H-NMR (CDCl₃) δ(ppm): 7.78 (1H, dd, J=6.8, 2.4 Hz), 7.48 (1H, d, J=7.8 Hz), 7.43 (1H, s), 7.38-7.34 (3H, m), 7.19 (1H, d, J=8.2 Hz), 5.43 (2H, s), 3.63 (3H, s), 2.60 (2H, q, J=7.6 Hz), 1.03 (3H, t, J=7.6 Hz).

Production Example 122

A mixture of 0.28 g of C11A, 0.18 g of C103A, 0.26 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.20 g of 1-{3-methyl-2-[1-(3-methylsulfanylphenyl)ethylideneaminooxymethyl]phenyl}-4-methyl-1,4-dihydrotetrazol-5-one (hereinafter referred to as the present compound 122)

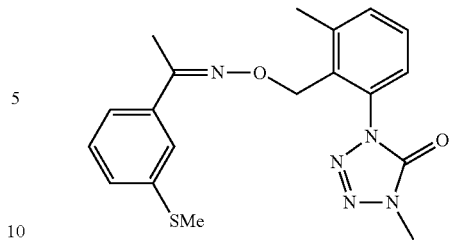

¹H-NMR (CDCl₃) δ(ppm): 7.47 (1H, t, J=1.6 Hz), 7.38-7.37 (2H, m), 7.32 (1H, dt, J=7.3, 1.77 Hz), 7.27-7.21 (3H, m), 5.25 (2H, s), 3.65 (3H, s), 2.55 (3H, s), 2.50 (3H, s), 2.09 (3H, s).

Production Example 123

A mixture of 0.28 g of C11A, 0.24 g of C104A, 0.26 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.30 g of 1-{2-[1-(4-cyclopropyl-3-trifluoromethylphenyl)ethylideneaminooxymethyl]-3-methylphenyl}-4-methyl-1,4-dihydrotetrazol-5-one (hereinafter referred to as the present compound 123).

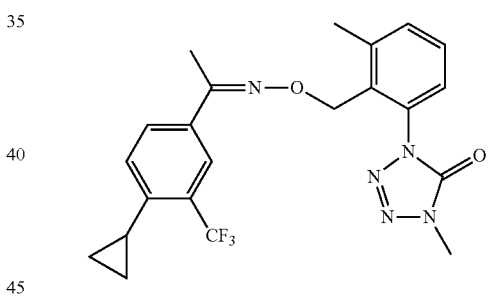

¹H-NMR (CDCl₃) δ(ppm): 7.81 (1H, s), 7.62 (1H, d, J=8.2 Hz), 7.39-7.36 (2H, m), 7.24-7.21 (1H, m), 6.97 (1H, d, J=8.2 Hz), 5.25 (2H, s), 3.66 (3H, s), 2.55 (3H, s), 2.23-2.16 (1H, m), 2.09 (3H, s), 1.07-1.02 (2H, m), 0.79-0.75 (2H, m).

Production Example 124

A mixture of 0.28 g of C14A, 0.18 g of C101A, 0.26 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.21 g of 1-[3-ethyl-2-(1-indan-4-ylethylideneaminooxymethyl)phenyl]-4-methyl-1,4-dihydrotetrazol-5-one (hereinafter referred to as the present compound 124).

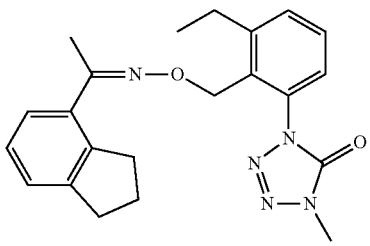

¹H-NMR (CDCl₃) δ(ppm): 7.44-7.39 (2H, m), 7.24 (1H, dd, J=6.3, 2.9 Hz), 7.21-7.18 (1H, m), 7.14 (2H, dd, J=8.1, 4.2 Hz), 5.28 (2H, s), 3.59 (3H, s), 2.92-2.86 (6H, m), 2.06 (3H, s), 1.99 (2H, sext, J=7.3 Hz), 1.28 (3H, t, J=7.6 Hz).

Production Example 125

A mixture of 0.30 g of C17A, 0.18 g of C101A, 0.26 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.18 g of 1-[3-cyclopropyl-2-(1-indan-4-ylethylideneaminooxymethyl)phenyl]-4-methyl-1,4-dihydrotetrazol-5-one (hereinafter referred to as the present compound 125).

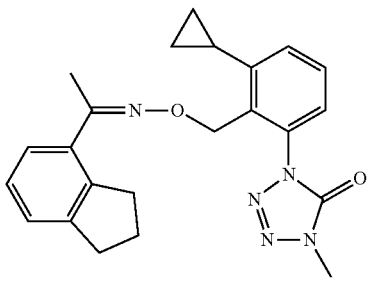 [SMILES: CC(=NOCc1c(C2CC2)cccc1-n1nnn(C)c1=O)c1cccc2c1CCC2]

¹H-NMR (CDCl₃) δ(ppm): 7.38 (1H, t, J=7.8 Hz), 7.25-7.17 (3H, m), 7.15-7.13 (2H, m), 5.49 (2H, s), 3.60 (3H, s), 2.90-2.85 (4H, m), 2.25-2.18 (1H, m), 2.07 (3H, s), 1.98 (2H, sext, J=7.3 Hz), 1.05-1.00 (2H, m), 0.79-0.75 (2H, m).

Production Example 126

A mixture of 0.28 g of C11A, 0.20 g of C105A, 0.26 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.25 g of 1-{3-methyl-2-[1-(5,6,7,8-tetrahydronaphthalen-1-yl)propylideneaminooxymethyl]phenyl}-4-methyl-1,4-dihydrotetrazol-5-one (hereinafter referred to as the present compound 126).

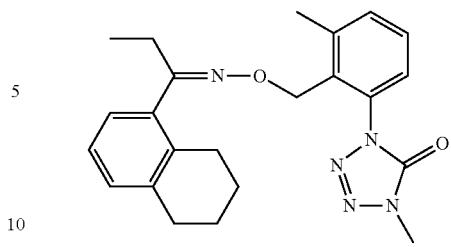

¹H-NMR (CDCl₃) δ(ppm): 7.40-7.35 (2H, m), 7.25-7.22 (1H, m), 7.10-7.03 (2H, m), 6.91 (1H, dd, J=7.2, 1.5 Hz), 5.18 (2H, s), 3.6 (3H, s), 2.77 (2H, t, J=6.1 Hz), 2.53 (3H, s), 2.57-2.48 (4H, m), 1.79-1.68 (4H, m), 0.89 (3H, t, J=7.6 Hz).

Production Example 127

A mixture of 0.28 g of C11A, 0.19 g of C106A, 0.26 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.25 g of 1-{3-methyl-2-[1-(5,6,7,8-tetrahydronaphthalen-1-yl)ethylideneaminooxymethyl]phenyl}-4-methyl-1,4-dihydrotetrazol-5-one (hereinafter referred to as the present compound 127).

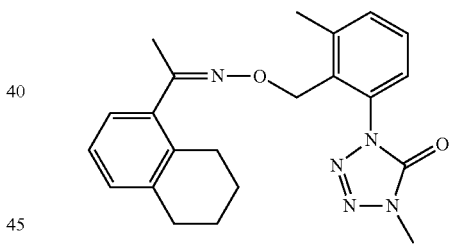

¹H-NMR (CDCl₃) δ(ppm): 7.37-7.36 (2H, m), 7.25-7.22 (1H, m), 7.09-7.02 (2H, m), 6.94 (1H, dd, J=7.1, 1.6 Hz), 5.22 (2H, s), 3.63 (3H, s), 2.77 (2H, t, J=6.2 Hz), 2.56 (2H, t, J=6.1 Hz), 2.53 (3H, s), 2.01 (3H, s), 1.78-1.67 (4H, m).

Production Example 128

A mixture of 0.31 g of C17A, 0.19 g of C106A, 0.27 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.23 g of 1-{3-cyclopropyl-2-[1-(5,6,7,8-tetrahydronaphthalen-1-yl)ethylideneaminooxymethyl]phenyl}-4-methyl-1,4-dihydrotetrazol-5-one (hereinafter referred to as the present compound 128).

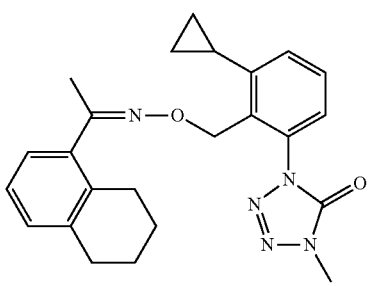 [SMILES: CC(=NOCc1c(C2CC2)cccc1-n1nnn(C)c1=O)c1cccc2c1CCCC2]

¹H-NMR (CDCl₃) δ(ppm): 7.38 (1H, t, J=7.8 Hz), 7.23 (2H, dd, J=7.8, 2.7 Hz), 7.09-7.02 (2H, m), 6.94 (1H, dd, J=7.2, 1.0 Hz), 5.45 (2H, s), 3.61 (3H, s), 2.77 (2H, t, J=6.1 Hz), 2.57 (2H, t, J=6.1 Hz), 2.25-2.18 (1H, m), 2.00 (3H, s), 1.78-1.67 (4H, m), 1.04-0.99 (2H, m), 0.78-0.74 (2H, m).

Production Example 129

A mixture of 0.30 g of C14A, 0.19 g of C106A, 0.26 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.36 g of 1-{3-ethyl-2-[1-(5,6,7,8-tetrahydronaphthalen-1-yl)ethylideneaminooxymethyl]phenyl}-4-methyl-1,4-dihydrotetrazol-5-one (hereinafter referred to as the present compound 129).

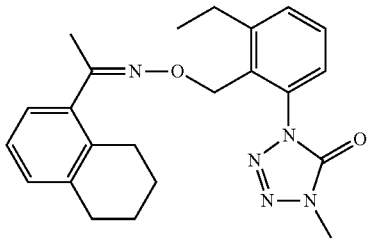 [SMILES: CCc1cccc(-n2nnn(C)c2=O)c1CON=C(C)c1cccc2c1CCCC2]

¹H-NMR (CDCl₃) δ(ppm): 7.45-7.40 (2H, m), 7.24 (1H, dd, J=6.8, 2.4 Hz), 7.10-7.03 (2H, m), 6.95 (1H, dd, J=7.1, 1.1 Hz), 5.24 (2H, s), 3.61 (3H, s), 2.88 (2H, q, J=7.6 Hz), 2.78 (2H, t, J=6.1 Hz), 2.58 (2H, t, J=6.1 Hz), 2.00 (3H, s), 1.79-1.68 (4H, m), 1.28 (3H, t, J=7.6 Hz).

Production Example 130

A mixture of 0.30 g of C8A, 0.19 g of C106A, 0.26 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.28 g of 1-{3-methoxy-2-[1-(5,6,7,8-tetrahydronaphthalen-1-yl)ethylideneaminooxymethyl]phenyl}-4-methyl-1,4-dihydrotetrazol-5-one (hereinafter referred to as the present compound 130).

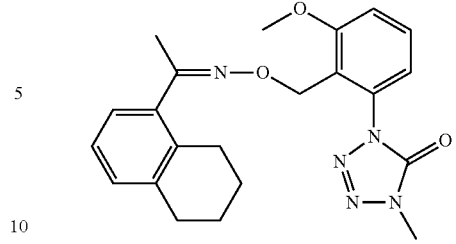

¹H-NMR (CDCl₃) δ(ppm): 7.43 (1H, t, J=8.2 Hz), 7.08-7.01 (4H, m), 6.92 (1H, dd, J=7.1, 1.4 Hz), 5.38 (2H, s), 3.89 (3H, s), 3.55 (3H, s), 2.76 (2H, t, J=6.1 Hz), 2.54 (2H, t, J=6.1 Hz), 1.94 (3H, s), 1.77-1.66 (4H, m).

Production Example 131

A mixture of 0.28 g of C11A, 0.16 g of C107A, 0.26 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.24 g of 1-{2-[1-(2,3-dimethylphenyl)ethylideneaminooxymethyl]-3-methylphen yl}-4-methyl-1,4-dihydrotetrazol-5-one (hereinafter referred to as the present compound 131).

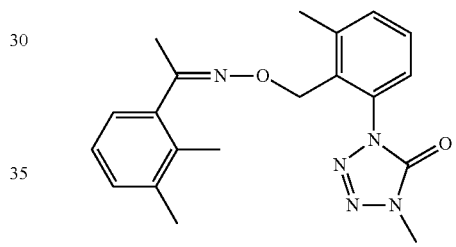

¹H-NMR (CDCl₃) δ(ppm): 7.40-7.36 (2H, m), 7.24 (1H, dd, J=6.0, 3.4 Hz), 7.13-7.05 (2H, m), 6.98 (1H, dd, J=7.4, 1.0 Hz), 5.23 (2H, s), 3.63 (3H, s), 2.53 (3H, s), 2.26 (3H, s), 2.10 (3H, s), 2.03 (3H, s).

Production Example 132

A mixture of 0.30 g of C8A, 0.18 g of C101A, 0.26 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.19 g of 1-[2-(1-indan-4-ylethylideneaminooxymethyl)-3-methoxyphenyl]-4-methyl-1,4-dihydrotetrazol-5-one (hereinafter referred to as the present compound 132).

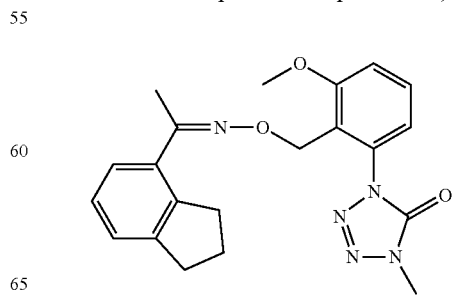

¹H-NMR (CDCl₃) δ(ppm): 7.42 (1H, t, J=8.2 Hz), 7.19-7.15 (1H, m), 7.14-7.10 (2H, m), 7.06 (1H, d, J=8.2 Hz), 7.02 (1H, d, J=8.0 Hz), 5.41 (2H, s), 3.90 (3H, s), 3.53 (3H, s), 2.89-2.82 (4H, m), 2.01 (3H, s), 1.98-1.93 (2H, m).

Production Example 133

A mixture of 0.28 g of C11A, 0.18 g of C108A, 0.26 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.18 g of 1-{2-[1-(3-chloro-2-methylphenyl)ethylideneaminooxymethyl]-3-methylphenyl}-4-methyl-1,4-dihydrotetrazol-5-one (hereinafter referred to as the present compound 133).

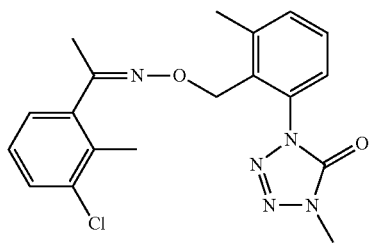

¹H-NMR (CDCl₃) δ(ppm): 7.41-7.36 (2H, m), 7.33 (1H, dd, J=7.8, 1.4 Hz), 7.24 (1H, dd, J=6.0, 3.2 Hz), 7.11 (1H, t, J=7.8 Hz), 7.04 (1H, dd, J=7.7, 1.3 Hz), 5.23 (2H, s), 3.63 (3H, s), 2.53 (3H, s), 2.23 (3H, s), 2.02 (3H, s).

Production Example 134

A mixture of 0.28 g of C11A, 0.22 g of C109A, 0.26 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.31 g of 1-{2-[1-(2,2-difluorobenzo[1,3]dioxan-4-yl)ethylideneaminooxymethyl]-3-methylphenyl}-4-methyl-1,4-dihydrotetrazol-5-one (hereinafter referred to as the present compound 134).

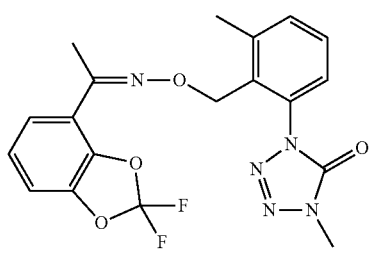 [SMILES: CC(=NOCc1c(C)cccc1-n1nnn(C)c1=O)c1cccc2c1OC(F)(F)O2]

¹H-NMR (CDCl₃) δ(ppm): 7.39 (2H, d, J=5.3 Hz), 7.27-7.20 (2H, m), 7.06-7.00 (2H, m), 5.27 (2H, s), 3.69 (3H, s), 2.56 (3H, s), 2.15 (3H, s).

Production Example 135

A mixture of 0.30 g of C8A, 0.22 g of C109A, 0.26 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.37 g of 1-{2-[1-(2,2-difluorobenzo[1,3]dioxan-4-yl)ethylideneaminooxymethyl]-3-methoxyphenyl}-4-methyl-1,4-dihydrotetrazol-5-one (hereinafter referred to as the present compound 135).

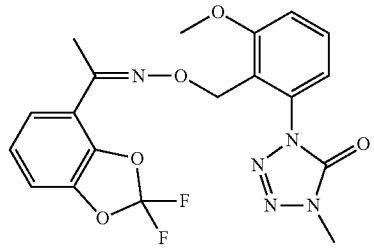 [SMILES: COc1cccc(-n2nnn(C)c2=O)c1CON=C(C)c1cccc2c1OC(F)(F)O2]

¹H-NMR (CDCl₃) δ(ppm): 7.45 (1H, t, J=8.24 Hz), 7.24 (1H, dd, J=7.4, 4.5 Hz), 7.08 (1H, d, J=8.0 Hz), 7.05-7.00 (3H, m), 5.40 (2H, s), 3.93 (3H, s), 3.63 (3H, s), 2.10 (3H, s).

Production Example 136

A mixture of 0.28 g of C11A, 0.21 g of C110A, 0.26 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.25 g of 1-{2-[1-(7-methoxyindan-4-yl)ethylideneaminooxymethyl]-3-methylphenyl}-4-methyl-1,4-dihydrotetrazol-5-one (hereinafter referred to as the present compound 136).

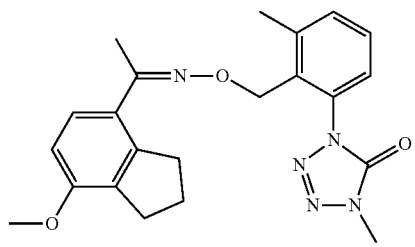 [SMILES: COc1ccc(C(C)=NOCc2c(C)cccc2-n2nnn(C)c2=O)c2c1CCC2]

¹H-NMR (CDCl₃) δ(ppm): 7.37-7.35 (2H, m), 7.25-7.20 (1H, m), 7.15 (1H, d, J=8.5 Hz), 6.66 (1H, d, J=8.5 Hz), 5.24 (2H, s), 3.82 (3H, s), 3.63 (3H, s), 2.88 (2H, t, J=7.4 Hz), 2.82 (2H, t, J=7.4 Hz), 2.53 (3H, s), 2.06 (3H, s), 2.02-1.94 (2H, m).

Production Example 137

A mixture of 0.30 g of C14A, 0.21 g of C110A, 0.26 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.13 g of 1-{3-ethyl-2-[1-(7-methoxyindan-4-yl)ethylideneaminooxymethyl]phen yl}-4-methyl-1,4-dihydrotetrazol-5-one (hereinafter referred to as the present compound 137).

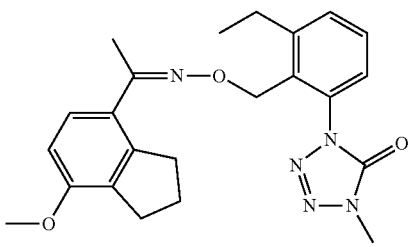 [SMILES: CCc1cccc(-n2nnn(C)c2=O)c1CON=C(C)c1ccc(OC)c2c1CCC2]

¹H-NMR (CDCl₃) δ(ppm): 7.41-7.39 (2H, m), 7.23 (1H, dd, J=6.1, 3.1 Hz), 7.15 (1H, d, J=8.2 Hz), 6.66 (1H, d, J=8.5 Hz), 5.26 (2H, s), 3.82 (3H, s), 3.60 (3H, s), 2.92-2.81 (6H, m), 2.04 (3H, s), 2.03-1.95 (2H, m), 1.32-1.24 (3H, t, J=7.5 Hz).

Production Example 138

A mixture of 0.31 g of C17A, 0.21 g of C110A, 0.26 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.24 g of 1-{3-cyclopropyl-2-[1-(7-methoxyindan-4-yl)ethylideneaminooxymethyl]phenyl}-4-methyl-1,4-dihydrotetrazol-5-one (hereinafter referred to as the present compound 138).

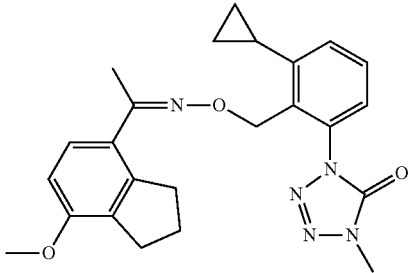 [SMILES: COc1ccc(C(C)=NOCc2c(C3CC3)cccc2-n2nnn(C)c2=O)c2c1CCC2]

¹H-NMR (CDCl₃) δ(ppm): 7.37 (1H, t, J=7.9 Hz), 7.22 (2H, dd, J=7.7, 1.9 Hz), 7.15 (1H, d, J=8.5 Hz), 6.65 (1H, d, J=8.5 Hz), 5.47 (2H, s), 3.82 (3H, s), 3.60 (3H, s), 2.89 (2H, t, J=7.5 Hz), 2.82 (2H, t, J=7.5 Hz), 2.25-2.18 (1H, m), 2.05 (3H, s), 2.02-1.94 (2H, m), 1.04-0.99 (2H, m), 0.78-0.74 (2H, m).

Production Example 139

A mixture of 0.28 g of C11A, 0.23 g of C111A, 0.26 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.38 g of 1-{2-[1-(4-methoxy-3-trifluoromethylphenyl)ethylideneaminooxymethy l]-3-methylphenyl}-4-methyl-1,4-dihydrotetrazol-5-one (hereinafter referred to as the present compound 139).

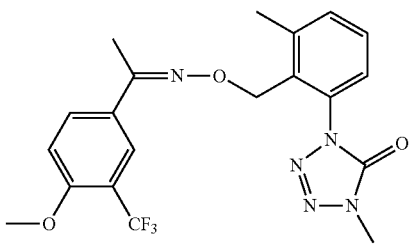 [SMILES: COc1ccc(C(C)=NOCc2c(C)cccc2-n2nnn(C)c2=O)cc1C(F)(F)F]

¹H-NMR (CDCl₃) δ(ppm): 7.80 (1H, d, J=2.1 Hz), 7.72 (1H, dd, J=8.7, 2.1 Hz), 7.38 (2H, d, J=5.3 Hz), 7.24-7.20 (1H, m), 6.96 (1H, d, J 25=8.7 Hz), 5.24 (2H, s), 3.91 (3H, s), 3.67 (3H, s), 2.55 (3H, s), 2.09 (3H, s).

Production Example 140

A mixture of 0.30 g of C14A, 0.23 g of C111A, 0.26 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.39 g of 1-{3-ethyl-2-[1-(4-methoxy-3-trifluoromethylphenyl)ethylideneaminooxymethyl]phenyl}-4-methyl-1,4-dihydrotetrazol-5-one (hereinafter referred to as the present compound 140).

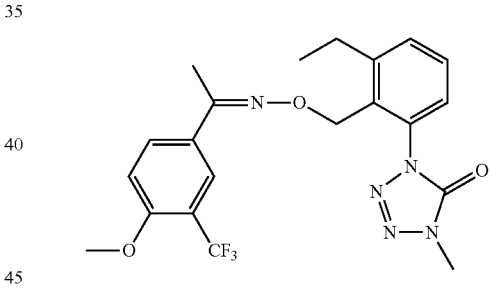

¹H-NMR (CDCl₃) δ(ppm): 7.80 (1H, s), 7.71 (1H, dd, J=8.6, 1.7 Hz), 7.43-7.41 (2H, m), 7.22 (1H, dd, J=6.0, 3.2 Hz), 6.96 (1H, d, J=8.9 Hz), 5.27 (2H, s), 3.92 (3H, s), 3.65 (3H, s), 2.90 (2H, q, J=7.6 Hz), 2.08 (3H, s), 1.30 (3H, t, J=7.6 Hz).

Production Example 141

A mixture of 0.28 g of C17A, 0.19 g of C111A, 0.26 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.40 g of 1-{3-cyclopropyl-2-[1-(4-methoxy-3-trifluoromethylphenyl)ethylideneaminooxymethyl]phenyl}-4-methyl-1,4-dihydrotetrazol-5-one (hereinafter referred to as the present compound 141).

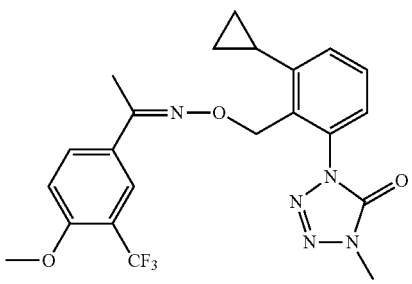 [SMILES: COc1ccc(C(C)=NOCc2c(C3CC3)cccc2-n2nnn(C)c2=O)cc1C(F)(F)F]

<sup>1</sup>H-NMR (CDCl₃) (ppm): 7.80 (1H, d, J=2.1 Hz), 7.71 (1H, dd, J=8.7, 2.3 Hz), 7.39 (1H, t, J=7.9 Hz), 7.24-7.20 (2H, m), 6.96 (1H, d, J=8.7 Hz), 5.47 (2H, s), 3.91 (3H, s), 3.65 (3H, s), 2.28-2.21 (1H, m), 2.08 (3H, s), 1.08-1.03 (2H, m), 0.80-0.76 (2H, m).

Production Example 142

A mixture of 0.30 g of C2A, 0.17 g of C101A, 0.26 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.28 g of 1-[3-chloro-2-(1-indan-4-ylethylideneaminooxymethyl)phenyl]-4-meth yl-1,4-dihydrotetrazol-5-one (hereinafter referred to as the present compound 142).

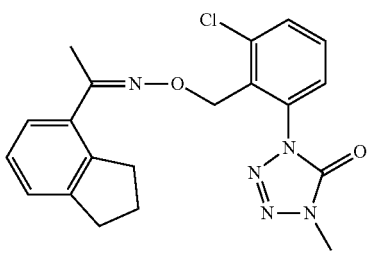 [SMILES: CC(=NOCc1c(Cl)cccc1-n1nnn(C)c1=O)c1cccc2c1CCC2]

$^1$H-NMR (CDCl₃) δ(ppm): 7.59-7.56 (1H, m), 7.41 (1H, t, J=7.9 Hz), 7.35-7.32 (1H, m), 7.19-7.17 (1H, m), 7.12-7.11 (2H, m), 5.48 (2H, s), 3.56 (3H, s), 2.87 (2H, t, J=7.5 Hz), 2.82 (2H, t, J=7.5 Hz), 2.03 (3H, s), 2.00-1.92 (2H, m).

Production Example 143

A mixture of 0.28 g of C11A, 0.21 g of C112A, 0.26 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.25 g of 1-{3-methyl-2-[1-(2-methy 3-difluoromethylphenyl)ethylideneaminooxymethyl]phenyl}-4-methyl-1,4-dihydrotetrazol-5-one (hereinafter referred to as the present compound 143).

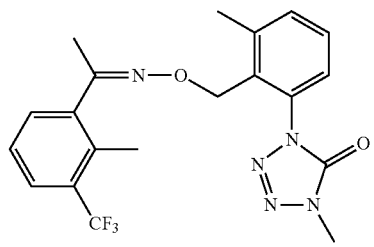

$^1$H-NMR (CDCl₃) δ(ppm): 7.60 (1H, d, J=7.3 Hz), 7.41-7.37 (2H, m), 7.31-7.23 (3H, m), 5.25 (2H, s), 3.62 (3H, s), 2.53 (3H, s), 2.30 (3H, d, J=1.6 Hz), 2.03 (3H, s).

Production Example 144

A mixture of 0.28 g of C11A, 0.19 g of C113A, 0.26 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.20 g of 1-{2-[1-(3-cyclopropyl-2-methylphenyl)ethylideneaminooxymethyl]-3-methylphenyl}-4-methyl-1,4-dihydrotetrazol-5-one (hereinafter referred to as the present compound 144).

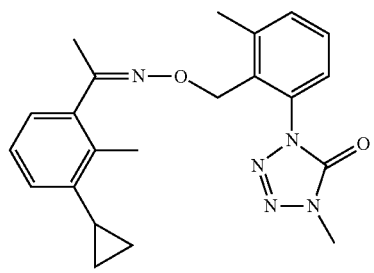 [SMILES: CC(=NOCc1c(C)cccc1-n1nnn(C)c1=O)c1cccc(C2CC2)c1C]

$^1$H-NMR (CDCl₃) δ(ppm): 7.41-7.36 (2H, m), 7.26-7.23 (1H, m), 7.09 (1H, t, J=7.6 Hz), 7.00 (1H, d, J=7.3 Hz), 6.98 (1H, d, J=7.6 Hz), 5.23 (2H, s), 3.63 (3H, s), 2.54 (3H, s), 2.28 (3H, s), 2.03 (3H, s), 1.89-1.82 (1H, m), 0.94-0.89 (2H, m), 0.63-0.59 (2H, m).

Production Example 145

A mixture of 0.28 g of C11A, 0.18 g of C114A, 0.26 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.18 g of 1-{2-[1-(3-ethyl-2-methylphenyl)ethylideneaminooxymethyl]-3-methyl phenyl}-4-methyl-1,4-dihydrotetrazol-5-one (hereinafter referred to as the present compound 145).

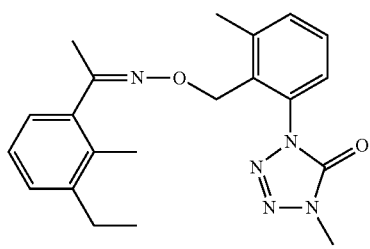 [SMILES: CCc1cccc(C(C)=NOCc2c(C)cccc2-n2nnn(C)c2=O)c1C]

¹H-NMR (CDCl₃) δ(ppm): 7.38-7.36 (2H, m), 7.26-7.23 (1H, m), 7.15-7.10 (2H, m), 6.97 (1H, dd, J=6.5, 2.4 Hz), 5.23 (2H, s), 3.62 (3H, s), 2.63 (2H, q, J=7.6 Hz), 2.53 (3H, s), 2.14 (3H, s), 2.02 (3H, s), 1.19 (3H, t, J=7.6 Hz).

Production Example 146

A mixture of 0.28 g of C11A, 0.16 g of C115A, 0.26 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.22 g of 1-{2-[1-(2,5-dimethylphenyl)ethylideneaminooxymethyl]-3-methylphenyl}-4-methyl-1,4-dihydrotetrazol-5-one (hereinafter referred to as the present compound 146).

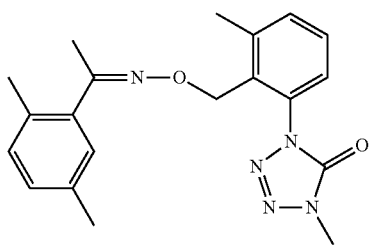 [SMILES: CC(=NOCc1c(C)cccc1-n1nnn(C)c1=O)c1cc(C)ccc1C]

¹H-NMR (CDCl₃) δ(ppm): 7.40-7.35 (2H, m), 7.25-7.22 (1H, m), 7.06-7.01 (2H, m), 6.97 (1H, s), 5.23 (2H, s), 3.62 (3H, s), 2.53 (3H, s), 2.30 (3H, s), 2.17 (3H, s), 2.03 (3H, s).

Production Example 147

A mixture of 0.05 g of C11A, 0.06 g of N-hydroxy-3-trifluoromethylthiobenzimidic acid methyl ester, 0.26 g of potassium carbonate, and 10 mL of acetonitrile was stirred while heating under reflux for 7 hours. After cooling to room temperature, the reaction mixture was filtered and the filtrate was concentrated.

The obtained residue was subjected to silica gel column chromatography to obtain 0.07 g of N-[2-methyl-6-(4-methoxy-5-oxo-4,5-dihydrotetrazol-1-yl)benzoyloxy]-3-trifluoromethylthiobenzimidic acid methyl ester (hereinafter referred to as the present compound 147).

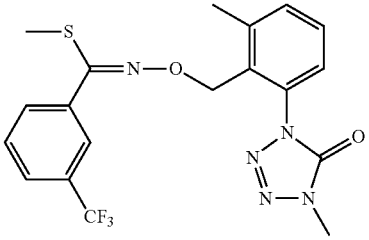 [SMILES: CSC(=NOCc1c(C)cccc1-n1nnn(C)c1=O)c1cccc(C(F)(F)F)c1]

MS, m/z: 438 (M+1).

Production Example 148

A mixture of 0.28 g of C11A, 0.22 g of C117A, 0.26 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.32 g of 1-{2-[1-(2-fluoro-3-trifluoromethylphenyl)ethylideneaminooxymethyl]-3-methylphenyl}-4-methyl-1,4-dihydrotetrazol-5-one (hereinafter referred to as the present compound 148).

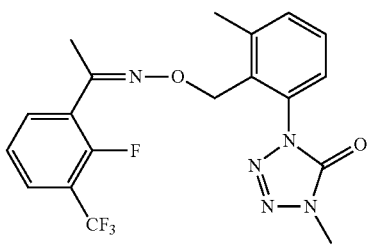 [SMILES: CC(=NOCc1c(C)cccc1-n1nnn(C)c1=O)c1cccc(C(F)(F)F)c1F]

¹H-NMR (CDCl₃) δ(ppm): 7.62-7.57 (2H, m), 7.40-7.36 (2H, m), 7.25-7.19 (2H, m), 5.26 (2H, s), 3.67 (3H, s), 2.54 (3H, s), 2.14 (3H, d, J=3.0 Hz).

Production Example 149

A mixture of 0.56 g of C11A, 0.27 g of acetophenone oxime, 0.52 g of potassium carbonate, and 10 mL of acetonitrile was stirred while heating under reflux for 7 hours. After cooling to room temperature, the reaction mixture was filtered and the filtrate was concentrated.

The obtained residue was subjected to silica gel column chromatography to obtain 0.47 g of 1-[2-(1-phenylethylideneaminooxymethyl)-3-methylphenyl]-4-methyl-1,4-dihydrotetrazol-5-one (hereinafter referred to as the present compound 149).

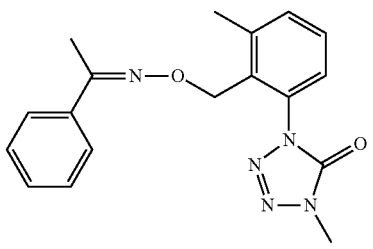 [SMILES: CC(=NOCc1c(C)cccc1-n1nnn(C)c1=O)c1ccccc1]

¹H-NMR (CDCl₃) δ(ppm): 7.59-7.56 (2H, m), 7.38-7.33 (5H, m), 7.25-7.21 (1H, m), 5.26 (2H, s), 3.63 (3H, s), 2.55 (3H, s), 2.11 (3H, s).

Production Example 150

A mixture of 0.28 g of C11A, 0.21 g of C118A, 0.26 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.08 g of 1-[2-(1-biphenyl-2-ylethylideneaminooxymethyl)-3-methylphenyl]-4-m ethyl-1,4-dihydrotetrazol-5-one (hereinafter referred to as the present compound 150).

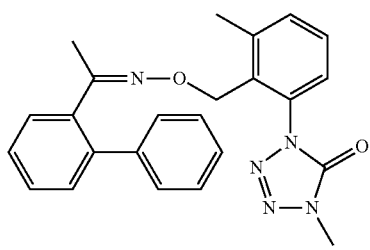 [SMILES: CC(=NOCc1c(C)cccc1-n1nnn(C)c1=O)c1ccccc1-c1ccccc1]

¹H-NMR (CDCl₃) δ(ppm): 7.44-7.23 (12H, m), 5.21 (2H, s), 3.64 (3H, s), 2.51 (3H, s), 1.50 (3H, s).

Production Example 151

A mixture of 0.33 g of C16A, 0.18 g of C101A, 0.26 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.18 g of 1-[3-difluoromethoxy-2-(1-indan-4-ylethylideneaminooxymethyl)phenyl]-4-methyl-1,4-dihydrotetrazol-5-one (hereinafter referred to as the present compound 151).

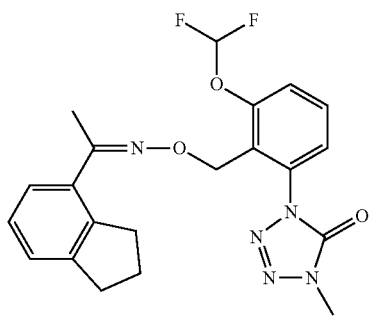 [SMILES: CC(=NOCc1c(OC(F)F)cccc1-n1nnn(C)c1=O)c1cccc2c1CCC2]

¹H-NMR (CDCl₃) δ(ppm): 7.50 (1H, t, J=8.1 Hz), 7.34 (2H, t, J=8.2 Hz), 7.19 (1H, d, J=6.6 Hz), 7.14-7.08 (2H, m), 6.56 (1H, t, J=73.5 Hz), 5.40 (2H, s), 3.56 (3H, s), 2.87 (2H, t, J=7.4 Hz), 2.80 (2H, t, J=7.3 Hz), 2.01 (3H, s), 1.98-1.92 (2H, m).

Production Example 152

A mixture of 0.28 g of C11A, 0.18 g of C119A, 0.26 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.11 g of 1-{2-[1-(2,3-dihydrobenzofuran-4-yl)ethylideneaminooxymethyl]-3-methylphenyl}-4-methyl-1,4-dihydrotetrazol-5-one (hereinafter referred to as the present compound 152).

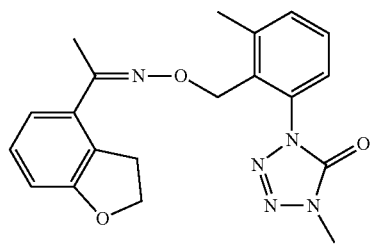

¹H-NMR (CDCl₃) δ(ppm): 7.37-7.36 (2H, m), 7.25-7.22 (1H, m), 7.10 (1H, t, J=7.7 Hz), 6.89 (1H, d, J=7.9 Hz), 6.76 (1H, d, J=7.9 Hz), 5.26 (2H, s), 4.48 (2H, t, J=8.8 Hz), 3.63 (3H, s), 3.12 (2H, t, J=8.8 Hz), 2.52 (3H, s), 2.09 (3H, s).

Production Example 153

A mixture of 0.30 g of C14A, 0.18 g of C119A, 0.26 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.13 g of 1-{2-[1-(2,3-dihydrobenzofuran-4-yl)ethylideneaminooxymethyl]-3-ethylphenyl}-4-methyl-1,4-dihydrotetrazol-5-one (hereinafter referred to as the present compound 153).

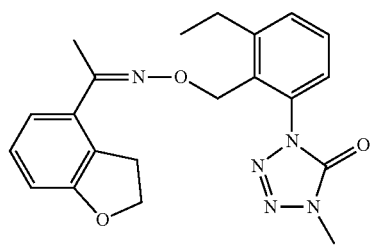 [SMILES: CCc1cccc(-n2nnn(C)c2=O)c1CON=C(C)c1cccc2c1CCO2]

¹H-NMR (CDCl₃) δ(ppm): 7.44-7.39 (2H, m), 7.23 (1H, dd, J=6.4, 2.8 Hz), 7.11 (1H, t, J=7.9 Hz), 6.89 (1H, d, J=8.0 Hz), 6.76 (1H, d, J=7.8 Hz), 5.29 (2H, s), 4.49 (2H, t, J=8.8 Hz), 3.59 (3H, s), 3.15 (2H, t, J=8.8 Hz), 2.88 (2H, q, J=7.5 Hz), 2.07 (3H, s), 1.28 (3H, t, J=7.5 Hz).

Production Example 154

A mixture of 0.31 g of C17A, 0.18 g of C119A, 0.26 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.13 g of 1-{3-cyclopropyl-2-[1-(2,3-dihydrobenzofuran-4-yl)ethylideneaminooxymethyl]phenyl}-4-methyl-1,4-dihydrotetrazol-5-one (hereinafter referred to as the present compound 154).

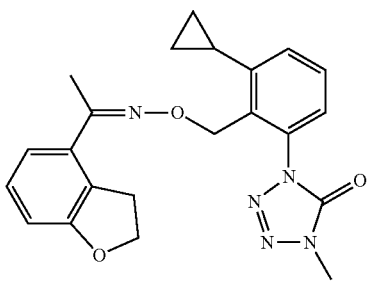 [SMILES: CC(=NOCc1c(C2CC2)cccc1-n1nnn(C)c1=O)c1cccc2c1CCO2]

¹H-NMR (CDCl₃) δ (ppm): 7.38 (1H, t, J=7.9 Hz), 7.23 (2H, dd, J=7.8, 2.3 Hz), 7.11 (1H, t, J=7.8 Hz), 6.90 (1H, d, J=7.8 Hz), 6.76 (1H, d, J=7.8 Hz), 5.50 (2H, s), 4.48 (2H, t, J=8.8 Hz), 3.60 (3H, s), 3.14 (2H, t, J=8.8 Hz), 2.24-2.17 (1H, m), 2.08 (3H, s), 1.05-1.00 (2H, m), 0.78-0.74 (2H, m).

Production Example 155

A mixture of 0.28 g of C11A, 0.23 g of C120A, 0.26 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.26 g of 1-[2-(1-biphenyl-3-ylethylideneaminooxymethyl)-3-methylphenyl]-4-m ethyl-1,4-dihydrotetrazol-5-one (hereinafter referred to as the present compound 155).

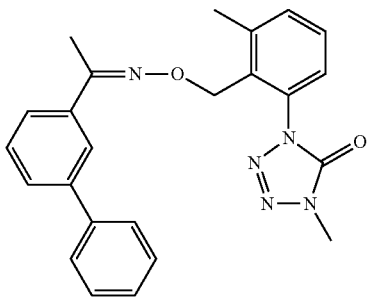 [SMILES: CC(=NOCc1c(C)cccc1-n1nnn(C)c1=O)c1cccc(-c2ccccc2)c1]

¹H-NMR (CDCl₃) δ(ppm): 7.37-7.27 (6H, m), 7.25-7.24 (1H, m), 7.21 (1H, dd, J=6.2, 3.0 Hz), 7.11 (1H, t, J=7.3 Hz), 7.01-6.95 (3H, m), 5.23 (2H, s), 3.65 (3H, s), 2.52 (3H, s), 2.07 (3H, s).

Production Example 156

A mixture of 0.12 g of C11A, 0.12 g of C121A, 0.10 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 1-{2-[1-(4-phenyl-3-trifluoromethylphenyl)ethylideneaminooxymethyl]-3-methylphenyl}-4-methyl-1,4-dihydrotetrazol-5-one (hereinafter referred to as the present compound 156).

¹H-NMR (CDCl₃) δ(ppm): 7.95 (1H, d, J=1.8 Hz), 7.75 (1H, dd, J=8.0, 1.4 Hz), 7.41-7.39 (5H, m), 7.32-7.29 (3H, m), 7.23 (1H, t, J=4.6 Hz), 5.29 (2H, s), 3.68 (3H, s), 2.57 (3H, s), 2.16 (3H, s).

Production Example 157

A mixture of 0.67 g of C9A, 0.41 g of C119A, 0.55 g of potassium carbonate, and 15 ml of acetonitrile was stirred while heating under reflux for 7 hours. After cooling to room temperature, the reaction mixture was filtered and the filtrate was concentrated. The obtained residue was subjected to silica gel column chromatography to obtain 0.17 g of 1-{3-trifluoromethyl-2-[1-(2,3-dihydrobenzofuran-4-yl)ethylideneaminooxymethyl]phenyl]-4-methyl-1,4-dihydrotetrazol-5-one (hereinafter referred to as the present compound 157).

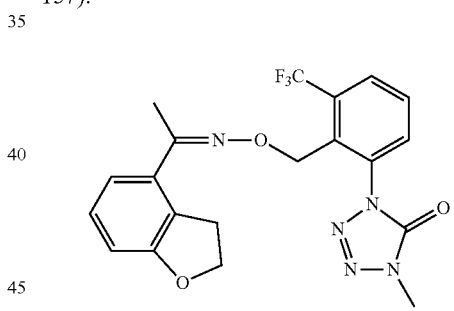

¹H-NMR (CDCl₃) δ(ppm): 7.88-7.86 (1H, m), 7.63-7.60 (2H, m), 7.10 (1H, t, J=7.9 Hz), 6.88 (1H, d, J=7.9 Hz), 6.76 (1H, d, J=8.0 Hz), 5.51 (2H, s), 4.46 (2H, t, J=8.8 Hz), 3.54 (3H, s), 3.09 (2H, t, J=8.7 Hz), 2.01 (3H, s).

Production Example 158

A mixture of 0.34 g of C11A, 0.21 g of C116A, 0.55 g of potassium carbonate, and 15 ml of acetonitrile was stirred at 70° C. for 24 hours. After cooling to room temperature, the reaction mixture was filtered and the filtrate was concentrated. The obtained residue was subjected to silica gel column chromatography to obtain 0.10 g of 1-{3-trifluoromethyl-2-[1-(2,2-dimethyl-2,3-dihydrobenzofuran-4-yl)ethylideneaminooxymethyl]phenyl]-4-methyl-1,4-dihydrotetrazol-5-one (hereinafter referred to as the present compound 158).

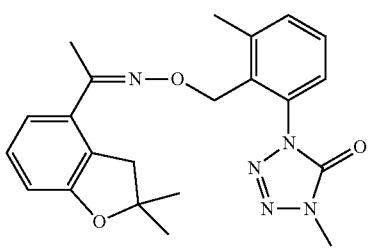 [SMILES: CC(=NOCc1c(C)cccc1-n1nnn(C)c1=O)c1cccc2c1CC(C)(C)O2]

$^1$H-NMR (CDCl$_3$) δ: 7.37-7.34 (2H, m), 7.25-7.22 (1H, m), 7.09 (1H, t, J=7.8 Hz), 6.87 (1H, dd, J=7.9, 0.8 Hz), 6.69 (1H, d, J=8.0 Hz), 5.25 (2H, s), 3.65 (3H, s), 2.84 (2H, s), 2.52 (3H, s), 2.08 (3H, s), 1.40 (6H, s).

Production Example 159

A mixture of 0.56 g of C11A, 0.36 g of C92A, 0.55 g of potassium carbonate, and 15 ml of acetonitrile was stirred at 70° C. for 24 hours. After cooling to room temperature, the reaction mixture was filtered and the filtrate was concentrated. The obtained residue was subjected to silica gel column chromatography to obtain 0.30 g of 1-[2-(1-benzo[1,3]dioxol-4-ylethylideneaminooxymethyl)-3-methylphenyl]-4-methyl-1,4-dihydrotetrazol-5-one (hereinafter referred to as the present compound 159).

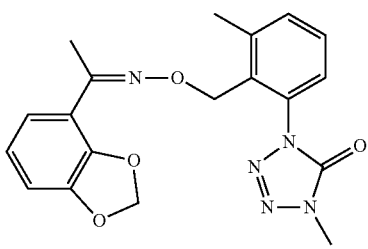

$^1$H-NMR (CDCl$_3$) δ: 7.38-7.36 (2H, m), 7.22 (1H, t, J=4.9 Hz), 7.04-7.00 (1H, m), 6.80-6.79 (2H, m), 5.96 (2H, s), 5.25 (2H, s), 3.66 (3H, s), 2.55 (3H, s), 2.13 (3H, s).

Production Example 201

A mixture of 0.42 g of C11A, 0.28 g of C201A, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.14 g of 1-[2-(1-cyclohexylethylideneaminooxymethyl)-3-methylphenyl]-4-methyl-1,4-dihydrotetrazol-5-one (hereinafter referred to as the present compound 201).

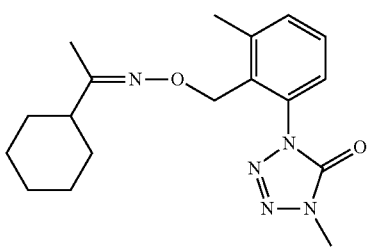 [SMILES: CC(=NOCc1c(C)cccc1-n1nnn(C)c1=O)C1CCCCC1]

$^1$H-NMR (CDCl$_3$) δ(ppm): 7.35-7.32 (2H, m), 7.21-7.17 (1H, m), 5.07 (2H, s), 3.69 (3H, s), 2.50 (3H, s), 2.07-2.00 (1H, m), 1.80-1.63 (5H, m), 1.64 (3H, s), 1.30-1.10 (5H, m).

Production Example 202

A mixture of 0.42 g of C11A, 0.21 g of C202A, 0.28 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.27 g of 1-[2-(1-cyclohex-1-enylethylideneaminooxymethyl)-3-methylphenyl]-4-methyl-1,4-dihydrotetrazol-5-one (hereinafter referred to as the present compound 202).

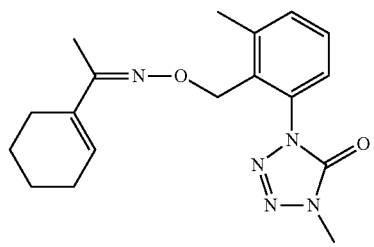 [SMILES: CC(=NOCc1c(C)cccc1-n1nnn(C)c1=O)C1=CCCCC1]

$^1$H-NMR (CDCl$_3$) δ(ppm): 7.37-7.34 (2H, m), 7.23-7.17 (1H, m), 6.07-6.05 (1H, m), 5.13 (2H, s), 3.69 (3H, s), 2.51 (3H, s), 2.17-2.11 (4H, m), 1.81 (3H, s), 1.61-1.55 (4H, m).

Production Example 203

A mixture of 0.84 g of C11A, 0.34 g of C203A, 0.56 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.54 g of 1-[2-(1,2-dimethylbutan-2-enylideneaminooxymethyl)-3-methylphenyl]-4-methyl-1,4-dihydrotetrazol-5-one (hereinafter referred to as the present compound 203).

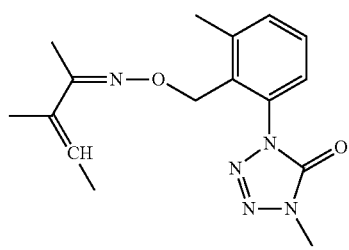 [SMILES: CC=C(C)C(C)=NOCc1c(C)cccc1-n1nnn(C)c1=O]

$^1$H-NMR (CDCl$_3$) δ(ppm): 7.36-7.35 (2H, m), 7.22-7.19 (1H, m), 5.91-5.85 (1H, m), 5.15 (2H, s), 3.69 (3H, s), 2.52 (3H, s), 1.82 (3H, s), 1.73 (3H, bs), 1.72 (3H, bs).

Production Example 204

A mixture of 0.84 g of C11A, 0.34 g of C204A, 0.56 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.53 g of 1-[2-(1,4-dimethylpentane-2-enylideneaminooxymethyl)-3-methylphenyl]-4-methyl-1,4-dihydrotetrazol-5-one (hereinafter referred to as the present compound 204).

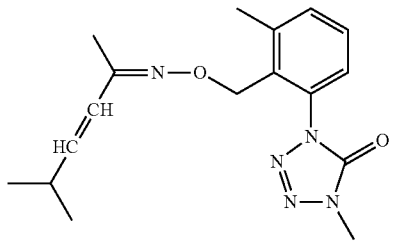 [SMILES: CC(C=CC(C)C)=NOCc1c(C)cccc1-n1nnn(C)c1=O]

$^1$H-NMR (CDCl$_3$) δ(ppm): 7.37-7.35 (2H, m), 7.22-7.20 (1H, m), 5.97-5.96 (2H, m), 5.11 (2H, s), 3.69 (3H, s), 2.50 (3H, s), 2.43-2.35 (1H, m), 1.81 (3H, s), 1.02 (6H, d, J=6.8 Hz).

Production Example 205

A mixture of 0.30 g of C11A, 0.16 g of 4-phenylbut-3-en-2-one oxime, 0.18 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.27 g of 1-methyl-4-[3-methyl-2-(1-methyl-3-phenylallylideneaminooxymethyl)phenyl]-1,4-dihydrotetrazol-5-one (hereinafter referred to as the present compound 205).

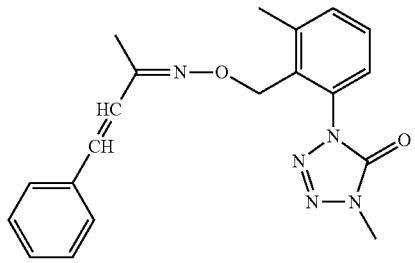 [SMILES: CC(C=Cc1ccccc1)=NOCc1c(C)cccc1-n1nnn(C)c1=O]

$^1$H-NMR (CDCl$_3$) δ(ppm): 7.45-7.22 (8H, m), 6.80 (1H, d, J=16.5 Hz), 6.72 (1H, d, J=16.5 Hz), 5.19 (2H, s), 3.70 (3H, s), 2.53 (3H, s), 1.95 (3H, s).

Production Example 206

A mixture of C11A, 4-(4-chlorophenyl)but-3-en-2-one oxime, potassium carbonate, and acetonitrile was stirred while heating under reflux for 7 hours. After cooling to room temperature, the reaction mixture was filtered and the filtrate was concentrated. The obtained residue was subjected to silica gel column chromatography to obtain 1-{2-[3-(4-chlorophenyl)-1-methylallylideneaminooxymethyl)-3-methylphenyl]-4-methyl-1,4-dihydrotetrazol-5-one (hereinafter referred to as the present compound 206).

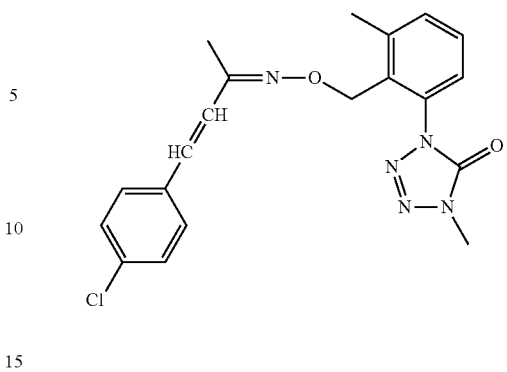

$^1$H-NMR (CDCl$_3$) δ(ppm): 7.39-7.35 (4H, m), 7.31-7.28 (2H, m), 7.25-7.21 (1H, m), 6.74 (1H, d, J=16.6 Hz), 6.68 (1H, d, J=16.6 Hz), 5.19 (2H, s), 3.70 (3H, s), 2.52 (3H, s), 1.93 (3H, s).

Production Example 207

A mixture of C8A, 4-(4-chlorophenyl)but-3-en-2-one oxime, potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 1-{2-[3-(4-chlorophenyl)-1-methylallylideneaminooxymethyl)-3-methoxyphenyl]-4-methyl-1,4-dihydrotetrazol-5-one (hereinafter referred to as the present compound 207).

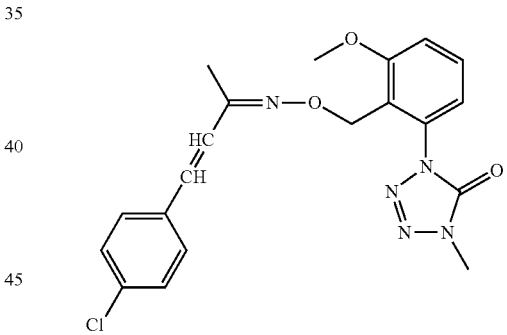

$^1$H-NMR (CDCl$_3$) δ(ppm): 7.44 (1H, t, J=8.2 Hz), 7.37-7.28 (4H, m), 7.07 (1H, d, J=8.0 Hz), 7.02 (1H, d, J=8.0 Hz), 6.69 (1H, d, J=16.4 Hz), 6.66 (1H, d, J=16.4 Hz), 5.33 (2H, s), 3.92 (3H, s), 3.67 (3H, s), 1.88 (3H, s).

Production Example 208

A mixture of 0.30 g of C11A, 0.23 g of 4-(2,6-dichlorophenyl)but-3-en-2-one oxime, 0.18 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.09 g of 1-{2-[3-(2,6-dichlorophenyl)-1-methylallylideneaminooxymethyl)-3-methylphenyl]-4-methyl-1,4-dihydrotetrazol-5-one (hereinafter referred to as the present compound 208).

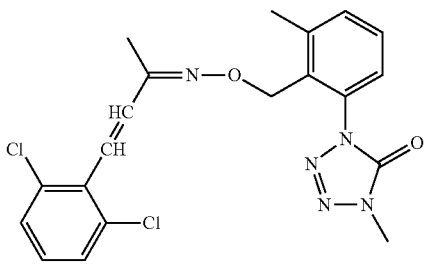 [SMILES: CC(C=Cc1c(Cl)cccc1Cl)=NOCc1c(C)cccc1-n1nnn(C)c1=O]

$^1$H-NMR (CDCl$_3$) δ(ppm): 7.39-7.37 (2H, m), 7.32 (2H, d, J=8.0 Hz), 7.23 (1H, dd, J=5.5, 3.4 Hz), 7.11 (1H, t, J=8.0 Hz), 6.84 (1H, d, J=16.7 Hz), 6.76 (1H, d, J=16.7 Hz), 5.20 (2H, s), 3.70 (3H, s), 2.53 (3H, s), 1.98 (3H, s).

Production Example 209

A mixture of 0.42 g of C11A, 0.24 g of C208A, 0.28 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.30 g of pentane-2,3-dione-3-{O-[2-methyl-6-(4-methyl-5-oxo-4,5-dihydrotetrazol-1-yl)benzyl]oxime}(hereinafter referred to as the present compound 209).

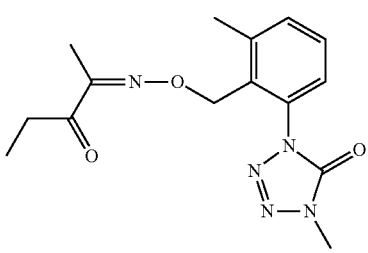 [SMILES: CCC(=O)C(C)=NOCc1c(C)cccc1-n1nnn(C)c1=O]

$^1$H-NMR (CDCl$_3$) δ(ppm): 7.40-7.39 (2H, m), 7.24-7.22 (1H, m), 5.29 (2H, s), 3.71 (3H, s), 2.83 (2H, q, J=7.6 Hz), 2.53 (3H, s), 1.81 (3H, s), 1.03 (3H, t, J=7.6 Hz).

Production Example 210

A mixture of 0.42 g of C11A, 0.24 g of C210A, 0.28 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.24 g of pentane-2,3,4-trione-2-{O-[2-methyl-6-(4-methyl-5-oxo-4,5-dihydrotetrazol-1-yl)benzyl]oxime}-4-(O-methyloxime) (hereinafter referred to as the present compound 210).

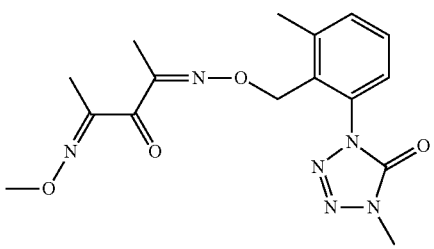 [SMILES: CON=C(C)C(=O)C(C)=NOCc1c(C)cccc1-n1nnn(C)c1=O]

$^1$H-NMR (CDCl$_3$) δ(ppm): 7.4-7.3 (2H, m), 7.2-7.3 (1H, m), 5.29 (2H, s), 3.98 (3H, s), 3.70 (3H, s), 2.51 (3H, s), 1.94 (3H, s), 1.91 (3H, s).

Production Example 211

A mixture of 0.28 g of C11A, 0.19 g of C211A, 0.18 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.27 g of pentane-2,3,4-trione-2-{O-[2-methyl-6-(4-methyl-5-oxo-4,5-dihydrotetrazol-1-yl)benzyl]oxime}-3,4-bis-(O-methyloxime): A (hereinafter referred to as the present compound 211)

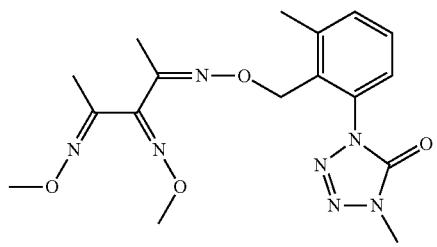 [SMILES: CON=C(C)C(=NOC)C(C)=NOCc1c(C)cccc1-n1nnn(C)c1=O]

$^1$H-NMR (CDCl$_3$) δ(ppm): 7.39-7.33 (2H, m), 7.21-7.18 (1H, m), 5.19 (2H, s), 3.92 (3H, s), 3.91 (3H, s), 3.71 (3H, s), 2.48 (3H, s), 1.91 (3H, s), 1.80 (3H, s).

Production Example 212

A mixture of 0.28 g of C11A, 0.19 g of C211B, 0.18 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.28 g of pentane-2,3,4-trione-2-{O-[2-methyl-6-(4-methyl-5-oxo-4,5-dihydrotetrazol-1-yl)benzyl]oxime}-3,4-bis-(O-methyloxime): B (hereinafter referred to as the present compound 212).

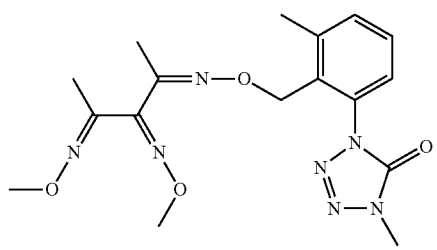 [SMILES: CON=C(C)C(=NOC)C(C)=NOCc1c(C)cccc1-n1nnn(C)c1=O]

$^1$H-NMR (CDCl$_3$) δ(ppm): 7.39-7.34 (2H, m), 7.23-7.21 (1H, m), 5.18 (2H, s), 3.93 (3H, s), 3.89 (3H, s), 3.69 (3H, s), 2.50 (3H, s), 2.00 (3H, s), 1.84 (3H, s).

Production Example 213

A mixture of C11A, 1-(4-chlorophenyl)propane-1,2-dione-1-(O-methyloxime)-2-oxime, potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 1-(4-chlorophenyl)propane-1,2-dione-2-{O-[2-methyl-6-(4-methyl-5-oxo-4,5-dihydrotetrazol-1-yl)benzyl]oxime}-1-(O-methyloxime) (hereinafter referred to as the present compound 213).

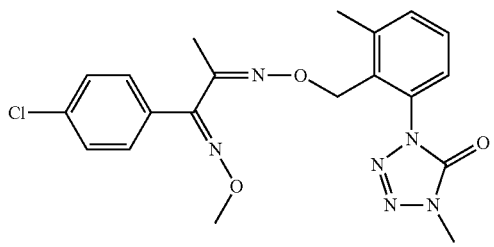 [SMILES: CON=C(C(C)=NOCc1c(C)cccc1-n1nnn(C)c1=O)c1ccc(Cl)cc1]

¹H-NMR (CDCl₃) δ(ppm): 7.43-7.34 (2.0H, m), 7.30-7.17 (4.0H, m), 7.01-6.99 (1.0H, m), 5.23 (0.5H, s), 5.06 (1.5H, s), 3.97 (0.8H, s), 3.88 (2.2H, s), 3.69 (2.2H, s), 3.67 (0.8H, s), 2.47 (0.8H, s), 2.23 (2.2H, s), 1.99 (2.2H, s), 1.93 (0.8H, s).

Production Example 214

A mixture of C2A, 1-(4-chlorophenyl)propane-1,2-dione-1-(O-methyloxime)-2-oxime, potassium carbonate, and acetonitrile was stirred while heating under reflux for 7 hours. After cooling to room temperature, the reaction mixture was filtered and the filtrate was concentrated. The obtained residue was subjected to silica gel column chromatography to obtain 1-(4-chlorophenyl)propane-1,2-dione-2-{O-[2-chloro-6-(4-methyl-5-oxo-4,5-dihydrotetrazol-1-yl)benzyl]oxime}-1-(O-methyloxime) (hereinafter referred to as the present compound 214).

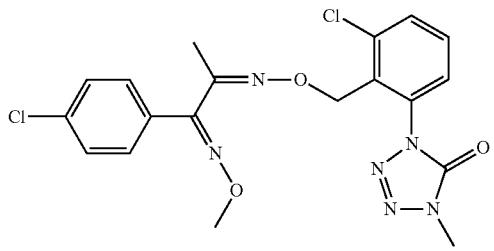 [SMILES: CON=C(C(C)=NOCc1c(Cl)cccc1-n1nnn(C)c1=O)c1ccc(Cl)cc1]

¹H-NMR (CDCl₃) δ(ppm): 7.58-7.49 (1.0H, m), 7.47-7.34 (2.0H, m), 7.31-7.23 (3.0H, m), 7.03-7.00 (1.0H, m), 5.43 (0.5H, s), 5.27 (1.5H, s), 3.97 (0.8H, s), 3.89 (2.2H, s), 3.68 (2.2H, s), 3.63 (0.8H, s), 1.97 (2.2H, s), 1.90 (0.8H, s).

Production Example 215

A mixture of C8A, 1-phenylpropane-1,2-dione-1-(O-methyloxime)-2-oxime, potassium carbonate, and acetonitrile was stirred while heating under reflux for 7 hours. After cooling to room temperature, the reaction mixture was filtered and the filtrate was concentrated. The obtained residue was subjected to silica gel column chromatography to obtain 1-phenylpropane-1,2-dion-2-{O-[2-methoxy-6-(4-methyl-5-oxo-4,5-dihydrotetrazol-1-yl)benzyl]oxime}-1-(O-methyloxime) (hereinafter referred to as the present compound 215).

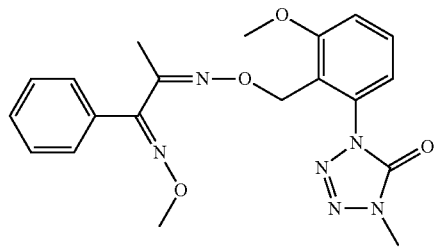 [SMILES: CON=C(C(C)=NOCc1c(OC)cccc1-n1nnn(C)c1=O)c1ccccc1]

¹H-NMR (CDCl₃) δ(ppm): 7.51-7.47 (1.0H, m), 7.45-7.40 (1.0H, m), 7.34-7.27 (3.0H, m), 7.11-7.09 (1.0H, m), 7.04 (1.0H, m), 7.01-6.98 (1H, m), 5.37 (0.9H, s), 5.21 (1.1H, s), 3.97 (1.3H, s), 3.88 (1.7H, s), 3.84 (1.3H, s), 3.70 (1.7H, s), 3.67 (1.7H, s), 3.61 (1.3H, s), 1.95 (1.7H, s), 1.89 (1.3H, s).

Production Example 216

A mixture of 0.28 g of C11A, 0.21 g of C215A, 0.28 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 1-(2-{1-[2-(4-chlorophenyl)cyclopropyl]ethylideneaminooxymethyl}-3-methylphenyl)-4-methyl-1,4-dihydrotetrazol-5-one (hereinafter referred to as the present compound 216).

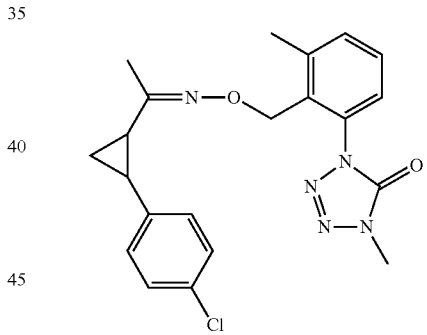

¹H-NMR (CDCl₃) δ(ppm): 7.37-7.35 (2H, m), 7.24-7.19 (3H, m), 7.01-6.98 (2H, m), 5.06 (2H, s), 3.67 (3H, s), 2.50 (3H, s), 2.09-2.06 (1H, m), 1.71-1.67 (1H, m), 1.66 (3H, s), 1.36-1.30 (1H, m), 1.11-1.06 (1H, m).

Production Example 217

A mixture of 0.28 g of C11A, 0.24 g of C216A, 0.28 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.22 g of 1-(2-{1-[2-(2,6-dichlorophenyl)cyclopropyl]ethylideneaminooxymethy 1}-3-methylphenyl)-4-methyl-1,4-dihydrotetrazol-5-one (hereinafter referred to as the present compound 217).

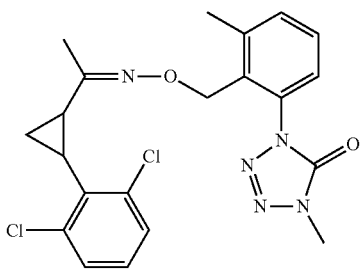 [SMILES: CC(=NOCc1c(C)cccc1-n1nnn(C)c1=O)C1CC1c1c(Cl)cccc1Cl]

¹H-NMR (CDCl₃) δ(ppm): 7.36-7.35 (2H, m), 7.25 (2H, d, J=8.2 Hz), 7.21 (1H, t, J=4.6 Hz), 7.08 (1H, t, J=8.0 Hz), 5.10 (2H, s), 3.70 (3H, s), 2.52 (3H, s), 2.07-2.00 (1H, m), 1.80-1.75 (1H, m), 1.73 (3H, s), 1.53-1.48 (1H, m), 1.21-1.16 (1H, m).

Production Example 218

A mixture of 0.28 g of C11A, C214A, 0.28 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.16 g of 1-{2-[1-(2-phenylcyclopropyl)ethylideneaminooxymethyl]-3-methylphenyl}-4-methyl-1,4-dihydrotetrazol-5-one (hereinafter referred to as the present compound 218).

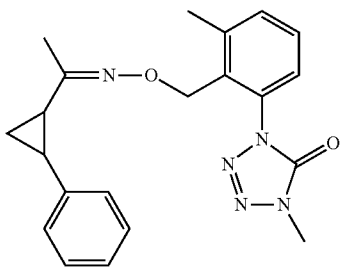 [SMILES: CC(=NOCc1c(C)cccc1-n1nnn(C)c1=O)C1CC1c1ccccc1]

¹H-NMR (CDCl₃) δ(ppm): 7.37-7.35 (2H, m), 7.27-7.13 (4H, m), 7.08-7.06 (2H, m), 5.07 (2H, s), 3.66 (3H, s), 2.50 (3H, s), 2.12-2.08 (1H, m), 1.75-1.70 (1H, m), 1.66 (3H, s), 1.36-1.31 (1H, m), 1.15-1.10 (1H, m).

Production Example 219

A mixture of 0.56 g of C11A, 0.48 g of C205A, 0.42 g of potassium carbonate, and 20 mL of acetonitrile was stirred while heating under reflux for 7 hours. After cooling to room temperature, the reaction mixture was filtered and the filtrate was concentrated. The obtained residue was subjected to silica gel column chromatography to obtain 0.61 g of 1-methyl-4-(3-methyl-2-{1-[1-(3-trifluoromethylphenyl)cyclopropyl]ethylideneaminooxymethyl]phenyl}1,4-dihydrotetrazol-5-one (hereinafter referred to as the present compound 219).

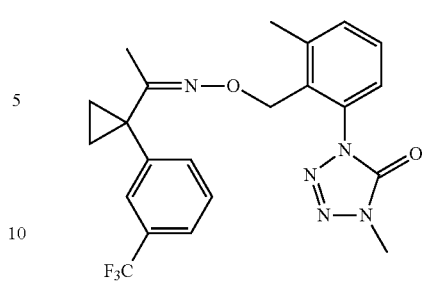

¹H-NMR (CDCl₃) δ: 7.46-7.43 (2H, m), 7.38-7.32 (4H, m), 7.20 (1H, dd, J=7.0, 2.0 Hz), 5.10 (2H, s), 3.69 (3H, s), 2.45 (3H, s), 1.61 (4H, s), 1.22 (2H, dd, J=6.6, 4.5 Hz), 0.98 (2H, dd, J=6.7, 4.6 Hz).

Production Example 251

A mixture of 0.42 g of C11A, 0.20 g of C251A, 0.28 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.16 g of 1-methyl-4-[3-methyl-2-(1-pyridin-3-ylethylideneaminooxymethyl)phenyl]-1,4-dihydrotetrazol-5-one (hereinafter referred to as the present compound 251).

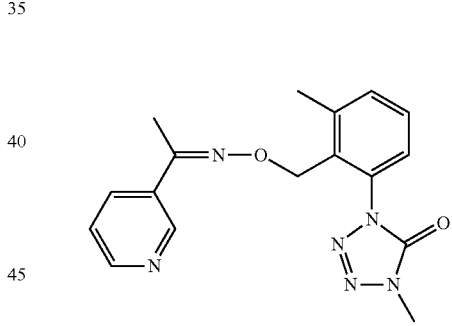

¹H-NMR (CDCl₃) δ(ppm): 8.78 (1H, d, J=2.2 Hz), 8.56 (1H, dd, J=4.8, 1.5 Hz), 7.87 (1H, dt, J=8.1, 1.9 Hz), 7.38-7.35 (2H, m), 7.28-7.21 (2H, m), 5.27 (2H, s), 3.66 (3H, s), 2.55 (3H, s), 2.12 (3H, s).

Production Example 252

A mixture of 0.50 g of C11A, 0.20 g of C252A, 0.28 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.37 g of 1-methyl-4-[3-methyl-2-(1-pyridin-2-ylethylideneaminooxymethyl)phenyl]-1,4-dihydrotetrazol-5-one (hereinafter referred to as the present compound 252).

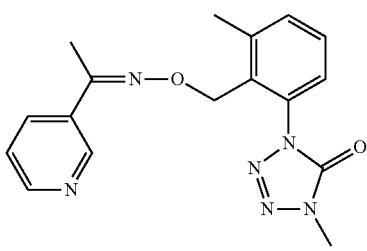 [SMILES: CC(=NOCc1c(C)cccc1-n1nnn(C)c1=O)c1cccnc1]

¹H-NMR (CDCl₃) δ(ppm): 8.55 (1H, dq, J=4.8, 1.0 Hz), 7.81 (1H, dt, J=8.1, 1.0 Hz), 7.64 (1H, td, J=7.8, 1.9 Hz), 7.39-7.38 (2H, m), 7.25-7.20 (2H, m), 5.28 (2H, s), 3.68 (3H, s), 2.56 (3H, s), 2.21 (3H, s).

Production Example 253

A mixture of 0.28 g of C11A, 0.20 g of C253A, 0.28 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.18 g of 1-methyl-4-{3-methyl-2-[1-(6-trifluoromethylpyridin-2-yl)ethylideneaminooxymethyl]phenyl}-1,4-dihydrotetrazol-5-one (hereinafter referred to as the present compound 253).

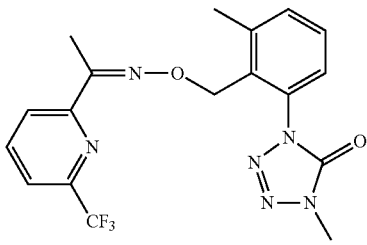

¹H-NMR (CDCl₃) δ(ppm): 8.01 (1H, d, J=7.9 Hz), 7.79 (1H, t, J=7.9 Hz), 7.59 (1H, dd, J=7.7, 0.7 Hz), 7.40-7.37 (2H, m), 7.25-7.21 (1H, m), 5.28 (2H, s), 3.70 (3H, s), 2.56 (3H, s), 2.23 (3H, s).

Production Example 254

A mixture of 0.56 g of C11A, 0.28 g of C254A, 0.56 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.31 g of 1-methyl-4-{3-methyl-2-[1-(1-methyl-1H-pyrrol-3-yl)ethylideneaminooxymethyl]phenyl}-1,4-dihydrotetrazol-5-one (hereinafter referred to as the present compound 254).

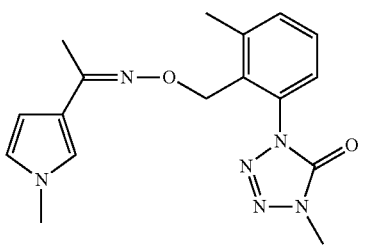 [SMILES: CC(=NOCc1c(C)cccc1-n1nnn(C)c1=O)c1ccn(C)c1]

¹H-NMR (CDCl₃) δ(ppm): 7.37-7.34 (2.0H, m), 7.30-7.27 (0.6H, m), 7.24-7.19 (1.0H, m), 6.80 (0.4H, t, J=2.1 Hz), 6.52 (0.4H, t, J=2.5 Hz), 6.50 (0.6H, t, J=2.5 Hz), 6.34 (0.4H, dd, J=2.8, 1.8 Hz), 6.32 (0.6H, dd, J=2.9, 1.7 Hz), 5.19 (1.2H, s), 5.14 (0.8H, s), 3.66 (1.2H, s), 3.62 (3.0H, s), 3.58 (1.8H, s), 2.54 (1.2H, s), 2.53 (1.8H, s), 2.09 (1.8H, s), 1.98 (1.2H, s).

Production Example 255

A mixture of 0.42 g of C11A, 0.21 g of C255A, 0.28 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.29 g of 1-methyl-4-{3-methyl-2-[1-(1-methyl-1H-pyrrol-2-yl)ethylideneaminooxymethyl]phenyl}-1,4-dihydrotetrazol-5-one (hereinafter referred to as the present compound 255).

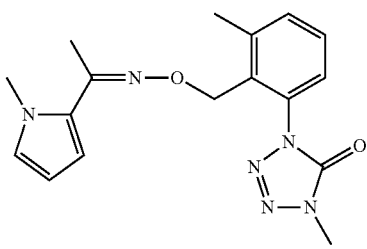 [SMILES: CC(=NOCc1c(C)cccc1-n1nnn(C)c1=O)c1cccn1C]

¹H-NMR (CDCl₃) δ(ppm): 7.35-7.32 (2H, m), 7.22-7.19 (1H, m), 6.58-6.56 (1H, m), 6.35-6.33 (1H, m), 6.05-6.03 (1H, m), 5.20 (2H, s), 3.64 (3H, s), 3.58 (3H, s), 2.51 (3H, s), 2.04 (3H, s).

Production Example 256

A mixture of 0.42 g of C11A, 0.23 g of C256A, 0.28 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.07 g of 1-methyl-4-{3-methyl-2-[1-(4-methyl-2-thienyl)ethylideneaminooxymethyl]phenyl}-1,4-dihydrotetrazol-5-one (hereinafter referred to as the present compound 256).

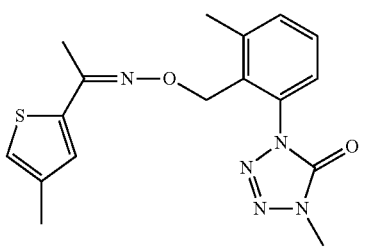 [SMILES: CC(=NOCc1c(C)cccc1-n1nnn(C)c1=O)c1cc(C)cs1]

¹H-NMR (CDCl₃) δ(ppm): 7.36-7.34 (2H, m), 7.21 (1H, t, J=4.4 Hz), 6.96 (1H, s), 6.80 (1H, s), 5.19 (2H, s), 3.66 (3H, s), 2.53 (3H, s), 2.20 (3H, s), 2.07 (3H, s).

Production Example 257

A mixture of 0.42 g of C11A, 0.21 g of C257A, 0.28 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.17 g of 1-methyl-4-{3-methyl-2-[1-(2-thienyl)ethylideneaminooxymethyl]phen yl}-1,4-dihydrotetrazol-5-one (hereinafter referred to as the present compound 257).

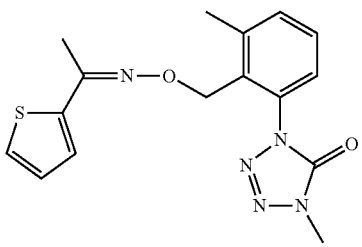 [SMILES: CC(=NOCc1c(C)cccc1-n1nnn(C)c1=O)c1cccs1]

$^1$H-NMR (CDCl$_3$) δ(ppm): 7.38-7.37 (2H, m), 7.25 (1H, dd, J=0.8, 5.6 Hz), 7.22 (1H, dd, J=4.4, 4.4 Hz), 7.16 (1H, dd, J=1.2, 3.6 Hz), 6.98 (1H, dd, J=3.6, 4.8 Hz), 5.21 (2H, s), 3.68 (3H, s), 2.55 (3H, s), 2.12 (3H, s).

Production Example 258

A mixture of 0.42 g of C11A, 0.23 g of C258A, 0.28 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.40 g of 1-methyl-4-{3-methyl-2-[1-(3-methyl-2-thienyl)ethylideneaminooxymethyl]phenyl}-1,4-dihydrotetrazol-5-one (hereinafter referred to as the present compound 258).

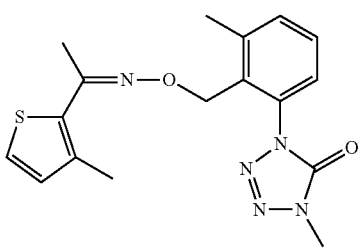 [SMILES: CC(=NOCc1c(C)cccc1-n1nnn(C)c1=O)c1sccc1C]

$^1$H-NMR (CDCl$_3$) δ(ppm): 7.37-7.35 (2H, m), 7.23-7.21 (1H, m), 7.14 (1H, d, J=5.2 Hz), 6.81 (1H, d, J=5.2 Hz), 5.24 (2H, s), 3.65 (3H, s), 2.53 (3H, s), 2.25 (3H, s), 2.12 (3H, s).

Production Example 259

A mixture of 0.56 g of C11A, 0.25 g of C259A, 0.36 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.49 g of 1-[2-(1-furan-2-yl-ethylideneaminooxymethyl) 3-methylphenyl]-4-meth yl-1,4-dihydrotetrazol-5-one (hereinafter referred to as the present compound 259).

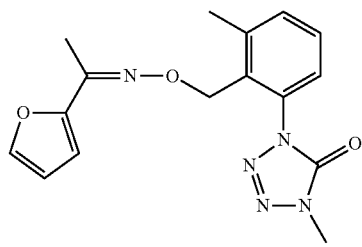 [SMILES: CC(=NOCc1c(C)cccc1-n1nnn(C)c1=O)c1ccco1]

$^1$H-NMR (CDCl$_3$) δ(ppm): 7.44 (1H, t, J=0.8 Hz), 7.44-7.37 (2H, m), 7.24-7.23 (1H, m), 6.60 (1H, d, J=3.2 Hz), 6.42-6.41 (1H, m), 5.23 (2H, s), 3.66 (3H, s), 2.53 (3H, s), 2.05 (3H, s).

Production Example 260

A mixture of 0.28 g of C11A, 0.19 g of C260A, 0.26 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.23 g of 1-{2-[1-(6-fluorobenzo[d]isoxazol-3-yl)ethylideneaminooxymethyl]-3-methylphenyl}-4-methyl-1,4-dihydrotetrazol-5-one (hereinafter referred to as the present compound 260).

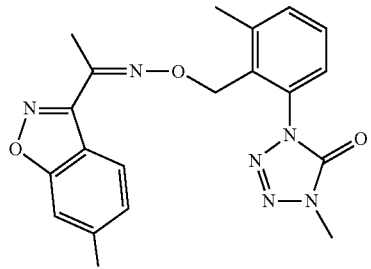

$^1$H-NMR (CHCl$_3$) δ(ppm): 7.90 (1H, dd, J=8.8, 5.4 Hz), 7.44-7.39 (2H, m), 7.29-7.26 (1H, m), 7.22 (1H, dd, J=8.4, 2.1 Hz), 7.09 (1H, td, J=8.9, 2.1 Hz), 5.40 (2H, s), 3.67 (3H, s), 2.57 (3H, s), 2.30 (3H, s).

Production Example 261

A mixture of 0.30 g of C14A, 0.19 g of C260A, 0.26 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.44 g of 1-{3-ethyl-2-[1-(6-fluorobenzo[d]isoxazol-3-yl)ethylideneaminooxymethyl]phenyl}-4-methyl-1,4-dihydrotetrazol-5-one (hereinafter referred to as the present compound 261).

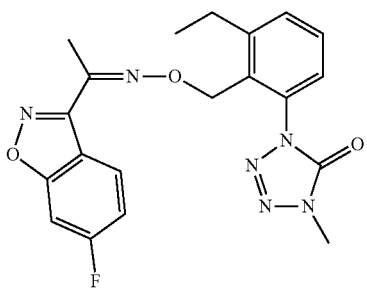 [SMILES: CCc1cccc(-n2nnn(C)c2=O)c1CON=C(C)c1noc2cc(F)ccc12]

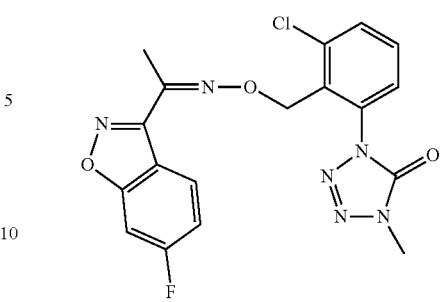

¹H-NMR (CDCl₃) δ(ppm): 7.91 (1H, dd, J=8.7, 5.5 Hz), 7.49-7.44 (2H, m), 7.28-7.26 (1H, m), 7.23 (1H, dd, J=8.4, 2.2 Hz), 7.09 (1H, td, J=8.9, 2.1 Hz), 5.43 (2H, s), 3.63 (3H, s), 2.92 (2H, q, J=7.6 Hz), 2.28 (3H, s), 1.31 (3H, t, J=7.6 Hz).

Production Example 262

A mixture of 0.31 g of C17A, 0.19 g of C260A, 0.26 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.33 g of 1-{3-cyclopropyl-2-[1-(6-fluorobenzo[d]isoxazol-3-yl)ethylideneaminooxymethyl]phenyl}-4-methyl-1,4-dihydrotetrazol-5-one (hereinafter referred to as the present compound 262).

¹H-NMR (CDCl₃) δ(ppm): 7.95 (1H, dd, J=8.8, 5.2 Hz), 7.63 (1H, d, J=8.2 Hz), 7.46 (1H, t, J=8.0 Hz), 7.37 (1H, d, J=7.9 Hz), 7.25-7.21 (1H, m), 7.12-7.06 (1H, m), 5.62 (2H, s), 3.65 (3H, s), 2.25 (3H, s).

Production Example 264

A mixture of 0.42 g of C11A, 0.23 g of C261A, 0.26 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.33 g of 1-{2-[1-(1,5-dimethyl-1H-pyrazol-3-yl)ethylideneaminooxymethyl]-3-methylphenyl}-4-methyl-1,4-dihydrotetrazol-5-one (hereinafter referred to as the present compound 264).

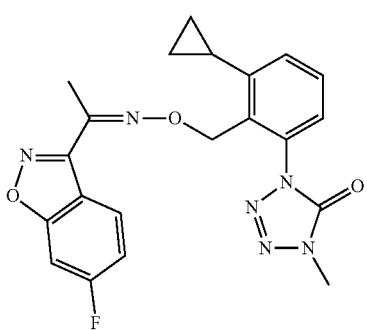 [SMILES: CC(=NOCc1c(C2CC2)cccc1-n1nnn(C)c1=O)c1noc2cc(F)ccc12]

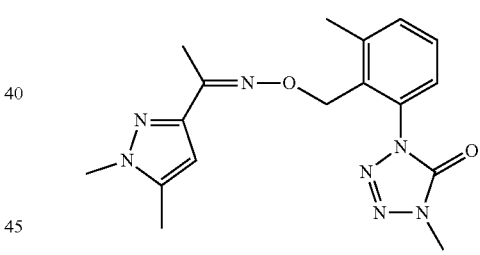

¹H-NMR (CDCl₃) δ(ppm): 7.90 (1H, dd, J=8.8, 5.4 Hz), 7.42 (1H, t, J=7.9 Hz), 7.26-7.21 (3H, m), 7.08 (1H, td, J=8.9, 2.1 Hz), 5.62 (2H, s), 3.64 (3H, s), 2.28 (3H, s), 2.26-2.21 (1H, m), 1.09-1.05 (2H, m), 0.82-0.78 (2H, m).

Production Example 263

A mixture of 0.30 g of C2A, 0.19 g of C260A, 0.26 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.16 g of 1-{3-chloro-2-[1-(6-fluorobenzo[d]isoxazol-3-yl)ethylideneaminooxy methyl]phenyl}-4-methyl-1,4-dihydrotetrazol-5-one (hereinafter referred to as the present compound 263).

¹H-NMR (CDCl₃) δ(ppm): 7.36 (2H, d, J=5.2 Hz), 7.21 (1H, t, J=4.6 Hz), 6.27 (1H, s), 5.19 (2H, s), 3.75 (3H, s), 3.68 (3H, s), 2.53 (3H, s), 2.25 (3H, s), 2.10 (3H, s).

Production Example 265

A mixture of 0.42 g of C11A, 0.25 g of C262A, 0.27 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.35 g of 1-[2-(5-mercapto-1,4-dimethylpenta-2,4-dienylideneaminooxymethyl)-3-methylphenyl]-4-methyl-1,4-dihydrotetrazol-5-one (hereinafter referred to as the present compound 265).

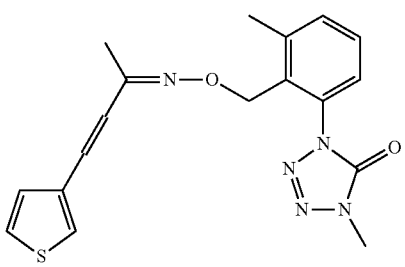 [SMILES: CC(C=Cc1ccsc1)=NOCc1c(C)cccc1-n1nnn(C)c1=O]

¹H-NMR (CDCl₃) δ(ppm): 7.39-7.37 (2H, m), 7.31-7.29 (1H, m), 7.25-7.21 (3H, m), 6.82 (1H, d, J=16.4 Hz), 6.57 (1H, d, J=16.4 Hz), 5.18 (2H, s), 3.70 (3H, s), 2.52 (3H, s), 1.92 (3H, s).

Production Example 266

A mixture of 0.28 g of C11A, 0.18 g of C263A, 0.26 g of potassium carbonate, and 10 mL of acetonitrile was stirred while heating under reflux for 7 hours. After cooling to room temperature, the reaction mixture was filtered and the filtrate was concentrated. The obtained residue was subjected to silica gel column chromatography to obtain 0.18 g of 1-methyl-4-{3-methyl-2-[1-(2-thiophenyl-3-ylcyclopropyl)ethylideneaminooxymethyl]phenyl)-1,4-dihydrotetrazol-5-one (hereinafter referred to as the present compound 266).

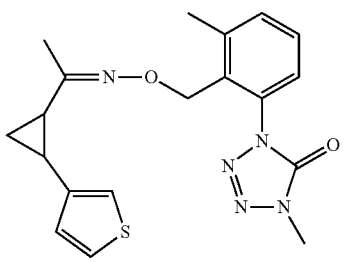 [SMILES: CC(=NOCc1c(C)cccc1-n1nnn(C)c1=O)C1CC1c1ccsc1]

¹H-NMR (CDCl₃) δ(ppm): 7.36-7.34 (2H, m), 7.25-7.19 (2H, m), 6.91-6.90 (1H, m), 6.83-6.81 (1H, m), 5.06 (2H, s), 3 the production of intermediates of the above present compounds. 66 (3H, s), 2.50 (3H, s), 2.18-2.13 (1H, m), 1.72-1.67 (1H, m), 1.64 (3H, s), 1.35-1.28 (1H, m), 1.08-1.03 (1H, m).

Regarding the production of the compound (2), Synthesis Example will be shown below.

Synthesis Example 1

A mixture of 7.88 g of C101A, 9.20 g of C151A, 11.06 g of potassium carbonate, and 100 mL of acetonitrile was stirred while heating under reflux for 7 hours. After cooling to room temperature, the reaction mixture was filtered and the filtrate was concentrated. The obtained residue was subjected to silica gel column chromatography to obtain 9.51 g of 1-indan-4-ylethanone O-(2-methyl-6-nitrobenzyl) oxime.

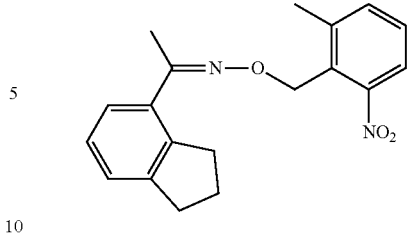

¹H-NMR (CDCl₃) δ(ppm): 7.57 (1H, d, J=7.9 Hz), 7.41 (1H, d, J=7.6 Hz), 7.33 (1H, t, J=7.9 Hz), 7.21-7.17 (1H, m), 7.15-7.11 (2H, m), 5.45 (2H, s), 2.88 (2H, t, J=7.5 Hz), 2.82 (2H, t, J=7.5 Hz), 2.53 (3H, s), 2.15 (3H, s), 1.96 (2H, sext, J=7.4 Hz).

Regarding the production of intermediates for producing the above present compounds, Reference Production Examples will be shown below.

Reference Production Example 1

Step (1)

Anhydrous aluminum trichloride (21.9 g) was added to 250 mL of N,N-dimethylformamide under ice cooling, followed by stirring for 15 minutes. To this was added 10.7 g of sodium azide and the mixture was stirred for 15 minutes, followed by the addition of 22.5 g of 1-fluoro-3-isocyanate-2-methylbenzene and further stirring at 80° C. for 3.5 hours. After cooling, the reaction solution was added in a mixture of 34 g of sodium nitrite, 2 L of water, and 500 g of ice while stirring. The mixture was acidified with 10% hydrochloric acid and then extracted with ethyl acetate. The organic layer was washed in turn with water and a saturated saline solution, dried over anhydrous magnesium sulfate, and then concentrated under reduced pressure to obtain 27.5 g of 1-(2-methyl-3-fluorophenyl)-1,4-dihydrotetrazol-5-one.

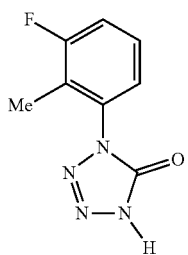

¹H-NMR (CDCl₃) δ(ppm): 12.93 (1H, s), 7.07-7.36 (3H, m), 2.21 (3H, s).

Step (2)

To a mixture of 10.00 g of 1-(2-methyl-3-fluorophenyl)-1,4-dihydrotetrazol-5-one and 100 mL of N,N-dimethylformamide, 2.47 g of 55% sodium hydride was added under ice cooling. The temperature of the mixture was raised to room temperature, followed by stirring for one hour. To the reaction mixture, 3.5 mL of methyl iodide was added under ice cooling. The temperature of the mixture was raised to room temperature, followed by stirring for 14 hours. Water was poured into the reaction mixture, followed by extraction with ethyl acetate. The organic layer was washed in turn with 10% hydrochloric acid, water, and a saturated saline solution, dried over anhydrous magnesiumsulfate, and then concentrated under reduced pressure. The obtained residue was subjected to silica gel column chromatography to obtain 2.19 g of 1-(2-methyl-3-fluorophenyl)-4-methyl-1,4-dihydrotetrazol-5-one.

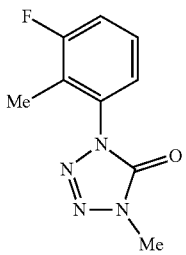

$^1$H-NMR (CDCl$_3$) δ(ppm): 7.29 (1H, dt, J=5.9, 8.3 Hz), 7.16-7.20 (2H, m), 3.70 (3H, s), 2.19 (3H, s).

Step (3)

A mixture of 2.19 g of 1-(2-methyl-3-fluorophenyl)-4-methyl-1,4-dihydrotetrazol-5-one, 0.52 g of 1,1'-azobis(cyclohexane-1-carbonitrile), 2.16 g of N-bromosuccinimide, and 40 mL of chlorobenzene was stirred while heating under reflux for 5 hours. After cooling, water was poured into the reaction mixture, followed by extraction with ethyl acetate. The organic layer was washed in turn with water and a saturated saline solution, dried over anhydrous magnesiumsulfate, and then concentrated under reduced pressure. The obtained residue was subjected to silica gel column chromatography to obtain 2.36 g of 1-(2-bromomethyl-3-fluorophenyl)-4-methyl-1,4-dihydrotetrazol-5-on e (C1A).

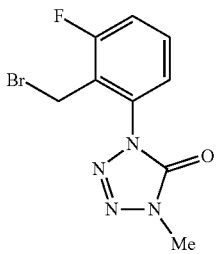 [SMILES: Cn1nnn(-c2cccc(F)c2CBr)c1=O]

$^1$H-NMR (CDCl$_3$) δ(ppm): 7.47 (1H, dt, J=5.9, 8.0 Hz), 7.23-7.30 (2H, m), 4.64 (2H, s), 3.75 (3H, s).

Reference Production Example 2

Step (1)

Anhydrous aluminum trichloride (21.9 g) was added to 250 mL of N,N-dimethylformamide under ice cooling, followed by stirring for 15 minutes. To this was added 10.7 g of sodium azide and the mixture was stirred for 15 minutes, followed by the addition of 25.0 g of 1-chloro-3-isocyanate-2-methylbenzene and further heating at 80° C. for 5 hours. After cooling, the reaction solution was added in a mixture of 35 g of sodium nitrite, 2 L of water, and 500 g of ice while stirring.

The mixture was acidified with 10% hydrochloric acid and then extracted with ethyl acetate. The organic layer was washed in turn with water and a saturated saline solution, dried over anhydrous magnesium sulfate, and then concentrated under reduced pressure to obtain 17.0 g of 1-(2-methyl-3-chlorophenyl)-1,4-dihydrotetrazol-5-one.

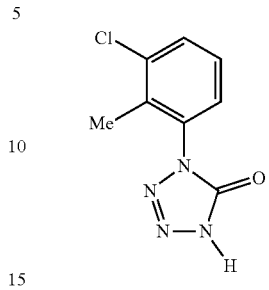

$^1$H-NMR (CDCl$_3$) δ(ppm): 13.08 (1H, s), 7.57 (1H, dd, J=6.8, 2.2 Hz), 7.28-7.36 (2H, m), 2.32 (3H, s).

Step (2)

To a mixture of 10.00 g of 1-(2-methyl-3-chlorophenyl)-1,4-dihydrotetrazol-5-one and 100 mL of N,N-dimethylformamide, 2.30 g of 55% sodium hydride was added under ice cooling. The temperature of the mixture was raised to room temperature, followed by stirring for one hour. To the reaction mixture, 3.2 mL of methyl iodide was added under ice cooling. The temperature of the mixture was raised to room temperature, followed by stirring for 14 hours. Water was poured into the reaction mixture, followed by extraction with ethyl acetate. The organic layer was washed in turn with 10% hydrochloric acid, water, and a saturated saline solution, dried over anhydrous magnesiumsulfate, and then concentrated under reduced pressure. The obtained residue was subjected to silica gel column chromatography to obtain 1.56 g of 1-(2-methyl-3-chlorophenyl)-4-methyl-1,4-dihydrotetrazol-5-one.

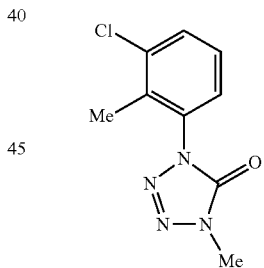

$^1$H-NMR (CDCl$_3$) δ(ppm): 7.52 (1H, dd, J=2.7, 6.8 Hz), 7.28 (1H, d, J=7.1 Hz), 7.27 (1H, d, J=2.7 Hz), 3.73 (3H, s), 2.30 (3H, s).

Step (3)

A mixture of 1.56 g of 1-(2-methyl-3-chlorophenyl)-4-methyl-1,4-dihydrotetrazol-5-one, 0.34 g of 1,1'-azobis(cyclohexane-1-carbonitrile), 1.42 g of N-bromosuccinimide, and 30 mL of chlorobenzene was stirred while heating under reflux for 5 hours. After cooling, water was poured into the reaction mixture, followed by extraction ethyl acetate. The organic layer was washed in turn with water and a saturated saline solution, dried over anhydrous magnesiumsulfate, and then concentrated under reduced pressure. The obtained residue was subjected to silica gel column chromatography to obtain 1.94 g of 1-(2-bromomethyl-3-chlorophenyl)-4-methyl-1,4-dihydrotetrazol-5-one (C2A).

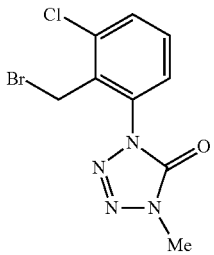 [SMILES: Cn1nnn(-c2cccc(Cl)c2CBr)c1=O]

$^1$H-NMR (CDCl$_3$) δ(ppm): 7.58 (1H, dd, J=1.2, 8.1 Hz), 7.43 (1H, t, J=8.1 Hz), 7.35 (1H, dd, J=1.2, 8.1 Hz), 4.69 (2H, s), 3.76 (3H, s).

Reference Production Example 3

A mixture of 21.5 g of 3-chloro-2-methylbenzoic acid, 17.6 g of oxalyl dichloride, about 50 mg of N,N-dimethylformamide and 300 mL of tetrahydrofuran was stirred at 25° C. for one hour. The reaction mixture was concentrated under reduced pressure to obtain 3-chloro-2-methylbenzoic acid chloride.

A mixture of 33.6 g of aluminum chloride, 49.2 g of sodium azide, and 100 mL of tetrahydrofuran was stirred while heating under reflux for 2 hours. After ice cooling of the reaction mixture, a mixture of 3-chloro-2-methylbenzoic acid chloride and 100 mL of tetrahydrofuran was added, followed by stirring while heating under reflux for 10 hours. After cooling, the reaction mixture was added in a mixture of 75.6 g of sodium nitrite and 500 mL of water while stirring. The mixture was acidified with concentrated hydrochloric acid and then extracted with ethyl acetate. The organic layer was dried over anhydrous sodium sulfate and then concentrated under reduced pressure to obtain 1-(2-methyl-3-chlorophenyl)-1,4-dihydrotetrazol-5-one.

The obtained mixture of 1-(2-methyl-3-chlorophenyl)-1,4-dihydrotetrazol-5-one, 57.5 g of potassium carbonate, 19.1 g of dimethylsulfuric acid, and 150 mL of N,N-dimethylformamide was stirred at 25° C. for one hour. An aqueous saturated sodium bicarbonate solution was poured into the reaction mixture, followed by extraction with ethyl acetate. The organic layer was washed with an aqueous saturated sodium bicarbonate solution, dried over anhydrous sodium sulfate, and then concentrated under reduced pressure to obtain 21.6 g of 1-(2-methyl-3-chlorophenyl)-4-methyl-1,4-dihydrotetrazol-5-one (C3A).

Reference Production Example 4

Under ice cooling, to a mixture of 30 mL of methyl chloroformate and 50 mL of tetrahydrofuran, 5.00 g of 3-amino-1-chloro-2-methylbenzene was added dropwise and the mixture was stirred at 25° C. for 0.5 hour. Water was poured into the reaction mixture, followed by extraction with ethyl acetate. The organic layer was washed with an aqueous saturated sodium bicarbonate solution, dried over anhydrous sodium sulfate, and then concentrated under reduced pressure to obtain 5.80 g of 1-chloro-2-methyl-3-methoxycarbonylaminobenzene.

A mixture of 5.80 g of 1-chloro-2-methyl-3-methoxycarbonylaminobenzene, 7.53 g of phosphorus pentachloride, and 50 mL of chlorobenzene was stirred while heating under reflux for one hour. The reaction mixture was concentrated under reduced pressure to obtain 1-chloro-3-isocyanate-2-methylbenzene.

A mixture of 4.71 g of aluminum chloride, 6.89 g of sodium azide, and 100 mL of tetrahydrofuran was stirred while heating under reflux for one hour. After ice cooling of the reaction mixture, a mixture of 1-chloro-3-isocyanate-2-methylbenzene obtained above and 10 mL of tetrahydrofuran was added, followed by stirring while heating under reflux for 5 hours. After cooling, the reaction mixture was added in a mixture of 10.59 g of sodium nitrite and 300 mL of water while stirring. The mixture was acidified with concentrated hydrochloric acid and then extracted with ethyl acetate. The organic layer was dried over anhydrous sodium sulfate and then concentrated under reduced pressure to obtain 1-(2-methyl-3-chlorophenyl)-1,4-dihydrotetrazol-5-one.

A mixture of the obtained 1-(2-methyl-3-chlorophenyl)-1,4-dihydrotetrazol-5-one, 16.11 g of potassium carbonate, 5.34 g of dimethylsulfuric acid, and 150 mL of N,N-dimethylformamide was stirred at 25° C. for one hour. An aqueous saturated sodium bicarbonate solution was poured into the reaction mixture, followed by extraction with ethyl acetate. The organic layer was washed with an aqueous saturated sodium bicarbonate solution, dried over anhydrous sodium sulfate, and then concentrated under reduced pressure to obtain 4.80 g of 1-(2-methyl-3-chlorophenyl)-4-methyl-1,4-dihydrotetrazol-5-one (C4A).

Reference Production Example 5

Step (1)

A mixture of 25.0 g of 1-bromo-2-methyl-3-aminobenzene, 60.0 g of triphosgene, and 400 mL of toluene was stirred while heating under reflux for 3 hours. The cooled reaction mixture was concentrated under reduced pressure to obtain 30.3 g of 1-bromo-3-isocyanate-2-methylbenzene.

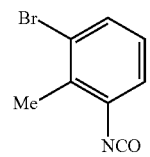

$^1$H-NMR (CDCl$_3$) δ(ppm): 7.39 (1H, dd, J=1.5, 7.7 Hz), 7.05 (1H, dd, J=1.7, 8.0 Hz), 7.00 (1H, dt, J=0.5, 8.0 Hz), 2.42 (3H, s).

Step (2)

Anhydrous aluminum trichloride (19.7 g) was added to 220 mL of N,N-dimethylformamide under ice cooling, followed by stirring for 15 minutes. To this was added 9.6 g of sodium azide and, after stirring for 15 minutes, 30.3 g of 1-bromo-3-isocyanate-2-methylbenzene was added, followed by heating at 80° C. for 5 hours. After cooling, the reaction solution was added in a mixture of 33 g of sodium nitrite, 2 L of water, and 500 g of ice while stirring. The mixture was acidified with 10% hydrochloric acid and then extracted with ethyl acetate. The organic layer was washed in turn with water and a saturated saline solution, dried over anhydrous magnesium sulfate, and then concentrated under reduced pressure to obtain 31.4 g of 1-(2-methyl-3-bromophenyl)-1,4-dihydrotetrazol-5-one.

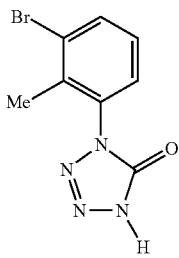 [SMILES: Cc1c(Br)cccc1-n1nn[nH]c1=O]

¹H-NMR (DMSO-d₆) δ(ppm): 14.72 (1H, s), 7.82 (1H, dd, J=8.0, 1.0 Hz), 7.49 (1H, dd, J=8.2, 1.1 Hz), 7.34 (1H, t, J=7.2 Hz), 2.22 (3H, s).

Step (3)

To a mixture of 31.4 g of 1-(2-methyl-3-bromophenyl)-1,4-dihydrotetrazol-5-one and 250 mL of N,N-dimethylformamide, 5.90 g of 60% sodium hydride was added under ice cooling. The temperature of the mixture was raised to room temperature, followed by stirring for one hour. Under ice cooling, 8.4 mL of methyl iodide was added to the reaction mixture. The temperature of the mixture was raised to room temperature, followed by stirring for 14 hours. Water was poured into the reaction mixture, followed by extraction with ethyl acetate. The organic layer was washed in turn with 10% hydrochloric acid, water, and a saturated saline solution, dried over anhydrous magnesiumsulfate, and then concentrated under reduced pressure. The obtained residue was subjected to silica gel column chromatography to obtain 8.47 g of C6A.

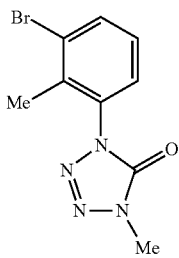 [SMILES: Cc1c(Br)cccc1-n1nnn(C)c1=O]

¹H-NMR (CDCl₃) δ(ppm): 7.71 (1H, dd, J=1.2, 8.3 Hz), 7.30 (1H, dd, J=1.0, 8.0 Hz), 7.21 (1H, dt, J=0.5, 7.8 Hz), 3.73 (3H, s), 2.33 (3H, s).

Step (4)

A mixture of 8.47 g of 1-(2-methyl-3-bromophenyl)-4-methyl-1,4-dihydrotetrazol-5-one, 1.54 g of 1,1'-azobis(cyclohexane-1-carbonitrile), 6.44 g of N-bromosuccinimide, and 125 mL of chlorobenzene was stirred while heating under reflux for 5 hours. After cooling, water was poured into the reaction mixture, followed by extraction with ethyl acetate. The organic layer was washed in turn with water and a saturated saline solution, dried over anhydrous magnesiumsulfate, and then concentrated under reduced pressure. The obtained residue was subjected to silica gel column chromatography to obtain 7.52 g of 1-(2-bromomethyl-3-bromophenyl)-4-methyl-1,4-dihydrotetrazol-5-one (C5A).

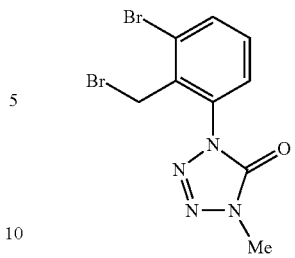

¹H-NMR (CDCl₃) δ(ppm): 3.76 (3H, s), 4.71 (2H, s), 7.34 (1H, t, J=7.8 Hz), 7.38 (1H, dd, J=8.0, 1.7 Hz), 7.77 (1H, dd, J=7.8, 1.7 Hz).

Reference Production Example 6

A mixture of 146.0 g of 3-bromo-2-methylbenzoic acid, 94.8 g of oxalyl dichloride, about 15 mg of N,N-dimethylformamide, and 500 mL of tetrahydrofuran was stirred at 25° C. for one hour. The reaction mixture was concentrated under reduced pressure to obtain 3-bromo-2-methylbenzoic acid chloride.

A mixture of 181.0 g of aluminum chloride, 265.0 g of sodium azide, and 300 mL of tetrahydrofuran was stirred while heating under reflux for 2 hours. After ice cooling of the reaction mixture, a mixture of 3-bromo-2-methylbenzoic acid chloride obtained above and 200 mL of tetrahydrofuran was added, followed by stirring while heating under reflux for 10 hours. After cooling, the reaction mixture was added in a mixture of 407 g of sodium nitrite and 1,500 mL of water while stirring. The mixture was acidified with concentrated hydrochloric acid and then extracted with ethyl acetate. The organic layer was dried over anhydrous sodium sulfate and then concentrated under reduced pressure to obtain 1-(2-methyl-3-bromophenyl)-1,4-dihydrotetrazol-5-one.

A mixture of 1-(2-methyl-3-bromophenyl)-1,4-dihydrotetrazol-5-one obtained above, 310.0 g of potassium carbonate, 103.0 g of dimethylsulfuric acid, and 500 mL of N,N-dimethylformamide was stirred at 25° C. for one hour. An aqueous saturated sodium bicarbonate solution was poured into the reaction mixture, followed by extraction with ethyl acetate. The organic layer was washed with an aqueous saturated sodium bicarbonate solution, dried over anhydrous sodium sulfate, and then concentrated under reduced pressure to obtain 142.0 g of 1-(2-methyl-3-bromophenyl)-4-methyl-1,4-dihydrotetrazol-5-one (C6A).

Reference Production Example 7

Step (1)

A mixture of 10.00 g of 3-iodo-2-methylbenzoic acid, 5.33 g of oxalyl dichloride, five drops of N,N-dimethylformamide, and 200 mL of tetrahydrofuran was stirred at 25° C. for one hour. The reaction mixture was concentrated under reduced pressure to obtain 3-iodo-2-methylbenzoic acid chloride.

A mixture of 10.20 g of aluminum trichloride, 14.90 g of sodium azide, and 100 mL of tetrahydrofuran was stirred while heating under reflux for 2 hours. After ice cooling of the reaction mixture, a mixture of 3-iodo-2-methylbenzoic acid chloride obtained above and 100 mL of tetrahydrofuran was added, followed by stirring while heating under reflux for 10 hours. After cooling, the reaction mixture was added in a mixture of 22.90 g of sodium nitrite and 200 mL of water while stirring. The mixture was acidified with concentrated hydrochloric acid and then extracted with ethyl acetate. The organic layer was dried over anhydrous sodium sulfate and then concentrated under reduced pressure to obtain 1-(2-methyl-3-iodophenyl)-1,4-dihydrotetrazol-5-one.

A mixture of 1-(2-methyl-3-iodophenyl)-1,4-dihydrotetrazol-5-one obtained above, 17.40 g of potassium carbonate, 5.78 g of dimethylsulfuric acid, and 150 mL of N,N-dimethylformamide was stirred at 25° C. for one hour. An aqueous saturated sodium bicarbonate solution was poured into the reaction mixture, followed by extraction with ethyl acetate. The organic layer was washed with an aqueous saturated sodium bicarbonate solution, dried over anhydrous sodium sulfate, and then concentrated under reduced pressure to obtain 8.10 g of 1-(2-methyl-3-iodophenyl)-4-methyl-1,4-dihydrotetrazol-5-one.

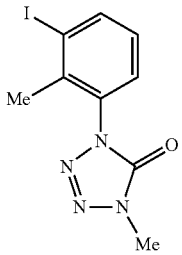 [SMILES: Cc1c(I)cccc1-n1nnn(C)c1=O]

$^1$H-NMR (CDCl$_3$) δ(ppm): 2.37 (3H, s), 3.72 (3H, s), 7.04 (1H, t, J=8.0 Hz), 7.32 (1H, d, J=7.7 Hz), 7.99 (1H, d, 8.0 Hz).

Step (2)

A mixture of 8.10 g of 1-(2-methyl-3-iodophenyl)-4-methyl-1,4-dihydrotetrazol-5-one, 1.25 g of 1,1'-azobis(cyclohexane-1-carbonitrile), 5.24 g of N-bromosuccinimide, and 100 mL of chlorobenzene was stirred while heating under reflux for 5 hours. After cooling, water was poured into the reaction solution, followed by extraction with ethyl acetate. The organic layer was washed in turn with water and a saturated saline solution, dried over anhydrous magnesium sulfate, and then concentrated under reduced pressure. The obtained residue was subjected to silica gel column chromatography to obtain 3.11 g of 1-(2-bromomethyl-3-iodophenyl)-4-methyl-1,4-dihydrotetrazol-5-one (C7A).

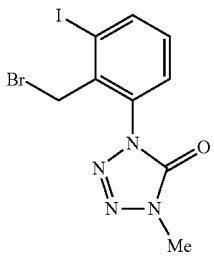 [SMILES: Cn1nnn(-c2cccc(I)c2CBr)c1=O]

$^1$H-NMR (CDCl$_3$) δ(ppm): 3.75 (3H, s), 4.71 (2H, s), 7.17 (1H, t, J=8.0 Hz), 7.39 (1H, d, J=8.0 Hz), 8.04 (1H, J=8.0 Hz).

Reference Production Example 8

Step (1)

A mixture of 15.0 g of 3-amino-1-methoxy-2-methylbenzene, 48.7 g of triphosgene, and 350 mL of toluene was stirred while heating under reflux for 3 hours. The cooled reaction mixture was concentrated under reduced pressure to obtain 17.0 g of 1-methoxy-3-isocyanate-2-methylbenzene.

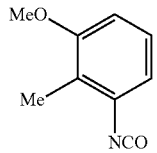

$^1$H-NMR (CDCl$_3$) δ(ppm): 2.19 (3H, s), 3.82 (3H, s), 6.69 (1H, d, J=8.2 Hz), 6.72 (1H, dd, J=0.5, 8.0 Hz), 7.09 (1H, t, J=8.2 Hz).

Step (2)

Under ice cooling, 16.0 g of anhydrous aluminum trichloride was added to 180 mL of N,N-dimethylformamide, followed by stirring for 15 minutes. To this was added 7.8 g of sodium azide and, after stirring for 15 minutes, 17.0 g of 1-methoxy-3-isocyanate-2-methylbenzene was added and the mixture was heated at 80° C. for 4.5 hours. After cooling, the reaction solution was added in a mixture of 25 g of sodium nitrite, 2 L of water, and 500 g of ice while stirring. The mixture was acidified with 10% hydrochloric acid and then extracted with ethyl acetate. The organic layer was washed in turn with water and a saturated saline solution, dried over anhydrous magnesiumsulfate, and then concentrated under reduced pressure to obtain 16.2 g of 1-(2-methyl-3-methoxyphenyl)-1,4-dihydrotetrazol-5-one.

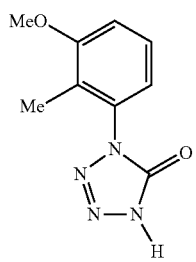 [SMILES: COc1cccc(-n2nn[nH]c2=O)c1C]

$^1$H-NMR (DMSO-d$_6$) δ(ppm): 1.99 (3H, s), 3.87 (3H, s), 7.01 (1H, d, J=8.1 Hz), 7.17 (1H, d, J=8.1 Hz). 7.36 (1H, t, J=8.3 Hz), 14.63 (1H, s).

Step (3)

To a mixture of 10.00 g of 1-(2-methyl-3-methoxyphenyl)-1,4-dihydrotetrazol-5-one and 100 mL of N,N-dimethylformamide, 2.47 g of 55% sodium hydride was added under ice cooling. The temperature of the mixture was raised to room temperature, followed by stirring for one hour. To the reaction mixture, 3.5 mL of methyl iodide was added under ice cooling. The temperature of the mixture was raised to room temperature, followed by stirring for 14 hours. Water was poured into the reaction mixture, followed by extraction with ethyl acetate. The organic layer was washed in turn with 10% hydrochloric acid, water, and a saturated saline solution, dried over anhydrous magnesiumsulfate, and then concentrated under reduced pressure. The obtained residue was subjected to silica gel column chromatography to obtain 2.19 g of 1-(2-methyl-3-methoxyphenyl)-4-methyl-1,4-dihydrotetrazol-5-one.

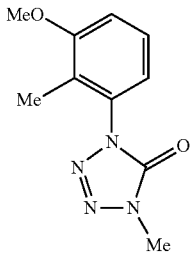 [SMILES: COc1cccc(-n2nnn(C)c2=O)c1C]

$^1$H-NMR (CDCl$_3$) δ(ppm): 2.11 (3H, s), 3, 72 (3H, s), 3.88 (3H, s), 6.95 (1H, d, J=8.2 Hz), 6.98 (1H, d, J=8.5 Hz), 7.29 (1H, t, J=8.2 Hz)

Step (4)

A mixture of 2.19 g of 1-(2-methyl-3-methoxyphenyl)-4-methyl-1,4-dihydrotetrazol-5-one, 0.52 g of 1,1'-azobis(cyclohexane-1-carbonitrile), 2.16 g of N-bromosuccinimide, and 40 mL of chlorobenzene was stirred while heating under reflux for 5 hours. After cooling, water was poured into the reaction solution, followed by extraction with ethyl acetate. The organic layer was washed in turn with water and a saturated saline solution, dried over anhydrous magnesium sulfate, and then concentrated under reduced pressure. The obtained residue was subjected to silica gel column chromatography to obtain 2.36 g of 1-(2-bromomethyl-3-methoxyphenyl)-4-methyl-1,4-dihydrotetrazol-5-one (C8A).

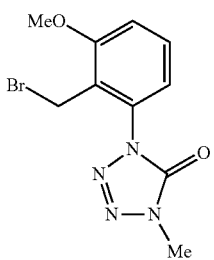 [SMILES: COc1cccc(-n2nnn(C)c2=O)c1CBr]

$^1$H-NMR (CDCl$_3$) δ(ppm): 3.74 (3H, s), 3.96 (3H, s), 4.93 (2H, s), 7.02 (1H, dd, J=1.0, 8.5 Hz), 7.04 (1H, d, J=9.0 Hz), 7.43 (1H, t, J=8.1 Hz).

Reference Production Example 9

Step (1)

A mixture of 5.00 g of 3-trifluoromethyl-2-methylbenzoic acid, 3.42 g of oxalyl dichloride, about 50 mg of N,N-dimethylformamide, and 200 mL of tetrahydrofuran was stirred at 25° C. for one hour. The reaction mixture was concentrated under reduced pressure to obtain 3-trifluoromethyl-2-methylbenzoic acid chloride.

A mixture of 6.53 g of aluminum trichloride, 9.55 g of sodium azide, and 100 mL of tetrahydrofuran was stirred while heating under reflux for 2 hours. After ice cooling of the reaction mixture, a mixture of 3-trifluoromethyl-2-methylbenzoic acid chloride obtained above and 100 mL of tetrahydrofuran was added, followed by stirring while heating under reflux for 10 hours. After cooling, the reaction mixture was added in a mixture of 14.7 g of sodium nitrite and 200 mL of water while stirring. The mixture was acidified with concentrated hydrochloric acid and then extracted with ethyl acetate. The organic layer was dried over anhydrous sodium sulfate and then concentrated under reduced pressure to obtain a crude product of 1-(2-methyl-3-trifluoromethylphenyl)-1,4-dihydrotetrazol-5-one. A mixture of the crude product of 1-(2-methyl-3-trifluoromethylphenyl)-1,4-dihydrotetrazol-5-one obtained above, 11.20 g of potassium carbonate, 3.71 g of dimethylsulfuric acid, and 150 mL of N,N-dimethylformamide was stirred at 25° C. for one hour. An aqueous saturated sodium bicarbonate solution was poured into the reaction mixture, followed by extraction with ethyl acetate. The organic layer was washed with an aqueous saturated sodium bicarbonate solution, dried over anhydrous sodium sulfate, and then concentrated under reduced pressure to obtain 5.13 g of 1-(2-methyl-3-trifluoromethylphenyl)-4-methyl-1,4-dihydrotetrazol-5-one.

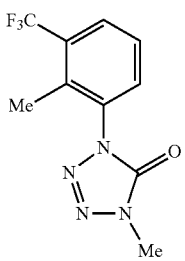

$^1$H-NMR (CDCl$_3$) δ(ppm): 2.42 (3H, s), 3.75 (3H, s), 7.52 (1H, t, J=8.2 Hz), 7.62 (1H, dd, J=1.2, 7.7 Hz), 8.02 (1H, dd, J=1.2, 8.2 Hz).

Step (2)

A mixture of 1.00 g of 1-(2-methyl-3-trifluoromethylphenyl)-4-methyl-1,4-dihydrotetrazol-5-one, 0.38 g of 1,1'-azobis(cyclohexane-1-carbonitrile), 0.79 g of N-bromosuccinimide, and 30 mL of chlorobenzene was stirred while heating under reflux for 5 hours. After cooling, water was poured into the reaction solution, followed by extraction with ethyl acetate. The organic layer was washed in turn with water and a saturated saline solution, dried over anhydrous magnesium sulfate, and then concentrated under reduced pressure. The obtained residue was subjected to silica gel column chromatography to obtain 1.21 g of 1-(2-bromomethyl-3-trifluoromethylphenyl)-4-methyl-1,4-dihydrotetrazol-5-one (C9A).

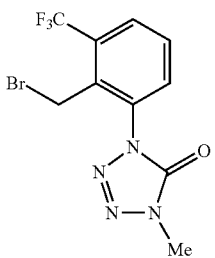 [SMILES: Cn1nnn(-c2cccc(C(F)(F)F)c2CBr)c1=O]

$^1$H-NMR (CDCl$_3$) δ(ppm): 3.77 (3H, s), 4.75 (2H, s), 7.62 (1H, d, J=5.5 Hz), 7.63 (1H, d, J=3.4 Hz), 7.85 (1H, dd, J=3.6, 5.8 Hz).

Reference Production Example 10

Step (1)

A mixture of 5.0 g of 3-nitro-2-methylbenzoic acid, 3.9 g of oxalyl dichloride, about 50 mg of N,N-dimethylformamide, and 200 mL of tetrahydrofuran was stirred at 25° C. for one hour. The reaction mixture was concentrated under reduced pressure to obtain 3-nitro-2-methylbenzoic acid chloride.

A mixture of 7.4 g of aluminumtrichloride, 11.0 g of sodiumazide, and 100 mL of tetrahydrofuran was stirred while heating under reflux for 2 hours. After ice cooling of the reaction mixture, a mixture of 3-nitro-2-methylbenzoic acid chloride obtained above and 100 mL of tetrahydrofuran was added, followed by stirring while heating under reflux for 10 hours. After cooling, the reaction mixture was added in a mixture of 16.6 g of sodium nitrite and 200 mL of water while stirring.

The mixture was acidified with concentrated hydrochloric acid and then extracted with ethyl acetate. The organic layer was dried over anhydrous sodium sulfate and then concentrated under reduced pressure to obtain 1-(2-methyl-3-nitrophenyl)-1,4-dihydrotetrazol-5-one.

A mixture of 1-(2-methyl-3-nitrophenyl)-1,4-dihydrotetrazol-5-one thus obtained, 12.6 g of potassium carbonate, 13.8 g of dimethylsulfuric acid, and 150 mL of N,N-dimethylformamide was stirred at 25° C. for one hour. An aqueous saturated sodium bicarbonate solution was poured into the reaction mixture, followed by extraction with ethyl acetate. The organic layer was washed with an aqueous saturated sodium bicarbonate solution, dried over anhydrous sodium sulfate, and then concentrated under reduced pressure to obtain 5.3 g of 1-(2-methyl-3-nitrophenyl)-4-methyl-1,4-dihydrotetrazol-5-one.

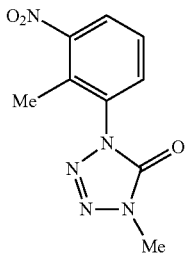 [SMILES: Cc1c(-n2nnn(C)c2=O)cccc1[N+](=O)[O-]]

$^1$H-NMR (CDCl$_3$) δ(ppm): 2.42 (3H, s), 3.75 (3H, s), 7.52 (1H, t, J=8.2 Hz), 7.62 (1H, dd, J=1.2, 7.7 Hz), 8.02 (1H, d, J=1.2, 8.2 Hz).

Step (2)

A mixture of 1.00 g of 1-(2-methyl-3-nitrophenyl)-4-methyl-1,4-dihydrotetrazol-5-one, 0.42 g of 1,1'-azobis(cyclohexane-1-carbonitrile), 0.87 g of N-bromosuccinimide, and 30 mL of chlorobenzene was stirred while heating under reflux for 5 hours. After allowing to cool, water was poured into the reaction solution, followed by extraction with ethyl acetate. The organic layer was washed in turn with water and an aqueous saturated sodium bicarbonate solution, dried over anhydrous magnesium sulfate, and then concentrated under reduced pressure. The obtained residue was subjected to silica gel column chromatography to obtain 1.00 g of 1-(2-bromomethyl-3-nitrophenyl)-4-methyl-1,4-dihydrotetrazol-5-one (C10A).

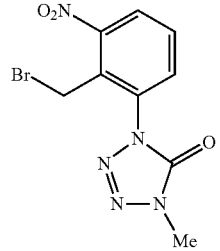 [SMILES: Cn1nnn(-c2cccc([N+](=O)[O-])c2CBr)c1=O]

$^1$H-NMR (CDCl$_3$) δ(ppm): 3.72 (3H, s), 5.63 (2H, s), 7.61 (1H, t, J=8.0 Hz), 7.70 (1H, d, J=8.1 Hz), 7.97 (1H, d, J=8.1 Hz).

Reference Production Example 11

Step (1)

A mixture of 45.0 g C5A, 37.4 g of sodium methoxide, and 600 mL of tetrahydrofuran was stirred at 25° C. for 3 hours. An aqueous saturated sodium bicarbonate solution was poured into the reaction mixture, followed by extraction with ethyl acetate. The organic layer was washed with an aqueous saturated sodium bicarbonate solution, dried over anhydrous sodium sulfate, and then concentrated under reduced pressure to obtain 1-(2-methoxymethyl-3-bromophenyl)-4-methyl-1,4-dihydrotetrazol-5-one.

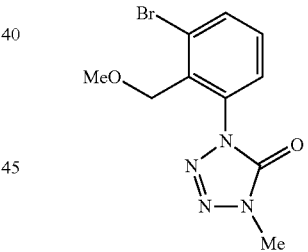

$^1$H-NMR (CDCl$_3$) δ(ppm): 3.23 (3H, s), 3.72 (3H, s), 4.67 (2H, s), 7.33 (1H, t, J=7.8 Hz), 7.38 (1H, dd, J=1.2, 8.1 Hz), 7.76 (1H, dd, J=1.5, 7.8 Hz).

Step (2)

A mixture of 1-(2-methoxymethyl-3-bromophenyl)-4-methyl-1,4-dihydrotetrazol-5-one obtained above, 23.2 g of methylboronic acid, 66.7 g of cesium fluoride, 10.6 g of [1,1'-bis(diphenylphosphino)ferrocene]palladium(II) dichloride dichloromethane adduct, and 500 mL of dioxane was stirred at 90° C. for 5.5 hours. After cooling, the reaction mixture was filtered and the filtrate was concentrated under reduced pressure. The obtained residue was subjected to silica gel column chromatography to obtain 1-(2-methoxymethyl-3-methylphenyl)-4-methyl-1,4-dihydrotetrazol-5-one.

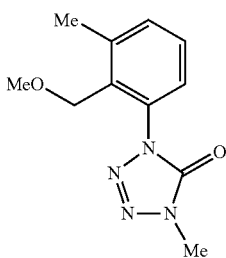 [SMILES: COCc1c(C)cccc1-n1nnn(C)c1=O]

$^1$H-NMR (CDCl$_3$) δ(ppm): 2.48 (3H, s), 3.23 (3H, s), 3.72 (3H, s), 4.42 (2H, s), 7.21 (1H, t, J=5.1 Hz), 7.35 (2H, d, J=4.8 Hz).

Step (3)

A mixture of 1-(2-methoxymethyl-3-methylphenyl)-4-methyl-1,4-dihydrotetrazol-5-one obtained above, 50 mL of acetic acid, and 50 mL of a 25% hydrogen bromide-acetic acid solution was stirred at 65° C. for one hour. An aqueous saturated sodium chloride solution was poured into the reaction mixture, followed by extraction with ethyl acetate. The organic layer was in turn washed with an aqueous saturated sodium bicarbonate solution and anhydrous sodium sulfate, dried over anhydrous sodium sulfate, and then concentrated under reduced pressure to obtain 27.9 g of 1-(2-bromomethyl-3-methylphenyl)-4-methyl-1,4-dihydro-tetrazol-5-one (C11A).

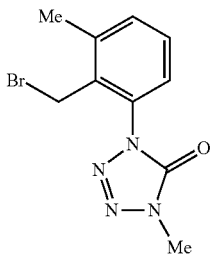

$^1$H-NMR (CDCl$_3$) δ(ppm): 2.51 (3H, s), 3.75 (3H, s), 4.51 (2H, s), 7.22-7.24 (1H, m), 7.36-7.39 (2H, m).

Reference Production Example 12

Step (1)

To a mixture of 15.1 g of 2-amino-6-methylbenzoic acid, 150 mL of ethyl acetate, and 150 mL of ethanol, a 2.0M diethyl ether solution of trimethylsilyldiazomethane was added under ice cooling. After stirring at room temperature for 4 hours, the mixture was concentrated under reduced pressure to obtain 16.5 of 2-amino-6-methylbenzoic acid methyl ester.

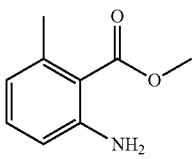

$^1$H-NMR (CDCl$_3$) δ(ppm): 6.94 (1H, t, J=8.0 Hz), 6.40-6.38 (2H, m), 4.96 (2H, s), 3.75 (3H, s), 2.29 (3H, s).

Step (2)

To a mixture of 16.5 g of 2-amino-6-methylbenzoic acid methyl ester and 300 mL of toluene, 44.5 g of triphosgene was added at room temperature, followed by stirring while heating under reflux for 2.5 hours. After concentration under reduced pressure, 2-isocyanate-6-methylbenzoic acid methyl ester was obtained.

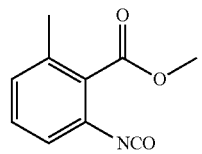

$^1$H-NMR (CDCl$_3$) δ(ppm): 7.28-7.24 (1H, m), 7.07-7.04 (1H, m), 6.98-6.95 (1H, m), 3.97 (3H, s), 2.36 (3H, s).

Step (3)

Under ice cooling, 16.0 g of aluminum trichloride was added to 200 mL of N,N-dimethylformamide, followed by stirring for 0.5 hour. Sodium azide (7.2 g) was added and, after stirring for 0.5 hour, 2-isocyanate-6-methylbenzoic acid methyl ester obtained above was added, followed by heating and stirring at 80° C. for 8 hours. After cooling, 11.5 g of sodium nitrite and 300 mL of ice water were added to the reaction solution, and the mixture was acidified with 10% hydrochloric acid and then extracted with ethyl acetate. The organic layer was washed in turn with water and a saturated saline solution, dried over anhydrous magnesium sulfate, and then concentrated under reduced pressure to obtain 2-methyl-6-(5-oxo-4,5-dihydrotetrazol-1-yl)benzoic acid methyl ester.

To a mixture of 2-methyl-6-(5-oxo-4,5-dihydrotetrazol-1-yl)benzoic acid methyl ester thus obtained and 300 mL of N,N-dimethylformamide, 42.0 g of potassium carbonate and 18.9 g of dimethylsulfuric acid were added at room temperature, followed by stirring for 24 hours. Water was poured into the reaction solution, followed by extraction with ethyl acetate. The organic layer was washed in turn with water and an aqueous saturated sodium bicarbonate solution, dried over anhydrous magnesium sulfate, and then concentrated under reduced pressure. The obtained residue was subjected to silica gel column chromatography to obtain 13.9 g of 2-methyl-6-(4-methyl-5-oxo-4,5-dihydrotetrazol-1-yl)benzoic acid methyl ester.

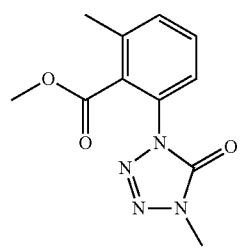 [SMILES: COC(=O)c1c(C)cccc1-n1nnn(C)c1=O]

$^1$H-NMR (CDCl$_3$) δ(ppm): 7.50-7.46 (2H, m), 7.35-7.33 (1H, m), 3.83 (3H, s), 3.69 (3H, s), 2.48 (3H, s).

Step (4)

To a mixture of 25 g of 2-methyl-6-(4-methyl-5-oxo-4,5-dihydro-tetrazol-1-yl)benzoic acid methyl ester and 300 mL of tetrahydrofuran, 201 mL of a 1.0M-tetrahydrofuran solution of lithiumtriethylborane hydride was added at 0° C., followed by stirring at room temperature for 0.5 hour.

Water was poured into the reaction solution, and the solution was acidified with 10% hydrochloric acid and extracted with ethyl acetate.

The organic layer was washed with water, dried over anhydrous magnesium sulfate, and then concentrated under reduced pressure to obtain 21.2 g of 1-(2-hydroxymethyl-3-methylphenyl)-4-methyl-1,4-dihydrotetrazol-5-one.

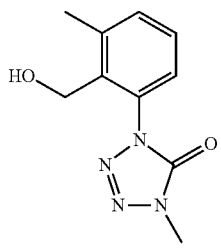 [SMILES: Cc1cccc(-n2nnn(C)c2=O)c1CO]

$^1$H-NMR (CDCl$_3$) δ(ppm): 7.39-7.34 (2H, m), 7.21 (1H, dd, J=6.5, 2.8 Hz), 4.48 (2H, s), 3.75 (3H, s), 2.57 (3H, s), 1.59 (1H, br s).

Step (5)

To a mixture of 21.2 g of 1-(2-hydroxymethyl-3-methylphenyl)-4-methyl-1,4-dihydrotetrazol-5-one and 300 mL of chloroform, 52.1 g of phosphorus tribromide was added, followed by stirring at room temperature for one hour. Ice water (200 mL) was poured into the reaction solution, followed by extraction with ethyl acetate. The organic layer was washed with water and a saturated saline solution, dried over anhydrous magnesium sulfate, and then concentrated under reduced pressure to obtain 26.0 g of C11A.

Reference Production Example 13

Step (1)

A mixture of 33.5 g of 2-methyl-3-nitrophenol, 41 g of iodoethane, 90 g of potassium carbonate, and 400 mL of acetone was stirred while heating under reflux for 10 hours. The mixture was cooled to room temperature and filtered, and the filtrate was concentrated. After extraction with ethyl acetate, the organic layer was washed in turn with water and a saturated saline solution, dried over anhydrous magnesium sulfate, and then concentrated under reduced pressure. The obtained residue was subjected to silica gel column chromatography to obtain 39.9 g of 1-ethoxy-2-methyl-3-nitrobenzene.

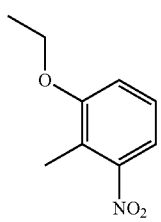

$^1$H-NMR (CDCl$_3$) δ(ppm): 7.39 (1H, dd, J=8.2, 1.0 Hz), 7.24 (1H, t, J=8.3 Hz), 7.02 (1H, d, J=8.2 Hz), 4.08 (2H, q, J=7.0 Hz), 2.37 (3H, s), 1.50-1.42 (3H, m).

Step (2)

A mixture of 39.9 g of 1-ethoxy-2-methyl-3-nitrobenzene, 4 g of palladium-carbon (palladium: 5%), and 200 mL of ethanol was stirred under hydrogen atmosphere at room temperature for 18 hours. The mixture was filtered and the filtrate was concentrated to obtain 33.0 g of 3-ethoxy-2-methylaniline.

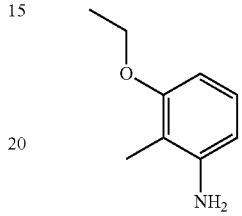

$^1$H-NMR (CDCl$_3$) δ(ppm): 6.95 (1H, t, J=8.1 Hz), 6.35 (1H, d, J=2.9 Hz), 6.33 (1H, d, J=3.1 Hz), 4.02-3.97 (2H, m), 3.61 (2H, br s), 2.05 (3H, s), 1.40 (3H, t, J=7.1 Hz).

Step (3)

To a mixture of 33.0 g of 3-ethoxy-2-methyl-aniline and 400 mL of toluene, 25 g of triphosgene was added at room temperature, followed by stirring while heating under reflux for 4 hours. The mixture was concentrated under reduced pressure to obtain 37.2 g of 1-ethoxy-3-isocyanate-2-methylbenzene.

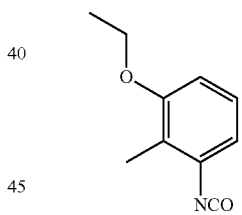

$^1$H-NMR (CDCl$_3$) δ(ppm): 7.07 (1H, t, J=8.2 Hz), 6.70 (1H, d, J=7.7 Hz), 6.68 (1H, d, J=8.2 Hz), 4.02 (2H, q, J=7.0 Hz), 2.20 (3H, s), 1.42 (3H, t, J=7.0 Hz).

Step (4)

To a mixture of 350 mL of N,N-dimethylformamide and 33.6 g of aluminum trichloride, 15 g of sodium azide was added at 0° C., followed by stirring for one hour. Thereafter, 37.2 g of 1-ethoxy-3-isocyanate-2-methylbenzene was added and the reaction mixture was raised to 80° C., followed by stirring for 5 hours. After cooling the mixture, 100 mL of ice water was added to the reaction mixture at 0° C. and a mixture of 23 g of sodium nitrite and 150 mL of water was added. Thereafter, the pH of the mixture was adjusted to about 4 by adding 10% hydrochloric acid. After extraction with ethyl acetate, the organic layer was washed in turn with water and a saturated saline solution, dried over anhydrous magnesium sulfate, and then concentrated under reduced pressure. The obtained residue was subjected to silica gel column chromatography to obtain 39.0 g of 1-(3-ethoxy-2-methylphenyl)-1,4-dihydrotetrazol-5-one.

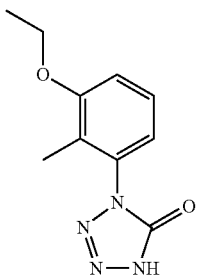 [SMILES: CCOc1cccc(-n2nn[nH]c2=O)c1C]

$^1$H-NMR (CDCl$_3$) δ(ppm): 7.30 (1H, t, J=8.1 Hz), 6.99 (1H, d, J=8.5 Hz), 6.96 (1H, d, J=8.0 Hz), 4.10 (2H, q, J=6.9 Hz), 2.13 (3H, s), 1.46 (3H, t, J=7.0 Hz).

Step (5)

To a mixture of 400 mL of N,N-dimethylformamide, 39.0 g of the above 1-(3-ethoxy-2-methylphenyl)-1,4-dihydrotetrazol-5-one, 36.7 g of potassium carbonate, and 400 mL of N,N-dimethylformamide, 44.7 g of dimethyl sulfate was added at 0° C. and the temperature was raised to room temperature, followed by stirring for 7 hours. Water (100 mL) was added, followed by extraction with ethyl acetate. The organic layer was washed in turn with water and a saturated saline solution, dried over anhydrous magnesium sulfate, and then concentrated under reduced pressure. The obtained residue was subjected to silica gel column chromatography to obtain 38.2 g of 1-(3-ethoxy-2-methylphenyl)-4-methyl-1,4-dihydrotetrazol-5-one.

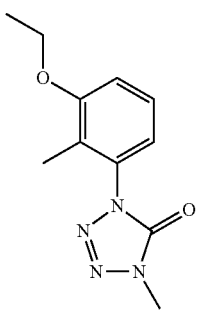 [SMILES: CCOc1cccc(-n2nnn(C)c2=O)c1C]

$^1$H-NMR (CDCl$_3$) δ(ppm): 7.29-7.23 (1H, m), 6.96 (1H, d, J=8.2 Hz), 6.93 (1H, d, J=8.2 Hz), 4.08 (2H, q, J=6.9 Hz), 3.72 (3H, s), 2.11 (3H, s), 1.45 (3H, t, J=7.1 Hz).

Step (6)

A mixture of 38.2 g of 1-(3-ethoxy-2-methylphenyl)-4-methyl-1,4-dihydrotetrazol-5-one, 7.95 g of 1,1'-azobis(cyclohexane-1-carbonitrile), 33.4 g of N-bromosuccinimide, and 380 mL of chlorobenzene was stirred at 120° C. for 5 hours. After cooling, water was poured into the reaction solution, followed by extraction with ethyl acetate. The organic layer was washed in turn with water and a saturated saline solution, dried over anhydrous magnesium sulfate, and then concentrated under reduced pressure. The obtained residue was subjected to silica gel column chromatography to obtain 38.2 g of 1-(3-ethoxy-2-bromomethylphenyl)-4-methyl-1,4-dihydrotetrazol-5-one (C13A).

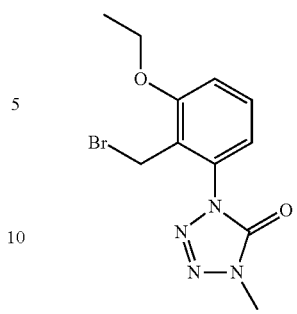

$^1$H-NMR (CDCl$_3$) δ(ppm): 7.40 (1H, t, J=8.2 Hz), 7.01 (2H, t, J=8.3 Hz), 4.64 (2H, s), 4.17 (2H, q, J=7.0 Hz), 3.74 (3H, s), 1.49 (3H, t, J=6.9 Hz).

Reference Production Example 14

Step (1)

A mixture of 29.8 g of 1-(2-methoxymethyl-3-bromophenyl)-4-methyl-1,4-dihydrotetrazol-5-one mentioned in Reference Production Example 11, 35.2 g of tributylvinyltin, 11.6 g of tetrakistriphenylphosphine palladium, and 500 mL of toluene was stirred while heating under reflux for 14 hours.

After cooling, an aqueous saturated ammonium chloride solution was poured into the reaction solution, followed by extraction with ethyl acetate. The organic layer was washed in turn with water and a saturated saline solution, dried over anhydrous magnesium sulfate, and then concentrated under reduced pressure. The obtained residue was subjected to silica gel column chromatography to obtain 19.7 g of 1-(2-methoxymethyl-3-ethenylphenyl)-4-methyl-1,4-dihydrotetrazol-5-one.

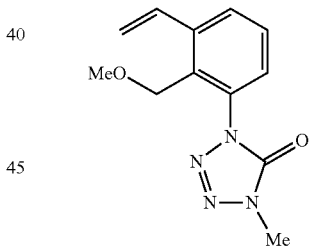

$^1$H-NMR (CDCl$_3$) δ(ppm): 7.67 (1H, dd, J=7.8, 1.3 Hz), 7.44 (1H, t, J=7.8 Hz), 7.29 (1H, dd, J=7.8, 1.3 Hz), 7.11 (1H, dd, J=17.4, 11.1 Hz), 5.72 (1H, dd, J=17.4, 1.3 Hz), 5.44 (1H, dd, J=11.1, 1.3 Hz), 4.45 (2H, s), 3.72 (3H, s), 3.23 (3H, s).

Step (2)

A mixture of 19.7 g of 1-(2-methoxymethyl-3-ethenylphenyl)-4-methyl-1,4-dihydrotetrazol-5-one, 3.02 g of palladium-fibroin complex, and 1 L of methanol was stirred under hydrogen atmosphere at room temperature for 11 hours.

The reaction mixture was filtered and the filtrate was concentrated under reduced pressure. The obtained residue was subjected to silica gel column chromatography to obtain 19.3 g of 1-(2-methoxymethyl-3-ethylphenyl)-4-methyl-1,4-dihydrotetrazol-5-one.

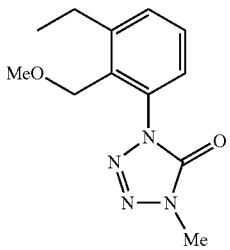

$^1$H-NMR (CDCl$_3$) δ(ppm): 7.42-7.38 (2H, m), 7.23-7.20 (1H, m), 4.44 (2H, s), 3.72 (3H, s), 3.22 (3H, s), 2.82 (2H, q, J=7.6 Hz), 1.27 (3H, t, J=7.6 Hz).

Step (3)

A mixture of 19.3 g of 1-(2-methoxymethyl-3-ethylphenyl)-4-methyl-1,4-dihydrotetrazol-5-one, 40 mL of acetic acid, and 40 mL of a 25% hydrogen bromide-acetic acid solution was stirred at 65° C. for 1.5 hours. An aqueous saturated sodium chloride solution was poured into the reaction mixture, followed by extraction with ethyl acetate. The organic layer was washed with an aqueous saturated sodium bicarbonate solution, dried over anhydrous sodium sulfate, and then concentrated under reduced pressure to obtain 23.3 g of 1-(2-bromomethyl-3-ethylphenyl)-4-methyl-1,4-dihydrotetrazol-5-one (C14A).

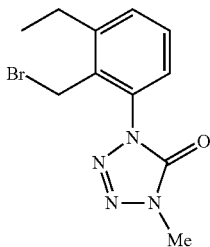

$^1$H-NMR (CDCl$_3$) δ(ppm): 7.44-7.37 (2H, m), 7.23 (1H, dd, J=7.1, 2.0 Hz), 4.56 (2H, s), 3.75 (3H, s), 2.85 (2H, q, J=7.6 Hz), 1.33 (3H, t, J=7.6 Hz).

Reference Production Example 15

Step (1)

A mixture of 9.4 g of sodium borohydride and 150 mL of tetrahydrofuran was stirred at 25° C. for 30 minutes. 2-methyl-3-nitrobenzoic acid (30.8 g) was added, followed by stirring at 25° C. for 30 minutes. After ice cooling of this mixed solution, 11.0 mL of methanesulfonic acid was slowly added over 45 minutes. The reaction mixture was stirred at 25° C. for 3 days. Water was poured into the reaction mixture, followed by extraction with ethyl acetate. The organic layer was washed in turn with 10% hydrochloric acid and a saturated saline solution, dried over anhydrous magnesium sulfate, and then concentrated under reduced pressure to obtain 27.0 g of 3-hydroxymethyl-2-methyl-1-nitrobenzene.

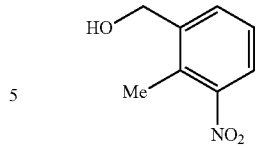

$^1$H-NMR (CDCl$_3$) δ(ppm): 1.81 (1H, s), 2.44 (3H, s), 4.79 (2H, s), 7.34 (1H, t, J=7.8 Hz), 7.65 (1H, d, 7.6 Hz), 7.72 (1H, d, J=8.1 Hz).

Step (2)

A mixture of 17.0 g of 3-hydroxymethyl-2-methyl-1-nitrobenzene, 65.0 g of manganese dioxide, and 170 mL of chloroform was stirred while heating under reflux for 5 hours. The cooled reaction mixture was filtered through cerite and then concentrated under reduced pressure to obtain 14.0 g of 3-formyl-2-methyl-1-nitrobenzene.

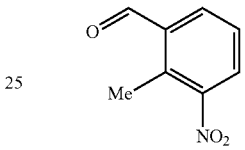

$^1$H-NMR (CDCl$_3$) δ(ppm): 2.78 (3H, s), 7.53 (1H, t, J=8.1 Hz), 7.97 (1H, dd, J=1.5, 8.1 Hz), 8.06 (1H, dd, J=1.5, 7.8 Hz), 10.39 (1H, s).

Step (3)

While cooling a mixture of 13.0 g of 3-formyl-2-methyl-1-nitrobenzene and 200 mL of chloroform at −78° C., 31.7 g of N,N-diethylaminosulfur trifluoride was added dropwise, followed by stirring at 25° C. for 16 hours. Water was poured into the reaction mixture, followed by extraction with chloroform. The organic layer was washed with a saturated saline solution, dried over anhydrous magnesium sulfate, and then concentrated under reduced pressure. The obtained residue was subjected to silica gel column chromatography to obtain 6.8 g of 3-difluoromethyl-2-methyl-1-nitrobenzene.

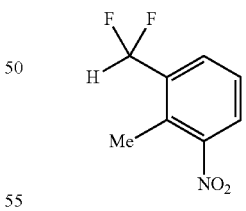

$^1$H-NMR (CDCl$_3$) δ(ppm): 2.54 (3H, s), 6.84 (1H, t, J=54.6 Hz), 7.45 (1H, t, J=7.7 Hz), 7.78 (1H, d, J=7.7 Hz), 7.89 (1H, d, J=8.0 Hz)

Step (4)

A mixture of 6.80 g of 3-difluoromethyl-2-methyl-1-nitrobenzene, 0.30 g of 5% platinum-activated carbon, and 50 mL of methanol was stirred under hydrogen atmosphere at 35° C. for 8 hours. The reaction mixture was filtered through cerite and the filtrate was concentrated under reduced pressure. The obtained residue was subjected to silica gel column chromatography to obtain 3.87 g of 3-difluoromethyl-2-methyl-1-aminobenzene.

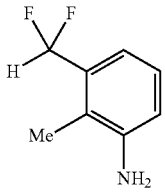

¹H-NMR (CDCl₃) δ(ppm): 2.20 (3H, s), 3.71 (2H, s), 6.72 (1H, t, J=55.5 Hz), 6.79 (1H, d, J=8.0 Hz), 6.92 (1H, d, J=7.7 Hz), 7.09 (1H, t, J=7.7 Hz).

Step (5)

A mixture of 3.87 g of 3-difluoromethyl-2-methyl-1-aminobenzene, 10.96 g of triphosgene, and 80 mL of toluene was stirred while heating under reflux for 3.5 hours. The cooled reaction mixture was concentrated under reduced pressure to obtain 3-difluoromethyl-2-methyl-1-isocyanatebenzene.

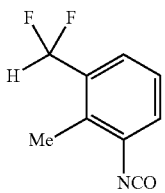

¹H-NMR (CDCl₃) δ(ppm): 2.39 (3H, s), 6.74 (1H, t, J=55.1 Hz), 7.21-7.27 (2H, m), 7.34 (1H, d, J=7.2 Hz).

Step (6)

Under ice cooling, 3.62 g of annhydrous aluminum trichloride was added to 40 mL of N,N-dimethylformamide, followed by stirring for 20 minutes. To this was added 1.76 g of sodium azide and, after stirring for 15 minutes, 3-difluoromethyl-2-methyl-1-isocyanatebenzene obtained above was added, followed by heating at 80° C. for 4 hours. After cooling, the reaction solution was added in a mixture of 6 g of sodium nitrite, 0.5 L of water, and 100 g of ice while stirring. The mixture was acidified with 10% hydrochloric acid and then extracted with ethyl acetate. The organic layer was washed in turn with water and a saturated saline solution, dried over anhydrous magnesium sulfate, and then concentrated under reduced pressure to obtain 3.22 g of 1-(2-methyl-3-difluoromethylphenyl)-1,4-dihydrotetrazol-5-one.

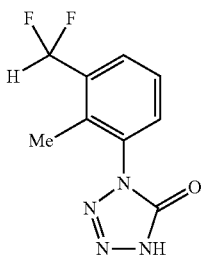 [SMILES: Cc1c(C(F)F)cccc1-n1nn[nH]c1=O]

Step (7)

A mixture of 3.22 g of 1-(2-methyl-3-difluoromethylphenyl)-1,4-dihydrotetrazol-5-one, 3.93 g of potassium carbonate, 4.04 g of methyl iodide, and 70 mL of N,N-dimethylformamide was stirred at 25° C. for 5 hours. Water was poured into the reaction mixture, followed by extraction with ethyl acetate. The organic layer was washed in turn with 10% hydrochloric acid, water, and a saturated saline solution, dried over anhydrous magnesium sulfate, and then concentrated under reduced pressure. The obtained residue was subjected to silica gel column chromatography to obtain 1.14 g of 1-(2-methyl-3-difluoromethylphenyl)-4-methyl-1,4-dihydrotetrazol-5-one.

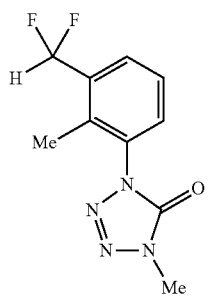 [SMILES: Cc1c(C(F)F)cccc1-n1nnn(C)c1=O]

¹H-NMR (CDCl₃) δ(ppm): 2.31 (3H, s), 3.73 (3H, s), 6.83 (1H, t, J=55.1 Hz), 7.44-7.46 (2H, m), 7.68-7.71 (1H, m).

Step (8)

A mixture of 1.14 g of 1-(2-methyl-3-difluoromethylphenyl)-4-methyl-1,4-dihydrotetrazol-5-one, 0.23 g of 1,1'-azobis(cyclohexane-1-carbonitrile), 0.97 g of N-bromosuccinimide, and 20 mL of chlorobenzene was stirred while heating under reflux for 5 hours. After cooling, water was poured into the reaction solution, followed by extraction with ethyl acetate. The organic layer was washed in turn with water and a saturated saline solution, dried over anhydrous magnesium sulfate, and then concentrated under reduced pressure. The obtained residue was subjected to silica gel column chromatography to obtain 1.21 g of 1-(2-bromomethyl-3-difluoromethylphenyl)-4-methyl-1,4-dihydrotetrazol-5-one (C15A).

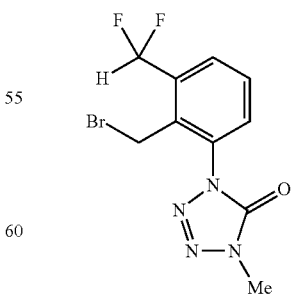

¹H-NMR (CDCl₃) δ(ppm): 3.76 (3H, s), 4.66 (2H, s), 6.99 (1H, t, J=54.8 Hz), 7.55 (1H, d, J=8.0 Hz), 7.60 (1H, t, J=7.7 Hz), 7.56 (1H, d, J=7.5 Hz).

Reference Production Example 16

Step (1)

A mixture of 7.17 g of 2-methyl-3-nitrophenol, 27 g of potassium hydroxide, 25 g of bromodifluoromethyl-diethylphosphonate, 100 mL of water, and 100 mL of acetonitrile was stirred at room temperature for 24 hours. After extraction with ethyl acetate, the organic layer was washed in turn with water and a saturated saline solution, dried over anhydrous magnesium sulfate, and then concentrated under reduced pressure. The obtained residue was subjected to silica gel column chromatography to obtain 7.50 g of 1-difluoromethoxy-2-methyl-3-nitrobenzene.

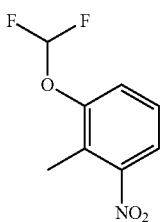

$^1$H-NMR (CDCl$_3$) δ(ppm): 7.74 (1H, dd, J=7.6, 1.8 Hz), 7.40-7.32 (2H, m), 6.56 (1H, t, J=72.4 Hz), 2.46 (3H, s).

Step (2)

A mixture of 7.50 g of 1-difluoromethoxy-2-methyl-3-nitrobenzene, 0.8 g of palladium-carbon (palladium: 5%), and 80 mL of ethanol was stirred under hydrogen atmosphere at room temperature for 8 hours. The mixture was filtered and the filtrate was concentrated to obtain 6.4 g of 3-difluoromethoxy-2-methylaniline

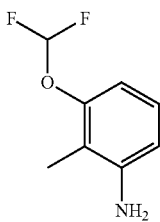

$^1$H-NMR (CDCl$_3$) δ(ppm): 6.99 (1H, t, J=8.1 Hz), 6.55 (1H, d, J=8.0 Hz), 6.51 (1H, d, J=8.2 Hz), 6.46 (1H, td, J=74.4, 0.4 Hz), 3.72 (2H, br s), 2.09 (3H, s).

Step (3)

To a mixture of 6.4 g of 3-difluoromethoxy-2-methylaniline and 100 mL of toluene, 5.48 g of triphosgene was added at room temperature, followed by stirring while heating under reflux for one hour. The mixture was concentrated under reduced pressure to obtain 7.36 g of 1-difluoromethoxy-3-isocyanate-2-methylbenzene.

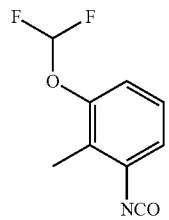

$^1$H-NMR (CDCl$_3$) δ(ppm): 7.14 (1H, t, J=8.1 Hz), 6.97 (2H, t, J=8.5 Hz), 6.50 (1H, td, J=73.6, 0.4 Hz), 2.27 (3H, s).

Step (4)

Under ice cooling, to a mixture of 200 mL of N,N-dimethylformamide and 5.91 g of anhydrous aluminum chloride, 2.64 g of sodium azide was added, followed by stirring for one hour. After the addition of 7.36 g of 1-difluoromethoxy-3-isocyanate-2-methylbenzene, the reaction mixture was raised to 75° C., followed by stirring for 9 hours. The mixture was cooled and 50 mL of ice water was added to the reaction mixture under ice cooling, followed by the addition of a mixture of 4.1 g of sodium nitrite and 100 mL of water. Thereafter, the pH of the mixture was adjusted to about 4 by adding concentrated hydrochloric acid. After extraction with ethyl acetate, the organic layer was washed in turn with water and a saturated saline solution, dried over anhydrous magnesium sulfate, and then concentrated under reduced pressure. To the obtained residue containing 1-(2-methyl-3-difluoromethoxyphenyl)-1,4-dihydrotetrazol-5-one, 100 mL of N,N-dimethylformamide, 7.66 g of potassium carbonate, and 9.32 g of dimethyl sulfate were added, followed by stirring at room temperature for 4 hours. After the addition of 100 mL of water and extraction with ethyl acetate, the organic layer was washed in turn with water and a saturated saline solution, dried over anhydrous magnesium sulfate, and then concentrated under reduced pressure. The obtained residue was subjected to silica gel column chromatography to obtain 1.0 g of 1-(2-methyl-3-difluoromethoxyphenyl)-4-methyl-1,4-dihydrotetrazol-5-one.

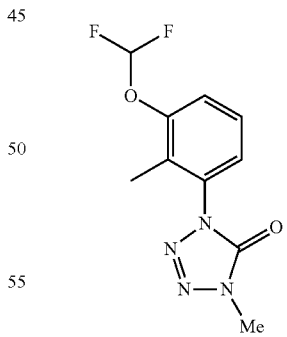

$^1$H-NMR (CDCl$_3$) δ(ppm): 7.34 (1H, t, J=8.1 Hz), 7.30-7.23 (2H, m), 6.55 (1H, t, J=72.8 Hz), 3.73 (3H, d, J=0.5 Hz), 2.21 (3H, s).

Step (5)

A mixture of 1.0 g of 1-(2-methyl-3-difluoromethoxyphenyl)-4-methyl-1,4-dihydrotetrazol-5-one, 0.19 g of 1,1'-azobis(cyclohexane-1-carbonitrile), 0.80 g of N-bromosuccinimide, and 50 mL of chlorobenzene was stirred while heating under reflux for 8 hours. After cooling, water was poured into the reaction solution, followed by extraction with ethyl acetate. The organic layer was washed in turn with water and a saturated saline solution, dried over anhydrous magnesium sulfate, and then concentrated under reduced pressure. The obtained residue was subjected to silica gel column chromatography to obtain 1.1 g of 1-(2-bromomethyl-3-difluoromethoxyphenyl)-4-methyl-1,4-dihydrotetrazol-5-one (C16A).

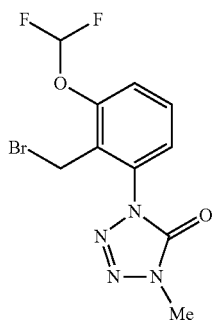 [SMILES: Cn1nnn(-c2cccc(OC(F)F)c2CBr)c1=O]

$^1$H-NMR (CDCl$_3$) δ(ppm): 7.50 (1H, t, J=8.2 Hz), 7.34 (2H, d, J=8.2 Hz), 6.62 (1H, t, J=72.8 Hz), 4.65 (2H, s), 3.76 (3H, d, J=0.5 Hz).

Reference Production Example 17

Step (1)

A mixture of 30.1 g of 1-(2-methoxymethyl-3-bromophenyl)-4-methyl-1,4-dihydrotetrazol-5-one mentioned in Reference Production Example 11, 12.9 g of cyclopropylboronic acid, 46.2 g of cesium fluoride, 8.2 g of a [1,1'-bis(diphenylphosphino)ferrocene]palladium(II) dichloride dichloromethane adduct, and 680 mL of dioxane was stirred at 90° C. for 4 hours. After cooling, the reaction mixture was filtered and the filtrate was concentrated under reduced pressure. The obtained residue was subjected to silica gel column chromatography to obtain 26.0 g of 1-(2-methoxymethyl-3-cyclopropylphenyl)-4-methyl-1,4-dihydrotetrazol-5-one.

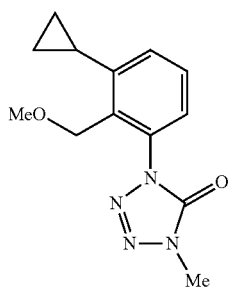 [SMILES: COCc1c(C2CC2)cccc1-n1nnn(C)c1=O]

$^1$H-NMR (CDCl$_3$) δ(ppm): 7.36 (1H, t, J=8.0 Hz), 7.20 (2H, d, J=8.0 Hz), 4.64 (2H, s), 3.72 (3H, s), 3.24 (3H, s), 2.20-2.13 (1H, m), 1.04-1.00 (2H, m), 0.76-0.72 (2H, m).

Step (2)

A mixture of 26.0 g of 1-(2-methoxymethyl-3-cyclopropylphenyl)-4-methyl-1,4-dihydrotetrazol-5-one, 40 mL of acetic acid, and 40 mL of a 25% hydrogen bromide-acetic acid solution was stirred at 65° C. for 2 hours. An aqueous saturated sodium chloride solution was poured into the reaction mixture, followed by extraction with ethyl acetate. The organic layer was washed with an aqueous saturated sodium bicarbonate solution, dried over anhydrous sodium sulfate, and then concentrated under reduced pressure to obtain 30.8 g of 1-(2-bromomethyl-3-cyclopropylphenyl)-4-methyl-1,4-dihydrotetrazol-5-one (C17A).

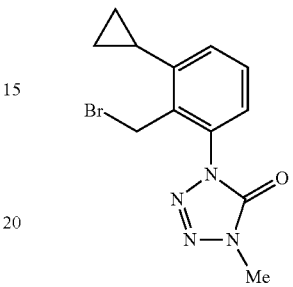

$^1$H-NMR (CDCl$_3$) δ(ppm): 7.38 (1H, t, J=7.8 Hz), 7.26-7.22 (2H, m), 4.77 (2H, s), 3.75 (3H, s), 2.16-2.09 (1H, m), 1.10-1.06 (2H, m), 0.82-0.78 (2H, m).

Reference Production Example 18

Step (1)

Under ice cooling, 0.63 g of 60% sodium hydride was added to a mixture of 4.99 g of triisopropylsilanethiol and 30 mL of toluene, followed by stirring for 30 minutes. To the reaction mixture, 2.82 g of 1-(2-methyl-3-bromophenyl)-4-methyl-1,4-dihydrotetrazol-5-one mentioned in Reference Production Example 5 and 0.856 g of a [1,1'-bis(diphenylphosphino)ferrocene]palladium(II) dichloride dichloromethane adduct was added, and then the temperature of the reaction mixture was raised to 90° C., followed by stirring for 4 hours.

After cooling, water was poured into the reaction mixture, followed by extraction with ethyl acetate. The organic layer was washed in turn with water and a saturated saline solution, dried over anhydrous magnesium sulfate, and then concentrated under reduced pressure. The obtained residue was subjected to silica gel column chromatography to obtain 3.64 g of 1-(2-methyl-3-triisopropylsilanylthiophenyl)-4-methyl-1,4-dihydrotetrazol-5-one.

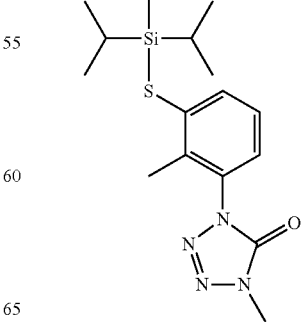

¹H-NMR (CDCl₃) δ(ppm): 1.09 (18H, d, J=6.6 Hz), 1.31 (3H, q, J=6.6 Hz), 2.45 (3H, s), 3.71 (3H, s), 7.16-7.21 (2H, m), 7.64 (1H, dd, J=6.6, 2.7 Hz).

Step (2)

A mixture of 3.63 g of 1-(2-methyl-3-triisopropylsilanyl-thiophenyl)-4-methyl-1,4-dihydrotetrazol-5-one, 2.91 g of cesium fluoride, and 10 mL of N,N-dimethylformamide was stirred at room temperature for 30 minutes.

To the mixture, 2.72 g of methyl iodide was added, followed by stirring at room temperature for 3 hours. Water was poured into the reaction mixture, followed by extraction with ethyl acetate. The organic layer was washed in turn with water and a saturated saline solution, dried over anhydrous magnesium sulfate, and then concentrated under reduced pressure. The obtained residue was subjected to silica gel column chromatography to obtain 1.65 g of 1-(2-methyl-3-methylthiophenyl)-4-methyl-1,4-dihydrotetrazol-5-one

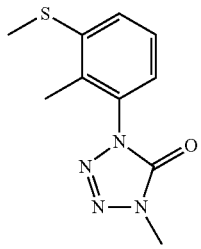 [SMILES: CSc1cccc(-n2nnn(C)c2=O)c1C]

¹H-NMR (CDCl₃) δ(ppm): 2.22 (3H, s), 2.51 (3H, s), 3.72 (3H, s), 7.10-7.16 (1H, m), 7.36-7.29 (2H, m).

Step (3)

A mixture of 1.50 g of 1-(2-methyl-3-methylthiophenyl)-4-methyl-1,4-dihydrotetrazol-5-one, 0.62 g of 1,1'-azobis(cyclohexane-1-carbonitrile), 1.30 g of N-bromosuccinimide, and 15 mL of chlorobenzene was stirred while heating under reflux for 4 hours. After cooling, water was poured into the reaction solution, followed by extraction with ethyl acetate. The organic layer was washed in turn with water and a saturated saline solution, dried over anhydrous magnesium sulfate, and then concentrated under reduced pressure. The obtained residue was subjected to silica gel column chromatography to obtain 0.40 g of 1-(2-bromomethyl-3-methylthiophenyl)-4-methyl-1,4-dihydrotetrazol-5-one (C18A).

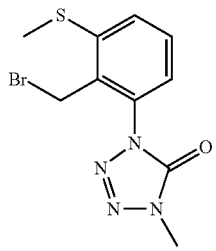

¹H-NMR (CDCl₃) δ(ppm): 2.57 (3H, s), 3.75 (3H, s), 4.69 (2H, s), 7.20 (1H, t, J=4.5 Hz), 7.44 (2H, d, J=4.5 Hz).

Reference Production Example 19

A mixture of 30 mL of ethanol, 5.0 g of 3'-bromo-4'-fluoroacetophenone, 2.4 g of hydroxylamine hydrochloride, and 4.6 mL of pyridine was stirred while heating under reflux for 4 hours. After the solvent was distilled off, hydrochloric acid (1M) was added, followed by extraction three times with ethyl acetate and further washing with a saturated saline solution. The obtained solution was dried over anhydrous magnesium sulfate and then concentrated to obtain a crude product of 1-(3-bromo-4-fluorophenyl)ethanone oxime (C19A).

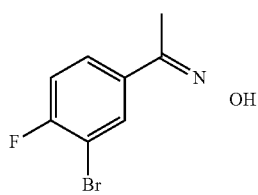

¹H-NMR (CDCl₃) δ(ppm): 9.00 (1H, bs), 7.83 (1H, dd, J=6.5, 2.2 Hz), 7.57-7.53 (1H, m), 7.12 (1H, t, J=8.5 Hz), 2.26 (3H, s).

Reference Production Examples 20 to 74

In the same manner as in Reference Production Example 19, except that each raw material was used in place of a ketone compound, production was performed.

3-(1-hydroxyiminoethyl)benzonitrile (C20A)

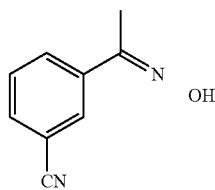

¹H-NMR (CDCl₃) δ(ppm): 8.87 (1H, s), 7.93-7.92 (1H, m), 7.88-7.85 (1H, m), 7.67-7.65 (1H, m), 7.51 (1H, t, J=7.9 Hz), 2.30 (3H, s).

1-(3-methoxyphenyl)ethanone oxime (C21A)

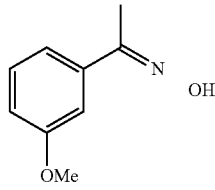

¹H-NMR (CDCl₃) δ(ppm): 7.30 (1H, t, J=7.9 Hz), 7.20-7.16 (2H, m), 6.95-6.92 (1H, m), 3.83 (3H, s), 2.30 (3H, s).

1-(3-nitrophenyl)ethanone oxime (C22A)

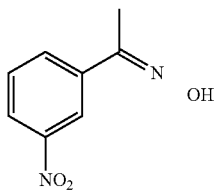

¹H-NMR (CDCl₃) δ(ppm): 8.50 (1H, t, J=2.0 Hz), 8.23 (1H, dq, J=8.2, 1.0 Hz), 8.00 (1H, dt, J=7.9, 1.2 Hz), 7.79 (1H, s), 7.56 (1H, t, J=8.1 Hz), 2.34 (3H, s).

1-(3,5-dimethylphenyl)ethanone oxime (C23A)

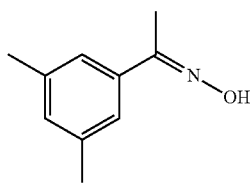

¹H-NMR (CDCl₃) δ(ppm): 7.23 (2H, s), 7.02 (1H, s), 2.34 (6H, s), 2.27 (3H, s).

indan-1-one oxime (C24A)

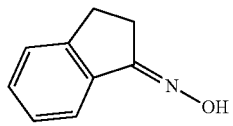 [SMILES: ON=C1CCc2ccccc21]

¹H-NMR (CDCl₃) δ(ppm): 7.77 (1H, d, J=7.8 Hz), 7.59 (1H, t, J=7.4 Hz), 7.49 (1H, d, J=7.8 Hz), 7.37 (1H, t, J=7.4 Hz), 3.17-3.14 (2H, m), 2.72-2.68 (2H, m).

6-methyl-indan-1-one oxime (C25A)

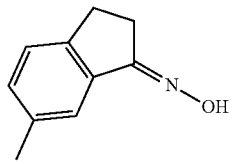

¹H-NMR (CDCl₃) δ(ppm): 7.56 (1H, s), 7.42-7.36 (2H, m), 3.11-3.08 (2H, m), 2.70-2.68 (2H, m), 2.41 (3H, s).

1-(naphthalen-2-yl)ethanone oxime (C26A)

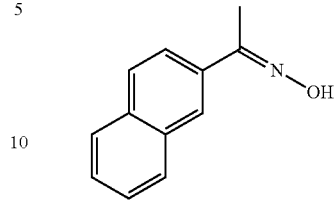

¹H-NMR (DMSO-D₆) δ(ppm): 11.34 (1H, s), 8.13 (1H, s), 7.99-7.97 (1H, m), 7.94-7.87 (3H, m), 7.53 (2H, t, J=4.4 Hz), 2.28 (3H, s).

1-(naphthalen-1-yl)ethanone oxime (C27A)

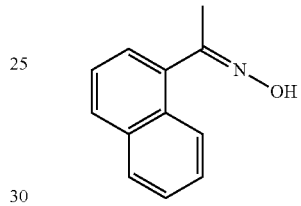

¹H-NMR (CDCl₃) δ(ppm): 8.62 (1H, s), 8.04-8.00 (1H, m), 7.90-7.84 (2H, m), 7.55-7.44 (4H, m), 2.38 (3H, s).

1-(3-chlorophenyl)ethanone oxime (C28A)

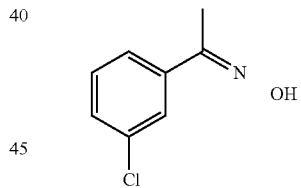

¹H-NMR (CDCl₃) δ(ppm): 8.23 (1H, s), 7.62 (1H, t, J=1.8 Hz), 7.51 (1H, dt, J=7.3, 1.6 Hz), 7.37-7.29 (2H, m), 2.27 (3H, s).

1-(2-trifluoromethylphenyl)ethanone oxime (C29A)

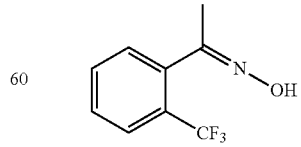

¹H-NMR (CDCl₃) δ(ppm): 8.33 (1H, s), 7.70 (1H, d, J=7.8 Hz), 7.56 (1H, t, J=7.6 Hz), 7.49 (1H, t, J=7.7 Hz), 7.36 (1H, d, J=7.6 Hz), 2.22 (3H, s).

309

1-(indan-5-yl)ethanone oxime (C30A)

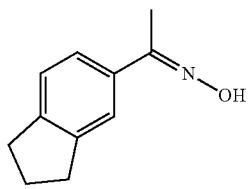

¹H-NMR (CDCl₃) δ(ppm): 7.49 (1H, s), 7.40 (1H, d, J=8.0 Hz), 7.23 (1H, d, J=7.7 Hz), 2.92 (4H, m), 2.29 (3H, s), 2.09 (2H, m).

1-(3,5-dichlorophenyl)ethanone oxime (C31A)

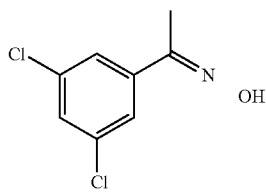

¹H-NMR (CDCl₃) δ(ppm): 8.06 (1H, s), 7.51 (2H, d, J=2.0 Hz), 7.36 (1H, t, J=1.8 Hz), 2.25 (3H, s).

6-chloroindan-1-one oxime (C32A)

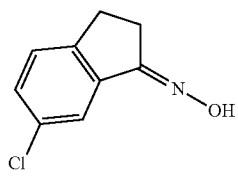 [SMILES: ON=C1CCc2ccc(Cl)cc21]

¹H-NMR (CDCl₃) δ(ppm): 7.63 (1H, d, J=2.0 Hz), 7.31 (1H, d, J=8.2, 2.1 Hz), 7.24 (1H, dd, J=8.2, 0.6 Hz), 3.05-2.97 (4H, m).

1-(3,5-ditrifluoromethylpheny)ethanone oxime (C33A)

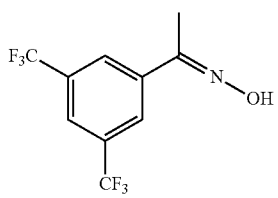 [SMILES: CC(=NO)c1cc(C(F)(F)F)cc(C(F)(F)F)c1]

¹H-NMR (CDCl₃) δ(ppm): 8.09 (2H, s), 7.88 (1H, s), 7.86 (1H, s), 2.33 (3H, s).

310

1-(3-trifluoromethoxyphenyl)ethanone oxime (C34A)

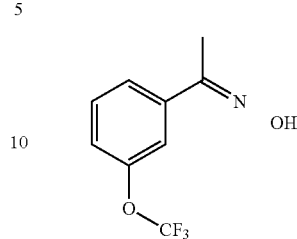

¹H-NMR (CDCl₃) δ(ppm): 8.38 (1H, bs), 7.56 (1H, d, J=7.7 Hz), 7.50 (1H, s), 7.41 (1H, t, J=8.0 Hz), 7.24 (1H, d, J=8.2 Hz), 2.29 (3H, s).

2,2,2-trifluoro-1-phenylethanone oxime (C35A)

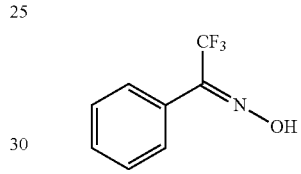

¹H-NMR (CDCl₃) δ(ppm): 7.53-7.40 (5H, m).

1-(4-trifluoromethylphenyl)ethanone oxime (C36A)

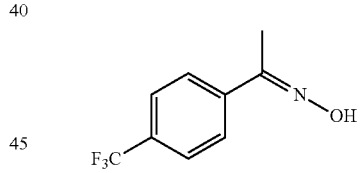

¹H-NMR (CDCl₃) δ(ppm): 7.74 (2H, d, J=8.2 Hz), 7.64 (2H, d, J=8.2 Hz), 2.32 (3H, s).

1-(3,5-difluorophenyl)ethanone oxime (C37A)

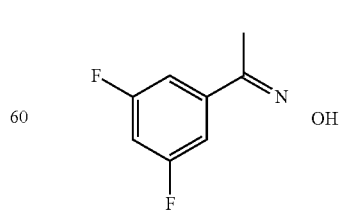

¹H-NMR (CDCl₃) δ(ppm): 7.98 (1H, s), 7.18-7.15 (2H, m), 6.82 (1H, tt, J=8.8, 2.3 Hz), 2.25 (3H, s).

3-trifluoromethylbenzaldehyde oxime (C38A)

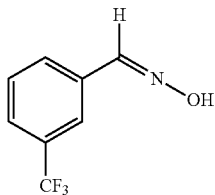 [SMILES: ON=Cc1cccc(C(F)(F)F)c1]

¹H-NMR (CDCl₃) δ(ppm): 8.17 (1H, s), 7.85 (1H, s), 7.75 (1H, d, J=7.6 Hz), 7.64 (1H, d, J=7.8 Hz), 7.52 (1H, m).

1-(3-trifluoromethylphenyl)propan-1-one oxime (C39A)

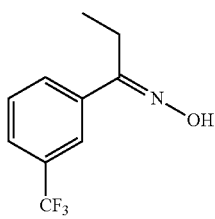

¹H-NMR (CDCl₃) δ(ppm): 8.30 (1H, bs), 7.88 (1H, s), 7.80 (1H, d, J=7.8 Hz), 7.63 (1H, d, J=7.8 Hz), 7.51 (1H, t, J=7.9 Hz), 2.84 (2H, q, J=7.6 Hz), 1.18 (3H, t, J=7.7 Hz).

1-(benzo[1,3]dioxan-5-yl)ethanone oxime (C40A)

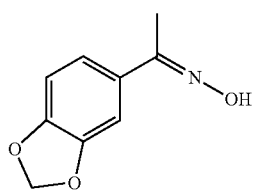

¹H-NMR (DMSO-D₆) δ(ppm): 11.04 (1H, bs), 7.20 (1H, d, J=1.6 Hz), 7.12 (1H, dd, J=8.1, 1.7 Hz), 6.91 (1H, d, J=8.0 Hz), 6.03 (2H, s), 2.10 (3H, s).

4-chloroindan-1-one oxime (C41A)

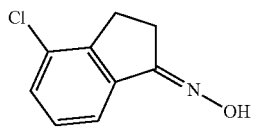 [SMILES: ON=C1CCc2c(Cl)cccc21]

¹H-NMR (CDCl₃) δ(ppm): 7.80 (1H, bs), 7.56 (1H, d, J=7.8 Hz), 7.34 (1H, d, J=7.8 Hz), 7.22 (1H, t, J=7.8 Hz), 3.10-3.06 (2H, m), 3.01-2.97 (2H, m).

1-(3-trifluoromethylphenyl)ethanone oxime (C42A)

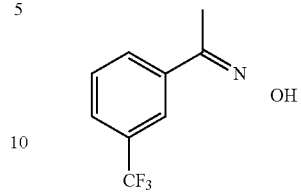

¹H-NMR (CDCl₃) δ(ppm): 7.97-7.90 (2H, m), 7.82 (1H, d, J=8.0 Hz), 7.63 (1H, d, J=7.7 Hz), 7.51 (1H, t, J=7.9 Hz), 2.31 (3H, s).

1-(3,4-dichlorophenyl)ethanone oxime (C43A)

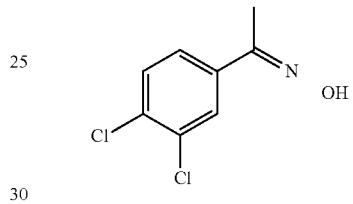

¹H-NMR (CDCl₃) δ(ppm): 7.78 (1H, bs), 7.73 (1H, d, J=1.8 Hz), 7.48 (1H, dd, J=8.4, 2.0 Hz), 7.44 (1H, d, J=8.5 Hz), 2.25 (3H, s).

1-(3,4-difluorophenyl)ethanone oxime (C44A)

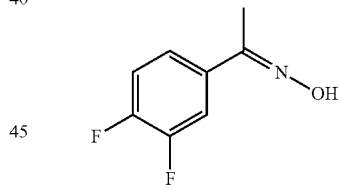

¹H-NMR (CDCl₃) δ(ppm): 8.58 (1H, bs), 7.51-7.45 (1H, m), 7.38-7.33 (1H, m), 7.20-7.13 (1H, m), 2.26 (3H, s).

1-(5,6,7,8-tetrahydronaphthalen-2-yl)ethanone oxime (C45A)

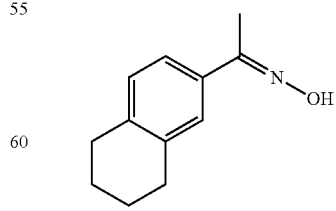

¹H-NMR (CDCl₃) δ(ppm): 8.61 (1H, bs), 7.34 (1H, d, J=8.0 Hz), 7.32 (1H, s), 7.07 (1H, d, J=8.0 Hz), 2.80-2.76 (4H, m), 2.27 (3H, s), 1.83-1.78 (4H, m).

1-(3-methylphenyl)ethanone oxime (C46A)

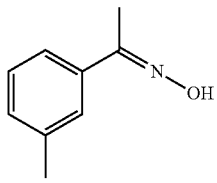

¹H-NMR (CDCl₃) δ(ppm): 8.51 (1H, bs), 7.44-7.41 (2H, m), 7.29 (1H, d, J=7.7 Hz), 7.19 (1H, d, J=7.5 Hz), 2.38 (3H, s), 2.29 (3H, s).

1-(2-trifluoromethylphenyl)propan-1-one oxime (C47A)

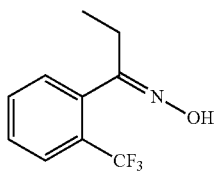

¹H-NMR (CDCl₃) δ(ppm): 7.72-7.70 (1H, m), 7.55-7.54 (1H, m), 7.50-7.48 (1H, m), 7.32 (1H, d, J=7.6 Hz), 2.76 (2H, q, J=7.7 Hz), 1.01 (3H, t, J=7.7 Hz).

1-(4-trifluoromethylphenyl)propan-1-one oxime (C48A)

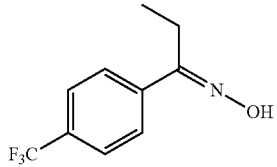

¹H-NMR (CDCl₃) δ(ppm): 8.13 (1H, bs), 7.74 (2H, d, J=8.2 Hz), 7.64 (2H, d, J=8.2 Hz), 2.84 (2H, q, J=7.6 Hz), 1.18 (3H, t, J=7.6 Hz).

1-(5-fluoro-3-trifluoromethylphenyl)propan-1-one oxime (C49A)

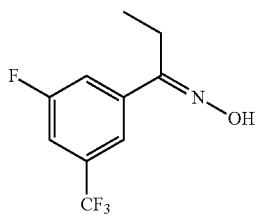

¹H-NMR (CDCl₃) δ(ppm): 7.67 (1H, s), 7.51 (1H, dt, J=9.5, 1.8 Hz), 7.34 (1H, d, J=8.2 Hz), 2.82 (2H, q, J=7.6 Hz), 1.18 (3H, t, J=7.7 Hz).

1-(3-iodophenyl)ethanone oxime (C50A)

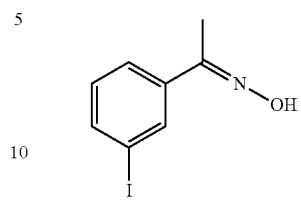

¹H-NMR (CDCl₃) δ(ppm): 8.95 (1H, bs), 7.96 (1H, s), 7.70 (1H, d, J=8.0 Hz), 7.58 (1H, d, J=7.8 Hz), 7.12 (1H, t, J=7.9 Hz), 2.26 (3H, s).

1-(3-bromophenyl)ethanone oxime (C51A)

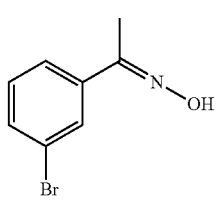

¹H-NMR (CDCl₃) δ(ppm): 8.93 (1H, bs), 7.76 (1H, t, J=1.8 Hz), 7.55 (1H, d, J=7.8 Hz), 7.51 (1H, d, J=8.0 Hz), 7.25 (1H, t, J=7.9 Hz), 2.28 (3H, s).

1-(2-methylphenyl)ethanone oxime (C52A)

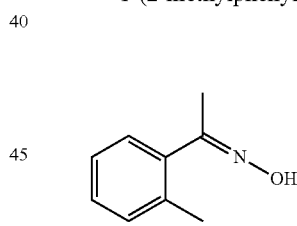

¹H-NMR (CDCl₃) δ(ppm): 7.26-7.20 (4H, m), 2.35 (3H, s), 2.23 (3H, s).

1-(2-chlorophenyl)ethanone oxime (C53A)

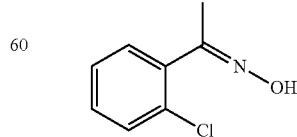

¹H-NMR (CDCl₃) δ(ppm): 7.91 (1H, bs), 7.42-7.39 (1H, m), 7.33-7.29 (3H, m), 2.27 (3H, s).

1-(2-methoxyphenyl)ethanone oxime (C54A)

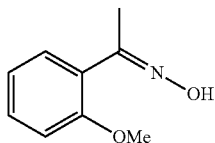

¹H-NMR (CDCl₃) δ(ppm): 8.98 (1H, bs), 7.36-7.29 (2H, m), 6.97-6.90 (2H, m), 3.84 (3H, s), 2.24 (3H, s).

1-(3-difluoromethylphenyl)ethanone oxime (C55A)

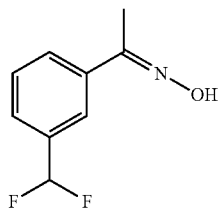

¹H-NMR (CDCl₃) δ(ppm): 8.39 (1H, s), 7.77-7.74 (2H, m), 7.54-7.46 (2H, m), 6.67 (1H, t, J=56.3 Hz), 2.32 (3H, s).

1-(2,2-difluorobenzo[1,3]dioxan-5-yl)ethanone oxime (C56A)

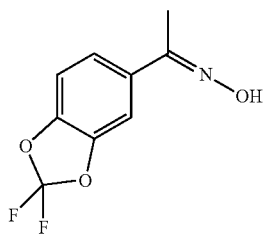

¹H-NMR (CDCl₃) δ(ppm): 7.92 (1H, bs), 7.41 (1H, d, J=1.7 Hz), 7.34 (1H, dd, J=8.5, 1.7 Hz), 7.06 (1H, d, J=8.3 Hz), 2.27 (3H, s).

1-[3-(1,1,2,2-tetrafluoroethoxyl)phenyl]ethanone oxime (C57A)

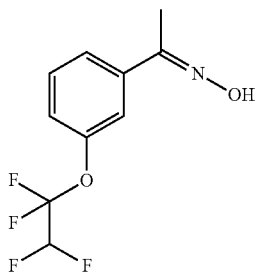 [SMILES: CC(=NO)c1cccc(OC(F)(F)C(F)F)c1]

¹H-NMR (CDCl₃) δ(ppm): 8.41 (1H, bs), 7.55 (1H, dt, J=7.8, 1.3 Hz), 7.49 (1H, s), 7.40 (1H, t, J=8.1 Hz), 7.25-7.22 (1H, m), 5.92 (1H, tt, J=53.2, 2.9 Hz), 2.29 (3H, s).

1-(3-difluoromethoxyphenyl)ethanone oxime (C58A)

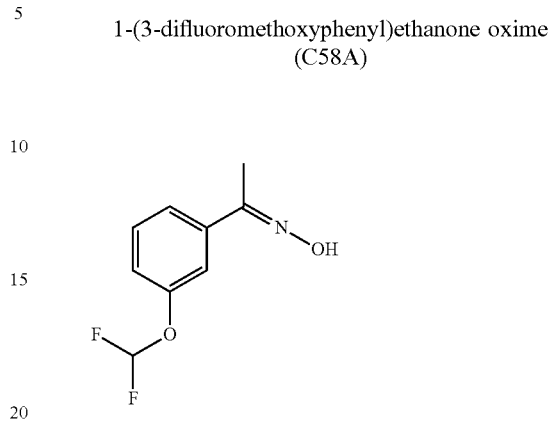

¹H-NMR (CDCl₃) δ(ppm): 7.47-7.44 (1H, m), 7.40-7.36 (2H, m), 7.14 (1H, dd, J=7.8, 1.7 Hz), 6.54 (1H, t, J=73.8 Hz), 2.29 (3H, s).

cyclopropyl (3-trifluoromethylphenyl)methanone oxime (C59A)

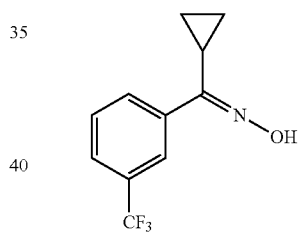

¹H-NMR (CDCl₃) δ(ppm): 7.74-7.46 (4H, m), 2.28-2.21 (0.7H, m), 1.76-1.70 (0.3H, m), 1.04-0.97 (1.3H, m), 0.90-0.81 (1.3H, m), 0.64 (1.4H, m).

2-methyl-1-(3-trifluoromethylphenyl)propan-1-one oxime (C60A)

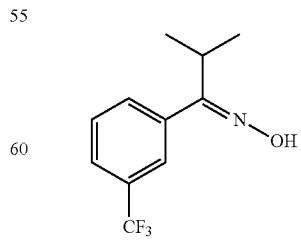

MS, m/z: 231 (M+).

1-(3-trifluoromethylphenyl)pentan-1-one oxime (C61A)

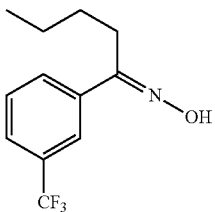 [SMILES: CCCCC(=NO)c1cccc(C(F)(F)F)c1]

$^1$H-NMR (CDCl$_3$) δ(ppm): 7.89 (1H, s), 7.79 (1H, d, J=7.8 Hz), 7.62 (1H, d, J=7.8 Hz), 7.50 (2H, t, J=7.8 Hz), 2.84-2.80 (2H, m), 1.53-1.50 (2H, m), 1.45-1.36 (2H, m), 0.93 (3H, t, J=7.3 Hz).

1-(3-trifluoromethylphenyl)heptan-1-one oxime (C62A)

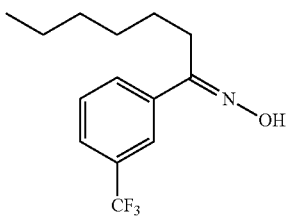 [SMILES: CCCCCCC(=NO)c1cccc(C(F)(F)F)c1]

$^1$H-NMR (CDCl$_3$) δ(ppm): 7.88 (1H, s), 7.78 (1H, d, J=7.6 Hz), 7.62 (1H, d, J=7.6 Hz), 7.52-7.48 (2H, m), 2.80 (2H, t, J=7.8 Hz), 1.55-1.51 (2H, m), 1.42-1.35 (2H, m), 1.30-1.27 (4H, m), 0.89-0.86 (3H, m). 3-methyl-1-(3-trifluoromethylphenyl)butan-1-one oxime (C63A)

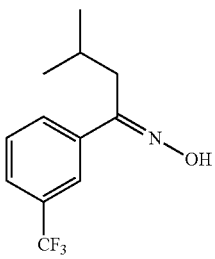 [SMILES: CC(C)CC(=NO)c1cccc(C(F)(F)F)c1]

$^1$H-NMR (CDCl$_3$) δ(ppm): 8.09 (1H, bs), 7.87 (1H, s), 7.78 (1H, d, J=7.8 Hz), 7.62 (1H, d, J=7.8 Hz), 7.50 (1H, t, J=7.8 Hz), 2.76 (2H, d, J=7.6 Hz), 1.95 (1H, sep, J=6.9 Hz), 0.94 (6H, d, J=6.6 Hz). 2,2-dimethyl-1-(3-trifluoromethylphenyl)propan-1-one oxime (C64A)

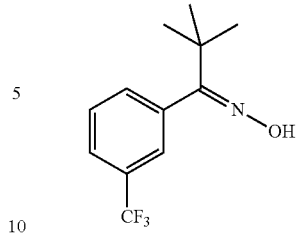

$^1$H-NMR (CDCl$_3$) δ(ppm): 7.63 (1H, d, J=8.1 Hz), 7.55 (1H, t, J=7.4 Hz), 7.36 (1H, s), 7.30 (1H, d, J=7.6 Hz), 7.23-7.16 (1H, m), 1.17 (9H, s).

N-[3-(1-hydroxyiminoethyl)phenyl]acetamide (C65A)

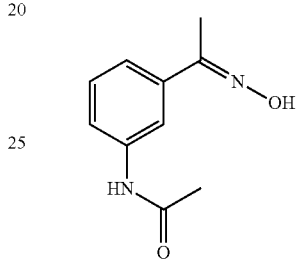

$^1$H-NMR (DMSO-D$_6$) δ(ppm): 11.21 (1H, bs), 9.99 (1H, s), 7.91 (1H, s), 7.58 (1H, t, J=7.8 Hz), 7.29-7.30 (2H, m), 2.13 (3H, s), 2.05 (3H, s).

N-[3-(1-hydroxyiminoethyl)phenyl]-N-methylacetamide (C66A)

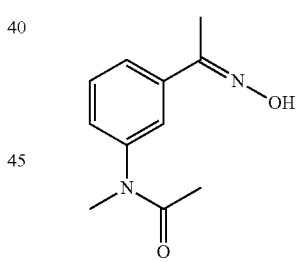

$^1$H-NMR (CDCl$_3$) δ(ppm): 7.57 (1H, d, J=7.8 Hz), 7.53-7.52 (1H, m), 7.43 (1H, t, J=7.9 Hz), 7.20 (1H, d, J=7.8 Hz), 3.29 (3H, s), 2.29 (3H, s), 1.91 (3H, s).

1-(3-hexyloxyphenyl)ethanone oxime (C67A)

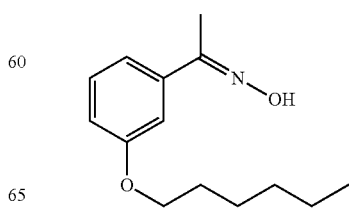

¹H-NMR (CDCl₃) δ(ppm): 7.81 (1H, bs), 7.30-7.26 (1H, m), 7.19-7.17 (2H, m), 6.93-6.90 (1H, m), 3.98 (2H, t, J=6.5 Hz), 2.27 (3H, s), 1.82-1.75 (2H, m), 1.50-1.43 (2H, m), 1.36-1.32 (4H, m), 0.92-0.89 (3H, m). 1-(3-isopropoxyphenyl)ethanone oxime (C68A)

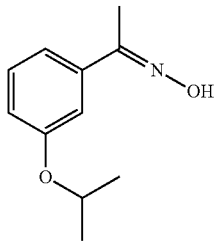

¹H-NMR (CDCl₃) δ(ppm): 7.29 (1H, d, J=8.2 Hz), 7.18-7.16 (2H, m), 6.92-6.89 (1H, m), 4.59 (1H, spt, J=6.1 Hz), 2.27 (3H, s), 1.35 (6H, d, J=6.2 Hz). 1-(3-pentyloxyphenyl)ethanone oxime (C69A)

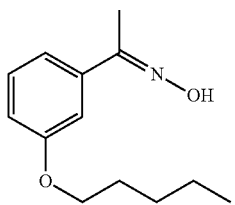 [SMILES: CCCCCOc1cccc(C(C)=NO)c1]

¹H-NMR (CDCl₃) δ(ppm): 8.45 (1H, bs), 7.30-7.28 (1H, m), 7.19-7.17 (2H, m), 6.92-6.90 (1H, m), 3.98 (2H, t, J=6.5 Hz), 2.28 (3H, s), 1.83-1.76 (2H, m), 1.48-1.34 (4H, m), 0.93 (3H, t, J=7.0 Hz). 1-(3-trifluoromethylphenyl)butan-1-one oxime (C70A)

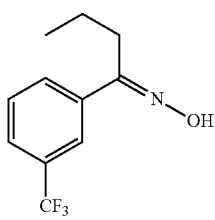 [SMILES: CCCC(=NO)c1cccc(C(F)(F)F)c1]

¹H-NMR (CDCl₃) δ(ppm): 7.86 (1H, s), 7.77 (1H, d, J=7.8 Hz), 7.63 (1H, d, J=7.8 Hz), 7.51 (1H, t, J=7.8 Hz), 2.81 (2H, t, J=7.8 Hz), 1.65-1.56 (2H, m), 0.99 (3H, t, J=7.4 Hz).

1-[3-(butyn-2-yloxy)phenyl]ethanone oxime (C71A)

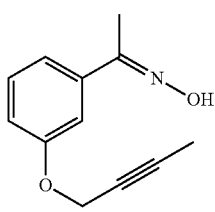

¹H-NMR (CDCl₃) δ(ppm): 8.79 (1H, bs), 7.31 (1H, t, J=8.1 Hz), 7.24-7.23 (2H, m), 7.00-6.97 (1H, m), 4.68 (2H, q, J=2.2 Hz), 2.28 (3H, s), 1.87 (3H, t, J=2.0 Hz).

1-[3-(pentyn-2-yloxy)phenyl]ethanone oxime (C72A)

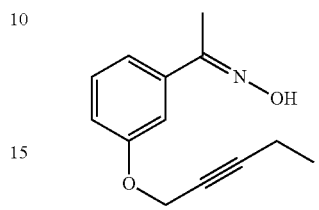

¹H-NMR (CDCl₃) δ(ppm): 7.30 (1H, t, J=8.1 Hz), 7.24-7.22 (2H, m), 7.01-6.98 (1H, m), 4.69 (2H, t, J=2.1 Hz), 2.29 (3H, s), 2.28-2.23 (2H, m), 1.14 (3H, t, J=7.4 Hz). 1-(3-dimethylaminophenyl)ethanone oxime (C73A)

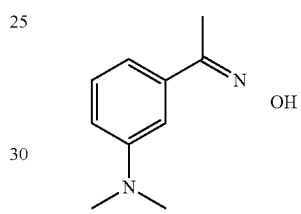

¹H-NMR (CDCl₃) δ(ppm): 7.27-7.23 (1H, m), 7.00 (1H, s), 6.94 (1H, d, J=7.8 Hz), 6.77 (1H, dd, J=8.2, 2.5 Hz), 2.98 (6H, s), 2.29 (3H, s).

1-(3-trifluoromethylphenyl)-1-hydroxyimino-2,2,2-trifluoroethane (C74A)

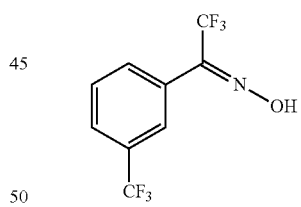

¹H-NMR (CDCl₃) δ(ppm): 7.73-7.50 (4H, m).

Reference Production Example 75

Under nitrogen atmosphere, to a mixture of 100 mL of chloroform and 1.89 g of C39A, 1.40 g of N-chlorosuccinimide was added at 0° C. and the temperature was raised to room temperature, followed by stirring for 2 hours. Water was added, followed by extraction three times with chloroform and further washing with a saturated saline solution. The obtained solution was dried over anhydrous sodium sulfate and then concentration to obtain a crude product. The crude product was subjected to silica gel column chromatography to obtain 1.86 g of α-chloro-(3-trifluoromethylbenzaldehyde)oxime (C75A).

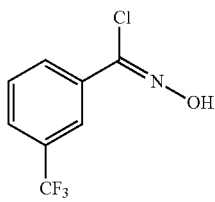 [SMILES: ON=C(Cl)c1cccc(C(F)(F)F)c1]

¹H-NMR (CDCl₃) δ(ppm): 8.12 (1H, s), 8.04 (1H, d, J=8.0 Hz), 7.88 (1H, s), 7.70 (1H, d, J=7.8 Hz), 7.55 (1H, t, J=7.9 Hz).

Reference Production Example 76

To a mixture of tetrahydrofuran and 4.66 g of C96A, 32 mL of 1M-methylmagnesium bromide tetrahydrofuran solvent was added dropwise at 0° C., followed by stirring while heating under reflux for 4 hours and further stirring at room temperature for 10 hours. After completion of the reaction, an aqueous saturated ammonium chloride solution was added, and the mixture was extracted three times with ethyl acetate, dried over anhydrous magnesium sulfate, and then concentrated to obtain a crude product of 1-(3-difluoromethylphenyl)ethanone (C76A).

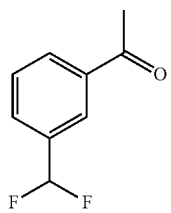

¹H-NMR (CDCl₃) δ(ppm): 8.10-8.07 (2H, m), 7.73 (1H, d, J=7.6 Hz), 7.58 (1H, t, J=7.8 Hz), 6.71 (1H, t, J=56.2 Hz), 2.65 (3H, s).

Reference Production Examples 77 to 78

In the same manner as in Reference Production Example 76, except that each raw material was used in place of an amide compound, production was performed.

1-(2,2-difluorobenzo[1,3]dioxol-5-yl)ethanone (C77A)

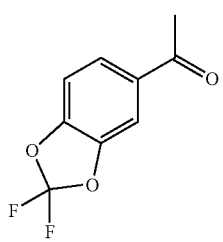

¹H-NMR (CDCl₃) δ(ppm): 7.78 (1H, dd, J=8.3, 1.7 Hz), 7.69 (1H, d, J=1.7 Hz), 7.14 (1H, d, J=8.3 Hz), 2.60 (3H, s).

1-[3-(1,1,2,2-tetrafluoroethoxyl)phenyl]ethanone (C78A)

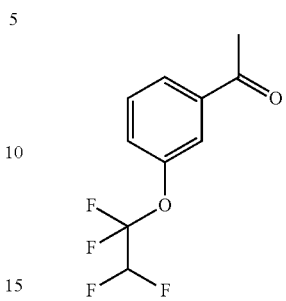

¹H-NMR (CDCl₃) δ(ppm): 7.88 (1H, dt, J=7.6, 1.3 Hz), 7.79 (1H, s), 7.51 (1H, t, J=7.9 Hz), 7.44-7.41 (1H, m), 5.94 (1H, tt, J=53.1, 2.8 Hz), 2.62 (3H, s).

Reference Production Example 79

To a mixture of 50 mL of acetonitrile, 50 mL of water, 10.5 g of potassium hydroxide, and 1.27 g of 3-hydroxyacetophenone, 5.0 g of bromodifluoromethyl diethylphosphonate was added dropwise at −78° C.

The temperature was raised to room temperature, followed by stirring for 3 hours. After completion of the reaction, the reaction solution was extracted with ethyl acetate and the obtained crude product was subjected to silica gel column chromatography to obtain 1-(3-difluoromethylphenyl)ethanone (C79A).

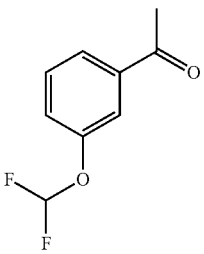

¹H-NMR (CDCl₃) δ(ppm): 7.80 (1H, dt, J=7.8, 1.2 Hz), 7.70 (1H, t, J=1.7 Hz), 7.48 (1H, t, J=7.9 Hz), 7.34 (1H, dd, J=8.2, 2.1 Hz), 6.57 (1H, t, J=73.3 Hz), 2.61 (3H, s).

Reference Production Example 80

Under nitrogen atmosphere, to a mixture of 200 mL of tetrahydrofuran and 4.66 g of C99A, 80 mL of a 0.5M-cyclopropylmagnesium bromide-tetrahydrofuran solution was added dropwise at 0° C., followed by stirring for 2 hours. After completion of the reaction, an aqueous saturated ammonium chloride solution was added, and the mixture was extracted three times with ethyl acetate, dried over anhydrous magnesium sulfate, and then concentration to obtain a crude product.

The obtained crude product was subjected to silica gel column chromatography to obtain 0.55 g of cyclopropyl(3-trifluoromethylphenyl)methanone (C80A).

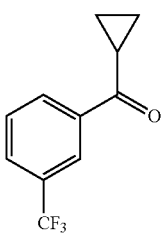

¹H-NMR (CDCl₃) δ(ppm): 8.26 (1H, s), 8.19 (1H, d, J=7.8 Hz), 7.82 (1H, d, J=7.8 Hz), 7.62 (1H, t, J=7.9 Hz), 2.71-2.63 (1H, m), 1.32-1.28 (2H, m), 1.14-1.10 (2H, m).

Reference Production Examples 81 to 85

In the same manner as in Reference Production Example 80, except that each raw material was used in place of a Grignard reagent, production was performed.

2-methyl-1-(3-trifluoromethylphenyl)propan-1-one (C81A)

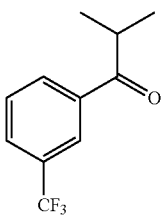

¹H-NMR (CDCl₃) δ(ppm): 8.20 (1H, s), 8.14 (1H, d, J=7.9 Hz), 7.82 (1H, d, J=7.8 Hz), 7.62 (1H, t, J=7.9 Hz), 3.56 (1H, sep, J=7.9 Hz), 1.24 (6H, d, J=7.9 Hz) 1-(3-trifluoromethylphenyl)butan-1-one (C82A)

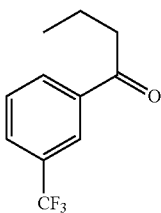

¹H-NMR (CDCl₃) δ(ppm): 8.21 (1H, s), 8.14 (1H, d, J=7.8 Hz), 7.81 (1H, d, J=7.8 Hz), 7.61 (1H, t, J=7.8 Hz), 2.98 (2H, t, J=7.3 Hz), 1.84-1.76 (2H, m), 1.02 (3H, t, J=7.4 Hz). 1-(3-trifluoromethylphenyl)pentan-1-one (C83A)

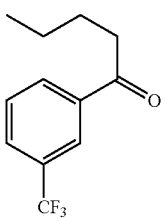

¹H-NMR (CDCl₃) δ(ppm): 8.21 (1H, s), 8.14 (1H, d, J=7.8 Hz), 7.81 (1H, d, J=7.1 Hz), 7.61 (1H, t, J=7.8 Hz), 3.00 (2H, t, J=7.3 Hz), 1.76-1.70 (2H, m), 1.47-1.38 (2H, m), 0.97 (3H, t, J=7.4 Hz).

1-(3-trifluoromethylphenyl)heptan-1-one (C84A)

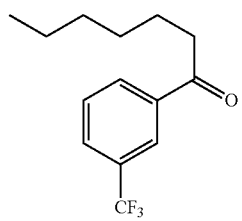 [SMILES: CCCCCCC(=O)c1cccc(C(F)(F)F)c1]

¹H-NMR (CDCl₃) δ(ppm): 8.20 (1H, s), 8.14 (1H, d, J=8.0 Hz), 7.81 (1H, d, J=7.8 Hz), 7.61 (1H, t, J=7.9 Hz), 2.99 (2H, t, J=7.4 Hz), 1.79-1.71 (2H, m), 1.43-1.30 (6H, m), 0.92-0.88 (3H, m). 3-methyl-1-(3-trifluoromethylphenyl)butan-1-one (C85A)

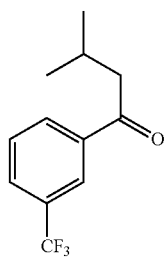

¹H-NMR (CDCl₃) δ(ppm): 8.20 (1H, s), 8.13 (1H, d, J=8.0 Hz), 7.81 (1H, d, J=7.8 Hz), 7.61 (1H, t, J=7.8 Hz), 2.87 (2H, d, J=6.8 Hz), 2.31 (1H, sep, J=6.8 Hz), 1.02 (6H, d, J=6.8 Hz).

Reference Production Example 86

Under nitrogen atmosphere, to a mixture of 30 mL of tetrahydrofuran and 0.73 g of magnesium, 4.2 mL of 1-bromo-3-trifluoromethylbenzene was slowly added dropwise at 0° C., followed by stirring at room temperature for one hour. The obtained solution was slowly added dropwise in a three-necked flask containing 4.7 g of pivaloyl chloride and 50 mL of tetrahydrofuran at 0° C., followed by stirring for one hour. After completion of the reaction, an aqueous saturated ammonium chloride solution was added, and the mixture was extracted three times with ethyl acetate, dried over anhydrous sodium sulfate, and then dried under reduced pressure to obtain a crude product.

The obtained crude product was subjected to silica gel column chromatography to obtain 1.10 g of 2,2-dimethyl-1-(3-trifluoromethylphenyl)propan-1-one (C86A).

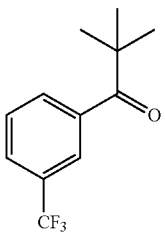

¹H-NMR (CDCl₃) δ(ppm): 7.92 (1H, s), 7.86 (1H, d, J=7.1 Hz), 7.72 (1H, d, J=7.8 Hz), 7.54 (1H, t, J=7.8 Hz), 1.36 (9H, s).

Reference Production Example 87

To a mixture of 50 mL of toluene and 6.76 g of 3-aminoacetophenone, 4.7 mL of acetic anhydride was added dropwise, followed by stirring at room temperature for 2 hours and further heating and stirring at 55° C. for one hour.

After cooling to room temperature, filtration, and washing with toluene, the obtained residue was dried under reduced pressure to obtain 6.39 g of N-(3-acetylphenyl)acetamide (C87A).

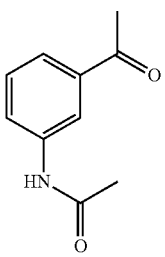

¹H-NMR (CDCl₃) δ(ppm): 8.00 (1H, s), 7.92 (1H, d, J=8.2 Hz), 7.69 (1H, d, J=7.8 Hz), 7.61 (1H, bs), 7.43 (1H, t, J=7.9 Hz), 2.61 (3H, s), 2.22 (3H, s).

Reference Production Example 88

Under nitrogen atmosphere, a mixture of 30 mL of toluene, 3.54 g of C87A, and 1.20 g of sodium hydroxide was stirred at room temperature. Here, methyl p-toluenesulfonate was added dropwise and the reaction was performed at 60° C. for 8 hours. After cooling to room temperature, water and an aqueous sodium sulfate solution were added, and the reaction solution was extracted three times with ethyl acetate, dried over anhydrous magnesium sulfate, and then concentrated to obtain a crude product of N-(3-acetylphenyl)-N-methylacetamide (C88A).

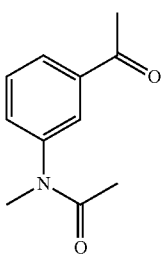

¹H-NMR (CDCl₃) δ(ppm): 7.92 (1H, s, J=7.9 Hz), 7.79 (1H, s), 7.54 (1H, t, J=7.9 Hz), 7.61 (1H, m), 3.29 (3H, s), 2.63 (3H, s), 1.88 (3H, s).

Reference Production Example 89

A mixture of 30 mL of acetonitrile, 3.45 g of 3-hydroxyacetophenone, 4.81 g of 1-bromohexane, and 3.45 g of potassium carbonate was stirred while heating under reflux for 6 hours. After cooling to room temperature, the reaction mixture was filtered and the filtrate was concentration to obtain 5.21 g of 1-(3-hexyloxyphenyl)ethanone (C89A).

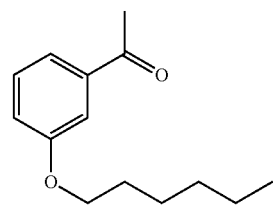 [SMILES: CCCCCCOc1cccc(C(C)=O)c1]

¹H-NMR (CDCl₃) δ(ppm): 7.52 (1H, d, J=7.6 Hz), 7.48 (1H, d, J=2.5 Hz), 7.36 (1H, t, J=8.0 Hz), 7.10 (1H, dd, J=8.2, 2.3 Hz), 4.00 (2H, t, J=6.5 Hz), 2.60 (3H, s), 1.83-1.76 (2H, m), 1.51-1.43 (2H, m), 1.37-1.32 (4H, m), 0.93-0.89 (3H, m).

Reference Production Examples 90 to 91 and 93 to 94

In the same manner as in Reference Production Example 89, except that each raw material was used in place of a halogen compound, production was performed.

1-(3-isopropoxyphenyl)ethanone (C90A)

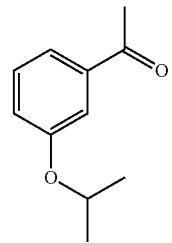

¹H-NMR (CDCl₃) δ(ppm): 7.52-7.47 (2H, m), 7.35 (1H, t, J=7.9 Hz), 7.09 (1H, dd, J=8.2, 1.8 Hz), 4.63 (1H, sep, J=6.1 Hz), 2.59 (3H, s), 1.35 (6H, d, J=6.0 Hz).

1-(3-pentloxphenyl)ethanone (C91A)

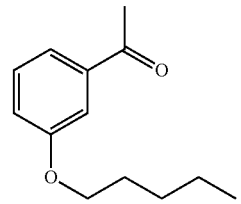

¹H-NMR (CDCl₃) δ(ppm): 7.52 (1H, dt, J=7.7, 1.2 Hz), 7.48 (1H, dd, J=2.1, 1.0 Hz), 7.36 (1H, t, J=7.9 Hz), 7.10 (1H, dq, J=8.2, 1.1 Hz), 4.00 (2H, t, J=6.5 Hz), 2.60 (3H, s), 1.84-1.77 (2H, m), 1.49-1.34 (4H, m), 0.94 (3H, t, J=7.1 Hz).

1-[3-(butyn-2-yloxy)phenyl]ethanone (C93A)

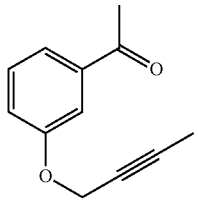

¹H-NMR (CDCl₃) δ(ppm): 7.58-7.54 (2H, m), 7.38 (1H, t, J=7.9 Hz), 7.17 (1H, dq, J=8.2, 1.1 Hz), 4.70 (2H, q, J=2.3 Hz), 2.60 (3H, s), 1.87 (3H, t, J=2.3 Hz).

1-[3-(pentyn-2-yloxy)phenyl]ethanone (C94A)

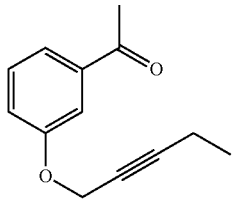

¹H-NMR (CDCl₃) δ(ppm): 7.58-7.56 (2H, m), 7.38 (1H, t, J=7.9 Hz), 7.19-7.16 (1H, m), 4.72 (2H, t, J=2.2 Hz), 2.60 (3H, s), 2.27-2.21 (2H, m), 1.14 (3H, t, J=7.4 Hz).

Reference Production Example 92

In the same manner as in Reference Production Example 19, except that a raw material was used in place of a ketone compound, production was performed.

1-(benzo[1,3]dioxan-4-yl)ethanone oxime (C92A)

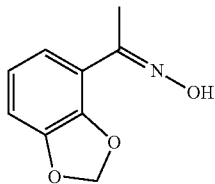

¹H-NMR (CDCl₃) δ: 7.02 (1H, dd, J=7.0, 2.3 Hz), 6.88-6.83 (2H, m), 6.03 (2H, s), 2.31 (3H, s).

Reference Production Example 95

In the same manner as in Reference Production Example 76, except that a raw material was used in place of an amide compound, production was performed.

1-(benzo[1,3]dioxan-4-yl)ethanone oxime (C95A)

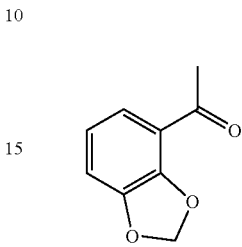

¹H-NMR (CDCl₃) δ: 7.38 (1H, dd, J=8.3, 1.2 Hz), 6.99 (1H, dd, J=7.6, 1.2 Hz), 6.89 (1H, t, J=7.9 Hz), 6.10 (2H, s), 2.61 (3H, s).

Reference Production Example 96

To a mixture of 100 mL of tetrahydrofuran, 3.89 g of C100A, a catalytic amount of DMF, 3.16 g of oxalylchloride was added dropwise at 0° C. After reacting at room temperature for one hour, the solvent was distilled off under reduced pressure. To this were added chloroform, 2.65 g of N,O-dimethylhydroxylamine hydrochloride, and 7.01 g of diisopropylamine, and the mixture was reacted at room temperature for 13 hours. After completion of the reaction, water was added and the reaction solution was stirred and then extracted with chloroform. The organic layer was dried over anhydrous sodium sulfate and then concentrated to obtain 3-difluoromethyl-N-methoxy-N-methylbenzamide (C96A)

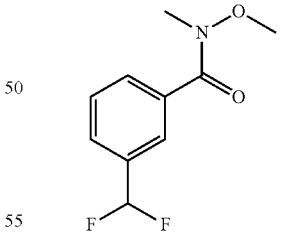

¹H-NMR (CDCl₃) δ(ppm): 7.84 (1H, s), 7.81 (1H, d, J=7.6 Hz), 7.62 (1H, t, J=3.9 Hz), 7.51 (1H, t, J=7.7 Hz), 6.68 (1H, t, J=56.3 Hz), 3.55 (3H, s), 3.38 (3H, s).

Reference Production Examples 97 to 98

In the same manner as in Reference Production Example 96, except that each raw material was used in place of carboxylic acid compound, production was performed.

N-methoxy-N-methyl-2,2-difluorobenzo[1,3]dioxane-5-carboxylic acid amide (C97A)

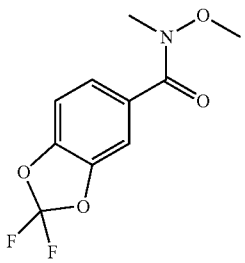 [SMILES: CON(C)C(=O)c1ccc2c(c1)OC(F)(F)O2]

$^1$H-NMR (CDCl$_3$) δ(ppm): 7.55 (1H, dd, J=8.3, 1.5 Hz), 7.49 (1H, d, J=1.7 Hz), 7.09 (1H, d, J=8.3 Hz), 3.55 (3H, s), 3.37 (3H, s).

N-methoxy-N-methyl-3-(1,1,2,2-tetrafluoroethoxyl)benzamide (C98A)

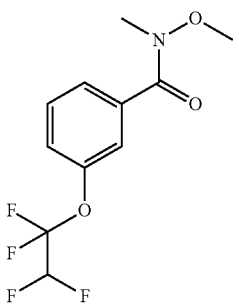 [SMILES: CON(C)C(=O)c1cccc(OC(F)(F)C(F)F)c1]

$^1$H-NMR (CDCl$_3$) δ(ppm): 7.62 (1H, d, J=7.8 Hz), 7.57 (1H, s), 7.44 (1H, t, J=7.9 Hz), 7.33-7.30 (1H, m), 5.93 (1H, tt, J=53.1, 2.8 Hz), 3.56 (3H, s), 3.37 (3H, s).

Reference Production Example 99

Under nitrogen atmosphere, to a mixture of 16.09 g of N,O-dimethylhydroxylamine hydrochloride in 300 mL of chloroform, 34.41 g of 3-trifluoromethyl benzoyl chloride was added dropwise at 0° C. and 50 mL of triethylamine was subsequently added dropwise. After stirring for 30 minutes while maintaining at 0° C., the temperature was raised to room temperature, followed by stirring for 4 hours. After completion of the reaction, the reaction solution was washed twice with hydrochloric acid (1M), washed twice with an aqueous sodium hydrogen carbonate solution, and further washed once with a saturated saline solution. The organic layer was dried over anhydrous sodium sulfate and then concentrated to obtain a crude product of N-methoxy-N-methyl-3-trifluoromethylbenzamide (C99A).

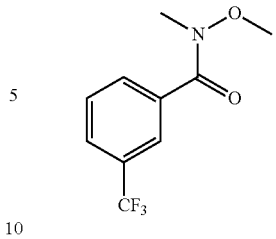

$^1$H-NMR (CDCl$_3$) δ(ppm): 7.97 (1H, s), 7.89 (1H, d, J=7.8 Hz), 7.72 (1H, d, J=7.8 Hz), 7.55 (1H, t, J=7.8 Hz), 3.55 (3H, s), 3.39 (3H, s).

Reference Production Example 100

3-difluoromethylbenzonitrile (3.80 g) was heated and stirred in an aqueous sodium hydroxide solution for 6 hours. After cooling to room temperature, an aqueous solution prepared by adding ice water to hydrochloric acid was poured thereinto, and the precipitated solid was filtered and then dried to obtain 3-difluoromethylbenzoic acid (C100A).

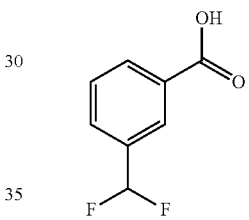

$^1$H-NMR (CDCl$_3$) δ(ppm): 8.27 (1H, s), 8.24 (1H, d, J=7.8 Hz), 7.79 (1H, d, J=7.8 Hz), 7.61 (1H, t, J=7.8 Hz), 6.72 (1H, t, J=56.2 Hz).

Reference Production Examples 101 to 121

In the same manner as in Reference Production Example 19, except that each raw material was used in place of a ketone compound, production was performed.

1-(indan-4-yl)ethanone oxime (C101A)

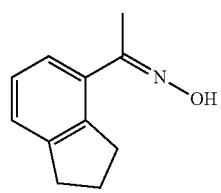

$^1$H-NMR (CDCl$_3$) δ(ppm): 9.89 (1H, bs), 7.30-7.27 (1H, m), 7.18-7.15 (2H, m), 2.97 (2H, t, J=7.4 Hz), 2.92 (2H, t, J=7.4 Hz), 2.33 (3H, s), 2.09-2.02 (2H, m).

1-(3-trifluoromethoxyphenyl)propan-1-one oxime (C102A)

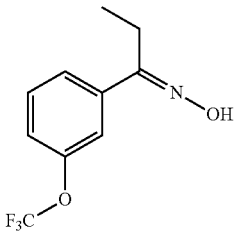 [SMILES: CCC(=NO)c1cccc(OC(F)(F)F)c1]

¹H-NMR (CDCl₃) δ(ppm): 8.20 (1H, bs), 7.56-7.54 (1H, m), 7.49 (1H, s), 7.42 (1H, t, J=8.0 Hz), 7.25-7.22 (1H, m), 2.81 (2H, q, J=7.6 Hz), 1.18 (3H, t, J=7.6 Hz).

1-(3-methylsulfanylphenyl)ethanone oxime (C103A)

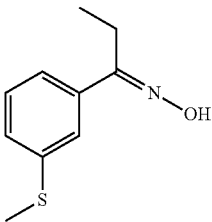

¹H-NMR (DMSO-D₆) δ(ppm): 7.49 (1H, t, J=1.7 Hz), 7.41 (1H, dt, J=7.6, 1.4 Hz), 7.33 (1H, t, J=7.7 Hz), 7.26 (1H, dq, J=7.8, 1.0 Hz), 2.49 (3H, s), 2.14 (3H, s).

1-(4-cyclopropyl-3-trifluoromethylphenyl)ethanone oxime (C104A)

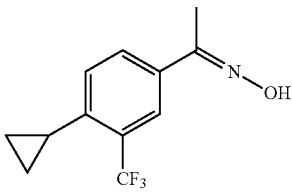 [SMILES: CC(=NO)c1ccc(C2CC2)c(C(F)(F)F)c1]

¹H-NMR (CDCl₃) δ(ppm): 7.88 (1H, s), 7.68 (1H, d, J=8.2 Hz), 7.01 (1H, d, J=8.2 Hz), 2.26 (3H, s), 2.23-2.18 (1H, m), 1.09-1.04 (2H, m), 0.81-0.77 (2H, m).

1-(5,6,7,8-tetrahydronaphthalen-1-yl)propan-1-one oxime (C105A)

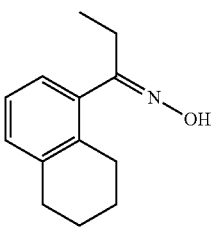

¹H-NMR (CDCl₃) δ(ppm): 8.13 (1H, bs), 7.12-7.06 (2H, m), 6.97 (1H, dd, J=6.9, 1.8 Hz), 2.82-2.78 (2H, m), 2.70-2.66 (2H, m), 2.68 (2H, q, J=7.6 Hz), 1.79-1.76 (4H, m), 1.02 (3H, t, J=7.6 Hz).

1-(5,6,7,8-tetrahydronaphthalen-1-yl)ethanone oxime (C106A)

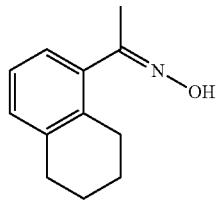

¹H-NMR (CDCl₃) δ(ppm): 7.92 (1H, bs), 7.13-7.00 (3H, m), 2.82-2.79 (2H, m), 2.74-2.70 (2H, m), 2.18 (3H, s), 1.81-1.77 (4H, m).

1-(2,3-dimethylphenyl)ethanone oxime (C107A)

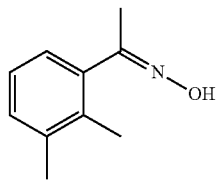

¹H-NMR (CDCl₃) δ(ppm): 7.15 (1H, d, J=5.0 Hz), 7.14 (1H, bs), 7.10 (1H, t, J=7.4 Hz), 7.05 (1H, d, J=7.4 Hz), 2.29 (3H, s), 2.22 (3H, s), 2.20 (3H, s).

1-(3-chloro-2-methylphenyl)ethanone oxime (C108A)

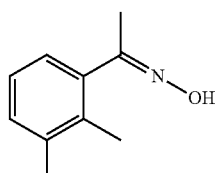

¹H-NMR (CDCl₃) δ(ppm): 7.64 (0.3H, bs), 7.38-7.35 (1.4H, m), 7.21-7.09 (2.0H, m), 6.98 (0.3H, d, J=8.0 Hz), 2.35 (2.0H, s), 2.28 (1.0H, s), 2.20 (2.0H, s), 2.14 (1.0H, s).

1-(2,2-difluorobenzo[1,3]dioxan-4-yl)ethanone oxime (C109A)

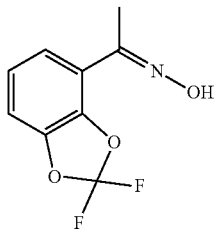

¹H-NMR (CDCl₃) δ(ppm): 7.29 (1H, dd, J=7.8, 1.6 Hz), 7.12-7.05 (2H, m), 2.33 (3H, s).

1-(7-methoxyindan-4-yl)ethanone oxime (C110A)

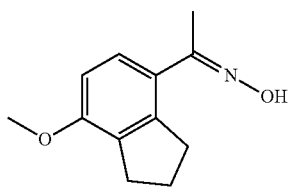

¹H-NMR (CDCl₃) δ(ppm): 7.22 (1H, d, J=8.5 Hz), 6.70 (1H, d, J=8.2 Hz), 3.85 (3H, s), 3.04 (2H, t, J=7.3 Hz), 2.86 (2H, t, J=7.4 Hz), 2.25 (3H, s), 2.09-2.02 (2H, m). 1-(4-methoxy-3-trifluoromethylphenyl)ethanone oxime (C111A)

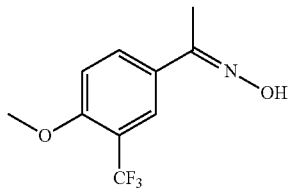 [SMILES: COc1ccc(C(C)=NO)cc1C(F)(F)F]

¹H-NMR (CDCl₃) δ(ppm): 7.88 (1H, d, J=2.3 Hz), 7.78 (1H, dd, J=8.7, 2.3 Hz), 7.00 (1H, d, J=8.7 Hz), 3.93 (3H, s), 2.26 (3H, s). 1-(2-methyl-3-trifluoromethylphenyl)ethanone oxime (C112A)

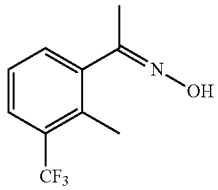

¹H-NMR (CDCl₃) δ(ppm): 7.64 (1.0H, d, J=7.6 Hz), 7.37-7.23 (2.0H, m), 2.42 (1.9H, d, J=1.60 Hz), 2.36 (1.1H, d, J=1.6 Hz), 2.21 (1.9H, s), 2.16 (1.1H, s). 1-(3-cyclopropyl-2-methylphenyl)ethanone oxime (C113A)

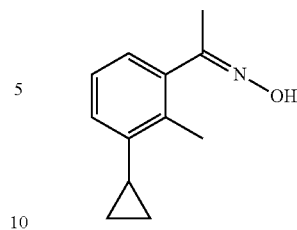

¹H-NMR (CDCl₃) δ(ppm): 7.19-7.10 (1.0H, m), 7.05-7.01 (1.7H, m), 6.91 (0.3H, d, J=7.8 Hz), 2.39 (2.2H, s), 2.32 (0.8H, s), 2.21 (2.2H, s), 2.15 (0.8H, s), 1.94-1.85 (1.0H, m), 0.96-0.91 (2.0H, m), 0.65-0.61 (2.0H, m).

1-(3-ethyl-2-methylphenyl)ethanone oxime (C114A)

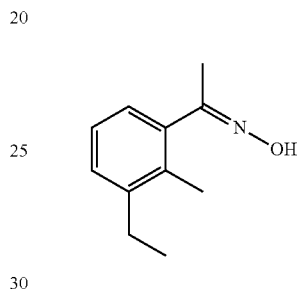

¹H-NMR (CDCl₃) δ(ppm): 7.21-7.13 (2.0H, m), 7.04 (0.7H, dd, J=6.8, 2.1 Hz), 6.92 (0.3H, dd, J=6.8, 2.1 Hz), 2.70-2.63 (2.0H, m), 2.25 (2.1H, s), 2.20 (2.1H, s), 2.19 (0.9H, s), 2.15 (0.9H, s), 1.25-1.19 (3.0H, m).

1-(2,5-dimethylphenyl)ethanone oxime (C115A)

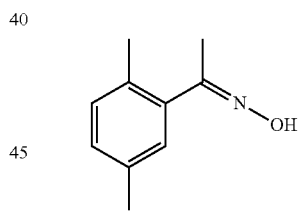

¹H-NMR (CDCl₃) δ: 8.86 (1H, bs), 7.10-7.04 (3H, m), 2.31 (3H, s), 2.30 (3H, s), 2.20 (3H, s). 1-(2,2-dimethyl-2,3-dihydrobenzofuran-4-yl)ethanone oxime (C116A)

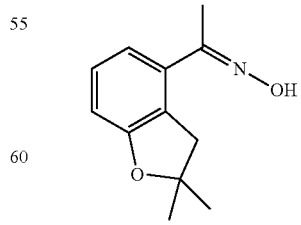

¹H-NMR (CDCl₃) δ: 7.19 (1H, bs), 7.15 (1H, t, J=7.9 Hz), 6.95 (1H, dd, J=7.9, 0.8 Hz), 6.75 (1H, d, J=8.0 Hz), 3.18 (2H, s), 2.26 (3H, s), 1.47 (6H, s).

1-(2-fluoro-3-trifluoromethylphenyl)ethanone oxime (C117A)

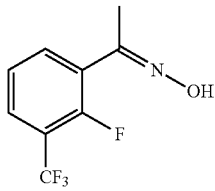

$^1$H-NMR (CDCl$_3$) δ(ppm): 7.83 (0.5H, dd, J=14.7, 7.7 Hz), 7.68-7.61 (1.5H, m), 7.45-7.41 (0.3H, m), 7.28-7.24 (0.7H, m), 2.64 (0.8H, s), 2.31 (2.2H, d, J=2.7 Hz).

1-biphenyl-2-ylethanone oxime (C118A)

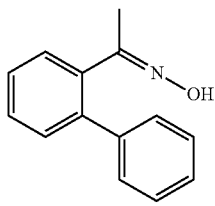 [SMILES: CC(=NO)c1ccccc1-c1ccccc1]

$^1$H-NMR (CDCl$_3$) δ(ppm): 8.87 (1H, bs), 7.47-7.28 (9H, m), 1.68 (3H, s).

1-(dihydrobenzofuran-4-yl)ethanone oxime (C119A)

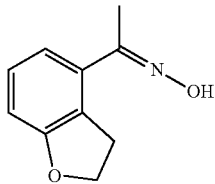

$^1$H-NMR (CDCl$_3$) δ(ppm): 7.70 (1H, bs), 7.16 (1H, t, J=7.9 Hz), 6.97 (1H, dd, J=7.9, 0.9 Hz), 6.81 (1H, d, J=7.9 Hz), 4.56 (2H, t, J=8.7 Hz), 3.36 (2H, t, J=8.7 Hz), 2.27 (3H, s).

1-biphenyl-3-ylethanone oxime (C120A)

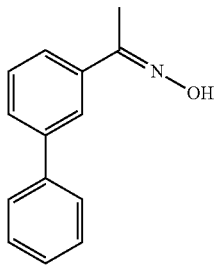 [SMILES: CC(=NO)c1cccc(-c2ccccc2)c1]

$^1$H-NMR (CDCl$_3$) δ(ppm): 7.36-7.31 (4H, m), 7.29-7.26 (1H, m), 7.28 (1H, d, J=5.0 Hz), 7.11 (1H, t, J=7.1 Hz), 7.02-6.98 (3H, m), 2.23 (3H, s).

1-(4-phenyl-3-trifluoromethylphenyl)ethanone oxime (C121A)

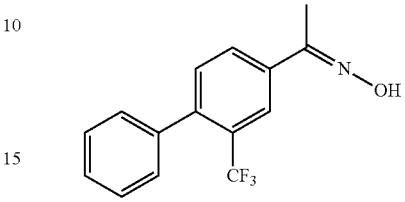

$^1$H-NMR (CDCl$_3$) δ(ppm): 8.03 (1H, bs), 7.82 (1H, dd, J=8.0, 1.4 Hz), 7.42-7.32 (7H, m), 2.34 (3H, s).

Reference Production Example 122

In the same manner as in Reference Production Example 76, except that a raw material was used in place of an amide compound, production was performed.

1-(3-trifluoromethoxyphenyl)propan-1-one (C122A)

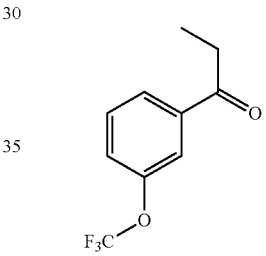

$^1$H-NMR (CDCl$_3$) δ(ppm): 7.90 (1H, dt, J=7.6, 1.3 Hz), 7.81 (1H, s), 7.51 (1H, t, J=8.0 Hz), 7.43-7.40 (1H, m), 3.01 (2H, q, J=7.2 Hz), 1.24 (3H, t, J=7.2 Hz).

Reference Production Example 123

A mixture of 0.46 g of 1-(3-sulfanylphenyl)ethanone, 0.12 g of sodium hydroxide, and 5 mL of ethanol was stirred at room temperature for one hour and then 0.43 g of iodomethane was added, followed by stirring for 2 hours. After completion of the reaction, an aqueous saturated sodium hydrogen carbonate solution was added, followed by stirring and further extraction with ethyl acetate. The organic layer was dried over anhydrous magnesium sulfate and then concentrated to obtain a crude product of 1-(3-methylsulfanylphenyl)ethanone (C123A).

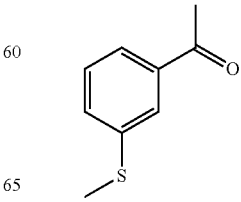

$^1$H-NMR (CDCl$_3$) δ(ppm): 7.83 (1H, s), 7.70 (1H, dd, J=7.6, 1.4 Hz), 7.46-7.43 (1H, m), 7.40-7.36 (1H, m), 2.61 (3H, s), 2.54 (3H, s).

Reference Production Example 124

A mixture of 0.45 g of 1-(4-chloro-3-trifluoromethylphenyl)ethanone, 0.22 g of cyclopropylboronic acid, 0.02 g of palladium acetate, 0.06 g of tricyclohexylphosphine, 1.49 g of potassiumphosphate, 10 mL of toluene, and 0.5 mL of water was reacted by heating under reflux for 5 hours and the thus obtained crude product was subjected to silica gel column chromatography to obtain 4'-cyclopropyl-3'-trifluoromethylacetophenone (C124A).

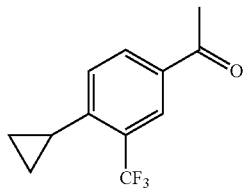 [SMILES: CC(=O)c1ccc(C2CC2)c(C(F)(F)F)c1]

$^1$H-NMR (CDCl$_3$) δ(ppm): 8.19 (1H, s), 8.01 (1H, d, J=7.8 Hz), 7.07 (1H, d, J=8.2 Hz), 2.61 (3H, s), 2.31-2.24 (1H, m), 1.18-1.13 (2H, m), 0.88-0.86 (2H, m).

Reference Production Examples 125 to 128

In the same manner as in Reference Production Example 76, except that each raw material was used in place of an amide compound, production was performed.

1-(5,6,7A-tetrahydronaphthalen-1-yl)propan-1-one (C125A)

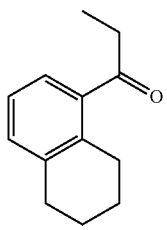

$^1$H-NMR (CDCl$_3$) δ(ppm): 7.33 (1H, dd, J=7.1, 2.1 Hz), 7.18-7.12 (2H, m), 2.89-2.80 (6H, m), 1.81-1.73 (4H, m), 1.18 (3H, t, J=7.3 Hz).

1-(5,6,7,8-tetrahydronaphthalen-1-yl)ethanone (C126A)

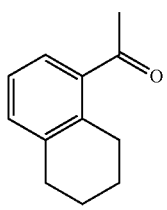

$^1$H-NMR (CDCl$_3$) δ(ppm): 7.43 (1H, d, J=7.5 Hz), 7.20-7.09 (2H, m), 2.96-2.93 (2H, m), 2.83-2.79 (2H, m), 2.55 (3H, s), 1.81-1.74 (4H, m).

3'-chloro-2'-methylacetophenone (C127A)

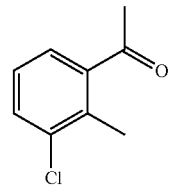

$^1$H-NMR (CDCl$_3$) δ(ppm): 7.46 (2H, t, J=7.7 Hz), 7.20 (1H, t, J=7.9 Hz), 2.57 (3H, s), 2.49 (3H, s).

1-(2,2-difluorobenzo[1,3]dioxan-4-yl)ethanone (C128A)

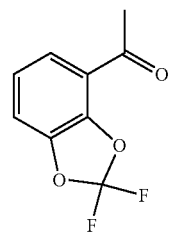

$^1$H-NMR (CDCl$_3$) δ(ppm): 7.64 (1H, dd, J=8.2, 1.4 Hz), 7.27-7.25 (1H, m), 7.17 (1H, t, J=8.0 Hz), 2.67 (3H, s).

Reference Production Example 129

To a mixture of 0.6 g of C141A, 2.67 g of aluminum chloride, and 20 mL of nitromethane, 0.78 g of acetyl chloride was added dropwise at 0° C., followed by stirring at room temperature for 13 hours. After completion of the reaction and cooling again to 0° C., water was added and the reaction solution was extracted with ethyl acetate. The organic layer was dried over anhydrous magnesium sulfate and then concentrated under reduced pressure. The obtained crude product was subjected to silica gel column chromatography to obtain 1-(7-methoxyindan-4-yl)ethanone (C129A).

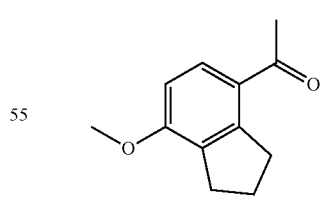

$^1$H-NMR (CDCl$_3$) δ(ppm): 7.75 (1H, d, J=8.5 Hz), 6.72 (1H, d, J=8.5 Hz), 3.89 (3H, s), 3.29 (2H, t, J=7.6 Hz), 2.83 (2H, t, J=7.6 Hz), 2.55 (3H, s), 2.12-2.04 (2H, m).

Reference Production Example 130

To a mixture of 1.0 g of 1-(4-hydroxy-3-trifluoromethylphenyl)ethanone, 0.18 g of sodium hydride, and 15 mL of dimethylformamide, 0.92 g of methyl iodide was added dropwise at 0° C., followed by stirring for 3 hours. After completion of the reaction, water was added and the reaction solution was extracted with ethyl acetate. The organic layer was dried over anhydrous magnesium sulfate and then concentrated under reduced pressure to obtain a crude product of 4'-methoxy-3'-trifluoromethylacetophenone (C130A).

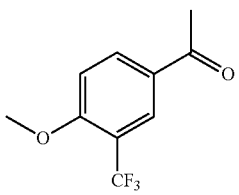

$^1$H-NMR (CDCl$_3$) δ(ppm): 8.20 (1H, d, J=2.1 Hz), 8.15 (1H, dd, J=8.7, 2.1 Hz), 7.06 (1H, d, J=8.7 Hz), 3.99 (3H, s), 2.60 (3H, s).

Reference Production Example 131

In the same manner as in Reference Production Example 76, except that a raw material was used in place of an amide compound, production was performed.

2'-methyl-3'-trifluoromethylacetophenone (C131A)

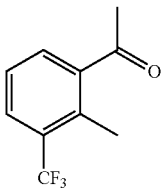

$^1$H-NMR (CDCl$_3$) δ(ppm): 7.73 (1H, d, J=7.8 Hz), 7.65 (1H, d, J=7.8 Hz), 7.36 (1H, t, J=7.8 Hz), 2.59 (3H, s), 2.53 (3H, d, J=1.4 Hz).

Reference Production Example 132

In the same manner as in Reference Production Example 124, except that a raw material was used in place of a ketone compound, production was performed.

3-cyclopropyl-2-methylacetophenone (C132A)

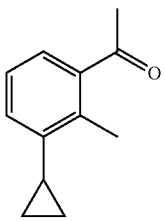

$^1$H-NMR (CDCl$_3$) δ(ppm): 7.40-7.36 (1H, m), 7.16 (2H, d, J=4.6 Hz), 2.57 (3H, s), 2.52 (3H, s), 1.94-1.87 (1H, m), 0.99-0.94 (2H, m), 0.65-0.61 (2H, m).

Reference Production Example 133

A mixture of 1.07 g of 3-ethyl-2-methylacetophenone, 0.73 g of ethylboronic acid, 0.61 g of a 1,1'-bis-diphenyl-hosphinoferrocene palladium (III) dichloride-dichloromethane complex, 3.18 g of potassium phosphate, 30 mL of 1,4-dioxane, and 3 mL of water was reacted while heating under reflux for 5 hours. The obtained crude product was subjected to silica gel column chromatography to obtain 3'-ethyl-2'-methylacetophenone (C133A)

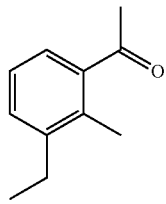

$^1$H-NMR (CDCl$_3$) δ(ppm): 7.39 (1H, d, J=7.6 Hz), 7.28 (1H, d, J=7.6 Hz), 7.19 (1H, t, J=7.6 Hz), 2.69 (2H, q, J=7.6 Hz), 2.56 (3H, s), 2.38 (3H, s), 1.21 (3H, t, J=7.6 Hz).

Reference Production Example 134

In the same manner as in Reference Production Example 76, except that a raw material was used in place of an amide compound, production was performed.

2'-fluoro-3'-trifluoromethylacetophenone (C134A)

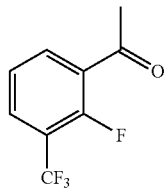

$^1$H-NMR (CDCl$_3$) δ(ppm): 8.11-8.07 (1H, m), 7.83-7.79 (1H, m), 7.35 (1H, t, J=7.8 Hz), 2.70 (3H, d, J=5.2 Hz).

Reference Production Example 135

A mixture of 1.62 g of C145A, 1.07 g of benzylamine, 10 g of 4A molecular sieves, and 30 mL of toluene was reacted while heating under reflux for 18 hours. After cooling to room temperature, the reaction mixture was filtered and the filtrate was concentrated. To the obtained crude product, 0.93 g of chlorotristriphenylphosphine rhodium and 30 mL of toluene were added, followed by stirring while heating under reflux for 12 hours. After cooling to room temperature, 1N hydrochloric acid was added and the mixture was extracted with ethyl acetate. The organic layer was dried over anhydrous magnesium sulfate and then concentrated under reduced pressure. The obtained crude product was subjected to silica gel column chromatography to obtain 0.86 g of 1-(dihydrobenzofuran-4-yl)ethanone (C135A).

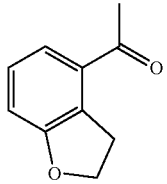

$^1$H-NMR (CDCl$_3$) δ(ppm): 7.38 (1H, dd, J=7.9, 0.9 Hz), 7.22 (1H, t, J=7.8 Hz), 6.98 (1H, d, J=7.9 Hz), 4.61 (2H, t, J=8.8 Hz), 3.55 (2H, t, J=8.8 Hz), 2.59 (3H, s).

Reference Production Example 136

A mixture of 0.45 g of 1-(4-chloro-3-trifluoromethylphenyl)ethanone, 0.22 g of phenylboronic acid, 0.02 g of palladium acetate, 2-(dichlorohexylphosphino)-2',4', 0.03 g of 6'-triisopropyl-1,1'-biphenyl, 0.52 g of potassium fluoride, and 5 mL of tetrahydrofuran was reacted while heating under reflux for 15 hours. The obtained crude product was subjected to silica gel column chromatography to obtain 1-(4-phenyl-3-trifluoromethylphenyl)ethanone (C136A).

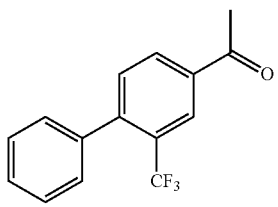 [SMILES: CC(=O)c1ccc(-c2ccccc2)c(C(F)(F)F)c1]

$^1$H-NMR (CDCl$_3$) δ(ppm): 8.34 (1H, s), 8.13 (1H, d, J=7.9 Hz), 7.47-7.41 (4H, m), 7.33-7.31 (2H, m), 2.67 (3H, s).

Reference Production Example 137

In the same manner as in Reference Production Example 99, except that a raw material was used in place of a halogenated acyl compound, production was performed.

N-methoxy-N-methyl-3-trifluoromethoxybenzamide (C137A)

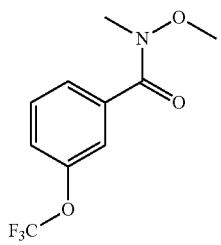 [SMILES: CON(C)C(=O)c1cccc(OC(F)(F)F)c1]

$^1$H-NMR (CDCl$_3$) δ(ppm): 7.64 (1H, dt, J=7.7, 1.2 Hz), 7.58 (1H, s), 7.45 (1H, t, J=8.0 Hz), 7.34-7.30 (1H, m), 3.55 (3H, s), 3.38 (3H, s).

Reference Production Examples 138 to 139

In the same manner as in Reference Production Example 96, except that each raw material was used in place of a carboxylic acid compound, production was performed.

N-methoxy-N-methyl-5,6,7,8-tetrahydronaphthalene-1-carboxylic acid amide (C138A)

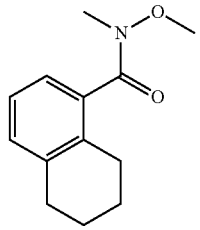 [SMILES: CON(C)C(=O)c1cccc2c1CCCC2]

$^1$H-NMR (CDCl$_3$) δ(ppm): 7.13-7.04 (3H, m), 3.47 (3H, bs), 3.31 (3H, bs), 2.81-2.70 (4H, m), 1.81-1.78 (4H, m).

3-chloro-N-methoxy-2, N-dimethylbenzamide (C139A)

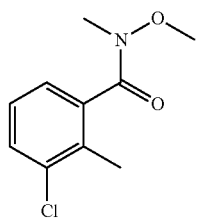

$^1$H-NMR (CDCl$_3$) δ(ppm): 7.40-7.38 (1H, m), 7.18-7.16 (2H, m), 3.41 (3H, bs), 3.38 (3H, bs), 2.34 (3H, s).

Reference Production Example 140

A mixture of 2.0 g of 2,2-difluorobenzo[1,3]dioxane-4-carboxylic acid and 10 mL of thionyl chloride was stirred while heating under reflux for 3 hours, and then the solvent was distilled off under reduced pressure. To this were added chloroform, 1.07 g of N,O-dimethylhydroxylamine hydrochloride, and 3 mL of triethylamine, followed by stirring at room temperature for 13 hours. After completion of the reaction, an aqueous saturated sodium hydrogen carbonate solution was added, followed by stirring and further extraction with chloroform. The organic layer was dried over anhydrous sodium sulfate and then concentrated to obtain a crude product. The obtained crude product was subjected to silica gel column chromatography to obtain N-methoxy-N-methyl-2,2-difluorobenzo[1,3]dioxane-4-carboxylic acid amide (C140A).

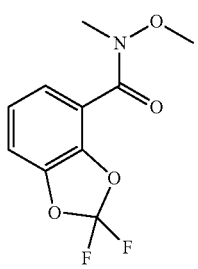 [SMILES: CON(C)C(=O)c1cccc2c1OC(F)(F)O2]

¹H-NMR (CDCl₃) δ(ppm): 7.29-7.25 (1H, m), 7.15-7.12 (2H, m), 3.63 (3H, s), 3.38 (3H, s).

Reference Production Example 141

To a mixture of 1.62 g of C146A and 8 mL of triethylsilane, 20 mL of trifluoroacetic acid was added dropwise at 0° C., followed by stirring while heating under reflux for 2 hours. After completion of the reaction, water was added, followed by stirring and further extraction with ethyl acetate. The organic layer was dried over anhydrous magnesium sulfate and then concentrated to obtain a crude product. The obtained crude product was subjected to silica gel column chromatography to obtain 4-methoxyindane (C141A).

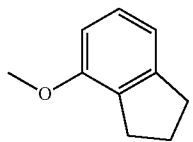

¹H-NMR (CDCl₃) δ(ppm): 7.13 (1H, t, J=7.8 Hz), 6.86 (1H, d, J=7.6 Hz), 6.67 (1H, d, J=8.0 Hz), 3.83 (3H, s), 2.92 (2H, t, J=7.4 Hz), 2.87 (2H, t, J=7.4 Hz), 2.11-2.03 (2H, m).

Reference Production Example 142

In the same manner as in Reference Production Example 140, except that a raw material was used in place of a carboxylic acid compound, production was performed.

N-methoxy-2,N-dimethyl-3-trifluoromethylbenzamide (C142A)

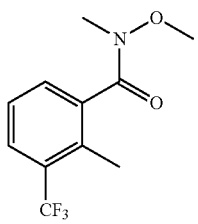 [SMILES: CON(C)C(=O)c1cccc(C(F)(F)F)c1C]

¹H-NMR (CDCl₃) δ(ppm): 7.67 (1H, d, J=7.8 Hz), 7.43 (1H, d, J=7.3 Hz), 7.33 (1H, t, J=7.6 Hz), 3.40 (6H, bs), 2.43 (3H, s).

Reference Production Example 143

In the same manner as in Reference Production Example 76, except that a raw material was used in place of an amide compound, production was performed.

3'-bromo-2'-methylacetophenone (C143A)

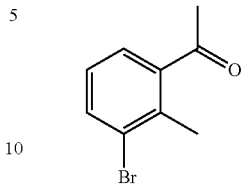

¹H-NMR (CDCl₃) δ(ppm): 7.66 (1H, dd, J=7.9, 1.3 Hz), 7.48 (1H, dd, J=7.8, 0.9 Hz), 7.12 (1H, t, J=7.8 Hz), 2.57 (3H, s), 2.51 (3H, s).

Reference Production Example 144

In the same manner as in Reference Production Example 140, except that a raw material was used in place of a carboxylic acid compound, production was performed.

2-fluoro-N-methoxy-N-methyl-3-trifluoromethyl-benzamide (C144A)

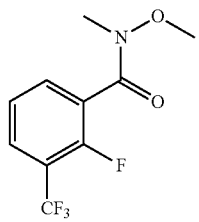 [SMILES: CON(C)C(=O)c1cccc(C(F)(F)F)c1F]

¹H-NMR (CDCl₃) δ(ppm): 7.69 (1H, t, J=7.3 Hz), 7.64 (1H, t, J=6.5 Hz), 7.32 (1H, t, J=7.8 Hz), 3.53 (3H, s), 3.39 (3H, s).

Reference Production Example 145

A mixture of 6.81 g of 3-hydroxyacetophenone, 8.61 g of vinyl acetate, 1.0 g of chloro(1,5-cyclooctadiene)iridium (I) dimer, 6.36 g of sodium carbonate, and 100 mL of toluene was stirred while heating at 100° C. for 3 hours. After cooling to room temperature, the solvent was distilled off and then the residue was subjected to silica gel column chromatography to obtain 1-(3-vinyloxyphenyl)ethanone (C145A).

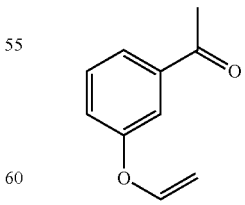

¹H-NMR (CDCl₃) δ(ppm): 7.67 (1H, dq, J=7.7, 0.9 Hz), 7.59 (1H, dd, J=2.3, 1.6 Hz), 7.43 (1H, t, J=7.9 Hz), 7.22 (1H, dq, J=8.2, 1.2 Hz), 6.68 (1H, dd, J=13.7, 6.0 Hz), 4.83 (1H, dd, J=13.7, 1.8 Hz), 4.52 (1H, dd, J=6.0, 1.8 Hz), 2.61 (3H, s).

Reference Production Example 146

In the same manner as in Reference Production Example 130, except that a raw material was used in place of a phenol compound, production was performed.

4-methoxyindan-1-one (C146A)

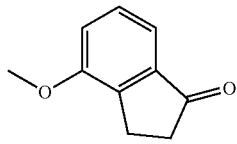

$^1$H-NMR (CDCl$_3$) δ(ppm): 7.36-7.35 (2H, m), 7.06-7.02 (1H, m), 3.91 (3H, s), 3.06-3.03 (2H, m), 2.71-2.68 (2H, m).

Reference Production Example 147

In the same manner as in Reference Production Example 140, except that a raw material was used in place of a carboxylic acid compound, production was performed.

3-bromo-N-methoxy-2, N-dimethylbenzamide (C147A)

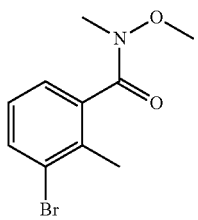

$^1$H-NMR (CDCl$_3$) δ(ppm): 7.59 (1H, d, J=8.0 Hz), 7.22 (1H, d, J=7.3 Hz), 7.09 (1H, t, J=7.8 Hz), 3.41 (3H, bs), 3.38 (3H, bs), 2.37 (3H, s).

Reference Production Example 148

Step (1)

To a mixture of 136.2 g of sodium sulfate, 480 mL of water, and 8.6 g of chloral hydrate, a mixture of 6.1 g of 2-fluoro-5-methylaniline, 4.2 mL of concentrated hydrochloric acid, and 24 mL of water was added and, furthermore, a mixture of 10.6 g of hydroxylamine hydrochloride and 30 mL of water was added, under stirring. After stirring while heating under reflux for 1.5 hours, the precipitated solid was collected by filtration to obtain N-(2-fluoro-5-methylphenyl)-2-hydroxyiminoacetamide. To a mixture of 19.5 mL of concentrated sulfuric acid and 4 mL of water, the N-(2-fluoro-5-methylphenyl)-2-hydroxyiminoacetamide was added, followed by stirring at 80° C. for one hour. After cooling, the reaction solution was poured into ice water and the precipitated solid was collected by filtration to obtain 4-methyl-7-fluoroisatin.

To a mixture of the obtained 4-methyl-7-fluoroisatin, 9.0 g of sodium hydroxide, and 40 mL of water, 3 mL of a 30% hydrogen peroxide solution was added. While maintaining the temperature at 70° C., the 25 pH of the reaction solution was adjusted to 4 by adding dropwise acetic acid. The precipitated solid was collected by filtration to obtain 2.3 q of 2-amino-3-fluoro-6-methylbenzoic acid.

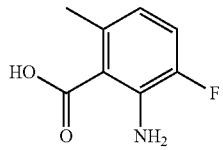

$^1$H-NMR (DMSO-D$_6$) δ(ppm): 7.03 (1H, dd, J=11.3, 8.2 Hz), 6.39 (1H, dd, J=8.2, 5.1 Hz), 2.32 (3H, s).

Step (2)

To a mixture of 2.3 g of 2-amino-3-fluoro-6-methylbenzoic acid, 70 mL of ethyl acetate, and 70 mL of ethanol, 13.7 mL of a 2.0M diethyl ether solution of trimethylsilyldiazomethane was added under ice cooling. After stirring at room temperature for 1.5 hours, the reaction solution was concentrated under reduced pressure. Water was poured into the obtained residue, followed by extraction with methyl tert-butyl ether. The organic layer was washed in turn with water and a saturated saline solution, dried over anhydrous magnesium sulfate, and then concentrated under reduced pressure. The obtained residue was subjected to silica gel column chromatography to obtain 0.81 g of 2-amino-3-fluoro-6-methylbenzoic acid methyl ester.

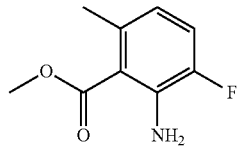

$^1$H-NMR (CDCl$_3$) δ(ppm): 6.94 (1H, dd, J=10.9, 8.2 Hz), 6.45-6.41 (1H, m), 5.26 (2H, br s), 3.91 (3H, s), 2.41 (3H, s).

Step (3)

To a mixture of 0.81 g of 2-amino-3-fluoro-6-methylbenzoic acid methyl ester and 15 mL of toluene, 2.0 g of triphosgene was added at room temperature, followed by stirring while heating under reflux for 3 hours. After concentration under reduced pressure, 0.92 g of 2-isocyanate-3-fluoro-6-methylbenzoic acid methyl ester was obtained.

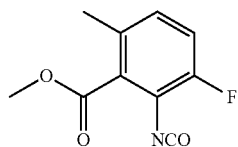

$^1$H-NMR (CDCl$_3$) δ(ppm): 7.09 (1H, t, J=8.7 Hz), 7.02-6.98 (1H, m), 3.96 (3H, s), 2.30 (3H, s).

Step (4)

Under ice cooling, 0.65 g of anhydrous aluminum chloride was added to 10 mL of N,N-dimethylformamide, followed by stirring for 20 minutes.

Sodium azide (0.32 g) was added and, after stirring for 15 minutes, 0.92 g of a 2-isocyanate-3-fluoro-6-methylbenzoic acid methyl ester was added and the mixture was heated and stirred at 80° C. for 4 hours.

After cooling, the reaction solution was added in a mixture of 1.0 g of sodium nitrite and 200 mL of ice water while stirring. The mixture was acidified with 10% hydrochloric acid and then extracted with ethyl acetate. The organic layer was washed in turn with water and a saturated saline solution, dried over anhydrous magnesium sulfate, and then concentrated under reduced pressure to obtain 1.4 g of 3-fluoro-6-methyl-2-(5-oxo-4,5-dihydrotetrazol-1-yl)benzoic acid methyl ester.

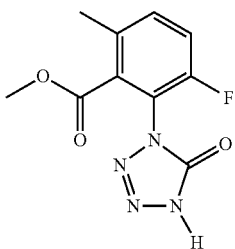 [SMILES: COC(=O)c1c(C)ccc(F)c1-n1nn[nH]c1=O]

$^1$H-NMR (DMSO-D$_6$) δ(ppm): 7.65-7.62 (1H, m), 7.59-7.56 (1H, m), 3.71 (3H, s), 2.38 (3H, s).

Step (5)

To a mixture of 1.4 g of 3-fluoro-6-methyl-2-(5-oxo-4,5-dihydrotetrazol-1-yl)benzoic acid methyl ester, and 20 mL of N,N-dimethylformamide, 1.2 g of potassium carbonate and 1.3 g of methyl iodide were added at room temperature, followed by stirring for 4 hours. Water was poured into the reaction solution, followed by extraction with ethyl acetate. The organic layer was washed in turn with water and a saturated saline solution, dried over anhydrous magnesium sulfate, and then concentrated under reduced pressure. The obtained residue was subjected to silica gel column chromatography to obtain 0.65 g of 3-fluoro-6-methyl-2-(4-methyl-5-oxo-4,5-dihydrotetrazol-1-yl)benzoic acid methyl ester.

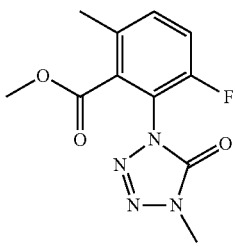 [SMILES: COC(=O)c1c(C)ccc(F)c1-n1nnn(C)c1=O]

$^1$H-NMR (CDCl$_3$) δ(ppm): 7.38 (1H, dd, J=8.6, 5.0 Hz), 7.28 (1H, t, J=8.6 Hz), 3.80 (3H, s), 3.71 (3H, s), 2.45 (3H, s).

Step (6)

Under ice cooling, to a mixture of 0.65 g of 3-fluoro-6-methyl-2-(4-methyl-5-oxo-4,5-dihydrotetrazol-1-yl)benzoic acid methyl ester and 11 mL of tetrahydrofuran, 5.4 mL of a 1.0M tetrahydrofuran solution of lithium triethylborohydride was added at room temperature, followed by stirring for one hour. Water was poured into the reaction solution, and the solution was acidified with 10% hydrochloric acid and then extracted with ethyl acetate. The organic layer was washed in turn with water and a saturated saline solution, dried over anhydrous magnesium sulfate, and then concentrated under reduced pressure to obtain 0.58 g of 1-(2-hydroxymethyl-3-methyl-6-fluorophenyl)-4-methyl-1,4-dihydrotetrazol-5-one.

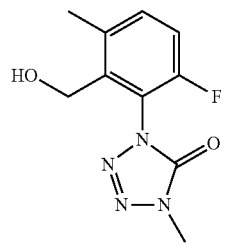

$^1$H-NMR (CDCl$_3$) δ(ppm): 7.37 (1H, dd, J=8.6, 5.4 Hz), 7.15 (1H, t, J=8.6 Hz), 4.54-4.36 (2H, m), 3.76 (3H, s), 3.28-3.24 (1H, m), 2.50 (3H, s).

Step (7)

To a mixture of 0.58 g of 1-(2-hydroxymethyl-3-methyl-6-fluorophenyl)-4-methyl-1,4-dihydrotetrazol-5-one and 8 mL of chloroform, 1.32 g of phosphorus tribromide was added, followed by stirring at room temperature for 20 hours. Ice water was poured into the reaction solution, followed by extraction with ethyl acetate. The organic layer was washed in turn with water and a saturated saline solution, dried over anhydrous magnesium sulfate, and then concentrated under reduced pressure. The obtained residue was subjected to silica gel column chromatography to obtain 0.66 g of 1-(2-bromomethyl-3-methyl-6-fluorophenyl)-4-methyl-, 4-dihydrotetrazol-5-one (C148A).

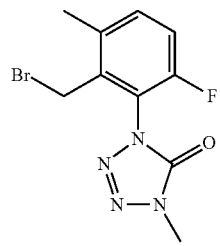 [SMILES: Cc1ccc(F)c(-n2nnn(C)c2=O)c1CBr]

$^1$H-NMR (CDCl$_3$) δ(ppm): 7.36 (1H, dd, J=8.7, 5.6 Hz), 7.16 (1H, t, J=8.7 Hz), 4.43 (1H, d, J=10.6 Hz), 4.32 (1H, d, J=10.6 Hz), 3.76 (3H, s), 2.46 (3H, s).

Reference Production Example 149

Step (1)

To a mixture of 272.4 g of sodium sulfate, 960 mL of water, and 17.2 g of chloral hydrate, a mixture of 12.2 g of 4-fluoro-3-methylaniline, 8.4 mL of concentrated hydrochloric acid, and 48 mL of water was added. Under stirring, a mixture of 21.1 g of hydroxylamine hydrochloride and 60 mL of water was further added.

After stirring while heating under reflux for 40 minutes, the precipitated solid was collected by filtration to obtain 25.4 g of N-(4-fluoro-3-methylphenyl)-2-hydroxyiminoacetamide.

To a mixture of 78 mL of concentrated sulfuric acid and 16 mL of water, 25.4 g of N-(4-fluoro-3-methylphenyl)-2-hydroxyiminoacetamide was added.

After stirring at 80° C. for one hour, the reaction solution was poured into 500 mL of ice water and the precipitated solid was collected by filtration to obtain a mixture of 4-methyl-5-fluoroisatin with 6-methyl-5-fluoroisatin.

The obtained mixture of 4-methyl-5-fluoroisatin with 6-methyl-5-fluoroisatin is mixed with a mixture of 18.0 g of sodium hydroxide and 80 mL of water, and then 6 mL of 30% hydrogen peroxide solution was added. While maintaining the temperature at 70° C., the pH of the reaction solution was adjusted to 4 by adding dropwise acetic acid. The precipitated solid was collected by filtration to obtain 11.5 g of a mixture of 6-amino-3-fluoro-2-methylbenzoic acid and 2-amino-5-fluoro-4-methylbenzoic acid.

To a mixture of 11.5 g of the mixture of 6-amino-3-fluoro-2-methylbenzoic acid and 2-amino-5-fluoro-4-methylbenzoic acid, 340 mL of ethyl acetate, and 340 mL ethanol, 68 mL of a 2.0M diethyl ether solution of trimethylsilyldiazomethane was added under ice cooling. After stirring at room temperature for 1.5 hours, the solution was concentrated under reduced pressure. The obtained residue was subjected to silica gel column chromatography to obtain 3.0 g of 6-amino-3-fluoro-2-methylbenzoic acid methyl ester.

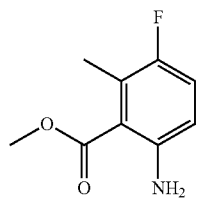

$^1$H-NMR (CDCl$_3$) δ(ppm): 6.93 (1H, t, J=9.0 Hz), 6.48 (1H, dd, J=9.0, 4.5 Hz), 4.82 (2H, br s), 3.91 (3H, s), 2.31 (3H, d, J=2.7 Hz).

Step (2)

To a mixture of 3.0 g of 6-amino-3-fluoro-2-methylbenzoic acid methyl ester and 60 mL of toluene, 7.6 g of triphosgene was added at room temperature, followed by stirring while heating under reflux for 3 hours. After concentration under reduced pressure, 3.6 g of 6-isocyanate-3-fluoro-2-methylbenzoic acid methyl ester was obtained.

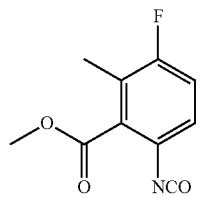

$^1$H-NMR (CDCl$_3$) δ(ppm): 7.04 (1H, t, J=8.8 Hz), 6.94 (1H, dd, J=8.8, 4.6 Hz), 3.98 (3H, s), 2.26 (3H, d, J=2.5 Hz).

Step (3)

Under ice cooling, 2.5 g of anhydrous aluminum chloride was added to 30 mL of N,N-dimethylformamide, followed by stirring for 20 minutes. Sodium azide (1.2 g) was added and, after stirring for 15 minutes, 3.6 g of 6-isocyanate-3-fluoro-2-methylbenzoic acid methyl ester was added, followed by heating and stirring at 80° C. for 4 hours. After cooling, the reaction solution was added in a mixture of 4.0 g of sodium nitrite and 500 mL of ice water while stirring. The mixture was acidified with 10% hydrochloric acid and then extracted with ethyl acetate. The organic layer was washed in turn with water and a saturated saline solution, dried over anhydrous magnesium sulfate, and then concentrated under reduced pressure to obtain 6.0 g of 2-methyl-3-fluoro-6-(5-oxo-4,5-dihydrotetrazol-1-yl)benzoic acid methyl ester.

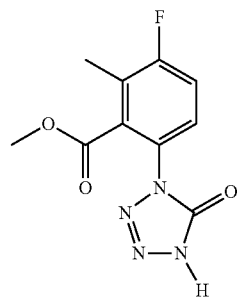 [SMILES: COC(=O)c1c(-n2nn[nH]c2=O)ccc(F)c1C]

$^1$H-NMR (DMSO-D$_6$) δ(ppm): 7.62-7.56 (2H, m), 5.29 (1H, br s), 3.73 (3H, s), 2.29 (3H, d, J=2.3 Hz).

Step (4)

To a mixture of 6.0 g of 2-methyl-3-fluoro-6-(5-oxo-4,5-dihydrotetrazol-1-yl)benzoic acid methyl ester and 85 mL of N,N-dimethylformamide, 4.7 g of potassium carbonate and 4.9 g of methyl iodide were added at room temperature, followed by stirring for 6 hours. Water was poured into the reaction solution, followed by extraction with ethyl acetate. The organic layer was washed in turn with water and a saturated saline solution, dried over anhydrous magnesium sulfate, and then concentrated under reduced pressure. The obtained residue was subjected to silica gel column chromatography to obtain 2.8 g of 2-methyl-3-fluoro-6-(4-methyl-5-oxo-4,5-dihydrotetrazol-1-yl)benzoic acid methyl ester.

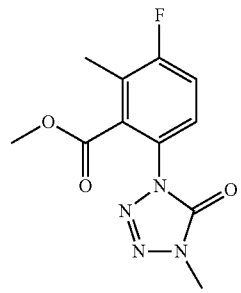 [SMILES: COC(=O)c1c(-n2nnn(C)c2=O)ccc(F)c1C]

$^1$H-NMR (CDCl$_3$) δ(ppm): 7.47 (1H, dd, J=8.9, 4.6 Hz), 7.25 (1H, t, J 25=8.9 Hz), 3.84 (3H, s), 3.69 (3H, s), 2.36 (3H, d, J=2.4 Hz).

Step (5)

Under ice cooling, to a mixture of 2.8 g of 2-methyl-3-fluoro-6-(4-methyl-5-oxo-4,5-dihydrotetrazol-1-yl)benzoic acid methyl ester and 46 mL of tetrahydrofuran, 22.9 mL of a 1.0M tetrahydrofuran solution of lithium triethylborohydride was added at room temperature, followed by stirring for one hour. Water was poured into the reaction solution, and the solution was acidified with 10% hydrochloric acid and then extracted with ethyl acetate. The organic layer was washed in turn with water and a saturated saline solution, dried over anhydrous magnesium sulfate, and then concentrated under reduced pressure to obtain 2.4 g of 1-(2-hydroxymethyl-3-methyl-4-fluorophenyl)-4-methyl-1,4-dihydrotetrazol-5-one.

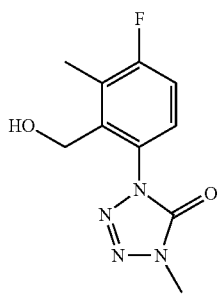 [SMILES: Cc1c(F)ccc(-n2nnn(C)c2=O)c1CO]

$^{1}$H-NMR (CDCl$_{3}$) δ(ppm): 7.21 (1H, dd, J=8.7, 5.1 Hz), 7.15 (1H, t, J 15=8.7 Hz), 4.47 (2H, dd, J=7.2, 1.0 Hz), 3.75 (3H, s), 2.45 (3H, d, J=2.4 Hz).

Step (6)

To a mixture of 2.4 g of 1-(2-hydroxymethyl-3-methyl-4-fluorophenyl)-4-methyl-1,4-dihydrotetrazol-5-one and 34 mL of chloroform, 5.5 g of phosphorus tribromide was added, followed by stirring at room temperature for 20 hours. Ice water was poured into the reaction solution, followed by extraction with ethyl acetate. The organic layer was washed in turn with water and a saturated saline solution, dried over anhydrous magnesium sulfate, and then concentrated under reduced pressure. The obtained residue was subjected to silica gel column chromatography to obtain 2.5 g of 1-(2-bromomethyl-3-methyl-4-fluorophenyl)-4-methyl-1,4-dihydrotetrazol-5-one (C149A).

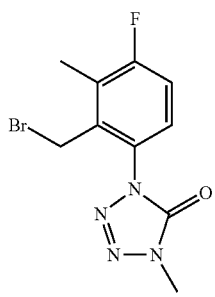 [SMILES: Cc1c(F)ccc(-n2nnn(C)c2=O)c1CBr]

$^{1}$H-NMR (CDCl$_{3}$) δ(ppm): 7.22 (1H, dd, J=8.7, 5.1 Hz), 7.16 (1H, t, J=8.7 Hz), 4.46 (2H, s), 3.75 (3H, s), 2.39 (3H, d, J=2.4 Hz).

Reference Production Example 150

To a mixture of 15.6 g of sodium tetrahydroborate and 200 ml of tetrahydrofuran, 50 g of 2-methyl-6-nitrobenzoic acid was added at room temperature. To the reaction mixture, 34 ml of dimethylsulfuric acid was added at 0° C., followed by stirring at room temperature for 20 hours. 5% Hydrochloric acid (300 ml) was added at 0° C., followed by stirring for one hour. After extraction with ethyl acetate, the organic layer was washed with water, dried over anhydrous magnesium sulfate, and then concentrated under reduced pressure to obtain 30.5 g of 2-methyl-6-nitrobenzyl alcohol (C150A).

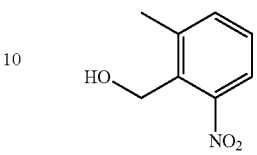

$^{1}$H-NMR (CDCl$_{3}$) δ(ppm): 7.71 (1H, d, J=7.7 Hz), 7.49 (1H, d, J=7.5 Hz), 7.36 (1H, t, J=7.9 Hz), 4.71 (2H, d, J=7.2 Hz), 2.62 (1H, t, J=7.4 Hz), 2.56 (3H, s).

Reference Production Example 151

To a mixture of 30.5 g of C150A and 100 ml of chloroform, 74.1 g of phosphorus tribromide was added at room temperature, followed by stirring for 10 hours. Ice water (200 ml) was added and the solution was extracted with chloroform. The organic layer was washed with water, dried over anhydrous magnesium sulfate, and then concentrated under reduced pressure to obtain 35 g of 2-methyl-6-nitrobenzyl bromide (C151A).

$^{1}$H-NMR (CDCl$_{3}$) δ(ppm): 7.75 (1H, d, J=8.2 Hz), 7.46 (1H, d, J=7.7 Hz), 7.36 (1H, t, J=7.8 Hz), 4.72 (2H, s), 2.54 (3H, s).

Reference Production Example 152

C153A (1.90 g) was heated and stirred at 220° C. for 36 hours. The obtained oily substance was subjected to silica gel column chromatography to obtain 0.43 g of 1-(2,2-dimethyl-2,3-dihydrobenzofuran-4-yl)ethanone (C152A).

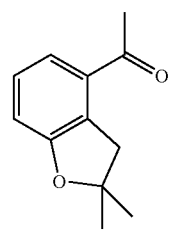

$^{1}$H-NMR (CDCl$_{3}$) δ: 7.37 (1H, d, J=7.9 Hz), 7.22 (1H, t, J=7.8 Hz), 6.92 (1H, d, J=7.9 Hz), 3.36 (2H, s), 2.59 (3H, s), 1.47 (6H, s).

Reference Production Example 153

A mixture of 20.4 g of 3-hydroxyacetophenone, 90.6 g of 3-chloro-2-methyl-1-propene, 24.9 g of potassium carbonate, and 150 mL of acetonitrile was stirred while heating under reflux for 17 hours. After cooling to room temperature, the reaction mixture was filtered to obtain 28.4 g of a crude 1-[3-(2-methylallyloxyl)phenyl]ethanone (C153A).

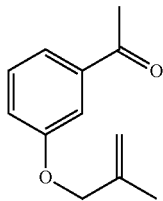

$^1$H-NMR (CDCl$_3$) δ: 7.54 (1H, dd, J=7.6, 0.7 Hz), 7.51 (1H, s), 7.37 (1H, t, J=7.9 Hz), 7.14 (1H, dd, J=8.2, 2.7 Hz), 5.12 (1H, s), 5.01 (1H, s), 4.49 (2H, s), 2.60 (3H, s), 1.84 (3H, s).

Reference Production Example 154

In the same manner as in Reference Production Example 96, except that a raw material was used in place of a carboxylic acid compound, production was performed.

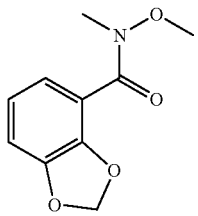

$^1$H-NMR (CDCl$_3$) δ: 7.01 (1H, dd, J=7.3, 1.8 Hz), 6.90-6.84 (2H, m), 6.02 (2H, s), 3.63 (3H, s), 3.35 (3H, s).

Reference Production Examples 201 to 204

In the same manner as in Reference Production Example 140, except that each raw material was used in place of a ketone compound, production was performed.

1-cyclohexylethanone oxime (C201A)

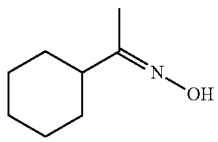

$^1$H-NMR (CDCl$_3$) δ(ppm): 9.18 (1H, bs), 2.18-2.10 (1H, m), 1.86 (3H, s), 1.83-1.77 (4H, m), 1.71-1.66 (1H, m), 1.33-1.15 (5H, m).

1-cyclohexan-1-enylethanone oxime (C202A)

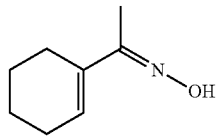

$^1$H-NMR (CDCl$_3$) δ(ppm): 8.98 (1H, bs), 6.21-6.18 (1H, m), 2.29-2.25 (2H, m), 2.21-2.16 (2H, m), 2.02 (3H, s), 1.69-1.58 (4H, m).

3-methylpent-3-en-2-one oxime (C203A)

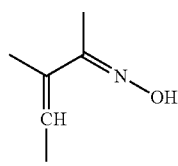

$^1$H-NMR (CDCl$_3$) δ(ppm): 6.04-5.97 (1H, m), 2.03 (3H, s), 1.84 (3H, s), 1.79 (3H, d, J=7.0 Hz).

5-methylhex-3-en-2-one oxime (C204A)

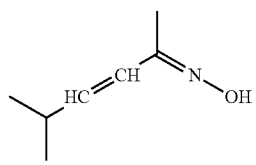

$^1$H-NMR (CDCl$_3$) δ(ppm): 8.36 (1H, bs), 6.10-6.00 (2H, m), 2.48-2.37 (1H, m), 1.99 (3H, s), 1.05 (6H, d, J=6.6 Hz).

Reference Production Example 205

In the same manner as in Reference Production Example 19, except that a raw material was used in place of a ketone compound, production was performed.

1-[1-(3-trifluoromethylphenyl)cyclopropyl]ethanone oxime (C205A)

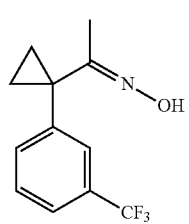 [SMILES: CC(=NO)C1(c2cccc(C(F)(F)F)c2)CC1]

¹H-NMR (CDCl₃) δ: 7.52-7.40 (5H, m), 1.80 (3H, s), 1.31 (2H, dd, J=6.7, 4.6 Hz), 1.08 (2H, dd, J=6.7, 4.6 Hz).

Reference Production Example 206

In the same manner as in Reference Production Example 140, except that a raw material was used in place of an amide compound, production was performed.

1-[1-(3-trifluoromethylphenyl)cyclopropyl]ethanone (C206A)

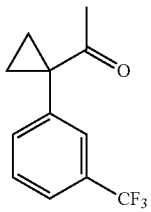

¹H-NMR (CDCl₃) δ: 7.62 (1H, s), 7.58-7.47 (3H, m), 2.00 (3H, s), 1.67 (2H, dd, J=7.0, 3.9 Hz), 1.21 (2H, dd, J=6.9, 4.0 Hz).

Reference Production Example 207

In the same manner as in Reference Production Example 96, except that a raw material was used in place of a carboxylic acid compound, production was performed.

N-methoxy-N-methyl-1-(3-trifluoromethylphenyl) cyclopropanecarboxylic acid amide (C207A)

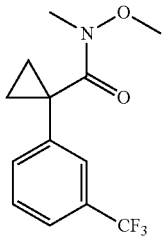 [SMILES: CON(C)C(=O)C1(c2cccc(C(F)(F)F)c2)CC1]

¹H-NMR (CDCl₃) δ: 7.52-7.47 (3H, m), 7.44-7.40 (1H, m), 3.14 (3H, s), 3.13 (3H, s), 1.50 (2H, dd, J=7.0, 4.7 Hz), 1.15 (2H, dd, J=7.0, 4.7 Hz).

Reference Production Example 208

To a mixture of 17.2 g of 3-pentanone, 20.6 g of tert-butyl nitrite, and 240 mL of methanol, 77.2 mL of a 28% sodium methoxide-methanol solution was added dropwise under ice cooling. After stirring at 0° C. for 4 hours, the temperature was raised to room temperature while stirring over 4 hours. The pH of the reaction mixture was adjusted to 7 by adding 1N hydrochloric acid and the mixture was extracted with chloroform. The organic layer was washed with a saturated saline solution, dried over anhydrous magnesiumsulfate, and then concentrated under reduced pressure. The obtained residue was subjected to silica gel chromatography to obtain 8.20 g of pentane-2,3-dione-2-oxime (C208A).

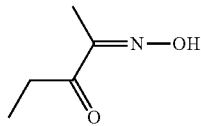

¹H-NMR (CDCl₃) δ(ppm): 8.48 (1H, s), 2.80 (2H, q, J=7.4 Hz), 1.99 (3H, s), 1.10 (3H, t, J=7.3 Hz).

Reference Production Example 209

To a mixture of 8.20 g of C208A, 19.6 g of potassium carbonate, and 140 mL of acetonitrile, 10.1 g of iodomethane was added dropwise under ice cooling, followed by stirring at room temperature for 2 hours. Water was added to the reaction mixture, followed by extraction with chloroform. The organic layer was washed with a saturated saline solution, dried over anhydrous magnesiumsulfate, and then concentrated under reduced pressure to obtain 9.04 g of pentane-2,3-dione-2-(O-methyloxime) (C209A).

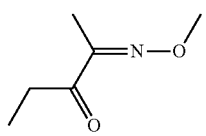

¹H-NMR (CDCl₃) δ(ppm): 4.04 (3H, s), 2.81 (2H, q, J=7.3 Hz), 1.91 (3H, s), 1.09 (3H, t, J=7.3 Hz).

Reference Production Example 210

To a mixture of 9.04 g of C209A, 7.22 g of tert-butyl nitrite, and 84 mL of methanol, 27.0 mL of a 28% sodium methoxide-methanol solution was added dropwise under ice cooling, followed by stirring at room temperature for 8 hours. The pH of the reaction mixture was adjusted to 7 by adding 1N hydrochloric acid, followed by extraction with chloroform. The organic layer was washed with a saturated saline solution, dried over anhydrous magnesium sulfate, and then concentrated under reduced pressure. The obtained residue was subjected to silica gel chromatography to obtain 3.37 g of pentane-2,3,4-trione-2-(O-methyloxime)-4-oxime (C210A).

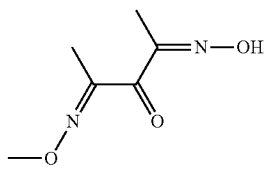

¹H-NMR (CDCl₃) δ(ppm): 9.96 (1H, bs), 4.07 (3H, s), 2.11 (3H, s), 2.05 (3H, s).

Reference Production Example 211

To a mixture of 3.16 g of C210A, 1.67 g of O-methylhydroxyamine hydrochloride and 40 mL of ethanol, 1.0 mL of hydrochloric acid was added, followed by stirring at room temperature for 2 hours. To the reaction mixture, an aqueous saturated sodium hydrogen carbonate solution was added, followed by extraction with chloroform. The organic layer was washed with a saturated saline solution, dried over anhydrous sodium sulfate, and then concentrated under reduced pressure.

The obtained residue was subjected to silica gel chromatography to obtain 1.23 g of one isomer (C211A) of pentane-2,3,4-trione-2,3-bis-(O-methyloxime)-4-oxime and 0.96 g of the other one isomer (C211B).

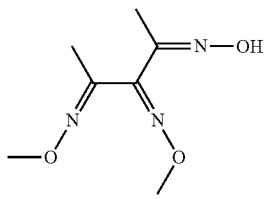

C211A:
$^1$H-NMR (CDCl$_3$) δ(ppm): 9.03 (1H, br s), 3.98 (3H, s), 3.95 (3H, s), 2.11 (3H, s), 1.97 (3H, s).
C211B:
$^1$H-NMR (CDCl$_3$) δ(ppm): 7.98 (1H, s), 3.97 (3H, s), 3.94 (3H, s), 2.04 (3H, s), 2.01 (3H, s).

Reference Production Examples 214 to 216

In the same manner as in Reference Production Example 19, except that each raw material was used in place of a ketoned compound, production was performed.

1-(2-phenylcyclopropyl)ethanone oxime (C214A)

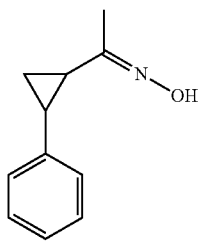

$^1$H-NMR (CDCl$_3$) δ(ppm): 7.45 (1.0H, bs), 7.30-7.26 (2.0H, m), 7.21-7.09 (3.0H, m), 2.76-2.71 (0.2H, m), 2.31-2.26 (0.2H, m), 2.22-2.17 (0.8H, m), 1.86 (2.2H, s), 1.85-1.80 (0.8H, m), 1.70 (0.8H, s), 1.44-1.17 (2.0H, m).

1-[2-(4-chlorophenyl)cyclopropyl]ethanone oxime (C215A)

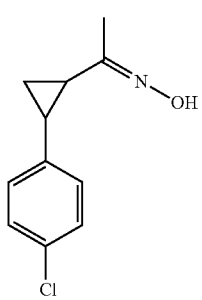

$^1$H-NMR (CDCl$_3$) δ(ppm): 7.25-7.22 (2H, m), 7.04-7.01 (2H, m), 2.19-2.14 (1H, m), 1.85 (3H, s), 1.81-1.76 (1H, m), 1.44-1.39 (1H, m), 1.19-1.14 (1H, m).

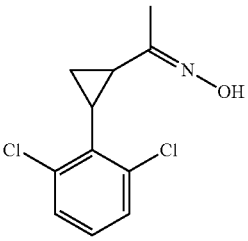

1-[2-(2,6-dichlorophenyl)cyclopropyl]ethanone oxime (C216A)

$^1$H-NMR (CDCl$_3$) δ(ppm): 7.29 (2H, d, J=7.9 Hz), 7.12 (1H, t, J=8.0 Hz), 2.77-2.71 (1H, m), 2.28-2.22 (1H, m), 1.74 (3H, s), 1.57-1.47 (2H, m).

Reference Production Examples 220 to 222

In the same manner as in Reference Production Example 76, except that each raw material was used in place of an amide compound, production was performed.

1-(2-phenylcyclopropyl)ethanone (C220A)

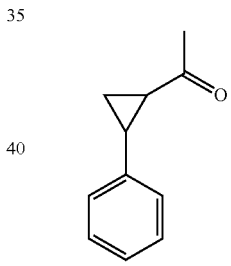

$^1$H-NMR (CDCl$_3$) δ(ppm): 7.31-7.27 (2H, m), 7.23-7.19 (1H, m), 7.11-7.09 (2H, m), 2.55-2.50 (1H, m), 2.31 (3H, s), 2.24-2.20 (1H, m), 1.70-1.65 (1H, m), 1.41-1.36 (1H, m).

1-[2-(4-chlorophenyl)cyclopropyl]ethanone (C221A)

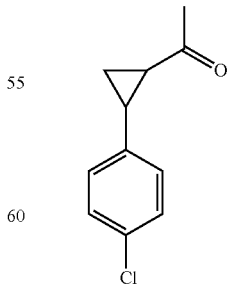

$^1$H-NMR (CDCl$_3$) δ(ppm): 7.26-7.23 (2H, m), 7.04-7.00 (2H, m), 2.52-2.47 (1H, m), 2.31 (3H, s), 2.20-2.16 (1H, m), 1.69-1.64 (1H, m), 1.36-1.32 (1H, m).

1-[2-(2,6-dichlorophenyl)cyclopropyl]ethanone (C222A)

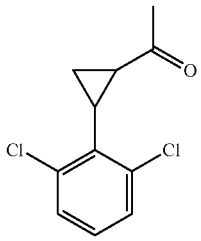

¹H-NMR (CDCl₃) δ(ppm): 7.29 (2H, d, J=7.8 Hz), 7.13 (1H, dd, J=8.5, 7.8 Hz), 2.42 (3H, s), 2.40-2.36 (1H, m), 2.27-2.23 (1H, m), 1.85-1.80 (1H, m), 1.46-1.41 (1H, m).

Reference Production Example 223

In the same manner as in Reference Production Example 99, except that a raw material was used in place of a halogenated acyl compound, production was performed.

3-phenyl-N-methoxy-N-methylacrylamide (C223A)

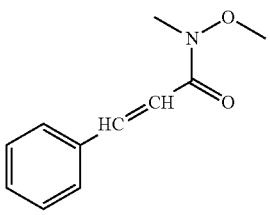

¹H-NMR (CDCl₃) δ(ppm): 7.74 (1H, d, J=15.8 Hz), 7.59-7.57 (2H, m), 7.42-7.36 (3H, m), 7.04 (1H, d, J=15.8 Hz), 3.77 (3H, s), 3.32 (3H, s).

Reference Production Examples 224 to 225

In the same manner as in Reference Production Example 140, except that a raw material was used in place of a carboxylic acid compound, production was performed.

3-(4-chlorophenyl)-N-methoxy-N-methylacrylamide (C224A)

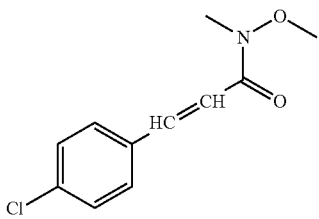

¹H-NMR (CDCl₃) δ(ppm): 7.68 (1H, d, J=15.8 Hz), 7.52-7.49 (2H, m), 7.37-7.34 (2H, m), 7.01 (1H, d, J=15.8 Hz), 3.77 (3H, s), 3.32 (3H, s).

3-(2,6-dichlorophenyl)-N-methoxy-N-methylacrylamide (C225A)

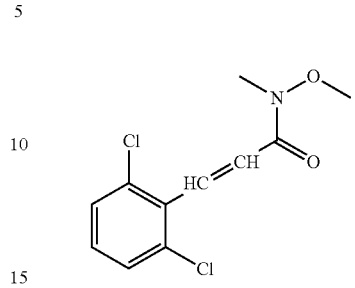

¹H-NMR (CDCl₃) δ(ppm): 7.79 (1H, d, J=16.3 Hz), 7.36 (2H, d, J=8.0 Hz), 7.20-7.14 (2H, m), 3.76 (3H, s), 3.33 (3H, s).

Reference Production Example 226

A mixture of 2.93 g of C223A, 6.60 g of trimethylsulfoxonium iodide, 0.72 g of sodium borohydride, and 30 mL of dimethylformamide was stirred at 0° C. for 6 hours. After completion of the reaction, an aqueous saturated ammonium chloride solution was added, followed by stirring and further extraction with ethyl acetate. The organic layer was dried over anhydrous magnesium sulfate and then concentrated to obtain a crude product. The obtained crude product was subjected to silica gel column chromatography to obtain N-methoxy-N-methyl-2-phenylcyclopropanecarboxylic acid amide (C226A).

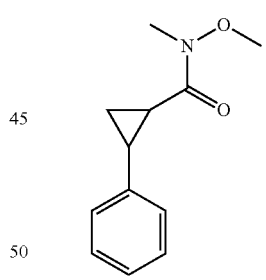

¹H-NMR (CDCl₃) δ(ppm): 7.31-7.27 (2H, m), 7.20 (1H, tt, J=7.4, 1.6 Hz), 7.15-7.13 (2H, m), 3.70 (3H, s), 3.24 (3H, s), 2.53-2.48 (1H, m), 2.42 (1H, bs), 1.66-1.61 (1H, m), 1.34-1.29 (1H, m).

Reference Production Examples 227 to 228

In the same manner as in Reference Production Example 226, except that each raw material was used in place of an amide compound, production was performed.

N-methoxy-N-methyl-2-(4-chlorophenyl)cyclopropanecarboxylic acid amide (C227A)

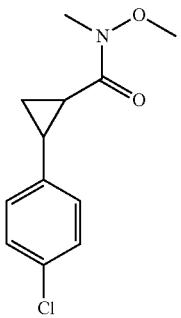 [SMILES: CON(C)C(=O)C1CC1c1ccc(Cl)cc1]

$^1$H-NMR (CDCl$_3$) δ(ppm): 7.26-7.23 (2H, m), 7.08-7.04 (2H, m), 3.69 (3H, s), 3.24 (3H, s), 2.49-2.45 (1H, m), 2.37 (1H, bs), 1.66-1.61 (1H, m), 1.30-1.25 (1H, m).

N-methoxy-N-methyl-2-(2,6-dichlorophenyl)cyclopropanecarboxylic acid amide (C228A)

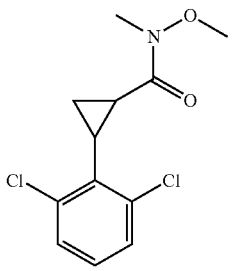 [SMILES: CON(C)C(=O)C1CC1c1c(Cl)cccc1Cl]

$^1$H-NMR (CDCl$_3$) δ(ppm): 7.28 (2H, d, J=8.0 Hz), 7.12 (1H, t, J=8.0 Hz), 3.79 (3H, s), 3.28 (3H, s), 2.54-2.49 (2H, m), 1.72-1.67 (1H, m), 1.47-1.42 (1H, m).

Reference Production Examples 251 to 259

In the same manner as in Reference Production Example 19, except that each raw material was used in place of a katone compound, production was performed.

1-pyridin-3-ylethanone oxime (C251A)

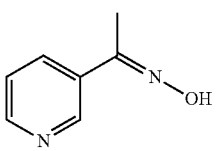

$^1$H-NMR (CDCl$_3$) δ(ppm): 8.93 (1H, d, J=2.1 Hz), 8.78 (1H, s), 8.61 (1H, dd, J=4.8, 1.6 Hz), 7.96 (1H, dt, J=8.0, 2.0 Hz), 7.33 (1H, dd, J=8.0, 4.8 Hz), 2.31 (3H, s).

1-pyridin-2-ylethanone oxime (C252A)

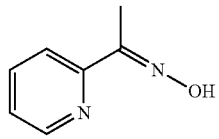

$^1$H-NMR (CDCl$_3$) δ(ppm): 8.63 (1H, dq, J=4.8, 0.8 Hz), 7.84 (1H, dt, J=8.1, 1.1 Hz), 7.69 (1H, td, J=7.7, 1.9 Hz), 7.28 (1H, ddd, J=7.5, 4.8, 1.1 Hz), 2.40 (3H, s).

1-(6-trifluoromethylpyridin-2-yl)ethanone oxime (C253A)

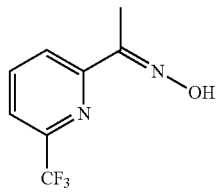

$^1$H-NMR (CDCl$_3$) δ(ppm): 8.09 (1H, d, J=7.8 Hz), 7.84 (1H, t, J=7.8 Hz), 7.64 (1H, d, J=7.8 Hz), 2.40 (3H, s).

1-(1-methyl-1H-pyrrol-3-yl)ethanone oxime (C254A)

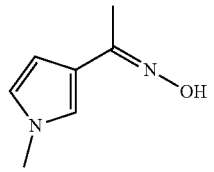

$^1$H-NMR (CDCl$_3$) δ(ppm): 7.62 (0.5H, t, J=1.8 Hz), 6.86 (0.5H, t, J=1.9 Hz), 6.59 (0.5H, t, J=2.5 Hz), 6.57 (0.5H, t, J=2.5 Hz), 6.48 (0.5H, dd, J=2.66, 1.69 Hz), 6.40 (0.5H, dd, J=2.8, 1.8 Hz), 3.69 (1.5H, s), 3.65 (1.5H, s), 2.19 (1.5H, s), 2.18 (1.5H, s).

1-(1-methyl-1H-pyrrol-2-yl)ethanone oxime (C255A)

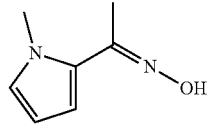

$^1$H-NMR (CDCl$_3$) δ(ppm): 7.64 (1H, bs), 6.66 (1H, t, J=2.2 Hz), 6.44 (1H, dd, J=3.9, 1.8 Hz), 6.12 (1H, dd, J=3.9, 2.8 Hz), 3.80 (3H, s), 2.23 (3H, s).

1-(4-methyl-2-thienyl)ethanone oxime (C256A)

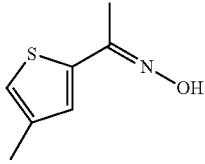

$^1$H-NMR (CDCl$_3$) δ(ppm): 8.41 (1H, bs), 7.06 (1H, s), 6.86 (1H, s), 2.28 (3H, s), 2.25 (3H, s).

1-(2-thienyl)ethanone oxime (C257A)

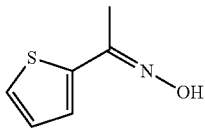

$^1$H-NMR (CDCl$_3$) δ(ppm): 8.63 (1H, bs), 7.58 (0.2H, dd, J=5.1, 1.0 Hz), 7.52 (0.2H, dd, J=3.7, 1.1 Hz), 7.29 (0.8H, dd, J=5.1, 1.0 Hz), 7.26 (0.8H, dd, J=3.7, 1.1 Hz), 7.12 (0.2H, dd, J=5.1, 3.8 Hz), 7.04 (0.8H, dd, J=5.1, 3.8 Hz), 2.39 (0.7H, s), 2.32 (2.3H, s). 1-(3-methyl-2-thienyl)ethanone oxime (C258A)

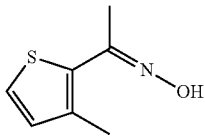

$^1$H-NMR (CDCl$_3$) δ(ppm): 8.52 (1H, bs), 7.19 (1H, d, J=5.4 Hz), 6.86 (1H, d, J=5.4 Hz), 2.39 (3H, s), 2.32 (3H, s). 1-(2-furyl)ethanone oxime (C259A)

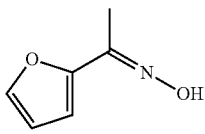

$^1$H-NMR (CDCl$_3$) δ(ppm): 9.00 (1H, bs), 7.47 (1H, dd, J=1.8, 0.8 Hz), 6.64 (1H, dd, J=3.4, 0.8 Hz), 6.44 (1H, dd, J=3.4, 1.8 Hz), 2.22 (3H, s).

Reference Production Example 260

A mixture of 2.14 g of C265A, 1.12 g of potassium hydroxide, and 40 mL of ethanol was stirred while heating under reflux for 2 hours. After completion of the reaction, water and 1N hydrochloric acid were added, followed by extraction with ethyl acetate. The organic layer was dried over anhydrous magnesium sulfate and then concentrated to obtain a crude product. The obtained crude product was subjected to silica gel column chromatography to obtain 1-(6-fluorobenzo[d]isoxazol-3-yl)ethanone oxime (C260A).

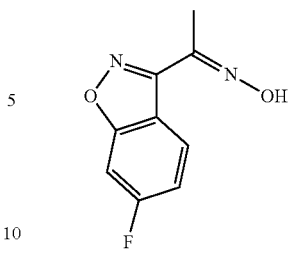

$^1$H-NMR (DMSO-D$_6$) δ(ppm): 12.31 (1H, s), 8.10 (1H, dd, J=8.8, 5.7 Hz), 7.78 (1H, dd, J=9.0, 1.9 Hz), 7.36 (1H, td, J=9.1, 2.2 Hz), 2.28 (3H, s).

Reference Production Examples 261 to 263

In the same manner as in Reference Production Example 19, except that each raw material was used in place of a ketone compound, production was performed.

1-(1,5-dimethyl-1H-pyrazol-3-yl)ethanone oxime (C261A)

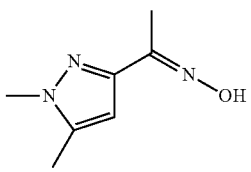

$^1$H-NMR (CDCl$_3$) δ(ppm): 6.30 (1H, s), 3.79 (3H, s), 2.28 (3H, d, J=3.2 Hz), 2.27 (3H, s).

4-(3-thienyl)butan-3-en-2-one oxime (C262A)

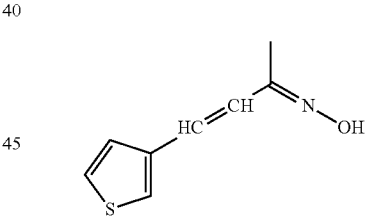

$^1$H-NMR (CDCl$_3$) δ(ppm): 7.33-7.28 (3H, m), 6.91 (1H, d, J=16.5 Hz), 6.67 (1H, d, J=16.3 Hz), 2.10 (3H, s).

1-[2-(3-thienyl)cyclopropyl]ethanone oxime (C263A)

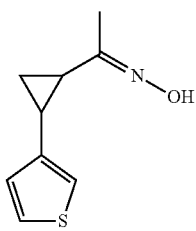

¹H-NMR (CDCl₃) δ(ppm): 7.64 (1.0H, s), 7.26-7.23 (1.0H, m), 6.99-6.97 (0.2H, m), 6.93-6.92 (0.8H, m), 6.90 (0.2H, dd, J=4.9, 1.0 Hz), 6.85 (0.8H, dd, J=5.0, 1.1 Hz), 2.72-2.68 (0.2H, m), 2.35-2.30 (0.2H, m), 2.27-2.22 (0.8H, m), 1.84 (2.2H, s), 1.82-1.77 (0.8H, m), 1.67 (0.8H, s), 1.39-1.32 (1.0H, m), 1.28-1.22 (0.2H, m), 1.16-1.11 (0.8H, m).

Reference Production 264

To a mixture of 5.0 g of 2-bromo-6-trifluoromethylpyridine, 3.1 mL of dimethylaceto, and amide diethyl ether, butyllithium (n-BuLi) was added dropwise at −78° C., followed by stirring for 6 hours. After completion of the reaction, water was added, followed by stirring and further extraction with ethyl acetate. The organic layer was dried over anhydrous magnesium sulfate and then concentrated to obtain a crude product. The obtained crude product was subjected to silica gel column chromatography to obtain 1-(6-trifluoromethylpyridin-2-yl)ethanone (C264A).

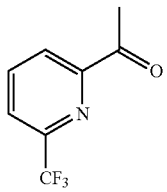

¹H-NMR (CDCl₃) δ(ppm): 8.22 (1H, d, J=7.8 Hz), 8.04 (1H, t, J=7.8 Hz), 7.86 (1H, d, J=7.8 Hz), 2.77 (3H, s).

Reference Production Example 265

In the same manner as in Reference Production Example 19, except that a raw material was used in place of a ketone compound, production was performed.

1-(2,4-difluorophenyl)propane-1,2-diondioxime (C265A)

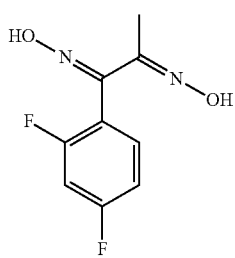

¹H-NMR (DMSO-D₆) δ(ppm): 11.87 (0.3H, s), 11.82 (0.7H, s), 11.58 (0.7H, s), 11.32 (0.3H, s), 7.54-7.47 (0.3H, m), 7.30-7.19 (1.7H, m), 7.14-7.05 (1.0H, m), 2.08 (0.9H, s), 2.06 (2.1H, s).

Reference Production Examples 266 to 268

In the same manner as in Reference Production Example 76, except that each raw material was used in place of an amide compound, production was performed.

1-(1,5-dimethyl-1H-pyrazol-3-yl)ethanone (C266A)

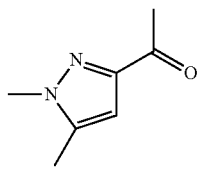

¹H-NMR (CDCl₃) δ(ppm): 6.53 (1H, d, J=0.7 Hz), 3.84 (3H, s), 2.54 (3H, s), 2.30 (3H, d, J=0.7 Hz).

4-(3-thienyl)butan-3-en-2-one (C267A)

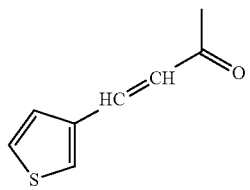

¹H-NMR (CDCl₃) δ(ppm): 7.55-7.54 (1H, m), 7.52 (1H, d, J=16.3 Hz), 7.37-7.35 (1H, m), 7.32-7.31 (1H, m), 6.55 (1H, d, J=16.3 Hz), 2.36 (3H, s).

1-[2-(3-thienyl)cyclopropyl]ethanone (C268A)

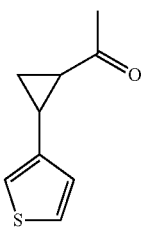

¹H-NMR (CDCl₃) δ(ppm): 7.27-7.25 (1H, m), 6.96-6.95 (1H, m), 6.84 (1H, d, J=5.0 Hz), 2.59-2.54 (1H, m), 2.31 (3H, s), 2.21-2.17 (1H, m), 1.66-1.61 (1H, m), 1.35-1.30 (1H, m).

Reference Production Example 269

A mixture of 14 mL of 1-(2,4-difluorophenyl)propan-1-one, 16 mL of amyl nitrite, 10 mL of concentrated hydrochloric acid, and 200 mL of tetrahydrofuran was stirred at room temperature for 6 hours. After completion of the reaction, water was added, followed by extraction with ethyl acetate. The organic layer was dried over anhydrous magnesium sulfate and then concentrated to obtain a crude product. The obtained crude product was subjected to silica gel column chromatography to obtain 1-(2,4-difluorophenyl)propane-1,2-dione-2-oxime (C269A).

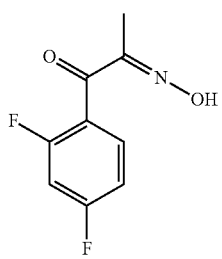

¹H-NMR (CDCl₃) δ(ppm): 8.16 (1H, s), 7.56-7.50 (1H, m), 6.97-6.92 (1H, m), 6.88-6.82 (1H, m), 2.14 (3H, s).

Reference Production Example 270

In the same manner as in Reference Production Example 140, except that a raw material was used in place of a carboxylic acid compound, production was performed.

N-methoxy-N-methyl-1,5-dimethyl-1H-pyrazole-3-carboxylic acid amide (C270A)

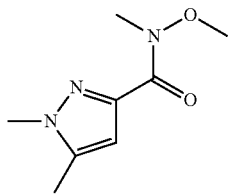

¹H-NMR (CDCl₃) δ(ppm): 6.51 (1H, s), 3.84 (3H, s), 3.75 (3H, s), 3.42 (3H, s), 2.30 (3H, s).

N-methoxy-N-methyl-3-(3-thienyl)acrylamide (C271A)

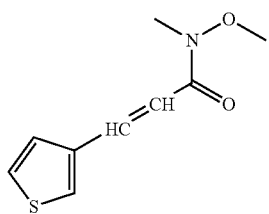

¹H-NMR (CDCl₃) δ(ppm): 7.72 (1H, d, J=15.7 Hz), 7.51-7.50 (1H, m), 7.36-7.32 (2H, m), 6.86 (1H, d, J=15.7 Hz), 3.76 (3H, s), 3.31 (3H, s).

Reference Production Example 272

In the same manner as in Reference Production Example 226, except that a raw material was used in place of an amide compound, production was performed.

N-methoxy-N-methyl-2-(3-thienyl)cyclopropanecarboxylic acid amide (C272A)

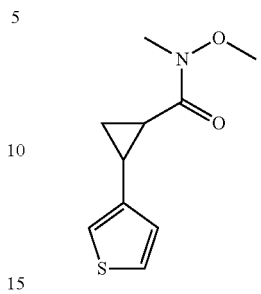

¹H-NMR (CDCl₃) δ(ppm): 7.25 (1H, dd, J=4.8, 3.0 Hz), 6.97 (1H, d, J=2.3 Hz), 6.88 (1H, dd, J=5.0, 0.9 Hz), 3.71 (3H, s), 3.24 (3H, s), 2.55-2.51 (1H, m), 2.37 (1H, bs), 1.61-1.57 (1H, m), 1.28-1.23 (1H, m).

According to the above method, compounds EP1A-001 to EP12G-513 can be obtained.

The compounds EP1A-001 to EP12G-513 are as follows:

(EP1A)

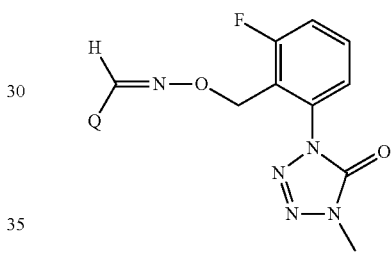

(EP1B)

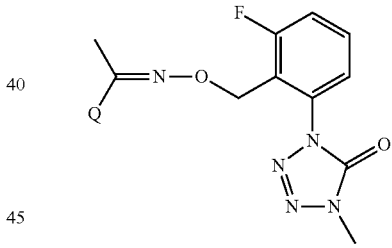

(EP1C)

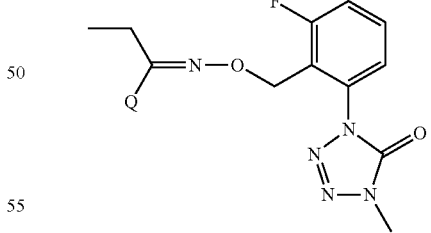

(EP1D)

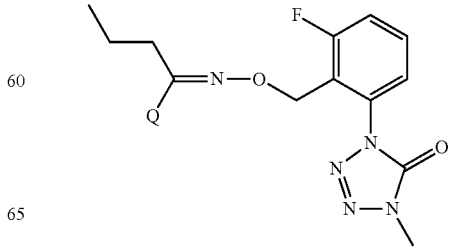

-continued
(EP1E)
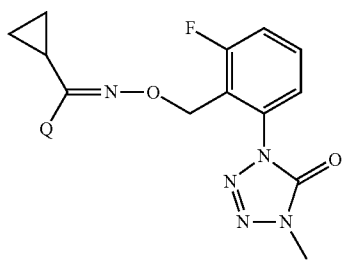
(EP1F)
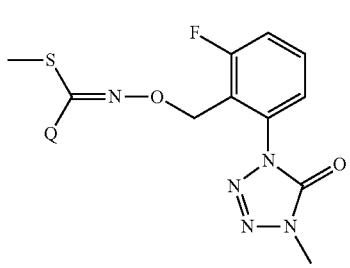
(EP1G)
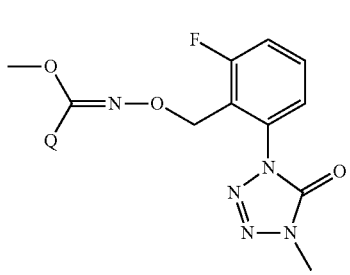
(EP2A)
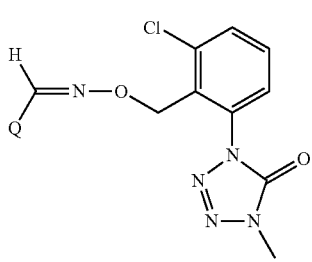
(EP2B)
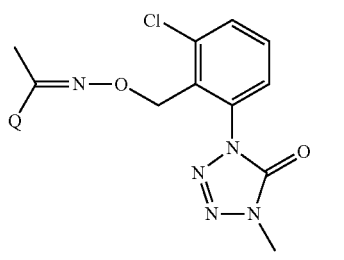
(EP2C)
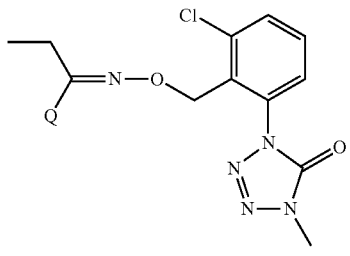
-continued
(EP2D)
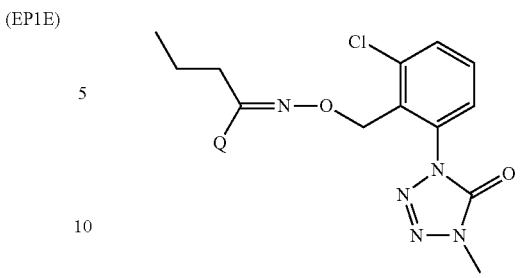
(EP2E)
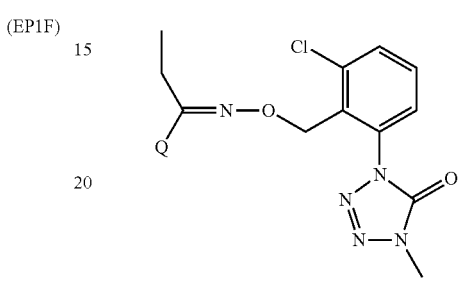
(EP2F)
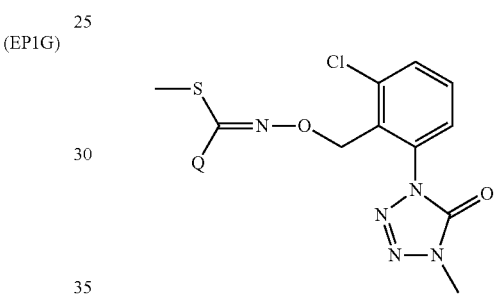
(EP2G)
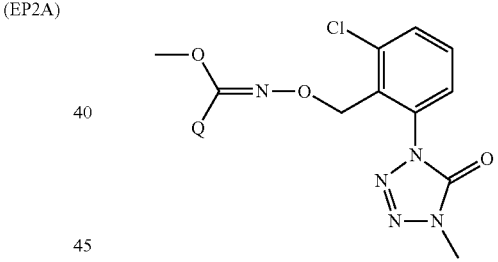
(EP3A)
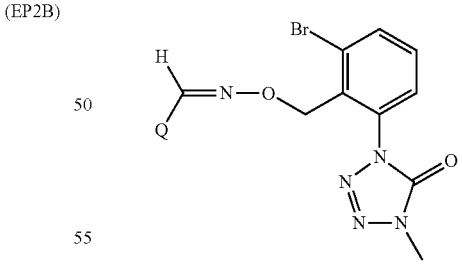
(EP3B)
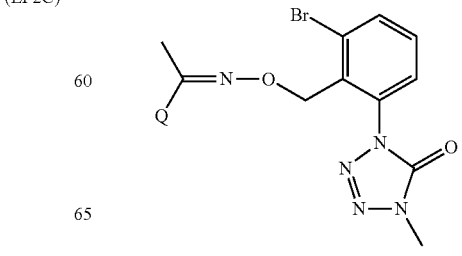

| 371 -continued | | 372 -continued | |
|---|---|---|---|
| 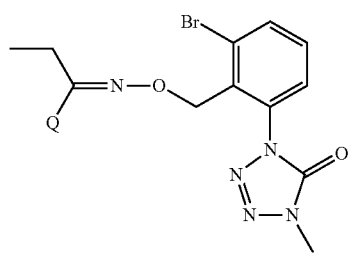 | (EP3C) | 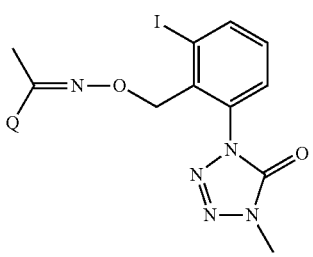 | (EP4B) |
| 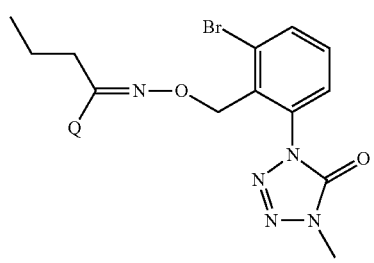 | (EP3D) | 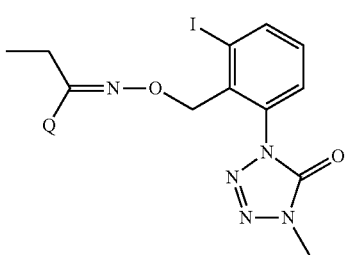 | (EP4C) |
| 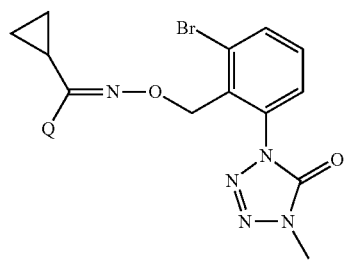 | (EP3E) | 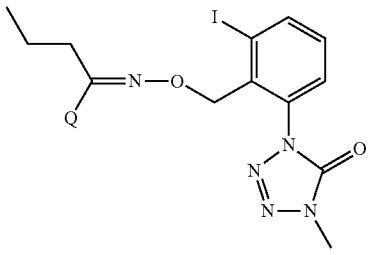 | (EP4D) |
| 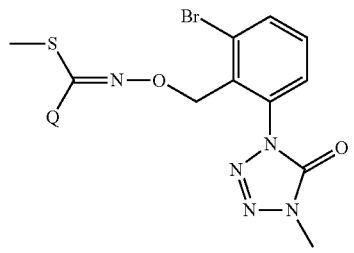 | (EP3F) | 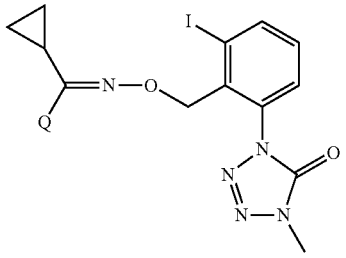 | (EP4E) |
| 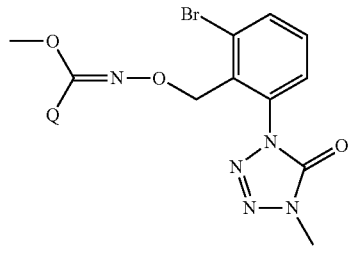 | (EP3G) | 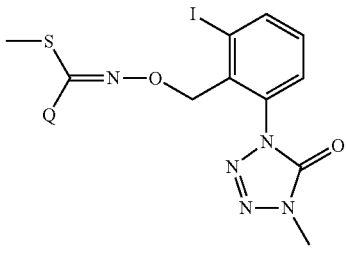 | (EP4F) |
| 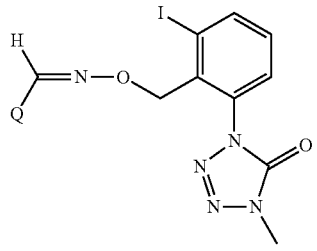 | (EP4A) | 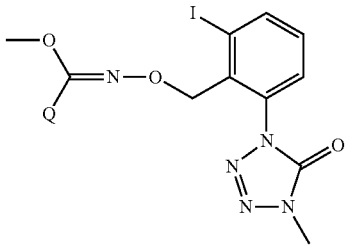 | (EP4G) |

(EP5A) 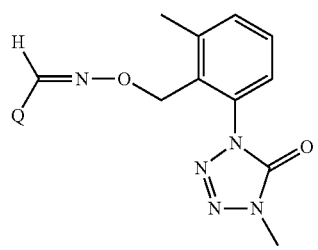
(EP5B) 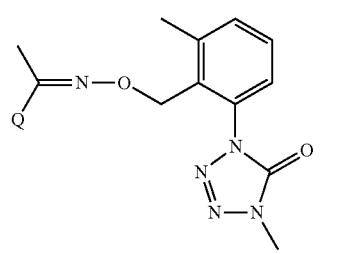
(EP5C) 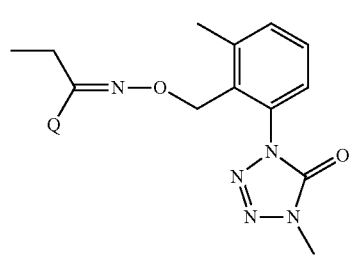
(EP5D) 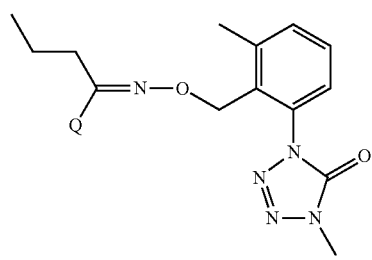
(EP5E) 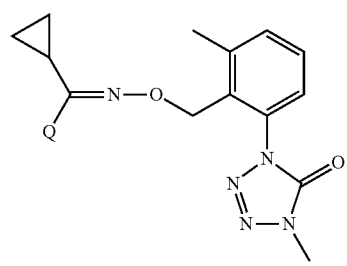
(EP5F) 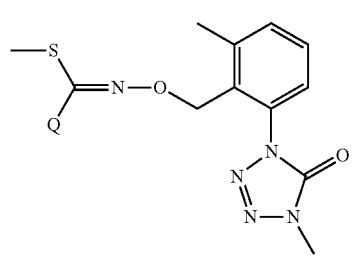
(EP5G) 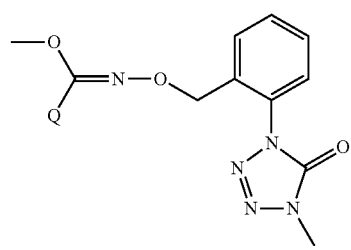
(EP6A) 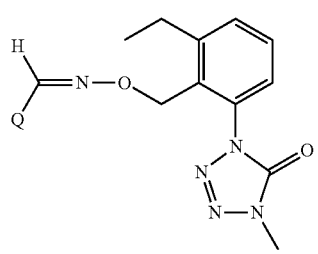
(EP6B) 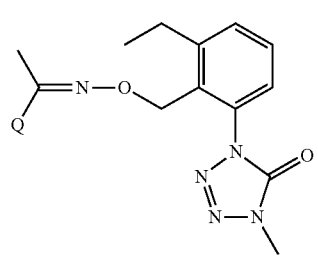
(EP6C) 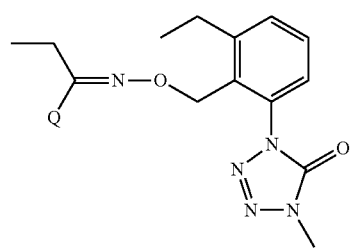
(EP6D) 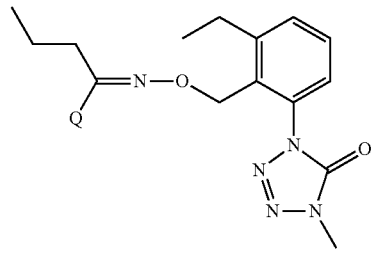
(EP6E) 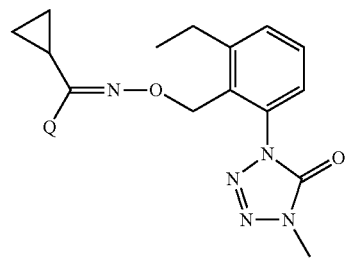

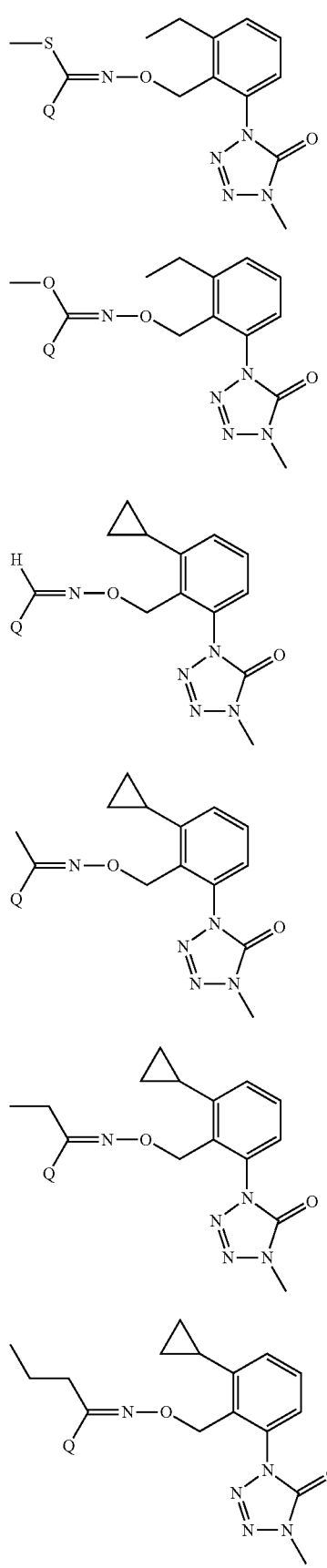
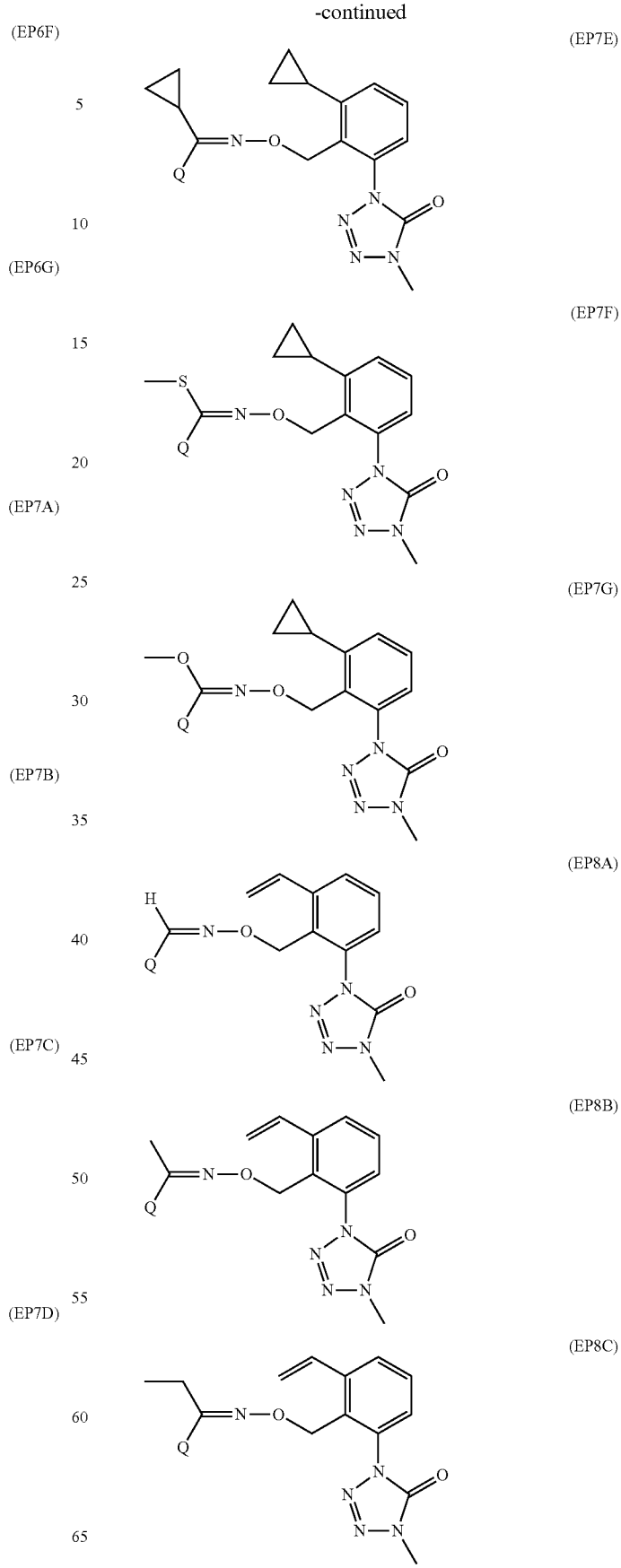

377
-continued
(EP8D)
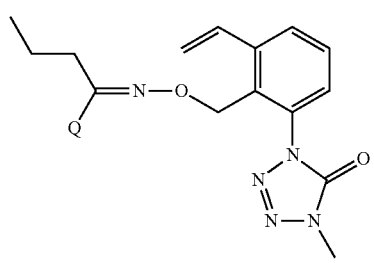
(EP8E)
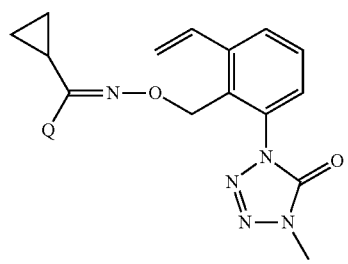
(EP8F)
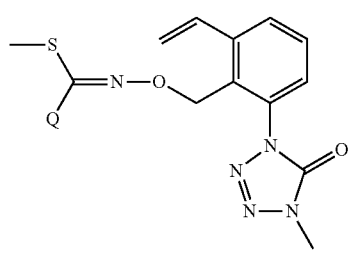
(EP8G)
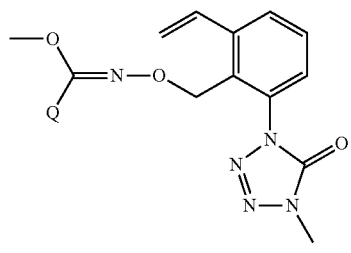
(EP9A)
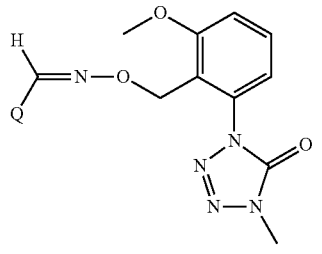
(EP9B)
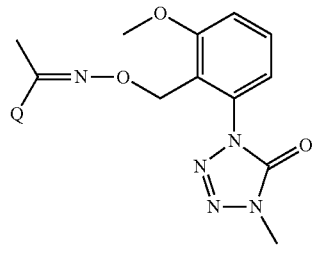
378
-continued
(EP9C)
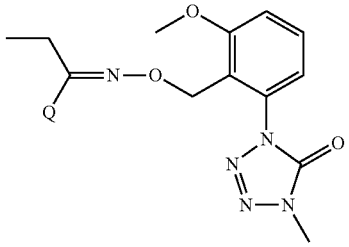
(EP9D)
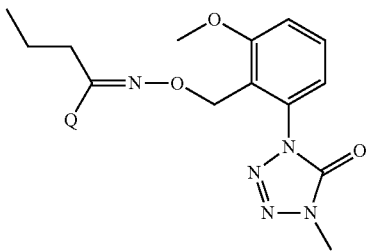
(EP9E)
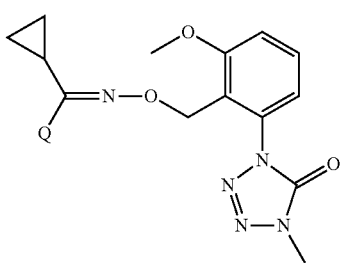
(EP9F)
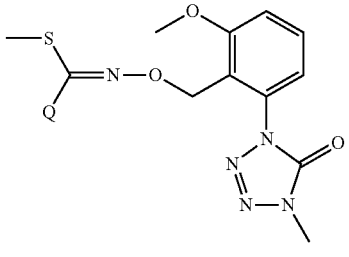
(EP9G)
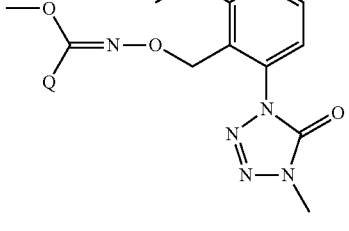
(EP10A)
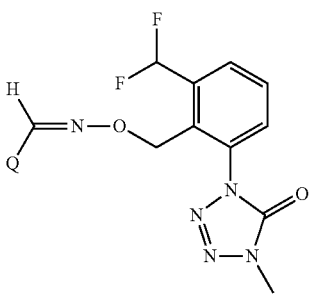

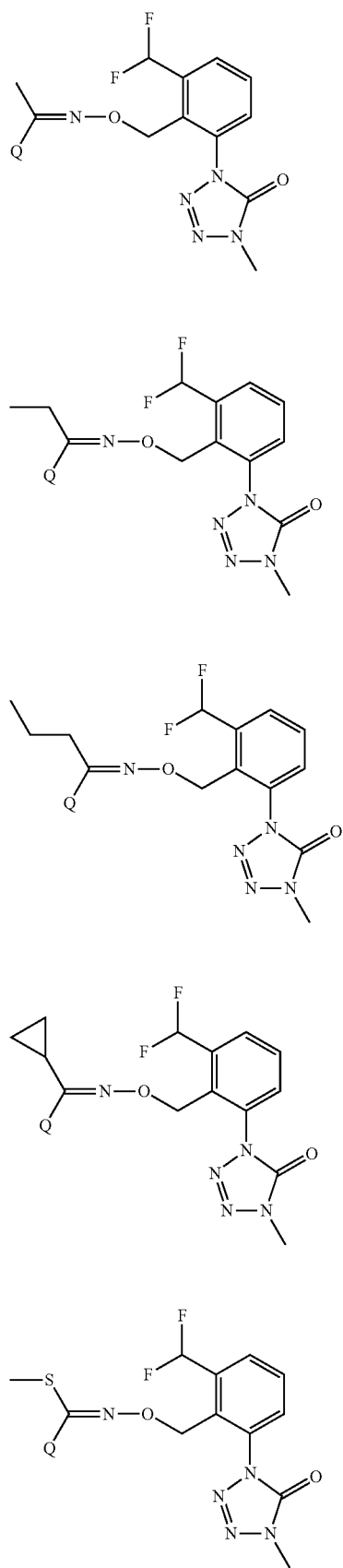
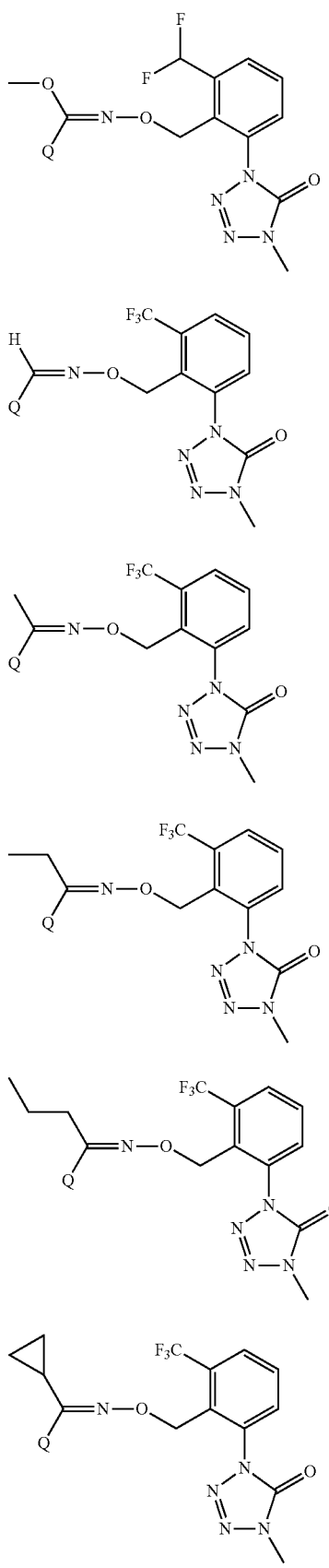

-continued (EP11F)
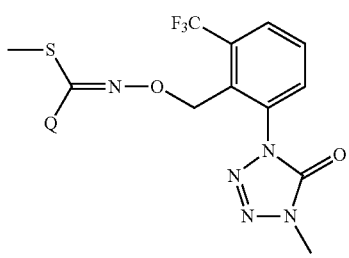

(EP11G)
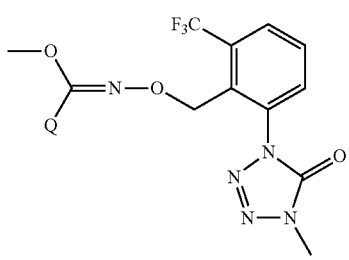

(EP12A)
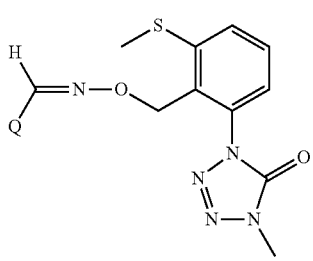

(EP12B)
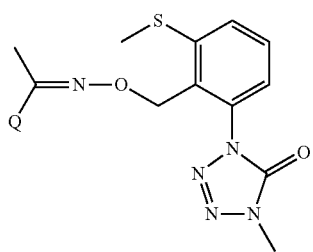

(EP12C)
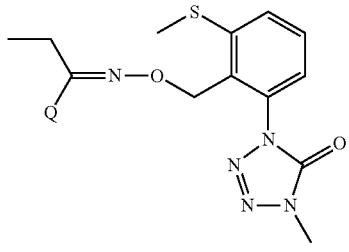

(EP12D)
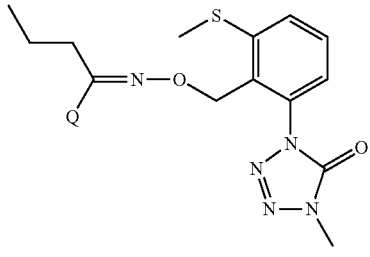

-continued (EP12E)
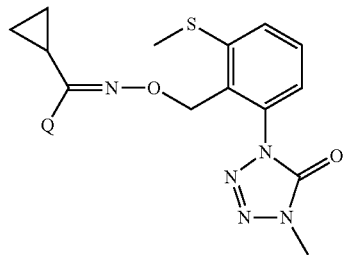

(EP12F)
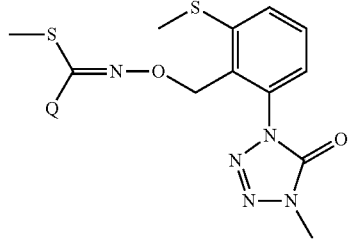

(EP12G)
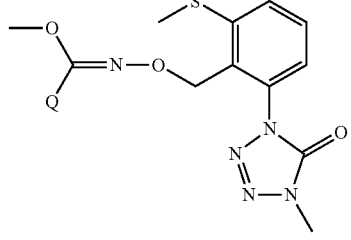

wherein Q is a compound represented by the substituent corresponding to each of the following substituent numbers 1 to 513: [substituent number; Q], [1; phenyl group], [2; 2-fluorophenyl group], [3; 3-fluorophenyl group], [4; 4-fluorophenyl group], [5; 2,3-difluorophenyl group], [6; 2,4-difluorophenyl group], [7; 2,5-difluorophenyl group], [8; 2,6-difluorophenyl group], [9; 3,4-difluorophenyl group], [10; 3,5-difluorophenyl group], [11; 2,3,4-trifluorophenyl group], [12; 2,3,5-trifluorophenyl group], [13; 2,4,5-trifluorophenyl group], [14; 2,3,6-trifluorophenyl group], [15; 2,4,6-trifluorophenyl group], [16; 3,4,5-trifluorophenyl group], [17; 3-chlorophenyl group], [18; 4-chlorophenyl group], [19; 3,4-dichlorophenyl group], [20; 3,5-dichlorophenyl group], [21; 3,4,5-trichlorophenyl group], [22; 3-bromophenyl group], [23; 4-bromophenyl group], [24; 3,4-dibromophenyl group], [25; 3,5-dibromophenyl group], [26; 3,4,5-tribromophenyl group], [27; 3-iodophenyl group], [28; 4-iodophenyl group], [29; 3,4-diiodophenyl group], [30; 3,5-diiodophenyl group], [31; 3,4,5-triiodophenyl group], [32; 2-fluoro-3-chlorophenyl group], [33; 2-fluoro-3-bromophenyl group], [34; 2-fluoro-3-iodophenyl group], [35; 2-fluoro-4-chlorophenyl group], [36; 2-fluoro-4-bromophenyl group], [37; 2-fluoro-4-iodophenyl group], [38; 2-fluoro-5-chlorophenyl group], [39; 2-fluoro-5-bromophenyl group], [40; 2-fluoro-5-iodophenyl group], [41; 2-fluoro-6-chlorophenyl group], [42; 2-fluoro-6-bromophenyl group], [43; 2-fluoro-6-iodophenyl group], [44; 3-fluoro-4-chlorophenyl group], [45; 3-fluoro-4-bromophenyl group], [46; 3-fluoro-4-iodophenyl group], [47; 3-fluoro-5-chlorophenyl group], [48; 3-fluoro-5-bromophenyl group], [49; 3-fluoro-5-iodophenyl group], [50; 3-chloro-4-fluorophenyl group], [51; 3-chloro-4-bromophenyl group], [52; 3-chloro-4-iodophenyl group], [53; 3-chloro-5-bromophenyl group], [54; 3-chloro-5-iodophenyl group], [55; 3-iodo-4-fluorophenyl group], [56; 3-iodo-4-chlorophenyl group], [57; 3-iodo-4-bromophenyl group], [58; 3-chloro-4,5-difluorophenyl group], [59; 3-bromo-4,5-difluorophenyl group], [60; 3-iodo-4,5-difluorophenyl group], [61; 3-fluoro-4,5-dichlorophenyl group], [62; 3-bromo-4,5-dichlorophenyl group], [63; 3-iodo-4,5-dichlorophenyl group], [64; 3-fluoro-4,5-dibromophenyl group], [65; 3-chloro-4,5-dibromophenyl group], [66; 3-iodo-4,5-dibromophenyl group], [67; 3-fluoro-4,5-diiodophenyl group], [68; 3-chloro-4,5-diiodophenyl group], [69; 3-bromo-4,5-diiodophenyl group], [70; 4-chloro-3,5-difluorophenyl group], [71; 4-bromo-3,5-difluorophenyl group], [72; 4-iodo-3,5-difluorophenyl group], [73; 4-fluoro-3,5-dichlorophenyl group], [74; 4-bromo-3,5-dichlorophenyl group], [75; 4-iodo-3,5-dichlorophenyl group], [76; 4-fluoro-3,5-dibromophenyl group], [77; 4-chloro-3,5-dibromophenyl group], [78; 4-iodo-3,5-dibromophenyl group], [79; 4-fluoro-3,5-diiodophenyl group], [80; 4-chloro-3,5-diiodophenyl group], [81; 4-bromo-3,5-diiodophenyl group], [82; 2-methylphenyl group], [83; 3-methylphenyl group], [84; 4-methylphenyl group], [85; 2,3-dimethylphenyl group], [86; 2,4-dimethylphenyl group], [87; 2,5-dimethylphenyl group], [88; 2,6-dimethylphenyl group], [89; 3,4-dimethylphenyl group], [90; 3,5-dimethylphenyl group], [91; 2,3,4-trimethylphenyl group], [92; 2,3,5-trimethylphenyl group], [93; 2,3,6-trimethylphenyl group], [94; 2,4,5-trimethylphenyl group], [95; 2,4,6-trimethylphenyl group], [96; 3,4,5-trimethylphenyl group], [97; 2-ethylphenyl group], [98; 3-ethylphenyl group], [99; 4-ethylphenyl group], [100; 2,3-diethylphenyl group], [101; 2,4-diethylphenyl group], [102; 2,5-diethylphenyl group], [103; 2,6-diethylphenyl group], [104; 3,4-diethylphenyl group], [105; 3,5-diethylphenyl group], [106; 2,3,4-triethylphenyl group], [107; 2,3,5-triethylphenyl group], [108; 2,3,6-triethylphenyl group], [109; 2,4,5-triethylphenyl group], [110; 2,4,6-triethylphenyl group], [111; 3,4,5-triethylphenyl group], [112; 3-propylphenyl group], [113; 4-propylphenyl group], [114; 3,4-dipropylphenyl group], [115; 3,5-dipropylphenyl group], [116; 3,4,5-tripropylphenyl group], [117; 3-isopropylphenyl group], [118; 4-isopropylphenyl group], [119; 3,4-diisopropylphenyl group], [120; 3,5-diisopropylphenyl group], [121; 3,4,5-triisopropylphenyl group], [122; 3-butylphenyl group], [123; 4-butylphenyl group], [124; 3,4-dibutylphenyl group], [125; 3,5-dibutylphenyl group], [126; 3-sec-butylphenyl group], [127; 4-sec-butylphenyl group], [128; 3,4-di-sec-butylphenyl group], [129; 3,5-di-sec-butylphenyl group], [130; 3-isobutylphenyl group], [131; 4-isobutylphenyl group], [132; 3,4-diisobutylphenyl group], [133; 3,5-diisobutylphenyl group], [134; 3-tert-butylphenyl group], [135; 4-tert-butylphenyl group], [136; 3,4-di-tert-butylphenyl group], [137; 3,5-di-tert-butylphenyl group], [138; 3-cyclopropylphenyl group], [139; 4-cyclopropylphenyl group], [140; 3,4-dicyclopropylphenyl group], [141; 3,5-dicyclopropylphenyl group], [142; 3-cyclobutylphenyl group], [143; 4-cyclobutylphenyl group], [144; 3,4-dicyclobutylphenyl group], [145; 3,5-dicyclobutylphenyl group], [146; 3-vinylphenyl group], [147; 4-vinylphenyl group], [148; 3-(1-propenyl)phenyl group], [149; 4-(1-propenyl)phenyl group], [150; 3-(2-propenyl)phenyl group], [151; 4-(2-propenyl)phenyl group], [152; 3-(1-butenyl)phenyl group], [153; 4-(1-butenyl)phenyl group], [154; 3-(2-butenyl)phenyl group], [155; 4-(2-butenyl)phenyl group], [156; 3-(3-butenyl)phenyl group], [157; 4-(3-butenyl)phenyl group], [158; 3-(1-methyl-1-propynyl)phenyl group], [159; 4-(1-methyl-1-propynyl)phenyl group], [160; 3-(1-ethyl-1-ethynyl)phenyl group], [161; 4-(1-ethyl-1-ethynyl)phenyl group], [162; 3-(2-methyl-1-propynyl)phenyl group], [163; 4-(2-methyl-1-propynyl)phenyl group], [164; 3-(2-methyl-2-propynyl)phenyl group], [165; 4-(2-methyl-2-propynyl)phenyl group], [166; 3-ethynylphenyl group], [167; 4-ethynylphenyl group], [168; 3-(1-propynyl)phenyl group], [169; 4-(1-propynyl)phenyl group], [170; 3-(2-propynyl)phenyl group], [171; 4-(2-propynyl)phenyl group], [172; 3-(1-butynyl)phenyl group], [173; 4-(1-butynyl)phenyl group], [174; 3-(2-butynyl)phenyl group], [175; 4-(2-butynyl)phenyl group], [176; 3-(3-butynyl)phenyl group], [177; 4-(3-butynyl)phenyl group], [178; 3-(1-methyl-2-propynyl)phenyl group], [179; 4-(1-methyl-2-propynyl)phenyl group], [180; 3-methoxyphenyl group], [181; 4-methoxyphenyl group], [182; 3-ethoxyphenyl group], [183; 4-ethoxyphenyl group], [184; 3-propoxyphenyl group], [185; 4-propoxyphenyl group], [186; 3-isopropoxyphenyl group], [187; 4-isopropoxyphenyl group], [188; 3-cyclopropoxyphenyl group], [189; 4-cyclopropoxyphenyl group], [190; 3-butoxyphenyl group], [191; 4-butoxyphenyl group], [192; 3-sec-butoxyphenyl group], [193; 4-sec-butoxyphenyl group], [194; 3-isobutoxyphenyl group], [195; 4-isobutoxyphenyl group], [196; 3-tert-butoxyphenyl group], [197; 4-tert-butoxyphenyl group], [198; 3,4-dimethoxyphenyl group], [199; 3,5-dimethoxyphenyl group], [200; 3,4,5-trimethoxyphenyl group], [201; 3-vinyloxyphenyl group], [202; 4-vinyloxyphenyl group], [203; 3-(1-propenyloxyl)phenyl group], [204; 4-(1-propenyloxyl)phenyl group], [205; 3-(2-propenyloxyl)phenyl group], [206; 4-(2-propenyloxyl)phenyl group], [207; 3-(1-butenyloxyl)phenyl group], [208; 4-(1-butenyloxyl)phenyl group], [209; 3-(2-butenyloxyl)phenyl group], [210; 4-(2-butenyloxyl)phenyl group], [211; 3-(3-butenyloxyl)phenyl group], [212; 4-(3-butenyloxyl)phenyl group], [213; 3-(1-methyl-1-propynyloxy)phenyl group], [214; 4-(1-methyl-1-propynyloxy)phenyl group], [215; 3-(1-ethyl-1-ethynyloxy)phenyl group], [216; 4-(1-ethyl-1-ethynyloxy)phenyl group], [217; 3-(2-methyl-1-propynyloxy)phenyl group], [218; 4-(2-methyl-1-propynyloxy)phenyl group], [219; 3-(2-methyl-2-propynyloxy)phenyl group], [220; 4-(2-methyl-2-propynyloxy)phenyl group], [221; 3-methoxymethylphenyl group], [222; 4-methoxymethylphenyl group], [223; 3-fluoromethylphenyl group], [224; 4-fluoromethylphenyl group], [225; 3-difluoromethylphenyl group], [226; 4-difluoromethylphenyl group], [227; 3-trifluoromethylphenyl group], [228; 4-trifluoromethylphenyl group], [229; 3-(1-fluoroethyl)phenyl group], [230; 4-(1-fluoroethyl)phenyl group], [231; 3-(2-fluoroethyl)phenyl group], [232; 4-(2-fluoroethyl)phenyl group], [233; 3-(1,1-difluoroethyl)phenyl group], [234; 4-(1,1-difluoroethyl)phenyl group], [235; 3-(1,2-difluoroethyl)phenyl group], [236; 4-(1,2-difluoroethyl)phenyl group], [237; 3-(2,2-difluoroethyl)phenyl group], [238; 4-(2,2-difluoroethyl)phenyl group], [239; 3-(1,1,2-trifluoroethyl)phenyl group], [240; 4-(1,1,2-trifluoroethyl)phenyl group], [241; 3-(1,2,2-trifluoroethyl)phenyl group], [242; 4-(1,2,2-trifluoroethyl)phenyl group], [243; 3-(2,2,2-trifluoroethyl)phenyl group], [244; 4-(2,2,2-trifluoroethyl)phenyl group], [245; 3-(1,1,2,2-tetrafluoroethyl)phenyl group], [246; 4-(1,1,2,2-tetrafluoroethyl)phenyl group], [247; 3-perfluoroethylphenyl group], [248; 4-perfluoroethylphenyl group], [249; 3-(1-fluoropropyl)phenyl group], [250; 4-(1-fluoropropyl)phenyl group], [251; 3-(2-fluoropropyl)phenyl group], [252; 4-(2-fluoropropyl)phenyl group], [253; 3-(3-fluoropropyl)phenyl group], [254; 4-(3-fluoropropyl)phenyl group], [255; 3-(1,1-difluoropropyl)phenyl group], [256; 4-(1,1-difluoropropyl)phenyl group], [257; 3-(1,2-difluoropropyl)phenyl group], [258; 4-(1,2-difluoropropyl)phenyl group], [259; 3-(1,3-difluoropropyl)phenyl group], [260; 4-(1,3-difluoropropyl)phenyl group], [261; 3-(2,2-difluoropropyl)phenyl group], [262; 4-(2,2-difluoropropyl)phenyl group], [263; 3-(2,3-difluoropropyl)phenyl group], [264; 4-(2,3-difluoropropyl)phenyl group], [265; 3-(3,3-difluoropropyl)phenyl group], [266; 4-(3,3-difluoropropyl)phenyl group], [267; 3-(1,1,2-trifluoropropyl)phenyl group], [268; 4-(1,1,2-trifluoropropyl)phenyl group], [269; 3-(1,1,3-trifluoropropyl)phenyl group], [270; 4-(1,1,3-trifluoropropyl)phenyl group], [271; 3-(1,2,2-trifluoropropyl)phenyl group], [272; 4-(1,2,2-trifluoropropyl)phenyl group], [273; 3-(1,2,3-trifluoropropyl)phenyl group], [274; 4-(1,2,3-trifluoropropyl)phenyl group], [275; 3-(1,3,3-trifluoropropyl)phenyl group], [276; 4-(1,3,3-trifluoropropyl)phenyl group], [277; 3-(2,2,3-trifluoropropyl)phenyl group], [278; 4-(2,2,3-trifluoropropyl)phenyl group], [279; 3-(2,3,3-trifluoropropyl)phenyl group], [280; 4-(2,3,3-trifluoropropyl)phenyl group], [281; 3-(3,3,3-trifluoropropyl)phenyl group], [282; 4-(3,3,3-trifluoropropyl)phenyl group], [283; 3-(1,1,2,2-tetrafluoropropyl)phenyl group], [284; 4-(1,1,2,2-tetrafluoropropyl)phenyl group], [285; 3-(1,1,3,3-tetrafluoropropyl)phenyl group], [286; 4-(1,1,3,3-tetrafluoropropyl)phenyl group], [287; 3-(2,2,3,3-tetrafluoropropyl)phenyl group], [288; 4-(2,2,3,3-tetrafluoropropyl)phenyl group], [289; 3-(1,1,3,3,3-pentafluoropropyl)phenyl group], [290; 4-(1,1,3,3,3-pentafluoropropyl)phenyl group], [291; 3-(2,2,3,3,3-pentafluoropropyl)phenyl group], [92; 4-(2,2,3,3,3-pentafluoropropyl)phenyl group], [293; 3-(1,1,2,2,3,3-hexafluoropropyl)phenyl group], [294; 4-(1,1,2,2,3,3-hexafluoropropyl)phenyl group], [295; 3-perfluoropropylphenyl group], [296; 4-perfluoropropylphenyl group], [297; 3-perfluoropropylphenyl group], [298; 4-perfluoropropylphenyl group], [299; 3-(2,2,2,2,2,2-hexafluoroisopropyl)phenyl group], [300; 4-(2,2,2,2,2,2-hexafluoroisopropyl)phenyl group], [301; 3-perfluoroisopropylphenyl group], [302; 4-perfluoroisopropylphenyl group], [303; 3-perfluorobutylphenyl group], [304; 4-perfluorobutylphenyl group], [305; 3-perfluoro-sec-butylphenyl group], [306; 4-perfluoro-sec-butylphenyl group], [307; 3-perfluoroisobutylphenyl group], [308; 4-perfluoroisobutylphenyl group], [309; 5-fluoro-3-trifluoromethylphenyl group], [310; 6-fluoro-3-trifluoromethylphenyl group], [311; 2,4-difluoro-3-trifluoromethylphenyl group], [312; 2,5-difluoro-3-trifluoromethylphenyl group], [313; 2,6-difluoro-3-trifluoromethylphenyl group], [314; 4,5-difluoro-3-trifluoromethylphenyl group], [315; 4,6-difluoro-3-trifluoromethylphenyl group], [316; 5,6-difluoro-3-trifluoromethylphenyl group], [317; 2,4,5-trifluoro-3-trifluoromethylphenyl group], [318; 2,4,6-trifluoro-3-trifluoromethylphenyl group], [319; 4,5,6-trifluoro-3-trifluoromethylphenyl group], [320; 2,4,5,6-tetrafluoro-3-trifluoromethylphenyl group], [321; 4-chloro-3-trifluoromethylphenyl group], [322; 5-chloro-3-trifluoromethylphenyl group], [323; 4-methyl-3-trifluoromethylphenyl group], [324; 5-methyl-3-trifluoromethylphenyl group], [325; 4-ethyl-3-trifluoromethylphenyl group], [326; 5-ethyl-3-trifluoromethylphenyl group], [327; 4-cyclopropyl-3-trifluoromethylphenyl group], [328; 5-cyclopropyl-3-trifluoromethylphenyl group], [329; 4-methoxy-3-trifluoromethylphenyl group], [330; 5-methoxy-3-trifluoromethylphenyl group], [331; 3-fluoromethoxyphenyl group], [332; 4-fluoromethoxyphenyl group], [333; 3-difluoromethoxyphenyl group], [334; 4-difluoromethoxyphenyl group], [335; 3-trifluoromethoxyphenyl group], [336; 4-trifluoromethoxyphenyl group], [337; 3-(1-fluoroethoxyl)phenyl group], [338; 4-(1-fluoroethoxyl)phenyl group], [339; 3-(2-fluoroethoxyl)phenyl group], [340; 4-(2-fluoroethoxyl)phenyl group], [341; 3-(1,1-difluoroethoxyl)phenyl group], [342; 4-(1,1-difluoroethoxyl)phenyl group], [343; 3-(1,2-difluoroethoxyl)phenyl group], [344; 4-(1,2-difluoroethoxyl)phenyl group], [345; 3-(2,2-difluoroethoxyl)phenyl group], [346; 4-(2,2-difluoroethoxyl)phenyl group], [347; 3-(1,1,2-trifluoroethoxyl)phenyl group], [348; 4-(1,1,2-trifluoroethoxy)phenyl group], [349; 3-(1,2,2-trifluoroethoxyl)phenyl group], [350; 4-(1,2,2-trifluoroethoxyl)phenyl group], [351; 3-(2,2,2-trifluoroethoxyl)phenyl group], [352; 4-(2,2,2-trifluoroethoxyl)phenyl group], [353; 3-(1,1,2,2-tetrafluoroethoxyl)phenyl group], [354; 4-(1,1,2,2-tetrafluoroethoxyl)phenyl group], [355; 3-(perfluoroethoxy)phenyl group], [356; 4-(perfluoroethoxy)phenyl group], [357; 3-(1-fluoropropoxyl)phenyl group], [358; 4-(1-fluoropropoxyl)phenyl group], [359; 3-(2-fluoropropoxyl)phenyl group], [360; 4-(2-fluoropropoxyl)phenyl group], [361; 3-(3-fluoropropoxyl)phenyl group], [362; 4-(3-fluoropropoxyl)phenyl group], [363; 3-(1,1-difluoropropoxyl)phenyl group], [364; 4-(1,1-difluoropropoxyl)phenyl group], [365; 3-(1,2-difluoropropoxyl)phenyl group], [366; 4-(1,2-difluoropropoxyl)phenyl group], [367; 3-(1,3-difluoropropoxyl)phenyl group], [368; 4-(1,3-difluoropropoxyl)phenyl group], [369; 3-(2,2-difluoropropoxyl)phenyl group], [370; 4-(2,2-difluoropropoxyl)phenyl group], [371; 3-(2,3-difluoropropoxyl)phenyl group], [372; 4-(2,3-difluoropropoxyl)phenyl group], [373; 3-(3,3-difluoropropoxyl)phenyl group], [374; 4-(3,3-difluoropropoxyl)phenyl group], [375; 3-(1,1,2-trifluoropropoxyl)phenyl group], [376; 4-(1,1,2-trifluoropropoxyl)phenyl group], [377; 3-(1,1,3-trifluoropropoxyl)phenyl group], [378; 4-(1,1,3-trifluoropropoxyl)phenyl group], [379; 3-(1,2,2-trifluoropropoxyl)phenyl group], [380; 4-(1,2,2-trifluoropropoxyl)phenyl group], [381; 3-(1,2,3-trifluoropropoxyl)phenyl group], [382; 4-(1,2,3-trifluoropropoxyl)phenyl group], [383; 3-(1,3,3-trifluoropropoxyl)phenyl group], [384; 4-(1,3,3-trifluoropropoxyl)phenyl group], [385; 3-(2,2,3-trifluoropropoxyl)phenyl group], [386; 4-(2,2,3-trifluoropropoxyl)phenyl group], [387; 3-(2,3,3-trifluoropropoxyl)phenyl group], [388; 4-(2,3,3-trifluoropropoxyl)phenyl group], [389; 3-(3,3,3-trifluoropropoxyl)phenyl group], [390; 4-(3,3,3-trifluoropropoxyl)phenyl group], [391; 3-(1,1,2,2-tetrafluoropropoxyl)phenyl group], [392; 4-(1,1,2,2-tetrafluoropropoxyl)phenyl group], [393; 3-(1,1,3,3-tetrafluoropropoxyl)phenyl group], [394; 4-(1,1,3,3-tetrafluoropropoxyl)phenyl group], [395; 3-(2,2,3,3-tetrafluoropropoxyl)phenyl group], [396; 4-(2,2,3,3-tetrafluoropropoxyl)phenyl group], [397; 3-(1,1,3,3,3-pentafluoropropoxyl)phenyl group], [398; 4-(1,1,3,3,3-pentafluoropropoxyl)phenyl group], [399; 3-(2,2,3,3,3-pentafluoropropoxyl)phenyl group], [400; 4-(2,2,3,3,3-pentafluoropropoxyl)phenyl group], [401; 3-(1,1,2,2,3,3-hexafluoropropoxyl)phenyl group], [402; 4-(1,1,2,2,3,3-hexafluoropropoxyl)phenyl group], [403; 3-perfluoropropoxyphenyl group], [404; 4-perfluoropropoxyphenyl group], [407; 3-(2,2,2,2,2,2-hexafluoroisopropoxyl)phenyl group], [408; 4-(2,2,2,2,2,2-hexafluoroisopropoxyl)phenyl group], [409; 3-perfluoroisopropoxyphenyl group], [410; 4-perfluoroisopropoxyphenyl group], [411; 3-perfluorobutoxyphenyl group], [412; 4-perfluorobutoxyphenyl group], [413; 3-perfluoro-sec-butoxyphenyl group], [414; 4-perfluoro-sec-butoxyphenyl group], [415; 3-perfluoroisobutoxyphenyl group], [416; 4-perfluoroisobutoxyphenyl group], [417; 4-chloro-3-trifluoromethoxyphenyl group], [418; 5-chloro-3-trifluoromethoxyphenyl group], [419; 4-methyl-3-trifluoromethoxyphenyl group], [420; 5-methyl-3-trifluoromethoxyphenyl group], [421; 4-ethyl-3-trifluoromethoxyphenyl group], [422; 5-ethyl-3-trifluoromethoxyphenyl group], [423; 4-cyclopropyl-3- trifluoromethoxyphenyl group], [424; 5-cyclopropyl-3-trifluoromethoxyphenyl group], [425; 4-methoxy-3-trifluoromethoxyphenyl group], [426; 5-methoxy-3-trifluoromethoxyphenyl group], [427; 3-nitrophenyl group], [428; 4-nitrophenyl group], [429; 3-cyanophenyl group], [430; 4-cyanophenyl group], [431; 3-methylthiophenyl group], [432; 4-methylthiophenyl group], [433; 3-trifluoromethylthiophenyl group], [434; 4-trifluoromethylthiophenyl group], [435; 3-aminophenyl group], [436; 4-aminophenyl group], [437; 3-(N-methylamino)phenyl group], [438; 4-(N-methylamino)phenyl group], [439; 3-(N,N-dimethylamino)phenyl group], [440; 4-(N,N-dimethylamino)phenyl group], [441; 3-(N-ethylamino)phenyl group], [442; 4-(N-ethylamino)phenyl group], [443; 3-(N,N-diethylamino)phenyl group], [444; 4-(N,N-diethylamino)phenyl group], [445; 3-(N-ethyl-N-methylamino)phenyl group], [446; 4-(N-ethyl-N-methylamino)phenyl group], [447; 3-(N-propylamino)phenyl group], [448; 4-(N-propylamino)phenyl group], [449; 3-(N-propylamino)phenyl group], [450; 4-(N-propylamino)phenyl group], [451; 3-(N-isopropylamino)phenyl group], [452; 4-(N-isopropylamino)phenyl group], [453; 3-(N,N-diisopropylamino)phenyl group], [454; 4-(N,N-diisopropylamino)phenyl group], [455; 3-phenol group], [456; 4-phenol group], [457; 3-methylthiophenyl group], [458; 4-methylthiophenyl group], [459; 3-(N-fluoromethylamino)phenyl group], [460; 4-(N-fluoromethylamino)phenyl group], [461; 3-(N-difluoromethylamino)phenyl group], [462; 4-(N-difluoromethylamino)phenyl group], [463; 3-(N-trifluoromethylamino)phenyl group], [464; 4-(N-trifluoromethylamino)phenyl group], [465; 3-methylcarbonylphenyl group], [466; 4-methylcarbonylphenyl group], [467; 3-ethylcarbonylphenyl group], [468; 4-ethylcarbonylphenyl group], [469; 3-methoxycarbonylphenyl group], [470; 4-methoxycarbonylphenyl group], [471; 3-ethoxycarbonylphenyl group], [472; 4-ethoxycarbonylphenyl group], [473; 3-aminocarbonylphenyl group], [474; 4-aminocarbonylphenyl group], [475; 3-methylaminocarbonylphenyl group], [476; 4-methylaminocarbonylphenyl group], [477; 3-(N-formylamino)phenyl group], [478; 4-(N-formylamino)phenyl group], [479; 3-(N-formyl-N-methylamino)phenyl group], [480; 4-(N-formyl-N-methylamino)phenyl group], [481; 3-trimethylsilylphenyl group], [482; 4-trimethylsilylphenyl group], [483; 1-naphthyl group], [484; 2-naphthyl group], [485; indan-1-yl group], [486; indan-2-yl group], [487; 1-(5,6,7,8-tetrahydro)naphthyl group], [488; 2-(5,6,7,8-tetrahydro)naphthyl group], [489; cyclohexenyl group], [490; cyclohexyl group], [491; 2-chlorocyclohex-1-enyl group], [492; 2-methylcyclohex-1-enyl group], [493; 4-chlorocyclohex-1-enyl group], [494; 4-methylcyclohex-1-enyl group], [495; 6-chlorocyclohex-1-enyl group], [496; 6-methylcyclohex-1-enyl group], [497; 3-chlorocyclohex-1-enyl group], [498; 3-methylcyclohex-1-enyl group], [499; 3-methoxycyclohex-1-enyl group], [500; 3-trifluoromethylcyclohex-1-enyl group], [501; 3-difluoromethylcyclohex-1-enyl group], [502; 3-trifluoromethoxycyclohex-1-enyl group], [503; 5-chlorocyclohex-1-enyl group], [504; 5-methylcyclohex-1-enyl group], [505; 5-methoxycyclohex-1-enyl group], [506; 5-trifluoromethylcyclohex-1-enyl group], [507; 5-difluoromethylcyclohex-1-enyl group], [508; 5-trifluoromethoxycyclohex-1-enyl group], [509; butyl-1-enyl group], [510; 3-methylbut-1-enyl group], [511; 4-chloro-3-chloromethylbut-1-enyl group], [512; 3-chlorocyclohexyl group], and [513; 3-trifluoromethylcyclohexyl group].

According to the above method, the compounds EP13A-001 to EP18C-513 can be obtained.

The compounds EP13A-001 to EP16C-513 will be shown below:

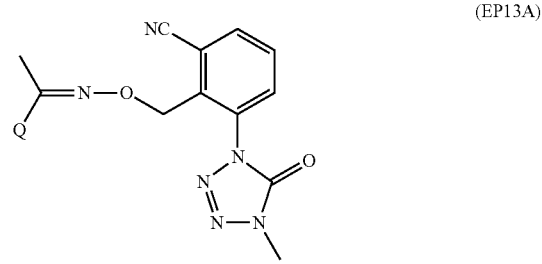

(EP13A)

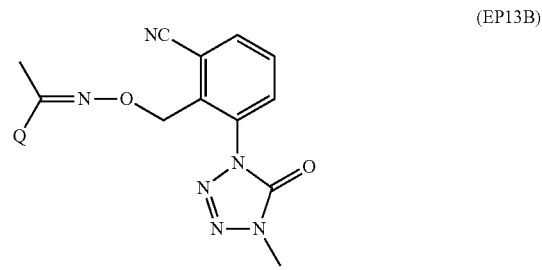

(EP13B)

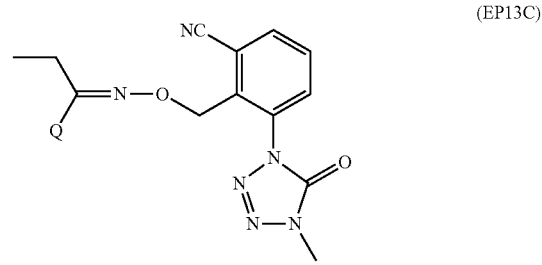

(EP13C)

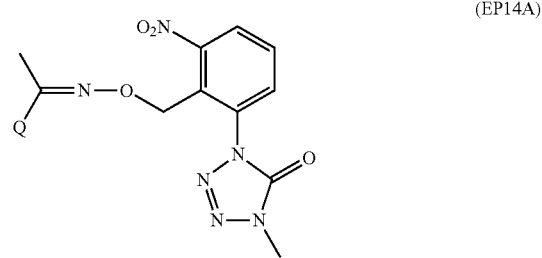

(EP14A)

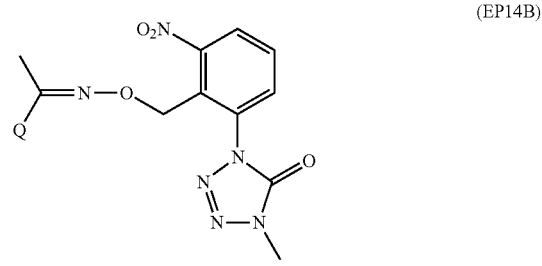

(EP14B)

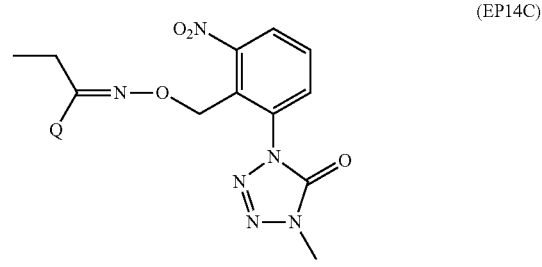

(EP14C)

389
-continued
(EP15A)
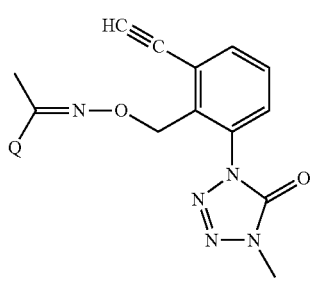
(EP15B)
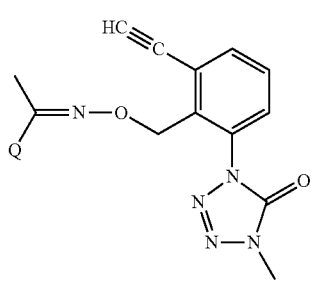
(EP15C)
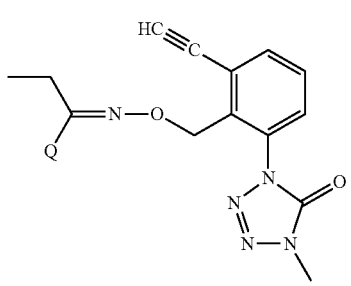
(EP16A)
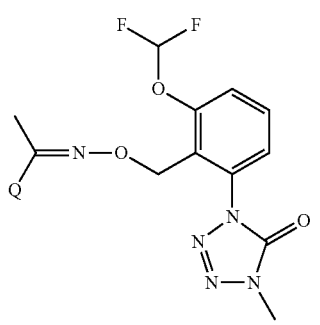
(EP16B)
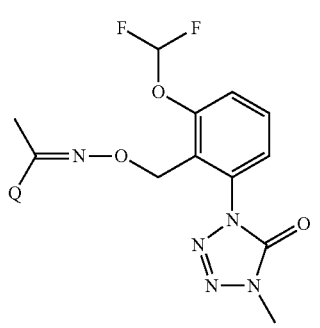
390
-continued
(EP15A)
(EP15B)
(EP16C)
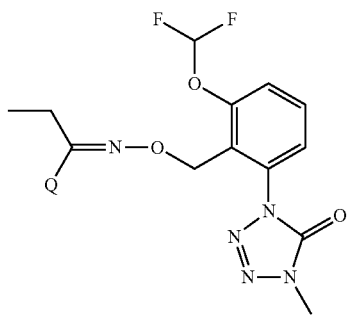
(EP16A)
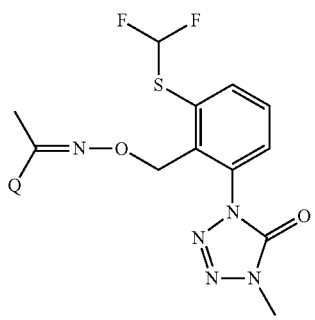
(EP16B)
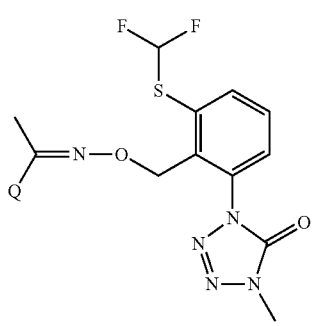
(EP16C)
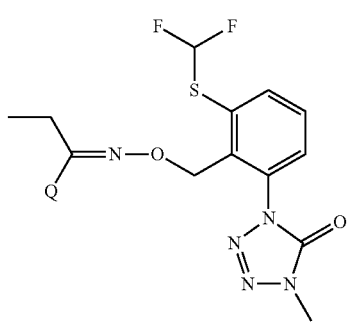
wherein Q is a compound corresponding to each of substituent numbers 1 to 513.
According to the above method, it is possible to obtain compounds EP1A-1001 to EP1C-3047, EP2A-1001 to EP2C-3047, EP3A-1001 to EP3C-3047, EP4A-1001 to EP4C-3047, EP5A-1001 to EP5C-3047, EP6A-1001 to EP6C-3047, EP7A-1001 to EP7C-3047, EP8A-1001 to EP8C-3047, EP9A-1001 to EP9C-3047, EP10A-1001 to EP10C-3047, EP11A-1001 to EP11C-3047, EP12A-1001 to EP12C-3047, EP13A-1001 to EP13C-3047, EP14A-1001 to EP14C-3047, EP15A-1001 to EP15C-3047, and EP16A-1001 to EP16C-3047:

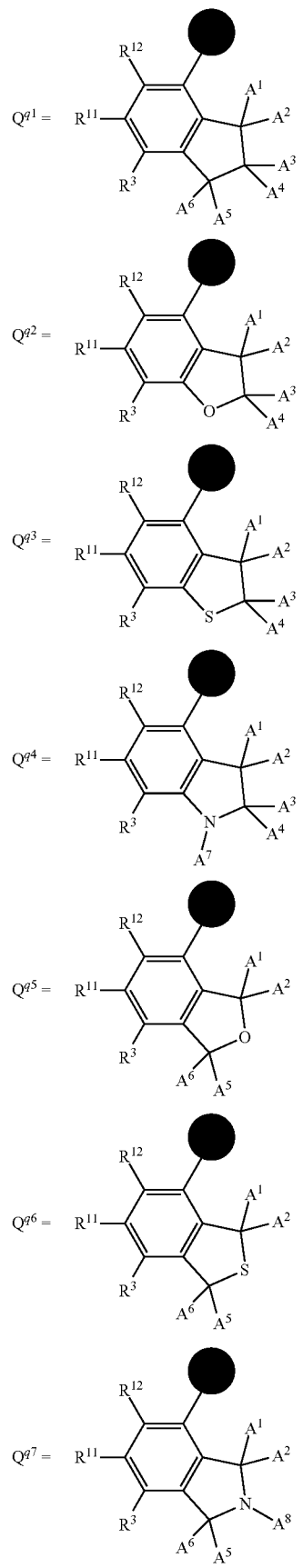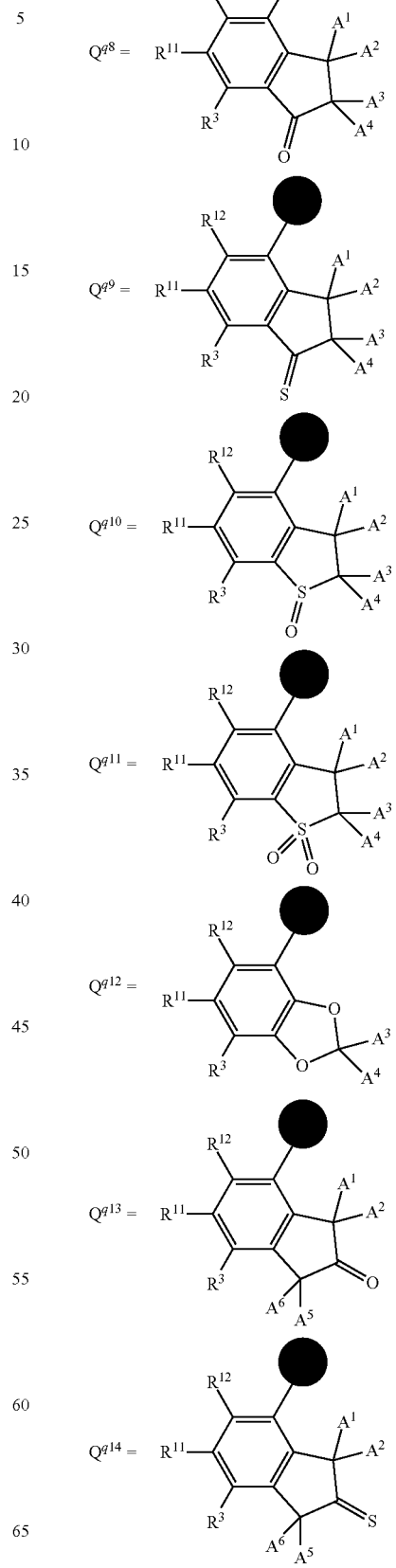

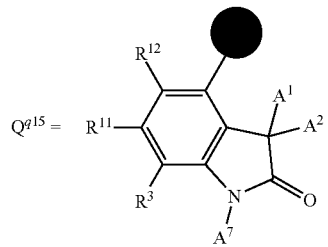
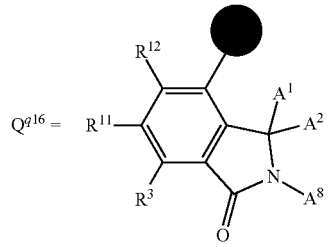
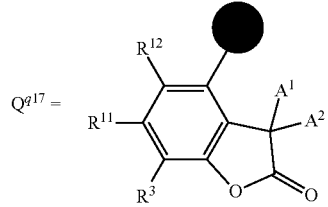
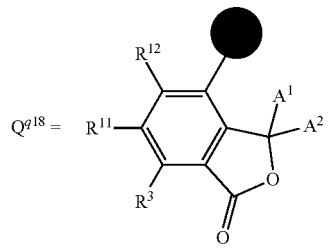
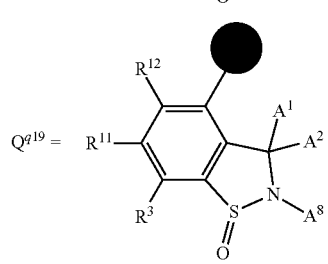
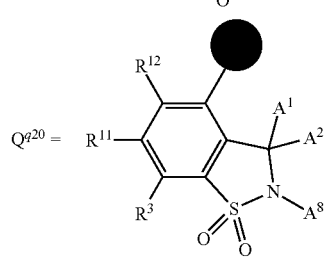
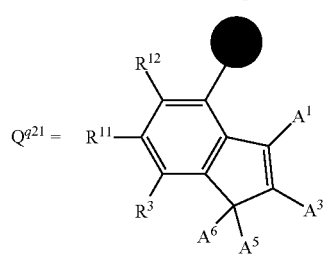
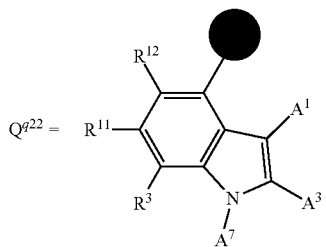
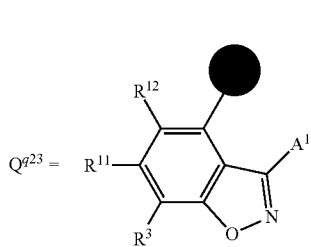
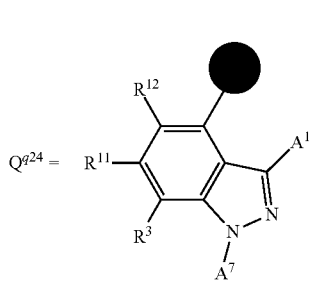
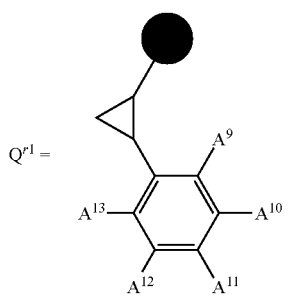
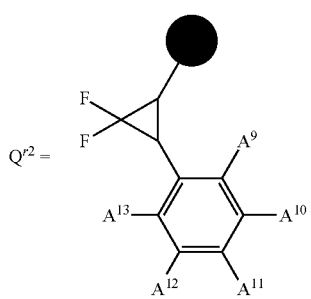
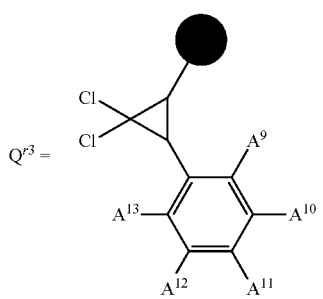

$Q^{r4} =$ 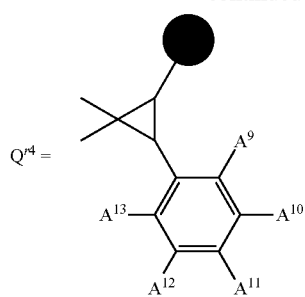
$Q^{r5} =$ 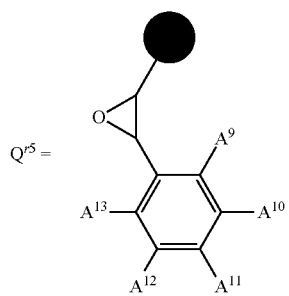
$Q^{r6} =$ 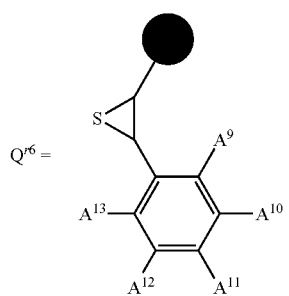
$Q^{r7} =$ 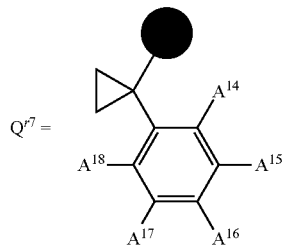
$Q^{r8} =$ 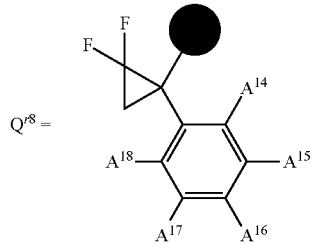
$Q^{r9} =$ 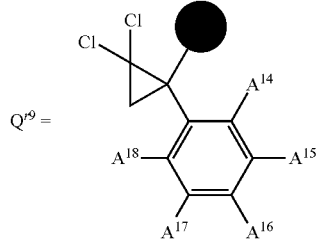
$Q^{r10} =$ 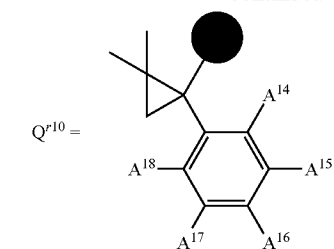
$Q^{r11} =$ 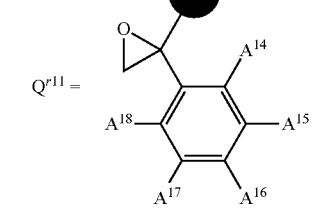
$Q^{r12} =$ 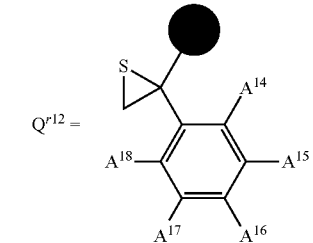
$Q^{r13} =$ $Q^{r14} =$ 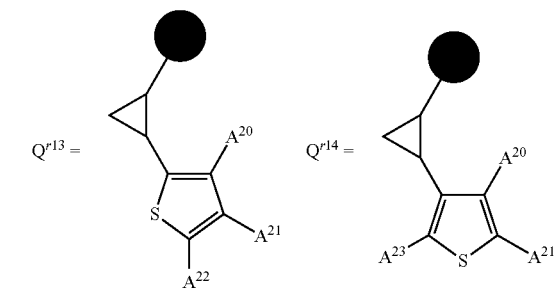
$Q^{r15} =$ $Q^{r16} =$ 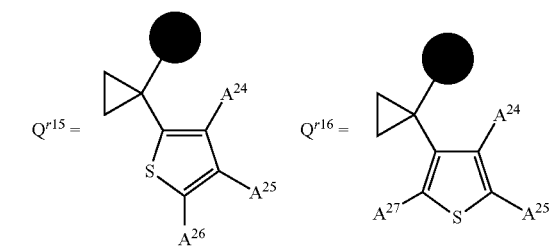
$Q^{s1} =$ 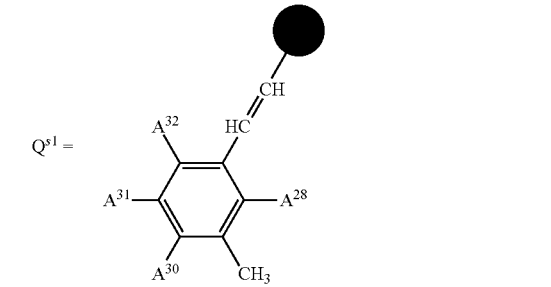

Q^{s2} = 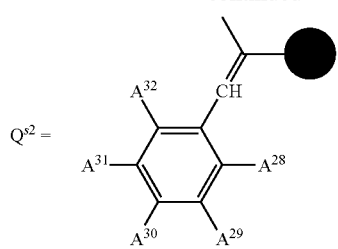
Q^{s3} = 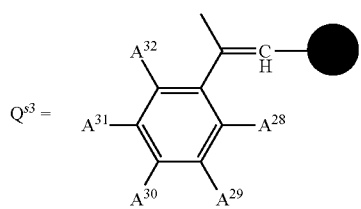
Q^{s4} = 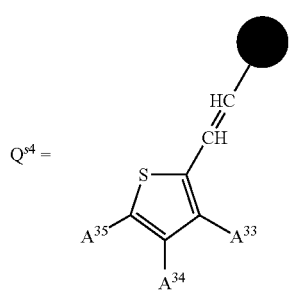
Q^{s5} = 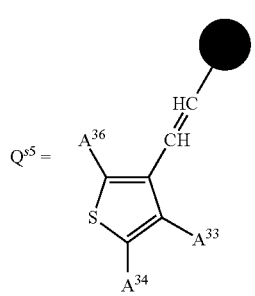
Q^{t1} = 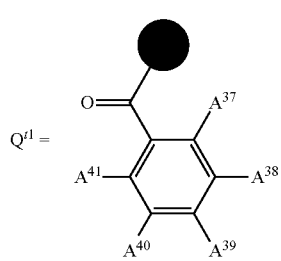
Q^{t2} = 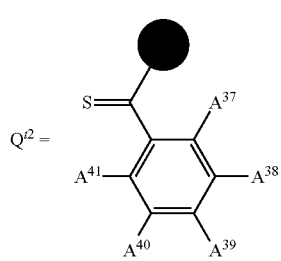
Q^{t3} = 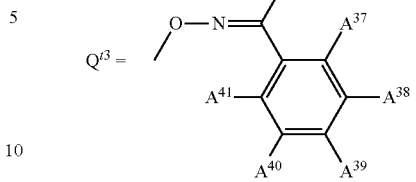
Q^{t4} = 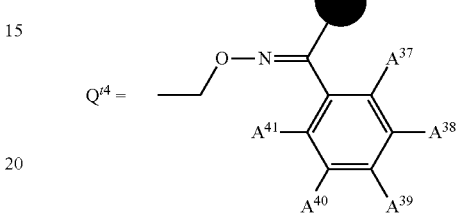
Q^{t5} = 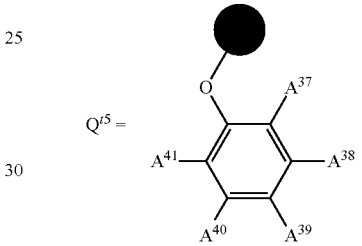
Q^{t6} = 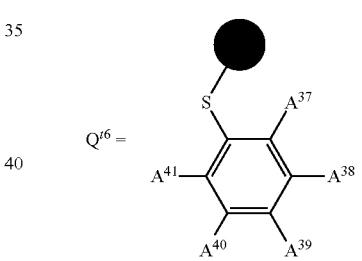
Q^{t7} = 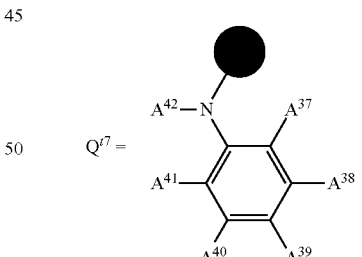
Q^{v1} = 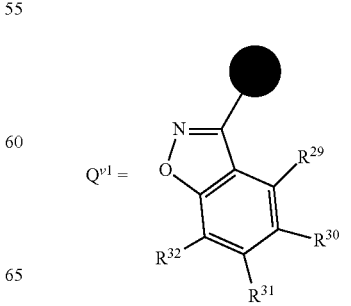

Q$^{v2}$ = 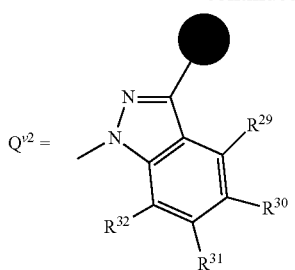

Q$^{v3}$ = 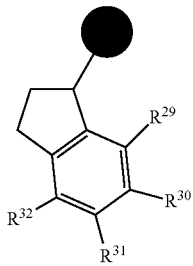 Q$^{v4}$ =

Q$^{v5}$ = 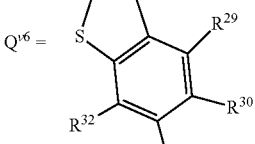 Q$^{v6}$ =

Q$^{v7}$ = 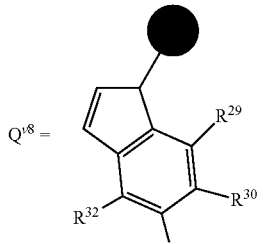

Q$^{v8}$ =

Q$^{v9}$ = 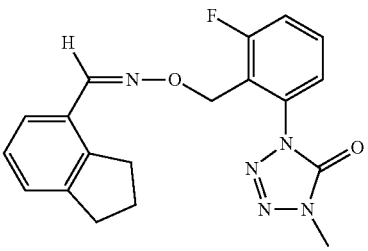

Q$^{v10}$ = 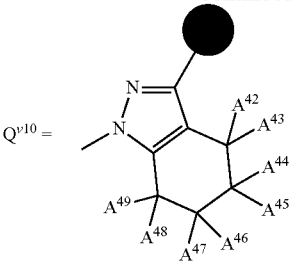

wherein Q represents any one of substituent numbers 1001 to 3047, Q$^{q1}$ to Q$^{v10}$ represent any one of the followings; and the symbol ○ represents a binding site.

Substituent numbers 1001 to 3047 will be shown below.

Here, Me represents a methyl group, OMe represents a methoxy group, CF$_3$ represents a trifluoromethyl group, OCF$_3$ represents a trifluoromethoxy group, OCHF$_2$ represents a difluoromethoxy group, for example, [1001; Q=Q$^{q1}$, A$^1$=H, A$^2$=H, A$^3$=H, A$^4$=H, A$^5$=H, A$^6$=H, R$^3$=H, R$^{11}$=H, R$^{12}$=H] represents a group in which Q is Q$^{q1}$, A$^1$, A$^2$, A$^3$, A$^4$, A$^5$, A$^6$, R$^3$, R$^{11}$, and R$^{12}$ are hydrogen atoms, and a compound in which the substituent number is 1,001 in EP1A represents the following compound:

(EP1A-1001)

wherein substituent number; Q
[1001; Q=Q$^{q1}$, A$^1$=H, A$^2$=H, A$^3$=H, A$^4$=H, A$^5$=H, A$^6$=H, R$^3$=H, R$^{11}$=H, R$^{12}$=H], [1002; Q=Q$^{q1}$, $^1$=F, A$^2$=H, A$^3$=H, A$^4$=H, A$^5$=H, A$^6$=H, R$^3$=H, R$^{11}$=H, R$^{12}$=H], [1003; Q=Q$^{q1}$, A$^1$=H, A$^2$=H, A$^3$=F, A$^4$=H, A$^5$=H, A$^6$=H, R$^3$=H, R$^{11}$=H, R$^{12}$=H], [1004; Q=Q$^{q1}$, A$^1$=H, A$^2$=H, A$^3$=H, A$^4$=H, A$^5$=F, A$^6$=H, R$^3$=H, R$^{11}$=H, R$^{12}$=H], [1005; Q=Q$^{q1}$, A$^1$=F, A$^2$=F, A$^3$=H, A$^4$=H, A$^5$=H, A$^6$=H, R$^3$=H, R$^{11}$=H, R$^{12}$=H], [1006; Q=Q$^{q1}$, A$^1$=H, A$^2$=H, A$^3$=F, A$^4$=F, A$^5$=H, A$^6$=H, R$^3$=H, R$^{11}$=H, R$^{12}$=H], [1007; Q=Q$^{q1}$, A$^1$=H, A$^2$=H, A$^3$=H, A$^4$=H, A$^5$=F, A$^6$=F, R$^3$=H, R$^{11}$=H, R$^{12}$=H], [1008; Q=Q$^{q1}$, A$^1$=H, A$^2$=H, A$^3$=Cl, A$^4$=H, A$^5$=H, A$^6$=H, R$^3$=H, R$^{11}$=H, R$^{12}$=H], [1009; Q=Q$^{q1}$, A$^1$=H, A$^2$=H, A$^3$=H, A$^4$=H, A$^5$=Cl, A$^6$=H, R$^3$=H, R$^{11}$=H, R$^{12}$=H], [1010; Q=Q$^{q1}$, A$^1$=H, A$^2$=H, A$^3$=Cl, A$^4$=Cl, A$^5$=H, A$^6$=H, R$^3$=H, R$^{11}$=H, R$^{12}$=H], [1011; Q=Q$^{q1}$, A$^1$=H, A$^2$=H, A$^3$=H, A$^4$=H, A$^5$=Cl, A$^6$=Cl, R$^3$=H, R$^{11}$=H, R$^{12}$=H], [1012; Q=Q$^{q1}$, A$^1$=H, A$^2$=H, A$^3$=Br, A$^4$=H, A$^5$=H, A$^6$=H, R$^3$=H, R$^{11}$=H, R$^{12}$=H], [1013; Q=Q$^{q1}$, A$^1$=H, A$^2$=H, A$^3$=H, A$^4$=H, A$^5$=Br, A$^6$=H, R$^3$=H, R$^{11}$=H, R$^{12}$=H], [1014; Q=Q$^{q1}$, A$^1$=H, A$^2$=H, A$^3$=Br, A$^4$=Br, A$^5$=H, A$^6$=H, R$^3$=H, R$^{11}$=H, R$^{12}$=H], [1015; Q=Q$^{q1}$, A$^5$=H, A$^2$=H, A$^3$=H, A$^4$=H, A$^5$=Br, A$^6$=Br, R$^3$=H, R$^{11}$=H, R$^{12}$=H], [1016; Q=Q$^{q1}$, A$^1$=H, A$^2$=H, A$^3$=Me, A$^4$=H, A$^5$=H, A$^6$=H, R$^3$=H, R$^{11}$=H, R$^{12}$=H], [1017; Q=Q$^{q1}$, A$^1$=H, A$^2$=H, A$^3$=H, A$^4$=H, A$^5$=Me, A$^6$=H, R$^3$=H, R$^{11}$=H, R$^{12}$=H], [1018; Q=Q$^{q1}$, A$^1$=H, A$^2$=H, A$^3$=Me, A$^4$=Me, A$^5$=H, A$^6$=H, R$^3$=H, R$^{11}$=H, R$^{12}$=H], [1019; Q=Q$^{q1}$, A$^1$=H, A$^2$=H, A$^3$=H, A$^4$=H, A$^5$=Me, A$^6$=Me, R³=H, R¹¹=H, R¹²=H], [1020; Q=Q^q1, A¹=H, A²=H, A³=OMe, A⁴=H, A⁵=H, A⁶=H, R³=H, R¹¹=H, R¹²=H], [1021; Q=Q^q1, A¹=H, A²=H, A³=H, A⁴=H, A⁵=OMe, A⁶=H, R³=H, R¹¹=H, R¹²=H], [1022; Q=Q^q1, A¹=H, A²=H, A³=H, A⁴=H, A⁵=H, A⁶=H, R³=F, R¹¹=H, R¹²=H], [1023; Q=Q^q1, A¹=F, A²=H, A³=H, A⁴=H, A⁵=H, A⁶=H, R³=F, R¹¹=H, R¹²=H], [1024; Q=Q^q1, A¹=H, A²=H, A³=F, A⁴=H, A⁵=H, A⁶=H, R³=F, R¹¹=H, R¹²=H], [1025; Q=Q^q1, A¹=H, A²=H, A³=H, A⁴=H, A⁵=F, A⁶=H, R³=F, R¹¹=H, R¹²=H], [1026; Q=Q^q1, A¹=F, A²=F, A³=H, A⁴=H, A⁵=H, A⁶=H, R³=F, R¹¹=H, R¹²=H], [1027; Q=Q^q1, A¹=H, A²=H, A³=F, A⁴=F, A⁵=H, A⁶=H, R³=F, R¹¹=H, R¹²=H], [1028; Q=Q^q1, A¹=H, A²=H, A³=H, A⁴=H, A⁵=F, A⁶=F, R³=F, R¹¹=H, R¹²=H], [1029; Q=Q^q1, A¹=H, A²=H, A³=Cl, A⁴=H, A⁵=H, A⁶=H, R³=F, R¹¹=H, R¹²=H], [1030; Q=Q^q1, A¹=H, A²=H, A³=H, A⁴=H, A⁵=Cl, A⁶=H, R³=F, R¹¹=H, R¹²=H], [1031; Q=Q^q1, A¹=H, A²=H, A³=Cl, A⁴=Cl, A⁵=H, A⁶=H, R³=F, R¹¹=H, R¹²=H], [1032; Q=Q^q1, A¹=H, A²=H, A³=H, A⁴=H, A⁵=Cl, A⁶=Cl, R³=F, R¹¹=H, R¹²=H], [1033; Q=Q^q1, A¹=H, A²=H, A³=Br, A⁴=H, A⁵=H, A⁶=H, R³=F, R¹¹=H, R¹²=H], [1034; Q=Q^q1, A¹=H, A²=H, A³=H, A⁴=H, A⁵=Br, A⁶=H, R³=F, R¹¹=H, R¹²=H], [1035; Q=Q^q1, A¹=H, A²=H, A³=Br, A⁴=Br, A⁵=H, A⁶=H, R³=F, R¹¹=H, R¹²=H], [1036; Q=Q^q1, A¹=H, A²=H, A³=H, A⁴=H, A⁵=Br, A⁶=Br, R³=F, R¹¹=H, R¹²=H], [1037; Q=Q^q1, A¹=H, A²=H, A³=Me, A⁴=H, A⁵=H, A⁶=H, R³=F, R¹¹=H, R¹²=H], [1038; Q=Q^q1, A¹=H, A²=H, A³=H, A⁴=H, A⁵=Me, A⁶=H, R³=F, R¹¹=H, R¹²=H], [1039; Q=Q^q1, A¹=H, A²=H, A³=Me, A⁴=Me, A⁵=H, A⁶=H, R³=F, R¹¹=H, R¹²=H], [1040; Q=Q^q1, A¹=H, A²=H, A³=H, A⁴=H, A⁵=Me, A⁶=Me, R³=F, R¹¹=H, R¹²=H], [1041; Q=Q^q1, A¹=H, A²=H, A³=H, A⁴=H, A⁵=OMe, A⁶=H, R³=F, R¹¹=H, R¹²=H], [1043; Q=Q^q1, A¹=H, A²=H, A³=H, A⁴=H, A⁵=H, A⁶=H, R³=Cl, R¹¹=H, R¹²=H], [1044; Q=Q^q1, A¹=F, A²=H, A³=H, A⁴=H, A⁵=H, A⁶=H, R³=C, R¹¹=H, R¹²=H], [1045; Q=Q^q1, A¹=H, A²=H, A³=F, A⁴=H, A⁵=H, A⁶=H, R³=Cl, R¹¹=H, R¹²=H], [1046; Q=Q^q1, A¹=H, A²=H, A³=H, A⁴=H, A⁵=F, A⁶=H, R³=Cl, R¹¹=H, R¹²=H], [1047; Q=Q^q1, A¹=F, A²=F, A³=H, A⁴=H, A⁵=H, A⁶=H, R³=Cl, R¹¹=H, R¹²=H], [1048; Q=Q^q1, A¹=H, A²=H, A³=F, A⁴=F, A⁵=H, A⁶=H, R³=Cl, R¹¹=H, R¹²=H], [1049; Q=Q^q1, A¹=H, A²=H, A³=H, A⁴=H, A⁵=F, A⁶=F, R³=Cl, R¹¹=H, R¹²=H], [1050; Q=Q^q1, A¹=H, A²=H, A³=Cl, A⁴=H, A⁵=H, A⁶=H, R³=Cl, R¹¹=H, R¹²=H], [1051; Q=Q^q1, A¹=H, A²=H, A³=H, A⁴=H, A⁵=Cl, A⁶=H, R³=Cl, R¹¹=H, R¹²=H], [1052; Q=Q^q1, A¹=H, A²=H, A³=Cl, A⁴=Cl, A⁵=H, A⁶=H, R³=Cl, R¹¹=H, R¹²=H], [1053; Q=Q^q1, A¹=H, A²=H, A³=H, A⁴=H, A⁵=Cl, A⁶=Cl, R³=Cl, R¹¹=H, R¹²=H], [1054; Q=Q^q1, A¹=H, A²=H, A³=Br, A⁴=H, A⁵=H, A⁶=H, R³=Cl, R¹¹=H, R¹²=H], [1055; Q=Q^q1, A¹=H, A²=H, A³=H, A⁴=H, A⁵=Br, A⁶=H, R³=Cl, R¹¹=H, R¹²=H], [1056; Q=Q^q1, A¹=H, A²=H, A³=Br, A⁴=Br, A⁵=H, A⁶=H, R³=Cl, R¹¹=H, R¹²=H], [1057; Q=Q^q1, A¹=H, A²=H, A³=H, A⁴=H, A⁵=Br, A⁶=Br, R³=Cl, R¹¹=H, R¹²=H], [1058; Q=Q^q1, A¹=H, A²=H, A³=Me, A⁴=H, A⁵=H, A⁶=H, R³=Cl, R¹¹=H, R¹²=H], [1059; Q=Q^q1, A¹=H, A²=H, A³=H, A⁴=H, A⁵=Me, A⁶=H, R³=Cl, R¹¹=H, R¹²=H], [1060; Q=Q^q1, A¹=H, A²=H, A³=Me, A⁴=Me, A⁵=H, A⁶=H, R³=Cl, R¹¹=H, R¹²=H], [1061; Q=Q^q1, A¹=H, A²=H, A³=H, A⁴=H, A⁵=Me, A⁶=Me, R³=C, R¹¹=H, R¹²=H], [1062; Q=Q^q1, A¹=H, A²=H, A³=OMe, A⁴=H, A⁵=H, A⁶=H, R³=C, R¹¹=H, R¹²=H], [1063; Q=Q^q1, A¹=H, A²=H, A³=H, A⁴=H, A⁵=OMe, A⁶=H, R³=Cl, R¹¹=H, R¹²=H], [1064; Q=Q^q1, A¹=H, A²=H, A³=H, A⁴=H, A⁵=H, A⁶=H, R³=Br, R¹¹=H, R¹²=H], [1065; Q=Q^q1, A¹=F, A²=H, A³=H, A⁴=H, A⁵=H, A⁶=H, R³=Br, R¹¹=H, R¹²=H], [1066; Q=Q^q1, A¹=H, A²=H, A³=F, A⁴=H, A⁵=H, A⁶=H, R³=Br, R¹¹=H, R¹²=H], [1067; Q=Q^q1, A¹=H, A²=H, A³=H, A⁴=H, A⁵=F, A⁶=H, R³=Br, R¹¹=H, R¹²=H], [1068; Q=Q^q1, A¹=F, A²=F, A³=H, A⁴=H, A⁵=H, A⁶=H, R³=Br, R¹¹=H, R¹²=H], [1069; Q=Q^q1, A¹=H, A²=H, A³=F, A⁴=F, A⁵=H, A⁶=H, R³=Br, R¹¹=H, R¹²=H], [1070; Q=Q^q1, A¹=H, A²=H, A³=H, A⁴=H, A⁵=F, A⁶=F, R³=Br, R¹¹=H, R¹²=H], [1071; Q=Q^q1, A¹=H, A²=H, A³=Cl, A⁴=H, A⁵=H, A⁶=H, R³=Br, R¹¹=H, R¹²=H], [1072; Q=Q^q1, A¹=H, A²=H, A³=H, A⁴=H, A⁵=Cl, A⁶=H, R³=Br, R¹¹=H, R¹²=H], [1073; Q=Q^q1, A¹=H, A²=H, A³=Cl, A⁴=Cl, A⁵=H, A⁶=H, R³=Br, R¹¹=H, R¹²=H], [1074; Q=Q^q1, A¹=H, A²=H, A³=H, A⁴=H, A⁵=Cl, A⁶=Cl, R³=Br, R¹¹=H, R¹²=H], [1075; Q=Q^q1, A¹=H, A²=H, A³=Br, A⁴=H, A⁵=H, A⁶=H, R³=Br, R¹¹=H, R¹²=H], [1076; Q=Q^q1, A¹=H, A²=H, A³=H, A⁴=H, A⁵=Br, A⁶=H, R³=Br, R¹¹=H, R¹²=H], [1077; Q=Q^q1, A¹=H, A²=H, A³=Br, A⁴=Br, A⁵=H, A⁶=H, R³=Br, R¹¹=H, R¹²=H], [1078; Q=Q^q1, A¹=H, A²=H, A³=H, A⁴=H, A⁵=Br, A⁶=Br, R³=Br, R¹¹=H, R¹²=H], [1079; Q=Q^q1, A¹=H, A²=H, A³=Me, A⁴=H, A⁵=H, A⁶=H, R³=Br, R¹¹=H, R¹²=H], [1080; Q=Q^q1, A¹=H, A²=H, A³=H, A⁴=H, A⁵=Me, A⁶=H, R³=Br, R¹¹=H, R¹²=H], [1081; Q=Q^q1, A¹=H, A²=H, A³=Me, A⁴=Me, A⁵=H, A⁶=H, R³=Br, R¹¹=H, R¹²=H], [1082; Q=Q^q1, A¹=H, A²=H, A³=H, A⁴=H, A⁵=Me, A⁶=Me, R³=Br, R¹¹=H, R¹²=H], [1083; Q=Q^q1, A¹=H, A²=H, A³=OMe, A⁴=H, A⁵=H, A⁶=H, R³=Br, R¹¹=H, R¹²=H], [1084; Q=Q^q1, A¹=H, A²=H, A³=H, A⁴=H, A⁵=OMe, A⁶=H, R³=Br, R¹¹=H, R¹²=H], [1085; Q=Q^q1, A¹=H, A²=H, A³=H, A⁴=H, A⁵=H, A⁶=H, R³=Me, R¹¹=H, R¹²=H], [1086; Q=Q^q1, A¹=F, A²=H, A³=H, A⁴=H, A⁵=H, A⁶=H, R³=Me, R¹¹=H, R¹²=H], [1087; Q=Q^q1, A¹=H, A²=H, A³=F, A⁴=H, A⁵=H, A⁶=H, R³=Me, R¹¹=H, R¹²=H], [1088; Q=Q^q1, A¹=H, A²=H, A³=H, A⁴=H, A⁵=F, A⁶=H, R³=Me, R¹¹=H, R¹²=H], [1089; Q=Q^q1, A¹=F, A²=F, A³=H, A⁴=H, A⁵=H, A⁶=H, R³=Me, R¹¹=H, R¹²=H], [1090; Q=Q^q1, A¹=H, A²=H, A³=F, A⁴=F, A⁵=H, A⁶=H, R³=Me, R¹¹=H, R¹²=H], [1091; Q=Q^q1, A¹=H, A²=H, A³=H, A⁴=H, A⁵=F, A⁶=F, R³=Me, R¹¹=H, R¹²=H], [1092; Q=Q^q1, A¹=H, A²=H, A³=C, A⁴=H, A⁵=H, A⁶=H, R³=Me, R¹¹=H, R¹²=H], [1093; Q=Q^q1, A¹=H, A²=H, A³=H, A⁴=H, A⁵=Cl, A⁶=H, R³=Me, R¹¹=H, R¹²=H], [1094; Q=Q^q1, A¹=H, A²=H, A³=C, A⁴=C, A⁵=H, A⁶=H, R³=Me, R¹¹=H, R¹²=H], [1095; Q=Q^q1, A¹=H, A²=H, A³=H, A⁴=H, A⁵=Cl, A⁶=Cl, R³=Me, R¹¹=H, R¹²=H], [1096; Q=Q^q1, A¹=H, A²=H, A³=Br, A⁴=H, A⁵=H, A⁶=H, R³=Me, R¹¹=H, R¹²=H], [1097; Q=Q^q1, A¹=H, A²=H, A³=H, A⁴=H, A⁵=Br, A⁶=H, R³=Me, R¹¹=H, R¹²=H], [1098; Q=Q^q1, A¹=H, A²=H, A³=Br, A⁴=Br, A⁵=H, A⁶=H, R³=Me, R¹¹=H, R¹²=H], [1099; Q=Q^q1, A¹=H, A²=H, A³=H, A⁴=H, A⁵=Br, A⁶=Br, R³=Me, R¹¹=H, R¹²=H], [1100; Q=Q^q1, A¹=H, A²=H, A³=Me, A⁴=H, A⁵=H, A⁶=H, R³=Me, R¹¹=H, R¹²=H], [1101; Q=Q^q1, A¹=H, A²=H, A³=H, A⁴=H, A⁵=Me, A⁶=H, R³=Me, R¹¹=H, R¹²=H], [1102; Q=Q^q1, A¹=H, A²=H, A³=Me, A⁴=Me, A⁵=H, A⁶=H, R³=Me, R¹¹=H, R¹²=H], [1103; Q=Q^q1, A¹=H, A²=H, A³=H, A⁴=H, A⁵=Me, A⁶=Me, R³=Me, R¹¹=H, R¹²=H], [1104; Q=Q^q1, A¹=H, A²=H, A³=OMe, A⁴=H, A⁵=H, A⁶=H, R³=Me, R¹¹=H, R¹²=H], [1105; Q=Q^q1, A¹=H, A²=H, A³=H, A⁴=H, A⁵=OMe, A⁶=H, R³=Me, R¹¹=H, R¹²=H], [1106; Q=Q^q1, A¹=H, A²=H, A³=H, A⁴=H, A⁵=H, A⁶=H, R³=CF₃, R¹¹=H, R¹²=H], [1107; Q=Q^q1, A¹=F, A²=H, A³=H, A⁴=H, A⁵=H, A⁶=H, R³=CF₃, R¹¹=H, R¹²=H], [1108; Q=Q^q1, A¹=H, A²=H, A³=F, A⁴=H, A⁵=H, A⁶=H, R³=CF₃, R¹¹=H, R¹²=H], [1109; Q=Q^q1, A¹=H, A²=H, A³=H, A⁴=H, A⁵=F, A⁶=H, R³=CF₃, R¹¹=H, R¹²=H], [1110; Q=Q^q1, A¹=F, A²=F, A³=H, A⁴=H, A⁵=H, A⁶=H, R³=CF₃, R¹¹=H, R¹²=H], [1111; Q=Q^q1, A¹=H, A²=H, A³=F, A⁴=F, A⁵=H, A⁶=H, R³=CF₃, R¹¹=H, R¹²=H], [1112; Q=Q^q1, A¹=H, A²=H, A³=H, A⁴=H, A⁵=F, A⁶=F, R³=CF₃, R¹¹=H, R¹²=H], [1113; Q=Q^q1, A¹=H, A²=H, A³=Cl, A⁴=H, A⁵=H, A⁶=H, R³=CF₃, R¹¹=H, R¹²=H], [1114; Q=Q^q1, A¹=H, A²=H, A³=H, A⁴=H, A⁵=Cl, $A^6$=H, $R^3$=CF$_3$, $R^{11}$=H, $R^{12}$=H], [1115; Q=Q$^{q1}$, $A^1$=H, $A^2$=H, $A^3$=Cl, $A^4$=C, $A^5$=H, $A^6$=H, $R^3$=CF$_3$, $R^{11}$=H, $R^{12}$=H], [1116; Q=Q$^{q1}$, $A^1$=H, $A^2$=H, $A^3$=H, $A^4$=H, $A^5$=Cl, $A^6$=Cl, $R^3$=CF$_3$, $R^{11}$=H, $R^{12}$=H], [1117; Q=Q$^{q1}$, $A^1$=H, $A^2$=H, $A^3$=Br, $A^4$=H, $A^5$=H, $A^6$=H, $R^3$=CF$_3$, $R^{11}$=H, $R^{12}$=H], [1118; Q=Q$^{q1}$, $A^1$=H, $A^2$=H, $A^3$=H, $A^4$=H, $A^5$=Br, $A^6$=H, $R^3$=CF$_3$, $R^{11}$=H, $R^{12}$=H], [1119; Q=Q$^{q1}$, $A^1$=H, $A^2$=H, $A^3$=Br, $A^4$=Br, $A^5$=H, $A^6$=H, $R^3$=CF$_3$, $R^{11}$=H, $R^{12}$=H], [1120; Q=Q$^{q1}$, $A^1$=H, $A^2$=H, $A^3$=H, $A^4$=H, $A^5$=Br, $A^6$=Br, $R^3$=CF$_3$, $R^{11}$=H, $R^{12}$=H], [1121; Q=Q$^{q1}$, $A^1$=H, $A^2$=H, $A^3$=Me, $A^4$=H, $A^5$=H, $A^6$=H, $R^3$=CF$_3$, $R^{11}$=H, $R^{12}$=H], [1122; Q=Q$^{q1}$, $A^1$=H, $A^2$=H, $A^3$=H, $A^4$=H, $A^5$=Me, $A^6$=H, $R^3$=CF$_3$, $R^{11}$=H, $R^{12}$=H], [1123; Q=Q$^{q1}$, $A^1$=H, $A^2$=H, $A^3$=Me, $A^4$=Me, $A^5$=H, $A^6$=H, $R^3$=CF$_3$, $R^{11}$=H, $R^{12}$=H], [1124; Q=Q$^{q1}$, $A^1$=H, $A^2$=H, $A^3$=H, $A^4$=H, $A^5$=Me, $A^6$=Me, $R^3$=CF$_3$, $R^{11}$=H, $R^{12}$=H], [1125; Q=Q$^{q1}$, $A^1$=H, $A^2$=H, $A^3$=OMe, $A^4$=H, $A^5$=H, $A^6$=H, $R^3$=CF$_3$, $R^{11}$=H, $R^{12}$=H], [1126; Q=Q$^{q1}$, $A^1$=H, $A^2$=H, $A^3$=H, $A^4$=H, $A^5$=OMe, $A^6$=H, $R^3$=CF$_3$, $R^{11}$=H, $R^{12}$=H], [1127; Q=Q$^{q1}$, $A^1$=H, $A^2$=H, $A^3$=H, $A^4$=H, $A^5$=H, $A^6$=H, $R^3$=OMe, $R^{11}$=H, $R^{12}$=H], [1128; Q=Q$^{q1}$, $A^1$=F, $A^2$=H, $A^3$=H, $A^4$=H, $A^5$=H, $A^6$=H, $R^3$=OMe, $R^{11}$=H, $R^{12}$=H], [1129; Q=Q$^{q1}$, $A^1$=H, $A^2$=H, $A^3$=F, $A^4$=H, $A^5$=H, $A^6$=H, $R^3$=OMe, $R^{11}$=H, $R^{12}$=H], [1130; Q=Q$^{q1}$, $A^1$=H, $A^2$=H, $A^3$=H, $A^4$=H, $A^5$=F, $A^6$=H, $R^3$=Me, $R^{11}$=H, $R^{12}$=H], [1131; Q=Q$^{q1}$, $A^1$=F, $A^2$=F, $A^3$=H, $A^4$=H, $A^5$=H, $A^6$=H, $R^3$=OMe, $R^{11}$=H, $R^{12}$=H], [1132; Q=Q$^{q1}$, $A^1$=H, $A^2$=H, $A^3$=F, $A^4$=F, $A^5$=H, $A^6$=H, $R^3$=OMe, $R^{11}$=H, $R^{12}$=H], [1133; Q=Q$^{q1}$, $A^1$=H, $A^2$=H, $A^3$=H, $A^4$=H, $A^5$=F, $A^6$=F, $R^3$=OMe, $R^{11}$=H, $R^{12}$=H], [1134; Q=Q$^{q1}$, $A^1$=H, $A^2$=H, $A^3$=C, $A^4$=H, $A^5$=H, $A^6$=H, $R^3$=OMe, $R^{11}$=H, $R^{12}$=H], [1135; Q=Q$^{q1}$, $A^1$=H, $A^2$=H, $A^3$=H, $A^4$=H, $A^5$=Cl, $A^6$=H, $R^3$=OMe, $R^{11}$=H, $R^{12}$=H], [1136; Q=Q$^{q1}$, $A^1$=H, $A^2$=H, $A^3$=Cl, $A^4$=Cl, $A^5$=H, $A^6$=H, $R^3$=OMe, $R^{11}$=H, $R^{12}$=H], [1137; Q=Q$^{q1}$, $A^1$=H, $A^2$=H, $A^3$=H, $A^4$=H, $A^5$=Cl, $A^6$=Cl, $R^3$=OMe, $R^{11}$=H, $R^{12}$=H], [1138; Q=Q$^{q1}$, $A^1$=H, $A^2$=H, $A^3$=Br, $A^4$=H, $A^5$=H, $A^6$=H, $R^3$=OMe, $R^{11}$=H, $R^{12}$=H], [1139; Q=Q$^{q1}$, $A^1$=H, $A^2$=H, $A^3$=H, $A^4$=H, $A^5$=Br, $A^6$=H, $R^3$=OMe, $R^{11}$=H, $R^{12}$=H], [1140; Q=Q$^{q1}$, $A^1$=H, $A^2$=H, $A^3$=Br, $A^4$=Br, $A^5$=H, $A^6$=H, $R^3$=OMe, $R^{11}$=H, $R^{12}$=H], [1141; Q=Q$^{q1}$, $A^1$=H, $A^2$=H, $A^3$=H, $A^4$=H, $A^5$=Br, $A^6$=Br, $R^3$=OMe, $R^{11}$=H, $R^{12}$=H], [1142; Q=Q$^{q1}$, $A^1$=H, $A^2$=H, $A^3$=Me, $A^4$=H, $A^5$=H, $A^6$=H, $R^3$=OMe, $R^{11}$=H, $R^{12}$=H], [1143; Q=Q$^{q1}$, $A^1$=H, $A^2$=H, $A^3$=H, $A^4$=H, $A^5$=Me, $A^6$=H, $R^3$=OMe, $R^{11}$=H, $R^{12}$=H], [1144; Q=Q$^{q1}$, $A^1$=H, $A^2$=H, $A^3$=Me, $A^4$=Me, $A^5$=H, $A^6$=H, $R^3$=OMe, $R^{11}$=H, $R^{12}$=H], [1145; Q=Q$^{q1}$, $A^1$=H, $A^2$=H, $A^3$=H, $A^4$=H, $A^5$=Me, $A^6$=Me, $R^3$=OMe, $R^{11}$=H, $R^{12}$=H], [1146; Q=Q$^{q1}$, $A^1$=H, $A^2$=H, $A^3$=OMe, $A^4$=H, $A^5$=H, $A^6$=H, $R^3$=OMe, $R^{11}$=H, $R^{12}$=H], [1147; Q=Q$^{q1}$, $A^1$=H, $A^2$=H, $A^3$=H, $A^4$=H, $A^5$=OMe, $A^6$=H, $R^3$=OMe, $R^{11}$=H, $R^{12}$=H], [1148; Q=Q$^{q1}$, $A^1$=H, $A^2$=H, $A^3$=H, $A^4$=H, $A^5$=H, $A^6$=H, $R^3$=OCF$_3$, $R^{11}$=H, $R^{12}$=H], [1149; Q=Q$^{q1}$, $A^1$=F, $A^2$=H, $A^3$=H, $A^4$=H, $A^5$=H, $A^6$=H, $R^3$=OCF$_3$, $R^{11}$=H, $R^{12}$=H], [1150; Q=Q$^{q1}$, $A^1$=H, $A^2$=H, $A^3$=F, $A^4$=H, $A^5$=H, $A^6$=H, $R^3$=OCF$_3$, $R^{11}$=H, $R^{12}$=H], [1151; Q=Q$^{q1}$, $A^1$=H, $A^2$=H, $A^3$=H, $A^4$=H, $A^5$=F, $A^6$=H, $R^3$=OCF$_3$, $R^{11}$=H, $R^{12}$=H], [1152; Q=Q$^{q1}$, $A^1$=F, $A^2$=F, $A^3$=H, $A^4$=H, $A^5$=H, $A^6$=H, $R^3$=OCF$_3$, $R^{11}$=H, $R^{12}$=H], [1153; Q=Q$^{q1}$, $A^1$=H, $A^2$=H, $A^3$=F, $A^4$=F, $A^5$=H, $A^6$=H, $R^3$=OCF$_3$, $R^{11}$=H, $R^{12}$=H], [1154; Q=Q$^{q1}$, $A^1$=H, $A^2$=H, $A^3$=H, $A^4$=H, $A^5$=F, $A^6$=F, $R^3$=OCF$_3$, $R^{11}$=H, $R^{12}$=H], [1155; Q=Q$^{q1}$, $A^1$=H, $A^2$=H, $A^3$=C, $A^4$=H, $A^5$=H, $A^6$=H, $R^3$=OCF$_3$, $R^{11}$=H, $R^{12}$=H], [1156; Q=Q$^{q1}$, $A^1$=H, $A^2$=H, $A^3$=H, $A^4$=H, $A^5$=Cl, $A^6$=H, $R^3$=OCF$_3$, $R^{11}$=H, $R^{12}$=H], [1157; Q=Q$^{q1}$, $A^1$=H, $A^2$=H, $A^3$=C, $A^4$=C, $A^5$=H, $A^6$=H, $R^3$=OCF$_3$, $R^{11}$=H, $R^{12}$=H], [1158; Q=Q$^{q1}$, $A^1$=H, $A^2$=H, $A^3$=H, $A^4$=H, $A^5$=Cl, $A^6$=Cl, $R^3$=OCF$_3$, $R^{11}$=H, $R^{12}$=H], [1159; Q=Q$^{q1}$, $A^1$=H, $A^2$=H, $A^3$=Br, $A^4$=H, $A^5$=H, $A^6$=H, $R^3$=OCF$_3$, $R^{11}$=H, $R^{12}$=H], [1160; Q=Q$^{q1}$, $A^1$=H, $A^2$=H, $A^3$=H, $A^4$=H, $A^5$=Br, $A^6$=H, $R^3$=OCF$_3$, $R^{11}$=H, $R^{12}$=H], [1161; Q=Q$^{q1}$, $A^1$=H, $A^2$=H, $A^3$=Br, $A^4$=Br, $A^5$=H, $A^6$=H, $R^3$=OCF$_3$, $R^{11}$=H, $R^{12}$=H], [1162; Q=Q$^{q1}$, $A^1$=H, $A^2$=H, $A^3$=H, $A^4$=H, $A^5$=Br, $A^6$=Br, $R^3$=OCF$_3$, $R^{11}$=H, $R^{12}$=H], [1163; Q=Q$^{q1}$, $A^1$=H, $A^2$=H, $A^3$=Me, $A^4$=H, $A^5$=H, $A^6$=H, $R^3$=OCF$_3$, $R^{11}$=H, $R^{12}$=H], [1164; Q=Q$^{q1}$, $A^1$=H, $A^2$=H, $A^3$=H, $A^4$=H, $A^5$=Me, $A^6$=H, $R^3$=OCF$_3$, $R^{11}$=H, $R^{12}$=H], [1165; Q=Q$^{q1}$, $A^1$=H, $A^2$=H, $A^3$=Me, $A^4$=Me, $A^5$=H, $A^6$=H, $R^3$=OCF$_3$, $R^{11}$=H, $R^{12}$=H], [1166; Q=Q$^{q1}$, $A^1$=H, $A^2$=H, $A^3$=H, $A^4$=H, $A^5$=Me, $A^6$=Me, $R^3$=OCF$_3$, $R^{11}$=H, $R^{12}$=H], [1167; Q=Q$^{q1}$, $A^1$=H, $A^2$=H, $A^3$=OMe, $A^4$=H, $A^5$=H, $A^6$=H, $R^3$=OCF$_3$, $R^{11}$=H, $R^{12}$=H], [1168; Q=Q$^{q1}$, $A^1$=H, $A^2$=H, $A^3$=H, $A^4$=H, $A^5$=OMe, $A^6$=H, $R^3$=OCF$_3$, $R^{11}$=H, $R^{12}$=H], [1169; Q=Q$^{q1}$, $A^1$=H, $A^2$=H, $A^3$=H, $A^4$=H, $A^5$=H, $A^6$=H, $R^3$=SMe, $R^{11}$=H, $R^{12}$=H], [1170; Q=Q$^{q1}$, $A^1$=F, $A^2$=H, $A^3$=H, $A^4$=H, $A^5$=H, $A^6$=H, $R^3$=SMe, $R^{11}$=H, $R^{12}$=H], [1171; Q=Q$^{q1}$, $A^1$=H, $A^2$=H, $A^3$=F, $A^4$=H, $A^5$=H, $A^6$=H, $R^3$=SMe, $R^{11}$=H, $R^{12}$=H], [1172; Q=Q$^{q1}$, $A^1$=H, $A^2$=H, $A^3$=H, $A^4$=H, $A^5$=F, $A^6$=H, $R^3$=SMe, $R^{11}$=H, $R^{12}$=H], [1173; Q=Q$^{q1}$, $A^1$=F, $A^2$=F, $A^3$=H, $A^4$=H, $A^5$=H, $A^6$=H, $R^3$=SMe, $R^{11}$=H, $R^{12}$=H], [1174; Q=Q$^{q1}$, $A^1$=H, $A^2$=H, $A^3$=F, $A^4$=F, $A^5$=H, $A^6$=H, $R^3$=SMe, $R^{11}$=H, $R^{12}$=H], [1175; Q=Q$^{q1}$, $A^1$=H, $A^2$=H, $A^3$=H, $A^4$=H, $A^5$=F, $A^6$=F, $R^3$=SMe, $R^{11}$=H, $R^{12}$=H], [1176; Q=Q$^{q1}$, $A^1$=H, $A^2$=H, $A^3$=Cl, $A^4$=H, $A^5$=H, $A^6$=H, $R^3$=SMe, $R^{11}$=H, $R^{12}$=H], [1177; Q=Q$^{q1}$, $A^1$=H, $A^2$=H, $A^3$=H, $A^4$=H, $A^5$=Cl, $A^6$=H, $R^3$=SMe, $R^{11}$=H, $R^{12}$=H], [1178; Q=Q$^{q1}$, $A^1$=H, $A^2$=H, $A^3$=Cl, $A^4$=Cl, $A^5$=H, $A^6$=H, $R^3$=SMe, $R^{11}$=H, $R^{12}$=H], [1179; Q=Q$^{q1}$, $A^1$=H, $A^2$=H, $A^3$=H, $A^4$=H, $A^5$=Cl, $A^6$=Cl, $R^3$=SMe, $R^{11}$=H, $R^{12}$=H], [1180; Q=Q$^{q1}$, $A^1$=H, $A^2$=H, $A^3$=Br, $A^4$=H, $A^5$=H, $A^6$=H, $R^3$=SMe, $R^{11}$=H, $R^2$=H], [1181; Q=Q$^{q1}$, $A^1$=H, $A^2$=H, $A^3$=H, $A^4$=H, $A^5$=Br, $A^6$=H, $R^3$=SMe, $R^{11}$=H, $R^{12}$=H], [1182; Q=Q$^{q1}$, $A^1$=H, $A^2$=H, $A^3$=Br, $A^4$=Br, $A^5$=H, $A^6$=H, $R^3$=SMe, $R^{11}$=H, $R^{12}$=H], [1183; Q=Q$^{q1}$, $A^1$=H, $A^2$=H, $A^3$=H, $A^4$=H, $A^5$=Br, $A^6$=Br, $R^3$=SMe, $R^{11}$=H, $R^{12}$=H], [1184; Q=Q$^{q1}$, $A^1$=H, $A^2$=H, $A^3$=Me, $A^4$=H, $A^5$=H, $A^6$=H, $R^3$=SMe, $R^{11}$=H, $R^{12}$=H], [1185; Q=Q$^{q1}$, $A^1$=H, $A^2$=H, $A^3$=H, $A^4$=H, $A^5$=Me, $A^6$=H, $R^3$=SMe, $R^{11}$=H, $R^{12}$=H], [1186; Q=Q$^{q1}$, $A^1$=H, $A^2$=H, $A^3$=Me, $A^4$=Me, $A^5$=H, $A^6$=H, $R^3$=SMe, $R^{11}$=H, $R^{12}$=H], [1187; Q=Q$^{q1}$, $A^1$=H, $A^2$=H, $A^3$=H, $A^4$=H, $A^5$=Me, $A^6$=Me, $R^3$=SMe, $R^{11}$=H, $R^{12}$=H], [1188; Q=Q$^{q1}$, $A^1$=H, $A^2$=H, $A^3$=OMe, $A^4$=H, $A^5$=H, $A^6$=H, $R^3$=SMe, $R^{11}$=H, $R^{12}$=H], [1189; Q=Q$^{q1}$, $A^1$=H, $A^2$=H, $A^3$=H, $A^4$=H, $A^5$=OMe, $A^6$=H, $R^3$=SMe, $R^{11}$=H, $R^{12}$=H], [1190; Q=Q$^{q1}$, $A^1$=H, $A^2$=H, $A^3$=H, $A^4$=H, $A^5$=H, $A^6$=H, $R^3$=H, $R^{11}$=F, $R^{12}$=H], [1191; Q=Q$^{q1}$, $A^1$=F, $A^2$=H, $A^3$=H, $A^4$=H, $A^5$=H, $A^6$=H, $R^3$=H, $R^{11}$=F, $R^{12}$=H], [1192; Q=Q$^{q1}$, $A^1$=H, $A^2$=H, $A^3$=F, $A^4$=H, $A^5$=H, $A^6$=H, $R^{11}$=H, $R^{11}$=F, $R^{12}$=H], [1193; Q=Q$^{q1}$, $A^1$=H, $A^2$=H, $A^3$=H, $A^4$=H, $A^5$=F, $A^6$=H, $R^3$=H, $R^{11}$=F, $R^{12}$=H], [1194; Q=Q$^{q1}$, $A^1$=F, $A^2$=F, $A^3$=H, $A^4$=H, $A^5$=H, $A^6$=H, $R^3$=H, $R^{11}$=F, $R^{12}$=H], [1195; Q=Q$^{q1}$, $A^1$=H, $A^2$=H, $A^3$=F, $A^4$=F, $A^5$=H, $A^6$=H, $R^3$=H, $R^{11}$=F, $R^{12}$=H], [1196; Q=Q$^{q1}$, $A^1$=H, $A^2$=H, $A^3$=H, $A^4$=H, $A^5$=F, $A^6$=F, $R^3$=H, $R^{11}$=F, $R^{12}$=H], [1197; Q=Q$^{q1}$, $A^1$=H, $A^2$=, $A^3$=H, $A^4$=H, $A^5$=H, $A^6$=H, $R^3$=H, $R^{11}$=F, $R^{12}$=H], [1198; Q=Q$^{q1}$, $A^1$=H, $A^2$=H, $A^3$=H, $A^4$=H, $A^5$=Cl, $A^6$=H, $R^3$=H, $R^{11}$=F, $R^{12}$=H], [1199; Q=Q 2, $A^1$=H, $A^2$=H, $A^3$=C, $A^4$=Cl, $A^5$=H, $A^6$=H, $R^3$=H, $R^{11}$=F, $R^{12}$=H], [1200; Q=Q$^{q1}$, $A^1$=H, $A^2$=H, $A^3$=H, $A^4$=H, $A^5$=Cl, $A^6$=Cl, $R^3$=H, $R^{11}$=F, $R^{12}$=H], [1201; Q=Q$^{q1}$, $A^1$=H, $A^2$=H, $A^3$=Br, $A^4$=H, $A^5$=H, $A^6$=H, $R^3$=H, $R^{11}$=F, $R^{12}$=H], [1202; Q=Q$^{q1}$, $A^1$=H, $A^2$=H, $A^3$=H, $A^4$=H, $A^5$=Br, $A^6$=H, $R^3$=H, $R^{11}$=F, $R^{12}$=H], [1203; Q=Q$^{q1}$, $A^1$=H, $A^2$=H, $A^3$=Br, $A^4$=Br, $A^5$=H, $A^6$=H, $R^3$=H, $R^{11}$=F, $R^{12}$=H], [1204; Q=Q$^{q1}$, $A^1$=H, $A^2$=H, $A^3$=H, $A^4$=H, $A^5$=Br, $A^6$=Br, $R^3$=H, $R^{11}$=F, $R^{12}$=H], [1205; Q=Q$^{q1}$, $A^1$=H, $A^2$=H, A³=Me, A⁴=H, A⁵=H, A⁶=H, R³=H, R¹¹=F, R¹²=H], [1206; Q=Q^{q1}, A¹=H, A²=H, A³=H, A⁴=H, A⁵=Me, A⁶=H, R³=H, R¹¹=F, R¹²=H], [1207; Q=Q^{q1}, A¹=H, A²=H, A³=Me, A⁴=Me, A⁵=H, A⁶=H, R³=H, R¹¹=F, R¹²=H], [1208; Q=Q^{q1}, A¹=H, A²=H, A³=H, A⁴=H, A⁵=Me, A⁶=Me, R³=H, R¹¹=F, R¹²=H], [1209; Q=Q^{q1}, A¹=H, A²=H, A³=OMe, A⁴=H, A⁵=H, A⁶=H, R³=H, R¹¹=F, R¹²=H], [1210; Q=Q^{q1}, A¹=H, A²=H, A³=H, A⁴=H, A⁵=OMe, A⁶=H, R³=H, R¹¹=F, R¹²=H], [1211; Q=Q^{q1}, A¹=H, A²=H, A³=H, A⁴=H, A⁵=H, A⁶=H, R³=H, R¹¹=Cl, R¹²=H], [1212; Q=Q^{q1}, A¹=F, A²=H, A³=H, A⁴=H, A⁵=H, A⁶=H, R³=H, R¹¹=Cl, R¹²=H], [1213; Q=Q^{q1}, A¹=H, A²=H, A³=F, A⁴=H, A⁵=H, A⁶=H, R³=H, R¹¹=Cl, R¹²=H], [1214; Q=Q^{q1}, A¹=H, A²=H, A³=H, A⁴=H, A⁵=F, A⁶=H, R³=H, R¹¹=Cl, R¹²=H], [1215; Q=Q^{q1}, A¹=F, A²=F, A³=H, A⁴=H, A⁵=H, A⁶=H, R³=H, R¹¹=Cl, R¹²=H], [1216; Q=Q^{q1}, A¹=H, A²=H, A³=F, A⁴=F, A⁵=H, A⁶=H, R³=H, R¹¹=Cl, R¹²=H], [1217; Q=Q^{q1}, A¹=H, A²=H, A³=H, A⁴=H, A⁵=F, A⁶=F, R³=H, R¹¹=Cl, R¹²=H], [1218; Q=Q^{q1}, A¹=H, A²=H, A³=Cl, A⁴=H, A⁵=H, A⁶=H, R³=H, R¹¹=Cl, R¹²=H], [1219; Q=Q^{q1}, A¹=H, A²=H, A³=H, A⁴=H, A⁵=Cl, A⁶=H, R³=H, R¹¹=Cl, R¹²=H], [1220; Q=Q^{q1}, A¹=H, A²=H, A³=Cl, A⁴=Cl, A⁵=H, A⁶=H, R³=H, R¹¹=Cl, R¹²=H], [1221; Q=Q^{q1}, A¹=H, A²=H, A³=H, A⁴=H, A⁵=Cl, A⁶=Cl, R³=H, R¹¹=Cl, R¹²=H], [1222; Q=Q^{q1}, A¹=H, A²=H, A³=H, A⁴=H, A⁵=H, A⁶=H, R³=H, R¹¹=Cl, R¹²=H], [1223; Q=Q^{q1}, A¹=H, A²=H, A³=H, A⁴=H, A⁵=Br, A⁶=H, R³=H, R¹¹=Cl, R¹²=H], [1224; Q=Q^{q1}, A¹=H, A²=H, A³=Br, A⁴=Br, A⁵=H, A⁶=H, R³=H, R¹¹=Cl, R¹²=H], [1225; Q=Q^{q1}, A¹=H, A²=H, A³=H, A⁴=H, A⁵=Br, A⁶=Br, R³=H, R¹¹=Cl, R¹²=H], [1226; Q=Q^{q1}, A¹=H, A²=H, A³=Me, A⁴=H, A⁵=H, A⁶=H, R³=H, R¹¹=Cl, R¹²=H], [1227; Q=Q^{q1}, A¹=H, A²=H, A³=H, A⁴=H, A⁵=Me, A⁶=H, R³=H, R¹¹=Cl, R¹²=H], [1228; Q=Q^{q1}, A¹=H, A²=H, A³=Me, A⁴=Me, A⁵=H, A⁶=H, R³=H, R¹¹=Cl, R¹²=H], [1229; Q=Q^{q1}, A¹=H, A²=H, A³=H, A⁴=H, A⁵=Me, A⁶=Me, R³=H, R¹¹=Cl, R¹²=H], [1230; Q=Q^{q1}, A¹=H, A²=H, A³=OMe, A⁴=H, A⁵=H, A⁶=H, R³=H, R¹¹=Cl, R¹²=H], [1231; Q=Q^{q1}, A¹=H, A²=H, A³=H, A⁴=H, A⁵=OMe, A⁶=H, R³=H, R¹¹=Cl, R¹²=H], [1232; Q=Q^{q1}, A¹=H, A²=H, A³=H, A⁴=H, A⁵=H, A⁶=H, R³=H, R¹¹=Br, R¹²=H], [1233; Q=Q^{q1}, A¹=F, A²=H, A³=H, A⁴=H, A⁵=H, A⁶=H, R³=H, R¹¹=Br, R¹²=H], [1234; Q=Q^{q1}, A¹=H, A²=H, A³=F, A⁴=H, A⁵=H, A⁶=H, R³=H, R¹¹=Br, R¹²=H], [1235; Q=Q^{q1}, A¹=H, A²=H, A³=H, A⁴=H, A⁵=F, A⁶=H, R³=H, R¹¹=Br, R¹²=H], [1236; Q=Q^{q1}, A¹=F, A²=F, A³=H, A⁴=H, A⁵=H, A⁶=H, R³=H, R¹¹=Br, R¹²=H], [1237; Q=Q^{q1}, A¹=H, A²=H, A³=F, A⁴=F, A⁵=H, A⁶=H, R³=H, R¹¹=Br, R¹²=H], [1238; Q=Q^{q1}, A¹=H, A²=H, A³=H, A⁴=H, A⁵=F, A⁶=F, R³=H, R¹¹=Br, R¹²=H], [1239; Q=Q^{q1}, A¹=H, A²=H, A³=Cl, A⁴=H, A⁵=H, A⁶=H, R³=H, R¹¹=Br, R¹²=H], [1240; Q=Q^{q1}, A¹=H, A²=H, A³=H, A⁴=H, A⁵=Cl, A⁶=H, R³=H, R¹¹=Br, R¹²=H], [1241; Q=Q^{q1}, A¹=H, A²=H, A³=Cl, A⁴=Cl, A⁵=H, A⁶=H, R³=H, R¹¹=Br, R¹²=H], [1242; Q=Q^{q1}, A¹=H, A²=H, A³=H, A⁴=H, A⁵=Cl, A⁶=Cl, R³=H, R¹¹=Br, R¹²=H], [1243; Q=Q^{q1}, A¹=H, A²=H, A³=Br, A⁴=H, A⁵=H, A⁶=H, R³=H, R¹¹=Br, R¹²=H], [1244; Q=Q^{q1}, A¹=H, A²=H, A³=H, A⁴=H, A⁵=Br, A⁶=H, R³=H, R¹¹=Br, R¹²=H], [1245; Q=Q^{q1}, A¹=H, A²=H, A³=Br, A⁴=Br, A⁵=H, A⁶=H, R³=H, R¹¹=Br, R¹²=H], [1246; Q=Q^{q1}, A¹=H, A²=H, A³=H, A⁴=H, A⁵=Br, A⁶=Br, R³=H, R¹¹=Br, R¹²=H], [1247; Q=Q^{q1}, A¹=H, A²=H, A³=Me, A⁴=H, A⁵=H, A⁶=H, R³=H, R¹¹=Br, R¹²=H], [1248; Q=Q^{q1}, A¹=H, A²=H, A³=H, A⁴=H, A⁵=Me, A⁶=H, R³=H, R¹¹=Br, R¹²=H], [1249; Q=Q^{q1}, A¹=H, A²=H, A³=Me, A⁴=Me, A⁵=H, A⁶=H, R³=H, R¹¹=Br, R¹²=H], [1250; Q=Q^{q1}, A¹=H, A²=H, A³=H, A⁴=H, A⁵=Me, A⁶=Me, R³=H, R¹¹=Br, R¹²=H], [1251; Q=Q^{q1}, A¹=H, A²=H, A³=OMe, A⁴=H, A⁵=H, A⁶=H, R³=H, R¹¹=Br, R¹²=H], [1252; Q=Q^{q1}, A¹=H, A²=H, A³=H, A⁴=H, A⁵=OMe, A⁶=H, R³=H, R¹¹=Br, R¹²=H], [1253; Q=Q^{q1}, A¹=H, A²=H, A³=H, A⁴=H, A⁵=H, A⁶=H, R³=H, R¹¹=Me, R¹²=H], [1254; Q=Q^{q1}, A¹=F, A²=H, A³=H, A⁴=H, A⁵=H, A⁶=H, R³=H, R¹¹=Me, R¹²=H], [1255; Q=Q^{q1}, A¹=H, A²=H, A³=F, A⁴=H, A⁵=H, A⁶=H, R³=H, R¹¹=Me, R¹²=H], [1256; Q=Q^{q1}, A¹=H, A²=H, A³=H, A⁴=H, A⁵=F, A⁶=H, R³=H, R¹¹=Me, R¹²=H], [1257; Q=Q^{q1}, A¹=F, A²=F, A³=H, A⁴=H, A⁵=H, A⁶=H, R³=H, R¹¹=Me, R¹²=H], [1258; Q=Q^{q1}, A¹=H, A²=H, A³=F, A⁴=F, A⁵=H, A⁶=H, R³=H, R¹¹=Me, R¹²=H], [1259; Q=Q^{q1}, A¹=H, A²=H, A³=H, A⁴=H, A⁵=F, A⁶=F, R³=H, R¹¹=Me, R¹²=H], [1260; Q=Q^{q1}, A¹=H, A²=H, A³=Cl, A⁴=H, A⁵=H, A⁶=H, R³=H, R¹¹=Me, R¹²=H], [1261; Q=Q^{q1}, A¹=H, A²=H, A³=H, A⁴=H, A⁵=Cl, A⁶=H, R³=H, R¹¹=Me, R¹²=H], [1262; Q=Q^{q1}, A¹=H, A²=H, A³=Cl, A⁴=Cl, A⁵=H, A⁶=H, R³=H, R¹¹=Me, R¹²=H], [1263; Q=Q^{q1}, A¹=H, A²=H, A³=H, A⁴=H, A⁵=Cl, A⁶=Cl, R³=H, R¹¹=Me, R¹²=H], [1264; Q=Q^{q1}, A¹=H, A²=H, A³=Br, A⁴=H, A⁵=H, A⁶=H, R³=H, R¹¹=Me, R¹²=H], [1265; Q=Q^{q1}, A¹=H, A²=H, A³=H, A⁴=H, A⁵=Br, A⁶=H, R³=H, R¹¹=Me, R¹²=H], [1266; Q=Q^{q1}, A¹=H, A²=H, A³=Br, A⁴=Br, A⁵=H, A⁶=H, R³=H, R¹¹=Me, R¹²=H], [1267; Q=Q^{q1}, A¹=H, A²=H, A³=H, A⁴=H, A⁵=Br, A⁶=Br, R³=H, R¹¹=Me, R¹²=H], [1268; Q=Q^{q1}, A¹=H, A²=H, A³=Me, A⁴=H, A⁵=H, A⁶=H, R³=H, R¹¹=Me, R¹²=H], [1269; Q=Q^{q1}, A¹=H, A²=H, A³=H, A⁴=H, A⁵=Me, A⁶=H, R³=H, R¹¹=Me, R¹²=H], [1270; Q=Q^{q1}, A¹=H, A²=H, A³=Me, A⁴=Me, A⁵=H, A⁶=H, R³=H, R¹¹=Me, R¹²=H], [1271; Q=Q^{q1}, A¹=H, A²=H, A³=H, A⁴=H, A⁵=Me, A⁶=Me, R³=H, R¹¹=Me, R¹²=H], [1272; Q=Q^{q1}, A¹=H, A²=H, A³=OMe, A⁴=H, A⁵=H, A⁶=H, R³=H, R¹¹=Me, R¹²=H], [1273; Q=Q^{q1}, A¹=H, A²=H, A³=H, A⁴=H, A⁵=OMe, A⁶=H, R³=H, R¹¹=Me, R¹²=H], [1274; Q=Q^{q1}, A¹=H, A²=H, A³=H, A⁴=H, A⁵=H, A⁶=H, R³=H, R¹¹=CF₃, R¹²=H], [1275; Q=Q^{q1}, A¹=F, A²=H, A³=H, A⁴=H, A⁵=H, A⁶=H, R³=H, R¹¹=CF₃, R¹²=H], [1276; Q=Q^{q1}, A¹=H, A²=H, A³=F, A⁴=H, A⁵=H, A⁶=H, R³=H, R¹¹=CF₃, R¹²=H], [1277; Q=Q^{q1}, A¹=H, A²=H, A³=H, A⁴=H, A⁵=F, A⁶=H, R³=H, R¹¹=CF₃, R¹²=H], [1278; Q=Q^{q1}, A¹=F, A²=F, A³=H, A⁴=H, A⁵=H, A⁶=H, R³=H, R¹¹=CF₃, R¹²=H], [1279; Q=Q^{q1}, A¹=H, A²=H, A³=F, A⁴=F, A⁵=H, A⁶=H, R³=H, R¹¹=CF₃, R¹²=H], [1280; Q=Q^{q1}, A¹=H, A²=H, A³=H, A⁴=H, A⁵=F, A⁶=F, R³=H, R¹¹=CF₃, R¹²=H], [1281; Q=Q^{q1}, A¹=H, A²=H, A³=Cl, A⁴=H, A⁵=H, A⁶=H, R³=H, R¹¹=CF₃, R¹²=H], [1282; Q=Q^{q1}, A¹=H, A²=H, A³=H, A⁴=H, A⁵=Cl, A⁶=H, R³=H, R¹¹=CF₃, R¹²=H], [1283; Q=Q^{q1}, A¹=H, A²=H, A³=Cl, A⁴=Cl, A⁵=H, A⁶=H, R³=H, R¹¹=CF₃, R¹²=H], [1284; Q=Q^{q1}, A¹=H, A²=H, A³=H, A⁴=H, A⁵=Cl, A⁶=Cl, R³=H, R¹¹=CF₃, R¹²=H], [1285; Q=Q^{q1}, A¹=H, A²=H, A³=Br, A⁴=H, A⁵=H, A⁶=H, R³=H, R¹¹=CF₃, R¹²=H], [1286; Q=Q^{q1}, A¹=H, A²=H, A³=H, A⁴=H, A⁵=Br, A⁶=H, R³=H, R¹¹=CF₃, R¹²=H], [1287; Q=Q^{q1}, A¹=H, A²=H, A³=Br, A⁴=Br, A⁵=H, A⁶=H, R³=H, R¹¹=CF₃, R¹²=H], [1288; Q=Q^{q1}, A¹=H, A²=H, A³=H, A⁴=H, A⁵=Br, A⁶=Br, R³=H, R¹¹=CF₃, R¹²=H], [1289; Q=Q^{q1}, A¹=H, A²=H, A³=Me, A⁴=H, A⁵=H, A⁶=H, R³=H, R¹¹=CF₃, R¹²=H], [1290; Q=Q^{q1}, A¹=H, A²=H, A³=H, A⁴=H, A⁵=Me, A⁶=H, R³=H, R¹¹=CF₃, R¹²=H], [1291; Q=Q^{q1}, A¹=H, A²=H, A³=Me, A⁴=Me, A⁵=H, A⁶=H, R³=H, R¹¹=CF₃, R¹²=H], [1292; Q=Q^{q1}, A¹=H, A²=H, A³=H, A⁴=H, A⁵=Me, A⁶=Me, R³=H, R¹¹=CF₃, R¹²=H], [1293; Q=Q^{q1}, A¹=H, A²=H, A³=OMe, A⁴=H, A⁵=H, A⁶=H, R³=H, R¹¹=CF₃, R¹²=H], [1294; Q=Q^{q1}, A¹=H, A²=H, A³=H, A⁴=H, A⁵=OMe, A⁶=H, R³=H, R¹¹=CF₃, R¹²=H], [1295; Q=Q^{q1}, A¹=H, A²=H, A³=H, A⁴=H, A⁵=H, A⁶=H, R³=H, R¹¹=OMe, R¹²=H], [1296; Q=Q^{q1}, A¹=F, A²=H, A³=H, A⁴=H, A⁵=H, A⁶=H, R³=H, R¹¹=OMe, R¹²=H], [1297; Q=Q^{q1}, A¹=H, A²=H, A³=F, A⁴=H, A⁵=H, A¹=H, R³=H, R$^{11}$=OMe, R$^{12}$=H], [1298; Q=Q$^{q1}$, A$^1$=H, A$^2$=H, A$^3$=H, A$^4$=H, A$^5$=F, A$^6$=H, R$^3$=H, R$^{11}$=OMe, R$^{12}$=H], [1299; Q=Q$^{q1}$, A$^1$=F, A$^2$=F, A$^3$=H, A$^4$=H, A$^5$=H, A$^6$=H, R$^3$=H, R$^{11}$=OMe, R$^{12}$=H], [1300; Q=Q$^{q1}$, A$^1$=H, A$^2$=H, A$^3$=F, A$^4$=F, A$^5$=H, A$^6$=H, R$^3$=H, R$^{11}$=OMe, R$^{12}$=H], [1301; Q=Q$^{q1}$, A$^1$=H, A$^2$=H, A$^3$=H, A$^4$=H, A$^5$=F, A$^6$=F, R$^3$=H, R$^{11}$=OMe, R$^{12}$=H], [1302; Q=Q$^{q1}$, A$^1$=H, A$^2$=H, A$^3$=Cl, A$^4$=H, A$^5$=H, A$^6$=H, R$^3$=H, R$^{11}$=OMe, R$^{12}$=H], [1303; Q=Q$^{q1}$, A$^1$=H, A$^2$=H, A$^3$=H, A$^4$=H, A$^5$=Cl, A$^6$=H, R$^3$=H, R$^{11}$=Me, R$^{12}$=H], [1304; Q=Q$^{q1}$, A$^1$=H, A$^2$=H, A$^3$=Cl, A$^4$=Cl, A$^5$=H, A$^6$=H, R$^3$=H, R$^{11}$=OMe, R$^{12}$=H], [1305; Q=Q$^{q1}$, A$^1$=H, A$^2$=H, A$^3$=H, A$^4$=H, A$^5$=Cl, A$^6$=Cl, R$^3$=H, R$^{11}$=OMe, R$^{12}$=H], [1306; Q=Q$^{q1}$, A$^1$=H, A$^2$=H, A$^3$=Br, A$^4$=H, A$^5$=H, A$^6$=H, R$^3$=H, R$^{11}$=OMe, R$^{12}$=H], [1307; Q=Q$^{q1}$, A$^1$=H, A$^2$=H, A$^3$=H, A$^4$=H, A$^5$=Br, A$^6$=H, R$^3$=H, R$^{11}$=OMe, R$^{12}$=H], [1308; Q=Q$^{q1}$, A$^1$=H, A$^2$=H, A$^3$=Br, A$^4$=Br, A$^5$=H, A$^6$=H, R$^3$=H, R$^{11}$=OMe, R$^{12}$=H], [1309; Q=Q$^{q1}$, A$^1$=H, A$^2$=H, A$^3$=H, A$^4$=H, A$^5$=Br, A$^6$=Br, R$^3$=H, R$^{11}$=OMe, R$^{12}$=H], [1310; Q=Q$^{q1}$, A$^1$=H, A$^2$=H, A$^3$=Me, A$^4$=H, A$^5$=H, A$^6$=H, R$^3$=H, R$^{11}$=OMe, R$^{12}$=H], [1311; Q=Q$^{q1}$, A$^1$=H, A$^2$=H, A$^3$=H, A$^4$=H, A$^5$=Me, A$^6$=H, R$^3$=H, R$^{11}$=OMe, R$^{12}$=H], [1312; Q=Q$^{q1}$, A$^1$=H, A$^2$=H, A$^3$=Me, A$^4$=Me, A$^5$=H, A$^6$=H, R$^3$=H, R$^{11}$=OMe, R$^{12}$=H], [1313; Q=Q$^{q1}$, A$^1$=H, A$^2$=H, A$^3$=H, A$^4$=H, A$^5$=Me, A$^6$=Me, R$^3$=H, R$^{11}$=OMe, R$^{12}$=H], [1314; Q=Q$^{q1}$, A$^1$=H, A$^2$=H, A$^3$=OMe, A$^4$=H, A$^5$=H, A$^6$=H, R$^3$=H, R$^{11}$=OMe, R$^{12}$=H], [1315; Q=Q$^{q1}$, A$^1$=H, A$^2$=H, A$^3$=H, A$^4$=H, A$^5$=OMe, A$^6$=H, R$^3$=H, R$^{11}$=OMe, R$^{12}$=H], [1316; Q=Q$^{q1}$, A$^1$=H, A$^2$=H, A$^3$=H, A$^4$=H, A$^5$=H, A$^6$=H, R$^3$=H, R$^{11}$=OCF$_3$, R$^{12}$=H], [1317; Q=Q$^{q1}$, A$^1$=F, A$^2$=H, A$^3$=H, A$^4$=H, A$^5$=H, A$^6$=H, R$^3$=H, R$^{11}$=OCF$_3$, R$^{12}$=H], [1318; Q=Q$^{q1}$, A$^1$=H, A$^2$=H, A$^3$=F, A$^4$=H, A$^5$=H, A$^6$=H, R$^3$=H, R$^{11}$=OCF$_3$, R$^{12}$=H], [1319; Q=Q$^{q1}$, A$^1$=H, A$^2$=H, A$^3$=H, A$^4$=H, A$^5$=F, A$^6$=H, R$^3$=H, R$^{11}$=OCF$_3$, R$^{12}$=H], [1320; Q=Q$^{q1}$, A$^1$=F, A$^2$=F, A$^3$=H, A$^4$=H, A$^5$=H, A$^6$=H, R$^3$=H, R$^{11}$=OCF$_3$, R$^{12}$=H], [1321; Q=Q$^{q1}$, A$^1$=H, A$^2$=H, A$^3$=F, A$^4$=F, A$^5$=H, A$^6$=H, R$^3$=H, R$^{11}$=OCF$_3$, R$^{12}$=H], [1322; Q=Q$^{q1}$, A$^1$=H, A$^2$=H, A$^3$=H, A$^4$=H, A$^5$=F, A$^6$=F, R$^3$=H, R$^{11}$=OCF$_3$, R$^{12}$=H], [1323; Q=Q$^{q1}$, A$^1$=H, A$^2$=H, A$^3$=Cl, A$^4$=H, A$^5$=H, A$^6$=H, R$^3$=H, R$^{11}$=OCF$_3$, R$^{12}$=H], [1324; Q=Q$^{q1}$, A$^1$=H, A$^2$=H, A$^3$=H, A$^4$=H, A$^5$=Cl, A$^6$=H, R$^3$=H, R$^{11}$=OCF$_3$, R$^{12}$=H], [1325; Q=Q$^{q1}$, A$^1$=H, A$^2$=H, A$^3$=Cl, A$^4$=Cl, A$^5$=H, A$^6$=H, R$^3$=H, R$^{11}$=OCF$_3$, R$^{12}$=H], [1326; Q=Q$^{q1}$, A$^1$=H, A$^2$=H, A$^3$=H, A$^4$=H, A$^5$=Cl, A$^6$=Cl, R$^3$=H, R$^{11}$=OCF$_3$, R$^{12}$=H], [1327; Q=Q$^{q1}$, A$^1$=H, A$^2$=H, A$^3$=Br, A$^4$=H, A$^5$=H, A$^6$=H, R$^3$=H, R$^{11}$=OCF$_3$, R$^{12}$=H], [1328; Q=Q$^{q1}$, A$^1$=H, A$^2$=H, A$^3$=H, A$^4$=H, A$^5$=Br, A$^6$=H, R$^3$=H, R$^{11}$=OCF$_3$, R$^{12}$=H], [1329; Q=Q$^{q1}$, A$^1$=H, A$^2$=H, A$^3$=Br, A$^4$=Br, A$^5$=H, A$^6$=H, R$^3$=H, R$^{11}$=OCF$_3$, R$^{12}$=H], [1330; Q=Q$^{q1}$, A$^1$=H, A$^2$=H, A$^3$=H, A$^4$=H, A$^5$=Br, A$^6$=Br, R$^3$=H, R$^{11}$=OCF$_3$, R$^{12}$=H], [1331; Q=Q$^{q1}$, A$^1$=H, A$^2$=H, A$^3$=Me, A$^4$=H, A$^5$=H, A$^6$=H, R$^3$=H, R$^{11}$=OCF$_3$, R$^{12}$=H], [1332; Q=Q$^{q1}$, A$^1$=H, A$^2$=H, A$^3$=H, A$^4$=H, A$^5$=Me, A$^6$=H, R$^3$=H, R$^{11}$=OCF$_3$, R$^{12}$=H], [1333; Q=Q$^{q1}$, A$^1$=H, A$^2$=H, A$^3$=Me, A$^4$=Me, A$^5$=H, A$^6$=H, R$^3$=H, R$^{11}$=OCF$_3$, R$^{12}$=H], [1334; Q=Q$^{q1}$, A$^1$=H, A$^2$=H, A$^3$=H, A$^4$=H, A$^5$=Me, A$^6$=Me, R$^3$=H, R$^{11}$=OCF$_3$, R$^{12}$=H], [1335; Q=Q$^{q1}$, A$^1$=H, A$^2$=H, A$^3$=OMe, A$^4$=H, A$^5$=H, A$^6$=H, R$^3$=H, R$^{11}$=OCF$_3$, R$^{12}$=H], [1336; Q=Q$^{q1}$, A$^1$=H, A$^2$=H, A$^3$=H, A$^4$=H, A$^5$=OMe, A$^6$=H, R$^3$=H, R$^{11}$=OCF$_3$, R$^{12}$=H], [1337; Q=Q$^{q1}$, A$^1$=H, A$^2$=H, A$^3$=H, A$^4$=H, A$^5$=H, A$^6$=H, R$^3$=H, R$^{11}$=SMe, R$^{12}$=H], [1338; Q=Q$^{q1}$, A$^1$=F, A$^2$=H, A$^3$=H, A$^4$=H, A$^5$=H, A$^6$=H, R$^3$=H, R$^{11}$=SMe, R$^{12}$=H], [1339; Q=Q$^{q1}$, A$^1$=H, A$^2$=H, A$^3$=F, A$^4$=H, A$^5$=H, A$^6$=H, R$^3$=H, R$^{11}$=SMe, R$^{12}$=H], [1340; Q=Q$^{q1}$, A$^1$=H, A$^2$=H, A$^3$=H, A$^4$=H, A$^5$=F, A$^6$=H, R$^3$=H, R$^{11}$=SMe, R$^{12}$=H], [1341; Q=Q$^{q1}$, A$^1$=F, A$^2$=F, A$^3$=H, A$^4$=H, A$^5$=H, A$^6$=H, R$^3$=H, R$^{11}$=SMe, R$^{12}$=H], [1342; Q=Q$^{q1}$, A$^1$=H, A$^2$=H, A$^3$=F, A$^4$=F, A$^5$=H, A$^6$=H, R$^3$=H, R$^{11}$=SMe, R$^{12}$=H], [1343; Q=Q$^{q1}$, A$^1$=H, A$^2$=H, A$^3$=H, A$^4$=H, A$^5$=F, A$^6$=F, R$^3$=H, R$^{11}$=SMe, R$^{12}$=H], [1344; Q=Q$^{q1}$, A$^1$=H, A$^2$=H, A$^3$=Cl, A$^4$=H, A$^5$=H, A$^6$=H, R$^3$=H, R$^{11}$=SMe, R$^{12}$=H], [1345; Q=Q$^{q1}$, A$^1$=H, A$^2$=H, A$^3$=H, A$^4$=H, A$^5$=Cl, A$^6$=H, R$^3$=H, R$^{11}$=SMe, R$^{12}$=H], [1346; Q=Q$^{q1}$, A$^1$=H, A$^2$=H, A$^3$=Cl, A$^4$=Cl, A$^5$=H, A$^6$=H, R$^3$=H, R$^{11}$=SMe, R$^{12}$=H], [1347; Q=Q$^{q1}$, A$^1$=H, A$^2$=H, A$^3$=H, A$^4$=H, A$^5$=Cl, A$^6$=Cl, R$^3$=H, R$^{11}$=SMe, R$^{12}$=H], [1348; Q=Q$^{q1}$, A$^1$=H, A$^2$=H, A$^3$=Br, A$^4$=H, A$^5$=H, A$^6$=H, R$^3$=H, R$^{11}$=SMe, R$^{12}$=H], [1349; Q=Q$^{q1}$, A$^1$=H, A$^2$=H, A$^3$=H, A$^4$=H, A$^5$=Br, A$^6$=H, R$^3$=H, R$^{11}$=SMe, R$^{12}$=H], [1350; Q=Q$^{q1}$, A$^1$=H, A$^2$=H, A$^3$=Br, A$^4$=Br, A$^5$=H, A$^6$=H, R$^3$=H, R$^{11}$=SMe, R$^{12}$=H], [1351; Q=Q$^{q1}$, A$^1$=H, A$^2$=H, A$^3$=H, A$^4$=H, A$^5$=Br, A$^6$=Br, R$^3$=H, R$^{11}$=SMe, R$^{12}$=H], [1352; Q=Q$^{q1}$, A$^1$=H, A$^2$=H, A$^3$=Me, A$^4$=H, A$^5$=H, A$^6$=H, R$^3$=H, R$^{11}$=SMe, R$^{12}$=H], [1353; Q=Q$^{q1}$, A$^1$=H, A$^2$=H, A$^3$=H, A$^4$=H, A$^5$=Me, A$^6$=H, R$^3$=H, R$^{11}$=SMe, R$^{12}$=H], [1354; Q=Q$^{q1}$, A$^1$=H, A$^2$=H, A$^3$=Me, A$^4$=Me, A$^5$=H, A$^6$=H, R$^3$=H, R$^{11}$=SMe, R$^{12}$=H], [1355; Q=Q$^{q1}$, A$^1$=H, A$^2$=H, A$^3$=H, A$^4$=H, A$^5$=Me, A$^6$=Me, R$^3$=H, R$^{11}$=SMe, R$^{12}$=H], [1356; Q=Q$^{q1}$, A$^1$=H, A$^2$=H, A$^3$=OMe, A$^4$=H, A$^5$=H, A$^6$=H, R$^3$=H, R$^{11}$=SMe, R$^{12}$=H], [1357; Q=Q$^{q1}$, A$^1$=H, A$^2$=H, A$^3$=H, A$^4$=H, A$^5$=OMe, A$^6$=H, R$^3$=H, R$^{11}$=SMe, R$^{12}$=H], [1358; Q=Q$^{q2}$, A$^1$=H, A$^2$=H, A$^4$=H, R$^3$=H, R$^{11}$=H, R$^{12}$=H], [1359; Q=Q$^{q2}$, A$^1$=H, A$^2$=H, A$^3$=F, A$^4$=H, R$^3$=H, R$^{11}$=H, R$^{12}$=H], [1360; Q=Q$^{q2}$, A$^1$=H, A$^2$=H, A$^3$=F, A$^4$=F, R$^3$=H, R$^{11}$=H, R$^{12}$=H], [1361; Q=Q$^{q2}$, A$^1$=H, A$^2$=H, A$^3$=Cl, A$^4$=H, R$^3$=H, R$^{11}$=H, R$^{12}$=H], [1362; Q=Q$^{q2}$, A$^1$=H, A$^2$=H, A$^3$=Cl, A$^4$=Cl, R$^3$=H, R$^{11}$=H, R$^{12}$=H], [1363; Q=Q$^{q2}$, A$^1$=H, A$^2$=H, A$^3$=Me, A$^4$=H, R$^3$=H, R$^{11}$=H, R$^{12}$=H], [1364; Q=Q$^{q2}$, A$^1$=H, A$^2$=H, A$^3$=Me, A$^4$=Me, R$^3$=H, R$^{11}$=H, R$^{12}$=H], [1395; Q=Q$^{q2}$, A$^1$=H, A$^2$=H, A$^3$=H, A$^4$=H, R$^3$=F, R$^{11}$=H, R$^{12}$=H], [1396; Q=Q$^{q2}$, A$^1$=H, A$^2$=H, A$^3$=F, A$^4$=H, R$^3$=F, R$^{11}$=H, R$^{12}$=H], [1397; Q=Q$^{q2}$, A$^1$=H, A$^2$=H, A$^3$=F, A$^4$=F, R$^3$=F, R$^{11}$=H, R$^{12}$=H], [1398; Q=Q$^{q2}$, A$^1$=H, A$^2$=H, A$^3$=Cl, A$^4$=H, R$^3$=F, R$^{11}$=H, R$^{12}$=H], [1399; Q=Q$^{q2}$, A$^1$=H, A$^2$=H, A$^3$=Cl, A$^4$=Cl, R$^3$=F, R$^{11}$=H, R$^{12}$=H], [1400; Q=Q$^{q2}$, A$^1$=H, A$^2$=H, A$^3$=Me, A$^4$=H, R$^3$=F, R$^{11}$=H, R$^{12}$=H], [1401; Q=Q$^{q2}$, A$^1$=H, A$^2$=H, A$^3$=Me, A$^4$=Me, R$^3$=F, R$^{11}$=H, R$^{12}$=H], [1402; Q=Q$^{q2}$, A$^1$=H, A$^2$=H, A$^3$=H, A$^4$=H, R$^3$=Cl, R$^{11}$=H, R$^{12}$=H], [1403; Q=Q$^{q2}$, A$^1$=H, A$^2$=H, A$^3$=F, A$^4$=H, R$^3$=Cl, R$^{11}$=H, R$^{12}$=H], [1404; Q=Q$^{q2}$, A$^1$=H, A$^2$=H, A$^3$=F, A$^4$=F, R$^3$=Cl, R$^{11}$=H, R$^{12}$=H], [1405; Q=Q$^{q2}$, A$^1$=H, A$^2$=H, A$^3$=Cl, A$^4$=H, R$^3$=Cl, R$^{11}$=H, R$^{12}$=H], [1406; Q=Q$^{q2}$, A$^1$=H, A$^2$=H, A$^3$=Cl, A$^4$=Cl, R$^3$=Cl, R$^{11}$=H, R$^{12}$=H], [1407; Q=Q$^{q2}$, A$^1$=H, A$^2$=H, A$^3$=Me, A$^4$=H, R$^3$=Cl, R$^{11}$=H, R$^{12}$=H], [1408; Q=Q$^{q2}$, A$^1$=H, A$^2$=H, A$^3$=Me, A$^4$=Me, R$^3$=Cl, R$^{11}$=H, R$^{12}$=H], [1409; Q=Q$^{q2}$, A$^1$=H, A$^2$=H, A$^3$=H, A$^4$=H, R$^3$=Br, R$^{11}$=H, R$^{12}$=H], [1410; Q=Q$^{q2}$, A$^1$=H, A$^2$=H, A$^3$=F, A$^4$=H, R$^3$=Br, R$^{11}$=H, R$^{12}$=H], [1411; Q=Q$^{q2}$, A$^1$=H, A$^2$=H, A$^3$=F, A$^4$=F, R$^3$=Br, R$^{11}$=H, R$^{12}$=H], [1412; Q=Q$^{q2}$, A$^1$=H, A$^2$=H, A$^3$=Cl, A$^4$=H, R$^3$=Br, R$^{11}$=H, R$^{12}$=H], [1413; Q=Q$^{q2}$, A$^1$=H, A$^2$=H, A$^3$=Cl, A$^4$=Cl, R$^3$=Br, R$^{11}$=H, R$^{12}$=H], [1414; Q=Q$^{q2}$, A$^1$=H, A$^2$=H, A$^3$=Me, A$^4$=H, R$^3$=Br, R$^{11}$=H, R$^{12}$=H], [1415; Q=Q$^{q2}$, A$^1$=H, A$^2$=H, A$^3$=Me, A$^4$=Me, R$^3$=Br, R$^{11}$=H, R$^{12}$=H], [1416; Q=Q$^{q2}$, A$^1$=H, A$^2$=H, A$^3$=H, A$^4$=H, R$^3$=Me, R$^{11}$=H, R$^{12}$=H], [1417; Q=Q$^{q2}$, A$^1$=H, A$^2$=H, A$^3$=F, A$^4$=H, R$^3$=Me, R$^{11}$=H, R$^{12}$=H], [1418; Q=Q$^{q2}$, A$^1$=H, A$^2$=H, A$^3$=F, A$^4$=F, R$^3$=Me, R$^{11}$=H, R$^{12}$=H], [1419; Q=Q$^{q2}$, A$^1$=H, A$^2$=H, A$^3$=Cl, A$^4$=H, R$^3$=Me, R$^{11}$=H, R$^{12}$=H], [1420; Q=Q$^{q2}$, A$^1$=H, A$^2$=H, A$^3$=Cl, A$^4$=Cl, R$^3$=Me, R$^{11}$=H, R$^{12}$=H], [1421; Q=Q$^{q2}$, A$^1$=H, A$^2$=H, A$^3$=Me, A$^4$=H, R$^3$=Me, R$^{11}$=H, R$^{12}$=H], [1422; Q=Q$^{q2}$, A$^1$=H, A$^2$=H, A$^3$=Me, A$^4$=Me, R$^3$=Me, R$^{11}$=H, R$^{12}$=H], [1423; Q=Q$^{q2}$, A$^1$=H, A$^2$=H, A$^3$=H, A$^4$=H, R$^3$=CF$_3$, R$^{11}$=H, R$^{12}$=H], [1424; Q=Q$^{q2}$, A$^1$=H, A$^2$=H, A$^3$=F, A$^4$=H, R$^3$=CF$_3$, R¹¹=H, R¹²=H], [1425; Q=$Q^{q2}$, A¹=H, A²=H, A³=F, A⁴=F, R³=CF₃, R¹¹=H, R¹²=H], [1426; Q=$Q^{q2}$, A¹=H, A²=H, A³=Cl, A⁴=H, R³=CF₃, R¹¹=H, R¹²=H], [1427; Q=$Q^{q2}$, A¹=H, A²=H, A³=Cl, A⁴=Cl, R³=CF₃, R¹¹=H, R¹²=H], [1428; Q=$Q^{q2}$, A¹=H, A²=H, A³=Me, A⁴=H, R³=CF₃, R¹¹=H, R¹²=H], [1429; Q=$Q^{q2}$, A¹=H, A²=H, A³=Me, A⁴=Me, R³=CF₃, R¹¹=H, R¹²=H], [1430; Q=$Q^{q2}$, A¹=H, A²=H, A³=H, A⁴=H, R³=OMe, R¹¹=H, R¹²=H], [1431; Q=$Q^{q2}$, A¹=H, A²=H, A³=F, A⁴=H, R³=OMe, R¹¹=H, R¹²=H], [1432; Q=$Q^{q2}$, A¹=H, A²=H, A³=F, A⁴=F, R³=OMe, R¹¹=H, R¹²=H], [1433; Q=$Q^{q2}$, A¹=H, A²=H, A³=Cl, A⁴=H, R³=OMe, R¹¹=H, R¹²=H], [1434; Q=$Q^{q2}$, A¹=H, A²=H, A³=Cl, A⁴=Cl, R³=OMe, R¹¹=H, R¹²=H], [1435; Q=$Q^{q2}$, A¹=H, A²=H, A³=Me, A⁴=H, R³=Me, R¹¹=H, R¹²=H], [1436; Q=$Q^{q2}$, A¹=H, A²=H, A³=Me, A⁴=Me, R³=Me, R¹¹=H, R¹²=H], [1437; Q=$Q^{q2}$, A¹=H, A²=H, A³=H, A⁴=H, R³=OCF₃, R¹¹=H, R¹²=H], [1438; Q=$Q^{q2}$, A¹=H, A²=H, A³=F, A⁴=H, R³=OCF₃, R¹¹=H, R¹²=H], [1439; Q=$Q^{q2}$, A¹=H, A²=H, A³=F, A⁴=F, R³=OCF₃, R¹¹=H, R¹²=H], [1440; Q=$Q^{q2}$, A¹=H, A²=H, A³=Cl, A⁴=H, R³=OCF₃, R¹¹=H, R¹²=H], [1441; Q=$Q^{q2}$, A¹=H, A²=H, A³=Cl, A⁴=Cl, R³=OCF₃, R¹¹=H, R¹²=H], [1442; Q=$Q^{q2}$, A¹=H, A²=H, A³=Me, A⁴=H, R³=OCF₃, R¹¹=H, R¹²=H], [1443; Q=$Q^{q2}$, A¹=H, A²=H, A³=Me, A⁴=Me, R³=OCF₃, R¹¹=H, R¹²=H], [1444; Q=$Q^{q2}$, A¹=H, A²=H, A³=H, A⁴=H, R³=SMe, R¹¹=H, R¹²=H], [1445; Q=$Q^{q2}$, A¹=H, A²=H, A³=F, A⁴=H, R³=SMe, R¹¹=H, R²=H], [1446; Q=$Q^{q2}$, A¹=H, A²=H, A³=F, A⁴=F, R³=SMe, R¹¹=H, R¹²=H], [1447; Q=$Q^{q2}$, A¹=H, A²=H, A³=Cl, A⁴=H, R³=SMe, R¹¹=H, R¹²=H], [1448; Q=$Q^{q2}$, A¹=H, A²=H, A³=Cl, A⁴=Cl, R³=SMe, R¹¹=H, R¹²=H], [1449; Q=$Q^{q2}$, A¹=H, A²=H, A³=Me, A⁴=H, R³=SMe, R¹¹=H, R¹²=H], [1450; Q=$Q^{q2}$, A¹=H, A²=H, A³=Me, A⁴=Me, R³=SMe, R¹¹=H, R¹²=H], [1451; Q=$Q^{q2}$, A¹=H, A²=H, A³=H, A⁴=H, R³=H, R¹¹=F, R¹²=H], [1452; Q=$Q^{q2}$, A¹=H, A²=H, A³=F, A⁴=H, R³=H, R¹=F, R¹²=H], [1453; Q=$Q^{q2}$, A¹=H, A²=H, A³=F, A⁴=F, R³=H, R¹¹=F, R¹²=H], [1454; Q=$Q^{q2}$, A¹=H, A²=H, A³=Cl, A⁴=H, R³=H, R¹¹=F, R¹²=H], [1455; Q=$Q^{q2}$, A¹=H, A²=H, A³=Cl, A⁴=Cl, R³=H, R¹¹=F, R¹²=H], [1456; Q=$Q^{q2}$, A¹=H, A²=H, A³=Me, A⁴=H, R³=H, R¹¹=F, R¹²=H], [1457; Q=$Q^{q1}2$, A¹=H, A²=H, A³=Me, A⁴=Me, R³=H, R¹¹=F, R¹²=H], [1458; Q=$Q^{q2}$, A¹=H, A²=H, A³=H, A⁴=H, R³=H, R¹¹=Cl, R¹²=H], [1459; Q=$Q^{q2}$, A¹=H, A²=H, A³=F, A⁴=H, R³=H, R¹¹=Cl, R¹²=H], [1460; Q=$Q^{q2}$, A¹=H, A²=H, A³=F, A⁴=F, R³=H, R¹¹=Cl, R¹²=H], [1461; Q=$Q^{q2}$, A¹=H, A²=H, A³=Cl, A⁴=H, R³=H, R¹¹=Cl, R¹²=H], [1462; Q=$Q^{q2}$, A¹=H, A²=H, A³=Cl, A⁴=Cl, R³=H, R¹¹=Cl, R¹²=H], [1463; Q=$Q^{q2}$, A¹=H, A²=H, A³=Me, A⁴=H, R³=H, R¹¹=Cl, R¹²=H], [1464; Q=$Q^{q2}$, A¹=H, A²=H, A³=Me, A⁴=Me, R³=H, R¹¹=Cl, R¹²=H], [1465; Q=$Q^{q2}$, A¹=H, A²=H, A³=H, A⁴=H, R³=H, R¹¹=Br, R¹²=H], [1466; Q=$Q^{q2}$, A¹=H, A²=H, A³=F, A⁴=H, R³=H, R¹¹=Br, R¹²=H], [1467; Q=$Q^{q2}$, A¹=H, A²=H, A³=F, A⁴=F, R³=H, R¹¹=Br, R¹²=H], [1468; Q=$Q^{q2}$, A¹=H, A²=H, A³=Cl, A⁴=H, R³=H, R¹¹=Br, R¹²=H], [1469; Q=$Q^{q2}$, A¹=H, A²=H, A³=Cl, A⁴=Cl, R³=H, R¹¹=Br, R¹²=H], [1470; Q=$Q^{q2}$, A¹=H, A²=H, A³=Me, A⁴=H, R³=H, R¹¹=Br, R¹²=H], [1471; Q=$Q^{q2}$, A¹=H, A²=H, A³=Me, A⁴=Me, R³=H, R¹¹=Br, R¹²=H], [1472; Q=$Q^{q2}$, A¹=H, A²=H, A³=H, A⁴=H, R³=H, R¹¹=Me, R¹²=H], [1473; Q=$Q^{q2}$, A¹=H, A²=H, A³=F, A⁴=H, R³=H, R¹¹=Me, R¹²=H], [1474; Q=$Q^{q2}$, A¹=H, A²=H, A³=F, A⁴=F, R³=H, R¹¹=Me, R¹²=H], [1475; Q=$Q^{q2}$, A¹=H, A²=H, A³=Cl, A⁴=H, R³=H, R¹¹=Me, R¹²=H][1476; Q=$Q^{q2}$, A¹=H, A²=H, A³=Cl, A⁴=Cl, R³=H, R¹¹=Me, R¹²=H], [1477; Q=$Q^{q2}$, A¹=H, A²=H, A³=Me, A⁴=H, R³=H, R¹¹=Me, R¹²=H], [1478; Q=$Q^{q2}$, A¹=H, A²=H, A³=Me, A⁴=Me, R³=H, R¹¹=Me, R¹²=H], [1479; Q=$Q^{q2}$, A¹=H, A²=H, A³=H, A⁴=H, R³=H, R¹¹=CF₃, R¹²=H], [1480; Q=$Q^{q2}$, A¹=H, A²=H, A³=F, A⁴=H, R³=H, R¹¹=CF₃, R¹²=H], [1481; Q=$Q^{q2}$, A¹=H, A²=H, A³=F, A⁴=F, R³=H, R¹¹=CF₃, R¹²=H], [1482; Q=$Q^{q2}$, A¹=H, A²=H, A³=Cl, A⁴=H, R³=H, R¹¹=CF₃, R¹²=H], [1483; Q=$Q^{q2}$, A¹=H, A²=H, A³=Cl, A⁴=Cl, R³=H, R¹¹=CF₃, R¹²=H], [1484; Q=$Q^{q2}$, A¹=H, A²=H, A³=Me, A⁴=H, R³=H, R¹¹=CF₃, R¹²=H], [1485; Q=$Q^{q2}$, A¹=H, A²=H, A³=Me, A⁴=Me, R³=H, R¹¹=CF₃, R¹²=H], [1486; Q=$Q^{q2}$, A¹=H, A²=H, A³=H, A⁴=H, R³=H, R¹¹=OMe, R¹²=H], [1487; Q=$Q^{q2}$, A¹=H, A²=H, A³=F, A⁴=H, R³=H, R¹¹=OMe, R¹²=H], [1488; Q=$Q^{q2}$, A¹=H, A²=H, A³=F, A⁴=F, R³=H, R¹¹=OMe, R¹²=H], [1489; Q=$Q^{q2}$, A¹=H, A²=H, A³=Cl, A⁴=H, R³=H, R¹¹=OMe, R¹²=H], [1490; Q=$Q^{q2}$, A¹=H, A²=H, A³=Cl, A⁴=Cl, R³=H, R¹¹=OMe, R¹²=H], [1491; Q=$Q^{q2}$, A¹=H, A²=H, A³=Me, A⁴=H, R³=H, R¹¹=OMe, R¹²=H], [1492; Q=$Q^{q2}$, A¹=H, A²=H, A³=Me, A⁴=Me, R³=H, R¹¹=OMe, R¹²=H], [1493; Q=$Q^{q2}$, A¹=H, A²=H, A³=H, A⁴=H, R³=H, R¹¹=OCF₃, R¹²=H], [1494; Q=$Q^{q2}$, A¹=H, A²=H, A³=F, A⁴=H, R³=H, R¹¹=OCF₃, R¹²=H], [1495; Q=$Q^{q2}$, A¹=H, A²=H, A³=F, A⁴=F, R³=H, R¹¹=OCF₃, R¹²=H], [1496; Q=$Q^{q2}$, A¹=H, A²=H, A³=Cl, A⁴=H, R³=H, R¹¹=OCF₃, R¹²=H], [1497; Q=$Q^{q2}$, A¹=H, A²=H, A³=Cl, A⁴=Cl, R³=H, R¹¹=OCF₃, R¹²=H], [1498; Q=$Q^{q2}$, A¹=H, A²=H, A³=Me, A⁴=H, R³=H, R¹¹=OCF₃, R¹²=H], [1499; Q=$Q^{q2}$, A¹=H, A²=H, A³=Me, A⁴=Me, R³=H, R¹¹=OCF₃, R¹²=H], [1500; Q=$Q^{q2}$, A¹=H, A²=H, A³=H, A⁴=H, R³=H, R¹¹=SMe, R¹²=H], [1501; Q=$Q^{q2}$, A¹=H, A²=H, A³=F, A⁴=H, R³=H, R¹¹=SMe, R¹²=H], [1502; Q=$Q^{q2}$, A¹=H, A²=H, A³=F, A⁴=F, R³=H, R¹¹=SMe, R¹²=H], [1503; Q=$Q^{q2}$, A¹=H, A²=H, A³=Cl, A⁴=H, R³=H, R¹¹=SMe, R¹²=H], [1504; Q=$Q^{q2}$, A¹=H, A²=H, A³=Cl, A⁴=Cl, R³=H, R¹¹=SMe, R¹²=H], [1505; Q=$Q^{q2}$, A¹=H, A²=H, A³=Me, A⁴=H, R³=H, R¹¹=SMe, R¹²=H], [1506; Q=$Q^{q2}$, A¹=H, A²=H, A³=Me, A⁴=Me, R³=H, R¹¹=SMe, R¹²=H], [1507; Q=$Q^{q3}$, A¹=H, A²=H, A³=H, A⁴=H, R³=H, R¹¹=H, R¹²=H], [1508; Q=$Q^{q3}$, A¹=H, A²=H, A³=F, A⁴=H, R³=H, R¹¹=H, R¹²=H], [1509; Q=$Q^{q3}$, A¹=H, A²=H, A³=F, A⁴=F, R³=H, R¹¹=H, R¹²=H], [1510; Q=$Q^{q3}$, A¹=H, A²=H, A³=Cl, A⁴=H, R³=H, R¹¹=H, R¹²=H], [1511; Q=$Q^{q3}$, A¹=H, A²=H, A³=Cl, A⁴=Cl, R³=H, R¹¹=H, R¹²=H], [1512; Q=$Q^{q3}$, A¹=H, A²=H, A³=Me, A⁴=H, R³=H, R¹¹=H, R¹²=H], [1513; Q=$Q^{q3}$, A¹=H, A²=H, A³=Me, A⁴=Me, R³=H, R¹¹=H, R¹²=H], [1514; Q=$Q^{q3}$, A¹=H, A²=H, A³=H, A⁴=H, R³=F, R¹¹=H, R¹²=H], [1515; Q=$Q^{q3}$, A¹=H, A²=H, A³=F, A⁴=H, R³=F, R¹¹=H, R¹²=H], [1516; Q=$Q^{q3}$, A¹=H, A²=H, A³=F, A⁴=F, R³=F, R¹¹=H, R¹²=H], [1517; Q=$Q^{v3}$, A¹=H, A²=H, A³=Cl, A⁴=H, R³=F, R¹¹=H, R¹²=H], [1518; Q=$Q^{q3}$, A¹=H, A²=H, A³=Cl, A⁴=Cl, R³=F, R¹¹=H, R¹²=H], [1519; Q=$Q^{q3}$, A¹=H, A²=H, A³=Me, A⁴=H, R³=F, R¹¹=H, R¹²=H], [1520; Q=$Q^{q3}$, A¹=H, A²=H, A³=Me, A⁴=Me, R³=F, R¹¹=H, R¹²=H], [1521; Q=$Q^{q3}$, A¹=H, A²=H, A³=H, A⁴=H, R³=Cl, R¹¹=H, R¹²=H], [1522; Q=$Q^{q3}$, A¹=H, A²=H, A³=F, A⁴=H, R³=Cl, R¹¹=H, R¹²=H], [1523; Q=$Q^{q3}$, A¹=H, A²=H, A³=F, A⁴=F, R³=Cl, R¹¹=H, R¹²=H], [1524; Q=$Q^{q3}$, A¹=H, A²=H, A³=Cl, A⁴=H, R³=Cl, R¹¹=H, R¹²=H], [1525; Q=$Q^{q3}$, A¹=H, A²=H, A³=Cl, A⁴=Cl, R³=Cl, R¹¹=H, R¹²=H], [1526; Q=$Q^{q3}$, A¹=H, A²=H, A³=Me, A⁴=H, R³=Cl, R¹¹=H, R¹²=H], [1527; Q=$Q^{q1}3$, A¹=H, A²=H, A³=Me, A⁴=Me, R³=Cl, R¹¹=H, R¹²=H], [1528; Q=$Q^{q3}$, A¹=H, A²=H, A³=H, A⁴=H, R³=Br, R¹¹=H, R¹²=H], [1529; Q=$Q^{q3}$, A¹=H, A²=H, A³=F, A⁴=H, R³=Br, R¹¹=H, R¹²=H], [1530; Q=$Q^{q3}$, A¹=H, A²=H, A³=F, A⁴=F, R³=Br, R¹¹=H, R¹²=H], [1531; Q=$Q^{q3}$, A¹=H, A²=H, A³=Cl, A⁴=H, R³=Br, R¹¹=H, R¹²=H], [1532; Q=$Q^{q3}$, A¹=H, A²=H, A³=Cl, A⁴=Cl, R³=Br, R¹¹=H, R¹²=H], [1533; Q=$Q^{q3}$, A¹=H, A²=H, A³=Me, A⁴=H, R³=Br, R¹¹=H, R¹²=H], [1534; Q=$Q^{q3}$, A¹=H, A²=H, A³=Me, A⁴=Me, $R^3$=Br, $R^{11}$=H, $R^{12}$=H], [1535; Q=$Q^{q3}$, $A^1$=H, $A^2$=H, $A^3$=H, $A^4$=H, $R^3$=Me, $R^{11}$=H, $R^{12}$=H], [1536; Q=$Q^{q1}$, $A^1$=H, $A^2$=H, $A^3$=F, $A^4$=H, $R^3$=Me, $R^{11}$=H, $R^{12}$=H], [1537; Q=$Q^{q1}$, $A^1$=H, $A^2$=H, $A^3$=F, $A^4$=F, $R^3$=Me, $R^{11}$=H, $R^{12}$=H], [1538; Q=$Q^{q3}$, $A^1$=H, $A^2$=H, $A^3$=Cl, $A^4$=H, $R^3$=Me, $R^{11}$=H, $R^{12}$=H], [1539; Q=$Q^{q3}$, $A^1$=H, $A^2$=H, $A^3$=Cl, $A^4$=Cl, $R^3$=Me, $R^{11}$=H, $R^{12}$=H], [1540; Q=$Q^{q3}$, $A^1$=H, $A^2$=H, $A^3$=Me, $A^4$=H, $R^3$=Me, $R^{11}$=H, $R^{12}$=H], [1541; Q=$Q^{q1}$3, $A^1$=H, $A^2$=H, $A^3$=Me, $A^4$=Me, $R^3$=Me, $R^{11}$=H, $R^{12}$=H] [1542; Q=$Q^{q3}$, $A^1$=H, $A^2$=H, $A^3$=H, $A^4$=H, $R^3$=$CF_3$, $R^{11}$=H, $R^{12}$=H], [1543; Q=$Q^{p3}$, $A^1$=H, $A^2$=H, $A^3$=F, $A^4$=H, $R^3$=$CF_3$, $R^{11}$=H, $R^{12}$=H], [1544; Q=$Q^{q1}$3, $A^1$=H, $A^2$=H, $A^3$=F, $A^4$=F, $R^3$=$CF_3$, $R^{11}$=H, $R^{12}$=H], [1545; Q=$Q^{q3}$, $A^1$=H, $A^2$=H, $A^3$=Cl, $A^4$=H, $R^3$=$CF_3$, $R^{11}$=H, $R^{12}$=H], [1546; Q=$Q^{q1}$3, $A^1$=H, $A^2$=H, $A^3$=Cl, $A^4$=Cl, $R^3$=$CF_3$, $R^{11}$=H, $R^{12}$=H], [1547; Q=$Q^{q3}$, $A^1$=H, $A^2$=H, $A^3$=Me, $A^4$=H, $R^3$=$CF_3$, $R^{11}$=H, $R^{12}$=H], [1548; Q=$Q^{q3}$, $A^1$=H, $A^2$=H, $A^3$=Me, $A^4$=Me, $R^3$=$CF_3$, $R^{11}$=H, $R^{12}$=H], [1549; Q=$Q^{q3}$, $A^1$=H, $A^2$=H, $A^3$=H, $A^4$=H, $R^3$=OMe, $R^{11}$=H, $R^{12}$=H], [1550; Q=$Q^{q3}$, $A^1$=H, $A^2$=H, $A^3$=F, $A^4$=H, $R^3$=OMe, $R^{11}$=H, $R^{12}$=H], [1551; Q=$Q^{q3}$, $A^1$=H, $A^2$=H, $A^3$=F, $A^4$=F, $R^3$=OMe, $R^{11}$=H, $R^{12}$=H], [1552; Q=$Q^{q3}$, $A^1$=H, $A^2$=H, $A^3$=Cl, $A^4$=H, $R^3$=OMe, $R^{11}$=H, $R^{12}$=H], [1553; Q=$Q^{q1}$3, $A^1$=H, $A^2$=H, $A^3$=Cl, $A^4$=C%, $R^3$=OMe, $R^{11}$=H, $R^{12}$=H], [1554; Q=$Q^{q3}$, $A^1$=H, $A^2$=H, $A^3$=Me, $A^4$=H, $R^3$=OMe, $R^{11}$=H, $R^{12}$=H], [1555; Q=$Q^{q3}$, $A^1$=H, $A^2$=H, $A^3$=Me, $A^4$=Me, $R^3$=OMe, $R^{11}$=H, $R^{12}$=H], [1556; Q=$Q^{q3}$, $A^1$=H, $A^2$=H, $A^3$=H, $A^4$=H, $R^3$=$OCF_3$, $R^{11}$=H, $R^{12}$=H], [1557; Q=$Q^{q1}$3, $A^1$=H, $A^2$=H, $A^3$=F, $A^4$=H, $R^3$=$OCF_3$, $R^{11}$=H, $R^{12}$=H], [1558; Q=$Q^{q3}$, $A^1$=H, $A^2$=H, $A^3$=F, $A^4$=F, $R^3$=$OCF_3$, $R^{11}$=H, $R^{12}$=H], [1559; Q=$Q^{q3}$, $A^1$=H, $A^2$=H, $A^3$=Cl, $A^4$=H, $R^3$=$OCF_3$, $R^{11}$=H, $R^{12}$=H], [1560; Q=$Q^{q3}$, $A^1$=H, $A^2$=H, $A^3$=Cl, $A^4$=Cl, $R^3$=$OCF_3$, $R^{11}$=H, $R^{12}$=H], [1561; Q=$Q^{q3}$, $A^1$=H, $A^2$=H, $A^3$=Me, $A^4$=H, $R^3$=$OCF_3$, $R^{11}$=H, $R^{12}$=H], [1562; Q=$Q^{q3}$, $A^1$=H, $A^2$=H, $A^3$=Me, $A^4$=Me, $R^3$=$OCF_3$, $R^{11}$=H, $R^{12}$=H], [1563; Q=$Q^{q3}$, $A^1$=H, $A^2$=H, $A^3$=H, $A^4$=H, $R^3$=SMe, $R^{11}$=H, $R^{12}$=H], [1564; Q=$Q^{q3}$, $A^1$=H, $A^2$=H, $A^3$=F, $A^4$=H, $R^3$=SMe, $R^{11}$=H, $R^{12}$=H], [1565; Q=$Q^{q3}$, $A^1$=H, $A^2$=H, $A^3$=F, $A^4$=F, $R^3$=SMe, $R^{11}$=H, $R^{12}$=H], [1566; Q=$Q^{q3}$, $A^1$=H, $A^2$=H, $A^3$=Cl, $A^4$=H, $R^3$=SMe, $R^{11}$=H, $R^{12}$=H], [1567; Q=$Q^{q3}$, $A^1$=H, $A^2$=H, $A^3$=Cl, $A^4$=Cl, $R^3$=SMe, $R^{11}$=H, $R^{12}$=H], [1568; Q=$Q^{q3}$, $A^1$=H, $A^2$=H, $A^3$=Me, $A^4$=H, $R^3$=SMe, $R^{11}$=H, $R^{12}$=H], [1569; Q=$Q^{q3}$, $A^1$=H, $A^2$=H, $A^3$=Me, $A^4$=Me, $R^3$=SMe, $R^{11}$=H, $R^{12}$=H], [1570; Q=$Q^{q3}$, $A^1$=H, $A^2$=H, $A^3$=H, $A^4$=H, $R^3$=H, $R^{11}$=F, $R^{12}$=H], [1571; Q=$Q^{q3}$, $A^1$=H, $A^2$=H, $A^3$=F, $A^4$=H, $R^3$=H, $R^{11}$=F, $R^{12}$=H], [1572; Q=$Q^{q3}$, $A^1$=H, $A^2$=H, $A^3$=F, $A^4$=F, $R^3$=H, $R^{11}$=F, $R^{12}$=H], [1573; Q=$Q^{q3}$, $A^1$=H, $A^2$=H, $A^3$=Cl, $A^4$=H, $R^3$=H, $R^1$=F, $R^{12}$=H], [1574; Q=$Q^{q3}$, $A^1$=H, $A^2$=H, $A^3$=Cl, $A^4$=Cl, $R^3$=H, $R^{11}$=F, $R^{12}$=H], [1575; Q=$Q^{q3}$, $A^1$=H, $A^2$=H, $A^3$=Me, $A^4$=H, $R^3$=H, $R^{11}$=F, $R^{12}$=H], [1576; Q=$Q^{q3}$, $A^1$=H, $A^2$=H, $A^3$=Me, $A^4$=Me, $R^3$=H, $R^{11}$=F, $R^2$=H], [1577; Q=$Q^{q3}$, $A^1$=H, $A^2$=H, $A^3$=H, $A^4$=H, $R^3$=H, $R^{11}$=Cl, $R^{12}$=H], [1578; Q=$Q^{q3}$, $A^1$=H, $A^2$=H, $A^3$=F, $A^4$=H, $R^3$=H, $R^{11}$=Cl, $R^{12}$=H], [1579; Q=$Q^{q3}$, $A^1$=H, $A^2$=H, $A^3$=F, $A^4$=F, $R^3$=H, $R^{11}$=Cl, $R^{12}$=H], [1580; Q=$Q^{q3}$, $A^1$=H, $A^2$=H, $A^3$=Cl, $A^4$=H, $R^3$=H, $R^{11}$=Cl, $R^{12}$=H], [1581; Q=$Q^{q3}$, $A^1$=H, $A^2$=H, $A^3$=Cl, $A^4$=Cl, $R^3$=H, $R^{11}$=Cl, $R^{12}$=H], [1582; Q=$Q^{q3}$, $A^1$=H, $A^2$=H, $A^3$=Me, $A^4$=H, $R^3$=H, $R^{11}$=Cl, $R^{12}$=H], [1583; Q=$Q^{q3}$, $A^1$=H, $A^2$=H, $A^3$=Me, $A^4$=Me, $R^3$=H, $R^{11}$=Cl, $R^{12}$=H], [1584; Q=$Q^{q3}$, $A^1$=H, $A^2$=H, $A^3$=H, $A^4$=H, $R^3$=H, $R^{11}$=Br, $R^{12}$=H], [1585; Q=$Q^{q3}$, $A^1$=H, $A^2$=H, $A^3$=F, $A^4$=H, $R^3$=H, $R^{11}$=Br, $R^{12}$=H], [1586; Q=$Q^{q3}$, $A^1$=H, $A^2$=H, $A^3$=F, $A^4$=F, $R^3$=H, $R^{11}$=Br, $R^{12}$=H], [1587; Q=$Q^{q3}$, $A^1$=H, $A^2$=H, $A^3$=Cl, $A^4$=H, $R^3$=H, $R^{11}$=Br, $R^{12}$=H], [1588; Q=$Q^{q3}$, $A^1$=H, $A^2$=H, $A^3$=Cl, $A^4$=Cl, $R^3$=H, $R^{11}$=Br, $R^{12}$=H], [1589; Q=$Q^{q3}$, $A^1$=H, $A^2$=H, $A^3$=Me, $A^4$=H, $R^3$=H, $R^{11}$=Br, $R^{12}$=H], [1590; Q=$Q^{q3}$, $A^1$=H, $A^2$=H, $A^3$=Me, $A^4$=Me, $R^3$=H, $R^{11}$=Br, $R^{12}$=H], [1591; Q=$Q^{q3}$, $A^1$=H, $A^2$=H, $A^3$=H, $A^4$=H, $R^3$=H, $R^{11}$=Me, $R^{12}$=H], [1592; Q=$Q^{q3}$, $A^1$=H, $A^2$=H, $A^3$=F, $A^4$=H, $R^3$=H, $R^{11}$=Me, $R^{12}$=H], [1593; Q=$Q^{q3}$, $A^1$=H, $A^2$=H, $A^3$=F, $A^4$=F, $R^3$=H, $R^{11}$=Me, $R^{12}$=H], [1594; Q=$Q^{q3}$, $A^1$=H, $A^2$=H, $A^3$=Cl, $A^4$=H, $R^3$=H, $R^{11}$=Me, $R^{12}$=H], [1595; Q=$Q^{q3}$, $A^1$=H, $A^2$=H, $A^3$=Cl, $A^4$=Cl, $R^3$=H, $R^{11}$=Me, $R^{12}$=H], [1596; Q=$Q^{q3}$, $A^1$=H, $A^2$=H, $A^3$=Me, $A^4$=H, $R^3$=H, $R^{11}$=Me, $R^{12}$=H][1597; Q=$Q^{q3}$, $A^1$=H, $A^2$=H, $A^3$=Me, $A^4$=Me, $R^3$=H, R=Me, $R^{12}$=H], [1598; Q=$Q^{q3}$, $A^1$=H, $A^2$=H, $A^3$=H, $A^4$=H, $R^3$=H, $R^{11}$=$CF_3$, $R^{12}$=H], [1599; Q=$Q^{q3}$, $A^1$=H, $A^2$=H, $A^3$=F, $A^4$=H, $R^3$=H, $R^{11}$=$CF_3$, $R^{12}$=H], [1600; Q=$Q^{q3}$, $A^1$=H, $A^2$=H, $A^3$=F, $A^4$=F, $R^3$=H, $R^{11}$=$CF_3$, $R^{12}$=H], [1601; Q=$Q^{q1}$3, $A^1$=H, $A^2$=H, $A^3$=Cl, $A^4$=H, $R^3$=H, $R^{11}$=$CF_3$, $R^{12}$=H], [1602; Q=$Q^{q1}$3, $A^1$=H, $A^2$=H, $A^3$=Cl, $A^4$=Cl, $R^3$=H, $R^{11}$=$CF_3$, $R^{12}$=H], [1603; Q=$Q^{q3}$, $A^1$=H, $A^2$=H, $A^3$=Me, $A^4$=H, $R^3$=H, $R^{11}$=$CF_3$, $R^{12}$=H], [1604; Q=$Q^{q3}$, $A^1$=H, $A^2$=H, $A^3$=Me, $A^4$=Me, $R^3$=H, $R^{11}$=$CF_3$, $R^{12}$=H], [1605; Q=$Q^{q3}$, $A^1$=H, $A^2$=H, $A^3$=H, $A^4$=H, $R^3$=H, $R^{11}$=OMe, $R^{12}$=H], [1606; Q=$Q^{q3}$, $A^1$=H, $A^2$=H, $A^3$=F, $A^4$=H, $R^3$=H, $R^{11}$=OMe, $R^{12}$=H], [1607; Q=$Q^{q3}$, $A^1$=H, $A^2$=H, $A^3$=F, $A^4$=F, $R^3$=H, $R^{11}$=OMe, $R^{12}$=H], [1608; Q=$Q^{q3}$, $A^1$=H, $A^2$=H, $A^3$=Cl, $A^4$=H, $R^3$=H, $R^{11}$=OMe, $R^{12}$=H], [1609; Q=$Q^{q3}$, $A^1$=H, $A^2$=H, $A^3$=Cl, $A^4$=Cl, $R^3$=H, $R^{11}$=OMe, $R^{12}$=H], [1610; Q=$Q^{q3}$, $A^1$=H, $A^2$=H, $A^3$=Me, $A^4$=H, $R^3$=H, $R^{11}$=OMe, $R^{12}$=H], [1611; Q=$Q^{q3}$, $A^1$=H, $A^2$=H, $A^3$=Me, $A^4$=Me, $R^3$=H, $R^{11}$=OMe, $R^{12}$=H], [1612; Q=$Q^{q3}$, $A^1$=H, $A^2$=H, $A^3$=H, $A^4$=H, $R^3$=H, $R^{11}$=$OCF_3$, $R^{12}$=H], [1613; Q=$Q^{q3}$, $A^1$=H, $A^2$=H, $A^3$=F, $A^4$=H, $R^3$=H, $R^{11}$=$OCF_3$, $R^{12}$=H], [1614; Q=$Q^{q3}$, $A^1$=H, $A^2$=H, $A^3$=F, $A^4$=F, $R^3$=H, $R^{11}$=$OCF_3$, $R^{12}$=H], [1615; Q=$Q^{q3}$, $A^1$=H, $A^2$=H, $A^3$=Cl, $A^4$=H, $R^3$=H, $R^{11}$=$OCF_3$, $R^{12}$=H], [1616; Q=$Q^{q3}$, $A^1$=H, $A^2$=H, $A^3$=Cl, $A^4$=Cl, $R^3$=H, $R^{11}$=$OCF_3$, $R^{12}$=H], [1617; Q=$Q^{q1}$, $A^1$=H, $A^2$=H, $A^3$=Me, $A^4$=H, $R^3$=H, $R^{11}$=$OCF_3$, $R^{12}$=H], [1618; Q=$Q^{q1}$3, $A^1$=H, $A^2$=H, $A^3$=Me, $A^4$=Me, $R^3$=H, $R^{11}$=$OCF_3$, $R^{12}$=H], [1619; Q=$Q^{q3}$, $A^1$=H, $A^2$=H, $A^3$=H, $A^4$=H, $R^3$=H, $R^{11}$=SMe, $R^{12}$=H], [1620; Q=$Q^{q3}$, $A^1$=H, $A^2$=H, $A^3$=F, $A^4$=H, $R^3$=H, $R^{11}$=SMe, $R^{12}$=H], [1621; Q=$Q^{q3}$, $A^1$=H, $A^2$=H, $A^3$=F, $A^4$=F, $R^3$=H, $R^{11}$=SMe, $R^{12}$=H], [1622; Q=$Q^{q3}$, $A^1$=H, $A^2$=H, $A^3$=Cl, $A^4$=H, $R^3$=H, $R^{11}$=SMe, $R^{12}$=H], [1623; Q=$Q^{q3}$, $A^1$=H, $A^2$=H, $A^3$=Cl, $A^4$=Cl, $R^3$=H, $R^{11}$=SMe, $R^{12}$=H], [1624; Q=$Q^{q3}$, $A^1$=H, $A^2$=H, $A^3$=Me, $A^4$=H, $R^3$=H, $R^{11}$=SMe, $R^{12}$=H], [1625; Q=$Q^{q1}$3, $A^1$=H, $A^2$=H, $A^3$=Me, $A^4$=Me, $R^3$=H, $R^{11}$=SMe, $R^{12}$=H], [1626; Q=$Q^{q1}$, $A^1$=H, $A^2$=H, $A^3$=H, $A^4$=H, $A^7$=Me, $R^3$=H, $R^{11}$=H, $R^{12}$=H], [1627; Q=$Q^{q1}$, $A^1$=H, $A^2$=H, $A^3$=F, $A^4$=H, $A^7$=Me, $R^3$=H, $R^{11}$=H, $R^{12}$=H], [1628; Q=$Q^{q4}$, $A^1$=H, $A^2$=H, $A^3$=F, $A^4$=F, $A^7$=Me, $R^3$=H, $R^{11}$=H, $R^{12}$=H], [1629; Q=$Q^{q4}$, $A^1$=H, $A^2$=H, $A^3$=Cl, $A^4$=H, $A^7$=Me, $R^3$=H, $R^{11}$=H, $R^{12}$=H], [1630; Q=$Q^{q4}$, $A^1$=H, $A^2$=H, $A^3$=Cl, $A^4$=Cl, $A^7$=Me, $R^3$=H, $R^{11}$=H, $R^{12}$=H], [1631; Q=$Q^{q4}$, $A^1$=H, $A^2$=H, $A^3$=Me, $A^4$=H, $A^7$=Me, $R^3$=H, $R^{11}$=H, $R^{12}$=H], [1632; Q=$Q^{q4}$, $A^1$=H, $A^2$=H, $A^3$=Me, $A^4$=Me, $A^7$=Me, $R^3$=H, $R^{11}$=H, $R^{12}$=H], [1633; Q=$Q^{q4}$, $A^1$=H, $A^2$=H, $A^3$=H, $A^4$=H, $A^7$=Et, $R^3$=H, $R^{11}$=H, $R^{12}$=H], [1634; Q=$Q^{q4}$, $A^1$=H, $A^2$=H, $A^3$=F, $A^4$=H, $A^7$=Et, $R^3$=H, $R^{11}$=H, $R^{12}$=H], [1635; Q=$Q^{q4}$, $A^1$=H, $A^2$=H, $A^3$=F, $A^4$=F, $A^7$=Et, $R^3$=H, $R^{11}$=H, $R^{12}$=H], [1636; Q=$Q^{q1}$, $A^1$=H, $A^2$=H, $A^3$=Cl, $A^4$=H, $A^7$=Et, $R^3$=H, $R^{11}$=H, $R^{12}$=H], [1637; Q=$Q^{q1}$, $A^1$=H, $A^2$=H, $A^3$=Cl, $A^4$=Cl, $A^7$=Et, $R^3$=H, $R^{11}$=H, $R^{12}$=H], [1638; Q=$Q^{q4}$, $A^1$=H, $A^2$=H, $A^3$=Me, $A^4$=H, $A^7$=Et, $R^3$=H, $R^{11}$=H, $R^{12}$=H], [1639; Q=$Q^{q4}$, $A^1$=H, $A^2$=H, $A^3$=Me, $A^4$=Me, $A^7$=Et, $R^3$=H, $R^{11}$=H, $R^{12}$=H], [1640; Q=$Q^{q4}$, $A^1$=H, $A^2$=H, $A^3$=H, $A^4$=H, $A^7$=cyclopropyl, $R^3$=H, $R^{11}$=H, $R^{12}$=H], [1641; Q=$Q^{q1}$, $A^1$=H, $A^2$=H, $A^3$=F, $A^4$=H, $A^7$=cyclopropyl, $R^3$=H, $R^{11}$=H, $R^{12}$=H], [1642;

Q=Q$^{q4}$, A$^1$=H, A$^2$=H, A$^3$=F, A$^4$=F, A$^7$=cyclopropyl, R$^3$=H, R$^{11}$=H, R$^{12}$=H], [1643; Q=Q$^{q4}$, A$^1$=H, A$^2$=H, A$^3$=Cl, A$^4$=H, A$^7$=cyclopropyl, R$^3$=H, R$^{11}$=H, R$^{12}$=H], [1644; Q=Q$^{q4}$, A$^1$=H, A$^2$=H, A$^3$=Cl, A$^4$=Cl, A$^7$=cyclopropyl, R$^3$=H, R$^{11}$=H, R$^{12}$=H], [1645; Q=Q$^4$, A$^1$=H, A$^2$=H, A$^3$=Me, A$^4$=H, A$^7$=cyclopropyl, R$^3$=H, R$^{11}$=H, R$^{12}$=H], [1646; Q=Q$^{q4}$, A$^1$=H, A$^2$=H, A$^3$=Me, A$^4$=Me, A$^7$=cyclopropyl, R$^3$=H, R$^{11}$=H, R$^{12}$=H], [1647; Q=Q$^{q4}$, A$^1$=H, A$^2$=H, A$^3$=H, A$^4$=H, A$^7$=Me, R$^3$=F, R$^{11}$=H, R$^{12}$=H], [1648; Q=Q$^{q4}$, A$^1$=H, A$^2$=H, A$^3$=F, A$^4$=H, A$^7$=Me, R$^3$=F, R$^{11}$=H, R$^{12}$=H], [1649; Q=Q$^{q4}$, A$^1$=H, A$^2$=H, A$^3$=F, A$^4$=F, A$^7$=Me, R$^3$=F, R$^{11}$=H, R$^{12}$=H], [1650; Q=Q$^{q4}$, A$^1$=H, A$^2$=H, A$^3$=Cl, A$^4$=H, A$^7$=Me, R$^3$=F, R$^{11}$=H, R$^{12}$=H], [1651; Q=Q$^{q4}$, A$^1$=H, A$^2$=H, A$^3$=Cl, A$^4$=Cl, A$^7$=Me, R$^3$=F, R$^{11}$=H, R$^{12}$=H], [1652; Q=Q$^{q4}$, A$^1$=H, A$^2$=H, A$^3$=Me, A$^4$=H, A$^7$=Me, R$^3$=F, R$^{11}$=H, R$^{12}$=H], [1653; Q=Q$^{q5}$, A$^1$=H, A$^2$=H, A$^3$=Me, A$^4$=Me, A$^7$=Me, R$^3$=F, R$^{11}$=H, R$^{12}$=H], [1654; Q=Q$^{q4}$, A$^1$=H, A$^2$=H, A$^3$=H, A$^4$=H, A$^7$=Et, R$^3$=F, R$^{11}$=H, R$^{12}$=H], [1655; Q=Q$^{q4}$, A$^1$=H, A$^2$=H, A$^3$=F, A$^4$=H, A$^7$=Et, R$^3$=F, R$^{11}$=H, R$^{12}$=H], [1656; Q=Q$^{q4}$, A$^1$=H, A$^2$=H, A$^3$=F, A$^4$=F, A$^7$=Et, R$^3$=F, R$^{11}$=H, R$^{12}$=H], [1657; Q=Q$^{q4}$, A$^1$=H, A$^2$=H, A$^3$=Cl, A$^4$=H, A$^7$=Et, R$^3$=F, R$^{11}$=H, R$^{12}$=H], [1658; Q=Q$^{q4}$, A$^1$=H, A$^2$=H, A$^3$=C, A$^4$=Cl, A$^7$=Et, R$^3$=F, R$^{11}$=H, R$^{12}$=H], [1659; Q=Q$^{q4}$, A$^1$=H, A$^2$=H, A$^3$=Me, A$^4$=H, A$^7$=Et, R$^3$=F, R$^{11}$=H, R$^{12}$=H], [1660; Q=Q$^{q4}$, A$^1$=H, A$^2$=H, A$^3$=Me, A$^4$=Me, A$^7$=Et, R$^3$=F, R$^{11}$=H, R$^{12}$=H], [1661; Q=Q$^{q4}$, A$^1$=H, A$^2$=H, A$^3$=H, A$^4$=H, A$^7$=Me, R$^3$=Cl, R$^{11}$=H, R$^{12}$=H], [1662; Q=Q$^{q4}$, A$^1$=H, A$^2$=H, A$^3$=F, A$^4$=H, A$^7$=Me, R$^3$=Cl, R$^{11}$=H, R$^{12}$=H], [1663; Q=Q$^{q4}$, A$^1$H, A$^2$=H, A$^3$=F, A$^4$=F, A$^7$=Me, R$^3$=Cl, R$^{11}$=H, R$^{12}$=H], [1664; Q=Q$^{q4}$, A$^1$=H, A$^2$=H, A$^3$=Cl, A$^4$=H, A$^7$=Me, R$^3$=Cl, R$^{11}$=H, R$^{12}$=H], [1665; Q=Q$^{q4}$, A$^1$=H, A$^2$=H, A$^3$=Cl, A$^4$=Cl, A$^7$=Me, R$^3$=C, R$^{11}$=H, R$^{12}$=H], [1666; Q=Q$^{q4}$, A$^1$=H, A$^2$=H, A$^3$=Me, A$^4$=H, A$^7$=Me, R$^3$=Cl, R$^{11}$=H, R$^{12}$=H], [1667; Q=Q$^{q4}$, A$^1$=H, A$^2$=H, A$^3$=Me, A$^4$=Me, A$^7$=Me, R$^3$=Cl, R$^{11}$=H, R$^{12}$=H], [1668; Q=Q$^{q4}$, A$^1$=H, A$^2$=H, A$^3$=H, A$^4$=H, A$^7$=Et, R$^3$=Cl, R$^{11}$=H, R$^{12}$=H], [1669; Q=Q$^{q4}$, A$^1$=H, A$^2$=H, A$^3$=F, A$^4$=H, A$^7$=Et, R$^3$=Cl, R$^{11}$=H, R$^{12}$=H], [1670; Q=Q$^{q4}$, A$^1$=H, A$^2$=H, A$^3$=F, A$^4$=F, A$^7$=Et, R$^3$=Cl, R$^{11}$=H, R$^{12}$=H], [1671; Q=Q$^{q4}$, A$^1$=H, A$^2$=H, A$^3$=Cl, A$^4$=H, A$^7$=Et, R$^3$=Cl, R$^{11}$=H, R$^{12}$=H], [1672; Q=Q$^{q4}$, A$^1$=H, A$^2$=H, A$^3$=Cl, A$^4$=Cl, A$^7$=Et, R$^3$=Cl, R$^{11}$=H, R$^{12}$=H], [1673; Q=Q$^{q4}$, A$^1$=H, A$^2$=H, A$^3$=Me, A$^4$=H, A$^7$=Et, R$^3$=Cl, R$^{11}$=H, R$^{12}$=H], [1674; Q=Q$^{q4}$, A$^1$=H, A$^2$=H, A$^3$=Me, A$^4$=Me, A$^7$=Et, R$^3$=Cl, R$^{11}$=H, R$^{12}$=H], [1675; Q=Q$^{q4}$, A$^1$=H, A$^2$=H, A$^3$=H, A$^4$=H, A$^7$=Me, R$^3$=Me, R$^{11}$=H, R$^{12}$=H], [1676; Q=Q$^{q4}$, A$^1$=H, A$^2$=H, A$^3$=F, A$^4$=H, A$^7$=Me, R$^3$=Me, R$^{11}$=H, R$^{12}$=H], [1677; Q=Q$^{q4}$, A$^1$=H, A$^2$=H, A$^3$=F, A$^4$=F, A$^7$=Me, R=Me, R$^{11}$=H, R$^{12}$=H], [1678; Q=Q$^{q4}$, A$^1$=H, A$^2$=H, A$^3$=Cl, A$^4$=H, A$^7$=Me, R$^3$=Me, R$^{11}$=H, R$^{12}$=H], [1679; Q=Q$^{q4}$, A$^1$=H, A$^2$=H, A$^3$=C, A$^4$=Cl, A$^7$=Me, R$^3$=Me, R$^{11}$=H, R$^{12}$=H], [1680; Q=Q$^{q4}$, A$^1$=H, A$^2$=H, A$^3$=Me, A$^4$=H, A$^7$=Me, R$^3$=Me, R$^{11}$=H, R$^{12}$=H], [1681; Q=Q$^{q4}$, A$^1$=H, A$^2$=H, A$^3$=Me, A$^4$=Me, A$^7$=Me, R$^3$=Me, R$^{11}$=H, R$^{12}$=H], [1682; Q=Q$^{q4}$, A$^1$=H, A$^2$=H, A$^3$=H, A$^4$=H, A$^7$=Et, R=Me, R$^{11}$=H, R$^{12}$=H], [1683; Q=Q$^{q4}$, A$^1$=H, A$^2$=H, A$^3$=F, A$^4$=H, A$^7$=Et, R$^3$=Me, R$^{11}$=H, R$^{12}$=H], [1684; Q=Q$^{q4}$, A$^1$=H, A$^2$=H, A$^3$=F, A$^4$=F, A$^7$=Et, R$^3$=Me, R$^{11}$=H, R$^{12}$=H], [1685; Q=Q$^{q4}$, A$^1$=H, A$^2$=H, A$^3$=Cl, A$^4$=H, A$^7$=Et, R$^3$=Me, R$^{11}$=H, R$^{12}$=H], [1686; Q=Q$^{q4}$, A$^1$=H, A$^2$=H, A$^3$=Cl, A$^4$=Cl, A$^7$=Et, R$^3$=Me, R$^{11}$=H, R$^{12}$=H], [1687; Q=Q$^{q4}$, A$^1$=H, A$^2$=H, A$^3$=Me, A$^4$=H, A$^7$=Et, R$^3$=Me, R$^{11}$=H, R$^{12}$=H], [1688; Q=Q$^{q4}$, A$^1$=H, A$^2$=H, A$^3$=Me, A$^4$=Me, A$^7$=Et, R$^3$=Me, R$^{11}$=H, R$^{12}$=H], [1689; Q=Q$^{q4}$, A$^1$=H, A$^2$=H, A$^3$=H, A$^4$=H, A$^7$=Me, R$^3$=CF$_3$, R$^{11}$=H, R$^{12}$=H], [1690; Q=Q$^{q4}$, A$^1$=H, A$^2$=H, A$^3$=F, A$^4$=H, A$^7$=Me, R$^3$=CF$_3$, R$^{11}$=H, R$^{12}$=H], [1691; Q=Q$^{q4}$, A$^1$=H, A$^2$=H, A$^3$=F, A$^4$=F, A$^7$=Me, R$^3$=CF$_3$, R$^{11}$=H, R$^{12}$=H], [1692; Q=Q$^{q4}$, A$^5$=H, A$^2$=H, A$^3$=Cl, A$^4$=H, A$^7$=Me, R$^3$=CF$_3$, R$^{11}$=H, R$^{12}$=H], [1693; Q=Q$^{q4}$, A$^1$=H, A$^2$=H, A$^3$=Cl, A$^4$=Cl, A$^7$=Me, R$^3$=CF$_3$, R$^{11}$=H, R$^{12}$=H], [1694; Q=Q$^{q4}$, A$^1$=H, A$^2$=H, A$^3$=Me, A$^4$=H, A$^7$=Me, R$^3$=CF$_3$, R$^{11}$=H, R$^{12}$=H], [1695; Q=Q$^{q4}$, A$^1$=H, A$^2$=H, A$^3$=Me, A$^4$=Me, A$^7$=Me, R$^3$=CF$_3$, R$^{11}$=H, R$^{12}$=H], [1696; Q=Q$^{q4}$, A$^1$=H, A$^2$=H, A$^3$=H, A$^4$=H, A$^7$=Et, R$^3$=CF$_3$, R$^{11}$=H, R$^{12}$=H], [1697; Q=Q$^{q4}$, A$^1$=H, A$^2$=H, A$^3$=F, A$^4$=H, A$^7$=Et, R$^3$=CF$_3$, R$^{11}$=H, R$^{12}$=H], [1698; Q=Q$^{q4}$, A$^1$=H, A$^2$=H, A$^3$=F, A$^4$=F, A$^7$=Et, R$^3$=CF$_3$, R$^{11}$=H, R$^{12}$=H], [1699; Q=Q$^{q4}$, A$^1$=H, A$^2$=H, A$^3$=Cl, A$^4$=H, A$^7$=Et, R$^3$=CF$_3$, R$^{11}$=H, R$^{12}$=H], [1700; Q=Q$^{q4}$, A$^1$=H, A$^2$=H, A$^3$=Cl, A$^4$=Cl, A$^7$=Et, R$^3$=CF$_3$, R$^{11}$=H, R$^{12}$=H], [1701; Q=Q$^{q4}$, A$^1$=H, A$^2$=H, A$^3$=Me, A$^4$=H, A$^7$=Et, R$^3$=CF$_3$, R$^{11}$=H, R$^{12}$=H], [1702; Q=Q$^{q4}$, A$^1$=H, A$^2$=H, A$^3$=Me, A$^4$=Me, A$^7$=Et, R$^3$=CF$_3$, R$^{11}$=H, R$^{12}$=H], [1703; Q=Q$^{q4}$, A$^1$=H, A$^2$=H, A$^3$=H, A$^4$=H, A$^7$=Me, R$^3$=OMe, R$^{11}$=H, R$^{12}$=H], [1704; Q=Q$^{q4}$, A$^1$=H, A$^2$=H, A$^3$=F, A$^4$=H, A$^7$=Me, R$^3$=OMe, R$^{11}$=H, R$^{12}$=H], [1705; Q=Q$^{q4}$, A$^1$=H, A$^2$=H, A$^3$=F, A$^4$=F, A$^7$=Me, R$^3$=OMe, R$^{11}$=H, R$^{12}$=H], [1706; Q=Q$^{q4}$, A$^1$=H, A$^2$=H, A$^3$=Cl, A$^4$=H, A$^7$=Me, R$^3$=OMe, R$^{11}$=H, R$^{12}$=H], [1707; Q=Q$^{q4}$, A$^1$=H, A$^2$=H, A$^3$=Cl, A$^4$=Cl, A$^7$=Me, R$^3$=OMe, R$^{11}$=H, R$^{12}$=H], [1708; Q=Q$^{q4}$, A$^1$=H, A$^2$=H, A$^3$=Me, A$^4$=H, A$^7$=Me, R$^3$=OMe, R$^{11}$=H, R$^{12}$=H], [1709; Q=Q$^{q4}$, A$^1$=H, A$^2$=H, A$^3$=Me, A$^4$=Me, A$^7$=Me, R$^3$=OMe, R$^{11}$=H, R$^{12}$=H], [1710; Q=Q$^{q4}$, A$^1$=H, A$^2$=H, A$^3$=H, A$^4$=H, A$^7$=Et, R$^3$=OMe, R$^{11}$=H, R$^{12}$=H], [1711; Q=Q$^{q4}$, A$^1$=H, A$^2$=H, A$^3$=F, A$^4$=H, A$^7$=Et, R$^3$=OMe, R$^{11}$=H, R$^{12}$=H], [1712; Q=Q$^{q4}$, A$^1$=H, A$^2$=H, A$^3$=F, A$^4$=F, A$^7$=Et, R$^3$=OMe, R$^{11}$=H, R$^{12}$=H], [1713; Q=Q$^{q4}$, A$^1$=H, A$^2$=H, A$^3$=Cl, A$^4$=H, A$^7$=Et, R$^3$=OMe, R$^{11}$=H, R$^{12}$=H], [1714; Q=Q$^{q4}$, A$^1$=H, A$^2$=H, A$^3$=Cl, A$^4$=Cl, A$^7$=Et, R$^3$=OMe, R$^{11}$=H, R$^{12}$=H], [1715; Q=Q$^{q4}$, A$^1$=H, A$^2$=H, A$^3$=Me, A$^4$=H, A$^7$=Et, R$^3$=OMe, R$^{11}$=H, R$^{12}$=H], [1716; Q=Q$^{q4}$, A$^1$=H, A$^2$=H, A$^3$=Me, A$^4$=Me, A$^7$=Et, R$^3$=OMe, R$^{11}$=H, R$^{12}$=H], [1717; Q=Q$^{q4}$, A$^1$=H, A$^2$=H, A$^3$=H, A$^4$=H, A$^7$=Me, R$^3$=H, R$^{11}$=F, R$^{12}$=H], [1718; Q=Q$^{q4}$, A$^1$=H, A$^2$=H, A$^3$=F, A$^4$=H, A$^7$=Me, R$^3$=H, R$^1$=F, R$^{12}$=H], [1719; Q=Q$^{q4}$, A$^1$=H, A$^2$=H, A$^3$=F, A$^4$=F, A$^7$=Me, R$^3$=H, R$^{11}$=F, R$^{12}$=H], [1720; Q=Q$^{q4}$, A$^1$=H, A$^2$=H, A$^3$=C, A$^4$=H, A$^7$=Me, R$^3$=H, R$^{11}$=F, R$^{12}$=H], [1721; Q=Q$^{q4}$, A$^1$=H, A$^2$=H, A$^3$=Cl, A$^4$=Cl, A$^7$=Me, R$^3$=H, R$^{11}$=F, R$^{12}$=H], [1722; Q=Q$^{q4}$, A$^1$=H, A$^2$=H, A$^3$=Me, A$^4$=H, A$^7$=Me, R$^3$=H, R$^{11}$=F, R$^{12}$=H], [1723; Q=Q$^{q4}$, A$^1$=H, A$^2$=H, A$^3$=Me, A$^4$=Me, A$^7$=Me, R$^3$=H, R$^{11}$=F, R$^{12}$=H], [1724; Q=Q$^{q4}$, A$^1$=H, A$^2$=H, A$^3$=H, A$^4$=H, A$^7$=Et, R$^3$=H, R$^{11}$=F, R$^{12}$=H], [1725; Q=Q$^{q4}$, A$^1$=H, A$^2$=H, A$^3$=F, A$^4$=H, A$^7$=Et, R$^3$=H, R$^{11}$=F, R$^{12}$=H], [1726; Q=Q$^{q4}$, A$^1$=H, A$^2$=H, A$^3$=F, A$^4$=F, A$^7$=Et, R$^3$=H, R$^{11}$=F, R$^{12}$=H], [1727; Q=Q$^{q4}$, A$^1$=H, A$^2$=H, A$^3$=Cl, A$^4$=H, A$^7$=Et, R$^3$=H, R$^{11}$=F, R$^{12}$=H], [1728; Q=Q$^{q4}$, A$^1$=H, A$^2$=H, A$^3$=Cl, A$^4$=Cl, A$^7$=Et, R$^3$=H, R$^{11}$=F, R$^{12}$=H], [1729; Q=Q$^{q4}$, A$^1$=H, A$^2$=H, A$^3$=Me, A$^4$=H, A$^7$=Et, R$^3$=H, R$^1$=F, R$^{12}$=H], [1730; Q=Q$^{q4}$, A$^1$=H, A$^2$=H, A$^3$=Me, A$^4$=Me, A$^7$=Et, R$^3$=H, R$^{11}$=F, R$^{12}$=H], [1731; Q=Q$^{q4}$, A$^1$=H, A$^2$=H, A$^3$=H, A$^4$=H, A$^7$=Me, R$^3$=H, R$^{11}$=Cl, R$^{12}$=H], [1732; Q=Q$^{q4}$, A$^1$=H, A$^2$=H, A$^3$=F, A$^4$=H, A$^7$=Me, R$^3$=H, R$^{11}$=Cl, R$^{12}$=H], [1733; Q=Q$^{q4}$, A$^1$=H, A$^2$=H, A$^3$=F, A$^4$=F, A$^7$=Me, R$^3$=H, R$^{11}$=Cl, R$^{12}$=H], [1734; Q=Q$^{q4}$, A$^1$=H, A$^2$=H, A$^3$=Cl, A$^4$=H, A$^7$=Me, R$^3$=H, R$^{11}$=Cl, R$^{12}$=H], [1735; Q=Q$^{q4}$, A$^1$=H, A$^2$=H, A$^3$=Cl, A$^4$=Cl, A$^7$=Me, R$^3$=H, R$^{11}$=Cl, R$^{12}$=H], [1736; Q=Q$^{q4}$, A$^1$=H, A$^2$=H, A$^3$=Me, A$^4$=H, A$^7$=Me, R$^3$=H, R$^{11}$=Cl, R$^{12}$=H], [1737; Q=Q$^{q4}$, A$^1$=H, A$^2$=H, A$^3$=Me, A$^4$=Me, A$^7$=Me, R$^3$=H, R$^{11}$=Cl, R$^{12}$=H], [1738; Q=Q$^{q4}$, A$^1$=H, A$^2$=H, A$^3$=H, A$^4$=H, A$^7$=Et, R$^3$=H, R$^{11}$=Cl, R$^{12}$=H], [1739; Q=Q$^{q4}$, A$^1$=H, A$^2$=H, A$^3$=F, A$^4$=H, A$^7$=Et, R$^3$=H, R$^{11}$=Cl, R$^{12}$=H], [1740; Q=Q$^{q4}$, A¹=H, A²=H, A³=F, A⁴=F, A⁷=Et, R³=H, R¹¹=Cl, R¹²=H], [1741; Q=Q^{q4}, A¹=H, A²=H, A³=Cl, A⁴=H, A⁷=Et, R³=H, R¹¹=Cl, R¹²=H], [1742; Q=Q^{q4}, A¹=H, A²=H, A³=Cl, A⁴=Cl, A⁷=Et, R³=H, R¹¹=Cl, R¹²=H], [1743; Q=Q^{q4}, A¹=H, A²=H, A³=Me, A⁴=H, A⁷=Et, R³=H, R¹¹=Cl, R¹²=H], [1744; Q=Q^{q4}, A¹=H, A²=H, A³=Me, A⁴=Me, A⁷=Et, R³=H, R¹¹=Cl, R¹²=H], [1745; Q=Q^{q4}, A¹=H, A²=H, A³=H, A⁴=H, A⁷=Me, R³=H, R¹¹=Me, R¹²=H], [1746; Q=Q^{q4}, A¹=H, A²=H, A³=F, A⁴=H, A⁷=Me, R³=H, R¹¹=Me, R¹²=H], [1747; Q=Q^{q4}, A¹=H, A²=H, A³=F, A⁴=F, A⁷=Me, R³=H, R¹¹=Me, R¹²=H], [1748; Q=Q^{q4}, A¹=H, A²=H, A³=Cl, A⁴=H, A⁷=Me, R³=H, R¹¹=Me, R¹²=H], [1749; Q=Q^{q4}, A¹=H, A²=H, A³=Cl, A⁴=Cl, A⁷=Me, R³=H, R¹¹=Me, R²=H], [1750; Q=Q^{q4}, A¹=H, A²=H, A³=Me, A⁴=H, A⁷=Me, R³=H, R¹¹=Me, R¹²=H], [1751; Q=Q^{q4}, A¹=H, A²=H, A³=Me, A³=Me, A⁷=Me, R³=H, R¹¹=Me, R¹²=H], [1752; Q=Q^{q4}, A¹=H, A²=H, A³=H, A⁴=H, A⁷=Et, R³=H, R¹¹=Me, R¹²=H], [1753; Q=Q^{q4}, A¹=H, A²=H, A³=F, A⁴=H, A⁷=Et, R³=H, R¹¹=Me, R¹²=H], [1754; Q=Q^{q4}, A¹=H, A²=H, A³=F, A⁴=F, A⁷=Et, R³=H, R¹¹=Me, R¹²=H], [1755; Q=Q^{q4}, A¹=H, A²=H, A³=H, A¹=H, A⁷=Et, R³=H, R¹¹=Me, R¹²=H], [1756; Q=Q^{q4}, A¹=H, A²=H, A³=Cl, A⁴=Cl, A⁷=Et, R³=H, R¹¹=Me, R¹²=H], [1757; Q=Q^{q4}, A¹=H, A²=H, A³=Me, A⁴=H, A⁷=Et, R³=H, R¹¹=Me, R¹²=H], [1758; Q=Q^{q4}, A¹=H, A²=H, A³=Me, A⁴=Me, A⁷=Et, R³=H, R¹¹=Me, R¹²=H], [1759; Q=Q^{q4}, A¹=H, A²=H, A³=H, A⁴=H, A⁷=Me, R³=H, R¹¹=CF₃, R¹²=H], [1760; Q=Q^{q4}, A⁵=H, A²=H, A³=F, A⁴=H, A⁷=Me, R³=H, R¹¹=CF₃, R¹²=H], [1761; Q=Q^{q4}, A¹=H, A²=H, A³=F, A⁵=F, A⁷=Me, R³=H, R¹¹=CF₃, R¹²=H], [1762; Q=Q^{q4}, A¹=H, A²=H, A³=Cl, A⁴=H, A⁷=Me, R³=H, R¹¹=CF₃, R¹²=H], [1763; Q=Q^{q4}, A¹=H, A²=H, A³=Cl, A⁴=Cl, A⁷=Me, R³=H, R¹¹=CF₃, R¹²=H], [1764; Q=Q^{q4}, A¹=H, A²=H, A³=Me, A⁴=H, A⁷=Me, R³=H, R¹¹=CF₃, R¹²=H], [1765; Q=Q^{q4}, A¹=H, A²=H, A³=Me, A⁴=Me, A⁷=Me, R³=H, R¹¹=CF₃, R¹²=H], [1766; Q=Q^{q4}, A¹=H, A²=H, A³=H, A⁴=H, A⁷=Et, R³=H, R¹¹=CF₃, R¹²=H], [1767; Q=Q^{q4}, A¹=H, A²=H, A³=F, A⁴=H, A⁷=Et, R³=H, R¹¹=CF₃, R¹²=H], [1768; Q=Q^{q4}, A¹=H, A²=H, A³=F, A⁴=F, A⁷=Et, R³=H, R¹¹=CF₃, R¹²=H], [1769; Q=Q^{q4}, A¹=H, A²=H, A³=Cl, A⁴=H, A⁷=Et, R³=H, R¹¹=CF₃, R¹²=H], [1770; Q=Q^{q4}, A¹=H, A²=H, A³=Cl, A⁴=Cl, A⁷=Et, R³=H, R¹¹=CF₃, R¹²=H], [1771; Q=Q^{q4}, A¹=H, A²=H, A³=Me, A⁴=H, A⁷=Et, R³=H, R¹¹=CF₃, R¹²=H], [1772; Q=Q^{q4}, A¹=H, A²=H, A³=Me, A⁴=Me, A⁷=Et, R³=H, R¹¹=CF₃, R¹²=H], [1773; Q=Q^{q4}, A¹=H, A²=H, A³=H, A⁴=H, A⁷=Me, R³=H, R¹¹=OMe, R¹²=H], [1774; Q=Q^{q4}, A¹=H, A²=H, A³=F, A⁴=H, A⁷=Me, R³=H, R¹¹=OMe, R¹²=H], [1775; Q=Q^{q4}, A¹=H, A²=H, A³=F, A⁴=F, A¹=Me, R³=H, R¹¹=OMe, R¹²=H][1776; Q=Q^{q4}, A¹=H, A²=H, A³=Cl, A⁴=H, A⁷=Me, R³=H, R¹¹=OMe, R¹²=H], [1777; Q=Q^{q4}, A¹=H, A²=H, A³=Cl, A⁴=Cl, A⁷=Me, R³=H, R¹¹=OMe, R¹²=H], [1778; Q=Q^{q4}, A¹=H, A²=H, A³=Me, A⁴=H, A⁷=Me, R³=H, R¹¹=OMe, R¹²=H], [1779; Q=Q^{q4}, A¹=H, A²=H, A³=Me, A⁴=Me, A⁷=Me, R³=H, R¹¹=OMe, R¹²=H], [1780; Q=Q^{q4}, A¹=H, A²=H, A³=H, A⁴=H, A⁷=Et, R³=H, R¹¹=OMe, R¹²=H], [1781; Q=Q^{q4}, A¹=H, A²=H, A³=F, A⁴=H, A⁷=Et, R³=H, R¹¹=OMe, R¹²=H], [1782; Q=Q^{q4}, A¹=H, A²=H, A³=F, A⁴=F, A⁷=Et, R³=H, R¹¹=OMe, R¹²=H], [1783; Q=Q^{q4}, A¹=H, A²=H, A³=Cl, A⁴=H, A⁷=Et, R³=H, R¹¹=OMe, R¹²=H], [1784; Q=Q^{q4}, A¹=H, A²=H, A³=Cl, A⁴=Cl, A⁷=Et, R³=H, R¹¹=OMe, R¹²=H], [1785; Q=Q^{q4}, A¹=H, A²=H, A³=Me, A⁴=H, A⁷=Et, R³=H, R¹¹=OMe, R¹²=H], [1786; Q=Q^{q4}, A¹=H, A²=H, A³=Me, A⁴=Me, A⁷=Et, R³=H, R¹¹=OMe, R¹²=H], [1787; Q=Q^{q5}, A¹=H, A²=H, A⁵=H, A⁶=H, R³=H, R¹¹=H, R¹²=H], [1788; Q=Q^{q5}, A¹=H, A²=H, A⁵=F, A⁶=H, R³=H, R¹¹=H, R¹²=H], [1789; Q=Q^{q5}, A¹=H, A²=H, A⁵=F, A⁶=F, R³=H, R¹¹=H, R¹²=H], [1790; Q=Q^{q5}, A¹=H, A²=H, A⁵=Cl, A⁶=Cl, R³=H, R¹¹=H, R¹²=H], [1791; Q=Q^{q5}, A¹=H, A²=H, A⁵=Me, A⁶=H, R³=H, R¹¹=H, R¹²=H], [1792; Q=Q^{q5}, A¹=H, A²=H, A⁵=Me, A⁶=Me, R³=H, R¹¹=H, R¹²=H], [1793; Q=Q^{q5}, A¹=H, A²=H, A⁵=H, A⁶=H, R³=Cl, R¹¹=H, R¹²=H], [1794; Q=Q^{q5}, A¹=H, A²=H, A⁵=F, A⁶=H, R³=Cl, R¹¹=H, R¹²=H], [1795; Q=Q^{q5}, A³=H, A²=H, A⁵=F, A⁶=F, R³=Cl, R¹¹=H, R¹²=H], [1796; Q=Q^{q5}, A¹=H, A²=H, A⁵=Cl, A⁶=Cl, R³=Cl, R¹¹=H, R¹²=H], [1797; Q=Q^{q5}, A¹=H, A²=H, A⁵=Me, A⁶=H, R³=Cl, R¹¹=H, R¹²=H], [1798; Q=Q^{q5}9, A¹=H, A²=H, A⁵=Me, A⁶=Me, R³=Cl, R¹¹=H, R¹²=H], [1799; Q=Q^{q5}5, A¹=H, A²=H, A¹=H, A¹=H, R³=OMe, R¹¹=H, R¹²=H], [1800; Q=Q^{q5}, A¹=H, A²=H, A⁵=F, A⁶=H, R³=OMe, R¹¹=H, R¹²=H], [1801; Q=Q^{q5}, A¹=H, A²=H, A⁵=F, A⁶=F, R³=OMe, R¹¹=H, R¹²=H], [1802; Q=Q^{q5}, A¹=H, A²=H, A⁵=Cl, A⁶=Cl, R³=OMe, R¹¹=H, R¹²=H] [1803; Q=Q^{q5}, A¹=H, A²=H, A⁵=Me, A⁶=H, R³=Me, R¹¹=H, R¹²=H], [1804; Q=Q^{q5}, A¹=H, A²=H, A⁵=Me, A⁶=Me, R³=OMe, R¹¹=H, R¹²=H], [1805; Q=Q^{q5}, A¹=H, A²=H, A⁵=H, A⁶=H, R³=CF₃, R¹¹=H, R¹²=H], [1806; Q=Q^{q5}, A¹=H, A²=H, A²=F, A⁶=H, R³=CF₃, R¹¹=H, R¹²=H], [1807; Q=Q^{q5}, A¹=H, A²=H, A⁵=F, A⁶=F, R³=CF₃, R¹¹=H, R¹²=H], [1808; Q=Q^{q5}, A¹=H, A²=H, A⁵=Cl, A⁶=Cl, R³=CF₃, R¹¹=H, R¹²=H], [1809; Q=Q^{q5}, A¹=H, A²=H, A⁵=Me, A⁶=H, R³=CF₃, R¹¹=H, R¹²=H], [1810; Q=Q^{q5}, A¹=H, A²=H, A⁵=Me, A⁶=Me, R³=CF₃, R¹¹=H, R¹²=H], [1811; Q=Q^{q5}, A¹=H, A²=H, A⁵=H, A⁶=H, R³=H, R¹¹=Cl, R¹²=H], [1812; Q=Q^{q5}, A¹=H, A²=H, A⁵=F, A⁶=H, R³=H, R¹¹=Cl, R¹²=H], [1813; Q=Q^{q5}, A¹=H, A²=H, A⁵=F, A⁶=F, R³=H, R¹¹=Cl, R¹²=H], [1814; Q=Q^{q5}, A¹=H, A²=H, A⁵=Cl, A⁶=Cl, R³=H, R¹¹=Cl, R¹²=H], [1815; Q=Q^{q5}, A¹=H, A²=H, A⁵=Me, A⁶=H, R³=H, R¹¹=Cl, R¹²=H], [1816; Q=Q^{q5}, A¹=H, A²=H, A⁵=Me, A⁶=Me, R³=H, R¹¹=Cl, R¹²=H], [1817; Q=Q^{q5}, A¹=H, A²=H, A⁵=H, A⁶=H, R³=H, R¹¹=OMe, R¹²=H], [1818; Q=Q^{q5}, A¹=H, A²=H, A⁵=F, A⁶=H, R³=H, R¹¹=OMe, R¹²=H], [1819; Q=Q^{q5}, A¹=H, A²=H, A⁵=F, A⁶=F, R³=H, R¹¹=OMe, R¹²=H], [1820; Q=Q^{q4}, A¹=H, A²=H, A³=Cl, A⁶=Cl, R³=H, R=n=OMe, R¹²=H], [1821; Q=Q^{q5}, A¹=H, A²=H, A⁵=Me, A⁶=H, R³=H, R¹¹=OMe, R¹²=H], [1822; Q=Q^{q5}, A¹=H, A²=H, A⁵=Me, A⁶=Me, R³=H, R¹¹=OMe, R¹²=H], [1823; Q=Q, A¹=H, A²=H, A⁵=H, A⁶=H, R³=H, R¹¹=CF₃, R¹²=H], [1824; Q=Q^{q4}, A¹=H, A²=H, A⁵=F, A⁶=H, R³=H, R¹¹=CF₃, R¹²=H], [1825; Q=Q^{q4}, A¹=H, A²=H, A⁵=F, A⁶=F, R³=H, R¹¹=CF₃, R¹²=H], [1826; Q=Q^{q4}, A¹=H, A²=H, A³=Cl, A⁶=Cl, R³=H, R¹¹=CF₃, R¹²=H], [1827; Q=Q^{q5}, A¹=H, A²=H, A⁵=Me, A⁶=H, R³=H, R¹¹=CF₃, R¹²=H], [1828; Q=Q^{q5}, A¹=H, A²=H, A⁵=Me, A⁶=Me, R³=H, R¹¹=CF₃, R¹²=H], [1829; Q=Q^{q6}, A¹=H, A²=H, A⁵=H, A⁶=H, R³=H, R¹¹=H, R¹²=H], [1830; Q=Q^{q6}, A¹=H, A²=H, A⁵=F, A⁶=H, R³=H, R¹¹=H, R¹²=H], [1831; Q=Q^{q6}, A¹=H, A²=H, A⁵=F, A⁶=F, R³=H, R¹¹=H, R¹²=H], [1832; Q=Q^{q6}, A¹=H, A²=H, A⁵=Cl, A⁶=Cl, R³=H, R¹¹=H, R¹²=H], [1833; Q=Q^{q6}, A¹=H, A²=H, A⁵=Me, A⁶=H, R³=H, R¹¹=H, R¹²=H], [1834; Q=Q^{q6}, A¹=H, A²=H, A⁵=Me, A⁶=Me, R³=H, R¹¹=H, R¹²=H], [1835; Q=Q^{q6}, A¹=H, A²=H, A⁵=H, A⁶=H, R³=Cl, R¹¹=H, R¹²=H], [1836; Q=Q^{q6}, A¹=H, A²=H, A⁵=F, A⁶=H, R³=Cl, R¹¹=H, R¹²=H], [1837; Q=Q^{q6}, A¹=H, A²=H, A⁵=F, A⁶=F, R³=Cl, R¹¹=H, R¹²=H], [1838; Q=Q^{q6}, A¹=H, A²=H, A⁵=Cl, A⁶=Cl, R³=Cl, R¹¹=H, R¹²=H], [1839; Q=Q^{q6}, A¹=H, A²=H, A⁵=Me, A⁶=H, R³=Cl, R¹¹=H, R¹²=H], [1840; Q=Q^{q6}, A¹=H, A²=H, A⁵=Me, A⁶=Me, R³=Cl, R¹¹=H, R¹²=H], [1841; Q=Q^{q6}, A¹=H, A²=H, A⁵=H, A⁶=H, R³=OMe, R¹¹=H, R¹²=H], [1842; Q=Q^{q6}, A¹=H, A²=H, A⁵=F, A⁶=H, R³=OMe, R¹¹=H, R¹²=H], [1843; Q=Q^{q6}, A¹=H, A²=H, A⁵=F, A⁶=F, R³=OMe, R¹¹=H, R¹²=H],

[1844; Q=$Q^{q6}$, $A^1$=H, $A^2$=H, $A^5$=Cl, $A^6$=Cl, $R^3$=OMe, $R^{11}$=H, $R^{12}$=H], [1845; Q=$Q^{q6}$, $A^1$=H, $A^2$=H, $A^5$=Me, $A^6$=H, $R^3$=OMe, $R^{11}$=H, $R^{12}$=H], [1846; Q=$Q^{q6}$, $A^1$=H, $A^2$=H, $A^5$=Me, $A^6$=Me, $R^3$=OMe, $R^{11}$=H, $R^{12}$=H], [1847; Q=$Q^{q6}$, $A^1$=H, $A^2$=H, $A^5$=H, $A^6$=H, $R^3$=$CF_3$, $R^{11}$=H, $R^{12}$=H], [1848; Q=$Q^{q6}$, $A^1$=H, $A^2$=H, $A^5$=F, $A^6$=H, $R^3$=$CF_3$, $R^{11}$=H, $R^{12}$=H], [1849; Q=$Q^{q6}$, $A^1$=H, $A^2$=H, $A^5$=F, $A^6$=F, $R^3$=$CF_3$, $R^{11}$=H, $R^{12}$=H], [1850; Q=$Q^{q6}$, $A^1$=H, $A^2$=H, $A^5$=Cl, $A^6$=Cl, $R^3$=$CF_3$, $R^{11}$=H, $R^{12}$=H], [1851; Q=$Q^{q6}$, $A^1$=H, $A^2$=H, $A^5$=Me, $A^6$=H, $R^3$=$CF_3$, $R^{11}$=H, $R^{12}$=H], [1852; Q=$Q^{q6}$, $A^1$=H, $A^2$=H, $A^5$=Me, $A^6$=Me, $R^3$=$CF_3$, $R^{11}$=H, $R^{12}$=H], [1853; Q=$Q^{q6}$, $A^1$=H, $A^2$=H, $A^5$=H, $A^6$=H, $R^3$=H, $R^{11}$=Cl, $R^{12}$=H], [1854; Q=$Q^{q6}$, $A^1$=H, $A^2$=H, $A^5$=F, $A^6$=H, $R^3$=H, $R^{11}$=Cl, $R^{12}$=H], [1855; Q=$Q^{q6}$, $A^1$=H, $A^2$=H, $A^5$=F, $A^6$=F, $R^3$=H, $R^{11}$=Cl, $R^{12}$=H], [1856; Q=$Q^{q6}$, $A^1$=H, $A^2$=H, $A^5$=Cl, $A^6$=Cl, $R^3$=H, $R^{11}$=Cl, $R^{12}$=H], [1857; Q=$Q^{q6}$, $A^1$=H, $A^2$=H, $A^5$=Me, $A^6$=H, $R^3$=H, $R^{11}$=Cl, $R^{12}$=H], [1858; Q=$Q^{q6}$, $A^1$=H, $A^2$=H, $A^5$=Me, $A^6$=Me, $R^3$=H, $R^{11}$=Cl, $R^{12}$=H], [1859; Q=$Q^{q6}$, $A^1$=H, $A^2$=H, $A^5$=H, $A^6$=H, $R^3$=H, $R^{11}$=OMe, $R^{12}$=H], [1860; Q=$Q^{q6}$, $A^1$=H, $A^2$=H, $A^5$=F, $A^6$=H, $R^3$=H, $R^{11}$=OMe, $R^{12}$=H], [1861; Q=$Q^{q6}$, $A^1$=H, $A^2$=H, $A^5$=F, $A^6$=F, $R^3$=H, $R^{11}$=OMe, $R^{12}$=H], [1862; Q=$Q^{q6}$, $A^1$=H, $A^2$=H, $A^5$=Cl, $A^6$=Cl, $R^3$=H, $R^{11}$=OMe, $R^{12}$=H], [1863; Q=$Q^{q6}$, $A^1$=H, $A^2$=H, $A^5$=Me, $A^6$=H, $R^3$=H, $R^{11}$=OMe, $R^2$=H], [1864; Q=$Q^{q6}$, $A^1$=H, $A^2$=H, $A^5$=Me, $A^6$=Me, $R^3$=H, $R^{11}$=OMe, $R^{12}$=H], [1865; Q=$Q^{q6}$, $A^1$=H, $A^2$=H, $A^5$=H, $A^6$=H, $R^3$=H, $R^{11}$=$CF_3$, $R^{12}$=H], [1866; Q=$Q^{q6}$, $A^1$=H, $A^2$=H, $A^5$=F, $A^6$=H, $R^3$=H, $R^{11}$=$CF_3$, $R^{12}$=H], [1867; Q=$Q^{q6}$, $A^1$=H, $A^2$=H, $A^5$=F, $A^6$=F, $R^3$=H, $R^{11}$=$CF_3$, $R^{12}$=H], [1868; Q=$Q^{q6}$, $A^1$=H, $A^2$=H, $A^5$=Cl, $A^6$=Cl, $R^3$=H, $R^{11}$=$CF_3$, $R^{12}$=H], [1869; Q=$Q^{q6}$, $A^1$=H, $A^2$=H, $A^5$=Me, $A^6$=H, $R^3$=H, $R^{11}$=$CF_3$, $R^{12}$=H], [1870; Q=$Q^{q6}$, $A^1$=H, $A^2$=H, $A^5$=Me, $A^6$=Me, $R^3$=H, $R^{11}$=$CF_3$, $R^{12}$=H], [1871; Q=$Q^{q7}$, $A^1$=H, $A^2$=H, $A^5$=H, $A^6$=H, $A^8$=Me, $R^3$=H, $R^{11}$=H, $R^{12}$=H], [1872; Q=$Q^{q7}$, $A^1$=H, $A^2$=H, $A^5$=Me, $A^6$=H, $A^8$=Me, $R^3$=H, $R^{11}$=H, $R^{12}$=H], [1873; Q=$Q^{q7}$, $A^1$=H, $A^2$=H, $A^5$=Me, $A^6$=Me, $A^8$=Me, $R^3$=H, $R^{11}$=H, $R^{12}$=H], [1874; Q=$Q^{q7}$, $A^1$=H, $A^2$=H, $A^5$=H, $A^6$=H, $A^8$=Me, $R^3$=Cl, $R^{11}$=H, $R^{12}$=H], [1875; Q=$Q^{q7}$, $A^1$=H, $A^2$=H, $A^5$=Me, $A^6$=H, $A^8$=Me, $R^3$=Cl, $R^{11}$=H, $R^{12}$=H], [1876; Q=$Q^{q7}$, $A^1$=H, $A^2$=H, $A^5$=Me, $A^6$=Me, $A^8$=Me, $R^3$=Cl, $R^{11}$=H, $R^{12}$=H], [1877; Q=$Q^{q7}$, $A^1$=H, $A^2$=H, $A^5$=H, $A^6$=H, $A^8$=Me, $R^3$=OMe, $R^{11}$=H, $R^{12}$=H], [1878; Q=$Q^{q7}$, $A^1$=H, $A^2$=H, $A^5$=Me, $A^6$=H, $A^1$=Me, $R^3$=OMe, $R^{11}$=H, $R^{12}$=H][1879; Q=$Q^{q7}$, $A^1$=H, $A^2$=H, $A^5$=Me, $A^6$=Me, $A^8$=Me, $R^3$=OMe, $R^{11}$=H, $R^{12}$=H], [1880; Q=$Q^{q4}$, $A^1$=H, $A^2$=H, $A^5$=H, $A^6$=H, $A^8$=Me, $R^3$=$CF_3$, $R^{11}$=H, $R^{12}$=H], [1881; Q=$Q^{q7}$, $A^1$=H, $A^2$=H, $A^5$=Me, $A^6$=H, $A^8$=Me, $R^3$=$CF_3$, $R^{11}$=H, $R^{12}$=H], [1882; Q=$Q^{q7}$, $A^1$=H, $A^2$=H, $A^5$=Me, $A^6$=Me, $A^8$=Me, $R^3$=$CF_3$, $R^{11}$=H, $R^{12}$=H], [1883; Q=$Q^{q8}$, $A^1$=H, $A^2$=H, $A^3$=H, $A^4$=H, $R^3$=H, $R^{11}$=H, $R^{12}$=H], [1884; Q=$Q^{q5}$, $A^1$=H, $A^2$=H, $A^3$=H, $A^4$=H, $R^3$=Cl, $R^{11}$=H, $R^{12}$=H], [1885; Q=$Q^{q8}$, $A^1$=H, $A^2$=H, $A^3$=H, $A^4$=H, $R^3$=$CF_3$, $R^{11}$=H, $R^{12}$=H], [1886; Q=$Q^{q5}$, $A^1$=H, $A^2$=H, $A^3$=H, $A^4$=H, $R^3$=OMe, $R^{11}$=H, $R^{12}$=H], [1887; Q=$Q^{q8}$, $A^1$=H, $A^2$=H, $A^3$=H, $A^4$=H, $R^3$=OCF_3, $R^{11}$=H, $R^{12}$=H], [1888; Q=$Q^{q8}$, $A^1$=H, $A^2$=H, $A^3$=H, $A^4$=H, $R^3$=SMe, $R^{11}$=H, $R^{12}$=H], [1889; Q=$Q^{q8}$, $A^1$=H, $A^2$=H, $A^3$=H, $A^4$=H, $R^3$=H, $R^{11}$=Cl, $R^{12}$=H], [1890; Q=$Q^{q5}$, $A^1$=H, $A^2$=H, $A^3$=H, $A^4$=H, $R^3$=H, $R^{11}$=$CF_3$, $R^{12}$=H], [1891; Q=$Q^{q8}$, $A^1$=H, $A^2$=H, $A^3$=H, $A^4$=H, $R^3$=H, $R^{11}$=OMe, $R^{12}$=H], [1892; Q=$Q^{q4}$, $A^1$=H, $A^2$=H, $A^3$=H, $A^4$=H, $R^3$=H, $R^{11}$=$OCF_3$, $R^{12}$=H], [1893; Q=$Q^{q9}$, $A^1$=H, $A^2$=H, $A^3$=H, $A^4$=H, $R^3$=H, $R^{11}$=SMe, $R^{12}$=H], [1894; Q=$Q^{q9}$, $A^1$=H, $A^2$=H, $A^3$=H, $A^4$=H, $R^3$=Cl, $R^{11}$=H, $R^{12}$=H], [1895; Q=$Q^{q9}$, $A^1$=H, $A^2$=H, $A^3$=H, $A^4$=H, $R^3$=$CF_3$, $R^{11}$=H, $R^{12}$=H], [1897; Q=$Q^{q9}$, $A^1$=H, $A^2$=H, $A^3$=H, $A^4$=H, $R^3$=OMe, $R^{11}$=H, $R^{12}$=H], [1898; Q=$Q^{q9}$, $A^1$=H, $A^2$=H, $A^3$=H, $A^4$=H, $R^3$=$OCF_3$, $R^{11}$=H, $R^{12}$=H], [1899; Q=$Q^{q9}$, $A^1$=H, $A^2$=H, $A^3$=H, $A^4$=H, $R^3$=SMe, $R^{11}$=H, $R^{12}$=H], [1900; Q=$Q^{q9}$, $A^1$=H, $A^2$=H, $A^3$=H, $A^4$=H, $R^3$=H, $R^{11}$=Cl, $R^{12}$=H], [1901; Q=$Q^{q9}$, $A^1$=H, $A^2$=H, $A^3$=H, $A^4$=H, $R^3$=H, $R^{11}$=$CF_3$, $R^{12}$=H], [1902; Q=$Q^{q9}$, $A^1$=H, $A^2$=H, $A^3$=H, $A^4$=H, $R^3$=H, $R^{11}$=OMe, $R^{12}$=H], [1903; Q=$Q^{q9}$, $A^1$=H, $A^2$=H, $A^3$=H, $A^4$=H, $R^3$=H, $R^{11}$=$OCF_3$, $R^{12}$=H], [1904; Q=$Q^{q9}$, $A^1$=H, $A^2$=H, $A^3$=H, $A^4$=H, $R^3$=H, $R^{11}$=SMe, $R^{12}$=H], [1905; Q=$Q^{q10}$, $A^1$=H, $A^2$=H, $A^3$=H, $A^4$=H, $R^3$=H, $R^{11}$=H, $R^{12}$=H], [1906; Q=$Q^{q10}$, $A^1$=H, $A^2$=H, $A^3$=H, $A^4$=H, $R^3$=Cl, $R^{11}$=H, $R^{12}$=H], [1907; Q=$Q^{q10}$, $A^1$=H, $A^2$=H, $A^3$=H, $A^4$=H, $R^3$=$CF_3$, $R^{11}$=H, $R^{12}$=H][1908; Q=$Q^{q10}$, $A^1$=H, $A^2$=H, $A^3$=H, $A^4$=H, $R^3$=OMe, $R^{11}$=H, $R^{12}$=H], [1909; Q=$Q^{q10}$, $A^1$=H, $A^2$=H, $A^3$=H, $A^4$=H, $R^3$=$OCF_3$, $R^{11}$=H, $R^{12}$=H], [1910; Q=$Q^{q10}$, $A^1$=H, $A^2$=H, $A^3$=H, $A^4$=H, $R^3$=SMe, $R^{11}$=H, $R^{12}$=H], [1911; Q=$Q^{q10}$, $A^1$=H, $A^2$=H, $A^3$=H, $A^4$=H, $R^3$=H, $R^{11}$=Cl, $R^{12}$=H], [1912; Q=$Q^{q10}$, $A^1$=H, $A^2$=H, $A^3$=H, $A^4$=H, $R^3$=H, $R^{11}$=$CF_3$, $R^{12}$=H], [1913; Q=$Q^{q10}$, $A^1$=H, $A^2$=H, $A^3$=H, $A^4$=H, $R^3$=H, $R^{11}$=OMe, $R^{12}$=H], [1914; Q=$Q^{q10}$, $A^1$=H, $A^2$=H, $A^3$=H, $A^4$=H, $R^3$=H, $R^{11}$=$OCF_3$, $R^{12}$=H], [1915; Q=$Q^{q10}$, $A^1$=H, $A^2$=H, $A^3$=H, $A^4$=H, $R^3$=H, $R^{11}$=SMe, $R^{12}$=H], [1916; Q=$Q^{q10}$, $A^1$=H, $A^2$=H, $A^3$=H, $A^4$=H, $R^{11}$=H, $R^{12}$=H], [1917; Q=$Q^{q9}$, $A^1$=H, $A^2$=H, $A^3$=H, $A^4$=H, $R^3$=Cl, $R^{11}$=H, $R^{12}$=H], [1918; Q=$Q^{q11}$, $A^1$=H, $A^2$=H, $A^3$=H, $A^4$=H, $R^3$=$CF_3$, $R^{11}$=H, $R^{12}$=H], [1919; Q=$Q^{q11}$, $A^1$=H, $A^2$=H, $A^3$=H, $A^4$=H, $R^3$=OMe, $R^{11}$=H, $R^{12}$=H], [1920; Q=$Q^{q11}$, $A^1$=H, $A^2$=H, $A^3$=H, $A^4$=H, $R^3$=$OCF_3$, $R^{11}$=H, $R^{12}$=H], [1921; Q=$Q^{q11}$, $A^1$=H, $A^2$=H, $A^3$=H, $A^4$=H, $R^3$=SMe, $R^{11}$=H, $R^{12}$=H], [1922; Q=$Q^{q11}$, $A^1$=H, $A^2$=H, $A^3$=H, $A^4$=H, $R^3$=H, $R^{11}$=Cl, $R^{12}$=H], [1923; Q=$Q^{q11}$, $A^1$=H, $A^2$=H, $A^3$=H, $A^4$=H, $R^3$=H, $R^{11}$=$CF_3$, $R^{12}$=H], [1924; Q=$Q^{q11}$, $A^1$=H, $A^2$=H, $A^3$=H, $A^4$=H, $R^3$=H, $R^{11}$=OMe, $R^{12}$=H], [1925; Q=$Q^{q11}$, $A^1$=H, $A^2$=H, $A^3$=H, $A^4$=H, $R^3$=H, $R^{11}$=$OCF_3$, $R^{12}$=H], [1926; Q=$Q^{q11}$, $A^1$=H, $A^2$=H, $A^3$=H, $A^4$=H, $R^3$=H, $R^{11}$=SMe, $R^{12}$=H], [1927; Q=$Q^{q12}$, $A^3$=H, $A^4$=H, $R^3$=H, $R^{11}$=H, $R^{12}$=H], [1928; Q=$Q^{q12}$, $A^3$=F, $A^4$=F, $R^3$=H, $R^{11}$=H, $R^{12}$=H], [1929; Q=$Q^{q12}$, $A^3$=Cl, $A^4$=Cl, $R^3$=H, $R^{11}$=H, $R^{12}$=H], [1930; Q=$Q^{q12}$, $A^3$=Me, $A^4$=Me, $R^3$=H, $R^{11}$=H, $R^{12}$=H], [1931; Q=$Q^{q2}$, $A^3$=H, $A^4$=H, $R^3$=Cl, $R^{11}$=H, $R^{12}$=H], [1932; Q=$Q^{q12}$, $A^3$=F, $A^4$=F, $R^3$=Cl, $R^{11}$=H, $R^{12}$=H], [1933; Q=$Q^{q12}$, $A^3$=Cl, $A^4$=Cl, $R^3$=Cl, $R^{11}$=H, $R^{12}$=H], [1934; Q=$Q^{q12}$, $A^3$=Me, $A^4$=Me, $R^3$=Cl, $R^{11}$=H, $R^{12}$=H], [1935; Q=$Q^{q12}$, $A^3$=H, $A^4$=H, $R^3$=$CF_3$, $R^{11}$=H, $R^{12}$=H], [1936; Q=$Q^{q12}$, $A^3$=F, $A^4$=F, $R^3$=$CF_3$, $R^{11}$=H, $R^{12}$=H], [1937; Q=$Q^{q12}$, $A^3$=Cl, $A^4$=Cl, $R^3$=$CF_3$, $R^{11}$=H, $R^{12}$=H], [1938; Q=$Q^{q12}$, $A^3$=Me, $A^7$=Me, $R^3$=$CF_3$, $R^{11}$=H, $R^{12}$=H], [1939; Q=$Q^{q12}$, $A^3$=H, $A^4$=H, $R^3$=OMe, $R^{11}$=H, $R^{12}$=H], [1940; Q=$Q^{q12}$, $A^3$=F, $A^4$=F, $R^3$=OMe, $R^{11}$=H, $R^{12}$=H], [1941; Q=$Q^{q12}$, $A^3$=C, $A^4$=Cl, $R^3$=OMe, $R^{11}$=H, $R^{12}$=H], [1942; Q=$Q^{q12}$, $A^3$=Me, $A^4$=Me, $R^3$=OMe, $R^{11}$=H, $R^{12}$=H], [1943; Q=$Q^{q12}$, $A^3$=H, $A^4$=H, $R^3$=H, $R^{11}$=Cl, $R^{12}$=H], [1944; Q=$Q^{q12}$, $A^3$=F, $A^4$=F, $R^3$=H, $R^{11}$=Cl, $R^{12}$=H], [1945; Q=$Q^{q12}$, $A^3$=Cl, $A^4$=Cl, $R^3$=H, $R^{11}$=Cl, $R^{12}$=H], [1946; Q=$Q^{q12}$, $A^3$=Me, $A^4$=Me, $R^3$=H, $R^{11}$=Cl, $R^{12}$=H], [1947; Q=$Q^{q12}$, $A^3$=H, $A^4$=H, $R^3$=H, $R^{11}$=$CF_3$, $R^{12}$=H], [1948; Q=$Q^{q12}$, $A^3$=F, $A^4$=F, $R^3$=H, $R^{11}$=$CF_3$, $R^{12}$=H], [1949; Q=$Q^{q12}$, $A^3$=Cl, $A^4$=Cl, $R^3$=H, $R^{11}$=$CF_3$, $R^{12}$=H], [1950; Q=$Q^{q12}$, $A^3$=Me, $A^7$=Me, $R^3$=H, $R^{11}$=$CF_3$, $R^{12}$=H], [1951; Q=$Q^{q12}$, $A^3$=H, $A^4$=H, $R^3$=H, $R^{11}$=OMe, $R^{12}$=H], [1952; Q=$Q^{q2}$, $A^3$=F, $A^4$=F, $R^3$=H, $R^{11}$=OMe, $R^{12}$=H], [1953; Q=$Q^{q12}$, $A^3$=Cl, $A^4$=Cl, $R^3$=H, $R^{11}$=OMe, $R^{12}$=H], [1954; Q=$Q^{q12}$, $A^3$=Me, $A^4$=Me, $R^3$=H, $R^{11}$=OMe, $R^{12}$=H], [1955; Q=$Q^{q13}$, $A^1$=H, $A^2$=H, $A^5$=H, $A^6$=H, $R^3$=H, $R^{11}$=H,

R$^{12}$=H], [1956; Q=Q$^{q14}$, A$^1$=H, A$^2$=H, A$^5$=H, A$^6$=H, R$^3$=H, R$^{11}$=H, R$^{12}$=H], [1957; Q=Q$^{q15}$, A$^1$=H, A$^2$=H, A$^7$=Me, R$^3$=H, R$^{11}$=H, R$^{12}$=H], [1958; Q=Q$^{q16}$, A$^1$=H, A$^2$=H, A$^8$=Me, R$^3$=H, R$^{11}$=H, R$^{12}$=H], [1959; Q=Q$^{q17}$, A$^1$=H, A$^2$=H, R$^3$=H, R$^{11}$=H, R$^{12}$=H], [1960; Q=Q$^{q18}$, A$^1$=H, A$^2$=H, R$^3$=H, R$^{11}$=H, R$^{12}$=H], [1961; Q=Q$^{q19}$, A$^1$=H, A$^2$=H, A$^8$=Me, R$^3$=H, R$^{11}$=H, R$^{12}$=H], [1962; Q=Q$^{q20}$, A$^1$=H, A$^2$=H, A$^8$=Me, R$^3$=H, R$^{11}$=H, R$^{12}$=H], [1963; Q=Q$^{q21}$, A$^1$=H, A$^3$=H, A$^5$=H, A$^6$=H, R$^3$=H, R$^{11}$=H, R$^{12}$=H], [1964; Q=Q$^{q21}$, A$^1$=H, A$^3$=Me, A$^5$=H, A$^6$=H, R$^3$=H, R$^{11}$=H, R$^{12}$=H], [1965; Q=Q$^{q21}$, A$^1$=H, A$^3$=H, A$^5$=F, A$^6$=F, R$^3$=H, R$^{11}$=H, R$^{12}$=H], [1966; Q=Q$^{q21}$, A$^1$=H, A$^3$=Me, A$^5$=F, A$^6$=F, R$^3$=H, R$^{11}$=H, R$^{12}$=H], [1967; Q=Q$^{q21}$, A$^1$=H, A$^3$=H, A$^5$=H, A$^6$=H, R$^3$=Cl, R$^{11}$=H, R$^{12}$=H], [1968; Q=Q$^{q21}$, A$^1$=H, A$^3$=Me, A$^5$=H, A$^6$=H, R$^3$=Cl, R$^{11}$=H, R$^{12}$=H], [1969; Q=Q$^{q21}$, A$^1$=H, A$^3$=H, A$^5$=F, A$^6$=F, R$^3$=Cl, R$^{11}$=H, R$^{12}$=H], [1970; Q=Q$^{q21}$, A$^1$=H, A$^3$=Me, A$^5$=F, A$^6$=F, R$^3$=C, R$^{11}$=H, R$^{12}$=H], [1971; Q=Q$^{q21}$, A$^1$=H, A$^3$=H, A$^5$=H, A$^6$=H, R$^3$=OMe, R$^{11}$=H, R$^{12}$=H], [1972; Q=Q$^{q21}$, A$^1$=H, A$^3$=Me, A$^5$=H, A$^6$=H, R$^3$=OMe, R$^{11}$=H, R$^{12}$=H], [1973; Q=Q$^{q21}$, A$^1$=H, A$^3$=H, A$^5$=F, A$^6$=F, R$^3$=OMe, R$^{11}$=H, R$^{12}$=H], [1974; Q=Q$^{q21}$, A$^1$=H, A$^3$=Me, A$^5$=F, A$^6$=F, R$^3$=OMe, R$^{11}$=H, R$^{12}$=H], [1975; Q=Q$^{q21}$, A$^1$=H, A$^3$=H, A$^5$=H, A$^6$=H, R$^3$=CF$_3$, R$^{11}$=H, R$^{12}$=H], [1976; Q=Q$^{q21}$, A$^1$=H, A$^3$=Me, A$^5$=H, A$^6$=H, R$^3$=CF$_3$, R$^{11}$=H, R$^{12}$=H], [1977; Q=Q$^{q21}$, A$^1$=H, A$^3$=H, A$^5$=F, A$^6$=F, R$^3$=CF$_3$, R$^{11}$=H, R$^{12}$=H], [1978; Q=Q$^{q21}$, A$^1$=H, A$^3$=Me, A$^5$=F, A$^6$=F, R$^3$=CF$_3$, R$^{11}$=H, R$^{12}$=H], [1979; Q=Q$^{q21}$, A$^1$=H, A$^3$=H, A$^5$=H, A$^6$=H, R$^3$=SMe, R$^{11}$=H, R$^{12}$=H], [1980; Q=Q$^{q21}$, A$^1$=H, A$^3$=Me, A$^5$=H, A$^6$=H, R$^3$=SMe, R$^{11}$=H, R$^{12}$=H], [1981; Q=Q$^{q21}$, A$^1$=H, A$^3$=H, A$^5$=F, A$^6$=F, R$^3$=SMe, R$^{11}$=H, R$^{12}$=H], [1982; Q=Q$^{q21}$, A$^1$=H, A$^3$=Me, A$^5$=F, A$^6$=F, R$^3$=SMe, R$^{11}$=H, R$^{12}$=H], [1983; Q=Q$^{q22}$, A$^1$=H, A$^3$=H, A$^7$=Me, R$^3$=H, R$^{11}$=H, R$^{12}$=H], [1984; Q=Q$^{q22}$, A$^1$=H, A$^3$=Me, A$^7$=Me, R$^3$=H, R$^{11}$=H, R$^{12}$=H], [1985; Q=Q$^{q22}$, A$^1$=H, A$^3$=H, A$^7$=Me, R$^3$=Cl, R$^{11}$=H, R$^{12}$=H], [1986; Q=Q$^{q22}$, A$^1$=H, A$^3$=Me, A$^7$=Me, R$^3$=Cl, R$^{11}$=H, R$^{12}$=H], [1987; Q=Q$^{q22}$, A$^1$=H, A$^3$=H, A$^7$=Me, R$^3$=OMe, R$^{11}$=H, R$^{12}$=H], [1988; Q=Q$^{q22}$, A$^1$=H, A$^3$=Me, A$^7$=Me, R$^3$=OMe, R$^{11}$=H, R$^{12}$=H], [1989; Q=Q$^{q22}$, A$^1$=H, A$^3$=H, A$^7$=Me, R$^3$=CF$_3$, R$^{11}$=H, R$^{12}$=H], [1990; Q=Q$^{q22}$, A$^1$=H, A$^3$=Me, A$^7$=Me, R$^3$=CF$_3$, R$^{11}$=H, R$^{12}$=H], [1991; Q=Q$^{q22}$, A$^1$=H, A$^3$=H, A$^7$=Me, R$^3$=SMe, R$^{11}$=H, R$^{12}$=H], [1992; Q=Q$^{q22}$, A$^1$=H, A$^3$=Me, A$^7$=Me, R$^3$=SMe, R$^{11}$=H, R$^{12}$=H], [1993; Q=Q$^{q22}$, A$^1$=H, A$^3$=H, A$^7$=Me, R$^3$=H, R$^{11}$=Cl, R$^{12}$=H], [1994; Q=Q$^{q22}$, A$^1$=H, A$^3$=Me, A$^7$=Me, R$^3$=H, R$^{11}$=Cl, R$^{12}$=H], [1995; Q=Q$^{q22}$, A$^1$=H, A$^3$=H, A$^7$=Me, R$^3$=H, R$^{11}$=OMe, R$^{12}$=H], [1996; Q=Q$^{q22}$, A$^1$=H, A$^3$=Me, A$^7$=Me, R$^3$=H, R$^{11}$=OMe, R$^{12}$=H], [1997; Q=Q$^{q22}$, A$^1$=H, A$^3$=H, A$^7$=Me, R$^3$=H, R$^{11}$=CF$_3$, R$^{12}$=H], [1998; Q=Q$^{q22}$, A$^1$=H, A$^3$=Me, A$^7$=Me, R$^3$=H, R$^{11}$=CF$_3$, R$^{12}$=H], [1999; Q=Q$^{q22}$, A$^1$=H, A$^3$=H, A$^7$=Me, R$^3$=H, R$^{11}$=SMe, R$^{12}$=H], [2000; Q=Q$^{q22}$, A$^1$=H, A$^3$=Me, A$^7$=Me, R$^3$=H, R$^{11}$=SMe, R$^{12}$=H], [2001; Q=Q$^{q23}$, A$^1$=H, R$^3$=H, R$^{11}$=H, R$^{12}$=H], [2002; Q=Q$^{q23}$, A$^1$=H, R$^3$=Cl, R$^{11}$=H, R$^{12}$=H], [2003; Q=Q$^{q23}$, A$^1$=H, R$^3$=OMe, R$^{11}$=H, R$^{12}$=H], [2004; Q=Q$^{q23}$, A$^1$=H, R$^3$=CF$_3$, R$^{11}$=H, R$^{12}$=H], [2005; Q=Q$^{q23}$, A$^1$=H, R$^3$=SMe, R$^{11}$=H, R$^{12}$=H], [2006; Q=Q$^{q23}$, A$^1$=H, R$^3$=H, R$^{11}$=Cl, R$^{12}$=H], [2007; Q=Q$^{q23}$, A$^1$=H, R$^3$=H, R$^{11}$=OMe, R$^{12}$=H], [2008; Q=Q$^{q23}$, A$^1$=H, R$^3$=H, R$^{11}$=CF$_3$, R$^{12}$=H], [2009; Q=Q$^{q23}$, A$^1$=H, R$^3$=H, R$^{11}$=SMe, R$^{12}$=H], [2010; Q=Q$^{q24}$, A$^1$=H, A$^7$=Me, R$^3$=H, R$^{11}$=H, R$^{12}$=H], [2011; Q=Q$^{q24}$, A$^1$=H, A$^7$=Me, R$^3$=Cl, R$^{11}$=H, R$^{12}$=H], [2012; Q=Q$^{q24}$, A$^1$=H, A$^7$=Me, R$^3$=OMe, R$^{11}$=H, R$^{12}$=H], [2013; Q=Q$^{q24}$, A$^1$=H, A$^7$=Me, R$^3$=CF$_3$, R$^{11}$=H, R$^{12}$=H], [2014; Q=Q$^{q24}$, A$^1$=H, A$^7$=Me, R$^3$=SMe, R$^{11}$=H, R$^{12}$=H], [2015; Q=Q$^{q24}$, A$^1$=H, A$^7$=Me, R$^3$=H, R$^{11}$=Cl, R$^{12}$=H], [2016; Q=Q$^{q24}$, A$^1$=H, A$^7$=Me, R$^3$=H, R$^{11}$=OMe, R$^{12}$=H], [2017; Q=Q$^{q24}$, A$^1$=H, A$^7$=Me, R$^3$=H, R$^{11}$=CF$_3$, R$^{12}$=H], [2018; Q=Q$^{q24}$, A$^1$=H, A$^7$=Me, R$^3$=H, R$^{11}$=SMe, R$^{12}$=H], 2019; Q=Q$^{r1}$, A$^9$=H, A$^{10}$=H, A$^{11}$=H, A$^{12}$=H, A$^{13}$=H], [2020; Q=Q$^{r1}$, A$^9$=F, A$^{10}$=H, A$^{11}$=H, A$^{12}$=H, A$^{13}$=H], [2021; Q=Q$^{r1}$, A$^9$=H, A$^{10}$=F, A$^{11}$=H, A$^{12}$=H, A$^{13}$=H], [2022; Q=Q$^{r1}$, A$^9$=H, A$^{10}$=H, A$^{11}$=F, A$^{12}$=H, A$^{13}$=H], [2023; Q=Q$^{r1}$, A$^9$=F, A$^{10}$=F, A$^{11}$=H, A$^{12}$=H, A$^{13}$=H], [2024; Q=Q$^{r1}$, A$^9$=F, A$^{10}$=H, A$^{11}$=F, A$^{12}$=H, A$^{13}$=H], [2025; Q=Q$^{q11}$, A$^9$=F, A$^{10}$=H, A$^{11}$=H, A$^{12}$=H, A$^{13}$=F], [2026; Q=Q$^{r1}$, A$^9$=H, A$^{10}$=F, A$^{11}$=F, A$^{12}$=H, A$^{13}$=H], [2027; Q=Q$^{r1}$, A$^9$=H, A$^{10}$=F, A$^{11}$=H, A$^{12}$=F, A$^{13}$=H], [2028; Q=Q$^{r1}$, A$^9$=Cl, A$^{10}$=H, A$^{11}$=H, A$^{12}$=H, A$^{13}$=H], [2029; Q=Q$^{r1}$, A$^9$=H, A$^{10}$=Cl, A$^{11}$=H, A$^{12}$=H, A$^{13}$=H], [2030; Q=Q$^{r1}$, A$^9$=H, A$^{10}$=H, A$^{11}$=Cl, A$^{12}$=H, A$^{13}$=H], [2031; Q=Q$^{r1}$, A$^9$=Cl, A$^{10}$=Cl, A$^{11}$=H, A$^{12}$=H, A$^{13}$=H], [2032; Q=Q$^{r1}$, A$^9$=Cl, A$^{10}$=H, A$^{11}$=Cl, A$^{12}$=H, A$^{13}$=H], [2033; Q=Q$^{r1}$, A$^9$=Cl, A$^{10}$=H, A$^{11}$=H, A$^{12}$=H, A$^{13}$=Cl], [2034; Q=Q$^{r1}$, A$^9$=H, A$^{10}$=Cl, A$^{11}$=Cl, A$^{12}$=H, A$^{13}$=H], [2035; Q=Q$^{r1}$, A$^9$=H, A$^{10}$=Cl, A$^{11}$=H, A$^{12}$=Cl, A$^{13}$=H], [2036; Q=Q$^{r1}$, A$^9$=CF$_3$, A$^{10}$=H, A$^{11}$=H, A$^{12}$=H, A$^{13}$=H], [2037; Q=Q$^{r1}$, A$^9$=H, A$^{10}$=CF$_3$, A$^{11}$=H, A$^{12}$=H, A$^{13}$=H], [2038; Q=Q$^{r1}$, A$^9$=H, A$^{10}$=H, A$^{11}$=CF$_3$, A$^{12}$=H, A$^{13}$=H], [2039; Q=Q$^{r1}$, A$^9$=CF$_3$, A$^{10}$=CF$_3$, A$^{11}$=H, A$^{12}$=H, A$^{13}$=H], [2040; Q=Q$^{r1}$, A$^9$=CF$_3$, A$^{10}$=H, A$^{11}$=CF$_3$, A$^{12}$=H, A$^{13}$=H], [2041; Q=Q$^{q11}$, A$^9$=CF$_3$, A$^{10}$=H, A$^{11}$=H, A$^{12}$=H, A$^{13}$=CF$_3$], [2042; Q=Q$^{r1}$, A$^9$=H, A$^{10}$=CF$_3$, A$^{11}$=CF$_3$, A$^{12}$=H, A$^{13}$=H], [2043; Q=Q$^{r1}$, A$^9$=H, A$^{10}$=CF$_3$, A$^{11}$=H, A$^{12}$=CF$_3$, A$^{13}$=H], [2044; Q=Q$^{r1}$, A$^9$=OMe, A$^{10}$=H, A$^{11}$=H, A$^{12}$=H, A$^{13}$=H], [2045; Q=Q$^{r1}$, A$^9$=H, A$^{10}$=OMe, A$^{11}$=H, A$^{12}$=H, A$^{13}$=H], [2046; Q=Q$^{r1}$, A$^9$=H, A$^{10}$=H, A$^{11}$=OMe, A$^{12}$=H, A$^{13}$=H], [2047; Q=Q$^{r1}$, A$^9$=OMe, A$^{10}$=OMe, A$^{11}$=H, A$^{12}$=H, A$^{13}$=H], [2048; Q=Q$^{r1}$, A$^9$=OMe, A$^{10}$=H, A$^{11}$=OMe, A$^{12}$=H, A$^{13}$=H], [2049; Q=Q$^{r1}$, A$^9$=OMe, A$^{10}$=H, A$^{11}$=H, A$^1$=H, A$^{13}$=OMe], [2050; Q=Q$^{r1}$, A$^9$=H, A$^{10}$=Me, A$^{11}$=OMe, A$^{12}$=H, A$^{13}$=H], [2051; Q=Q$^{r1}$, A$^9$=H, A$^{10}$=OMe, A$^{11}$=H, A$^{12}$=OMe, A$^{13}$=H], [2052; Q=Q$^{q11}$, A$^9$=H, A$^{10}$=Br, A$^{11}$=H, A$^{12}$=H, A$^{13}$=H], [2053; Q=Q$^{r1}$, A$^9$=H, A$^{10}$=H, A$^{11}$=Br, A$^{12}$=H, A$^{13}$=H], [2054; Q=Q$^{r1}$, A$^9$=Br, A$^{10}$=H, A$^{11}$=H, A$^{12}$=H, A$^{13}$=Br], [2055; Q=Q$^{r1}$, A$^9$=H, A$^{10}$=Me, A$^{11}$=H, A$^{12}$=H, A$^{13}$=H], [2056; Q=Q$^{r1}$, A$^9$=H, A$^{10}$=H, A$^{11}$=Me, A$^{12}$=H, A$^{13}$=H], [2057; Q=Q$^{r1}$, A$^9$=Me, A$^{10}$=H, A$^{11}$=H, A$^{12}$=H, A$^{13}$=Me], [2058; Q=Q$^{r1}$, A$^9$=H, A$^{10}$=cyclopropyl, A$^{11}$=H, A$^{12}$=H, A$^{13}$=H], [2059; Q=Q$^{r1}$, A$^9$=H, A$^{10}$=H, A$^{11}$=cyclopropyl, A$^{12}$=H, A$^{13}$=H], [2060; Q=Q$^{r1}$, A$^7$=cyclopropyl, A$^{10}$=H, A$^{11}$=H, A$^{12}$=H, A$^{13}$=cyclopropyl], [2061; Q=Q$^{r1}$, A$^9$=H, A$^{10}$=OCHF$_2$, A$^{11}$=H, A$^{12}$=H, A$^{13}$=H], [2062; Q=Q$^{r1}$, A$^9$=H, A$^{10}$=H, A$^{11}$=OCHF$_2$, A$^{12}$=H, A$^{13}$=H], [2063; Q=Q$^{r1}$, A$^9$=H, A$^{10}$=OCF$_3$, A$^{11}$=H, A$^{12}$=H, A$^{13}$=H], [2064; Q=Q$^{r1}$, A$^9$=H, A$^{10}$=H, A$^{11}$=OCF$_3$, A$^{12}$=H, A$^{13}$=H], [2065; Q=Q$^{r2}$, A$^9$=H, A$^{10}$=H, A$^{11}$=H, A$^{12}$=H, A$^{13}$=H], [2066; Q=Q$^{r2}$, A$^9$=F, A$^{10}$=H, A$^{11}$=H, A$^{12}$=H, A$^{13}$=H], [2067; Q=Q$^{r2}$, A$^9$=H, A$^{10}$=F, A$^{11}$=H, A$^{12}$=H, A$^{13}$=H], [2068; Q=Q$^{r2}$, A$^9$=H, A$^{10}$=H, A$^{11}$=F, A$^{12}$=H, A$^{13}$=H], [2069; Q=Q$^{r2}$, A$^9$=F, A$^{10}$=F, A$^{11}$=H, A$^{12}$=H, A$^{13}$=H], [2070; Q=Q$^{r2}$, A$^9$=F, A$^{10}$=H, A$^{11}$=F, A$^{12}$=H, A$^{13}$=H], [2071; Q=Q$^{r2}$, A$^9$=F, A$^{10}$=H, A$^{11}$=H, A$^{12}$=H, A$^{13}$=F], [2072; Q=Q$^{r2}$, A$^9$=H, A$^{10}$=F, A$^1$=F, A$^{12}$=H, A$^{13}$=H], [2073; Q=Q$^{r2}$, A$^9$=H, A$^1$=F, A$^{11}$=H, A$^{12}$=F, A$^{13}$=H], [2074; Q=Q$^{r2}$, A$^9$=Cl, A$^{10}$=H, A$^{11}$=H, A$^{12}$=H, A$^{13}$=H], [2075; Q=Q$^{r2}$, A$^9$=H, A$^{10}$=Cl, A$^{11}$=H, A$^{12}$=H, A$^{13}$=H], [2076; Q=Q$^{r2}$, A$^9$=H, A$^{10}$=H, A$^{11}$=Cl, A$^{12}$=H, A$^{13}$=H], [2077; Q=Q$^{r2}$, A$^9$=Cl, A$^{10}$=H, A$^{11}$=Cl, A$^{12}$=H, A$^{13}$=H], [2078; Q=Q$^{r2}$, A$^9$=Cl, A$^{10}$=H, A$^{11}$=H, A$^{12}$=H, A$^{13}$=Cl], [2079; Q=Q$^{r2}$, A$^9$=H, A$^{10}$=Cl, A$^{11}$=Cl, A$^{12}$=H, A$^{13}$=H], [2080; Q=Q$^{r2}$, A$^9$=H, A$^{10}$=Cl, A$^{11}$=Cl, A$^{12}$=H, A$^{13}$=H], [2081; Q=Q$^{r2}$, A$^9$=H, $A^{10}$=Cl, $A^{11}$=H, $A^{12}$=Cl, $A^{13}$=H], [2082; Q=$Q^{r2}$, $A^{9}$=CF$_3$, $A^{10}$=H, $A^{11}$=H, $A^{12}$=H, $A^{13}$=H], [2083; Q=$Q^{r2}$, $A^{9}$=H, $A^{10}$=CF$_3$, $A^{11}$=H, $A^{12}$=H, $A^{13}$=H], [2084; Q=$Q^{r2}$, $A^{9}$=H, $A^{10}$=H, $A^{11}$=CF$_3$, $A^{12}$=H, $A^{13}$=H], [2085; Q=$Q^{r2}$, $A^{9}$=CF$_3$, $A^{10}$=CF$_3$, $A^{11}$=H, $A^{12}$=H, $A^{13}$=H], [2086; Q=$Q^{r2}$, $A^{9}$=CF$_3$, $A^{10}$=H, $A^{11}$=CF$_3$, $A^{12}$=H, $A^{13}$=H], [2087; Q=$Q^{r2}$, $A^{9}$=CF$_3$, $A^{10}$=H, $A^{11}$=H, $A^{12}$=H, $A^{13}$=CF$_3$], [2088; Q=$Q^{r2}$, $A^{9}$=H, $A^{10}$=CF$_3$, $A^{1}$=CF$_3$, $A^{12}$=H, $A^{13}$=H], [2089; Q=$Q^{r2}$, $A^{9}$=H, $A^{10}$=CF$_3$, $A^{11}$=H, $A^{12}$=CF$_3$, $A^{13}$=H], [2090; Q=$Q^{r2}$, $A^{9}$=OMe, $A^{10}$=H, $A^{11}$=H, $A^{12}$=H, $A^{13}$=H], [2091; Q=$Q^{r2}$, $A^{9}$=H, $A^{10}$=OMe, $A^{11}$=H, $A^{12}$=H, $A^{13}$=H], [2092; Q=$Q^{r2}$, $A^{9}$=H, $A^{10}$=H, $A^{11}$=OMe, $A^{12}$=H, $A^{13}$=H], [2093; Q=$Q^{r2}$, $A^{9}$=OMe, $A^{10}$=OMe, $A^{11}$=H, $A^{12}$=H, $A^{13}$=H], [2094; Q=$Q^{r2}$, $A^{9}$=OMe, $A^{10}$=H, $A^{11}$=OMe, $A^{12}$=H, $A^{13}$=H], [2095; Q=$Q^{r2}$, $A^{9}$=OMe, $A^{10}$=H, $A^{11}$=H, $A^{12}$=H, $A^{13}$=OMe], [2096; Q=$Q^{r2}$, $A^{9}$=H, $A^{10}$=OMe, $A^{11}$=OMe, $A^{12}$=H, $A^{13}$=H], [2097; Q=$Q^{r2}$, $A^{9}$=H, $A^{10}$=OMe, $A^{1}$=H, $A^{12}$=OMe, $A^{13}$=H], [2098; Q=$Q^{r2}$, $A^{9}$=H, $A^{10}$=Br, $A^{11}$=H, $A^{12}$=H, $A^{13}$=H], [2099; Q=$Q^{r2}$, $A^{9}$=H, $A^{10}$=H, $A^{11}$=Br, $A^{12}$=H, $A^{13}$=H], [2100; Q=$Q^{r2}$, $A^{1}$=Br, $A^{10}$=H, $A^{11}$=H, $A^{12}$=H, $A^{13}$=Br], [2101; Q=$Q^{r2}$, $A^{9}$=H, $A^{10}$=Me, $A^{11}$=H, $A^{12}$=H, $A^{13}$=H], [2102; Q=$Q^{r2}$, $A^{9}$=H, $A^{10}$=H, $A^{11}$=Me, $A^{12}$=H, $A^{13}$=H], [2103; Q=$Q^{r2}$, $A^{9}$=Me, $A^{10}$=H, $A^{11}$=H, $A^{12}$=H, $A^{13}$=Me], [2104; Q=$Q^{r2}$, $A^{9}$=H, $A^{10}$=cyclopropyl, $A^{11}$=H, $A^{12}$=H, $A^{13}$=H], [2105; Q=$Q^{r2}$, $A^{9}$=H, $A^{10}$=H, $A^{11}$=cyclopropyl, $A^{12}$=H, $A^{13}$=H], [2106; Q=$Q^{r2}$, $A^{9}$=cyclopropyl, $A^{10}$=H, $A^{11}$=H, $A^{12}$=H, $A^{13}$=cyclopropyl], [2107; Q=$Q^{r2}$, $A^{1}$=H, $A^{10}$=OCHF$_2$, $A^{11}$=H, $A^{12}$=H, $A^{13}$=H], [2108; Q=$Q^{r2}$, $A^{9}$=H, $A^{10}$=H, $A^{11}$=OCHF$_2$, $A^{12}$=H, $A^{13}$=H], [2109; Q=$Q^{r2}$, $A^{9}$=H, $A^{10}$=OCF$_3$, $A^{11}$=H, $A^{12}$=H, $A^{13}$=H], [2110; Q=$Q^{r2}$, $A^{9}$=H, $A^{10}$=H, $A^{11}$=OCF$_3$, $A^{12}$=H, $A^{13}$=H], [2111; Q=$Q^{r3}$, $A^{9}$=H, $A^{10}$=H, $A^{11}$=H, $A^{12}$=H, $A^{3}$=H], [2112; Q=$Q^{r3}$, $A^{9}$=F, $A^{10}$=H, $A^{11}$=H, $A^{12}$=H, $A^{13}$=H], [2113; Q=$Q^{q11}$, $A^{9}$=H, $A^{10}$=F, $A^{11}$=H, $A^{12}$=H, $A^{13}$=H], [2114; Q=$Q^{r3}$, $A^{9}$=H, $A^{10}$=H, $A^{11}$=F, $A^{12}$=H, $A^{13}$=H], [2115; Q=$Q^{r3}$, $A^{9}$=F, $A^{10}$=F, $A^{11}$=H, $A^{12}$=H, $A^{13}$=H], [2116; Q=$Q^{r3}$, $A^{9}$=F, $A^{10}$=H, $A^{11}$=F, $A^{12}$=H, $A^{13}$=H], [2117; Q=$Q^{r3}$, $A^{9}$=F, $A^{10}$=H, $A^{11}$=H, $A^{12}$=H, $A^{13}$=F], [2118; Q=$Q^{r3}$, $A^{9}$=H, $A^{10}$=F, $A^{11}$=F, $A^{12}$=H, $A^{13}$=H], [2119; Q=$Q^{r3}$, $A^{9}$=H, $A^{10}$=F, $A^{1}$=H, $A^{12}$=F, $A^{13}$=H], [2120; Q=$Q^{r3}$, $A^{9}$=Cl, $A^{10}$=H, $A^{11}$=H, $A^{12}$=H, $A^{13}$=H], [2121; Q=$Q^{r3}$, $A^{9}$=H, $A^{10}$=Cl, $A^{11}$=H, $A^{12}$=H, $A^{13}$=H], [2122; Q=$Q^{r3}$, $A^{9}$=H, $A^{10}$=H, $A^{11}$=Cl, $A^{12}$=H, $A^{13}$=H], [2123; Q=$Q^{q11}$, $A^{9}$=Cl, $A^{10}$=Cl, $A^{11}$=H, $A^{12}$=H, $A^{13}$=H], [2124; Q=$Q^{r3}$, $A^{9}$=Cl, $A^{10}$=H, $A^{11}$=Cl, $A^{12}$=H, $A^{13}$=H], [2125; Q=$Q^{r3}$, $A^{9}$=Cl, $A^{10}$=H, $A^{11}$=H, $A^{12}$=H, $A^{13}$=Cl], [2126; Q=$Q^{r3}$, $A^{9}$=H, $A^{10}$=Cl, $A^{11}$=Cl, $A^{12}$=H, $A^{13}$=H], [2127; Q=$Q^{r3}$, $A^{9}$=H, $A^{10}$=Cl, $A^{11}$=H, $A^{12}$=Cl, $A^{13}$=H], [2128; Q=$Q^{r3}$, $A^{9}$=CF$_3$, $A^{10}$=H, $A^{11}$=H, $A^{12}$=H, $A^{13}$=H], [2129; Q=$Q^{r3}$, $A^{9}$=H, $A^{10}$=CF$_3$, $A^{11}$=H, $A^{12}$=H, $A^{13}$=H], [2130; Q=$Q^{r3}$, $A^{9}$=H, $A^{10}$=H, $A^{11}$=CF$_3$, $A^{12}$=H, $A^{13}$=H], [2131; Q=$Q^{r3}$, $A^{9}$=CF$_3$, $A^{10}$=CF$_3$, $A^{1}$=H, $A^{12}$=H, $A^{13}$=H], [2132; Q=$Q^{r3}$, $A^{9}$=CF$_3$, $A^{10}$=H, $A^{11}$=CF$_3$, $A^{12}$=H, $A^{13}$=H], [2133; Q=$Q^{r3}$, $A^{9}$=CF$_3$, $A^{10}$=H, $A^{11}$=H, $A^{12}$=H, $A^{13}$=CF$_3$], [2134; Q=$Q^{r3}$, $A^{9}$=H, $A^{10}$=CF$_3$, $A^{11}$=CF$_3$, $A^{12}$=H, $A^{13}$=H], [2135; Q=$Q^{r3}$, $A^{9}$=H, $A^{10}$=CF$_3$, $A^{11}$=H, $A^{12}$=CF$_3$, $A^{13}$=H], [2136; Q=$Q^{r3}$, $A^{9}$=OMe, $A^{10}$=H, $A^{11}$=H, $A^{12}$=H, $A^{13}$=H], [2137; Q=$Q^{r3}$, $A^{9}$=H, $A^{10}$=OMe, $A^{11}$=H, $A^{12}$=H, $A^{13}$=H], [2138; Q=$Q^{r3}$, $A^{9}$=H, $A^{10}$=H, $A^{11}$=OMe, $A^{12}$=H, $A^{13}$=H], [2139; Q=$Q^{r3}$, $A^{9}$=OMe, $A^{10}$=OMe, $A^{11}$=H, $A^{12}$=H, $A^{13}$=H], [2140; Q=$Q^{r3}$, $A^{9}$=OMe, $A^{10}$=H, $A^{11}$=OMe, $A^{12}$=H, $A^{13}$=H], [2141; Q=$Q^{r3}$, $A^{9}$=OMe, $A^{10}$=H, $A^{11}$=H, $A^{12}$=H, $A^{13}$=OMe], [2142; Q=$Q^{r3}$, $A^{9}$=H, $A^{10}$=OMe, $A^{1}$=OMe, $A^{12}$=H, $A^{13}$=H], [2143; Q=$Q^{r3}$, $A^{9}$=H, $A^{10}$=OMe, $A^{11}$=H, $A^{12}$=OMe, $A^{13}$=H], [2144; Q=$Q^{r3}$, $A^{9}$=H, $A^{10}$=Br, $A^{11}$=H, $A^{12}$=H, $A^{13}$=H], [2145; Q=$Q^{r3}$, $A^{9}$=H, $A^{10}$=H, $A^{11}$=Br, $A^{12}$=H, $A^{13}$=H], [2146; Q=$Q^{r3}$, $A^{9}$=Br, $A^{10}$=H, $A^{11}$=H, $A^{12}$=H, $A^{13}$=Br], [2147; Q=$Q^{r3}$, $A^{9}$=H, $A^{10}$=Me, $A^{11}$=H, $A^{12}$=H, $A^{13}$=H], [2148; Q=$Q^{r3}$, $A^{9}$=H, $A^{10}$=H, $A^{11}$=Me, $A^{12}$=H, $A^{13}$=H], [2149; Q=$Q^{r3}$, $A^{9}$=Me, $A^{10}$=H, $A^{11}$=H, $A^{12}$=H, $A^{13}$=Me], [2150; Q=$Q^{r3}$, $A^{9}$=H, $A^{11}$=cyclopropyl, $A^{11}$=H, $A^{12}$=H, $A^{13}$=H], [2151; Q=$Q^{r3}$, $A^{9}$=H, $A^{10}$=H, $A^{7}$=cyclopropyl, $A^{12}$=H, $A^{13}$=H], [2152; Q=$Q^{r3}$, $A^{7}$=cyclopropyl, $A^{10}$=H, $A^{11}$=H, $A^{12}$=H, $A^{13}$=cyclopropyl], [2153; Q=$Q^{r3}$, $A^{9}$=H, $A^{10}$=OCHF$_2$, $A^{11}$=H, $A^{12}$=H, $A^{13}$=H], [2154; Q=$Q^{r3}$, $A^{9}$=H, $A^{10}$=H, $A^{11}$=OCHF$_2$, $A^{12}$=H, $A^{13}$=H], [2155; Q=$Q^{r3}$, $A^{9}$=H, $A^{10}$=OCF$_3$, $A^{11}$=H, $A^{12}$=H, $A^{13}$=H], [2156; Q=$Q^{r3}$, $A^{9}$=H, $A^{10}$=H, $A^{11}$=OCF$_3$, $A^{12}$=H, $A^{13}$=H], [2157; Q=$Q^{r4}$, $A^{9}$=H, $A^{10}$=H, $A^{11}$=H, $A^{12}$=H, $A^{13}$=H], [2158; Q=$Q^{r4}$, $A^{9}$=F, $A^{10}$=H, $A^{11}$=H, $A^{12}$=H, $A^{13}$=H], [2159; Q=$Q^{r4}$, $A^{9}$=H, $A^{10}$=F, $A^{11}$=H, $A^{12}$=H, $A^{13}$=H], [2160; Q=$Q^{r4}$, $A^{9}$=H, $A^{10}$=H, $A^{11}$=F, $A^{12}$=H, $A^{13}$=H], [2161; Q=$Q^{r4}$, $A^{9}$=F, $A^{10}$=F, $A^{11}$=H, $A^{12}$=H, $A^{13}$=H], [2162; Q=$Q^{r4}$, $A^{9}$=F, $A^{10}$=H, $A^{11}$=F, $A^{12}$=H, $A^{13}$=H], [2163; Q=$Q^{r4}$, $A^{9}$=F, $A^{10}$=H, $A^{11}$=H, $A^{12}$=H, $A^{13}$=F], [2164; Q=$Q^{r4}$, $A^{9}$=H, $A^{10}$=F, $A^{11}$=F, $A^{12}$=H, $A^{13}$=H], [2165; Q=$Q^{r4}$, $A^{9}$=H, $A^{10}$=F, $A^{11}$=H, $A^{12}$=F, $A^{13}$=H], [2166; Q=$Q^{r4}$, $A^{9}$=Cl, $A^{10}$=H, $A^{11}$=H, $A^{12}$=H, $A^{13}$=H], [2167; Q=$Q^{r4}$, $A^{9}$=H, $A^{10}$=Cl, $A^{11}$=H, $A^{12}$=H, $A^{13}$=H], [2168; Q=$Q^{r4}$, $A^{9}$=H, $A^{10}$=H, $A^{11}$=Cl, $A^{12}$=H, $A^{13}$=H], [2169; Q=$Q^{r4}$, $A^{9}$=Cl, $A^{10}$=Cl, $A^{11}$=H, $A^{12}$=H, $A^{13}$=H], [2170; Q=$Q^{r4}$, $A^{9}$=Cl, $A^{10}$=H, $A^{11}$=Cl, $A^{12}$=H, $A^{13}$=H], [2171; Q=$Q^{r4}$, $A^{9}$=Cl, $A^{10}$=H, $A^{11}$=H, $A^{12}$=H, $A^{13}$=Cl], [2172; Q=$Q^{r4}$, $A^{9}$=H, $A^{10}$=Cl, $A^{11}$=Cl, $A^{12}$=H, $A^{13}$=H], [2173; Q=$Q^{r4}$, $A^{9}$=H, $A^{1}$=Cl, $A^{1}$=H, $A^{2}$=Cl, $A^{13}$=H], [2174; Q=$Q^{r4}$, $A^{9}$=CF$_3$, $A^{10}$=H, $A^{11}$=H, $A^{12}$=H, $A^{13}$=H], [2175; Q=$Q^{r4}$, $A^{9}$=H, $A^{10}$=CF$_3$, $A^{11}$=H, $A^{12}$=H, $A^{13}$=H], [2176; Q=$Q^{r4}$, $A^{9}$=H, $A^{10}$=H, $A^{11}$=CF$_3$, $A^{12}$=H, $A^{13}$=H], [2177; Q=$Q^{q11}$, $A^{9}$=CF$_3$, $A^{10}$=CF$_3$, $A^{11}$=H, $A^{12}$=H, $A^{13}$=H], [2178; Q=$Q^{r4}$, $A^{9}$=CF$_3$, $A^{10}$=H, $A^{11}$=CF$_3$, $A^{12}$=H, $A^{13}$=H], [2179; Q=$Q^{r4}$, $A^{9}$=CF$_3$, $A^{10}$=H, $A^{11}$=H, $A^{12}$=H, $A^{13}$=CF$_3$], [2180; Q=$Q^{r4}$, $A^{9}$=H, $A^{10}$=CF$_3$, $A^{11}$=CF$_3$, $A^{12}$=H, $A^{13}$=H], [2181; Q=$Q^{r4}$, $A^{9}$=H, $A^{10}$=CF$_3$, $A^{11}$=H, $A^{12}$=CF$_3$, $A^{13}$=H], [2182; Q=$Q^{r4}$, $A^{9}$=OMe, $A^{10}$=H, $A^{11}$=H, $A^{12}$=H, $A^{13}$=H], [2183; Q=$Q^{r4}$, $A^{9}$=H, $A^{10}$=OMe, $A^{11}$=H, $A^{12}$=H, $A^{13}$=H], [2184; Q=$Q^{r4}$, $A^{9}$=H, $A^{10}$=H, $A^{11}$=OMe, $A^{12}$=H, $A^{13}$=H], [2185; Q=$Q^{r4}$, $A^{9}$=OMe, $A^{10}$=OMe, $A^{11}$=H, $A^{12}$=H, $A^{13}$=H], [2186; Q=$Q^{r4}$, $A^{9}$=OMe, $A^{10}$=H, $A^{11}$=OMe, $A^{12}$=H, $A^{13}$=H], [2187; Q=$Q^{r1}$, $A^{9}$=OMe, $A^{10}$=H, $A^{11}$=H, $A^{12}$=H, $A^{13}$=OMe], [2188; Q=$Q^{r4}$, $A^{9}$=H, $A^{10}$=OMe, $A^{1}$=OMe, $A^{12}$=H, $A^{13}$=H], [2189; Q=$Q^{r4}$, $A^{9}$=H, $A^{10}$=OMe, $A^{11}$=H, $A^{12}$=OMe, $A^{13}$=H], [2190; Q=$Q^{r4}$, $A^{9}$=H, $A^{10}$=Br, $A^{11}$=H, $A^{12}$=H, $A^{13}$=H], [2191; Q=$Q^{r4}$, $A^{9}$=H, $A^{10}$=H, $A^{11}$=Br, $A^{12}$=H, $A^{13}$=H], [2192; Q=$Q^{r4}$, $A^{9}$=Br, $A^{10}$=H, $A^{11}$=H, $A^{12}$=H, $A^{13}$=Br], [2193; Q=$Q^{r4}$, $A^{9}$=H, $A^{10}$=Me, $A^{11}$=H, $A^{12}$=H, $A^{13}$=H], [2194; Q=$Q^{r4}$, $A^{9}$=H, $A^{10}$=H, $A^{11}$=Me, $A^{12}$=H, $A^{13}$=H], [2195; Q=$Q^{r4}$, $A^{9}$=Me, $A^{10}$=H, $A^{11}$=H, $A^{12}$=H, $A^{13}$=Me], [2196; Q=$Q^{r1}$, $A^{9}$=H, $A^{11}$=cyclopropyl, $A^{11}$=H, $A^{12}$=H, $A^{13}$=H], [2197; Q=$Q^{r4}$, $A^{9}$=H, $A^{10}$=H, $A^{7}$=cyclopropyl, $A^{12}$=H, $A^{13}$=H], [2198; Q=$Q^{r4}$, $A^{9}$=cyclopropyl, $A^{10}$=H, $A^{11}$=H, $A^{12}$=H, $A^{13}$=cyclopropyl], [2199; Q=$Q^{r4}$, $A^{9}$=H, $A^{10}$=OCHF$_2$, $A^{11}$=H, $A^{12}$=H, $A^{13}$=H], [2200; Q=$Q^{r4}$, $A^{9}$=H, $A^{10}$=H, $A^{11}$=OCHF$_2$, $A^{12}$=H, $A^{13}$=H], [2201; Q=$Q^{r4}$, $A^{9}$=H, $A^{10}$=OCF$_3$, $A^{11}$=H, $A^{12}$=H, $A^{13}$=H], [2202; Q=$Q^{r4}$, $A^{9}$=H, $A^{10}$=H, $A^{11}$=OCF$_3$, $A^{12}$=H, $A^{13}$=H], [2203; Q=$Q^{r5}$, $A^{9}$=H, $A^{10}$=H, $A^{11}$=H, $A^{12}$=H, $A^{13}$=H], [2204; Q=$Q^{r5}$, $A^{9}$=F, $A^{10}$=H, $A^{11}$=H, $A^{12}$=H, $A^{13}$=H], [2205; Q=$Q^{r5}$, $A^{9}$=H, $A^{10}$=F, $A^{11}$=H, $A^{12}$=H, $A^{13}$=H], [2206; Q=$Q^{r5}$, $A^{9}$=H, $A^{10}$=H, $A^{11}$=F, $A^{12}$=H, $A^{13}$=H], [2207; Q=$Q^{r5}$, $A^{9}$=F, $A^{10}$=F, $A^{11}$=H, $A^{12}$=H, $A^{13}$=H], [2208; Q=$Q^{r5}$, $A^{9}$=F, $A^{10}$=H, $A^{11}$=F, $A^{12}$=H, $A^{13}$=H], [2209; Q=$Q^{r5}$, $A^{9}$=F, $A^{10}$=H, $A^{11}$=H, $A^{12}$=H, $A^{13}$=F], [2210; Q=$Q^{r5}$, $A^{9}$=H, $A^{10}$=F, $A^{11}$=F, $A^{12}$=H, $A^{13}$=H], [2211; Q=$Q^{r5}$, $A^{9}$=H, $A^{10}$=F, $A^{11}$=H, $A^{12}$=F, $A^{13}$=H], [2212;

Q=Q$^{r5}$, A$^9$=Cl, A$^{10}$=H, A$^{11}$=H, A$^{12}$=H, A$^{13}$=H], [2213; Q=Q$^{r5}$, A$^9$=H, A$^{10}$=Cl, A$^{11}$=H, A$^{12}$=H, A$^{13}$=H], [2214; Q=Q$^{r5}$, A$^9$=H, A$^{10}$=H, A$^{11}$=Cl, A$^{12}$=H, A$^{13}$=H], [2215; Q=Q$^{r5}$, A$^9$=Cl, A$^{10}$=Cl, A$^{11}$=H, A$^{12}$=H, A$^{13}$=H], [2216; Q=Q$^{r5}$, A$^9$=Cl, A$^{10}$=H, A$^{11}$=Cl, A$^{12}$=H, A$^{13}$=H], [2217; Q=Q$^{r5}$, A$^9$=Cl, A$^{10}$=H, A$^{11}$=H, A$^{12}$=H, A$^{13}$=Cl], [2218; Q=Q$^{r5}$, A$^9$=H, A$^{10}$=Cl, A$^{11}$=Cl, A$^{12}$=H, A$^{13}$=H], [2219; Q=Q$^{r5}$, A$^9$=H, A$^{10}$=Cl, A$^{11}$=H, A$^{12}$=Cl, A$^{13}$=H], [2220; Q=Q$^{r5}$, A$^9$=CF$_3$, A$^{10}$=H, A$^{11}$=H, A$^{12}$=H, A$^{13}$=H], [2221; Q=Q$^{r5}$, A$^9$=H, A$^{10}$=CF$_3$, A$^{11}$=H, A$^{12}$=H, A$^{13}$=H], [2222; Q=Q$^{r5}$, A$^9$=H, A$^{10}$=H, A$^{11}$=CF$_3$, A$^{12}$=H, A$^{13}$=H], [2223; Q=Q$^{r5}$, A$^9$=CF$_3$, A$^{10}$=CF$_3$, A$^1$=H, A$^{12}$=H, A$^{13}$=H], [2224; Q=Q$^{r5}$, A$^9$=CF$_3$, A$^{10}$=H, A$^{11}$=CF$_3$, A$^{12}$=H, A$^{13}$=H], [2225; Q=Q$^{r5}$, A$^9$=CF$_3$, A$^{10}$=H, A$^{11}$=H, A$^{12}$=H, A$^{13}$=CF$_3$], [2226; Q=Q$^{r5}$, A$^9$=H, A$^{10}$=CF$_3$, A$^1$=CF$_3$, A$^{12}$=H, A$^{13}$=H], [2227; Q=Q$^{r5}$, A$^9$=H, A$^{10}$=CF$_3$, A$^{11}$=H, A$^{12}$=CF$_3$, A$^{13}$=H], [2228; Q=Q 5, A$^9$=OMe, A$^{10}$=H, A$^{11}$=H, A$^{12}$=H, A$^{13}$=H], [2229; Q=Q$^{q5}$, A$^9$=H, A$^{10}$=OMe, A$^{11}$=H, A$^{12}$=H, A$^{13}$=H], [2230; Q=Q$^{r5}$, A$^9$=H, A$^{10}$=H, A$^{11}$=OMe, A$^{12}$=H, A$^{13}$=H], [2231; Q=Q$^{r5}$, A$^9$=OMe, A$^{10}$=OMe, A$^{11}$=H, A$^{12}$=H, A$^{13}$=H], [2232; Q=Q$^{r5}$, A$^9$=OMe, A$^{10}$=H, A$^{11}$=OMe, A$^{12}$=H, A$^{13}$=H], [2233; Q=Q$^{q5}$, A$^9$=OMe, A$^{10}$=H, A$^{11}$=H, A$^{12}$=H, A$^{13}$=OMe], [2234; Q=Q$^{r5}$, A$^9$=H, A$^{10}$=OMe, A$^1$=OMe, A$^{12}$=H, A$^{13}$=H], [2235; Q=Q$^{r5}$, A$^9$=H, A$^{10}$=OMe, A$^{11}$=H, A$^{12}$=OMe, A$^{13}$=H], [2236; Q=Q$^{r5}$, A$^9$=H, A$^{10}$=Br, A$^{11}$=H, A$^{12}$=H, A$^1$=H], [2237; Q=Q$^{r5}$, A$^9$=H, A$^{10}$=H, A$^{11}$=Br, A$^{12}$=H, A$^{13}$=H], [2238; Q=Q$^{r1}$, A$^9$=Br, A$^{10}$=H, A$^{11}$=H, A$^{12}$=H, A$^{13}$=Br], [2239; Q=Q$^{r5}$, A$^9$=H, A$^{10}$=Me, A$^1$=H, A$^{12}$=H, A$^{13}$=H], [2240; Q=Q$^{r5}$, A$^9$=H, A$^{10}$=H, A$^{11}$=Me, A$^{12}$=H, A$^{13}$=H], [2241; Q=Q$^{r5}$, A$^9$=Me, A$^{10}$=H, A$^{11}$=H, A$^{12}$=H, A$^{13}$=Me], [2242; Q=Q$^{r5}$, A$^9$=H, A$^{10}$=cyclopropyl, A$^{11}$=H, A$^{12}$=H, A$^{13}$=H], [2243; Q=Q$^{q5}$, A$^9$=H, A$^{10}$=H, A$^7$=cyclopropyl, A$^{12}$=H, A$^{13}$=H], [2244; Q=Q$^{q5}$, A$^7$=cyclopropyl, A$^{10}$=H, A$^{11}$=H, A$^{12}$=H, A$^{13}$=cyclopropyl], [2245; Q=Q$^{r5}$, A$^9$=H, A$^{10}$=OCHF$_2$, A$^{11}$=H, A$^{12}$=H, A$^{13}$=H], [2246; Q=Q$^{r5}$, A$^9$=H, A$^{10}$=H, A$^{11}$=OCHF$_2$, A$^{12}$=H, A$^{13}$=H], [2247; Q=Q$^{r5}$, A$^9$=H, A$^{10}$=OCF$_3$, A$^{11}$=H, A$^{12}$=H, A$^{13}$=H], [2248; Q=Q$^{r1}$, A$^9$=H, A$^{10}$=H, A$^{11}$=OCF$_3$, A$^{12}$=H, A$^{13}$=H], [2249; Q=Q$^{r6}$, A$^9$=H, A$^{10}$=H, A$^{11}$=H, A$^{12}$=H, A$^{13}$=H], [2250; Q=Q$^{r6}$, A$^9$=F, A$^{10}$=H, A$^{11}$=H, A$^{12}$=H, A$^{13}$=H], [2251; Q=Q$^{r6}$, A$^9$=H, A$^{10}$=F, A$^{11}$=H, A$^{12}$=H, A$^{13}$=H], [2252; Q=Q$^{r6}$, A$^9$=H, A$^{10}$=H, A$^{11}$=F, A$^{12}$=H, A$^{13}$=H], [2253; Q=Q$^{r6}$, A$^9$=F, A$^{10}$=F, A$^{11}$=H, A$^{12}$=H, A$^{13}$=H], [2254; Q=Q$^{r6}$, A$^9$=F, A$^{10}$=H, A$^{11}$=F, A$^{12}$=H, A$^{13}$=H], [2255; Q=Q$^{r6}$, A$^9$=F, A$^{10}$=H, A$^{11}$=H, A$^{12}$=H, A$^{13}$=F], [2256; Q=Q$^{r6}$, A$^9$=H, A$^{10}$=F, A$^{11}$=F, A$^{13}$=H], [2257; Q=Q$^{r6}$, A$^9$=H, A$^{10}$=F, A$^1$=H, A$^2$=F, A$^{13}$=H], [2258; Q=Q$^{r6}$, A$^9$=Cl, A$^{10}$=H, A$^{11}$=H, A$^{12}$=H, A$^{13}$=H], [2259; Q=Q$^{r6}$, A$^9$=H, A$^{10}$=Cl, A$^{11}$=H, A$^{12}$=H, A$^{13}$=H], [2260; Q=Q$^{r6}$, A$^9$=H, A$^{10}$=H, A$^{11}$=Cl, A$^{12}$=H, A$^{13}$=H], [2261; Q=Q$^{r6}$, A$^9$=Cl, A$^{10}$=Cl, A$^{11}$=H, A$^{12}$=H, A$^{13}$=H], [2262; Q=Q$^{r6}$, A$^9$=Cl, A$^{10}$=H, A$^{11}$=Cl, A$^{12}$=H, A$^{13}$=H], [2263; Q=Q$^{r6}$, A$^9$=Cl, A$^{10}$=H, A$^{11}$=H, A$^{12}$=H, A$^{13}$=Cl], [2264; Q=Q$^{r6}$, A$^9$=H, A$^{10}$=Cl, A$^{11}$=Cl, A$^{12}$=H, A$^{13}$=H], [2265; Q=Q$^{r6}$, A$^9$=H, A$^{10}$=Cl, A$^{11}$=H, A$^{12}$=Cl, A$^{13}$=H], [2266; Q=Q$^{r6}$, A$^9$=CF$_3$, A$^{10}$=H, A$^{11}$=H, A$^{12}$=H, A$^{13}$=H], [2267; Q=Q$^{r6}$, A$^9$=H, A$^{10}$=CF$_3$, A$^{11}$=H, A$^{12}$=H, A$^{13}$=H], [2268; Q=Q$^{r6}$, A$^9$=H, A$^{10}$=H, A$^{11}$=CF$_3$, A$^{12}$=H, A$^{13}$=H], [2269; Q=Q$^{r6}$, A$^9$=CF$_3$, A$^{10}$=CF$_3$, A$^{11}$=H, A$^{12}$=H, A$^{13}$=H], [2270; Q=Q$^{r6}$, A$^9$=CF$_3$, A$^{10}$=H, A$^1$=CF$_3$, A$^{12}$=H, A$^{13}$=H], [2271; Q=Q$^{r6}$, A$^9$=CF$_3$, A$^{10}$=H, A$^1$=H, A$^{12}$=H, A$^{13}$=CF$_3$], [2272; Q=Q$^{r6}$, A$^9$=H, A$^{10}$=CF$_3$, A$^{11}$=CF$_3$, A$^2$=H, A$^{13}$=H], [2273; Q=Q$^{r6}$, A$^9$=H, A$^{10}$=CF$_3$, A$^{11}$=H, A$^{12}$=CF$_3$, A$^{13}$=H], [2274; Q=Q$^{r6}$, A$^9$=OMe, A$^{10}$=H, A$^5$=H, A$^{12}$=H, A$^{13}$=H], [2275; Q=Q$^{r6}$, A$^9$=H, A$^{10}$=OMe, A$^{11}$=H, A$^{12}$=H, A$^{13}$=H], [2276; Q=Q$^{r1}$, A$^9$=H, A$^{10}$=H, A$^{11}$=OMe, A$^{12}$=H, A$^{13}$=H], [2277; Q=Q$^{r1}$, A$^9$=OMe, A$^{10}$=OMe, A$^{11}$=H, A$^{12}$=H, A$^{13}$=H], [2278; Q=Q$^{r6}$, A$^9$=OMe, A$^{10}$=H, A$^{11}$=OMe, A$^{12}$=H, A$^{13}$=H], [2279; Q=Q$^{r6}$, A$^9$=OMe, A$^{10}$=H, A$^{11}$=H, A$^{12}$=H, A$^{13}$=OMe], [2280; Q=Q$^{r6}$, A$^9$=H, A$^{10}$=OMe, A$^1$=OMe, A$^{12}$=H, A$^{13}$=H], [2281; Q=Q$^{r6}$, A$^9$=H, A$^{10}$=OMe, A$^1$=H, A$^{12}$=OMe, A$^{13}$=H], [2282; Q=Q$^{r1}$, A$^9$=H, A$^{10}$=Br, A$^{11}$=H, A$^{12}$=H, A$^{13}$=H], [2283; Q=Q$^{r6}$, A$^9$=H, A$^{10}$=H, A$^{11}$=Br, A$^{12}$=H, A$^{13}$=H], [2284; Q=Q$^{r6}$, A$^9$=Br, A$^{10}$=H, A$^{11}$=H, A$^{12}$=H, A$^{13}$=Br], [2285; Q=Q$^{r6}$, A$^9$=H, A$^{10}$=Me, A$^{11}$=H, A$^{12}$=H, A$^{13}$=H], [2286; Q=Q$^{r6}$, A$^9$=H, A$^{10}$=H, A$^{11}$=Me, A$^{12}$=H, A$^{13}$=H], [2287; Q=Q$^{r6}$, A$^9$=Me, A$^{10}$=H, A$^{11}$=H, A$^{12}$=H, A$^{13}$=Me], [2288; Q=Q$^{r6}$, A$^9$=H, A$^{10}$=cyclopropyl, A$^{11}$=H, A$^{12}$=H, A$^{13}$=H], [2289; Q=Q$^{r6}$, A$^9$=H, A$^{10}$=H, A$^7$=cyclopropyl, A$^{12}$=H, A$^{13}$=H], [2290; Q=Q$^{r6}$, A$^9$=cyclopropyl, A$^{10}$=H, A$^{11}$=H, A$^{12}$=H, A$^{13}$=cyclopropyl], [2291; Q=Q$^{r6}$, A$^9$=H, A$^{10}$=OCHF$_2$, A$^{11}$=H, A$^{12}$=H, A$^1$=H], [2292; Q=Q$^{r6}$, A$^9$=H, A$^{10}$=H, A$^{11}$=OCHF$_2$, A$^2$=H, A$^{13}$=H], [2293; Q=Q$^{r1}$, A$^9$=H, A$^{10}$=OCF$_3$, A$^{11}$=H, A$^{12}$=H, A$^{13}$=H], [2294; Q=Q$^{r6}$, A$^9$=H, A$^{10}$=H, A$^{11}$=OCF$_3$, A$^{12}$=H, A$^{13}$=H], [2295; Q=Q$^{r7}$, A$^{14}$=H, A$^{15}$=H, A$^{16}$=H, A$^{17}$=H, A$^{18}$=H], [2296; Q=Q$^{r7}$, A$^{14}$=F, A$^{15}$=H, A$^{16}$=H, A$^{17}$=H, A$^{18}$=H], [2297; Q=Q$^{r7}$, A$^{14}$=H, A$^{15}$=F, A$^{16}$=H, A$^{17}$=H, A$^{18}$=H], [2298; Q=Q$^{r7}$, A$^{14}$=H, A$^{15}$=H, A$^{16}$=F, A$^{17}$=H, A$^{18}$=H], [2299; Q=Q$^{r7}$, A$^{14}$=F, A$^{15}$=F, A$^{16}$=H, A$^{17}$=H, A$^{18}$=H], [2300; Q=Q$^{r7}$, A$^{14}$=F, A$^{15}$=H, A$^{16}$=F, A$^{17}$=H, A$^{18}$=H], [2301; Q=Q$^{r7}$, A$^{14}$=F, A$^{15}$=H, A$^{16}$=H, A$^{17}$=H, A$^{18}$=F], [2302; Q=Q$^{r7}$, A$^{14}$=H, A$^{15}$=F, A$^{16}$=F, A$^1$=H, A$^1$=H], [2303; Q=Q$^{r7}$, A$^{14}$=H, A$^{15}$=F, A$^{16}$=H, A$^{17}$=F, A$^{18}$=H], [2304; Q=Q$^{r7}$, A$^{14}$=Cl, A$^{15}$=H, A$^{16}$=H, A$^{17}$=H, A$^{18}$=H], [2305; Q=Q$^{r7}$, A$^{14}$=H, A$^{15}$=Cl, A$^{16}$=H, A$^{17}$=H, A$^{18}$=H], [2306; Q=Q$^{r7}$, A$^{14}$=H, A$^{15}$=H, A$^{16}$=Cl, A$^{17}$=H, A$^{18}$=H], [2307; Q=Q$^{r7}$, A$^{14}$=Cl, A$^{15}$=Cl, A$^{16}$=H, A$^{17}$=H, A$^{18}$=H], [2308; Q=Q$^{r7}$, A$^{14}$=Cl, A$^{15}$=H, A$^{16}$=Cl, A$^{17}$=H, A$^{18}$=H], [2309; Q=Q$^{r7}$, A$^{14}$=Cl, A$^{15}$=H, A$^{16}$=H, A$^{17}$=H, A$^{18}$=Cl], [2310; Q=Q$^{r7}$, A$^{14}$=H, A$^{15}$=Cl, A$^{16}$=Cl, A$^{17}$=H, A$^{18}$=H], [2311; Q=Q$^{r7}$, A$^{14}$=H, A$^{15}$=Cl, A$^1$=H, A$^1$=Cl, A$^{18}$=H], [2312; Q=Q$^{r7}$, A$^{14}$=CF$_3$, A$^{15}$=H, A$^{16}$=H, A$^{17}$=H, A$^{18}$=H], [2313; Q=Q$^{r7}$, A$^{14}$=H, A$^{15}$=CF$_3$, A$^{16}$=H, A$^{17}$=H, A$^{18}$=H], [2314; Q=Q$^{r7}$, A$^{14}$=H, A$^{15}$=H, A$^{16}$=CF$_3$, A$^{17}$=H, A$^{18}$=H], [2315; Q=Q$^{r7}$, A$^{14}$=CF$_3$, A$^{15}$=CF$_3$, A$^{16}$=H, A$^{17}$=H, A$^{18}$=H], [2316; Q=Q$^{r7}$, A$^{14}$=CF$_3$, A$^{15}$=H, A$^{16}$=CF$_3$, A$^{17}$=H, A$^{18}$=H], [2317; Q=Q$^{r7}$, A$^{14}$=CF$_3$, A$^{15}$=H, A$^{16}$=H, A$^{17}$=H, A$^{18}$=CF$_3$], [2318; Q=Q$^{r7}$, A$^{14}$=H, A$^{15}$=CF$_3$, A$^{16}$=CF$_3$, A$^{17}$=H, A$^{18}$=H], [2319; Q=Q$^{r7}$, A$^{14}$=H, A$^{15}$=CF$_3$, A$^{16}$=H, A$^{17}$=CF$_3$, A$^{18}$=H], [2320; Q=Q$^{r7}$, A$^{14}$=Me, A$^{15}$=H, A$^{16}$=H, A$^{17}$=H, A$^{18}$=H], [2321; Q=Q$^{r7}$, A$^{14}$=H, A$^{15}$=OMe, A$^{16}$=H, A$^{17}$=H, A$^{18}$=H], [2322; Q=Q$^{r7}$, A$^{14}$=H, A$^{15}$=H, A$^{16}$=OMe, A$^{17}$=H, A$^{18}$=H], [2323; Q=Q$^{r7}$, A$^{14}$=OMe, A$^{15}$=OMe, A$^{16}$=H, A$^{17}$=H, A$^{18}$=H], [2324; Q=Q$^{r7}$, A$^{14}$=OMe, A$^{15}$=H, A$^{16}$=OMe, A$^{17}$=H, A$^{18}$=H], [2325; Q=Q$^{r7}$, A$^{14}$=OMe, A$^5$=H, A$^1$=H, A$^{17}$=H, A$^{18}$=OMe], [2326; Q=Q$^{r7}$, A$^{14}$=H, A$^{15}$=OMe, A$^{16}$=OMe, A$^{17}$=H, A$^{18}$=H], [2327; Q=Q$^{r7}$, A$^{14}$=H, A$^{15}$=OMe, A$^{16}$=H, A$^{17}$=OMe, A$^{18}$=H], [2328; Q=Q$^{r7}$, A$^{14}$=H, A$^{15}$=Br, A$^{16}$=H, A$^{17}$=H, A$^{18}$=H], [2329; Q=Q$^{r7}$, A$^{14}$=H, A$^{15}$=H, A$^{16}$=Br, A$^{17}$=H, A$^{18}$=H], [2330; Q=Q$^{r7}$, A$^{14}$=Br, A$^{15}$=H, A$^{16}$=H, A$^{17}$=H, A$^{18}$=Br], [2331; Q=Q$^{r7}$, A$^{14}$=H, A$^{15}$=Me, A$^{16}$=H, A$^{17}$=H, A$^{18}$=H], [2332; Q=Q$^{q7}$, A$^{14}$=H, A$^{15}$=H, A$^{16}$=Me, A$^{17}$=H, A$^{18}$=H], [2333; Q=Q$^{r7}$, A$^{14}$=Me, A$^{15}$=H, A$^{16}$=H, A$^{17}$=H, A$^{18}$=Me], [2334; Q=Q$^{r7}$, A$^{14}$=H, A$^{15}$=cyclopropyl, A$^{16}$=H, A$^{17}$=H, A$^{18}$=H], [2335; Q=Q$^{r7}$, A$^{14}$=H, A$^{15}$=H, A$^{16}$=cyclopropyl, A$^{17}$=H, A$^{18}$=H], [2336; Q=Q$^{r7}$, A$^{14}$=cyclopropyl, A$^{15}$=H, A$^{16}$=H, A$^{17}$=H, A$^{18}$=cyclopropyl], [2337; Q=Q$^{r7}$, A$^{14}$=H, A$^{15}$=OCHF$_2$, A$^{16}$=H, A$^{17}$=H, A$^{18}$=H], [2338; Q=Q$^{r7}$, A$^{14}$=H, A$^{15}$=OCHF$_2$, A$^{17}$=H, A$^{18}$=H], [2339; Q=Q$^{r7}$, A$^{14}$=H, A$^{15}$=OCF$_3$, A$^{16}$=H, A$^{17}$=H, A$^{18}$=H], [2340; Q=Q$^{r7}$, A$^{14}$=H, A$^{15}$=H, A$^{16}$=OCF$_3$, A$^{17}$=H, A$^{18}$=H], [2341; Q=Q$^{r8}$, A$^{14}$=H, A$^{15}$=H, A$^{16}$=H, A$^{17}$=H, A$^{18}$=H], [2342; Q=Q$^{r8}$, A$^{14}$=F, $A^{15}$=H, $A^{16}$=H, $A^{17}$=H, $A^{18}$=H], [2343; Q=$Q^{r8}$, $A^{14}$=H, $A^{15}$=F, $A^{16}$=H, $A^{17}$=H, $A^{18}$=H], [2344; Q=$Q^{r8}$, $A^{14}$=H, $A^{15}$=H, $A^{16}$=F, $A^{17}$=H, $A^{18}$=H], [2345; Q=$Q^{r8}$, $A^{14}$=F, $A^{15}$=F, $A^{16}$=F, $A^{17}$=H, $A^{18}$=H], [2346; Q=$Q^{r8}$, $A^{14}$=F, $A^{15}$=F, $A^{16}$=F, $A^{17}$=H, $A^{5}$=H], [2347; Q=$Q^{r8}$, $A^{14}$=F, $A^{15}$=H, $A^{16}$=H, $A^{17}$=H, $A^{18}$=F], [2348; Q=$Q^{r8}$, $A^{14}$=H, $A^{15}$=F, $A^{16}$=F, $A^{17}$=H, $A^{18}$=H], [2349; Q=$Q^{r8}$, $A^{14}$=H, $A^{15}$=F, $A^{16}$=H, $A^{17}$=F, $A^{18}$=H], [2350; Q=$Q^{r8}$, $A^{14}$=Cl, $A^{15}$=H, $A^{16}$=H, $A^{17}$=H, $A^{18}$=H], [2351; Q=$Q^{r8}$, $A^{14}$=H, $A^{15}$=Cl, $A^{16}$=H, $A^{17}$=H, $A^{5}$=H], [2352; Q=$Q^{r8}$, $A^{14}$=H, $A^{15}$=H, $A^{16}$=Cl, $A^{17}$=H, $A^{5}$=H], [2353; Q=$Q^{r8}$, $A^{14}$=Cl, $A^{15}$=Cl, $A^{16}$=H, $A^{17}$=H, $A^{18}$=H], [2354; Q=$Q^{r8}$, $A^{14}$=Cl, $A^{15}$=H, $A^{16}$=Cl, $A^{17}$=H, $A^{18}$=H], [2355; Q=$Q^{r8}$, $A^{14}$=Cl, $A^{15}$=H, $A^{16}$=H, $A^{17}$=H, $A^{18}$=Cl], [2356; Q=$Q^{r8}$, $A^{14}$=H, $A^{15}$=Cl, $A^{16}$=Cl, $A^{17}$=H, $A^{18}$=H], [2357; Q=$Q^{r8}$, $A^{14}$=H, $A^{15}$=Cl, $A^{16}$=H, $A^{17}$=Cl, $A^{18}$=H], [2358; Q=$Q^{r8}$, $A^{14}$=CF$_3$, $A^{15}$=H, $A^{16}$=H, $A^{17}$=H, $A^{18}$=H], [2359; Q=$Q^{r5}$, $A^{14}$=H, $A^{15}$=CF$_3$, $A^{16}$=H, $A^{17}$=H, $A^{18}$=H], [2360; Q=$Q^{r8}$, $A^{4}$=H, $A^{5}$=H, $A^{16}$=CF$_3$, $A^{17}$=H, $A^{18}$=H], [2361; Q=$Q^{r8}$, $A^{14}$=CF$_3$, $A^{15}$=CF$_3$, $A^{16}$=H, $A^{17}$=H, $A^{18}$=H], [2362; Q=$Q^{r8}$, $A^{14}$=CF$_3$, $A^{15}$=H, $A^{16}$=CF$_3$, $A^{17}$=H, $A^{18}$=H], [2363; Q=$Q^{r8}$, $A^{14}$=CF$_3$, $A^{15}$=H, $A^{16}$=H, $A^{17}$=H, $A^{18}$=CF$_3$], [2364; Q=$Q^{r1}$, $A^{14}$=H, $A^{15}$=CF$_3$, $A^{16}$=CF$_3$, $A^{17}$=H, $A^{18}$=H], [2365; Q=$Q^{r8}$, $A^{14}$=H, $A^{15}$=CF$_3$, $A^{16}$=H, $A^{17}$=CF$_3$, $A^{18}$=H], [2366; Q=$Q^{r8}$, $A^{14}$=OMe, $A^{15}$=H, $A^{16}$=H, $A^{17}$=H, $A^{18}$=H], [2367; Q=$Q^{r8}$, $A^{14}$=H, $A^{15}$=OMe, $A^{16}$=H, $A^{17}$=H, $A^{18}$=H], [2368; Q=$Q^{r8}$, $A^{14}$=H, $A^{15}$=H, $A^{16}$=OMe, $A^{17}$=H, $A^{18}$=H], [2369; Q=$Q^{r1}$, $A^{14}$=OMe, $A^{15}$=OMe, $A^{16}$=H, $A^{17}$=H, $A^{18}$=H], [2370; Q=$Q^{r5}$, $A^{14}$=OMe, $A^{15}$=H, $A^{6}$=OMe, $A^{17}$=H, $A^{18}$=H], [2371; Q=$Q^{r8}$, $A^{14}$=OMe, $A^{15}$=H, $A^{16}$=H, $A^{17}$=H, $A^{18}$=OMe], [2372; Q=$Q^{r8}$, $A^{14}$=H, $A^{15}$=OMe, $A^{16}$=OMe, $A^{17}$=H, $A^{18}$=H], [2373; Q=$Q^{r8}$, $A^{14}$=H, $A^{15}$=OMe, $A^{16}$=H, $A^{17}$=OMe, $A^{18}$=H], [2374; Q=$Q^{r8}$, $A^{14}$=H, $A^{15}$=Br, $A^{16}$=H, $A^{17}$=H, $A^{18}$=H], [2375; Q=$Q^{r8}$, $A^{14}$=H, $A^{15}$=H, $A^{16}$=Br, $A^{17}$=H, $A^{18}$=H], [2376; Q=$Q^{r8}$, $A^{14}$=Br, $A^{15}$=H, $A^{16}$=H, $A^{17}$=H, $A^{18}$=Br], [2377; Q=$Q^{r8}$, $A^{1}$=H, $A^{15}$=Me, $A^{16}$=H, $A^{17}$=H, $A^{18}$=H], [2378; Q=$Q^{r8}$, $A^{14}$=H, $A^{15}$=H, $A^{16}$=Me, $A^{17}$=H, $A^{18}$=H], [2379; Q=$Q^{r8}$, $A^{14}$=Me, $A^{15}$=H, $A^{16}$=H, $A^{17}$=H, $A^{18}$=Me], [2380; Q=$Q^{r8}$, $A^{14}$=H, $A^{15}$=cyclopropyl, $A^{16}$=H, $A^{17}$=H, $A^{18}$=H], [2381; Q=$Q^{r8}$, $A^{14}$=H, $A^{15}$=H, $A^{16}$=cyclopropyl, $A^{17}$=H, $A^{18}$=H], [2382; Q=$Q^{r8}$, $A^{14}$=cyclopropyl, $A^{15}$=H, $A^{16}$=H, $A^{17}$=H, $A^{18}$=cyclopropyl], [2383; Q=$Q^{r1}$, $A^{14}$=H, $A^{15}$=OCHF$_2$, $A^{16}$=H, $A^{17}$=H, $A^{18}$=H], [2384; Q=$Q^{r8}$, $A^{14}$=H, $A^{15}$=H, $A^{16}$=OCHF$_2$, $A^{17}$=H, $A^{18}$=H], [2385; Q=$Q^{r8}$, $A^{14}$=H, $A^{15}$=OCF$_3$, $A^{16}$=H, $A^{17}$=H, $A^{18}$=H], [2386; Q=$Q^{r8}$, $A^{14}$=H, $A^{15}$=H, $A^{16}$=OCF$_3$, $A^{17}$=H, $A^{18}$=H], [2387; Q=$Q^{r9}$, $A^{14}$=H, $A^{15}$=H, $A^{16}$=H, $A^{17}$=H, $A^{18}$=H], [2388; Q=$Q^{r9}$, $A^{14}$=F, $A^{15}$=H, $A^{16}$=H, $A^{17}$=H, $A^{18}$=H], [2389; Q=$Q^{r9}$, $A^{14}$=H, $A^{15}$=F, $A^{16}$=H, $A^{17}$=H, $A^{18}$=H], [2390; Q=$Q^{r9}$, $A^{14}$=H, $A^{15}$=H, $A^{16}$=F, $A^{17}$=H, $A^{18}$=H], [2391; Q=$Q^{r9}$, $A^{14}$=F, $A^{15}$=F, $A^{16}$=H, $A^{17}$=H, $A^{18}$=H], [2392; Q=$Q^{r9}$, $A^{14}$=F, $A^{15}$=H, $A^{16}$=F, $A^{17}$=H, $A^{18}$=H], [2393; Q=$Q^{r9}$, $A^{14}$=F, $A^{15}$=H, $A^{16}$=H, $A^{17}$=H, $A^{5}$=H], [2394; Q=$Q^{r9}$, $A^{14}$=F, $A^{15}$=H, $A^{16}$=H, $A^{17}$=H, $A^{18}$=F], [2395; Q=$Q^{r9}$, $A^{14}$=H, $A^{15}$=F, $A^{16}$=F, $A^{17}$=H, $A^{18}$=H], [2396; Q=$Q^{r9}$, $A^{14}$=H, $A^{15}$=F, $A^{16}$=H, $A^{17}$=F, $A^{18}$=H], [2397; Q=$Q^{r9}$, $A^{14}$=Cl, $A^{15}$=H, $A^{16}$=H, $A^{17}$=H, $A^{18}$=H], [2398; Q=$Q^{r1}$, $A^{14}$=H, $A^{15}$=Cl, $A^{16}$=H, $A^{17}$=H, $A^{18}$=H], [2399; Q=$Q^{r9}$, $A^{14}$=Cl, $A^{15}$=H, $A^{16}$=Cl, $A^{17}$=H, $A^{18}$=H], [2400; Q=$Q^{r9}$, $A^{14}$=Cl, $A^{15}$=H, $A^{16}$=Cl, $A^{17}$=H, $A^{18}$=H], [2401; Q=$Q^{r9}$, $A^{14}$=Cl, $A^{15}$=H, $A^{16}$=H, $A^{17}$=H, $A^{18}$=Cl], [2402; Q=$Q^{r9}$, $A^{14}$=H, $A^{15}$=Cl, $A^{16}$=Cl, $A^{17}$=H, $A^{18}$=H], [2403; Q=$Q^{r9}$, $A^{14}$=H, $A^{15}$=Cl, $A^{16}$=H, $A^{17}$=Cl, $A^{18}$=H], [2404; Q=$Q^{r9}$, $A^{14}$=CF$_3$, $A^{15}$=H, $A^{16}$=H, $A^{17}$=H, $A^{18}$=H], [2405; Q=$Q^{r1}$, $A^{14}$=H, $A^{15}$=CF$_3$, $A^{16}$=H, $A^{17}$=H, $A^{18}$=H], [2406; Q=$Q^{r9}$, $A^{4}$=H, $A^{5}$=H, $A^{16}$=CF$_3$, $A^{17}$=H, $A^{18}$=H], [2407; Q=$Q^{r9}$, $A^{14}$=CF$_3$, $A^{15}$=CF$_3$, $A^{6}$=H, $A^{17}$=H, $A^{18}$=H], [2408; Q=$Q^{r9}$, $A^{14}$=CF$_3$, $A^{15}$=H, $A^{16}$=CF$_3$, $A^{17}$=H, $A^{18}$=H], [2409; Q=$Q^{r9}$, $A^{14}$=CF$_3$, $A^{15}$=H, $A^{16}$=H, $A^{17}$=H, $A^{18}$=CF$_3$], [2410; Q=$Q^{r9}$, $A^{14}$=H, $A^{15}$=CF$_3$, $A^{16}$=CF$_3$, $A^{17}$=H, $A^{18}$=H], [2411; Q=$Q^{r9}$, $A^{14}$=H, $A^{15}$=CF$_3$, $A^{16}$=H, $A^{17}$=CF$_3$, $A^{18}$=H], [2412; Q=$Q^{r9}$, $A^{14}$=OMe, $A^{15}$=H, $A^{16}$=H, $A^{17}$=H, $A^{18}$=H], [2413; Q=$Q^{r9}$, $A^{14}$=H, $A^{15}$=OMe, $A^{16}$=H, $A^{17}$=H, $A^{18}$=H], [2414; Q=$Q^{r9}$, $A^{14}$=H, $A^{15}$=H, $A^{16}$=OMe, $A^{17}$=H, $A^{18}$=H], [2415; Q=$Q^{r9}$, $A^{14}$=OMe, $A^{15}$=OMe, $A^{16}$=H, $A^{17}$=H, $A^{18}$=H], [2416; Q=$Q^{r9}$, $A^{14}$=OMe, $A^{15}$=H, $A^{6}$=OMe, $A^{17}$=H, $A^{18}$=H], [2417; Q=$Q^{r9}$, $A^{14}$=OMe, $A^{15}$=H, $A^{16}$=H, $A^{17}$=H, $A^{18}$=OMe], [2418; Q=$Q^{r9}$, $A^{14}$=H, $A^{15}$=OMe, $A^{16}$=OMe, $A^{17}$=H, $A^{18}$=H], [2419; Q=$Q^{r9}$, $A^{14}$=H, $A^{15}$=OMe, $A^{16}$=H, $A^{17}$=OMe, $A^{18}$=H], [2420; Q=$Q^{r9}$, $A^{14}$=H, $A^{15}$=Br, $A^{16}$=H, $A^{17}$=H, $A^{18}$=H], [2421; Q=$Q^{r9}$, $A^{14}$=H, $A^{15}$=H, $A^{16}$=Br, $A^{17}$=H, $A^{18}$=H], [2422; Q=$Q^{r9}$, $A^{14}$=Br, $A^{15}$=H, $A^{16}$=H, $A^{17}$=H, $A^{18}$=Br], [2423; Q=$Q^{r9}$, $A^{14}$=H, $A^{15}$=Me, $A^{16}$=H, $A^{17}$=H, $A^{18}$=H], [2424; Q=$Q^{r9}$, $A^{14}$=H, $A^{15}$=H, $A^{16}$=Me, $A^{17}$=H, $A^{18}$=H], [2425; Q=$Q^{r9}$, $A^{1}$=Me, $A^{15}$=H, $A^{16}$=H, $A^{17}$=H, $A^{18}$=Me], [2426; Q=$Q^{r9}$, $A^{14}$=H, $A^{15}$=cyclopropyl, $A^{16}$=H, $A^{17}$=H, $A^{18}$=H], [2427; Q=$Q^{r9}$, $A^{14}$=H, $A^{16}$=cyclopropyl, $A^{17}$=H, $A^{18}$=H], [2428; Q=$Q^{r9}$, $A^{14}$=cyclopropyl, $A^{15}$=H, $A^{16}$=H, $A^{17}$=H, $A^{18}$=cyclopropyl], [2429; Q=$Q^{r9}$, $A^{14}$=H, $A^{15}$=OCHF$_2$, $A^{16}$=H, $A^{17}$=H, $A^{18}$=H], [2430; Q=$Q^{r9}$, $A^{14}$=H, $A^{15}$=H, $A^{16}$=OCHF$_2$, $A^{17}$=H, $A^{18}$=H], [2431; Q=$Q^{r9}$, $A^{14}$=H, $A^{15}$=OCF$_3$, $A^{16}$=H, $A^{17}$=H, $A^{18}$=H], [2432; Q=$Q^{r9}$, $A^{14}$=H, $A^{15}$=H, $A^{16}$=OCF$_3$, $A^{17}$=H, $A^{18}$=H], [2433; Q=$Q^{r10}$, $A^{14}$=H, $A^{15}$=H, $A^{16}$=H, $A^{17}$=H, $A^{18}$=H], [2434; Q=$Q^{r10}$, $A^{14}$=F, $A^{15}$=H, $A^{16}$=H, $A^{17}$=H, $A^{18}$=H], [2435; Q=$Q^{r10}$, $A^{14}$=H, $A^{15}$=F, $A^{16}$=H, $A^{17}$=H, $A^{18}$=H], [2436; Q=$Q^{r10}$, $A^{14}$=H, $A^{15}$=H, $A^{16}$=F, $A^{17}$=H, $A^{18}$=H], [2437; Q=$Q^{r10}$, $A^{14}$=F, $A^{15}$=F, $A^{16}$=H, $A^{17}$=H, $A^{18}$=H], [2438; Q=$Q^{r10}$, $A^{14}$=F, $A^{15}$=H, $A^{16}$=F, $A^{17}$=H, $A^{18}$=H], [2439; Q=$Q^{r10}$, $A^{14}$=F, $A^{15}$=H, $A^{16}$=H, $A^{17}$=H, $A^{18}$=F], [2440; Q=$Q^{r10}$, $A^{14}$=H, $A^{15}$=F, $A^{16}$=F, $A^{17}$=H, $A^{18}$=H], [2441; Q=$Q^{r10}$, $A^{14}$=H, $A^{15}$=F, $A^{16}$=H, $A^{17}$=F, $A^{18}$=H], [2442; Q=$Q^{r10}$, $A^{14}$=Cl, $A^{15}$=H, $A^{16}$=H, $A^{17}$=H, $A^{18}$=H], [2443; Q=$Q^{r10}$, $A^{14}$=H, $A^{15}$=Cl, $A^{16}$=H, $A^{17}$=H, $A^{18}$=H], [2444; Q=$Q^{r10}$, $A^{14}$=H, $A^{15}$=H, $A^{16}$=Cl, $A^{17}$=H, $A^{18}$=H], [2445; Q=$Q^{r10}$, $A^{14}$=Cl, $A^{15}$=Cl, $A^{16}$=H, $A^{17}$=H, $A^{18}$=H], [2446; Q=$Q^{r10}$, $A^{14}$=Cl, $A^{15}$=H, $A^{16}$=Cl, $A^{17}$=H, $A^{18}$=H], [2447; Q=$Q^{r10}$, $A^{14}$=Cl, $A^{15}$=H, $A^{6}$=H, $A^{17}$=H, $A^{18}$=Cl], [2448; Q=$Q^{r10}$, $A^{14}$=H, $A^{15}$=Cl, $A^{16}$=Cl, $A^{17}$=H, $A^{18}$=H], [2449; Q=$Q^{r10}$, $A^{14}$=H, $A^{15}$=Cl, $A^{16}$=H, $A^{17}$=Cl, $A^{18}$=H], [2450; Q=$Q^{r10}$, $A^{14}$=CF$_3$, $A^{15}$=H, $A^{16}$=H, $A^{17}$=H, $A^{18}$=H], [2451; Q=$Q^{r10}$, $A^{14}$=H, $A^{15}$=CF$_3$, $A^{16}$=H, $A^{17}$=H, $A^{18}$=H], [2452; Q=$Q^{r10}$, $A^{14}$=H, $A^{15}$=H, $A^{16}$=CF$_3$, $A^{17}$=H, $A^{18}$=H], [2453; Q=$Q^{r10}$, $A^{14}$=CF$_3$, $A^{15}$=CF$_3$, $A^{16}$=H, $A^{17}$=H, $A^{18}$=H], [2454; Q=$Q^{r10}$, $A^{14}$=CF$_3$, $A^{15}$=H, $A^{16}$=CF$_3$, $A^{17}$=H, $A^{18}$=H], [2455; Q=$Q^{r10}$, $A^{14}$=CF$_3$, $A^{15}$=H, $A^{16}$=H, $A^{17}$=H, $A^{18}$=CF$_3$], [2456; Q=$Q^{r10}$, $A^{14}$=H, $A^{15}$=CF$_3$, $A^{16}$=CF$_3$, $A^{17}$=H, $A^{18}$=H], [2457; Q=$Q^{r10}$, $A^{14}$=H, $A^{15}$=CF$_3$, $A^{16}$=H, $A^{17}$=CF$_3$, $A^{18}$=H], [2458; Q=$Q^{r10}$, $A^{14}$=OMe, $A^{15}$=H, $A^{16}$=H, $A^{17}$=H, $A^{18}$=H], [2459; Q=$Q^{r10}$, $A^{14}$=H, $A^{15}$=OMe, $A^{16}$=H, $A^{17}$=H, $A^{18}$=H], [2460; Q=$Q^{r10}$, $A^{14}$=H, $A^{15}$=H, $A^{16}$=OMe, $A^{17}$=H, $A^{18}$=H], [2461; Q=$Q^{r10}$, $A^{14}$=OMe, $A^{15}$=OMe, $A^{16}$=H, $A^{17}$=H, $A^{18}$=H], [2462; Q=$Q^{r10}$, $A^{14}$=OMe, $A^{15}$=H, $A^{16}$=OMe, $A^{17}$=H, $A^{18}$=H], [2463; Q=$Q^{r10}$, $A^{14}$=OMe, $A^{15}$=H, $A^{16}$=H, $A^{17}$=H, $A^{18}$=OMe], [2464; Q=$Q^{r10}$, $A^{14}$=H, $A^{15}$=OMe, $A^{16}$=OMe, $A^{17}$=H, $A^{18}$=H], [2465; Q=$Q^{r10}$, $A^{14}$=H, $A^{15}$=OMe, $A^{16}$=H, $A^{17}$=OMe, $A^{1}$=H], [2466; Q=$Q^{r10}$, $A^{14}$=H, $A^{15}$=Br, $A^{16}$=H, $A^{17}$=H, $A^{18}$=H], [2467; Q=$Q^{r10}$, $A^{14}$=H, $A^{15}$=H, $A^{16}$=Br, $A^{17}$=H, $A^{18}$=H], [2468; Q=$Q^{r10}$, $A^{14}$=Br, $A^{15}$=H, $A^{16}$=H, $A^{17}$=H, $A^{18}$=Br], [2469; Q=$Q^{r10}$, $A^{14}$=H, $A^{15}$=Me, $A^{16}$=H, $A^{17}$=H, $A^{18}$=H], [2470; Q=$Q^{r10}$, $A^{14}$=H, $A^{15}$=H, $A^{16}$=Me, $A^{17}$=H, $A^{18}$=H], [2471; Q=$Q^{r10}$, $A^{14}$=Me, $A^{15}$=H, $A^{16}$=H, $A^{17}$=H, $A^{18}$=Me], [2472; Q=$Q^{r10}$, $A^{14}$=H, $A^{15}$=cyclopropyl, $A^{16}$=H, $A^{17}$=H, $A^{18}$=H], [2473; Q=$Q^{r10}$, $A^{14}$=H, $A^{15}$=H, $A^{16}$=cyclopropyl, $A^{17}$=H, $A^{18}$=H], [2474; Q=$Q^{r10}$, $A^{14}$=cyclopropyl, $A^{15}$=H, $A^{16}$=H, $A^{17}$=H, $A^{18}$=cyclopropyl], [2475; Q=$Q^{r10}$, $A^{14}$=H, $A^{15}$=OCHF$_2$, $A^{16}$=H, $A^{17}$=H, $A^{18}$=H], [2476; Q=$Q^{r10}$, $A^{14}$=H, $A^{15}$=H, $A^{16}$=OCHF$_2$, $A^{17}$=H, $A^{18}$=H], [2477; Q=$Q^{r10}$, $A^{14}$=H, $A^{15}$=OCF$_3$, $A^{16}$=H, $A^{17}$=H, $A^{18}$=H], [2478; Q=$Q^{r10}$, $A^{14}$=H, $A^{15}$=H, $A^{16}$=OCF$_3$, $A^{17}$=H, $A^{18}$=H], [2479; Q=$Q^{r10}$, $A^{14}$=H, $A^{15}$=H, $A^{16}$=H, $A^{17}$=H, $A^{18}$=H], [2480; Q=$Q^{r11}$, $A^{14}$=F, $A^{15}$=H, $A^{16}$=H, $A^{17}$=H, $A^{18}$=H], [2481; Q=$Q^{r11}$, $A^{14}$=H, $A^{15}$=F, $A^{16}$=H, $A^{17}$=H, $A^{18}$=H], [2482; Q=$Q^{r11}$, $A^{14}$=H, $A^{15}$=H, $A^{16}$=F, $A^{17}$=H, $A^{18}$=H], [2483; Q=$Q^{r11}$, $A^{14}$=F, $A^{15}$=F, $A^{16}$=H, $A^{17}$=H, $A^{18}$=H], [2484; Q=$Q^{r11}$, $A^{14}$=F, $A^{15}$=H, $A^{16}$=F, $A^{17}$=H, $A^5$=H], [2485; Q=$Q^{r11}$, $A^{14}$=F, $A^{15}$=H, $A^{16}$=H, $A^{17}$=H, $A^{18}$=F], [2486; Q=$Q^{r11}$, $A^{14}$=H, $A^{15}$=F, $A^{16}$=F, $A^{17}$=H, $A^{18}$=H], [2487; Q=$Q^{r11}$, $A^{14}$=H, $A^{15}$=F, $A^{16}$=H, $A^{17}$=F, $A^{18}$=H], [2488; Q=$Q^{r11}$, $A^{14}$=Cl, $A^{15}$=H, $A^{16}$=H, $A^{17}$=H, $A^{18}$=H], [2489; Q=$Q^{r11}$, $A^{14}$=H, $A^{15}$=Cl, $A^{16}$=H, $A^{17}$=H, $A^{18}$=H], [2490; Q=$Q^{r11}$, $A^{14}$=H, $A^{15}$=H, $A^{16}$=Cl, $A^{17}$=H, $A^{18}$=H], [2491; Q=$Q^{r11}$, $A^{14}$=Cl, $A^{15}$=Cl, $A^{16}$=H, $A^{17}$=H, $A^{18}$=H], [2492; Q=$Q^{r11}$, $A^{14}$=Cl, $A^{15}$=H, $A^{16}$=Cl, $A^{17}$=H, $A^{18}$=H], [2493; Q=$Q^{r11}$, $A^{14}$=Cl, $A^{15}$=H, $A^{16}$=H, $A^{17}$=H, $A^{18}$=Cl], [2494; Q=$Q^{r11}$, $A^{14}$=H, $A^{15}$=Cl, $A^{16}$=Cl, $A^{17}$=H, $A^{18}$=H], [2495; Q=$Q^{r11}$, $A^{14}$=H, $A^{15}$=Cl, $A^{16}$=H, $A^{17}$=Cl, $A^{18}$=H], [2496; Q=$Q^{r11}$, $A^{14}$=CF$_3$, $A^{15}$=H, $A^{16}$=H, $A^{17}$=H, $A^{18}$=H], [2497; Q=$Q^{r11}$, $A^{14}$=H, $A^{15}$=CF$_3$, $A^{16}$=H, $A^{17}$=H, $A^{18}$=H], [2498; Q=$Q^{r11}$, $A^{14}$=H, $A^{15}$=H, $A^{16}$=CF$_3$, $A^{17}$=H, $A^{18}$=H], [2499; Q=$Q^{r11}$, $A^{14}$=CF$_3$, $A^{15}$=CF$_3$, $A^{16}$=H, $A^{17}$=H, $A^{18}$=H], [2500; Q=$Q^{r11}$, $A^{14}$=CF$_3$, $A^{15}$=H, $A^{16}$=CF$_3$, $A^{17}$=H, $A^{18}$=H], [2501; Q=$Q^{r11}$, $A^{14}$=CF$_3$, $A^{15}$=H, $A^{16}$=H, $A^{17}$=H, $A^{18}$=CF$_3$], [2502; Q=$Q^{r11}$, $A^{14}$=H, $A^{15}$=CF$_3$, $A^{16}$=CF$_3$, $A^{17}$=H, $A^{18}$=H], [2503; Q=$Q^{r11}$, $A^{14}$=H, $A^{15}$=CF$_3$, $A^{16}$=H, $A^{17}$=CF$_3$, $A^{18}$=H], [2504; Q=$Q^{r1}$, $A^{14}$=OMe, $A^{15}$=H, $A^{16}$=H, $A^{17}$=H, $A^{18}$=H], [2505; Q=$Q^{r11}$, $A^{14}$=H, $A^{15}$=OMe, $A^{16}$=H, $A^{17}$=H, $A^{18}$=H], [2506; Q=$Q^{r11}$, $A^{14}$=H, $A^{15}$=H, $A^{16}$=OMe, $A^{17}$=H, $A^{18}$=H], [2507; Q=$Q^{r11}$, $A^{14}$=Me, $A^{15}$=OMe, $A^{16}$=H, $A^{17}$=H, $A^{18}$=H], [2508; Q=$Q^{r11}$, $A^{14}$=OMe, $A^{15}$=H, $A^{16}$=OMe, $A^{17}$=H, $A^{18}$=H], [2509; Q=$Q^{r11}$, $A^{14}$=OMe, $A^{15}$=H, $A^{16}$=H, $A^{17}$=H, $A^{18}$=OMe], [2510; Q=$Q^{r11}$, $A^{14}$=H, $A^{15}$=OMe, $A^{16}$=OMe, $A^{17}$=H, $A^{18}$=H], [2511; Q=$Q^{r11}$, $A^{14}$=H, $A^{15}$=OMe, $A^{16}$=H, $A^{17}$=OMe, $A^{18}$=H], [2512; Q=$Q^{r11}$, $A^{14}$=H, $A^{15}$=Br, $A^{16}$=H, $A^{17}$=H, $A^{18}$=H], [2513; Q=$Q^{r11}$, $A^{14}$=H, $A^{15}$=H, $A^{16}$=Br, $A^{17}$=H, $A^{18}$=H], [2514; Q=$Q^{r11}$, $A^{14}$=Br, $A^{15}$=H, $A^{16}$=H, $A^{17}$=H, $A^{18}$=Br], [2515; Q=$Q^{r11}$, $A^{14}$=H, $A^{15}$=Me, $A^{16}$=H, $A^{17}$=H, $A^{18}$=H], [2516; Q=$Q^{r11}$, $A^{14}$=H, $A^{15}$=H, $A^{16}$=Me, $A^{17}$=H, $A^{18}$=H], [2517; Q=$Q^{r11}1$, $A^{14}$=Me, $A^{15}$=H, $A^{16}$=H, $A^{17}$=H, $A^{18}$=Me], [2518; Q=$Q^{r11}$, $A^{14}$=H, $A^{15}$=cyclopropyl, $A^{16}$=H, $A^{17}$=H, $A^{18}$=H], [2519; Q=$Q^{r11}$, $A^{14}$=H, $A^{15}$=H, $A^{16}$=cyclopropyl, $A^{17}$=H, $A^{18}$=H], [2520; Q=$Q^{r11}$, $A^{17}$=cyclopropyl, $A^{15}$=H, $A^{16}$=H, $A^{17}$=H, $A^{18}$=cyclopropyl], [2521; Q=$Q^{r11}$, $A^{14}$=H, $A^{15}$=OCHF$_2$, $A^{16}$=H, $A^{17}$=H, $A^{18}$=H], [2522; Q=$Q^{r1}$, $A^{14}$=H, $A^{15}$=H, $A^{16}$=OCHF$_2$, $A^{17}$=H, $A^{18}$=H], [2523; Q=$Q^{r11}$, $A^{14}$=H, $A^{15}$=OCF$_3$, $A^6$=H, $A^{17}$=H, $A^{18}$=H], [2524; Q=$Q^{r11}$, $A^{14}$=H, $A^{15}$=H, $A^{16}$=OCF$_3$, $A^{17}$=H, $A^{18}$=H], [2525; Q=$Q^{r12}$, $A^{14}$=H, $A^{15}$=H, $A^{16}$=H, $A^{17}$=H, $A^{18}$=H], [2526; Q=$Q^{r12}$, $A^{14}$=F, $A^{15}$=H, $A^{16}$=H, $A^{17}$=H, $A^{18}$=H], [2527; Q=$Q^{r12}$, $A^{14}$=H, $A^{15}$=F, $A^{16}$=H, $A^{17}$=H, $A^{18}$=H], [2528; Q=$Q^{r12}$, $A^{14}$=H, $A^{15}$=H, $A^{16}$=F, $A^{17}$=H, $A^{18}$=H], [2529; Q=$Q^{r12}$, $A^{14}$=F, $A^{15}$=F, $A^{16}$=H, $A^{17}$=H, $A^{18}$=H], [2530; Q=$Q^{r12}$, $A^{14}$=F, $A^{15}$=H, $A^{16}$=F, $A^{17}$=H, $A^{18}$=H], [2531; Q=$Q^{r12}$, $A^{14}$=F, $A^{15}$=H, $A^{16}$=H, $A^{17}$=H, $A^1$=F], [2532; Q=$Q^{r12}$, $A^{14}$=H, $A^{15}$=F, $A^{16}$=F, $A^{17}$=H, $A^{18}$=H], [2533; Q=$Q^{r12}$, $A^{14}$=H, $A^{15}$=F, $A^{16}$=H, $A^{17}$=F, $A^{18}$=H], [2534; Q=$Q^{r12}$, $A^{14}$=Cl, $A^{15}$=H, $A^{16}$=H, $A^{17}$=H, $A^{18}$=H], [2535; Q=$Q^{r12}$, $A^{14}$=H, $A^{15}$=Cl, $A^{16}$=H, $A^{17}$=H, $A^{18}$=H], [2536; Q=$Q^{r12}$, $A^{14}$=H, $A^{15}$=H, $A^{16}$=Cl, $A^{17}$=H, $A^{18}$=H], [2537; Q=$Q^{r12}$, $A^{14}$=Cl, $A^{15}$=Cl, $A^{16}$=H, $A^{17}$=H, $A^{18}$=H], [2538; Q=$Q^{r12}$, $A^{14}$=Cl, $A^{15}$=H, $A^{16}$=Cl, $A^{17}$=H, $A^{18}$=H], [2539; Q=$Q^{r12}$, $A^{14}$=Cl, $A^{15}$=H, $A^{16}$=H, $A^{17}$=H, $A^{18}$=Cl], [2540; Q=$Q^{r12}$, $A^{14}$=Cl, $A^{15}$=Cl, $A^{16}$=Cl, $A^{17}$=H, $A^{18}$=H], [2541; Q=$Q^{r12}$, $A^{14}$=Cl, $A^{15}$=Cl, $A^{16}$=H, $A^{17}$=Cl, $A^{18}$=H], [2542; Q=$Q^{r12}$, $A^{14}$=CF$_3$, $A^{15}$=H, $A^{16}$=H, $A^{17}$=H, $A^{18}$=H], [2543; Q=$Q^{r2}$, $A^{14}$=H, $A^{15}$=CF$_3$, $A^{16}$=H, $A^{17}$=H, $A^{18}$=H], [2544; Q=$Q^{r12}$, $A^{14}$=H, $A^{15}$=H, $A^{16}$=CF$_3$, $A^{17}$=H, $A^{18}$=H], [2545; Q=$Q^{r12}$, $A^{14}$=CF$_3$, $A^{15}$=CF$_3$, $A^{16}$=H, $A^{17}$=H, $A^{18}$=H], [2546; Q=$Q^{r12}$, $A^{14}$=CF$_3$, $A^{15}$=H, $A^{16}$=CF$_3$, $A^{17}$=H, $A^{18}$=H], [2547; Q=$Q^{r2}$, $A^{14}$=CF$_3$, $A^{15}$=H, $A^{16}$=H, $A^{17}$=H, $A^{18}$=CF$_3$], [2548; Q=$Q^{r12}$, $A^{14}$=H, $A^{15}$=CF$_3$, $A^{16}$=CF$_3$, $A^{17}$=H, $A^{18}$=H], [2549; Q=$Q^{r12}$, $A^{14}$=H, $A^{15}$=CF$_3$, $A^{16}$=H, $A^{17}$=CF$_3$, $A^{18}$=H], [2550; Q=$Q^{r12}$, $A^{14}$=OMe, $A^{15}$=H, $A^{16}$=H, $A^{17}$=H, $A^{18}$=H], [2551; Q=$Q^{r12}$, $A^{18}$=H, $A^1$=OMe, $A^{16}$=H, $A^{17}$=H, $A^{18}$=H], [2552; Q=$Q^{r12}$, $A^{14}$=H, $A^{15}$=H, $A^{16}$=OMe, $A^{17}$=H, $A^{18}$=H], [2553; Q=$Q^{r2}$, $A^{14}$=OMe, $A^{15}$=OMe, $A^{16}$=H, $A^{17}$=H, $A^{18}$=H], [2554; Q=$Q^{r12}$, $A^{14}$=OMe, $A^{15}$=H, $A^{16}$=OMe, $A^{17}$=H, $A^{18}$=H], [2555; Q=$Q^{r12}$, $A^{14}$=OMe, $A^{15}$=H, $A^{16}$=H, $A^{17}$=H, $A^{18}$=OMe], [2556; Q=$Q^{r12}$, $A^{14}$=H, $A^{15}$=OMe, $A^{16}$=OMe, $A^{17}$=H, $A^{18}$=H], [2557; Q=$Q^{r12}$, $A^{18}$=H, $A^{15}$=OMe, $A^{16}$=H, $A^{17}$=OMe, $A^{18}$=H], [2558; Q=$Q^{r12}$, $A^{14}$=H, $A^{15}$=Br, $A^{16}$=H, $A^{17}$=H, $A^{18}$=H], [2559; Q=$Q^{r12}$, $A^{14}$=H, $A^{15}$=H, $A^{16}$=Br, $A^{17}$=H, $A^{18}$=H], [2560; Q=$Q^{r12}$, $A^{14}$=Br, $A^{15}$=H, $A^{16}$=H, $A^{17}$=H, $A^{18}$=Br], [2561; Q=$Q^{r12}$, $A^{14}$=H, $A^{15}$=Me, $A^{16}$=H, $A^{17}$=H, $A^{18}$=H], [2562; Q=$Q^{r12}$, $A^{14}$=H, $A^{15}$=H, $A^{16}$=Me, $A^{17}$=H, $A^{18}$=H], [2563; Q=$Q^{r12}$, $A^{14}$=Me, $A^{15}$=H, $A^{16}$=H, $A^{17}$=H, $A^{18}$=Me], [2564; Q=$Q^{r12}$, $A^{14}$=H, $A^{15}$=cyclopropyl, $A^{16}$=H, $A^{17}$=H, $A^{18}$=H], [2565; Q=$Q^{r12}$, $A^{14}$=H, $A^{15}$=H, $A^{16}$=cyclopropyl, $A^{17}$=H, $A^{18}$=H], [2566; Q=$Q^{r12}$, $A^{14}$=cyclopropyl, $A^{15}$=H, $A^{16}$=H, $A^{17}$=H, $A^{18}$=cyclopropyl], [2567; Q=$Q^{r12}$, $A^{14}$=H, $A^{15}$=OCHF$_2$, $A^{16}$=H, $A^{17}$=H, $A^{18}$=H], [2568; Q=$Q^{r12}$, $A^{14}$=H, $A^{15}$=H, $A^{16}$=OCHF$_2$, $A^{17}$=H, $A^{18}$=H], [2569; Q=$Q^{r12}$, $A^{14}$=H, $A^{15}$=OCF$_3$, $A^{16}$=H, $A^{17}$=H, $A^{18}$=H], [2570; Q=$Q^{r12}$, $A^{14}$=H, $A^{15}$=H, $A^{16}$=OCF$_3$, $A^{17}$=H, $A^{18}$=H], [2571; Q=$Q^{r13}$, $A^{20}$=H, $A^{21}$=H, $A^{22}$=H], [2572; Q=$Q^{r13}$, $A^{20}$=Me, $A^{21}$=H, $A^{22}$=H], [2573; Q=$Q^{r13}$, $A^{20}$=H, $A^{21}$=Me, $A^{22}$=H], [2574; Q=$Q^{r13}$, $A^{20}$=H, $A^{21}$=H, $A^{22}$=Me], [2575; Q=$Q^{r3}$, $A^{20}$=Me, $A^{21}$=Me, $A^{22}$=H], [2576; Q=$Q^{r13}$, $A^{20}$=Me, $A^{21}$=H, $A^{22}$=Me], [2577; Q=$Q^{r13}$, $A^{20}$=H, $A^{21}$=Me, $A^{22}$=Me], [2578; Q=$Q^{r13}$, $A^{20}$=Me, $A^{21}$=Me, $A^{22}$=Me], [2579; Q=$Q^{r13}$, $A^{20}$=H, $A^{21}$=H, $A^{22}$=Cl], [2580; Q=$Q^{r13}$, $A^{20}$=H, $A^{21}$=H, $A^{22}$=CF$_3$], [2581; Q=$Q^{r13}$, $A^{20}$=H, $A^{21}$=H, $A^{22}$=OMe], [2582; Q=$Q^{r14}$, $A^{20}$=H, $A^{21}$=H, $A^{23}$=H], [2583; Q=$Q^{r14}$, $A^{20}$=Me, $A^{21}$=H, $A^{23}$=H], [2584; Q=$Q^{r14}$, $A^{20}$=H, $A^{21}$=Me, $A^{23}$=H], [2585; Q=$Q^{r14}$, $A^{20}$=H, $A^{21}$=H, $A^{23}$=Me], [2586; Q=$Q^{r14}$, $A^{20}$=Me, $A^{21}$=Me, $A^{23}$=H], [2587; Q=$Q^{r14}$, $A^{20}$=Me, $A^{21}$=H, $A^{23}$=Me], [2588; =$Q^{r14}$, $A^{20}$=H, $A^{21}$=Me, $A^{23}$=Me], [2589; Q=$Q^{r4}$, $A^{20}$=Me, $A^{21}$=Me, $A^{23}$=Me], [2590; Q=$Q^{r14}$, $A^{20}$=H, $A^{21}$=Cl, $A^{23}$=H], [2591; Q=$Q^{q11}$, $A^{20}$=H, $A^{21}$=CF$_3$, $A^{23}$=H], [2592; Q=$Q^{r14}$, $A^{20}$=H, $A^{21}$=OMe, $A^{23}$=H], [2593; Q=$Q^{r14}$, $A^{20}$=H, $A^{21}$=H, $A^{23}$=Cl], [2594; Q=$Q^{r14}$, $A^{20}$=H, $A^{21}$=H, $A^{23}$=CF$_3$], [2595; Q=$Q^{r14}$, $A^{20}$=H, $A^{21}$=H, $A^{23}$=OMe], [2596; Q=$Q^{r15}$, $A^{24}$=H, $A^{25}$=H, $A^{26}$=H], [2597; Q=$Q^{r15}$, $A^{24}$=Me, $A^{25}$=H, $A^{26}$=H], [2598; Q=$Q^{r15}$, $A^{24}$=H, $A^{25}$=Me, $A^{26}$=H], [2599; Q=$Q^{r15}$, $A^{24}$=H, $A^{25}$=H, $A^{26}$=Me], [2600; Q=$Q^{r15}$, $A^{24}$=Me, $A^{25}$=Me, $A^{26}$=H], [2601; Q=$Q^{r15}$, $A^{24}$=Me, $A^{25}$=H, $A^{26}$=Me], [2602; Q=$Q^{r15}$, $A^{24}$=H, $A^{25}$=Me, $A^{26}$=Me], [2603; Q=$Q^{r5}$, $A^{24}$=Me, $A^{25}$=Me, $A^{26}$=Me], [2604; Q=$Q^{r15}$, $A^{24}$=H, $A^{25}$=H, $A^{26}$=Cl], [2605; Q=$Q^{r1}$, $A^{24}$=H, $A^{25}$=H, $A^{26}$=CF$_3$], [2606; Q=Q$^{r15}$, $A^{24}$=H, $A^{25}$=H, $A^{26}$=OMe], [2607; Q=Q$^{r16}$, $A^{24}$=H, $A^{25}$=H, $A^{27}$=H], [2608; Q=Q$^{r16}$, $A^{24}$=Me, $A^{25}$=H, $A^{27}$=Me], [2609; Q=Q$^{r16}$, $A^{24}$=H, $A^{25}$=Me, $A^{27}$=H], [2610; Q=Q$^{r1}$, $A^{24}$=H, $A^{25}$=H, $A^{27}$=Me], [2611; Q=Q$^{r1}$, $A^{24}$=Me, $A^{25}$=Me, $A^{27}$=H], [2612; Q=Q$^{r16}$, $A^{24}$=Me, $A^{25}$=H, $A^{27}$=Me], [2613; Q=Q$^{r16}$, $A^{24}$=H, $A^{25}$=Me, $A^{27}$=Me], [2614; Q=Q$^{r16}$, $A^{24}$=Me, $A^{25}$=Me, $A^{27}$=Me], [2615; Q=Q$^{r16}$, $A^{24}$=H, $A^{25}$=Cl, $A^{27}$=H], [2616; Q=Q$^{r16}$, $A^{24}$=H, $A^{25}$=CF$_3$, $A^{27}$=H], [2617; Q=Q$^{r16}$, $A^{24}$=H, $A^{25}$=OMe, $A^{27}$=H], [2618; Q=Q$^{r1}$, $A^{24}$=H, $A^{25}$=H, $A^{27}$=Cl], [2619; Q=Q$^{r16}$, $A^{24}$=H, $A^{25}$=H, $A^{27}$=CF$_3$], [2620; Q=Q$^{r16}$, $A^{24}$=H, $A^{25}$=H, $A^{27}$=OMe], [2630; Q=Q$^{s1}$, $A^{28}$=H, $A^{29}$=H, $A^{30}$=H, $A^{31}$=H, $A^{32}$=H], [2631; Q=Q$^{s19}$, $A^{28}$=H, $A^{29}$=F, $A^{30}$=H, $A^{31}$=H, $A^{32}$=H], [2632; Q=Q$^{s1}$, $A^{28}$=H, $A^{29}$=H, $A^{30}$=F, $A^{31}$=H, $A^{32}$=H], [2633; Q=Q$^{s1}$, $A^{28}$=F, $A^{29}$=H, $A^{30}$=H, $A^{31}$=H, $A^{32}$=F], [2634; Q=Q$^{s1}$, $A^{28}$=H, $A^{29}$=F, $A^{30}$=H, $A^1$=F, $A^{32}$=H], [2635; Q=Q$^{s1}$, $A^{28}$=H, $A^{29}$=Cl, $A^{30}$=H, $A^{31}$=H, $A^{32}$=H], [2636; Q=Q$^{s1}$, $A^{28}$=H, $A^{29}$=H, $A^{30}$=Cl, $A^{31}$=H, $A^{32}$=H], [2637; Q=Q$^{s1}$, $A^{28}$=Cl, $A^{29}$=Cl, $A^{30}$=H, $A^{31}$=H, $A^{32}$=H], [2638; Q=Q$^{s1}$, $A^{28}$=Cl, $A^{29}$=H, $A^{30}$=H, $A^3$=H, $A^{32}$=Cl], [2639; Q=Q$^{s1}$, $A^{28}$=H, $A^{29}$=Cl, $A^{30}$=H, $A^{31}$=Cl, $A^{32}$=H], [2640; Q=Q$^{s1}$, $A^{28}$=H, $A^{29}$=CF$_3$, $A^{30}$=H, $A^{31}$=H, $A^{32}$=H], [2641; Q=Q$^{s1}$, $A^{28}$=H, $A^{29}$=H, $A^{30}$=CF$_3$, $A^{31}$=H, $A^{32}$=H], [2642; Q=Q$^{s1}$, $A^{28}$=H, $A^{29}$=OMe, $A^{30}$=H, $A^{31}$=H, $A^{32}$=H], [2643; Q=Q$^{s1}$, $A^{28}$=H, $A^{29}$=H, $A^{30}$=OMe, $A^{31}$=H, $A^{32}$=H], [2644; Q=Q$^{s1}$, $A^{28}$=OMe, $A^{29}$=H, $A^{30}$=H, $A^{31}$=H, $A^{32}$=OMe], [2645; Q=Q$^{q11}$, $A^{28}$=H, $A^{29}$=OMe, $A^{30}$=H, $A^{31}$=OMe, $A^{32}$=H], [2646; Q=Q$^{s1}$, $A^{28}$=H, $A^{29}$=Br, $A^{30}$=H, $A^{31}$=H, $A^{32}$=H], [2647; Q=Q$^{s1}$, $A^{28}$=H, $A^{29}$=H, $A^{30}$=Br, $A^{31}$=H, $A^{32}$=H], [2648; Q=Q$^{s1}$, $A^{28}$=Br, $A^{29}$=H, $A^{30}$=H, $A^{31}$=H, $A^{32}$=Br], [2649; Q=Q$^{q5}$, $A^{28}$=H, $A^{29}$=Me, $A^{30}$=H, $A^{31}$=H, $A^{32}$=H], [2650; Q=Q$^{s1}$, $A^{28}$=H, $A^{29}$=H, $A^{30}$=Me, $A^{31}$=H, $A^{32}$=H], [2651; Q=Q$^{s1}$, $A^{28}$=Me, $A^{29}$=H, $A^{30}$=H, $A^{31}$=H, $A^{32}$=Me], [2652; Q=Q$^{s1}$, $A^{28}$=H, $A^{29}$=cyclopropyl, $A^{30}$=H, $A^{31}$=H, $A^{32}$=H], [2653; Q=Q$^{s1}$, $A^{28}$=H, $A^{29}$=H, $A^{30}$=cyclopropyl, $A^{31}$=H, $A^{32}$=H], [2654; Q=Q$^{s1}$, $A^{28}$=cyclopropyl, $A^{29}$=H, $A^{30}$=H, $A^{31}$=H, $A^{32}$=cyclopropyl], [2655; Q=Q$^{s1}$, $A^{28}$=H, $A^{29}$=OCHF$_2$, $A^{30}$=H, $A^{31}$=H, $A^{32}$=H], [2656; Q=Q$^{s1}$, $A^{28}$=H, $A^{29}$=H, $A^{30}$=OCHF$_2$, $A^{31}$=H, $A^{32}$=H], [2657; Q=Q$^{s1}$, $A^{28}$=H, $A^{29}$=OCF$_3$, $A^{30}$=H, $A^{31}$=H, $A^{32}$=H], [2658; Q=Q$^{s1}$, $A^{28}$=H, $A^{29}$=H, $A^{30}$=OCF$_3$, $A^{31}$=H, $A^{32}$=H], [2659; Q=Q$^{s2}$, $A^{28}$=H, $A^{29}$=H, $A^{30}$=H, $A^{31}$=H, $A^{32}$=H], [2660; Q=Q$^{s2}$, $A^{28}$=H, $A^{29}$=F, $A^{30}$=H, $A^{31}$=H, $A^{32}$=H], [2661; Q=Q$^{q2}$, $A^{28}$=H, $A^{29}$=H, $A^{30}$=F, $A^{31}$=H, $A^{32}$=H], [2662; Q=Q$^{s2}$, $A^{28}$=F, $A^{29}$=H, $A^{30}$=H, $A^{31}$=H, $A^{32}$=F], [2663; Q=Q$^{s2}$, $A^{28}$=H, $A^{29}$=F, $A^{30}$=H, $A^1$=F, $A^{32}$=H], [2664; Q=Q$^{s2}$, $A^{28}$=H, $A^{29}$=Cl, $A^{30}$=H, $A^{31}$=H, $A^{32}$=H], [2665; Q=Q$^{s2}$, $A^{28}$=H, $A^{29}$=H, $A^{30}$=Cl, $A^{31}$=H, $A^{32}$=H], [2666; Q=Q$^{s2}$, $A^{28}$=Cl, $A^{29}$=Cl, $A^{30}$=H, $A^{31}$=H, $A^{32}$=H], [2667; Q=Q$^{s2}$, $A^{28}$=Cl, $A^{29}$=H, $A^{30}$=H, $A^{31}$=H, $A^{32}$=Cl], [2668; Q=Q$^{s2}$, $A^{28}$=H, $A^{29}$=Cl, $A^{30}$=H, $A^{31}$=Cl, $A^{32}$=H], [2669; Q=Q$^{s2}$, $A^{28}$=H, $A^{29}$=CF$_3$, $A^{30}$=H, $A^{31}$=H, $A^{32}$=H], [2670; Q=Q$^{s2}$, $A^{28}$=H, $A^{29}$=H, $A^{30}$=CF$_3$, $A^{31}$=H, $A^{32}$=H], [2671; Q=Q$^{s2}$, $A^{28}$=H, $A^{29}$=OMe, $A^{30}$=H, $A^{31}$=H, $A^{32}$=H], [2672; Q=Q$^{s2}$, $A^{28}$=H, $A^{29}$=H, $A^{30}$=OMe, $A^{31}$=H, $A^{32}$=H], [2673; Q=Q$^{s2}$, $A^{28}$=Me, $A^{29}$=H, $A^{30}$=H, $A^{31}$=H, $A^{32}$=OMe], [2674; Q=Q$^{s2}$, $A^{28}$=H, $A^{29}$=OMe, $A^{30}$=H, $A^{31}$=OMe, $A^{32}$=H], [2675; Q=Q$^{q2}$, $A^{28}$=H, $A^{29}$=Br, $A^{30}$=H, $A^{31}$=H, $A^{32}$=H], [2676; Q=Q$^{q2}$, $A^{28}$=H, $A^{29}$=H, $A^{30}$=Br, $A^{31}$=H, $A^{32}$=H], [2677; Q=Q$^{q2}$, $A^{28}$=Br, $A^{29}$=H, $A^{30}$=H, $A^{31}$=H, $A^{32}$=Br], [2678; Q=Q$^{s2}$, $A^{28}$=H, $A^{29}$=Me, $A^{30}$=H, $A^{31}$=H, $A^{32}$=H], [2679; Q=Q$^{s2}$, $A^{28}$=H, $A^{29}$=H, $A^{30}$=Me, $A^{31}$=H, $A^{32}$=H], [2680; Q=Q$^{s2}$, $A^{28}$=Me, $A^{29}$=H, $A^{30}$=H, $A^{31}$=H, $A^{32}$=Me], [2681; Q=Q$^{s2}$, $A^{28}$=H, $A^{29}$=cyclopropyl, $A^{30}$=H, $A^{31}$=H, $A^{32}$=H], [2682; Q=Q$^{s2}$, $A^{28}$=H, $A^{29}$=H, $A^{30}$=cyclopropyl, $A^{31}$=H, $A^{32}$=H], [2683; Q=Q$^{s2}$, $A^{28}$=cyclopropyl, $A^{29}$=H, $A^{30}$=H, $A^{31}$=H, $A^{32}$=cyclopropyl], [2684; Q=Q$^{s2}$, $A^{28}$=H, $A^{29}$=OCHF$_2$, $A^{30}$=H, $A^{31}$=H, $A^{32}$=H], [2685; Q=Q$^{s2}$, $A^{28}$=H, $A^{29}$=H, $A^{30}$=OCHF$_2$, $A^{31}$=H, $A^{32}$=H], [2686; Q=Q$^{s2}$, $A^{28}$=H, $A^{29}$=OCF$_3$, $A^{30}$=H, $A^{31}$=H, $A^{32}$=H], [2687; Q=Q$^{s2}$, $A^{28}$=H, $A^{29}$=H, $A^{30}$=OCF$_3$, $A^{31}$=H, $A^{32}$=H], [2688; Q=Q$^{s1}$, $A^{28}$=H, $A^{29}$=H, $A^{30}$=H, $A^{31}$=H, $A^{32}$=H], [2689; Q=Q$^{s1}$, $A^{28}$=H, $A^{29}$=F, $A^{30}$=H, $A^{31}$=H, $A^{32}$=H], [2690; Q=Q$^{s1}$, $A^{28}$=H, $A^{29}$=H, $A^{30}$=F, $A^{31}$=H, $A^{32}$=H], [2691; Q=Q$^{s1}$, $A^{28}$=F, $A^{29}$=H, $A^{30}$=H, $A^{31}$=H, $A^{32}$=F], [2692; Q=Q$^{s1}$, $A^{28}$=H, $A^{29}$=F, $A^{30}$=H, $A^{31}$=F, $A^{32}$=H], [2693; Q=Q$^{s1}$, $A^{28}$=H, $A^{29}$=Cl, $A^{30}$=H, $A^{31}$=H, $A^{32}$=H], [2694; Q=Q$^{s3}$, $A^{28}$=H, $A^{29}$=H, $A^{30}$=Cl, $A^{31}$=H, $A^{32}$=H], [2695; Q=Q$^{s1}$, $A^{28}$=Cl, $A^{29}$=Cl, $A^{30}$=H, $A^{31}$=H, $A^{32}$=H], [2696; Q=Q$^{s3}$, $A^{28}$=Cl, $A^{29}$=H, $A^{30}$=H, $A^{31}$=H, $A^{32}$=Cl], [2697; Q=Q$^{s3}$, $A^{28}$=H, $A^{29}$=Cl, $A^{30}$=H, $A^{31}$=Cl, $A^{32}$=H], [2698; Q=Q$^{s3}$, $A^{28}$=H, $A^{29}$=CF$_3$, $A^{30}$=H, $A^{31}$=H, $A^{32}$=H], [2699; Q=Q$^{s3}$, $A^{28}$=H, $A^{29}$=H, $A^{30}$=CF$_3$, $A^{31}$=H, $A^{32}$=H], [2700; Q=Q$^{s3}$, $A^{28}$=H, $A^{29}$=OMe, $A^{30}$=H, $A^{31}$=H, $A^{32}$=H], [2701; Q=Q$^{s3}$, $A^{28}$=H, $A^{29}$=H, $A^{30}$=, $A^{31}$=H, $A^{32}$=H], [2702; Q=Q$^{s3}$, $A^{28}$=OMe, $A^{29}$=H, $A^{30}$=H, $A^{31}$=H, $A^{32}$=OMe], [2703; Q=Q$^{s1}$, $A^{28}$=H, $A^{29}$=OMe, $A^{30}$=H, $A^{31}$=OMe, $A^{32}$=H], [2704; Q=Q$^{s1}$, $A^{28}$=H, $A^{29}$=Br, $A^{30}$=H, $A^{31}$=H, $A^{32}$=H], [2705; Q=Q$^{s3}$, $A^{28}$=H, $A^{29}$=H, $A^{30}$=Br, $A^{31}$=H, $A^{32}$=H], [2706; Q=Q$^{s3}$, $A^{28}$=Br, $A^{29}$=H, $A^{30}$=H, $A^{31}$=H, $A^{32}$=Br], [2707; Q=Q$^{s3}$, $A^{28}$=H, $A^{29}$=Me, $A^{30}$=H, $A^{31}$=H, $A^{32}$=H], [2708; Q=Q$^{s3}$, $A^{28}$=H, $A^{29}$=H, $A^{30}$=Me, $A^{31}$=H, $A^{32}$=H], [2709; Q=Q$^{s3}$, $A^{28}$=Me, $A^{29}$=H, $A^{30}$=H, $A^{31}$=H, $A^{32}$=Me], [2710; Q=Q$^{s3}$, $A^{28}$=H, $A^{29}$=cyclopropyl, $A^{30}$=H, $A^{31}$=H, $A^{32}$=H], [2711; Q=Q$^{s3}$, $A^{28}$=H, $A^{29}$=H, $A^{30}$=cyclopropyl, $A^{31}$=H, $A^{32}$=H], [2712; Q=Q$^{s3}$, $A^{28}$=cyclopropyl, $A^{29}$=H, $A^{30}$=H, $A^{31}$=H, $A^{32}$=cyclopropyl], [2713; Q=Q$^{s3}$, $A^{28}$=H, $A^{29}$=OCHF$_2$, $A^{30}$=H, $A^{31}$=H, $A^{32}$=H], [2714; Q=Q$^{s1}$, $A^{28}$=H, $A^{29}$=H, $A^{30}$=OCHF$_2$, $A^{31}$=H, $A^{32}$=H], [2715; Q=Q$^{s1}$, $A^{28}$=H, $A^{29}$=OCF$_3$, $A^{30}$=H, $A^{31}$=H, $A^{32}$=H], [2716; Q=Q$^{s3}$, $A^{28}$=H, $A^{29}$=H, $A^{30}$=OCF$_3$, $A^{31}$=H, $A^{32}$=H], [2717; Q=Q$^{s3}$, $A^{33}$=H, $A^{34}$=H, $A^{35}$=H], [2718; Q=Q$^{s4}$, $A^{33}$=Me, $A^{34}$=H, $A^{35}$=H], [2719; Q=Q$^{s4}$, $A^{33}$=H, $A^{34}$=Me, $A^{35}$=H], [2720; Q=Q$^{s4}$, $A^{33}$=H, $A^{34}$=H, $A^{35}$=Me], [2721; Q=Q$^{s4}$, $A^{33}$=Me, $A^{34}$=Me, $A^{35}$=H], [2722; Q=Q$^{s4}$, $A^{33}$=Me, $A^{34}$=H, $A^{35}$=Me], [2723; Q=Q$^{s4}$, $A^{33}$=H, $A^{34}$=Me, $A^{35}$=Me], [2724; Q=Q$^{s4}$, $A^{33}$=Me, $A^{34}$=Me, $A^{35}$=Me], [2725; Q=Q$^{s4}$, $A^{33}$=H, $A^{34}$=H, $A^{35}$=Cl], [2726; Q=Q$^{s4}$, $A^{33}$=H, $A^{34}$=H, $A^{35}$=CF$_3$], [2727; Q=Q$^{s4}$, $A^{33}$=H, $A^{34}$=H, $A^{35}$=OMe], [2728; Q=Q$^{s5}$, $A^{33}$=H, $A^{34}$=H, $A^{36}$=H], [2729; Q=Q$^{s1}$, $A^{33}$=Me, $A^{34}$=H, $A^{36}$=H], [2730; Q=Q$^{s5}$, $A^{33}$=H, $A^{34}$=Me, $A^{36}$=H], [2731; Q=Q$^{q5}$, $A^{33}$=H, $A^{34}$=H, $A^{36}$=Me], [2732; Q=Q$^{s5}$, $A^{33}$=Me, $A^{34}$=Me, $A^{36}$=H], [2733; Q=Q$^{s5}$, $A^{33}$=Me, $A^{34}$=H, $A^{36}$=Me], [2734; Q=Q$^{s5}$, $A^{33}$=H, $A^{34}$=Me, $A^{36}$=Me], [2735; Q=Q$^{s5}$, $A^{33}$=Me, $A^{34}$=Me, $A^{36}$=Me], [2736; Q=Q$^{s5}$, $A^{33}$=H, $A^{34}$=Cl, $A^{36}$=H], [2737; Q=Q$^{q5}$, $A^{33}$=H, $A^{34}$=CF$_3$, $A^{36}$=H], [2738; Q=Q$^{s5}$, $A^{33}$=H, $A^{34}$=OMe, $A^{36}$=H], [2739; Q=Q$^{s5}$, $A^{33}$=H, $A^{34}$=H, $A^{36}$=Cl], [2740; Q=Q$^{s5}$, $A^{33}$=H, $A^{34}$=H, $A^{36}$=CF$_3$], [2741; Q=Q$^{s1}$, $A^{33}$=H, $A^{34}$=H, $A^{36}$=OMe], [2742; Q=Q$^{r1}$, $A^{37}$=H, $A^{38}$=H, $A^{39}$=H, $A^{40}$=H, $A^{41}$=H], [2743; Q=Q$^{r1}$, $A^{37}$=Cl, $A^{38}$=H, $A^{39}$=H, $A^{40}$=H, $A^{41}$=H], [2744; Q=Q$^{r1}$, $A^{37}$=H, $A^{38}$=Cl, $A^{39}$=H, $A^{40}$=H, $A^{41}$=H], [2745; Q=Q$^{r1}$, $A^{37}$=H, $A^{38}$=H, $A^{39}$=Cl, $A^{40}$=H, $A^{41}$=H], [2746; Q=Q$^{r1}$, $A^{37}$=Cl, $A^{38}$=H, $A^{39}$=H, $A^{40}$=H, $A^{41}$=Cl], [2747; Q=Q$^{r1}$, $A^{37}$=H, $A^{38}$=Cl, $A^{39}$=H, $A^{40}$=Cl, $A^{41}$=H], [2748; Q=Q$^{r1}$, $A^{37}$=Me, $A^{38}$=H, $A^{39}$=H, $A^{40}$=H, $A^{41}$=H], [2749; Q=Q$^{r1}$, $A^{37}$=H, $A^{38}$=Me, $A^{39}$=H, $A^{40}$=H, $A^{41}$=H], [2750; Q=Q$^{r1}$, $A^{37}$=H, $A^{38}$=H, $A^{39}$=Me, $A^{40}$=H, $A^{41}$=H], [2751; Q=Q$^{r1}$, $A^{37}$=Me, $A^{38}$=H, $A^{39}$=H, $A^{40}$=H, $A^{41}$=Me], [2752; Q=Q$^{r1}$, $A^{37}$=H, $A^{38}$=Me, $A^{39}$=H, $A^{40}$=Me, $A^{41}$=H], [2753; Q=Q$^{r1}$, $A^{37}$=H, $A^{38}$=H, $A^{39}$=H, $A^{40}$=H, $A^{41}$=H], [2754; Q=Q$^{r2}$, $A^{37}$=H, $A^{38}$=H, $A^{39}$=H, $A^{40}$=H, $A^{41}$=H], [2755; Q=Q$^{r2}$, $A^{37}$=Cl, A³⁸=H, A³⁹=H, A⁴⁰=H, A⁴¹=H], [2756; Q=Q^{r2}, A³⁷=H, A³⁸=Cl, A³⁹=H, A⁴⁰=H, A⁴¹=H], [2757; Q=Q^{r2}, A³⁷=H, A³⁸=H, A³⁹=Cl, A⁴⁰=H, A⁴¹=H], [2758; Q=Q^{r2}, A³⁷=Cl, A³⁸=H, A³⁹=H, A⁴⁰=H, A⁴¹=Cl], [2759; Q=Q^{r2}, A³⁷=H, A³⁸=Cl, A³⁹=H, A⁴⁰=Cl, A⁴¹=H], [2760; Q=Q^{r2}, A³⁷=Me, A³⁸=H, A³⁹=H, A⁴⁰=H, A⁴¹=H], [2761; Q=Q^{r2}, A³⁷=H, A³⁸=Me, A³⁹=H, A⁴⁰=H, A⁴¹=H], [2762; Q=Q^{r2}, A³⁷=H, A³⁸=H, A³⁹=Me, A⁴⁰=H, A⁴¹=H], [2763; Q=Q^{r2}, A³⁷=Me, A³⁸=H, A³⁹=H, A⁴⁰=H, A⁴¹=Me], [2764; Q=Q^{r2}, A³⁷=H, A³⁸=Me, A³⁹=H, A⁴⁰=Me, A⁴¹=H], [2765; Q=Q^{r3}, A³⁷=H, A³⁸=H, A³⁹=H, A⁴⁰=H, A⁴¹=H], [2766; Q=Q^{r3}, A³⁷=H, A³⁸=H, A³⁹=H, A⁴⁰=H, A⁴¹=H], [2767; Q=Q^{r3}, A³⁷=Cl, A³⁸=H, A³⁹=H, A⁴⁰=H, A⁴¹=H], [2768; Q=Q^{r3}, A³⁷=H, A³⁸=Cl, A³⁹=H, A⁴⁰=H, A⁴¹=H], [2769; Q=Q^{r3}, A³⁷=H, A³⁸=H, A³⁹=Cl, A⁴⁰=H, A⁴¹=H], [2770; Q=Q^{r3}, A³⁷=Cl, A³⁸=H, A³⁹=H, A⁴⁰=H, A⁴¹=Cl], [2771; Q=Q^{r3}, A³⁷=H, A³⁸=Cl, A³⁹=H, A⁴⁰=Cl, A¹=H], [2772; Q=Q^{r3}, A³⁷=Me, A³⁸=H, A³⁹=H, A⁴⁰=H, A⁴¹=H], [2773; Q=Q^{r3}, A³⁷=H, A³⁸=Me, A³⁹=H, A⁴⁰=H, A⁴¹=H], [2774; Q=Q^{r3}, A³⁷=H, A³⁸=H, A³⁹=Me, A⁴⁰=H, A⁴¹=H], [2775; Q=Q^{r3}, A³⁷=Me, A³⁸=H, A³⁹=H, A⁴⁰=H, A⁴¹=Me], [2776; Q=Q^{r3}, A³⁷=H, A³⁸=Me, A³⁹=H, A⁴⁰=Me, A⁴¹=H], [2777; Q=Q^{r3}, A³⁷=H, A³⁸=H, A³⁹=H, A⁴⁰=H, A⁴¹=H], [2778; Q=Q^{r4}, A³⁷=H, A³⁸=H, A³⁹=H, A⁴⁰=H, A⁴¹=H], [2779; Q=Q^{r4}, A³⁷=Cl, A³⁸=H, A³⁹=H, A⁴⁰=H, A⁴¹=H], [2780; Q=Q^{r4}, A³⁷=H, A³⁸=Cl, A³⁹=H, A⁴⁰=H, A⁴¹=H], [2781; Q=Q^{r4}, A³⁷=H, A³⁸=H, A³⁹=Cl, A⁴⁰=H, A⁴⁹=H], [2782; Q=Q^{r4}, A³⁷=Cl, A³⁸=H, A³⁹=H, A⁴⁰=H, A⁴¹=Cl], [2783; Q=Q^{r4}, A³⁷=H, A³⁸=Cl, A³⁹=H, A⁴⁰=Cl, A⁴¹=H], [2784; Q=Q^{r4}, A³⁷=Me, A³⁸=H, A³⁹=H, A⁴⁰=H, A⁴¹=H], [2785; Q=Q^{r4}, A³⁷=H, A³⁸=Me, A³⁹=H, A⁴⁰=H, A⁴¹=H], [2786; Q=Q^{r4}, A³⁷=H, A³⁸=H, A³⁹=Me, A⁴⁰=H, A⁴¹=H], [2787; Q=Qt, A³⁷=Me, A³⁸=H, A³⁹=H, A⁴⁰=H, A⁴¹=Me], [2788; Q=Q^{r4}, A³⁷=H, A³⁸=Me, A³⁹=H, A⁴⁰=Me, A⁴¹=H], [2789; Q=Q^{r4}, A³⁷=H, A³⁸=H, A³⁹=H, A⁴⁰=H, A⁴¹=H], [2790; Q=Q^{r5}, A³⁷=H, A³⁸=H, A³⁹=H, A⁴⁰=H, A⁴¹=H], [2791; Q=Q^{r5}, A³⁷=Cl, A³⁸=H, A³⁹=H, A⁴⁰=H, A⁴¹=H], [2792; Q=Q^{r5}, A³⁷=H, A³⁸=Cl, A³⁹=H, A⁴⁰=H, A⁴¹=H], [2793; Q=Q^{r5}, A³⁷=H, A³⁸=H, A³⁹=Cl, A⁴⁰=H, A⁴¹=H], [2794; Q=Q^{r5}, A³⁷=Cl, A³⁸=H, A³⁹=H, A⁴⁰=H, A⁴¹=Cl], [2795; Q=Q^{r5}, A³⁷=H, A³⁸=Cl, A³⁹=H, A⁴⁰=Cl, A⁴¹=H], [2796; Q=Q^{r5}, A³⁷=Me, A³⁸=H, A³⁹=H, A⁴⁰=H, A⁴¹=H], [2797; Q=Q^{r5}, A³⁷=H, A³⁸=Me, A³⁹=H, A⁴⁰=H, A⁴¹=H], [2798; Q=Q^{r5}, A³⁷=H, A³⁸=H, A³⁹=Me, A⁴⁰=H, A⁴¹=H], [2799; Q=Q^{r5}, A³⁷=Me, A³⁸=H, A³⁹=H, A⁴⁰=H, A⁴¹=Me], [2800; Q=Q^{r5}, A³⁷=H, A³⁸=Me, A³⁹=H, A⁴⁰=Me, A⁴¹=H], [2801; Q=Q^{r5}, A³⁷=H, A³⁸=H, A³⁹=H, A⁴⁰=H, A⁴¹=H], [2802; Q=Q^{r6}, A³⁷=H, A³⁸=H, A³⁹=H, A⁴⁰=H, A⁴¹=H], [2803; Q=Q^{r6}, A³⁷=Cl, A³⁸=H, A³⁹=H, A⁴⁰=H, A⁴¹=H], [2804; Q=Q^{r6}, A³⁷=H, A³⁸=Cl, A³⁹=H, A⁴⁰=H, A⁴¹=H], [2805; Q=Q^{r6}, A³⁷=H, A³⁸=H, A³⁹=Cl, A⁴⁰=H, A⁴¹=H], [2806; Q=Q^{r6}, A³⁷=Cl, A³⁸=H, A³⁹=H, A⁴⁰=H, A⁴¹=Cl], [2807; Q=Q^{r6}, A³⁷=H, A³⁸=Cl, A³⁹=H, A⁴⁰=Cl, A⁴¹=H], [2808; Q=Q^{r6}, A³⁷=Me, A³⁸=H, A³⁹=H, A⁴⁰=H, A⁴¹=H], [2809; Q=Q^{r6}, A³⁷=H, A³⁸=Me, A³⁹=H, A⁴⁰=H, A⁴¹=H], [2810; Q=Q^{r6}, A³⁷=H, A³⁸=H, A³⁹=Me, A⁴⁰=H, A⁴¹=H], [2811; Q=Q^{r6}, A³⁷=Me, A³⁸=H, A³⁹=H, A⁴⁰=H, A⁴¹=Me], [2812; Q=Q^{r6}, A³⁷=H, A³⁸=Me, A³⁹=H, A⁴⁰=Me, A⁴¹=H], [2813; Q=Q^{r6}, A³⁷=H, A³⁸=H, A³⁹=H, A⁴⁰=H, A⁴¹=H], [2814; Q=Q^{r7}, A³⁷=H, A³⁸=H, A³⁹=H, A⁴⁰=H, A⁴¹=H, A⁴²=H], [2815; Q=Q^{r7}, A³⁷=Cl, A³⁸=H, A³⁹=H, A⁴⁰=H, A⁴¹=H, A⁴²=H], [2816; Q=Q^{r7}, A³⁷=H, A³⁸=Cl, A³⁹=H, A⁴⁰=H, A⁴¹=H, A⁴²=H], [2817; Q=Q^{r7}, A³⁷=H, A³⁸=H, A³⁹=Cl, A⁴⁰=H, A⁴¹=H, A⁴²=H], [2818; Q=Q^{r7}, A³⁷=Cl, A³⁸=H, A³⁹=H, A⁴⁰=H, A⁴¹=Cl, A⁴²=H], [2819; Q=Q^{r7}, A³⁷=H, A³⁸=Cl, A³⁹=H, A⁴⁰=Cl, A⁴¹=H, A⁴²=H], [2820; Q=Q^{r7}, A³⁷=Me, A³⁸=H, A³⁹=H, A⁴⁰=H, A⁴¹=H, A⁴²=H], [2821; Q=Q^{r7}, A³⁷=H, A³⁸=Me, A³⁹=H, A⁴⁰=H, A⁴¹=H, A⁴²=H], [2822; Q=Q^{r7}, A³⁷=H, A³⁸=H, A³⁹=Me, A⁴⁰=H, A⁴¹=H, A⁴²=H], [2823; Q=Q^{r7}, A³⁷=Me, A³⁸=H, A³⁹=H, A⁴⁰=H, A⁴¹=Me, A⁴²=H], [2824; Q=Q^{r7}, A³⁷=H, A³⁸=Me, A³⁹=H, A⁴⁰=Me, A⁴=H, A⁴²=H], [2825; Q=Q^{r7}, A³⁷=H, A³⁸=H, A³⁹=H, A⁴⁰=H, A⁴¹=H, A⁴²=Me], [2826; Q=Q^{r7}, A³⁷=H, A³⁸=H, A³⁹=H, A⁴⁰=H, A⁴¹=H, A⁴²=Me], [2827; Q=Q^{r7}, A³⁷=Cl, A³⁸=H, A³⁹=H, A⁴⁰=H, A⁴¹=H, A⁴²=Me], [2828; Q=Q^{r7}, A³⁷=H, A³⁸=Cl, A³⁹=H, A⁴⁰=H, A⁴¹=H, A⁴²=Me], [2829; Q=Q^{r7}, A³⁷=H, A³⁸=H, A³⁹=Cl, A⁴⁰=H, A⁴¹=H, A⁴²=Me], [2830; Q=Q^{r7}, A³⁷=Cl, A³⁸=H, A³⁹=H, A⁴⁰=H, A⁴¹=Cl, A⁴²=Me], [2831; Q=Q^{r7}, A³⁷=H, A³⁸=Cl, A³⁹=H, A⁴⁰=Cl, A⁴=H, A⁴²=Me], [2832; Q=Q^{r7}, A³⁷=Me, A³⁸=H, A³⁹=H, A⁴⁰=H, A⁴¹=H, A⁴²=Me], [2833; Q=Q^{r7}, A³⁷=H, A³⁸=Me, A³⁹=H, A⁴⁰=H, A⁴¹=H, A⁴²=Me], [2834; Q=Q^{r7}, A³⁷=H, A³⁸=H, A³⁹=Me, A⁴⁰=H, A⁴¹=H, A⁴²=Me], [2835; Q=Q^{r7}, A³⁷=Me, A³⁸=H, A³⁹=H, A⁴⁰=H, A⁴¹=Me, A⁴²=Me], [2836; Q=Q^{r7}, A³⁷=H, A³⁸=Me, A³⁹=H, A⁴⁰=Me, A⁴¹=H, A⁴²=Me], [2837; Q=Q^{r7}, A³⁷=H, A³⁸=H, A³⁹=H, A⁴⁰=H, A⁴¹=H, A⁴²=Me], [2838; Q=Q^{v1}, R²⁹=H, R³⁰=H, R³¹=H, R³²=H][2839; Q=Q^{v1}, R²⁹=F, R³⁰=H, R³¹=H, R³²=H], [2840; Q=Q^{v1}, R²⁹=H, R³⁰=F, R³¹=H, R³²=H], [2841; Q=Q^{v1}, R²⁹=H, R³⁰=H, R³¹=F, R³²=H], [2842; Q=Q^{v1}, R²⁹=H, R³⁰=H, R³¹=H, R³²=F], [2843; Q=Q^{v1}, R²⁹=Cl, R³⁰=H, R³¹=H, R³²=H], [2844; Q=Q^{v1}, R²⁹=H, R³⁰=Cl, R³¹=H, R³²=H], [2845; Q=Q^{v1}, R²⁹=H, R³⁰=H, R³¹=Cl, R³²=H], [2846; Q=Q^{v1}, R²⁹=H, R³⁰=H, R³¹=H, R³²=Cl], [2847; Q=Q^{v1}, R²⁹=Me, R³⁰=H, R³¹=H, R³²=H], [2848; Q=Q^{v1}, R²⁹=H, R³⁰=Me, R³¹=H, R³²=H], [2849; Q=Q^{v1}, R²⁹=H, R³⁰=H, R³¹=Me, R³²=H], [2850; Q=Q^{v1}, R²⁹=H, R³⁰=H, R³¹=H, R³²=Me], [2851; Q=Q^{v1}, R²⁹=OMe, R³⁰=H, R³¹=H, R³²=H], [2852; Q=Q^{v1}, R²⁹=H, R³⁰=OMe, R³¹=H, R³²=H], [2853; Q=Q^{v1}, R²⁹=H, R³⁰=H, R³¹=OMe, R³²=H], [2854; Q=Q^{v1}, R²⁹=H, R³⁰=H, R³¹=H, R³²=OMe], [2855; Q=Q^{v1}, R²⁹=CF₃, R³⁰=H, R³¹=H, R³²=H][2856; Q=Q^{v1}, R²⁹=H, R³⁰=CF₃, R³¹=H, R³²=H], [2857; Q=Q^{v1}, R²⁹=H, R³⁰=H, R³¹=CF₃, R³²=H], [2858; Q=Q^{v1}, R²⁹=H, R³⁰=H, R³¹=H, R³²=CF₃], [2859; Q=Q^{v2}, R²⁹=H, R³⁰=H, R³¹=H, R³²=H], [2860; Q=Q^{v2}, R²⁹=F, R³⁰=H, R³¹=H, R³²=H], [2861; Q=Q^{v2}, R²⁹=H, R³⁰=F, R³¹=H, R³²=H], [2862; Q=Q^{v2}, R²⁹=H, R³⁰=H, R³¹=F, R³²=H], [2863; Q=Q^{v2}, R²⁹=H, R³⁰=H, R³¹=H, R³²=F], [2864; Q=Q^{v2}, R²⁹=Cl, R³⁰=H, R³¹=H, R³²=H], [2865; Q=Q^{v2}, R²⁹=H, R³⁰=Cl, R³¹=H, R³²=H], [2866; Q=Q^{v2}, R²⁹=H, R³⁰=H, R³¹=Cl, R³²=H], [2867; Q=Q^{v2}, R²⁹=H, R³⁰=H, R³¹=H, R³²=Cl], [2868; Q=Q^{v2}, R²⁹=Me, R³⁰=H, R³¹=H, R³²=H], [2869; Q=Q^{v2}, R²⁹=H, R³⁰=Me, R³¹=H, R³²=H], [2870; Q=Q^{v2}, R²⁹=H, R³⁰=H, R=Me, R³²=H], [2871; Q=Q^{v2}, R²⁹=H, R³⁰=H, R³¹=H, R³²=Me], [2872; Q=Q^{v2}, R²⁹=Me, R³⁰=H, R³¹=H, R³²=H], [2873; Q=Q^{v2}, R²⁹=H, R³⁰=OMe, R³¹=H, R³²=H], [2874; Q=Q^{v2}, R²⁹=H, R³⁰=H, R³¹=Me, R³²=H], [2875; Q=Q^{v2}, R²⁹=H, R³⁰=H, R³¹=H, R³²=OMe], [2876; Q=Q^{v2}, R²⁹=CF₃, R³⁰=H, R³¹=H, R³²=H], [2877; Q=Q 29=H, R²⁹=H, R³⁰=CF₃, R³¹=H, R³²=H], [2878; Q=Q^{v2}, R²⁹=H, R³⁰=H, R³¹=CF₃, R³²=H], [2879; Q=Q^{v2}, R²⁹=H, R³⁰=H, R³¹=H, R³²=CF₃], [2880; Q=Q^{v3}, R²⁹=H, R³⁰=H, R³¹=H, R³²=H], [2881; Q=Q^{v3}, R²⁹=F, R³⁰=H, R³¹=H, R³²=H][2882; Q=Q^{v3}, R²⁹=H, R³⁰=F, R³¹=H, R³²=H], [2883; Q=Q^{v3}, R²⁹=H, R³⁰=H, R³¹=F, R³²=H], [2884; Q=Q^{v3}, R²⁹=H, R³⁰=H, R³¹=H, R³²=F], [2885; Q=Q^{v3}, R²⁹=Cl, R³⁰=H, R³¹=H, R³²=H], [2886; Q=Q^{v3}, R²⁹=H, R³⁰=Cl, R³¹=H, R³²=H], [2887; Q=Q^{v3}, R²⁹=H, R³⁰=H, R³¹=Cl, R³²=H], [2888; Q=Q^{v3}, R²⁹=H, R³⁰=H, R³¹=H, R³²=Cl], [2889; Q=Q^{v3}, R²⁹=Me, R³⁰=H, R³¹=H, R³²=H], [2890; Q=Q^{v3}, R²⁹=H, R³⁰=Me, R³¹=H, R³²=H], [2891; Q=Q^{v3}, R²⁹=H, R³⁰=H, R³¹=Me, R³²=H], [2892; Q=Q^{v3}, R²⁹=H, R³⁰=H, R³¹=H, R³²=Me], [2893; Q=Q^{v3}, R²⁹=OMe, R³⁰=H, $R^{31}$=H, $R^{32}$=H], [2894; Q=$Q^{v3}$, $R^{29}$=H, $R^{30}$=OMe, $R^{31}$=H, $R^{32}$=H], [2895; Q=$Q^{v3}$, $R^{29}$=H, $R^{30}$=H, $R^{31}$=OMe, $R^{32}$=H], [2896; Q=$Q^{v3}$, $R^{29}$=H, $R^{30}$=H, $R^{31}$=H, $R^{32}$=OMe], [2897; Q=$Q^{v3}$, $R^{29}$=CF$_3$, $R^{30}$=H, $R^{31}$=H, $R^{32}$=H], [2898; Q=$Q^{v3}$, $R^{29}$=H, $R^{30}$=CF$_3$, $R^{31}$=H, $R^{32}$=H], [2899; Q=$Q^{v3}$, $R^{29}$=H, $R^{30}$=H, $R^{31}$=CF$_3$, $R^{32}$=H], [2900; Q=$Q^{v3}$, $R^{29}$=H, $R^{30}$=H, $R^{31}$=H, $R^{32}$=CF$_3$], [2901; Q=$Q^{s1}$, $R^{29}$=H, $R^{30}$=H, $R^{31}$=H, $R^{32}$=H], [2902; Q=$Q^{v4}$, $R^{29}$=F, $R^{30}$=H, $R^{31}$=H, $R^{32}$=H], [2903; Q=$Q^{v4}$, $R^{29}$=H, $R^{30}$=F, $R^{31}$=H, $R^{32}$=H], [2904; Q=$Q^{v4}$, $R^{29}$=H, $R^{30}$=H, $R^{31}$=F, $R^{32}$=H], [2905; Q=$Q^{v4}$, $R^{29}$=H, $R^{30}$=H, $R^{31}$=H, $R^{32}$=F], [2906; Q=$Q^{v4}$, $R^{29}$=Cl, $R^{30}$=H, $R^{31}$=H, $R^{32}$=H], [2907; Q=$Q^{v4}$, $R^{29}$=H, $R^{30}$=Cl, $R^{31}$=H, $R^{32}$=H], [2908; Q=$Q^{v4}$, $R^{29}$=H, $R^{30}$=H, $R^{31}$=Cl, $R^{32}$=H], [2909; Q=$Q^{v4}$, $R^{29}$=H, $R^{30}$=H, $R^{31}$=H, $R^{32}$=Cl], [2910; Q=$Q^{v4}$, $R^{29}$=Me, $R^{30}$=H, $R^{31}$=H, $R^{32}$=H], [2911; Q=$Q^{v4}$, $R^{29}$=H, $R^{30}$=Me, $R^{31}$=H, $R^{32}$=H], [2912; Q=$Q^{v4}$, $R^{29}$=H, $R^{30}$=H, $R^{31}$=Me, $R^{32}$=H], [2913; Q=$Q^{v4}$, $R^{29}$=H, $R^{30}$=H, $R^{31}$=H, $R^{32}$=Me], [2914; Q=$Q^{s1}$, $R^{29}$=OMe, $R^{30}$=H, $R^{31}$=H, $R^{32}$=H], [2915; Q=$Q^{v4}$, $R^{29}$=H, $R^{30}$=OMe, $R^{31}$=H, $R^{32}$=H], [2916; Q=$Q^{v4}$, $R^{29}$=H, $R^{30}$=H, $R^{31}$=OMe, $R^{32}$=H], [2917; Q=$Q^{s1}$, $R^{29}$=H, $R^{30}$=H, $R^{31}$=H, $R^{32}$=OMe], [2918; Q=$Q^{v4}$, $R^{29}$=CF$_3$, $R^{30}$=H, $R^{31}$=H, $R^{32}$=H], [2919; Q=$Q^{v4}$, $R^{29}$=H, $R^{30}$=CF$_3$, $R^{31}$=H, $R^{32}$=H], [2920; Q=$Q^{v4}$, $R^{29}$=H, $R^{30}$=H, $R^{31}$=CF$_3$, $R^{32}$=H], [2921; Q=$Q^{v4}$, $R^{29}$=H, $R^{30}$=H, $R^{31}$=H, $R^{32}$=CF$_3$], [2922; Q=$Q^{v5}$, $R^{29}$=H, $R^{30}$=H, $R^{31}$=H, $R^{32}$=H], [2923; Q=$Q^{v5}$, $R^{29}$=F, $R^{30}$=H, $R^{31}$=H, $R^{32}$=H], [2924; Q=$Q^{v5}$, $R^{29}$=H, $R^{30}$=F, $R^{31}$=H, $R^{32}$=H], [2925; Q=$Q^{v5}$, $R^{29}$=H, $R^{30}$=H, $R^{31}$=F, $R^{32}$=H], [2926; Q=$Q^{v5}$, $R^{29}$=H, $R^{30}$=H, $R^{31}$=H, $R^{32}$=F], [2927; Q=$Q^{v5}$, $R^{29}$=Cl, $R^{30}$=H, $R^{31}$=H, $R^{32}$=H], [2928; Q=$Q^{v5}$, $R^{29}$=H, $R^{30}$=Cl, $R^{31}$=H, $R^{32}$=H], [2929; Q=$Q^{v5}$, $R^{29}$=H, $R^{30}$=H, $R^{31}$=Cl, $R^{32}$=H], [2930; Q=$Q^{v5}$, $R^{29}$=H, $R^{30}$=H, $R^{31}$=H, $R^{32}$=Cl], [2931; Q=$Q^{q5}$, $R^{29}$=Me, $R^{30}$=H, $R^{31}$=H, $R^{32}$=H], [2932; Q=$Q^{v1}$, $R^{29}$=H, $R^{30}$=Me, $R^{31}$=H, $R^{32}$=H], [2933; Q=$Q^{v5}$, $R^{29}$=H, $R^{30}$=H, $R^{31}$=Me, $R^{32}$=H], [2934; Q=$Q^{v5}$, $R^{29}$=H, $R^{30}$=H, $R^{31}$=H, $R^{32}$=Me], [2935; Q=$Q^{v5}$, $R^{29}$=OMe, $R^{30}$=H, $R^{31}$=H, $R^{32}$=H], [2936; Q=$Q^{v5}$, $R^{29}$=H, $R^{30}$=OMe, $R^{31}$=H, $R^{32}$=H], [2937; Q=$Q^{v5}$, $R^{29}$=H, $R^{30}$=H, $R^{31}$=OMe, $R^{32}$=H], [2938; Q=$Q^{v5}$, $R^{29}$=H, $R^{30}$=H, $R^{31}$=H, $R^{32}$=OMe], [2939; Q=$Q^{q5}$, $R^{29}$=CF$_3$, $R^{30}$=H, $R^{31}$=H, $R^{32}$=H], [2940; Q=$Q^{v5}$, $R^{29}$=H, $R^{30}$=CF$_3$, $R^{31}$=H, $R^{32}$=H], [2941; Q=$Q^{v5}$, $R^{29}$=H, $R^{30}$=H, $R^{31}$=CF$_3$, $R^{32}$=H], [2942; Q=$Q^{v5}$, $R^{29}$=H, $R^{30}$=H, $R^{31}$=H, $R^{32}$=CF$_3$], [2943; Q=$Q^{v6}$, $R^{29}$=H, $R^{30}$=H, $R^{31}$=H, $R^{32}$=H], [2944; Q=$Q^{v6}$, $R^{29}$=F, $R^{30}$=H, $R^{31}$=H, $R^{32}$=H], [2945; Q=$Q^{v6}$, $R^{29}$=H, $R^{30}$=F, $R^{31}$=H, $R^{32}$=H], [2946; Q=$Q^{v6}$, $R^{29}$=H, $R^{30}$=H, $R^{31}$=F, $R^{32}$=H], [2947; Q=$Q^{v1}$, $R^{29}$=H, $R^{30}$=H, $R^{31}$=H, $R^{32}$=F], [2948; Q=$Q^{v6}$, $R^{29}$=Cl, $R^{30}$=H, $R^{31}$=H, $R^{32}$=H], [2949; Q=$Q^{v6}$, $R^{29}$=H, $R^{30}$=Cl, $R^{31}$=H, $R^{32}$=H], [2950; Q=$Q^{v6}$, $R^{29}$=H, $R^{30}$=H, $R^{31}$=Cl, $R^{32}$=H], [2951; Q=$Q^{v6}$, $R^{29}$=H, $R^{30}$=H, $R^{31}$=H, $R^{32}$=Cl], [2952; Q=$Q^{v6}$, $R^{29}$=Me, $R^{30}$=H, $R^{31}$=H, $R^{32}$=H], [2953; Q=$Q^{v6}$, $R^{29}$=H, $R^{30}$=Me, $R^{31}$=H, $R^{32}$=H], [2954; Q=$Q^{v6}$, $R^{29}$=H, $R^{30}$=H, $R^{31}$=Me, $R^{32}$=H], [2955; Q=$Q^{v6}$, $R^{29}$=H, $R^{30}$=H, $R^{31}$=H, $R^{32}$=Me], [2956; Q=$Q^{v6}$, $R^{29}$=OMe, $R^{30}$=H, $R^{31}$=H, $R^{32}$=H], [2957; Q=$Q^{v6}$, $R^{29}$=H, $R^{30}$=OMe, $R^{31}$=H, $R^{32}$=H], [2958; Q=$Q^{v6}$, $R^{29}$=H, $R^{30}$=H, $R^{31}$=OMe, $R^{32}$=H], [2959; Q=$Q^{v6}$, $R^{29}$=H, $R^{30}$=H, $R^{31}$=H, $R^{32}$=OMe], [2960; Q=$Q^{v6}$, $R^{29}$=CF$_3$, $R^{30}$=H, $R^{31}$=H, $R^{32}$=H][2961; Q=$Q^{v6}$, $R^{29}$=H, $R^{30}$=CF$_3$, $R^{31}$=H, $R^{32}$=H], [2962; Q=$Q^{v6}$, $R^{29}$=H, $R^{30}$=H, $R^{31}$=CF$_3$, $R^{32}$=H], [2963; Q=$Q^{v6}$, $R^{29}$=H, $R^{30}$=H, $R^{31}$=H, $R^{32}$=CF$_3$], [2964; Q=$Q^{v7}$, $R^{29}$=H, $R^{30}$=H, $R^{31}$=H, $R^{32}$=H], [2965; Q=$Q^{v7}$, $R^{29}$=F, $R^{30}$=H, $R^{31}$=H, $R^{32}$=H], [2966; Q=$Q^{v1}$, $R^{29}$=H, $R^{30}$=F, $R^{31}$=H, $R^{32}$=H], [2967; Q=$Q^{v7}$, $R^{29}$=H, $R^{30}$=H, $R^{31}$=F, $R^{32}$=H], [2968; Q=$Q^{v7}$, $R^{29}$=H, $R^{30}$=H, $R^{31}$=H, $R^{32}$=F], [2969; Q=$Q^{v7}$, $R^{29}$=Cl, $R^{30}$=H, $R^{31}$=H, $R^{32}$=H], [2970; Q=$Q^{v7}$, $R^{29}$=H, $R^{30}$=Cl, $R^{31}$=H, $R^{32}$=H], [2971; Q=$Q^{v7}$, $R^{29}$=H, $R^{30}$=H, $R^{31}$=Cl, $R^{32}$=H], [2972; Q=$Q^{v7}$, $R^{29}$=H, $R^{30}$=H, $R^{31}$=H, $R^{32}$=Cl], [2973; Q=$Q^{v7}$, $R^{29}$=Me, $R^{30}$=H, $R^{31}$=H, $R^{32}$=H], [2974; Q=$Q^{v7}$, $R^{29}$=H, $R^{30}$=Me, $R^{31}$=H, $R^{32}$=H], [2975; Q=$Q^{v7}$, $R^{29}$=H, $R^{30}$=H, $R^{31}$=Me, $R^{32}$=H], [2976; Q=$Q^{v7}$, $R^{29}$=H, $R^{30}$=H, $R^{31}$=H, $R^{32}$=Me], [2977; Q=$Q^{v7}$, $R^{29}$=OMe, $R^{30}$=H, $R^{31}$=H, $R^{32}$=H], [2978; Q=$Q^{v7}$, $R^{29}$=H, $R^{30}$=OMe, $R^{31}$=H, $R^{32}$=H], [2979; Q=$Q^{v7}$, $R^{29}$=H, $R^{30}$=H, $R^{31}$=Me, $R^{32}$=H], [2980; Q=$Q^{v7}$, $R^{29}$=H, $R^{30}$=H, $R^{31}$=H, $R^{32}$=OMe], [2981; Q=$Q^{v7}$, $R^{29}$=CF$_3$, $R^{30}$=H, $R^{31}$=H, $R^{32}$=H], [2982; Q=$Q^{v1}$, $R^{29}$=H, $R^{30}$=CF$_3$, $R^{31}$=H, $R^{32}$=H], [2983; Q=$Q^{v7}$, $R^{29}$=H, $R^{30}$=H, $R^{31}$=CF$_3$, $R^{32}$=H], [2984; Q=$Q^{v7}$, $R^{29}$=H, $R^{30}$=H, $R^{31}$=H, $R^{32}$=CF$_3$], [2985; Q=$Q^{v5}$, $R^{29}$=H, $R^{30}$=H, $R^{31}$=H, $R^{32}$=H], [2986; Q=$Q^{v8}$, $R^{29}$=F, $R^{30}$=H, $R^{31}$=H, $R^{32}$=H], [2987; Q=$Q^{v8}$, $R^{29}$=H, $R^{30}$=F, $R^{31}$=H, $R^{32}$=H], [2988; Q=$Q^{v8}$, $R^{29}$=H, $R^{30}$=H, $R^{31}$=F, $R^{32}$=H], [2989; Q=$Q^{v1}$, $R^{29}$=H, $R^{30}$=H, $R^{31}$=H, $R^{32}$=F], [2990; Q=$Q^{v8}$, $R^{29}$=Cl, $R^{30}$=H, $R^{31}$=H, $R^{32}$=H], [2991; Q=$Q^{v8}$, $R^{29}$=H, $R^{30}$=Cl, $R^{31}$=H, $R^{32}$=H], [2992; Q=$Q^{v8}$, $R^{29}$=H, $R^{30}$=H, $R^{31}$=Cl, $R^{32}$=H], [2993; Q=$Q^{v8}$, $R^{29}$=H, $R^{30}$=H, $R^{31}$=H, $R^{32}$=Cl], [2994; Q=$Q^{v8}$, $R^{29}$=Me, $R^{30}$=H, $R^{31}$=H, $R^{32}$=H], [2995; Q=$Q^{v8}$, $R^{29}$=H, $R^{30}$=Me, $R^{31}$=H, $R^{32}$=H], [2996; Q=$Q^{v8}$, $R^{29}$=H, $R^{30}$=H, $R^{31}$=Me, $R^{32}$=H], [2997; Q=$Q^{v8}$, $R^{29}$=H, $R^{30}$=H, $R^{31}$=H, $R^{32}$=Me], [2998; Q=$Q^{v8}$, $R^{29}$=OMe, $R^{30}$=H, $R^{31}$=H, $R^{32}$=H][2999; Q=$Q^{v8}$, $R^{29}$=H, $R^{30}$=OMe, $R^{31}$=H, $R^{32}$=H], [3000; Q=$Q^{v8}$, $R^{29}$=H, $R^{30}$=H, $R^{31}$=OMe, $R^{32}$=H], [3001; Q=$Q^{v8}$, $R^{29}$=H, $R^{30}$=H, $R^{31}$=H, $R^{32}$=OMe], [3002; Q=$Q^{v8}$, $R^{29}$=CF$_3$, $R^{30}$=H, $R^{31}$=H, $R^{32}$=H], [3003; Q=$Q^{v8}$, $R^{29}$=H, $R^{30}$=CF$_3$, $R^{31}$=H, $R^{32}$=H], [3004; Q=$Q^{v8}$, $R^{29}$=H, $R^{30}$=H, $R^{31}$=CF$_3$, $R^{32}$=H], [3005; Q=$Q^{v8}$, $R^{29}$=H, $R^{30}$=H, $R^{31}$=H, $R^{32}$=CF$_3$], [3006; Q=$Q^{v8}$, $A^{42}$=H, $A^{43}$=H, $A^{44}$=H, $A^{45}$=H, $A^{46}$=H, $A^{47}$=H, $A^{48}$=H, $A^{49}$=H], [3007; Q=$Q^{v9}$, $A^{42}$=F, $A^{43}$=H, $A^{44}$=H, $A^{45}$=H, $A^{6}$=H, $A^{47}$=H, $A^{8}$=H, $A^{49}$=H], [3008; Q=$Q^{v9}$, $A^{42}$=H, $A^{43}$=H, $A^{44}$=F, $A^{45}$=H, $A^{46}$=H, $A^{47}$=H, $A^{48}$=H, $A^{49}$=H], [3009; Q=$Q^{v9}$, $A^{42}$=H, $A^{43}$=H, $A^{44}$=H, $A^{45}$=H, $A^{46}$=F, $A^{47}$=H, $A^{48}$=H, $A^{49}$=H], [3010; Q=$Q^{v9}$, $A^{42}$=H, $A^{43}$=H, $A^{44}$=H, $A^{45}$=H, $A^{46}$=H, $A^{47}$=H, $A^{48}$=F, $A^{49}$=H], [3011; Q=$Q^{v9}$, $A^{42}$=Cl, $A^{43}$=H, $A^{44}$=H, $A^{45}$=H, $A^{46}$=H, $A^{47}$=H, $A^{48}$=H, $A^{49}$=H], [3012; Q=$Q^{v9}$, $A^{42}$=H, $A^{43}$=H, $A^{44}$=Cl, $A^{45}$=H, $A^{46}$=H, $A^{47}$=H, $A^{48}$=H, $A^{49}$=H], [3013; Q=$Q^{v9}$, $A^{42}$=H, $A^{43}$=H, $A^{44}$=H, $A^{45}$=H, $A^{46}$=Cl, [$A^{47}$=H, $A^{48}$=H, $A^{49}$=H], [3014; Q=$Q^{v9}$, $A^{42}$=H, $A^{43}$=H, $A^{44}$=H, $A^{45}$=H, $A^{46}$=H, $A^{47}$=H, $A^{48}$=Cl, $A^{49}$=H], [3015; Q=$Q^{v9}$, $A^{42}$=Me, $A^{43}$=H, $A^{44}$=H, $A^{45}$=H, $A^{46}$=H, $A^{47}$=H, $A^{48}$=H, $A^{49}$=H], [3016; Q=$Q^{v9}$, $A^{42}$=H, $A^{43}$=H, $A^{44}$=Me, $A^{45}$=H, $A^{46}$=H, $A^{47}$=H, $A^{48}$=H, $A^{49}$=H], [3017; Q=$Q^{v9}$, $A^{42}$=H, $A^{13}$=H, $A^{44}$=H, $A^{45}$=H, $A^{46}$=Me, $A^{47}$=H, $A^{48}$=H, $A^{49}$=H], [3018; Q=$Q^{v9}$, $A^{42}$=H, $A^{43}$=H, $A^{44}$=H, $A^{45}$=H, $A^{46}$=H, $A^{47}$=H, $A^{48}$=Me, $A^{49}$=H], [3019; Q=$Q^{v9}$, $A^{42}$=OMe, $A^{43}$=H, $A^{44}$=H, $A^{45}$=H, $A^{46}$=H, $A^{47}$=H, $A^{48}$=H, $A^{49}$=H], [3020; Q=$Q^{v9}$, $A^{42}$=H, $A^{43}$=H, $A^{44}$=OMe, $A^{45}$=H, $A^{46}$=H, $A^{47}$=H, $A^{48}$=H, $A^{49}$=H], [3021; Q=$Q^{v9}$, $A^{2}$=H, $A^{43}$=H, $A^{44}$=H, $A^{45}$=H, $A^{46}$=OMe, $A^{47}$=H, $A^{48}$=H, $A^{49}$=H], [3022; Q=$Q^{r9}$, $A^{42}$=H, $A^{43}$=H, $A^{44}$=H, $A^{45}$=H, $A^{46}$=H, $A^{47}$=H, $A^{48}$=OMe, $A^{49}$=H], [3023; Q=$Q^{v9}$, $A^{42}$=CF$_3$, $A^{43}$=H, $A^{44}$=H, $A^{45}$=H, $A^{46}$=H, $A^{47}$=H, $A^{48}$=H, $A^{9}$=H], [3024; Q=$Q^{v9}$, $A^{42}$=H, $A^{43}$=H, $A^{44}$=CF$_3$, $A^{45}$=H, $A^{46}$=H, $A^{47}$=H, $A^{48}$=H, $A^{49}$=H], [3025; Q=$Q^{v9}$, $A^{42}$=H, $A^{43}$=H, $A^{44}$=H, $A^{45}$=H, $A^{46}$=CF$_3$, $A^{47}$=H, $A^{48}$=H, $A^{49}$=H], [3026; Q=$Q^{v9}$, $A^{42}$=H, $A^{43}$=H, $A^{1}$=H, $A^{45}$=H, $A^{46}$=H, $A^{47}$=H, $A^{48}$=CF$_3$, $A^{49}$=H], [3027; Q=$Q^{v9}$, $A^{42}$=F, $A^{43}$=F, $A^{44}$=H, $A^{45}$=H, $A^{46}$=H, $A^{47}$=H, $A^{48}$=H, $A^{49}$=H], [3028; Q=$Q^{v9}$, $A^{42}$=H, $A^{43}$=H, $A^{44}$=F, $A^{45}$=F, $A^{46}$=H, $A^{47}$=H, $A^{48}$=H, $A^{49}$=H], [3029; Q=$Q^{v9}$, $A^{42}$=H, $A^{43}$=H, $A^{44}$=H, $A^{45}$=H, $A^{46}$=F, $A^{47}$=F, $A^{48}$=H, $A^{4}$=H], [3030; Q=$Q^{v1}$, $A^{42}$=H, $A^{43}$=H, $A^{44}$=H, $A^{45}$=H, $A^{46}$=H, $A^{47}$=H, $A^{48}$=F, $A^{49}$=F], [3031; Q=$Q^{v10}$, $A^{42}$=H, $A^{43}$=H, $A^{44}$=H, $A^{45}$=H, $A^{46}$=H, $A^{47}$=H, $A^{48}$=H, $A^{49}$=H], [3032; Q=$Q^{v10}$, $A^{42}$=F, $A^{43}$=H, $A^{44}$=H, $A^{45}$=H, $A^{46}$=H, $A^{47}$=H, $A^{48}$=H, $A^{49}$=H], [3033; Q=$Q^{v10}$, $A^{42}$=H, $A^{43}$=H, $A^{44}$=F, $A^{45}$=H, $A^{46}$=H, $A^{47}$=H, $A^{48}$=H, $A^{1}$=H], [3034; Q=$Q^{v10}$, $A^{42}$=H, $A^{43}$=H, $A^{44}$=H, $A^{45}$=H, $A^{46}$=F, $A^{47}$=H, $A^{48}$=H, $A^{49}$=H], [3035; Q=$Q^{v10}$, $A^{42}$=H, $A^{43}$=H, $A^{44}$=H, $A^{45}$=H, $A^{46}$=H, $A^{47}$=H, $A^{48}$=F, $A^{49}$=H], [3036; Q=$Q^{v10}$, $A^{42}$=Cl, $A^{43}$=H, $A^{44}$=H, $A^{45}$=H, $A^{46}$=H, $A^{47}$=H, $A^{48}$=H, $A^{49}$=H], [3037; Q=$Q^{v10}$, $A^{42}$=H, $A^{43}$=H, $A^{44}$=Cl, $A^{45}$=H, $A^{46}$=H, $A^{47}$=H, $A^{48}$=H, $A^{49}$=H], [3038; Q=$Q^{v10}$, $A^{42}$=H, $A^{43}$=H, $A^{44}$=H, $A^{45}$=H, $A^{46}$=Cl, $A^{47}$=H, $A^{48}$=H, $A^{49}$=H], [3039; Q=$Q^{v10}$, $A^{42}$=H, $A^{43}$=H, $A^{44}$=H, $A^{45}$=H, $A^{46}$=H, $A^{47}$=H, $A^{48}$=Cl, $A^{49}$=H], [3040; Q=$Q^{v10}$, $A^{42}$=Me, $A^{43}$=H, $A^{44}$=H, $A^{45}$=H, $A^{46}$=H, $A^{47}$=H, $A^{48}$=H, $A^{49}$=H], [3041; Q=$Q^{v10}$, $A^{42}$=H, $A^{43}$=H, $A^{44}$=Me, $A^{45}$=H, $A^{46}$=H, $A^{47}$=H, $A^{48}$=H, $A^{49}$=H], [3042; Q=$Q^{v10}$, $A^{42}$=H, $A^{43}$=H, $A^{44}$=H, $A^{45}$=H, $A^{46}$=Me, $A^{47}$=H, $A^{48}$=H, $A^{49}$=H], [3043; Q=$Q^{v10}$, $A^{42}$=H, $A^{43}$=H, $A^{44}$=H, $A^{45}$=H, $A^{46}$=H, $A^{47}$=H, $A^{48}$=Me, $A^{49}$=H], [3044; Q=$Q^{v10}$, $A^{42}$=OMe, $A^{43}$=H, $A^{44}$=H, $A^{45}$=H, $A^{46}$=H, $A^{47}$=H, $A^{48}$=H, $A^{49}$=H], [3045; Q=$Q^{v10}$, $A^{42}$=H, $A^{43}$=H, $A^{44}$=OMe, $A^{45}$=H, $A^{46}$=H, $A^{47}$=H, $A^{48}$=H, $A^{49}$=H], [3046; Q=$Q^{v10}$, $A^{42}$=H, $A^{43}$=H, $A^{44}$=H, $A^{45}$=H, $A^{46}$=OMe, $A^{47}$=H, $A^{48}$=H, $A^{49}$=H], [3047; Q=$Q^{v10}$, $A^{42}$=H, $A^{43}$=H, $A^{44}$=H, $A^{45}$=H, $A^{46}$=H, $A^{47}$=H, $A^{48}$=OMe, $A^{49}$=H], [3048; Q=$Q^{v10}$, $A^{42}$=$CF_3$, $A^{43}$=H, $A^{44}$=H, $A^{45}$=H, $A^{46}$=H, $A^{47}$=H, $A^{48}$=H, $A^{4}$=H], [3049; Q=$Q^{v10}$, $A^{42}$=H, $A^{4}$=H, $A^{44}CF_3$, $A^{45}$=H, $A^{46}$=H, $A^{47}$=H, $A^{48}$=H, $A^{49}$=H], [3050; Q=$Q^{v10}$, $A^{42}$=H, $A^{43}$=H, $A^{44}$=H, $A^{45}$=H, $A^{46}$=H, $A^{47}$=H, $A^{48}$=H, $A^{49}$=H], [3051; Q=$Q^{v10}$, $A^{42}$=H, $A^{43}$=H, $A^{44}$=H, $A^{45}$=H, $A^{46}$=H, $A^{47}$=H, $A^{48}$=$CF_3$, $A^{49}$=H], [3052; Q=$Q^{v10}$, $A^{42}$=F, $A^{43}$=F, $A^{44}$=H, $A^{45}$=H, $A^{46}$=H, $A^{47}$=H, $A^{48}$=H, $A^{49}$=H], [3053; Q=$Q^{v10}$, $A^{42}$=H, $A^{43}$=H, $A^{44}$=F, $A^{45}$=F, $A^{46}$=H, $A^{47}$=H, $A^{48}$=H, $A^{49}$=H], [3054; Q=$Q^{v10}$, $A^{42}$=H, $A^{43}$=H, $A^{44}$=H, $A^{45}$=H, $A^{46}$=F, $A^{47}$=F, $A^{48}$=H, $A^{49}$=H], and [3055; Q=$Q^{v10}$, $A^{42}$=H, $A^{43}$=H, $A^{44}$=H, $A^{45}$=H, $A^{46}$=H, $A^{47}$=H, $A^{48}$=F, $A^{49}$=F]

According to the above method, it is possible to obtain compounds EC1B-5001 to EO7C-5107:

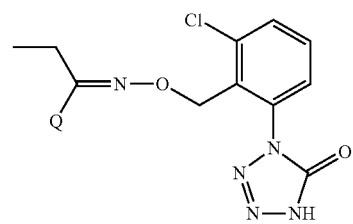
(EC1B)

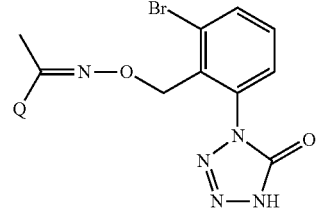
(EC1C)

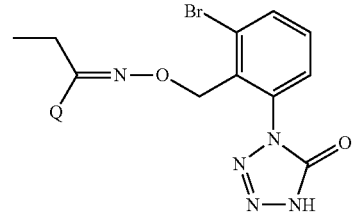
(EC2B)

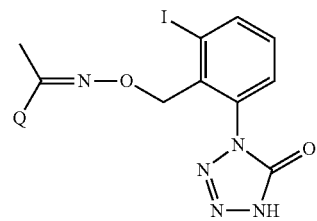
(EC2C)

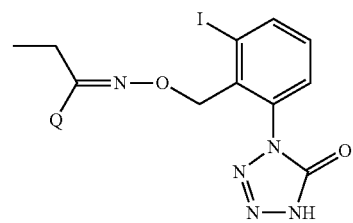
(EC3B)

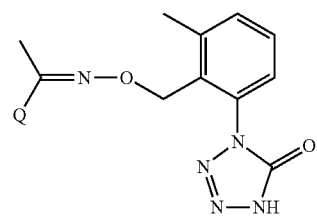
(EC3C)

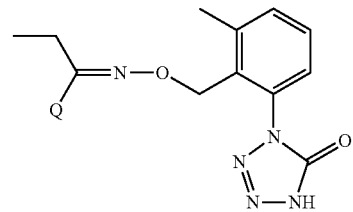
(EC4B)

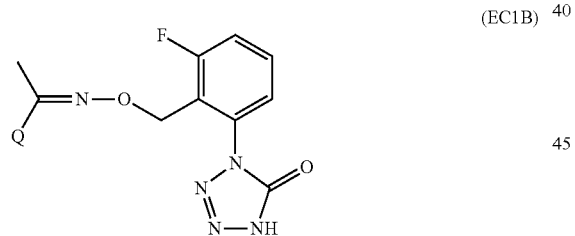
(EC4C)

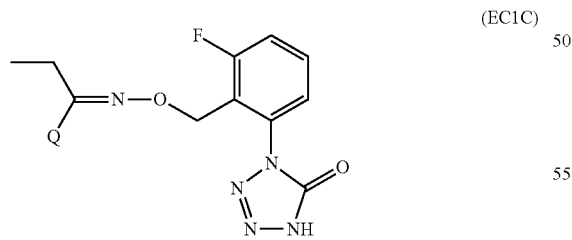
(EC5B)

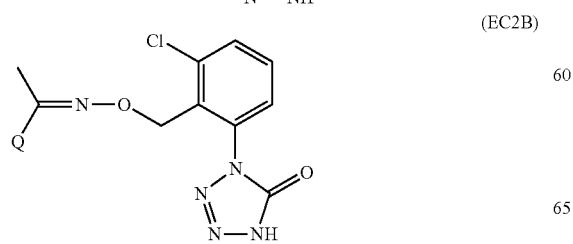
(EC5C)

-continued

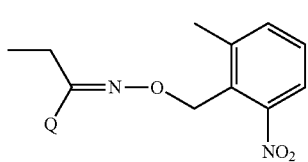
(ED5C)
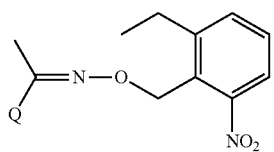
(ED6B)
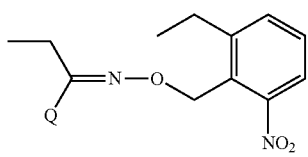
(ED6C)
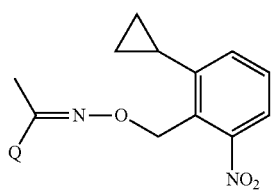
(ED7B)
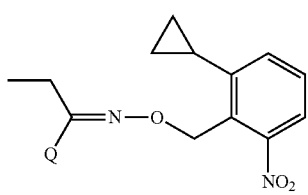
(ED7C)
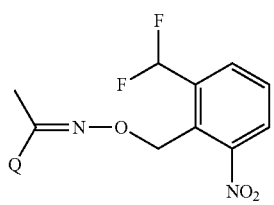
(ED8B)
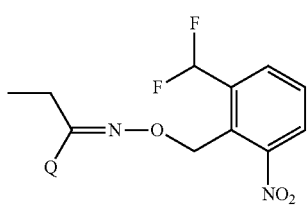
(ED8C)
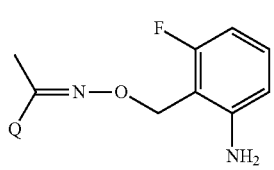
(EE1B)
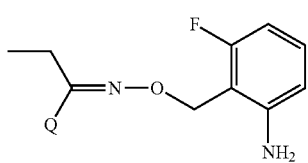
(EE1C)
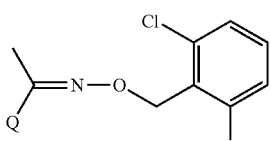
(EE2B)
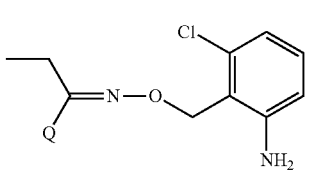
(EE2C)
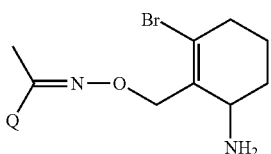
(EE3B)
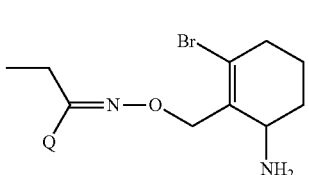
(EE3C)
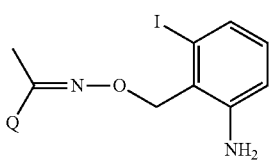
(EE4B)
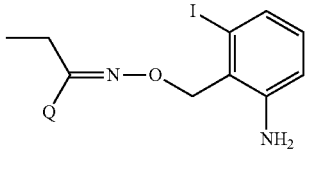
(EE4C)
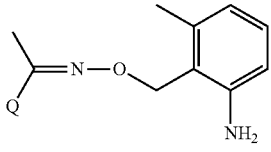
(EE5B)
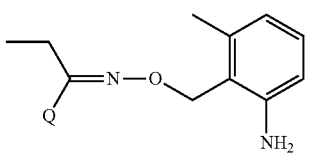
(EE5C)
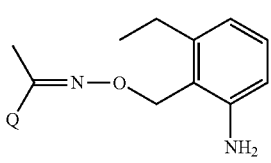
(EE6B)

441
-continued
(EE6C)
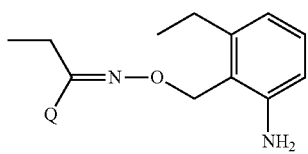
(EE7B)
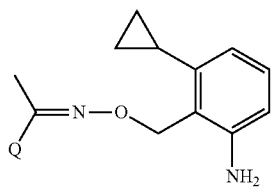
(EE7C)
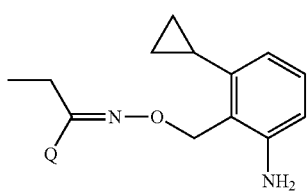
(EE8B)
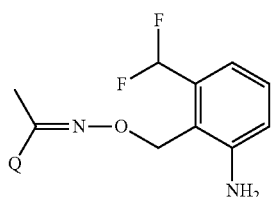
(EE8C)
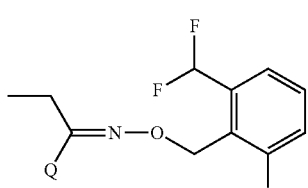
(EF1B)
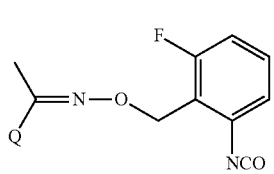
(EF1C)
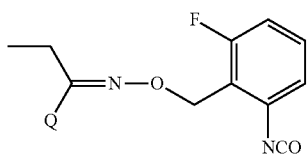
(EF2B)
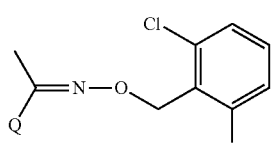
(EF2C)
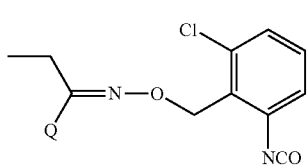
442
-continued
(EF3B)
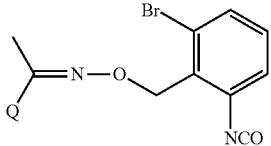
(EF3C)
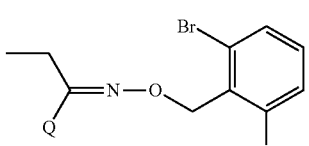
(EF4B)
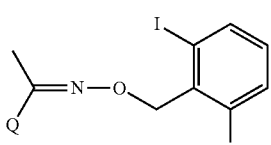
(EF4C)
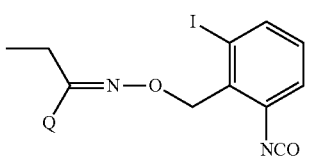
(EF5B)
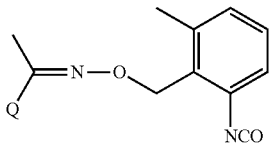
(EF5C)
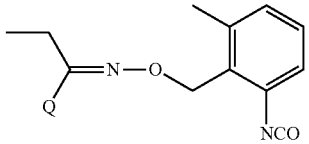
(EF6B)
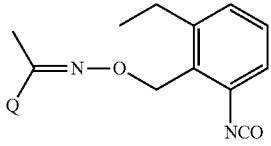
(EF6C)
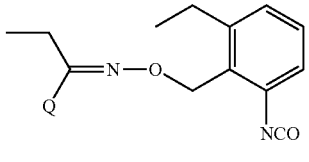
(EF7B)
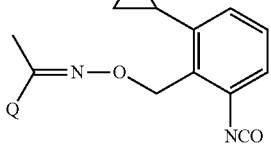

-continued
(EF7C)
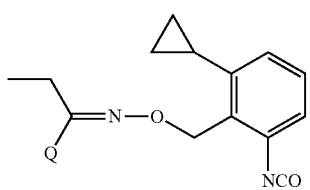
(EF8B)
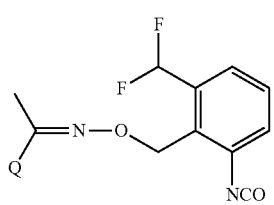
(EF8C)
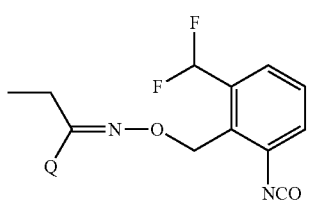
(EG1B)
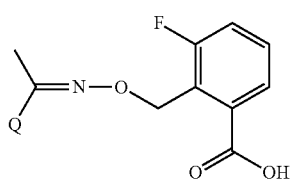
(EG1C)
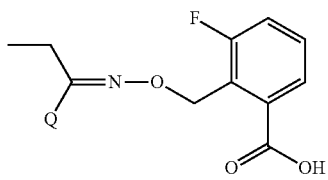
(EG2B)
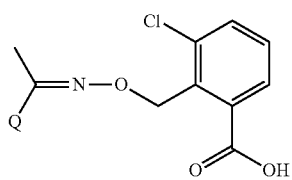
(EG2C)
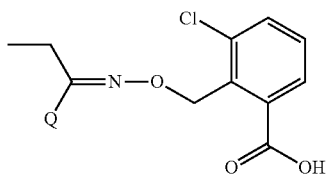
(EG3B)
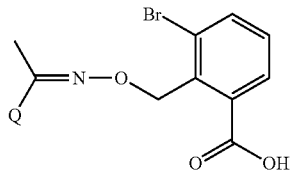
-continued
(EG3C)
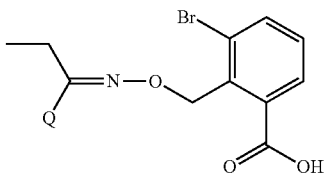
(EG4B)
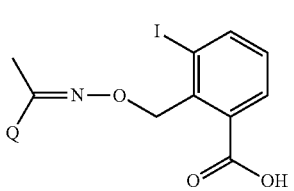
(EG4C)
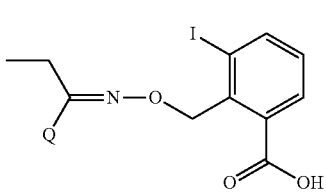
(EG5B)
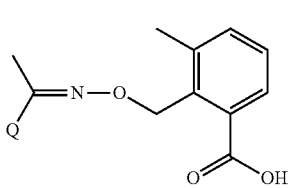
(EG5C)
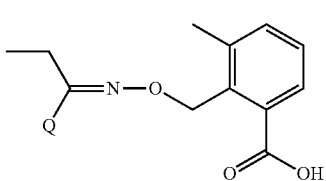
(EG6B)
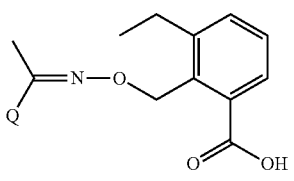
(EG6C)
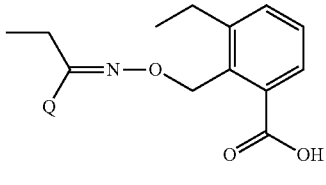
(EG7B)
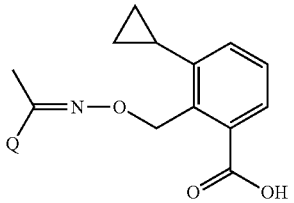

| 445 -continued | | 446 -continued | |
|---|---|---|---|
| 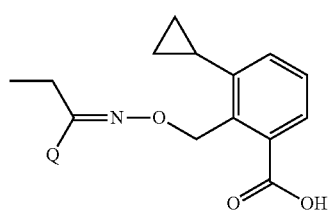 | (EG7C) | 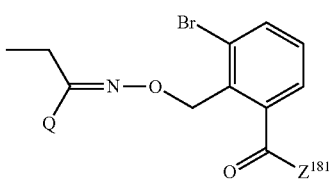 | (EH3C) |
| 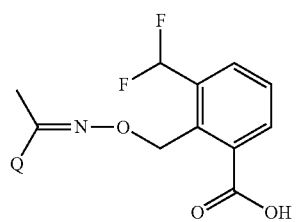 | (EG8B) | 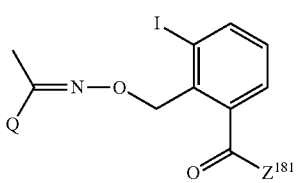 | (EH4B) |
| 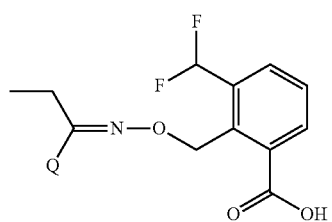 | (EG8C) | 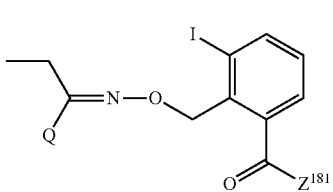 | (EH4C) |
| 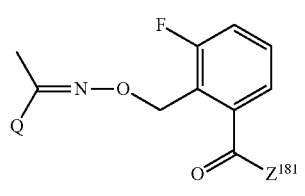 | (EH1B) | 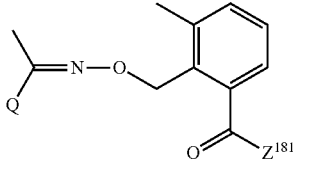 | (EH5B) |
| 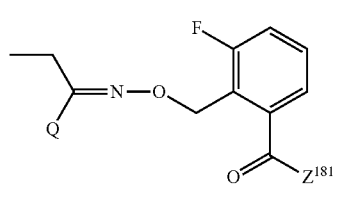 | (EH1C) | 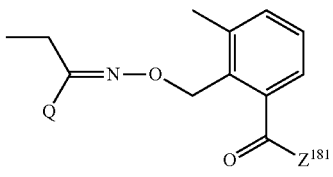 | (EH5C) |
| 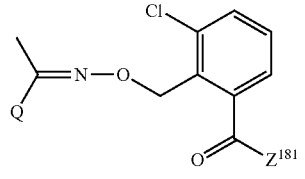 | (EH2B) | 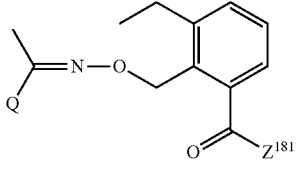 | (EH6B) |
| 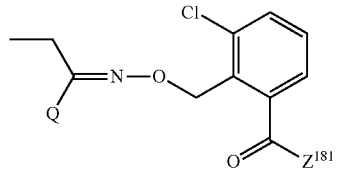 | (EH2C) | 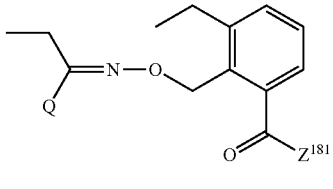 | (EH6C) |
| 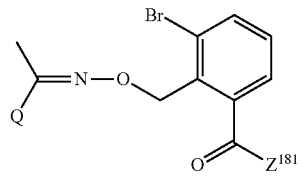 | (EH3B) | 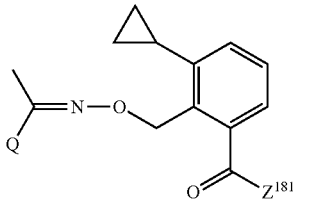 | (EH7B) |

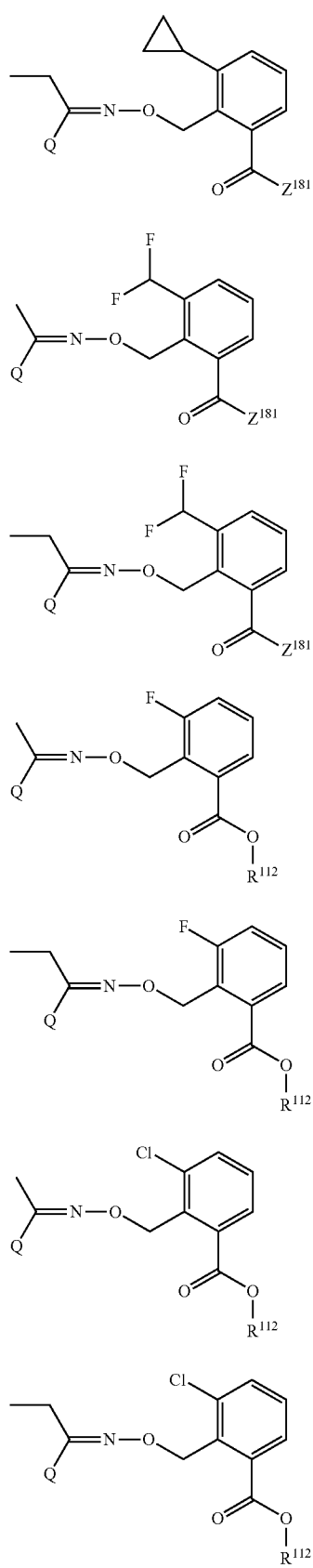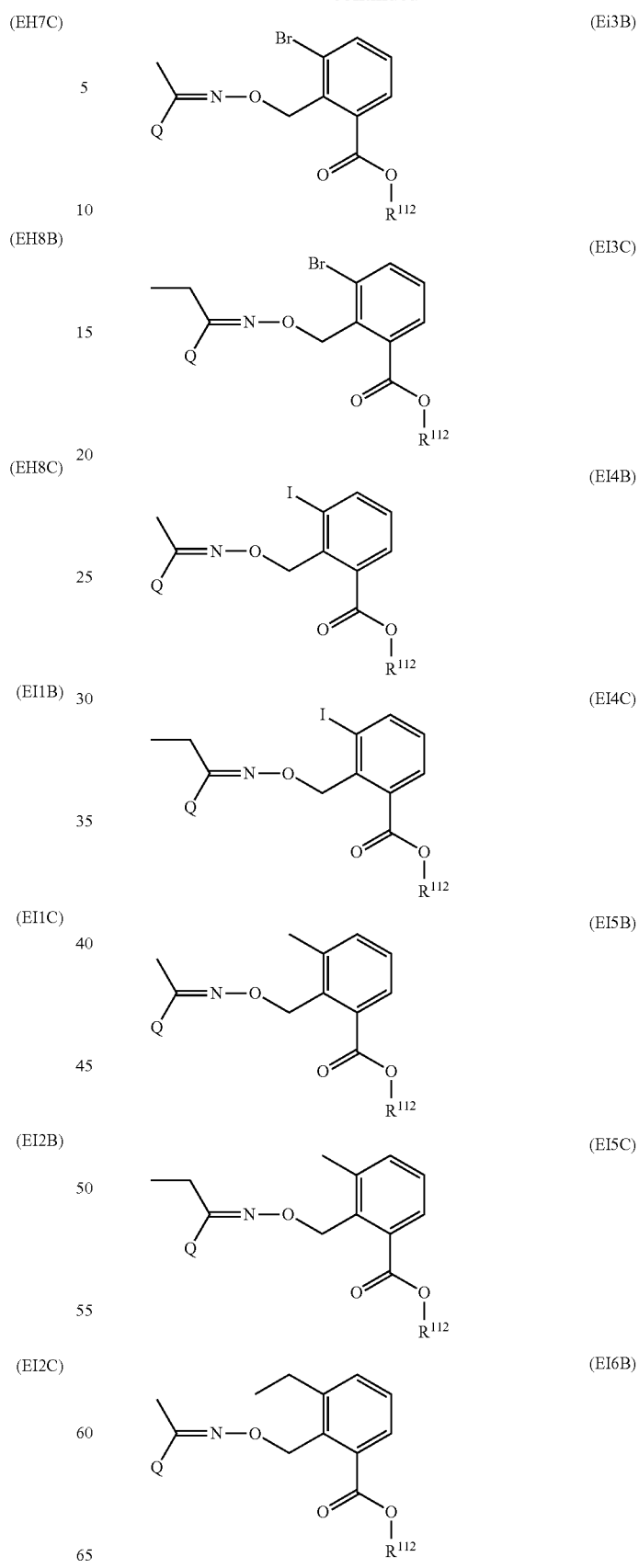

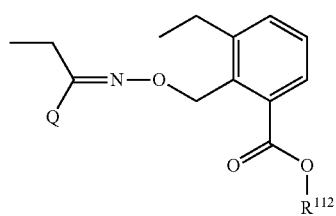
(EI6C)
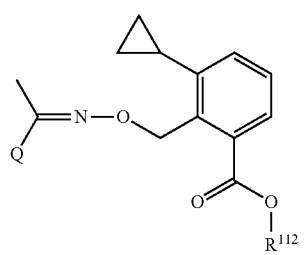
(EI7B)
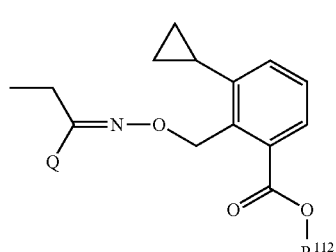
(EI7C)
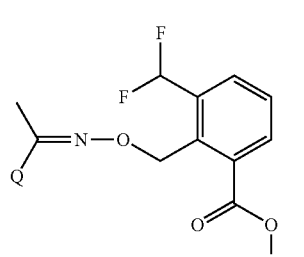
(EI8B)
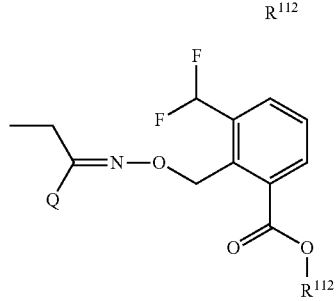
(EI8C)
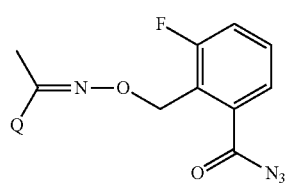
(EJ1B)
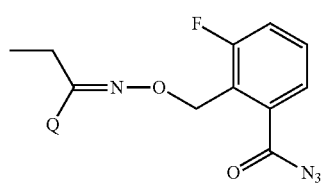
(EJ1C)
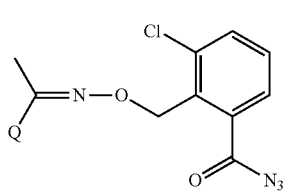
(EJ2B)
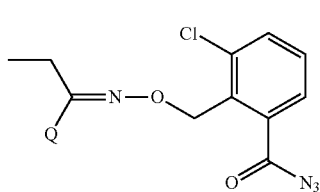
(EJ2C)
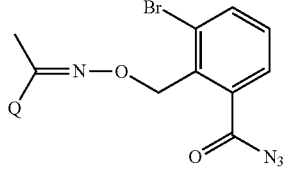
(EJ3B)
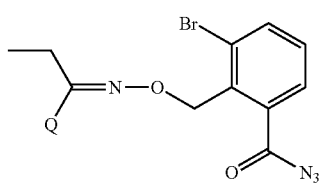
(EJ3C)
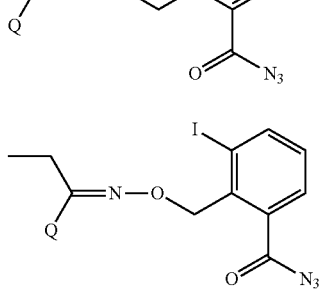
(EJ4B)
(EJ4C)
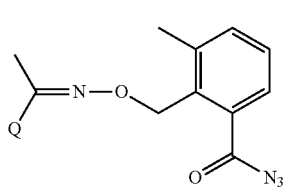
(EJ5B)
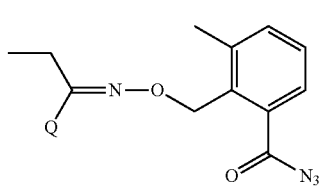
(EJ5C)

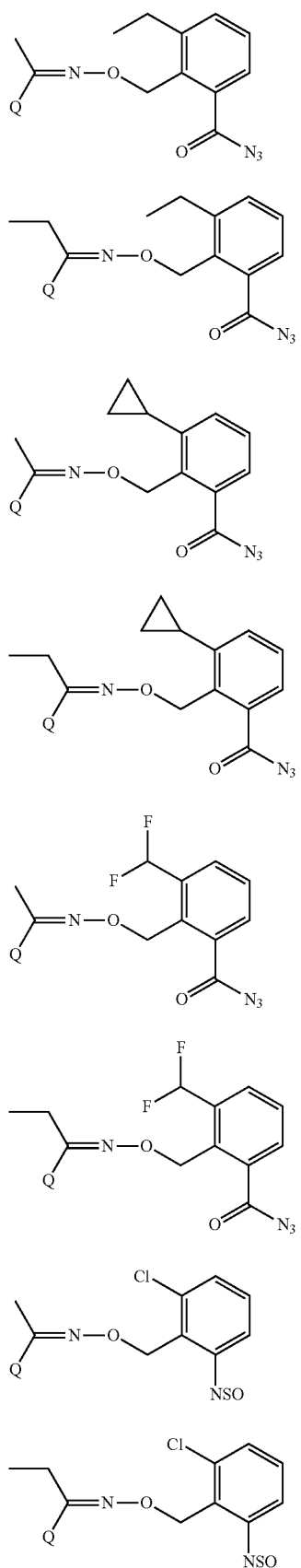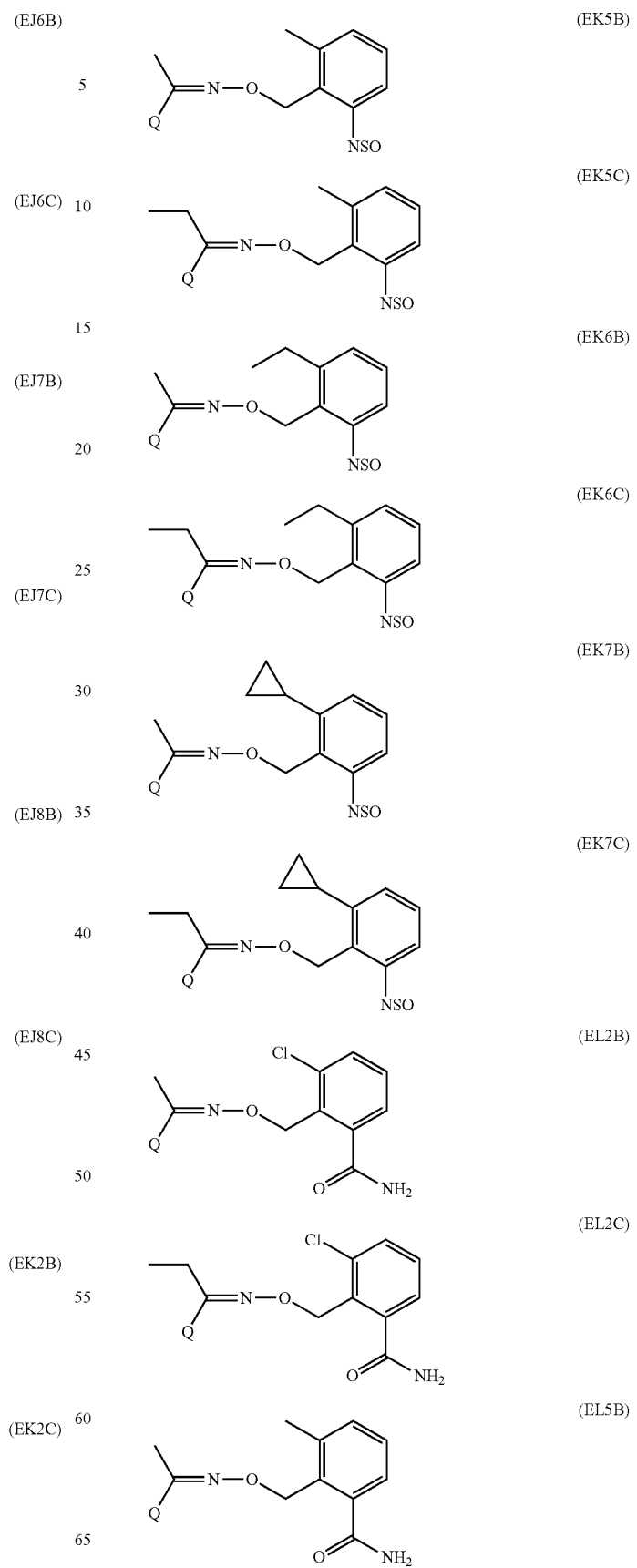

(EL5C)
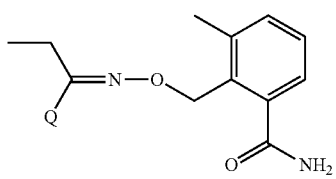
(EL6B)
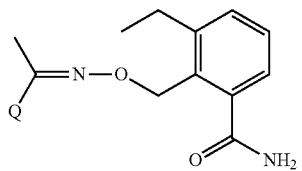
(EL6C)
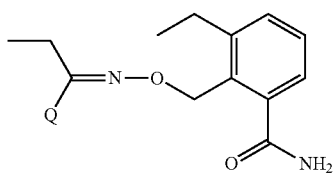
(EL7B)
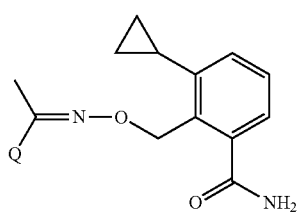
(EL7C)
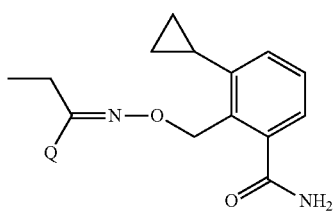
(EM2B)
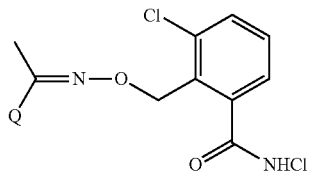
(EM2C)
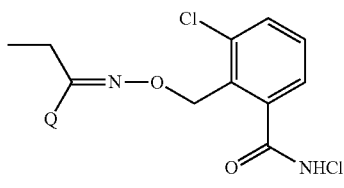
(EM5B)
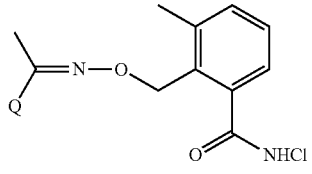
(EM5C)
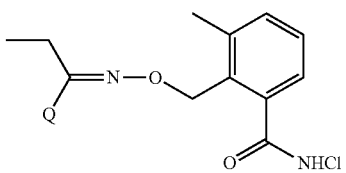
(EM6B)
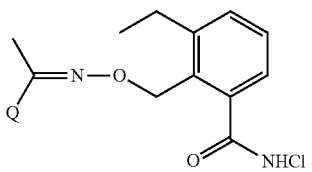
(EM6C)
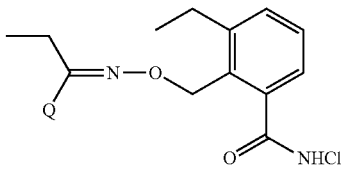
(EM7B)
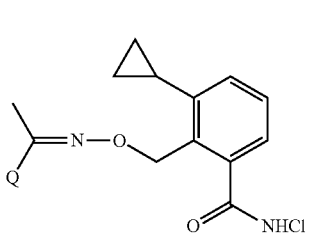
(EM7C)
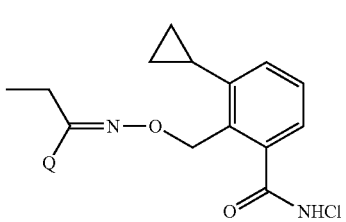
(EN2B)
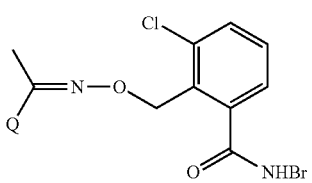
(EN2C)
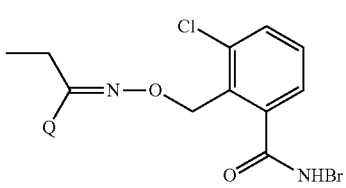
(EN5B)
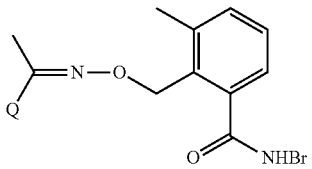

-continued
(EN5C) 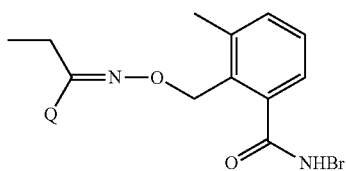
(EN6B) 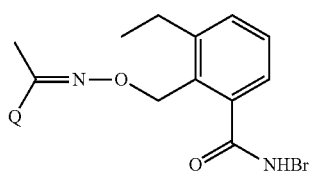
(EN6C) 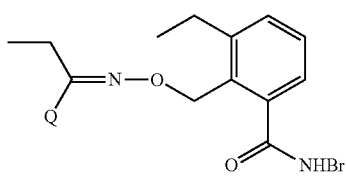
(EN7B) 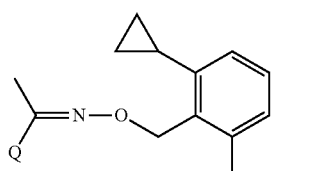
(EN7C) 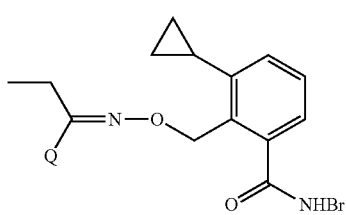
(EO2B) 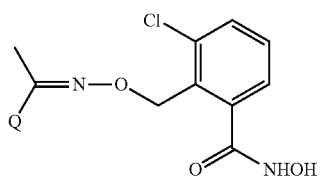
(EO2C) 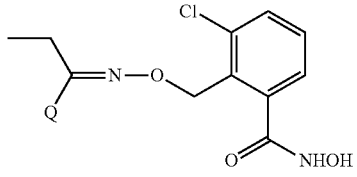
(EO5B) 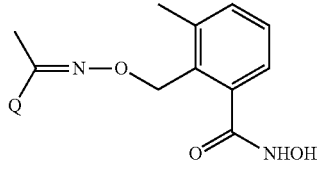
-continued
(EO5C) 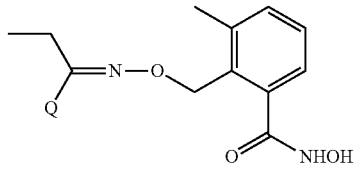
(EO6B) 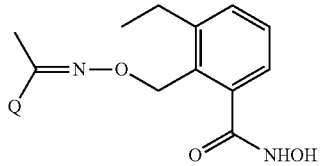
(EO6C) 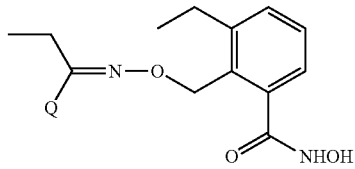
(EO7B) 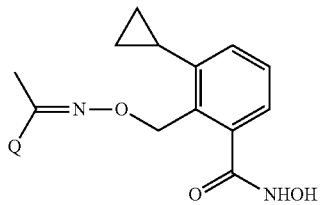
(EO7C) 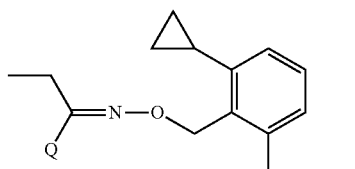
wherein Q represents any one of substituent numbers 5001 to 5107, and $Q^{P1}$ to $Q^{p10}$ represent any one of the followings.
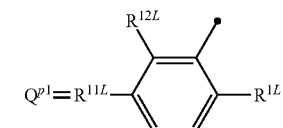 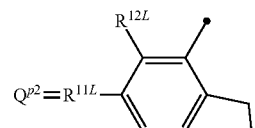
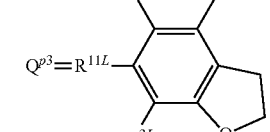 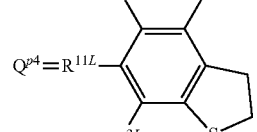
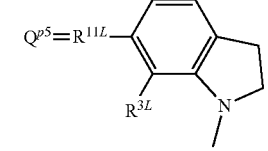 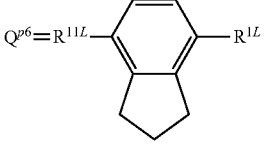

-continued

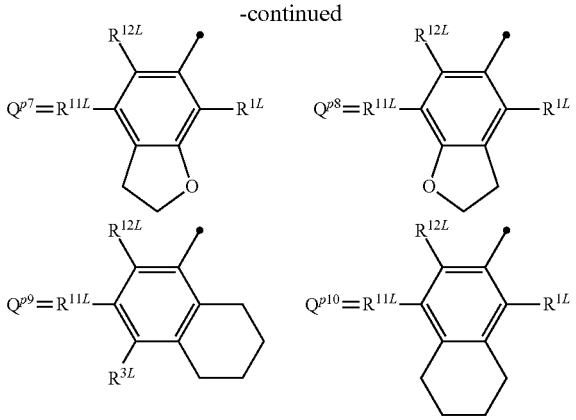

The substituent numbers 5001 to 5107 will be shown below.

Here, Me, $OCF_3$, OMe, $OCHF_2$, $OCF_3$, and SMe are as defined above, $CHF_2$ represents a difluoromethyl group, $NO_2$ represents a nitro group, CN represents a cyano group, $SCF_3$ represents a trifluoromethylthio group and, for example, [5001; $Q=Q^{p1}$, $R^{1L}=H$, $R^{2L}=H$, $R^{3L}=H$, $R^{11L}=H$, $R^{12L}=H$] represents a group in which Q is $Q^{p1}$, and $R^{1L}$, $R^{2L}$, $R^{3L}$, $R^{11L}$, and $R^{12L}$ are hydrogen atoms, and a compound in which the substituent number is 5001 in EC1B represents the following compound.

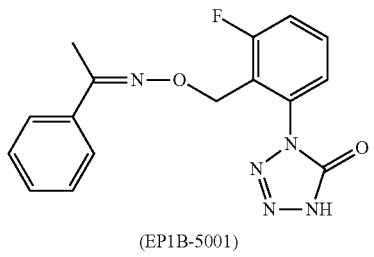 [SMILES: CC(=NOCc1c(F)cccc1-n1nn[nH]c1=O)c1ccccc1]

(EP1B-5001)

[substituent number; Q], [5001; $Q=Q^{p1}$, $R^{1L}=H$, $R^{2L}=H$, $R^{3L}=H$, $R^{11L}=H$, $R^{12L}=H$], [5002; $Q=Q^{p1}$, $R^{1L}=F$, $R^{2L}=H$, $R^{3L}=H$, $R^{11L}=H$, $R^{12L}=H$], [5003; $Q=Q^{p1}$, $R^{1L}=H$, $R^{2L}=F$, $R^{3L}=H$, $R^{11L}=H$, $R^{12L}=H$], [5004; $Q=Q^{p1}$, $R^{1L}=H$, $R^{2L}=H$, $R^{3L}=F$, $R^{11L}=H$, $R^{12L}=H$], [5005; $Q=Q^{p1}$, $R^{1L}=H$, $R^{2L}=Cl$, $R^{3L}=H$, $R^{11L}=H$, $R^{12L}=H$], [5006; $Q=Q^{p1}$, $R^{1L}=H$, $R^{2L}=H$, $R^{3L}=Cl$, $R^{11L}=H$, $R^{12L}=H$], [5007; $Q=Q^{p1}$, $R^{1L}=Me$, $R^{2L}=H$, $R^{3L}=H$, $R^{11L}=H$, $R^{12L}=H$], [5008; $Q=Q^{p1}$, $R^{1L}=H$, $R^{2L}=Me$, $R^{3L}=H$, $R^{11L}=H$, $R^{12L}=H$], [5009; $Q=Q^{p1}$, $R^{1L}=H$, $R^{2L}=H$, $R^{3L}=Me$, $R^{11L}=H$, $R^{12L}=H$], [5010; $Q=Q^{p1}$, $R^{1L}=H$, $R^{2L}=CHF_2$, $R^{3L}=H$, $R^{11L}=H$, $R^{12L}=H$], [5011; $Q=Q^{p1}$, $R^{1L}=H$, $R^{2L}=H$, $R^{3L}=CHF_2$, $R^{11L}=H$, $R^{12L}=H$], [5012; $Q=Q^{p1}$, $R^{1L}=H$, $R^{2L}=CF_3$, $R^{3L}=H$, $R^{11L}=H$, $R^{12L}=H$], [5013; $Q=Q^{p1}$, $R^{1L}=H$, $R^{2L}=H$, $R^{3L}=CF_3$, $R^{11L}=H$, $R^{12L}=H$], [5014; $Q=Q^{p1}$, $R^{1L}=H$, $R^{2L}=Me$, $R^{3L}=H$, $R^{11L}=H$, $R^{12L}=H$], [5015; $Q=Q^{p1}$, $R^{1L}=H$, $R^{2L}=H$, $R^{3L}=OMe$, $R^{11L}=H$, $R^{12L}=H$], [5016; $Q=Q^{p1}$, $R^{1L}=H$, $R^{2L}=OCHF_2$, $R^{3L}=H$, $R^{11L}=H$, $R^{12L}=H$], [5017; $Q=Q^{p1}$, $R^{1L}=H$, $R^{2L}=H$, $R^{3L}=OCHF_2$, $R^{11L}=H$, $R^{12L}=H$], [5018; $Q=Q^{p1}$, $R^{1L}=H$, $R^{2L}=OCF_3$, $R^{3L}=H$, $R^{11L}=H$, $R^{12L}=H$], [5019; $Q=Q^{p1}$, $R^{1L}=H$, $R^{2L}=H$, $R^{3L}=OCF_3$, $R^{11L}=H$, $R^{12L}=H$], [5020; $Q=Q^{p1}$, $R^{1L}=H$, $R^{2L}=SMe$, $R^{3L}=H$, $R^{11L}=H$, $R^{12L}=H$], [5021; $Q=Q^{p1}$, $R^{1L}=H$, $R^{2L}=H$, $R^{3L}=SMe$, $R^{11L}=H$, $R^{12L}=H$], [5022; $Q=Q^{p1}$, $R^{1L}=H$, $R^{2L}=SCF_3$, $R^{3L}=H$, $R^{11L}=H$, $R^{12L}=H$], [5023; $Q=Q^{p1}$, $R^{1L}=H$, $R^{2L}=H$, $R^{3L}=SCF_3$, $R^{11L}=H$, $R^{12L}=H$], [5024; $Q=Q^{p1}$, $R^{1L}=H$, $R^{2L}=N$, $R^{3L}=H$, $R^{11L}=H$, $R^{12L}=H$], [5025; $Q=Q^{p1}$, $R^{1L}=H$, $R^{2L}=H$, $R^{3L}=N$, $R^{11L}=H$, $R^{12L}=H$], [5026; $Q=Q^{p1}$, $R^{1L}=H$, $R^{2L}=H$, $R^{3L}=H$, $R^{11L}=H$, $R^{12L}=H$], [5027; $Q=Q^{p1}$, $R^{1L}=H$, $R^{2L}=H$, $R^{3L}=NO_2$, $R^{11L}=H$, $R^{12L}=H$], [5028; $Q=Q^{p1}$, $R^{1L}=H$, $R^{2L}=Cl$, $R^{3L}=H$, $R^{11L}=Cl$, $R^{12L}=H$], [5029; $Q=Q^{p1}$, $R^{1L}=H$, $R^{2L}=Me$, $R^{3L}=H$, $R^{11L}=Me$, $R^{12L}=H$], [5030; $Q=Q^{p2}$, $R^{3L}=H$, $R^{11L}=H$, $R^{12L}=H$], [5031; $Q=Q^{p2}$, $R^{3L}=F$, $R^{11L}=H$, $R^{12L}=H$], [5032; $Q=Q^{p2}$, $R^{3L}=H$, $R^{11L}=F$, $R^{12L}=H$], [5033; $Q=Q^{p2}$, $R^{3L}=H$, $R^{11L}=H$, $R^{12L}=F$], [5034; $Q^{p2}$, $R^{3L}=Cl$, $R^{11L}=H$, $R^{12L}=H$], [5035; $Q=Q^{p2}$, $R^{3L}=H$, $R^{11L}=Cl$, $R^{12L}=H$], [5036; $Q=Q^{p2}$, $R^{3L}=H$, $R^{11L}=H$, $R^{12L}=H$], [5037; $Q=Q^{p2}$, $R^{3L}=H$, $R^{11L}=OMe$, $R^{12L}=H$], [5038; $Q=Q^{p2}$, $R^{3L}=CF_3$, $R^{11L}=H$, $R^{12L}=H$], [5039; $Q=Q^{p2}$, $R^{3L}=H$, $R^{11L}=CF_3$, $R^{12L}=H$], [5040; $Q=Q^{p3}$, $R^{3L}=H$, $R^{11L}=H$, $R^{12L}=H$], [5041; $Q=Q^{p3}$, $R^{3L}=F$, $R^{11L}=H$, $R^{12L}=H$], [5042; $Q=Q^{p3}$, $R^{3L}=H$, $R^{11}=F$, $R^{12L}=H$], [5043; $Q=Q^{p3}$, $R^{3L}=H$, $R^{11L}=H$, $R^{12L}=F$], [5044; $Q=Q^{p3}$, $R^{3L}=Cl$, $R^{11L}=H$, $R^{12L}=H$], [5045; $Q=Q^{p3}$, $R^{3L}=H$, $R^{11L}=Cl$, $R^{12L}=H$], [5046; $Q=Q^{p3}$, $R^{3L}=OMe$, $R^{11L}=H$, $R^{12L}=H$], [5047; $Q=Q^{p3}$, $R^{3L}=H$, $R^{11L}=OMe$, $R^{12L}=H$], [5048; $Q=Q^{p3}$, $R^{3L}=CF_3$, $R^{11L}=H$, $R^{12L}=H$], [5049; $Q=Q^{p3}$, $R^{3L}=H$, $R^{11L}=CF_3$, $R^{12L}=H$], [5050; $Q=Q^{p3}$, $R^{3L}=H$, $R^{11L}=H$, $R^{12L}=H$], [5051; $Q=Q^{p4}$, $R^3=F$, $R^{11L}=H$, $R^{12L}=H$], [5052; $Q=Q^{p4}$, $R^{3L}=H$, $R^{11L}=F$, $R^{12L}=H$], [5053; $Q=Q^{p4}$, $R^{3L}=H$, $R^{11L}=H$, $R^{12L}=F$], [5054; $Q=Q^{p4}$, $R^{3L}=Cl$, $R^{11L}=H$, $R^{12L}=H$], [5055; $Q=Q^{p4}$, $R^{3L}=H$, $R^{11L}=Cl$, $R^{12L}=H$], [5056; $Q=Q^{p4}$, $R^{3L}=OMe$, $R^{11L}=H$, $R^{12L}=H$], [5057; $Q=Q^{p4}$, $R^{3L}=H$, $R^{11L}=OMe$, $R^{12L}=H$], [5058; $Q=Q^{p4}$, $R^{3L}=CF_3$, $R^{11L}=H$, $R^{12L}=H$], [5059; $Q=Q^{p4}$, $R^{3L}=H$, $R^{11L}=CF_3$, $R^{12L}=H$], [5060; $Q=Q^{p5}$, $R^{3L}=H$, $R^{11L}=H$, $R^{12L}=H$], [5061; $Q=Q^{p5}$, $R^{3L}=F$, $R^{11L}=H$, $R^{12L}=H$], [5062; $Q=Q^{p5}$, $R^{3L}=H$, $R^{11L}=F$, $R^{12L}=H$], [5063; $Q=Q^{p5}$, $R^{3L}=H$, $R^{11L}=H$, $R^{12L}=F$], [5064; $Q=Q^{p5}$, $R^{3L}=Cl$, $R^{11L}=H$, $R^{12L}=H$], [5065; $Q=Q^{p5}$, $R^{3L}=H$, $R^{11L}=Cl$, $R^{12L}=H$], [5066; $Q=Q^{p5}$, $R^{3L}=OMe$, $R^{11L}=H$, $R^{12L}=H$], [5067; $Q=Q^{p5}$, $R^{3L}=H$, $R^{11L}=OMe$, $R^{12L}=H$], [5068; $Q=Q^{p5}$, $R^{3L}=CF_3$, $R^{11L}=H$, $R^{12L}=H$], [5069; $Q=Q^{p5}$, $R^{3L}=H$, $R^{11L}=CF_3$, $R^{12L}=H$], [5070; $Q=Q^{p5}$, $R^{1L}=H$, $R^{11L}=H$, $R^{12L}=H$], [5071; $Q=Q^{p6}$, $R^{1L}=F$, $R^{11L}=H$, $R^{12L}=H$], [5072; $Q=Q^{p6}$, $R^{1L}=H$, $R^{11L}=F$, $R^{12L}=H$], [5073; $Q=Q^{p6}$, $R^{1L}=H$, $R^{11L}=H$, $R^{12L}=F$], [5074; $Q=Q^{p6}$, $R^{1L}=H$, $R^{11L}=Cl$, $R^{12L}=H$], [5075; $Q=Q^{p6}$, $R^{1L}=H$, $R^{11L}=OMe$, $R^{12L}=H$], [5076; $Q=Q^{p6}$, $R^{1L}=H$, $R^{11L}=CF_3$, $R^{12L}=H$], [5077; $Q=Q^{p7}$, $R^{1L}=H$, $R^{11L}=H$, $R^{12L}=H$], [5078; $Q=Q^{p7}$, $R^{1L}=F$, $R^{11L}=H$, $R^{12L}=H$], [5079; $Q=Q^{p7}$, $R^{1L}=H$, $R^{11L}=F$, $R^{12L}=H$], [5080; $Q=Q^{p7}$, $R^{1L}=H$, $R^{11L}=H$, $R^{12L}=F$], [5081; $Q=Q^{p7}$, $R^{1L}=H$, $R^{11L}=Cl$, $R^{12L}=H$], [5082; $Q=Q^{p7}$, $R^{1L}=H$, $R^{11L}=OMe$, $R^{12L}=H$], [5083; $Q=Q^{p7}$, $R^{1L}=H$, $R^{11L}=CF_3$, $R^{12L}=H$], [5084; $Q=Q^{p8}$, $R^{1L}=H$, $R^{11L}=H$, $R^{12L}=H$], [5085; $Q=Q^{p8}$, $R^{1L}=F$, $R^{11L}=H$, $R^{12L}=H$], [5086; $Q=Q^{p8}$, $R^{1L}=H$, $R^{11L}=F$, $R^{12L}=H$], [5087; $Q=Q^{p8}$, $R^{1L}=H$, $R^{11L}=H$, $R^{12L}=F$], [5088; $Q=Q^{p8}$, $R^{1L}=H$, $R^{11L}=Cl$, $R^{12L}=H$], [5089; $Q=Q^{p8}$, $R^{1L}=H$, $R^{11L}=OMe$, $R^{12L}=H$], [5090; $Q=Q^{p8}$, $R^{1L}=H$, $R^{11L}=CF_3$, $R^{12L}=H$], [5091; $Q=Q^{p9}$, $R^{3L}=H$, $R^{11L}=H$, $R^{12L}=H$], [5092; $Q=Q^{p9}$, $R^{3L}=F$, $R^{11L}=H$, $R^{12L}=H$], [5093; $Q=Q^{p9}$, $R^{3L}=H$, $R^{1L}=F$, $R^{12L}=H$], [5094; $Q=Q^{p9}$, $R^{3L}=H$, $R^{11L}=H$, $R^{12L}=F$], [5095; $Q=Q^{p9}$, $R^{3L}=Cl$, $R^{11L}=H$, $R^{12L}=H$], [5096; $Q=Q^{p9}$, $R^{3L}=H$, $R^{11L}=Cl$, $R^{12L}=H$], [5097; $Q=Q^{p9}$, $R^{3L}=OMe$, $R^{11L}=H$, $R^{12L}=H$], [5098; $Q=Q^{p9}$, $R^{3L}=H$, $R^{11L}=OMe$, $R^{12L}=H$], [5099; $Q=Q^{p9}$, $R^{3L}=CF_3$, $R^{11L}=H$, $R^{12L}=H$], [5100; $Q=Q^{p9}$, $R^{3L}=H$, $R^{11L}=CF_3$, $R^{12L}=H$], [5101; $Q=Q^{p10}$, $R^{1L}=H$, $R^{11L}=H$, $R^{12L}=H$], [5102; $Q=Q^{p10}$, $R^{1L}=F$, $R^{11L}=H$, $R^{12L}=H$], [5103; $Q=Q^{p10}$, $R^{1L}=H$, $R^{11L}=F$, $R^{12L}=H$], [5104; $Q=Q^{p10}$, $R^{1L}=H$, $R^{11L}=H$, $R^{12L}=F$], [5105; $Q=Q^{p10}$, $R^{1L}=H$, $R^{11L}=Cl$, $R^{12L}=H$], [5106; $Q=Q^{p10}$, $R^{1L}=H$, $R^{11L}=OMe$, $R^{12L}=H$], and [5107; $Q=Q^{p10}$, $R^{1L}=H$, $R^{11L}=CF_3$, $R^{12L}=H$]

Formulation Examples will be shown below. Parts are by weight.

Formulation Example 1

Fifty parts (50 parts) of any one of the present compounds 1 to 159, 201 to 219, and 251 to 266, 3 parts of calcium ligninsulfoate, 2 parts of laurylmagnesium sulfate, and 45 parts of synthetic hydrated silicon oxide are thoroughly ground and mixed to obtain each formulation.

Formulation Example 2

Twenty parts (20 parts) of any one of the present compounds 1 to 159, 201 to 219, and 251 to 266, and 1.5 parts of sorbitan trioleate were mixed with 28.5 parts of an aqueous solution containing 2 parts of polyvinyl alcohol and the mixture was finely ground by a wet grinding method. Then, 40 parts of an aqueous solution containing 0.05 part of xanthan gum and 0.1 part of aluminum magnesium silicate is added thereto and 10 parts of propylene glycol is further added, followed by stirring and mixing to obtain each formulation.

Formulation Example 3

Two parts (2 parts) of any one of the present compounds 1 to 159, 201 to 219, and 251 to 266, 88 parts of kaolin clay, and 10 parts of talc are thoroughly ground and mixed to obtain each formulation.

Formulation Example 4

Five parts (5 parts) of any one of the present compounds 1 to 159, 201 to 219, and 251 to 266, 14 parts of polyoxyethylene styryl phenyl ether, 6 parts of calcium dodecylbenzenesulfonate, and 75 parts of xylene are thoroughly ground and mixed to obtain each formulation.

Formulation Example 5

Two parts (2 parts) of any one of the present compounds 1 to 159, 201 to 219, and 251 to 266, 1 part of synthetic hydrated silicon oxide, 2 parts of calcium ligninsulfoate, 30 parts of bentonite, and 65 parts of kaolin clay are thoroughly ground and mixed. After the addition of water, the mixture is thoroughly kneaded and further and granulated and dried to obtain each formulation.

Formulation Example 6

Ten parts (10 parts) of any one of the present compounds 1 to 159, 201 to 219, and 251 to 266, 35 parts of white carbon containing 50 parts of a polyoxyethylene alkyl ether sulfate ammonium salt, and 55 parts of water were finely ground by a wet grinding method to obtain each formulation.

The following Test Examples will show that the present compounds are useful for controlling pests.

The control effect was evaluated by visually observing the area of lesion spots on each of test plants at the time of investigation, and comparing the area of lesion spots on a plant treated with the present control compound with that on an untreated plant.

Test Example 1

Each of plastic pots was filled with soil and rice (cultivar: NIHONBARE) was sowed therein and grown in a greenhouse for 20 days. Each of the present compounds 5, 7, 24, 30, 31, 32, 34, 37, 44, 69, 71, 76, 85, 96, 97, 110, 124, 127, 129, 133, 136, 137, 139, 142, 143, 144, 149, 152, 153, 154, 202, 203, 204, 211, 215, 217, and 265 was formulated into a formulation according to Formulation Example, which was diluted with water to adjust to a prescribed concentration of 500 ppm. The obtained diluted solutions were sprayed over stems and leaves so that they sufficiently adhered to the surface of the leaves of the rice. After spraying, the plant was air-dried and subjected to a spraying treatment and the rice seedling (cultivar: NIHONBARE) infected by the rice blast fungus (*Magnaporthe grisea*) were left to stand for 6 days at 24° C. in the daytime and 20° C. at night under high humidity condition, while being in contact with each other, and then the area of lesion spots was investigated. As a result, the lesion areas on all of the plant treated with the present compounds 5, 7, 24, 30, 31, 32, 34, 37, 44, 69, 71, 76, 85, 96, 97, 110, 124, 127, 129, 133, 136, 137, 139, 142, 143, 144, 149, 152, 153, 154, 265, 202, 203, 204, 211, 215, 217, and 265 showed 30% or less with respect to the lesion area on the non-treated plant.

Test Example 2

Each of plastic pots was filled with soil and wheat (cultivar: SHIROGANE) was sowed therein and grown in a greenhouse for 9 days. Each of the present compounds 24, 30, 31, 34, 38, 44, 101, 110, 119, 137, 138, 152, 153, 154, 202, 203, 204, 215, and 217 was formulated into a formulation according to Formulation Example, which was diluted with water to adjust to a prescribed concentration of 500 ppm. The obtained diluted solution was sprayed over stems and leaves of the wheat so that they sufficiently adhered to the surface of the leaves of the wheat. After spraying, the plant was air-dried and cultivated at 20° C. for 5 days under illumination, and then inoculated by sprinkling with spores of the wheat rust fungus (*Puccinia recondita*). After the inoculation, the plant was left to stand at 23° C. for one day under dark and high humidity condition, and cultivated under illumination at 20° C. for 8 days, and then the area of lesion spots was investigated. As a result, it has been found that the area of lesion spots on all of the plant treated with each of the present compounds 24, 30, 31, 34, 38, 44, 101, 110, 119, 137, 138, 152, 153, 154, 202, 203, 204, 215, and 217 showed 30% or less of that on an untreated plant.

Test Example 3

Each of plastic pots was filled with soil and barley (cultivar: MIKAMO GOLDEN) was sowed therein and grown in a greenhouse for 7 days. Each of the present compounds 1, 2, 5, 7, 9, 11, 12, 15, 16, 17, 19, 23, 24, 25, 28, 29, 30, 31, 32, 33, 34, 35, 36, 37, 38, 39, 40, 41, 42, 43, 44, 45, 46, 47, 48, 49, 50, 51, 53, 54, 55, 56, 57, 58, 59, 60, 61, 64, 65, 66, 67, 68, 69, 70, 71, 72, 75, 76, 78, 79, 80, 82, 84, 85, 86, 87, 88, 89, 92, 93, 95, 96, 97, 99, 101, 105, 106, 107, 109, 110, 112, 113, 114, 115, 116, 118, 119, 120, 122, 123, 124, 125, 127, 129, 131, 132, 133, 134, 135, 136, 137, 138, 139, 141, 142, 143, 144, 145, 146, 148, 149, 151, 152, 153, 154, 155, 156, 159, 202, 203, 204, 205, 206, 207, 209, 210, 213, 215, 216, 217, 257, 258, 259, 260, 261, 262, 263, 264, and 265 was formulated into a formulation according to Formulation Example, which was diluted with water to adjust to a prescribed concentration of 500 ppm. The obtained diluted solution was sprayed over stems and leaves of the barley so that they sufficiently adhered to the surface of the leaves of the barley. After spraying, the plant was air-dried. Two days later, an aqueous suspension containing conidiospores of barley net blotch fungus (*Pyrenophora teres*) was sprayed to inoculate the spores. After completion of the inoculation, the plant was left to stand for 3 days in a greenhouse at 23° C. in the daytime and 20° C. at night under high humidity condition and cultivated in a greenhouse for 7 days, and then the area of lesion spots was investigated. As a result, it has been found that the area of lesion spots on all of the plant treated with each of the present compounds 1, 2, 5, 7, 9, 11, 12, 15, 16, 17, 19, 23, 24, 25, 28, 29, 30, 31, 32, 33, 34, 35, 36, 37, 38, 39, 40, 41, 42, 43, 44, 45, 46, 47, 48, 49, 50, 51, 53, 54, 55, 56, 57, 58, 59, 60, 61, 64, 65, 66, 67, 68, 69, 70, 71, 72, 75, 76, 78, 79, 80, 82, 84, 85, 86, 87, 88, 89, 92, 93, 95, 96, 97, 99, 101, 105, 106, 107, 109, 110, 112, 113, 114, 115, 116, 118, 119, 120, 122, 123, 124, 125, 127, 129, 131, 132, 133, 134, 135, 136, 137, 138, 139, 141, 142, 143, 144, 145, 146, 148, 149, 151, 152, 153, 154, 155, 156, 159, 202, 203, 204, 205, 206, 207, 209, 210, 213, 215, 216, 217, 257, 258, 259, 260, 261, 262, 263, 264, and 265 showed 30% or less of that on an untreated plant.

Test Example 4

Each of plastic pots was filled with soil and kidney bean (cultivar: NAGAUZURA INGEN) was sowed therein and grown in a greenhouse for 8 days. Each of the present compounds 1, 2, 5, 7, 8, 9, 10, 11, 12, 16, 17, 19, 24, 27, 30, 31, 32, 33, 34, 35, 36, 37, 38, 39, 42, 44, 46, 47, 48, 49, 50, 53, 54, 55, 56, 58, 61, 65, 67, 68, 69, 70, 71, 76, 78, 79, 84, 85, 86, 89, 90, 92, 93, 95, 96, 97, 101, 105, 107, 108, 109, 110, 118, 119, 122, 123, 124, 125, 127, 128, 129, 130, 131, 132, 133, 135, 136, 137, 138, 139, 142, 143, 144, 145, 146, 149, 151, 152, 153, 202, 203, 204, 205, 206, 208, 214, 215, 216, 217, 257, 258, and 259 was formulated into a formulation according to Formulation Example, which was diluted with water to adjust to a prescribed concentration of 500 ppm. The obtained diluted solution was sprayed over stems and leaves of the kidney bean so that they sufficiently adhered to the surface of the leaves of the kidney bean. After spraying, the plant was air-dried and a PDA medium containing hyphae of the kidney bean stem rot fungus (*Sclerotinia sclerotiorum*) was placed on the leaves of the kidney bean. After the inoculation, all kidney beans are left to stand under high humidity condition only at night. Four days after the inoculation, the area of lesion spots was investigated. As a result, the area of lesion spots on all of the plant treated with each of the present compounds 1, 2, 5, 7, 8, 9, 10, 11, 12, 16, 17, 19, 24, 27, 30, 31, 32, 33, 34, 35, 36, 37, 38, 39, 42, 44, 46, 47, 48, 49, 50, 53, 54, 55, 56, 58, 61, 65, 67, 68, 69, 70, 71, 76, 78, 79, 84, 85, 86, 89, 90, 92, 93, 95, 96, 97, 101, 105, 107, 108, 109, 110, 118, 119, 122, 123, 124, 125, 127, 128, 129, 130, 131, 132, 133, 135, 136, 137, 138, 139, 142, 143, 144, 145, 146, 149, 151, 152, 153, 202, 203, 204, 205, 206, 208, 214, 215, 216, 217, 257, 258, and 259 showed 30% or less of that on an untreated plant.

Test Example 5

Each of plastic pots was filled with soil and wheat (cultivar: APOGEE) was sowed therein and grown in a greenhouse for 10 days. Each of the present compounds 1, 5, 7, 9, 10, 11, 12, 15, 16, 17, 19, 23, 24, 25, 29, 30, 31, 32, 34, 35, 36, 37, 38, 39, 41, 42, 44, 45, 46, 47, 48, 49, 50, 51, 53, 54, 55, 56, 57, 58, 59, 60, 61, 64, 65, 67, 68, 69, 70, 71, 72, 75, 77, 78, 79, 84, 85, 86, 88, 89, 90, 91, 92, 93, 95, 96, 97, 99, 100, 101, 102, 105, 106, 107, 108, 109, 110, 111, 112, 113, 114, 115, 116, 117, 118, 119, 120, 122, 123, 124, 125, 126, 127, 128, 129, 130, 131, 132, 133, 134, 135, 136, 137, 138, 139, 140, 141, 142, 143, 144, 145, 146, 148, 149, 151, 152, 153, 154, 155, 156, 202, 203, 204, 207, 211, 215, 216, 217, 257, 258, 259, 261, 262, 264, and 265 was formulated into a formulation according to Formulation Example, which was diluted with water to adjust to a prescribed concentration of 500 ppm. The obtained diluted solution was sprayed over stems and leaves of the wheat so that they sufficiently adhered to the surface of the leaves of the wheat. After spraying, the plant was air-dried. Four days later, an aqueous suspension containing conidiospores of the wheat leaf blotch fungus (*Septoria tritici*) was sprayed to inoculate the spores. After completion of the inoculation, the plant was left to stand at 18° C. under high humidity condition for 3 days and left to stand under illumination for 14 to 18 days, and then the area of lesion spots was investigated. As a result, the area of lesion spots on all of the plant treated with each of the present compounds 1, 5, 7, 9, 10, 11, 12, 15, 16, 17, 19, 23, 24, 25, 29, 30, 31, 32, 34, 35, 36, 37, 38, 39, 41, 42, 44, 45, 46, 47, 48, 49, 50, 51, 53, 54, 55, 56, 57, 58, 59, 60, 61, 64, 65, 67, 68, 69, 70, 71, 72, 75, 77, 78, 79, 84, 85, 86, 88, 89, 90, 91, 92, 93, 95, 96, 97, 99, 100, 101, 102, 105, 106, 107, 108, 109, 110, 111, 112, 113, 114, 115, 116, 117, 118, 119, 120, 122, 123, 124, 125, 126, 127, 128, 129, 130, 131, 132, 133, 134, 135, 136, 137, 138, 139, 140, 141, 142, 143, 144, 145, 146, 148, 149, 151, 152, 153, 154, 155, 156, 202, 203, 204, 207, 211, 215, 216, 217, 257, 258, 259, 261, 262, 264, and 265 showed 30% or less of that on an untreated plant.

Test Example 6

Each of plastic pots was filled with soil and cucumber (cultivar: SAGAMI HANJIRO) was sowed therein and grown in a greenhouse for 12 days. Each of the present compounds 1, 2, 5, 7, 9, 10, 11, 12, 15, 16, 17, 19, 23, 24, 25, 27, 29, 30, 31, 32, 33, 34, 35, 38, 39, 40, 44, 45, 46, 48, 49, 51, 53, 54, 55, 56, 58, 59, 60, 61, 62, 64, 65, 66, 67, 68, 69, 70, 71, 72, 73, 76, 77, 78, 79, 83, 84, 85, 86, 88, 89, 90, 91, 92, 93, 95, 96, 99, 100, 101, 102, 105, 106, 107, 108, 109, 110, 111, 112, 113, 114, 115, 116, 118, 119, 120, 123, 124, 125, 126, 127, 128, 129, 131, 132, 133, 134, 135, 136, 137, 138, 139, 142, 143, 144, 145, 148, 149, 151, 153, 154, 155, 156, 202, 203, 204, 205, 208, 211, 212, 213, 214, 215, 216, 217, 257, 258, 260, 261, 262, and 263 was formulated into a formulation according to Formulation Example, which was diluted with water to adjust to a prescribed concentration of 500 ppm. The obtained diluted solution was sprayed over stems and leaves of the cucumber so that they sufficiently adhered to the surface of the leaves of the cucumber. After spraying, the plant was air-dried and then inoculated by sprinkling with spores of the cucumber powdery mildew fungus (*Sphaerotheca fuliginea*). After the inoculation, the plant was cultivated in a greenhouse at 24° C. in the daytime and 20° C. at night for 8 days, and then the area of lesion spots was investigated. As a result, the area of lesion spots on all of the plant treated with each of the present compounds 1, 2, 5, 7, 9, 10, 11, 12, 15, 16, 17, 19, 23, 24, 25, 27, 29, 30, 31, 32, 33, 34, 35, 38, 39, 40, 44, 45, 46, 48, 49, 51, 53, 54, 55, 56, 58, 59, 60, 61, 62, 64, 65, 66, 67, 68, 69, 70, 71, 72, 73, 76, 77, 78, 79, 83, 84, 85, 86, 88, 89, 90, 91, 92, 93, 95, 96, 99, 100, 101, 102, 105, 106, 107, 108, 109, 110, 111, 112, 113, 114, 115, 116, 118, 119, 120, 123, 124, 125, 126, 127, 128, 129, 131, 132, 133, 134, 135, 136, 137, 138, 139, 142, 143, 144, 145, 148, 149, 151, 153, 154, 155, 156, 202, 203, 204, 205, 208, 211, 212, 213, 214,

Test Example 7

Each of plastic pots was filled with soil and rice (cultivar: NIHONBARE) was sowed therein and grown in a greenhouse for 20 days. Each of the present compounds 2, 3, 6, 9, 10, 13, 16, 17, 19, 23, 47, 48, 53, 54, 55, 56, 57, 58, 60, 65, 70, 72, 73, 84, 94, 95, 101, 107, 112, 118, 119, 126, 131, 132, 134, 135, 138, 148, 150, 151, 155, 201, 214, 216, 258, and 260 was formulated into a formulation according to Formulation Example, which was diluted with water to adjust to a prescribed concentration of 200 ppm. The obtained diluted solutions were sprayed over stems and leaves so that they sufficiently adhered to the surface of the leaves of the rice. After spraying, the plant was air-dried and subjected to a spraying treatment and the rice seedling (cultivar: NIHONBARE) infected by the rice blast fungus (*Magnaporthe grisea*) were left to stand for 6 days at 24° C. in the daytime and 20° C. at night under high humidity condition, while being in contact with each other, and then the area of lesion spots was investigated. As a result, the lesion areas on all of the plant treated with the present compounds 2, 3, 6, 9, 10, 13, 16, 17, 19, 23, 47, 48, 53, 54, 55, 56, 57, 58, 60, 65, 70, 72, 73, 84, 94, 95, 101, 107, 112, 118, 119, 126, 131, 132, 134, 135, 138, 148, 150, 151, 155, 201, 214, 216, 258, and 260 showed 30% or less with respect to the lesion area on the non-treated plant.

Test Example 8

Each of plastic pots was filled with soil and wheat (cultivar: SHIROGANE) was sowed therein and grown in a greenhouse for 9 days. Each of the present compounds 7, 10, 39, 54, 56, 61, 75, 78, 86, 88, 90, 92, 94, 99, 100, 105, 106, 107, 118, 120, 124, 125, 127, 132, 134, 136, 142, 143, 144, 148, 149, 206, 213, 216, and 258 was formulated into a formulation according to Formulation Example, which was diluted with water to adjust to a prescribed concentration of 200 ppm. The obtained diluted solution was sprayed over stems and leaves of the wheat so that they sufficiently adhered to the surface of the leaves of the wheat. After spraying, the plant was air-dried and cultivated at 20° C. for 5 days under illumination, and then inoculated by sprinkling with spores of the wheat rust fungus (*Puccinia recondita*). After the inoculation, the plant was left to stand at 23° C. for one day under dark and high humidity condition, and cultivated under illumination at 20° C. for 8 days, and then the area of lesion spots was investigated. As a result, it has been found that the area of lesion spots on all of the plant treated with each of the present compounds 7, 10, 39, 54, 56, 61, 75, 78, 86, 88, 90, 92, 92, 99, 94, 99, 100, 105, 106, 107, 118, 120, 124, 125, 127, 132, 134, 136, 142, 143, 144, 148, 149, 206, 213, 216, and 258 showed 30% or less of that on an untreated plant.

Test Example 9

Each of plastic pots was filled with soil and barley (cultivar: MIKAMO GOLDEN) was sowed therein and grown in a greenhouse for 7 days. Each of the present compounds 3, 10, 27, 62, 90, 94, 108, 121, 126, 128, 130, 147, 151, 201, and 205 was formulated into a formulation according to Formulation Example, which was diluted with water to adjust to a prescribed concentration of 200 ppm. The obtained diluted solution was sprayed over stems and leaves of the barley so that they sufficiently adhered to the surface of the leaves of the barley. After spraying, the plant was air-dried. Two days later, an aqueous suspension containing conidiospores of barley net blotch fungus (*Pyrenophora teres*) was sprayed to inoculate the spores. After completion of the inoculation, the plant was left to stand for 3 days in a greenhouse at 23° C. in the daytime and 20° C. at night under high humidity condition and cultivated in a greenhouse for 7 days, and then the area of lesion spots was investigated. As a result, the area of lesion spots on all of the plant treated with each of the present compounds 3, 10, 27, 62, 90, 94, 108, 121, 126, 128, 130, 147, 151, 201, and 205 showed 30% or less of that on an untreated plant.

Test Example 10

Each of plastic pots was filled with soil and kidney bean (cultivar: NAGAUZURA INGEN) was sowed therein and grown in a greenhouse for 8 days. Each of the present compounds 63, 66, 72, 87, 88, 91, 116, 117, 155, and 201 was formulated into a formulation according to Formulation Example, which was diluted with water to adjust to a prescribed concentration of 200 ppm. The obtained diluted solution was sprayed over stems and leaves of the kidney bean so that they sufficiently adhered to the surface of the leaves of the kidney bean. After spraying, the plant was air-dried and a PDA medium containing hyphae of the kidney bean stem rot fungus (*Sclerotinia sclerotiorum*) was placed on the leaves of the kidney bean. After the inoculation, all kidney beans are left to stand under high humidity condition only at night. Four days after the inoculation, the area of lesion spots was investigated. As a result, the area of lesion spots on all of the plant treated with any one of the present compounds 63, 66, 72, 87, 88, 91, 116, 117, 155, and 201 showed 30% or less of that on an untreated plant.

Test Example 11

Each of plastic pots was filled with soil and wheat (cultivar: APOGEE) was sowed therein and grown in a greenhouse for 10 days. Each of the present compounds 2, 3, 27, 28, 43, 62, 63, 66, 76, 94, 121, 147, 159, 205, and 260 was formulated into a formulation according to Formulation Example, which was diluted with water to adjust to a prescribed concentration of 200 ppm. The obtained diluted solution was sprayed over stems and leaves of the wheat so that they sufficiently adhered to the surface of the leaves of the wheat. After spraying, the plant was air-dried. Four days later, an aqueous suspension containing conidiospores of the wheat leaf blotch fungus (*Septoria tritici*) was sprayed to inoculate the spores. After completion of the inoculation, the plant was left to stand at 18° C. under high humidity condition for 3 days and left to stand under illumination for 14 to 18 days, and then the area of lesion spots was investigated. As a result, the area of lesion spots on all of the plant treated with each of the present compounds 2, 3, 27, 28, 43, 62, 63, 65, 66, 76, 94, 121, 147, 159, 205, and 260 showed 30% or less of that on an untreated plant.

Test Example 12

Each of plastic pots was filled with soil and cucumber (cultivar: SAGAMI HANJIRO) was sowed therein and grown in a greenhouse for 12 days. Each of the present compounds 42, 57, 94, 121, and 152 was formulated into a formulation according to Formulation Example, which was diluted with water to adjust to a prescribed concentration of 200 ppm. The obtained diluted solution was sprayed over stems and leaves of the cucumber so that they sufficiently adhered to the surface of the leaves of the cucumber. After spraying, the plant was air-dried and then inoculated by sprinkling with spores of the cucumber powdery mildew fungus (*Sphaerotheca fuliginea*). After the inoculation, the plant was cultivated in a greenhouse at 24° C. in the daytime and 20° C. at night for 8 days, and then the area of lesion spots was investigated. As a result, the area of lesion spots on all of the plant treated with each of the present compounds 42, 57, 94, 121, and 152 showed 30% or less of that on an untreated plant.

Test Example 13

Each of plastic pots was filled with soil and soybean (cultivar: KUROSENGOKU) was sowed therein and grown in a greenhouse for 13 days. Each of the present compounds 38, 110, 144, 152, 203, 215, and 217 was formulated into a formulation according to Formulation Example, which was diluted with water to adjust to a prescribed concentration of 200 ppm. The obtained diluted solution was sprayed over stems and leaves of the soybean so that they sufficiently adhered to the surface of the leaves of the soybean. After spraying, the plant was air-dried. Two days later, an aqueous suspension containing conidiospores of soybean rust fungus (*Phakopsora pachyrhizi*) was sprayed to inoculate the spores. After completion of the inoculation, the plant was left to stand for 3 days in a greenhouse at 23° C. in the daytime and 20° C. at night under high humidity condition and cultivated in a greenhouse for 14 days, and then the area of lesion spots was investigated. As a result, it has been found that the area of lesion spots on all of the plant treated with each of the present compounds 38, 110, 144, 152, 203, 215, and 217 showed 30% or less of that on an untreated plant.

Test Example 14

Each of plastic pots was filled with soil and barley (cultivar: MIKAMO GOLDEN) was sowed therein and grown in a greenhouse for 7 days. Each of the present compounds 1, 2, 5, 7, 8, 9, 10, 11, 12, 16, 17, 19, 23, 25, 27, 29, 30, 31, 32, 33, 34, 35, 36, 37, 38, 39, 40, 41, 42, 43, 44, 46, 47, 48, 49, 51, 53, 54, 55, 56, 58, 59, 60, 61, 64, 65, 66, 68, 69, 70, 71, 72, 73, 75, 76, 77, 78, 79, 84, 85, 88, 92, 93, 94, 95, 96, 97, 98, 99, 103, 105, 106, 107, 108, 109, 110, 112, 113, 114, 115, 116, 117, 118, 119, 120, 121, 122, 123, 124, 125, 126, 127, 128, 129, 130, 131, 132, 133, 134, 136, 137, 138, 139, 140, 141, 142, 143, 144, 145, 146, 147, 148, 149, 151, 152, 155, 201, 202, 203, 205, 206, 207, 209, 211, 213, 214, 215, 216, 217, 219, 257, 258, 259, 260, and 262 was formulated into a formulation according to Formulation Example, which was diluted with water to adjust to a prescribed concentration of 200 ppm. The obtained diluted solution was sprayed over stems and leaves of the barley so that they sufficiently adhered to the surface of the leaves of the barley. After spraying, the plant was air-dried. Two days later, an aqueous suspension containing conidiospores of barley scald fungus (*Rhynchosporium secalis*) was sprayed to inoculate the spores. After completion of the inoculation, the plant was left to stand for 3 days in a greenhouse at 23° C. in the daytime and 20° C. at night under high humidity condition and cultivated in a greenhouse for 7 days, and then the area of lesion spots was investigated. As a result, it has been found that the area of lesion spots on all of the plant treated with each of the present compounds 1, 2, 5, 7, 8, 9, 10, 11, 12, 16, 17, 19, 23, 25, 27, 29, 30, 31, 32, 33, 34, 35, 36, 37, 38, 39, 40, 41, 42, 43, 44, 46, 47, 48, 49, 51, 53, 54, 55, 56, 58, 59, 60, 61, 64, 65, 66, 68, 69, 70, 71, 72, 73, 75, 76, 77, 78, 79, 84, 85, 88, 92, 93, 94, 95, 96.97, 98, 99, 103, 105, 106, 107, 108, 109, 110, 112, 113, 114, 115, 116, 117, 118, 119, 120, 121, 122, 123, 124, 125, 126, 127, 128, 129, 130, 131, 132, 133, 134, 136, 137, 138, 139, 140, 141, 142, 143, 144, 145, 146, 147, 148, 149, 151, 152, 155, 201, 202, 203, 205, 206, 207, 209, 211, 213, 214, 215, 216, 217, 219, 257, 258, 259, 260, and 262 showed 30% or less of that on an untreated plant.

Test Example 15

Each of formulations of the present compounds 6, 9, 26, 28, 31, 32, 33, 36, 71, 109, 114, 115, 125, and 149 obtained in Formulation Example 6 was diluted with water so that the concentration of the active ingredient is controlled to 500 ppm to prepare a test spraying solution. Meanwhile, the above test chemical solution was sprayed over three-leaf stage cabbage sowed in a polyethylene cup in the proportion of 20 mL/cup. After drying the chemical solution, stem and leaf portions were cut off and put in a 50 mL cup and five second-instar larvae of diamondback moth (*Plutella xylostella*) were released, and then the cup was capped. The cup was stored at 25° C. and, after 5 days, the number of surviving worms was counted and mortality was determined by the following equation.

Mortality (%)=[(Number of dead insects)/(Number of tested insects)]×100

As a result, the treated area of the test spraying solutions of the present compounds 6, 9, 26, 28, 31, 32, 33, 36, 71, 109, 114, 115, 125, and 149 exhibited mortality of 80% or more.

Comparative Test Example

Each of plastic pots was filled with soil and cucumber (cultivar: SAGAMI HANJIRO) was sowed therein and grown in a greenhouse for 12 days.

Each of 1-methyl-4-{2-methyl-6-[1-(3-trifluoromethylphenyl)ethylideneaminooxymethyl]phenyl}-1,4-dihydrotetrazol-5-one and 1-{3-methyl-2-[1-(3-trifluoromethylphenyl)ethylideneaminooxymethyl]phenyl}-4-methyl-1,4-dihydrotetrazol-5-one was formulated into a formulation according to Formulation Example, which was diluted with water to adjust to a prescribed concentration of 200 ppm. The obtained diluted solution was sprayed over stems and leaves of the cucumber so that they sufficiently adhered to the surface of the leaves of the cucumber. After spraying, the plant was air-dried and then inoculated by sprinkling with spores of the cucumber powdery mildew fungus (*Sphaerotheca fuliginea*). After the inoculation, the plant was cultivated in a greenhouse at 24° C. in the daytime and 20° C. at night for 8 days, and then the area of lesion spots was investigated. As a result, the area of lesion spots on the plant treated with 1-methyl-4-{2-methyl-6-[1-(3-trifluoromethylphenyl)ethylideneaminooxymethyl]phenyl}-1,4-dihydrotetrazol-5-one was 70% or more of that on an untreated plant, whereas, the area of lesion spots on the plant treated with 1-{3-methyl-2-[1-(3-trifluoromethylphenyl)ethylideneaminooxymethyl]phenyl}-4-methyl-1,4-dihydrotetrazol-5-one was 30% or less of that on an untreated plant.

The invention claimed is:

1. A tetrazolinone compound represented by formula (1):

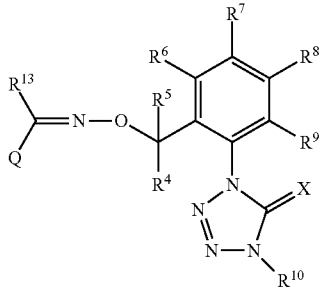

(1)

wherein,
$R^4$, $R^5$, $R^7$, $R^8$, and $R^9$ are hydrogen atoms;
$R^{10}$ is a methyl group; X is an oxygen atom;
$R^6$ is a C1-C3 alkyl group optionally having one or more halogen atoms,
a C3-C4 cycloalkyl group optionally having one or more halogen atoms,
a C1-C3 alkoxy group optionally having one or more halogen atoms,
a halogen atom, a C2-C3 alkenyl group, a C2-C3 alkynyl group, or a C1-C3 alkylthio group; and either
(a) R13 is methyl; and
Q is the following structure

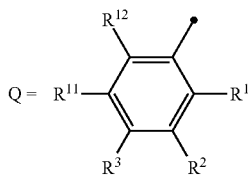

wherein,
$R^1$, $R^3$, $R^{11}$ and $R^{12}$ each represent a hydrogen atom and $R^2$ is $CF_3$; or
(b) $R^{13}$ is a C1-C4 alkyl group, a C3-C4 cycloalkyl group, a hydrogen atom, a C2-C4 alkenyl group, a C2-C4 alkynyl group, a C1-C4 alkoxy group, or a C1-C4 alkylthio group; and
Q is the following structure:

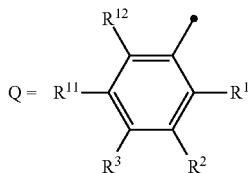

wherein,
$R^3$, $R^{11}$, and $R^{12}$ each represents a hydrogen atom, a halogen atom, a cyano group, a nitro group,
a C1-C3 alkoxy group optionally having one or more halogen atoms,
a C1-C3 alkylthio group optionally having one or more halogen atoms,
a C1-C3 alkyl group optionally having one or more halogen atoms, or a C3-C4 cycloalkyl group optionally having one or more halogen atoms;
$R^1$ and $R^2$ form a four-membered ring or a five-membered ring together with the carbon atom to which they are attached; and the ring may contain one or more atoms selected from the group consisting of an oxygen atom, a sulfur atom, and a nitrogen atom as a ring-constituent atom, and may have an oxo group, a thioxo group, or a C1-C3 alkoxyimino group on the same carbon atom, and may have one or two oxide groups on the same sulfur atom; and the phenyl moiety and the ring may have one or more atoms or groups selected from Group $P^4$ and, when the number of atoms or groups selected from Group $P^4$ is two or more, the atoms or groups may be the same or different; and the symbol o represents a binding site; and Group $P^4$ consisting of a halogen atom, a cyano group, a nitro group, a C1-C4 alkyl group, a C3-C6 cycloalkyl group, a C1-C4 haloalkyl group, a C3-C6 halocycloalkyl group, a C1-C4 alkoxy group, a C1-C4 haloalkoxy group, a C1-C4 alkylthio group, and a C1-C4 haloalkylthio group.

2. The tetrazolinone compound according to claim 1, wherein $R^6$ is C1-C3 alkyl group, a C3-C4 cycloalkyl group, a C1-C3 haloalkyl group, a halogen atom, or a methoxy group;
$R^{13}$ is a C1-C3 alkyl group;
$R^1$ and $R^2$ are bonded to form -E-CH$_2$—CH$_2$— (provided that E is bonded with the carbon atom to which $R^2$ is attached, and represents CH$_2$ or an oxygen atom); and
$R^3$, $R^{11}$, and $R^{12}$ each represents a hydrogen atom, a halogen atom, a C1-C3 alkyl group optionally having one or more halogen atoms, or a C1-C3 alkoxy group optionally having one or more halogen atoms.

3. A pest control agent comprising the tetrazolinone compound according to claim 1 as an active ingredient.

4. A method for controlling pests, which comprises treating the plant body or a cultivation area of the plant with an effective amount of the tetrazolinone compound according to claim 1.

5. The tetrazolinone compound according to claim 1, which is 1-{3-methyl-2-[1-(3-trifluoromethylphenyl)ethylideneaminooxymethyl]phenyl}-4-methyl-1,4-dihydrotetrazol-5-one.

* * * * *